US012807570B2

(12) United States Patent
Ji

(10) Patent No.: US 12,807,570 B2
(45) **Date of Patent: *Nov. 24, 2026**

(54) SMALL-MOLECULE INHIBITORS FOR THE B-CATENIN/B-CELL LYMPHOMA 9 PROTEIN-PROTEIN INTERACTION

(71) Applicant: H. Lee Moffitt Cancer Center and Research Institute, Inc., Tampa, FL (US)

(72) Inventor: Haitao Ji, Tampa, FL (US)

(73) Assignee: H. Lee Moffitt Cancer Center and Research Institute, Inc., Tampa, FL (US)

(*) Notice: Subject to any disclaimer, the term of this patent is extended or adjusted under 35 U.S.C. 154(b) by 965 days.

This patent is subject to a terminal disclaimer.

(21) Appl. No.: 17/761,737

(22) PCT Filed: Sep. 21, 2020

(86) PCT No.: PCT/US2020/051782

§ 371 (c)(1),
(2) Date: Mar. 18, 2022

(87) PCT Pub. No.: WO2021/055936

PCT Pub. Date: Mar. 25, 2021

(65) Prior Publication Data

US 2022/0411372 A1 Dec. 29, 2022

Related U.S. Application Data

(60) Provisional application No. 62/903,228, filed on Sep. 20, 2019.

(51) Int. Cl.

| | |
|---|---|
| ***C07D 401/12*** | (2006.01) |
| ***A61P 35/00*** | (2006.01) |
| ***C07D 211/60*** | (2006.01) |
| ***C07D 401/06*** | (2006.01) |
| ***C07D 401/10*** | (2006.01) |
| ***C07D 401/14*** | (2006.01) |
| ***C07D 405/12*** | (2006.01) |
| ***C07D 409/12*** | (2006.01) |
| ***C07D 413/12*** | (2006.01) |
| ***C07D 471/04*** | (2006.01) |
| ***C07D 471/10*** | (2006.01) |
| ***C07D 487/04*** | (2006.01) |
| ***C07D 487/10*** | (2006.01) |

(52) U.S. Cl.

CPC ............ *C07D 211/60* (2013.01); *A61P 35/00* (2018.01); *C07D 401/10* (2013.01); *C07D 401/12* (2013.01); *C07D 401/14* (2013.01); *C07D 409/12* (2013.01); *C07D 471/04* (2013.01); *C07D 487/04* (2013.01)

(58) Field of Classification Search

None

See application file for complete search history.

(56) References Cited

U.S. PATENT DOCUMENTS

| | | | | |
|---|---|---|---|---|
| 4,559,157 | A | 12/1985 | Smith et al. | |
| 4,608,392 | A | 8/1986 | Jacquet et al. | |
| 4,820,508 | A | 4/1989 | Wortzman | |
| 4,938,949 | A | 7/1990 | Borch | |
| 4,992,478 | A | 2/1991 | Geria | |
| 5,167,649 | A | 12/1992 | Zook | |
| 6,960,648 | B2 | 11/2005 | Bonny | |
| 2002/0035243 | A1 | 3/2002 | Imfeld et al. | |
| 2002/0120100 | A1 | 8/2002 | Bonny | |
| 2003/0032594 | A1 | 2/2003 | Bonny | |
| 2004/0157885 | A1 | 8/2004 | Bagley et al. | |
| 2007/0249580 | A1 * | 10/2007 | Nomura ............... | C07D 211/26 514/315 |
| 2011/0118314 | A1 | 5/2011 | Yun | |

FOREIGN PATENT DOCUMENTS

WO 2019139961 A1 7/2019

OTHER PUBLICATIONS

Barratt, Gillian., Therapeutic applications of colloidal drug carriers, PSTT vol. 3, No. 5 May 2000 (Year: 2000).*

Zhang et al., AlphaScreen selectivity assay for b-catenin/B-cell lymphoma 9 inhibitors, Analytical Biochemistry 469 (2015) 43-53 (Year: 2015).*

Adachi, S.; Jigami, T.; Yasui, T.; Nakano, T.; Ohwada, S.; Omori, Y.; Sugano, S.; Ohkawara, B.; Shibuya, H.; Nakamura, T.; Akiyama, T. Role of a BCL9-related beta-catenin-binding protein, B9L, in tumorigenesis induced by aberrant activation of Wnt signaling. Cancer research 2004, 64, 8496-8501.

Anastas, J. N.; Moon, R. T. WNT signalling pathways as therapeutic targets in cancer. Nature reviews. Cancer 2013, 13, 11-26.

Brembeck, F. H.; Schwarz-Romond, T.; Bakkers, J.; Wilhelm, S.; Hammerschmidt, M.; Birchmeier, W. Essential role of BCL9-2 in the switch between beta-catenin's adhesive and transcriptional functions. Genes & development 2004, 18, 2225-2230.

Brembeck, F. H.; Wiese, M.; Zatula, N.; Grigoryan, T.; Dai, Y.; Fritzmann, J.; Birchmeier, W. BCL9-2 promotes early stages of intestinal tumor progression. Gastroenterology 2011, 141, 1359-1370, 1370.e1351-1353.

(Continued)

*Primary Examiner* — Kortney L. Klinkel

*Assistant Examiner* — Alison Azar Hastings

(74) *Attorney, Agent, or Firm* — Meunier Carlin & Curfman LLC

(57) ABSTRACT

Disclosed are inhibitors for the β-catenin/B-cell lymphoma 9 interaction. The inhibitors are selective for β-catenin/B-cell lymphoma 9 over β-catenin/E-cadherin PPI interaction. Methods of using the disclosed compounds to treat cancer are also disclosed.

19 Claims, 7 Drawing Sheets

Specification includes a Sequence Listing.

(56) References Cited

OTHER PUBLICATIONS

Chen, B.; Dodge, M. E.; Tang, W.; Lu, J.; Ma, Z.; Fan, C. W.; Wei, S.; Hao, W.; Kilgore, J.; Williams, N. S.; Roth, M. G.; Amatruda, J. F.; Chen, C.; Lum, L. Small molecule-mediated disruption of Wnt-dependent signaling in tissue regeneration and cancer. Nature chemical biology 2009, 5, 100-107.
Chen, H. J.; Hsu, L. S.; Shia, Y. T.; Lin, M. W.; Lin, C. M. The beta-catenin/TCF complex as a novel target of resveratrol in the Wnt/beta-catenin signaling pathway. Biochemical pharmacology 2012, 84, 1143-1153.
Choi, H. J.; Gross, J. C.; Pokutta, S.; Weis, W. I. Interactions of plakoglobin and beta-catenin with desmosomal cadherins: basis of selective exclusion of alpha- and beta-catenin from desmosomes. The Journal of biological chemistry 2009, 284, 31776-31788.
Choi, H. J.; Huber, A. H.; Weis, W. I. Thermodynamics of beta-catenin-ligand interactions: the roles of the N- and C-terminal tails in modulating binding affinity. The Journal of biological chemistry 2006, 281, 1027-1038.
De la Roche, M.; Ibrahim, A. E.; Mieszczanek, J.; Bienz, M. LEF1 and B9L shield beta-catenin from inactivation by Axin, desensitizing colorectal cancer cells to tankyrase inhibitors. Cancer research 2014, 74, 1495-1505.
De la Roche, M.; Rutherford, T. J.; Gupta, D.; Veprintsev, D. B.; Saxty, B.; Freund, S. M.; Bienz, M. An intrinsically labile alpha-helix abutting the BCL9-binding site of beta-catenin is required for its inhibition by carnosic acid. Nat Commun 2012, 3, 680.
De la Roche, M.; Worm, J.; Bienz, M. The function of BCL9 in Wnt/beta-catenin signaling and colorectal cancer cells. BMC cancer 2008, 8, 199.
Deka, J.; Wiedemann, N.; Anderle, P.; Murphy-Seiler, F.; Bultinck, J.; Eyckerman, S.; Stehle, J. C.; Andre, S.; Vilain, N.; Zilian, O.; Robine, S.; Delorenzi, M.; Basler, K.; Aguet, M. Bc19/Bc191 are critical for Wnt-mediated regulation of stem cell traits in colon epithelium and adenocarcinomas. Cancer research 2010, 70, 6619-6628.
Dow, L. E.; O'Rourke, K. P.; Simon, J.; Tschaharganeh, D. F.; van Es, J. H.; Clevers, H.; Lowe, S. W. Apc Restoration Promotes Cellular Differentiation and Reestablishes Crypt Homeostasis in Colorectal Cancer. Cell 2015, 161, 1539-1552.
Drees, F.; Pokutta, S.; Yamada, S.; Nelson, W. J.; Weis, W. I. Alpha-catenin is a molecular switch that binds E-cadherin-beta-catenin and regulates actin-filament assembly. Cell 2005, 123, 903-915.
Eklof Spink, K.; Fridman, S. G.; Weis, W. I. Molecular mechanisms of beta-catenin recognition by adenomatous polyposis coli revealed by the structure of an APC-beta-catenin complex. The EMBO journal 2001, 20, 6203-6212.
Fearnhead, N. S.; Wilding, J. L.; Bodmer, W. F. Genetics of colorectal cancer: hereditary aspects and overview of colorectal tumorigenesis. British medical bulletin 2002, 64, 27-43.
Feng, M.; Jin, J. Q.; Xia, L.; Xiao, T.; Mei, S.; Wang, X.; Huang, X.; Chen, J.; Liu, M.; Chen, C.; Rafi, S.; Zhu, A. X.; Feng, Y. X.; Zhu, D. Pharmacological inhibition of beta-catenin/BCL9 interaction overcomes resistance to immune checkpoint blockades by modulating Treg cells. Science advances 2019, 5, eaau5240.
Fiedler, M.; Graeb, M.; Mieszczanek, J.; Rutherford, T. J.; Johnson, C. M.; Bienz, M. An ancient Pygo-dependent Wnt enhanceosome integrated by Chip/LDB-SSDP. eLife 2015, 4.
Fujii, N.; You, L.; Xu, Z.; Uematsu, K.; Shan, J.; He, B.; Mikami, I.; Edmondson, L. R.; Neale, G.; Zheng, J.; Guy, R. K.; Jablons, D. M. An antagonist of dishevelled protein-protein interaction suppresses beta-catenin-dependent tumor cell growth. Cancer research 2007, 67, 573-579.
Galluzzi, L.; Spranger, S.; Fuchs, E.; Lopez-Soto, A. WNT Signaling in Cancer Immunosurveillance. Trends in cell biology 2019, 29, 44-65.
Gay, D. M.; Ridgway, R. A.; Muller, M.; Hodder, M. C.; Hedley, A.; Clark, W.; Leach, J. D.; Jackstadt, R.; Nixon, C.; Huels, D. J.; Campbell, A. D.; Bird, T. G.; Sansom, O. J. Loss of BCL9/91 suppresses Wnt driven tumourigenesis in models that recapitulate human cancer. Nat Commun 2019, 10, 723.
Ha, N. C.; Tonozuka, T.; Stamos, J. L.; Choi, H. J.; Weis, W. I. Mechanism of phosphorylation-dependent binding of APC to beta-catenin and its role in beta-catenin degradation. Molecular cell 2004, 15, 511-521.
Hoggard, L. R.; Zhang, Y.; Zhang, M.; Panic, V.; Wisniewski, J. A.; Ji, H. Rational design of selective small-molecule inhibitors for beta-catenin/B-cell lymphoma 9 protein-protein interactions. J. Am. Chem. Soc. 2015, 137, 12249-12260.
Huang, S. M.;et al., Tankyrase inhibition stabilizes axin and antagonizes Wnt signalling. Nature 2009, 461, 614-620.
Huang, Z.; Zhang, M.; Burton, S. D.; Katsakhyan, L. N.; Ji, H. Targeting the Tcf4 G13ANDE17 binding site to selectively disrupt beta-catenin/T-cell factor protein-protein interactions. ACS chemical biology 2014, 9, 193-201.
Huber, A. H.; Weis, W. I. The structure of the beta-catenin/E-cadherin complex and the molecular basis of diverse ligand recognition by beta-catenin. Cell 2001, 105, 391-402.
Hwang, S. Y.; Deng, X.; Byun, S.; Lee, C.; Lee, S. J.; Suh, H.; Zhang, J.; Kang, Q.; Zhang, T.; Westover, K. D.; Mandinova, A.; Lee, S. W. Direct Targeting of beta-Catenin by a Small Molecule Stimulates Proteasomal Degradation and Suppresses Oncogenic Wnt/beta-Catenin Signaling. Cell Rep 2016, 16, 28-36.
Kawamoto, S. A.; Coleska, A.; Ran, X.; Yi, H.; Yang, C. Y.; Wang, S. Design of triazole-stapled BCL9 alpha-helical peptides to target the beta-catenin/B-cell CLL/lymphoma 9 (BCL9) protein-protein interaction. J Med Chem 2012, 55, 1137-1146.
Knapp, S.; Zamai, M.; Volpi, D.; Nardese, V.; Avanzi, N.; Breton, J.; Plyte, S.; Flocco, M.; Marconi, M.; Isacchi, A.; Caiolfa, V. R. Thermodynamics of the high-affinity interaction of TCF4 with beta-catenin. Journal of molecular biology 2001, 306, 1179-1189.
Liu, J.; Xing, Y.; Hinds, T. R.; Zheng, J.; Xu, W. The third 20 amino acid repeat is the tightest binding site of APC for beta-catenin. Journal of molecular biology 2006, 360, 133-144.
Lu, D.; Choi, M. Y.; Yu, J.; Castro, J. E.; Kipps, T. J.; Carson, D. A. Salinomycin inhibits Wnt signaling and selectively induces apoptosis in chronic lymphocytic leukemia cells. Proceedings of the National Academy of Sciences of the United States of America 2011, 108, 13253-13257.
Lu, D.; Zhao, Y.; Tawatao, R.; Cottam, H. B.; Sen, M.; Leoni, L. M.; Kipps, T. J.; Corr, M.; Carson, D. A. Activation of the Wnt signaling pathway in chronic lymphocytic leukemia. Proceedings of the National Academy of Sciences of the United States of America 2004, 101, 3118-3123.
Lum, L.; Clevers, H. Cell biology. The unusual case of Porcupine. Science (New York, N.Y.) 2012, 337, 922-923.
Lyou, Y.; Habowski, A. N.; Chen, G. T.; Waterman, M. L. Inhibition of nuclear Wnt signalling: challenges of an elusive target for cancer therapy. British journal of pharmacology 2017, 174, 4589-4599.
Mani, M.; Carrasco, D. E.; Zhang, Y.; Takada, K.; Gatt, M. E.; Dutta-Simmons, J.; Ikeda, H.; Diaz-Griffero, F.; Pena-Cruz, V.; Bertagnolli, M.; Myeroff, L. L.; Markowitz, S. D.; Anderson, K. C.; Carrasco, D. R. BCL9 promotes tumor progression by conferring enhanced proliferative, metastatic, and angiogenic properties to cancer cells. Cancer research 2009, 69, 7577-7586.
Mieszczanek, J.; van Tienen, L. M.; Ibrahim, A. E. K.; Winton, D. J.; Bienz, M. Bcl9 and Pygo synergise downstream of Apc to effect intestinal neoplasia in FAP mouse models. Nat Commun 2019, 10, 724.
Moor, A. E.; Anderle, P.; Cantu, C.; Rodriguez, P.; Wiedemann, N.; Baruthio, F.; Deka, J.; Andre, S.; Valenta, T.; Moor, M. B.; Gyorffy, B.; Barras, D.; Delorenzi, M.; Basler, K.; Aguet, M. BCL9/9L-beta-catenin Signaling is Associated With Poor Outcome in Colorectal Cancer. EBioMedicine 2015, 2, 1932-1943.
Nusse, R.; Clevers, H. Wnt/beta-Catenin Signaling, Disease, and Emerging Therapeutic Modalities. Cell 2017, 169, 985-999.
Orsulic, S.; Huber, O.; Aberle, H.; Arnold, S.; Kemler, R. E-cadherin binding prevents beta-catenin nuclear localization and beta-catenin/LEF-1-mediated transactivation. Journal of cell science 1999, 112 ( Pt 8), 1237-1245.

(56) References Cited

OTHER PUBLICATIONS

Proffitt, K. D.; Madan, B.; Ke, Z.; Pendharkar, V.; Ding, L.; Lee, M. A.; Hannoush, R. N.; Virshup, D. M. Pharmacological inhibition of the Wnt acyltransferase PORCN prevents growth of WNT-driven mammary cancer. Cancer research 2013, 73, 502-507.

Sampietro, J.; Dahlberg, C. L.; Cho, U. S.; Hinds, T. R.; Kimelman, D.; Xu, W. Crystal structure of a beta-catenin/BCL9/Tcf4 complex. Molecular cell 2006, 24, 293-300.

Sang, P.; Zhang, M.; Shi, Y.; Li, C.; Abdulkadir, S.; Li, Q.; Ji, H.; Cai, J. Inhibition of beta-catenin/B cell lymphoma 9 protein-protein interaction using alpha-helix-mimicking sulfono-gamma-AApeptide inhibitors. Proceedings of the National Academy of Sciences of the United States of America 2019, 116, 10757-10762.

Shin, S. H.; Lim, D. Y.; Reddy, K.; Malakhova, M.; Liu, F.; Wang, T.; Song, M.; Chen, H.; Bae, K. B.; Ryu, J.; Liu, K.; Lee, M. H.; Bode, A. M.; Dong, Z. A Small Molecule Inhibitor of the beta-Catenin-TCF4 Interaction Suppresses Colorectal Cancer Growth In Vitro and In Vivo. EBioMedicine 2017, 25, 22-31.

Smith, M. C.; Gestwicki, J. E. Features of protein-protein interactions that translate into potent inhibitors: topology, surface area and affinity. Expert reviews in molecular medicine 2012, 14, e16.

Sukhdeo, K.; Mani, M.; Zhang, Y.; Dutta, J.; Yasui, H.; Rooney, M. D.; Carrasco, D. E.; Zheng, M.; He, H.; Tai, Y. T.; Mitsiades, C.; Anderson, K. C.; Carrasco, D. R. Targeting the beta-catenin/TCF transcriptional complex in the treatment of multiple myeloma. Proceedings of the National Academy of Sciences of the United States of America 2007, 104, 7516-7521.

Sun, J.; Weis, W. I. Biochemical and structural characterization of beta-catenin interactions with nonphosphorylated and CK2-phosphorylated Lef-1. Journal of molecular biology 2011, 405, 519-530.

Takada, K.; Zhu, D.; Bird, G. H.; Sukhdeo, K.; Zhao, J. J.; Mani, M.; Lemieux, M.; Carrasco, D. E.; Ryan, J.; Horst, D.; Fulciniti, M.; Munshi, N. C.; Xu, W.; Kung, A. L.; Shivdasani, R. A.; Walensky, L. D.; Carrasco, D. R. Targeted disruption of the BCL9/beta-catenin complex inhibits oncogenic Wnt signaling. Science translational medicine 2012, 4, 148ra117.

Thorne, C. A.; Hanson, A. J.; Schneider, J.; Tahinci, E.; Orton, D.; Cselenyi, C. S.; Jernigan, K. K.; Meyers, K. C.; Hang, B. I.; Waterson, A. G.; Kim, K.; Melancon, B.; Ghidu, V. P.; Sulikowski, G. A.; LaFleur, B.; Salic, A.; Lee, L. A.; Miller, D. M., 3rd; Lee, E. Small-molecule inhibition of Wnt signaling through activation of casein kinase 1alpha. Nature chemical biology 2010, 6, 829-836.

Tickenbrock, L.; Kossmeier, K.; Rehmann, H.; Herrmann, C.; Muller, O. Differences between the interaction of beta-catenin with non-phosphorylated and single-mimicked phosphorylated 20-amino acid residue repeats of the APC protein. Journal of molecular biology 2003, 327, 359-367.

Toyoizumi, et al., "Combined therapy with chemotherapeutic agents and herpes simplex virus type IICP34.5 mutant (HSV-1716) in human non-small cell lung cancer," Human Gene Therapy, 1999, 10(18):17.

Van de Wetering, M.; Sancho, E.; Verweij, C.; de Lau, W.; Oving, I.; Hurlstone, A.; van der Horn, K.; Batlle, E.; Coudreuse, D.; Haramis, A. P.; Tjon-Pon-Fong, M.; Moerer, P.; van den Born, M.; Soete, G.; Pals, S.; Eilers, M.; Medema, R.; Clevers, H. The beta-catenin/TCF-4 complex imposes a crypt progenitor phenotype on colorectal cancer cells. Cell 2002, 111, 241-250.

Van Tienen, L. M.; Mieszczanek, J.; Fiedler, M.; Rutherford, T. J.; Bienz, M. Constitutive scaffolding of multiple Wnt enhanceosome components by Legless/BCL9. eLife 2017, 6.

Waaler, J.; Machon, O.; Tumova, L.; Dinh, H.; Korinek, V.; Wilson, S. R.; Paulsen, J. E.; Pedersen, N. M.; Eide, T. J.; Machonova, O.; Gradl, D.; Voronkov, A.; von Kries, J. P.; Krauss, S. A novel tankyrase inhibitor decreases canonical Wnt signaling in colon carcinoma cells and reduces tumor growth in conditional APC mutant mice. Cancer research 2012, 72, 2822-2832.

Wang, Z.; Zhang, M.; Wang, J.; Ji, H. Optimization of Peptidomimetics as Selective Inhibitors for the beta-Catenin/T-Cell Factor Protein-Protein Interaction. Journal of medicinal chemistry 2019, 62, 3617-3635.

Xing, Y.; Clements, W. K.; Le Trong, I.; Hinds, T. R.; Stenkamp, R.; Kimelman, D.; Xu, W. Crystal structure of a beta-catenin/APC complex reveals a critical role for APC phosphorylation in APC function. Molecular cell 2004, 15, 523-533.

Yu, B.; Huang, Z.; Zhang, M.; Dillard, D. R.; Ji, H. Rational design of small-molecule inhibitors for beta-catenin/T-cell factor protein-protein interactions by bioisostere replacement. ACS chemical biology 2013, 8, 524-529.

Zhang, M.; Wang, Z.; Zhang, Y.; Guo, W.; Ji, H. Structure-Based Optimization of Small-Molecule Inhibitors for the beta-Catenin/B-Cell Lymphoma 9 Protein-Protein Interaction. J. Med. Chem. 2018, 61, 2989-3007.

International Search Report and Written Opinion in PCT/US2020/051782, mailed Jan. 29, 2021, 10 pages.

PUBCHEM, CID 71192680. Mar. 21, 2013. pp. 1-8. Retrieved from the internet , URL: https://pubchem.ncbi.nlm.nih.gov/compound/71192680; p. 2, formula.

* cited by examiner

37

A

| Compound | $K_i$ ± SD (μM) | | Selectivity |
|---|---|---|---|
| | β-catenin/BCL9 | β-catenin/E-cadherin | BCL9/E-cadherin |
| **37** | 0.76 ± 0.044 | 174 ± 38 | 229 |

A

| Cmpd. | $t_{1/2}$ (min) | | $CL_{int}$ ($\mu$M/min/mg) | |
|---|---|---|---|---|
| | human | mouse | human | mouse |
| sunitinib | 27.8 | 13.0 | 25 | 53 |
| **25** | 35.3 | 18.2 | 20 | 38 |
| **37** | 38.4 | 9.6 | 18 | 72 |
| **46** | 28.3 | 7.7 | 24 | 90 |

B

| Cmpd. | route | dose (mg/kg) | $C_{max}$ ($\mu$M) | AUC ($\mu$M · h) | Vd (L/kg) | CL (mL/min/kg) | $t_{1/2}$ (h) | %F |
|---|---|---|---|---|---|---|---|---|
| **37** | iv | 1 | 0.79 | 0.71 | 8.0 | 44.20 | 3.51 | |
| **37** | po | 20 | 3.21 | 11.71 | — | 51.10 | 3.07 | 83 |

FIGURES 5A-5B

SMALL-MOLECULE INHIBITORS FOR THE B-CATENIN/B-CELL LYMPHOMA 9 PROTEIN-PROTEIN INTERACTION

CROSS REFERENCE TO RELATED APPLICATIONS

This application is a United States National Phase Patent Application of International Patent Application Number PCT/US2020/051782, filed on Sep. 21, 2020 which claims the benefit of priority to U.S. Provisional Application No. 62/903,228, filed Sep. 20, 2019, both of which are incorporated by reference herein in their entireties.

SEQUENCE LISTING

A Sequence Listing conforming to the rules of WIPO Standard ST.25 is hereby incorporated by reference. Said Sequence Listing has been filed as an electronic document via Patent Center encoded as a .txt file. The electronic document, created on Jul. 17, 2025, is entitled "10110-242US1_ST25.txt", and is 5,263 bytes in size.

BACKGROUND

The protein β-catenin plays essential roles in canonical Wnt signaling and cell-cell adhesion in mammalian cells. β-Catenin is a structural component of adherens junctions, where it binds to the cytoplasmic domain of E-cadherin in epithelial cells to recruit and organize actin filaments. β-Catenin is also the central mediator of the canonical Wnt signaling pathway and essential in directing cell proliferation, differentiation, and survival. In the absence of Wnt ligands, almost all β-catenin binds with the cell membrane. The free cytosolic β-catenin is continuously phosphorylated by the destruction complex that includes adenomatous polysis *coli* (APC), Axin, glycogen synthase kinase 3β (GSK38), and casein kinase 1α (CK1α), ubiquitinylated by β-TrCP, and degraded by the 26S proteasome. When the suppressor genes APC and Axin suffer from the loss-of-function mutations and/or the N-terminal phosphorylation sites of the β-catenin gene (CTNNB1) are mutated inappropriately, β-catenin is stabilized into the dephosphorylated state and then translocated into the cell nucleus. Unphosphorylated β-catenin associates with the DNA-binding T-cell factor (Tcf)/lymphoid enhancer factor (Lef) to recruit co-activators, B-cell lymphoma 9 (BCL9), Pygo, CREB-binding protein (CBP), etc. to activate transcription of specific Wnt/β-catenin target genes. These target genes can promote self-renewal of cancer stem cells, induce epithelial-to-mesenchymal transition, activate tumor cell invasion and metastasis, foster tumor vascularization, confer treatment resistance, and cause tumor immune evasion. The autocrine/paracrine activation of Wnt ligands, frizzled (Fzd), and disheveled (Dvl), and the epigenetic silencing of Wnt antagonist genes can also cause hyperactivation of Wnt/β-catenin signaling.

Although extensive efforts have been made to discover inhibitors for the upstream effectors of the Wnt/β-catenin signaling pathway, inhibition of the upstream Wnt effectors: 1) cannot confer efficacy to most disease-causing mutations including more downstream APC and Axin loss-of-function mutations and β-catenin activation mutations; 2)) are ineffective against cancer with upregulation of downstream Wnt effectors, such as β-catenin, by crosstalk with the other signaling pathways; and 3) can increase the risk of undesirable off-pathway effects by inhibiting noncanonical Wnt signaling pathways. The most effective target to develop inhibitors is the β-catenin-containing transcriptional complex, because the formation of this transcriptional complex in the cell nucleus is the penultimate step of this pathway, and the transcriptional activation of Wnt/β-catenin signaling is dependent on the formation of this complex. However, direct targeting of oncogenic β-catenin has proven to be a formidable challenge. Most β-catenin-directed efforts focused on discovering inhibitors for its main ligand interaction surface with Tcf/Lef but none of these compounds have advanced beyond the early stage of preclinical development, probably due to two great challenges: 1) β-catenin and Tcf have a very large contacting surface area (3500 $Å^2$) and the tight binding affinity ($K_D$=7-10 nM), indicating it might be too difficult to be disrupted by a small molecule; and 2) β-catenin uses the same surface area for binding with Tcf, APC, and E-cadherin, and Tcf has much higher affinity for β-catenin than APC and E-cadherin, indicating achieving selectivity might be a tough issue. To avoid these challenges, β-catenin/BCL9 PPI represents a promising alternative target for the Wnt/β-catenin pathway. BCL9 or B9L (BCL9-like, a BCL9 paralog) is the scaffolding protein of the Wnt enhanceosome that captures newly stabilized, nuclear-localized β-catenin, facilitates β-catenin access to Tcf/Lef, and activates the β-catenin-containing transcriptional complex. BCL9 and B9L adopts a single α-helical structure to interact with β-catenin. The contacting area between β-catenin and BCL9 is much smaller (1450 $Å^2$) and this PPI has a moderate binding affinity ($K_D$=0.47 μM). The binding surface of β-catenin for BCL9 interaction has little overlap with the other β-catenin partners with E-cadherin region V being the only reported additional binding partner at this PPI interface. The β-catenin/BCL9 complex is predominantly found in tumor tissues, and eliminating BCL9/B9L in the murine gut had no overt phenotypic consequences and no impact on normal intestinal homeostasis. Use of siRNAs and shRNAs against BCL9/B9L markedly decreases β-catenin-dependent gene expression and diminishes cancer cell growth in vitro and in vivo. BCL9/B9L loss suppresses Wnt driven tumorigenesis and extends disease-free survival in models that recapitulate human cancer.

While several peptide-based inhibitors have been reported to disrupt the β-catenin/BCL9 PPI, small-molecule inhibitors are scarce. Bienz and coworkers discovered a natural product carnosic acid as an inhibitor of the β-catenin/BCL9 PPI by screening two compound libraries. Recently 3-(4-fluorophenyl)-N-phenylbenzamide (PNPB) derivatives have been reported as inhibitors of β-catenin/BCL9 PPI by rational design and optimization. There is a need for inhibitors that binds with β-catenin and selectively disrupt the β-catenin/BCL9 PPI. The compositions and methods disclosed herein address these and other needs. Herein, disclosed are novel small-molecule inhibitors that binds with β-catenin and selectively disrupt the β-catenin/BCL9 PPI, and the proteolysis-targeting chimera (PROTAC) based on this series of compounds to degrade β-catenin.

SUMMARY

In accordance with the purposes of the disclosed materials and methods, as embodied and broadly described herein, the disclosed subject matter, in one aspect, relates to compounds, compositions and methods of making and using compounds and compositions. The compounds can have a structure represented by Formula I below:

Formula I

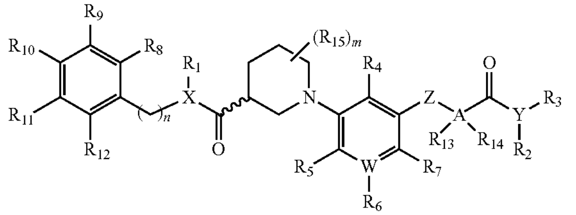

wherein n is 1 or 2;

m is 0, 1, or 2;

W is selected from C or N, wherein when W is N, then $R_6$ is absent;

X is selected from O, N, —R'O, or —R'N, wherein R' is selected from $C_1$-$C_3$ alkyl;

Y is selected from O, N;

Z is absent or O;

A is absent or selected from $C_1$-$C_3$ alkyl, preferably $C_1$ alkyl;

$R_1$ is absent or selected from hydrogen, halogen, $C_1$-$C_6$ alkyl, $C_1$-$C_6$ alkoxy, $C_1$-$C_6$ haloalkyl, $C_1$-$C_6$ haloalkoxy, $C_1$-$C_6$ alkylamine, $C_2$-$C_6$ ether, $C_3$-$C_6$ cycloalkyl, $C_3$-$C_6$ cycloalkenyl, heteroaryl, or a linker conjugated to a PROTAC moiety; wherein $R_1$ is optionally substituted with halogen, hydroxyl, carboxyl, amino, cyano, nitro, isocyano, alkyl, haloalkyl, haloalkoxy, cycloalkyl, a linker conjugated to a PROTAC moiety, heterocycloalkyl, aryl, or heteroaryl;

$R_2$ and $R_3$ are independently absent or selected from hydrogen, $C_1$-$C_6$ alkyl, $C_3$-$C_{10}$ cycloalkyl, a $C_2$-$C_8$ heterocycloalkyl, $C_5$-$C_{10}$ aryl, $C_2$-$C_8$ heteroaryl, a linker conjugated to a PROTAC moiety, or $R_2$ and $R_3$ combine together with the atoms to which they are attached to form a heterocycloalkyl, a heterocycloalkenyl, or a heteroaryl, wherein $R_2$ and $R_3$ are optionally substituted with halogen, hydroxyl, carboxyl, amino, cyano, nitro, isocyano, alkyl, haloalkyl, haloalkoxy, a linker conjugated to a PROTAC moiety, cycloalkyl, heterocycloalkyl, aryl, or heteroaryl;

$R_4$, $R_5$, $R_6$, and $R_7$ are independently selected from hydrogen, hydroxyl, halogen, cyano, $C_1$-$C_3$ alkyl, $C_1$-$C_3$ alkoxy, $C_1$-$C_3$ alkylhalide, or a linker conjugated to a PROTAC moiety;

$R_8$ and $R_9$ are independently selected from hydrogen, $C_1$-$C_6$ alkyl, $C_1$-$C_6$ alkoxy, $C_3$-$C_8$ cycloalkyl, a $C_1$-$C_7$ heterocycloalkyl, $C_5$-$C_8$ aryl, $C_1$-$C_8$ heteroaryl, a linker conjugated to a PROTAC moiety, or $R_1$ and $R_8$ combine together with the atoms to which they are attached to form a heterocycloalkyl, or a heterocycloalkenyl, wherein $R_8$ and $R_9$ are optionally substituted with halogen, hydroxyl, amino, cyano, nitro, isocyano, carboxyl, hydroxyl, alkyl, alkoxy, alkenyl, haloalkyl, haloalkoxy, a linker conjugated to a PROTAC moiety, cycloalkyl, heterocycloalkyl, aryl, or heteroaryl;

$R_{10}$ is selected from hydrogen, $C_1$-$C_6$ alkyl, $C_1$-$C_6$ haloalkyl, $C_1$-$C_6$ alkylamine, $C_1$-$C_6$ alkoxy, $C_1$-$C_6$ haloalkoxy, $C_3$-$C_{10}$ cycloalkyl, a $C_2$-$C_8$ heterocycloalkyl, $C_5$-$C_{10}$ aryl, $C_2$-$C_8$ heteroaryl, or a linker conjugated to a PROTAC moiety, wherein $R_{10}$ is optionally substituted with halogen, hydroxyl, amino, cyano, nitro, isocyano, carboxyl, hydroxyl, alkyl, alkoxy, alkenyl, haloalkyl, haloalkoxy, a linker conjugated to a PROTAC moiety, cycloalkyl, heterocycloalkyl, aryl, or heteroaryl;

$R_{11}$ and $R_{12}$ are independently selected from hydrogen, hydroxyl, halogen, cyano, $C_1$-$C_3$ alkyl, $C_1$-$C_3$ alkoxy, $C_1$-$C_3$ heteroalkyl, $C_1$-$C_3$ alkylhalide, or a linker conjugated to a PROTAC moiety;

$R_{13}$ and $R_{14}$ are independently selected from hydrogen, hydroxyl, halogen, cyano, $C_1$-$C_6$ alkyl, $C_1$-$C_6$ alkoxy, $C_1$-$C_6$ alkylhalide, aryl, alkylaryl, heteroaryl, alkylheteroaryl, a linker conjugated to a PROTAC moiety, or $R_{13}$ and $R_{14}$ combine together with the atoms to which they are attached to form a cycloalkyl, a cycloalkenyl, a heterocycloalkyl, or a heterocycloalkenyl, wherein $R_{13}$ and $R_{14}$ are optionally substituted with halogen, hydroxyl, amino, cyano, nitro, isocyano, carboxyl, hydroxyl, alkyl, alkoxy, alkenyl, haloalkyl, haloalkoxy, a linker conjugated to a PROTAC moiety, cycloalkyl, heterocycloalkyl, aryl, or heteroaryl, and $R_{15}$ is absent or for each occurrence, independently selected from hydroxyl, halogen, cyano, $C_1$-$C_6$ alkyl, $C_1$-$C_6$ alkoxy, $C_1$-$C_6$ alkylhalide, aryl, heteroaryl, a linker conjugated to a PROTAC moiety, wherein $R_{15}$ is optionally substituted with halogen, hydroxyl, amino, cyano, nitro, isocyano, carboxyl, hydroxyl, alkyl, alkoxy, alkenyl, haloalkyl, haloalkoxy, a linker conjugated to a PROTAC moiety, cycloalkyl, heterocycloalkyl, aryl, or heteroaryl.

The compound can have a chiral designation of R, S, or the racemic mixture.

Pharmaceutical compositions comprising a therapeutically effective amount of a compound as disclosed herein or a pharmaceutically acceptable salt thereof, and a pharmaceutically acceptable carrier are also disclosed.

In specific aspects, the disclosed subject matter relates to cancer therapy and to anti-cancer compounds. More specifically, the subject matter disclosed herein relates to inhibitors for the β-catenin/B-cell lymphoma 9 interaction. Further, the subject matter disclosed herein relates to inhibitors that are selective for β-catenin/B-cell lymphoma 9 interactions over β-catenin/E-cadherin PPI interaction. Also disclosed are methods of inhibiting the β-catenin/B-cell lymphoma 9 interaction, as well as methods of treating certain cancers.

In specific aspects, the disclosed subject matter relates to cancer therapy and to anti-cancer compounds. More specifically, the subject matter disclosed herein relates to degradation of β-catenin. Also disclosed are methods of degrading nuclear β-catenin as methods of treating certain cancers.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DESCRIPTION OF THE FIGURES

FIG. 5A shows hepatic microsome stability of compound 11 and positive control sunitinib. FIG. 5B shows mouse PK data of compound 11. Male C57BL/6 mice were administrated with compound 11 through intravenous injection (iv) via tail vein or through oral gavage (po).

DETAILED DESCRIPTION

Figure 1A:
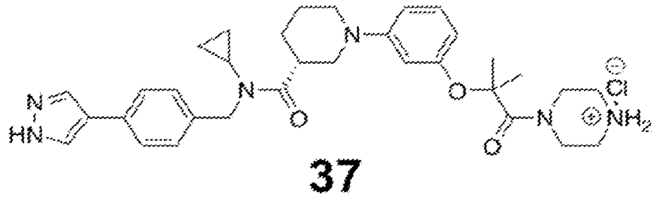
FIG. 1A shows the selectivity of inhibitor 37 between β-catenin/BCL9 and β-catenin/E-cadherin interactions. Wnt-responsive TOPFlash luciferase reporter assay results of inhibitor 37 in β-catenin activated HEK293 cells (FIG. 1B) and SW480 cells (FIG. 1C) and of positive control compound ICG-001 in SW480 cells (FIG. 1D) are also shown. Wnt-responsive FOPFlash luciferase reporter assay results of inhibitor 37 in β-catenin activated HEK293 cells (FIG. 1E) and SW480 cells (FIG. 1F) and of ICG-001 in SW480 cells (FIG. 1G) are further shown.

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, “treatment” refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, delaying occurrence or recurrence of cancer, delay or slowing of cancer progression, amelioration of the cancer state, and remission (whether partial or total).

The term “patient” preferably refers to a human in need of treatment with an anti-cancer agent or treatment for any purpose, and more preferably a human in need of such a treatment to treat cancer, or a precancerous condition or lesion. However, the term “patient” can also refer to non-human animals, preferably mammals such as dogs, cats, horses, cows, pigs, sheep and non-human primates, among others, that are in need of treatment with an anti-cancer agent or treatment.

It is understood that throughout this specification the identifiers “first” and “second” are used solely to aid in distinguishing the various components and steps of the disclosed subject matter. The identifiers “first” and “second” are not intended to imply any particular order, amount, preference, or importance to the components or steps modified by these terms.

Chemical Definitions

As used herein, the term “composition” is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term “substituted” is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms “substitution” or “substituted with” include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term “aliphatic” as used herein refers to a non-aromatic hydrocarbon group and includes branched and unbranched, alkyl, alkenyl, or alkynyl groups.

The term “alkyl” as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A^n$ is used herein as merely a generic substituent in the definitions below.

The term “alkoxy” as used herein is an alkyl group bound through a single, terminal ether linkage; that is, an “alkoxy” group can be defined as $—OA^1$ where $A^1$ is alkyl as defined above.

The term “alkenyl” as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This may be presumed in structural formulae herein wherein an asymmetric alkene is present, or it may be explicitly indicated by the bond symbol C═C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term “alkynyl” as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term “aryl” as used herein is a group that contains any carbon-based aromatic group including, but not limited to, benzene, naphthalene, phenyl, biphenyl, phenoxybenzene, and the like. The term “heteroaryl” is defined as a group that contains an aromatic group that has at least one heteroatom incorporated within the ring of the aromatic group. Examples of heteroatoms include, but are not limited to, nitrogen, oxygen, sulfur, and phosphorus. The term “non-heteroaryl,” which is included in the term “aryl,” defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term “biaryl” is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C═O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula $—C(O)O^-$.

The term "ester" as used herein is represented by the formula $—OC(O)\ A^1$ or $—C(O)OA^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)\ A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula $—NO_2$.

The term "cyano" as used herein is represented by the formula —CN The term "azido" as used herein is represented by the formula $—N_3$.

The term "sulfonyl" is used herein to refer to the sulfo-oxo group represented by the formula $—S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula $—S(O)_2NH_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Compounds

In certain aspects, disclosed herein are compounds having Formula I.

Formula I

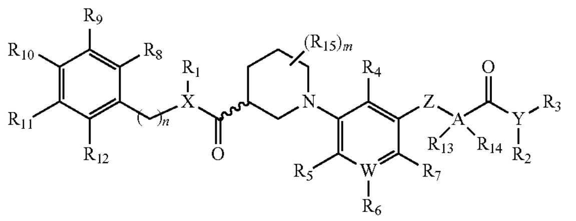

wherein n is 1 or 2;

m is 0, 1, or 2;

W is selected from C or N, wherein when W is N, then $R_6$ is absent;

X is selected from O, N, —R'O, or —R'N, wherein R' is selected from $C_1$-$C_3$ alkyl;

Y is selected from O, N;

Z is absent or O;

A is absent or selected from $C_1$-$C_3$ alkyl, preferably $C_1$ alkyl;

$R_1$ is absent or selected from hydrogen, halogen, $C_1$-$C_6$ alkyl, $C_1$-$C_6$ alkoxy, $C_1$-$C_6$ haloalkyl, $C_1$-$C_6$ haloalkoxy, $C_1$-$C_6$ alkylamine, $C_2$-$C_6$ ether, $C_3$-$C_6$ cycloalkyl, $C_3$-$C_6$ cycloalkenyl, heteroaryl, or a linker conjugated to a PROTAC moiety; wherein $R_1$ is optionally substituted with halogen, hydroxyl, carboxyl, amino, cyano, nitro, isocyano, alkyl, haloalkyl, haloalkoxy, cycloalkyl, a linker conjugated to a PROTAC moiety, heterocycloalkyl, aryl, or heteroaryl;

$R_2$ and $R_3$ are independently absent or selected from hydrogen, $C_1$-$C_6$ alkyl, $C_3$-$C_{10}$ cycloalkyl, a $C_2$-$C_8$ heterocycloalkyl, $C_5$-$C_{10}$ aryl, $C_2$-$C_8$ heteroaryl, a linker conjugated to a PROTAC moiety, or $R_2$ and $R_3$ combine together with the atoms to which they are attached to form a heterocycloalkyl, a heterocycloalkenyl, or a heteroaryl, wherein $R_2$ and $R_3$ are optionally substituted with halogen, hydroxyl, carboxyl, amino, cyano, nitro, isocyano, alkyl, haloalkyl, haloalkoxy, a linker conjugated to a PROTAC moiety, cycloalkyl, heterocycloalkyl, aryl, or heteroaryl;

$R_4$, $R_5$, $R_6$, and $R_7$ are independently selected from hydrogen, hydroxyl, halogen, cyano, $C_1$-$C_3$ alkyl, $C_1$-$C_3$ alkoxy, $C_1$-$C_3$ alkylhalide, or a linker conjugated to a PROTAC moiety;

$R_8$ and $R_9$ are independently selected from hydrogen, $C_1$-$C_6$ alkyl, $C_1$-$C_6$ alkoxy, $C_3$-$C_8$ cycloalkyl, a $C_1$-$C_7$ heterocycloalkyl, $C_5$-$C_8$ aryl, $C_1$-$C_8$ heteroaryl, a linker conjugated to a PROTAC moiety, or $R_1$ and $R_8$ combine together with the atoms to which they are attached to form a heterocycloalkyl, or a heterocycloalkenyl, wherein $R_8$ and $R_9$ are optionally substituted with halogen, hydroxyl, amino, cyano, nitro, isocyano, carboxyl, hydroxyl, alkyl, alkoxy, alkenyl, haloalkyl, haloalkoxy, a linker conjugated to a PROTAC moiety, cycloalkyl, heterocycloalkyl, aryl, or heteroaryl;

$R_{10}$ is selected from hydrogen, $C_1$-$C_6$ alkyl, $C_1$-$C_6$ haloalkyl, $C_1$-$C_6$ alkylamine, $C_1$-$C_6$ alkoxy, $C_1$-$C_6$ haloalkoxy, $C_3$-$C_{10}$ cycloalkyl, a $C_2$-$C_8$ heterocycloalkyl, $C_5$-$C_{10}$ aryl, $C_2$-$C_8$ heteroaryl, or a linker conjugated to a PROTAC moiety, wherein $R_{10}$ is optionally substituted with halogen, hydroxyl, amino, cyano, nitro, isocyano, carboxyl, hydroxyl, alkyl, alkoxy, alkenyl, haloalkyl, haloalkoxy, a linker conjugated to a PROTAC moiety, cycloalkyl, heterocycloalkyl, aryl, or heteroaryl;

$R_{11}$ and $R_{12}$ are independently selected from hydrogen, hydroxyl, halogen, cyano, $C_1$-$C_3$ alkyl, $C_1$-$C_3$ alkoxy, $C_1$-$C_3$ heteroalkyl, $C_1$-$C_3$ alkylhalide, or a linker conjugated to a PROTAC moiety;

$R_{13}$ and $R_{14}$ are independently selected from hydrogen, hydroxyl, halogen, cyano, $C_1$-$C_6$ alkyl, $C_1$-$C_6$ alkoxy, $C_1$-$C_6$ alkylhalide, aryl, alkylaryl, heteroaryl, alkylheteroaryl, a linker conjugated to a PROTAC moiety, or $R_{13}$ and $R_{14}$ combine together with the atoms to which they are attached to form a cycloalkyl, a cycloalkenyl, a heterocycloalkyl, or a heterocycloalkenyl, wherein $R_{13}$ and $R_{14}$ are optionally substituted with halogen, hydroxyl, amino, cyano, nitro, isocyano, carboxyl, hydroxyl, alkyl, alkoxy, alkenyl, haloalkyl, haloalkoxy, a linker conjugated to a PROTAC moiety, cycloalkyl, heterocycloalkyl, aryl, or heteroaryl, and $R_{15}$ is absent or for each occurrence, independently selected from hydroxyl, halogen, cyano, $C_1$-$C_6$ alkyl, $C_1$-$C_6$ alkoxy, $C_1$-$C_6$ alkylhalide, aryl, heteroaryl, a linker conjugated to a PROTAC moiety, wherein $R_{15}$ is optionally substituted with halogen, hydroxyl, amino, cyano, nitro, isocyano, carboxyl, hydroxyl, alkyl, alkoxy, alkenyl, haloalkyl, haloalkoxy, a linker conjugated to a PROTAC moiety, cycloalkyl, heterocycloalkyl, aryl, or heteroaryl.

In some aspects, the compound of Formula I can have a structure according to Formula I-A.

Formula I-A

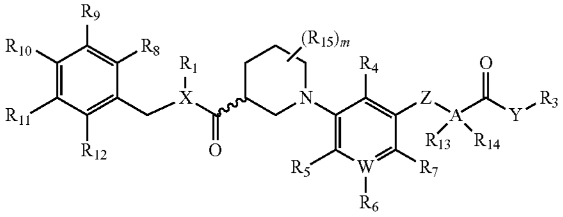

wherein m is 0, 1, or 2;

W is selected from C or N, wherein when W is N, then $R_6$ is absent;

X is selected from O, N, —R'O, or —R'N, wherein R' is selected from $C_1$-$C_3$ alkyl;

Y is selected from O, N;

Z is absent or O;

A is absent or selected from $C_1$-$C_3$ alkyl, preferably $C_1$ alkyl;

$R_1$ is absent or selected from hydrogen, halogen, $C_1$-$C_6$ alkyl, $C_1$-$C_6$ alkoxy, $C_1$-$C_6$ haloalkyl, $C_1$-$C_6$ haloalkoxy, $C_1$-$C_6$ alkylamine, $C_3$-$C_6$ cycloalkyl, $C_3$-$C_6$ cycloalkenyl, heteroaryl, or a linker conjugated to a PROTAC moiety; wherein $R_1$ is optionally substituted with halogen, hydroxyl, carboxyl, amino, cyano, nitro, isocyano, alkyl, haloalkyl, haloalkoxy, a linker conjugated to a PROTAC moiety, cycloalkyl, heterocycloalkyl, aryl, or heteroaryl;

$R_3$ is selected from hydrogen, $C_1$-$C_6$ alkyl, $C_3$-$C_{10}$ cycloalkyl, a $C_2$-$C_8$ heterocycloalkyl, $C_5$-$C_{10}$ aryl, $C_2$-$C_8$ heteroaryl, or a linker conjugated to a PROTAC moiety, wherein $R_3$ is optionally substituted with halogen, hydroxyl, carboxyl, amino, cyano, nitro, isocyano, alkyl, haloalkyl, haloalkoxy, cycloalkyl, heterocycloalkyl, aryl, or heteroaryl;

$R_4$, $R_5$, $R_6$, and $R_7$ are independently selected from hydrogen, hydroxyl, halogen, cyano, $C_1$-$C_3$ alkyl, $C_1$-$C_3$ alkoxy, $C_1$-$C_3$ alkylhalide, or a linker conjugated to a PROTAC moiety;

$R_8$ and $R_9$ are independently selected from hydrogen, $C_1$-$C_6$ alkyl, $C_1$-$C_6$ alkoxy, $C_3$-$C_8$ cycloalkyl, a $C_1$-$C_7$ heterocycloalkyl, $C_5$-$C_8$ aryl, $C_1$-$C_8$ heteroaryl, a linker conjugated to a PROTAC moiety, or $R_1$ and $R_8$ combine together with the atoms to which they are attached to form a heterocycloalkyl, or a heterocycloalkenyl, wherein $R_8$ and $R_9$ are optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

$R_{10}$ is selected from hydrogen, $C_1$-$C_6$ alkyl, $C_1$-$C_6$ alkoxy, $C_3$-$C_{10}$ cycloalkyl, a $C_2$-$C_8$ heterocycloalkyl, $C_5$-$C_{10}$ aryl, $C_2$-$C_8$ heteroaryl, or a linker conjugated to a PROTAC moiety, wherein $R_{10}$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

$R_{11}$ and $R_{12}$ are independently selected from hydrogen, hydroxyl, halogen, cyano, $C_1$-$C_3$ alkyl, $C_1$-$C_3$ alkoxy, $C_1$-$C_3$ heteroalkyl, $C_1$-$C_3$ alkylhalide, or a linker conjugated to a PROTAC moiety;

$R_{13}$ and $R_{14}$ are independently selected from hydrogen, hydroxyl, halogen, cyano, $C_1$-$C_6$ alkyl, $C_1$-$C_6$ alkoxy, $C_1$-$C_6$ alkylhalide, aryl, heteroaryl, a linker conjugated to a PROTAC moiety, or $R_{13}$ and $R_{14}$ combine together with the atoms to which they are attached to form a cycloalkyl, a heterocycloalkyl, or a heterocycloalkenyl, wherein $R_{13}$ and $R_{14}$ are optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl, and $R_{15}$ is absent or for each occurrence, independently selected from hydroxyl, halogen, cyano, $C_1$-$C_6$ alkyl, $C_1$-$C_6$ alkoxy, $C_1$-$C_6$ alkylhalide, aryl, heteroaryl, a linker conjugated to a PROTAC moiety, wherein $R_{15}$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl.

In other aspects, the compound of Formula I can have a structure according to Formula I-B.

Formula I-B

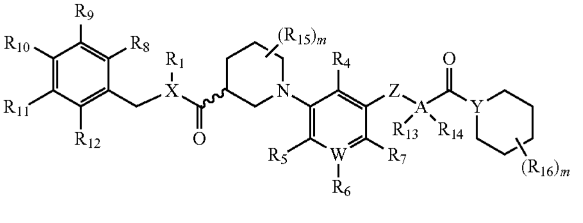

wherein m is independently for each occurrence 0, 1, or 2;

W is selected from C or N, wherein when W is N, then $R_6$ is absent;

X is selected from O, N, —R'O, or —R'N, wherein R' is selected from $C_1$-$C_3$ alkyl;

Y is selected from O, N;

$Y_1$ is selected from O, NR'R", wherein R' and R" are independently absent or present, which when present is selected from hydrogen, halogen, hydroxyl, alkyl, or alkoxy;

Z is absent or O;

A is absent or selected from $C_1$-$C_3$ alkyl, preferably $C_1$ alkyl;

$R_1$ is absent or selected from hydrogen, halogen, $C_1$-$C_6$ alkyl, $C_1$-$C_6$ alkoxy, $C_1$-$C_6$ haloalkyl, $C_1$-$C_6$ haloalkoxy, $C_1$-$C_6$ alkylamine, $C_3$-$C_6$ cycloalkyl, $C_3$-$C_6$ cycloalkenyl, heteroaryl, or a linker conjugated to a PROTAC moiety; wherein $R_1$ is optionally substituted with halogen, hydroxyl, carboxyl, amino, cyano, nitro, isocyano, alkyl, haloalkyl, haloalkoxy, a linker conjugated to a PROTAC moiety, cycloalkyl, heterocycloalkyl, aryl, or heteroaryl;

$R_4$, $R_5$, $R_6$, and $R_7$ are independently selected from hydrogen, hydroxyl, halogen, cyano, $C_1$-$C_3$ alkyl, $C_1$-$C_3$ alkoxy, $C_1$-$C_3$ alkylhalide, or a linker conjugated to a PROTAC moiety;

$R_8$ and $R_9$ are independently selected from hydrogen, $C_1$-$C_6$ alkyl, $C_1$-$C_6$ alkoxy, $C_3$-$C_8$ cycloalkyl, a $C_1$-$C_7$ heterocycloalkyl, $C_5$-$C_8$ aryl, $C_1$-$C_8$ heteroaryl, a linker conjugated to a PROTAC moiety, or $R_1$ and R& combine together with the atoms to which they are attached to form a heterocycloalkyl, or a heterocycloalkenyl, wherein $R_8$ and $R_9$ are optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

$R_{10}$ is selected from hydrogen, $C_1$-$C_6$ alkyl, $C_1$-$C_6$ alkoxy, $C_3$-$C_{10}$ cycloalkyl, a $C_2$-$C_8$ heterocycloalkyl, $C_5$-$C_{10}$ aryl, $C_2$-$C_8$ heteroaryl, or a linker conjugated to a PROTAC moiety, wherein $R_{10}$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

$R_{11}$ and $R_{12}$ are independently selected from hydrogen, hydroxyl, halogen, cyano, $C_1$-$C_3$ alkyl, $C_1$-$C_3$ alkoxy, $C_1$-$C_3$ heteroalkyl, $C_1$-$C_3$ alkylhalide, or a linker conjugated to a PROTAC moiety;

$R_{13}$ and $R_{14}$ are independently selected from hydrogen, hydroxyl, halogen, cyano, $C_1$-$C_6$ alkyl, $C_1$-$C_6$ alkoxy, $C_1$-$C_6$ alkylhalide, aryl, heteroaryl, a linker conjugated to a PROTAC moiety, or $R_{13}$ and $R_{14}$ combine together with the atoms to which they are attached to form a cycloalkyl, a heterocycloalkyl, or a heterocycloalkenyl, wherein $R_{13}$ and $R_{14}$ are optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl, $R_{15}$ is absent or for each occurrence, independently selected from hydroxyl, halogen, cyano, $C_1$-$C_6$ alkyl, $C_1$-$C_6$ alkoxy, $C_1$-$C_6$ alkylhalide, aryl, heteroaryl, a linker conjugated to a PROTAC moiety, wherein $R_{15}$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl, and $R_{16}$ for each occurrence is independently selected from halogen, hydroxyl, carboxyl, amino, cyano, nitro, isocyano, alkyl, haloalkyl, haloalkoxy, a linker conjugated to a PROTAC moiety, cycloalkyl, heterocycloalkyl, aryl, or heteroaryl.

In some aspects of the compounds disclosed herein, the compounds of Formula I, I-A, or I-B can have a structure according to Formula I-C.

Formula I-C

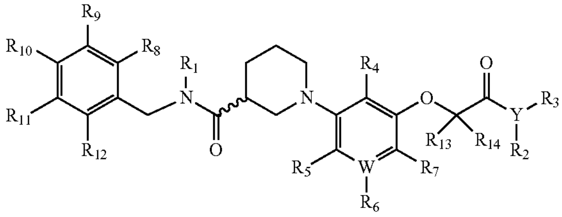

wherein

W is selected from C or N, wherein when W is N, then $R_6$ is absent;

Y is selected from O, N;

$R_1$ is absent or selected from hydrogen, halogen, $C_1$-$C_6$ alkyl, $C_1$-$C_6$ alkoxy, $C_1$-$C_6$ haloalkyl, $C_1$-$C_6$ haloalkoxy, $C_1$-$C_6$ alkylamine, $C_2$-$C_6$ ether, $C_3$-$C_6$ cycloalkyl, $C_3$-$C_6$ cycloalkenyl, heteroaryl, or a linker conjugated to a PROTAC moiety; wherein $R_1$ is optionally substituted with halogen, hydroxyl, carboxyl, amino, cyano, nitro, isocyano, alkyl, haloalkyl, haloalkoxy, cycloalkyl, heterocycloalkyl, aryl, or heteroaryl;

$R_2$ and $R_3$ are independently absent or selected from hydrogen, $C_1$-$C_6$ alkyl, $C_3$-$C_{10}$ cycloalkyl, a $C_2$-$C_8$ heterocycloalkyl, $C_5$-$C_{10}$ aryl, $C_2$-$C_8$ heteroaryl, a linker conjugated to a PROTAC moiety, or $R_2$ and $R_3$ combine together with the atoms to which they are attached to form a heterocycloalkyl, a heterocycloalkenyl, or a heteroaryl, wherein $R_2$ and $R_3$ are optionally substituted with halogen, hydroxyl, carboxyl, amino, cyano, nitro, isocyano, alkyl, haloalkyl, haloalkoxy, cycloalkyl, heterocycloalkyl, aryl, or heteroaryl;

$R_4$, $R_5$, $R_6$, and $R_7$ are independently selected from hydrogen, hydroxyl, halogen, cyano, $C_1$-$C_3$ alkyl, $C_1$-$C_3$ alkoxy, $C_1$-$C_3$ alkylhalide, or a linker conjugated to a PROTAC moiety;

$R_8$ and $R_9$ are independently selected from hydrogen, $C_1$-$C_6$ alkyl, $C_1$-$C_6$ alkoxy, $C_3$-$C_8$ cycloalkyl, a $C_1$-$C_7$ heterocycloalkyl, $C_5$-$C_8$ aryl, $C_1$-$C_8$ heteroaryl, a linker conjugated to a PROTAC moiety, or $R_1$ and R& combine together with the atoms to which they are attached to form a heterocycloalkyl, or a heterocycloalkenyl, wherein $R_8$ and $R_9$ are optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

$R_{10}$ is selected from hydrogen, $C_1$-$C_6$ alkyl, $C_1$-$C_6$ alkoxy, $C_3$-$C_{10}$ cycloalkyl, a $C_2$-$C_8$ heterocycloalkyl, $C_5$-$C_{10}$ aryl, $C_2$-$C_8$ heteroaryl, or a linker conjugated to a PROTAC moiety, wherein $R_{10}$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

$R_{11}$ and $R_{12}$ are independently selected from hydrogen, hydroxyl, halogen, cyano, $C_1$-$C_3$ alkyl, $C_1$-$C_3$ alkoxy, $C_1$-$C_3$ heteroalkyl, $C_1$-$C_3$ alkylhalide, or a linker conjugated to a PROTAC moiety;

$R_{13}$ and $R_{14}$ are independently selected from hydrogen, hydroxyl, halogen, cyano, $C_1$-$C_6$ alkyl, $C_1$-$C_6$ alkoxy, $C_1$-$C_6$ alkylhalide, aryl, alkylaryl, heteroaryl, alkylheteroaryl, a linker conjugated to a PROTAC moiety, or $R_{13}$ and $R_{14}$ combine together with the atoms to which they are attached to form a cycloalkyl, a cycloalkenyl, a heterocycloalkyl, or a heterocycloalkenyl, wherein $R_{13}$ and $R_{14}$ are optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl, and $R_{15}$ is absent or for each occurrence, independently selected from hydroxyl, halogen, cyano, $C_1$-$C_6$ alkyl, $C_1$-$C_6$ alkoxy, $C_1$-$C_6$ alkylhalide, aryl, heteroaryl, a linker conjugated to a PROTAC moiety, wherein $R_{15}$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl.

As described herein, the compounds can include a proteolysis-targeting chimera (also known as PROTAC). PROTACs are hetero-bifunctional molecules that recruit an E3 ubiquitin ligase to a given substrate protein resulting in its targeted degradation. In some embodiments, PROTACs couple a small molecule binder of a target protein to an E3 ubiquitin ligase-recruiting moiety via an intervening chemical linker. High-affinity small molecules for E3 ubiquitin ligases, in particular against von Hippel-Lindau include VH032 and against cereblon includes pomalidomide.

In some examples, the linker conjugated to the PROTAC moiety comprises a linker selected from a substituted or unsubstituted $C_4$-$C_{24}$ alkyl, a substituted or unsubstituted $C_4$-$C_{24}$ alkoxy. In some examples, the PROTAC moiety is selected from a cereblon binder (such as thalidomide, lenalidomide, or pomalidomide), or a von Hippel-Lindau E3 ligase (VHL) ligand (such as VH032, or VH298). In some embodiments of Formula I, I-A, I-B or I-C, the compounds comprise at least one linker conjugated to a PROTAC moiety.

In some embodiments of Formula I, I-A, I-B or I-C, n is 1. In other embodiments of the compounds described herein, n is 2.

In some embodiments of Formula I, I-A, I-B or I-C, m is 0. In other embodiments of the compounds described herein, m is 1. In further embodiments of the compounds described herein, m is 2.

In some embodiments of Formula I, I-A, I-B or I-C, W is C.

In some embodiments of Formula I, I-A, I-B or I-C, X can be O. In some embodiments of Formula I, I-A, I-B or I-C, X can be N. In some embodiments of Formula I, I-A, I-B or I-C, X can be —R'N, such as —$CH_2N$—. In some embodiments of the compounds described herein, X is selected from O or N. Preferably, X is N.

In some embodiments of the compounds described herein, Y is N.

In some embodiments of Formula I, I-A, I-B or I-C, Z can be absent. In some embodiments of Formula I, I-A, I-B or I-C, Z can be O.

In some embodiments of Formula I, Y can be O. In some embodiments of Formula I, Y can be N.

In some embodiments of Formula I, I-A, I-B or I-C, A can be absent. In some embodiments of Formula I, I-A, I-B or I-C, A can be methyl, ethyl, or propyl, preferably methyl.

In some embodiments of Formula I, I-A, I-B or I-C, $R_1$ can be absent, for example when X is O. In some embodiments of Formula I, I-A, I-B or I-C, $R_1$ can be hydrogen. In some embodiments of Formula I, I-A, I-B or I-C, $R_1$ can be halogen such as chloro or bromo or fluoro. In some embodiments of Formula I, I-A, I-B or I-C, $R_1$ can be $C_1$-$C_6$ alkyl, such as methyl, ethyl, propyl. In some embodiments of Formula I, I-A, I-B or I-C, $R_1$ can be $C_1$-$C_6$ alkoxy, such as methoxy, ethoxy, or propoxy. In some embodiments of Formula I, I-A, I-B or I-C, $R_1$ can be cycloalkyl, such as cyclopropyl. In some embodiments of Formula I, I-A, I-B or I-C, $R_1$ can be selected from hydrogen, $C_1$-$C_6$ alkyl, $C_1$-$C_6$ alkoxy, $C_1$-$C_6$ alkylamine, $C_3$-$C_6$ cycloalkyl, or a linker conjugated to a PROTAC moiety. In some examples of Formula I, I-A, I-B or I-C, $R_1$ can be selected from hydrogen, $C_1$-$C_6$ alkyl, or $C_3$-$C_6$ cycloalkyl.

In some embodiments of Formula I, I-A, I-B or I-C, one of $R_2$ and $R_3$ can be absent, such as when Y is O. In some embodiments of Formula I, I-A, I-B or I-C, at least one of $R_2$ and $R_3$ can be hydrogen. In some embodiments of Formula I, I-A, I-B or I-C, at least one of $R_2$ and $R_3$ can be $C_3$-$C_{10}$ cycloalkyl. In some embodiments of Formula I, I-A, I-B or I-C, at least one of $R_2$ and $R_3$ can be a $C_2$-$C_8$ heterocycloalkyl. In some embodiments of Formula I, I-A, I-B or I-C, at least one of $R_2$ and $R_3$ can be $C_5$-$C_{10}$ aryl. In some embodiments' of Formula I, I-A, I-B or I-C, at least one of $R_2$ and $R_3$ can be $C_2$-$C_8$ heteroaryl. In some embodiments of Formula I, I-A, I-B or I-C, $R_2$ and $R_3$ combine together with the atoms to which they are attached to form a heterocycloalkyl, or a heterocycloalkenyl. In some embodiments of Formula I, I-A, I-B or I-C, $R_2$ and $R_3$ are independently absent or selected from hydrogen, $C_1$-$C_6$ alkyl, a linker conjugated to a PROTAC moiety, or $R_2$ and $R_3$ combine together with the atoms to which they are attached to form a heterocycloalkyl, a heterocycloalkenyl, or a heteroaryl. In some embodiments of Formula I, I-A, I-B or I-C, $R_2$ is absent and $R_3$ is selected from hydrogen, $C_1$-$C_6$ alkyl, or a linker conjugated to a PROTAC moiety. In some embodiments of Formula I, I-A, I-B or I-C, $R_2$ and $R_3$ combine together with the atoms to which they are attached to form a heterocycloalkyl, a heterocycloalkenyl, or a heteroaryl, wherein $R_2$ and $R_3$ are optionally substituted with halogen, hydroxyl, carboxyl, amino, cyano, nitro, isocyano, alkyl, haloalkyl, haloalkoxy, cycloalkyl, heterocycloalkyl, aryl, heteroaryl, or a linker conjugated to a PROTAC moiety.

In some embodiments of Formula I, I-A, I-B or I-C, $R_4$ is selected from hydrogen, hydroxyl, halogen, cyano, $C_1$-$C_3$ alkyl, $C_1$-$C_3$ alkoxy, or $C_1$-$C_3$ alkylhalide.

In some embodiments of Formula I, I-A, I-B or I-C, $R_5$ is selected from hydrogen, hydroxyl, halogen, cyano, $C_1$-$C_3$ alkyl, $C_1$-$C_3$ alkoxy, or $C_1$-$C_3$ alkylhalide.

In some embodiments of Formula I, I-A, I-B or I-C, $R_6$ is selected from hydrogen, hydroxyl, halogen, cyano, $C_1$-$C_3$ alkyl, $C_1$-$C_3$ alkoxy, or $C_1$-$C_3$ alkylhalide.

In some embodiments of Formula I, I-A, I-B or I-C, $R_7$ is selected from hydrogen, hydroxyl, halogen, cyano, $C_1$-$C_3$ alkyl, $C_1$-$C_3$ alkoxy, or $C_1$-$C_3$ alkylhalide.

In some embodiments of Formula I, I-A, I-B or I-C, at least one of $R_4$, $R_5$, $R_6$, and $R_7$ are hydrogen.

In some embodiments of Formula I, I-A, I-B or I-C, at least two of $R_4$, $R_5$, $R_6$, and $R_7$ are hydrogen.

In some embodiments of Formula I, I-A, I-B or I-C, at least three of $R_4$, $R_5$, $R_6$, and $R_7$ are hydrogen.

In some embodiments of Formula I, I-A, I-B or I-C, all of $R_4$, $R_5$, $R_6$, and $R_7$ are hydrogen.

In some embodiments of Formula I, I-A, I-B or I-C, $R_8$ and $R_9$ are both hydrogen. In some embodiments of Formula I, I-A, I-B or I-C, $R_8$ and $R_9$ are independently selected from hydrogen or a $C_1$-$C_6$ alkyl. In some embodiments of Formula I, I-A, I-B or I-C, $R_1$ and $R_8$ combine together with the atoms to which they are attached to form a heterocycloalkyl, or a heterocycloalkenyl.

In some embodiments of Formula I, I-A, I-B or I-C, $R_{10}$ is hydrogen. In some embodiments of Formula I, $R_{10}$ is a $C_1$-$C_6$ alkyl, such as methyl, ethyl, n-propyl, or isopropyl. In some embodiments of Formula I, I-A, I-B or I-C, $R_{10}$ is selected from $C_3$-$C_{10}$ cycloalkyl, a $C_2$-$C_8$ heterocycloalkyl, $C_5$-$C_{10}$ aryl, or $C_2$-$C_8$ heteroaryl. In some embodiments of Formula I, I-A, I-B or I-C, $R_{10}$ is selected from $C_1$-$C_6$ alkyl, $C_1$-$C_6$ alkoxy, $C_3$-$C_{10}$ cycloalkyl, a $C_2$-$C_8$ heterocycloalkyl, $C_5$-$C_{10}$ aryl, $C_2$-$C_8$ heteroaryl, or a linker conjugated to a PROTAC moiety. In some embodiments of Formula I, I-A, I-B or I-C, $R_{10}$ is selected from $C_1$-$C_6$ alkyl, $C_1$-$C_6$ alkoxy, or $C_2$-$C_8$ heteroaryl.

In some embodiments of Formula I, I-A, I-B or I-C, $R_1$ is selected from hydrogen, hydroxyl, halogen, cyano, $C_1$-$C_3$ alkyl, $C_1$-$C_3$ alkoxy, or $C_1$-$C_3$ alkylhalide.

In some embodiments of Formula I, I-A, I-B or I-C, $R_{12}$ is selected from hydrogen, hydroxyl, halogen, cyano, $C_1$-$C_3$ alkyl, $C_1$-$C_3$ alkoxy, or $C_1$-$C_3$ alkylhalide.

In some embodiments of Formula I, I-A, I-B or I-C, at least one of $R_{11}$ and $R_{12}$ are hydrogen.

In some embodiments of Formula I, I-A, I-B or I-C, both $R_{13}$ and $R_{14}$ can be independently selected from hydrogen, hydroxyl, halogen, cyano, $C_1$-$C_6$ alkyl, $C_1$-$C_6$ alkoxy, $C_1$-$C_6$ alkylhalide, aryl, heteroaryl, a linker conjugated to a PROTAC moiety, or $R_{13}$ and $R_{14}$ combine together with the atoms to which they are attached to form a cycloalkyl, a heterocycloalkyl, or a heterocycloalkenyl. $R_{13}$ and $R_{14}$ are optionally and independently substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl.

In some embodiments of Formula I, I-A, I-B or I-C, $R_{15}$ is absent. In some embodiments of Formula I, I-A, I-B or I-C, $R_{15}$ can be selected from hydroxyl, halogen, cyano, $C_1$-$C_6$ alkyl, $C_1$-$C_6$ alkoxy, $C_1$-$C_6$ alkylhalide, or a linker conjugated to a PROTAC moiety.

In some embodiments of Formula I, I-A, I-B or I-C, $R_{16}$ for each occurrence can be independently selected from halogen, hydroxyl, carboxyl, amino, cyano, nitro, isocyano, alkyl, haloalkyl, haloalkoxy, a linker conjugated to a PROTAC moiety, cycloalkyl, heterocycloalkyl, aryl, or heteroaryl.

As described herein, the compound can have a chiral designation of R or S or in some cases, is a racemic mixture.

For example, the compound can be as described below in Tables 1-8:

TABLE 1

Inhibitors 1-14. [a]

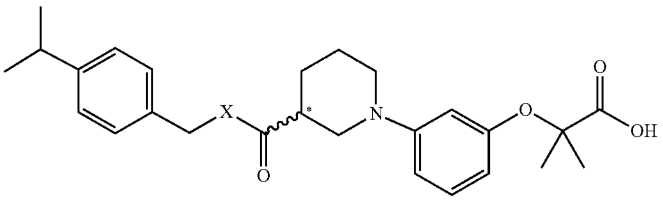

| No. | X | *R/S | $K_i$(μM) |
|---|---|---|---|
| 1 | 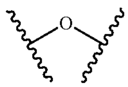 [SMILES: *O*] | R | >90 |
| 2 | 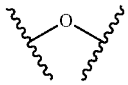 [SMILES: *O*] | S | >90 |
| 3 | 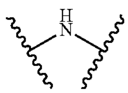 [SMILES: *N*] | R | ≤50 |
| 4 | 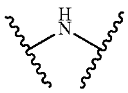 [SMILES: *N*] | S | >90 |
| 5 | 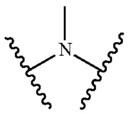 [SMILES: *N(*)C] | R | <50 |

TABLE 1-continued
Inhibitors 1-14. [a]
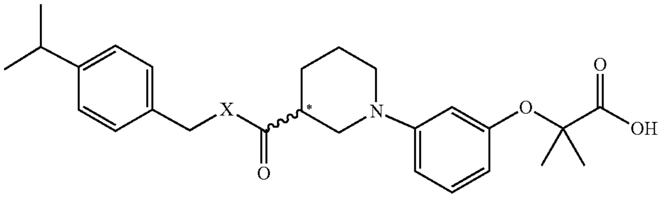
| No. | X | *R/S | $K_i$(μM) |
|---|---|---|---|
| 6 | 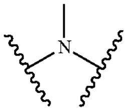 [SMILES: *N(*)C] | S | ≤30 |
| 7 | 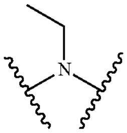 | R | >90 |
| 8 | 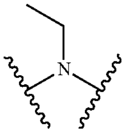 [SMILES: *N(*)CC] | S | >90 |
| 9 | 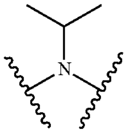 [SMILES: *N(*)C(C)C] | R | >90 |
| 10 | 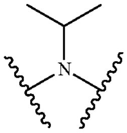 [SMILES: *N(*)C(C)C] | S | ≤50 |
| 11 | 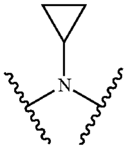 [SMILES: *N(*)C1CC1] | R | ≤50 |
| 12 | 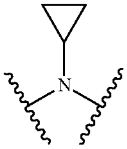 [SMILES: *N(*)C1CC1] | S | >90 |
| 13 | 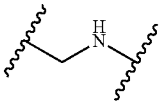 [SMILES: *CN*] | R | ≤50 |
| 14 | 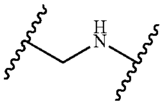 | S | ≤90 |

TABLE 2
Inhibitors 15-26. [a]
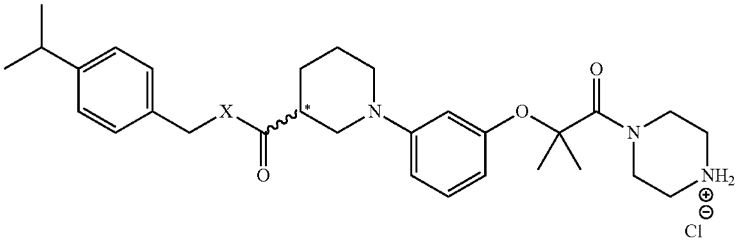
| No. | X | *R/S | $K_i$(μM) |
|---|---|---|---|
| 15 | 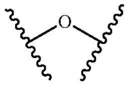 [SMILES: *O*] | R | ≤10 |
| 16 | 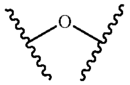 [SMILES: *O*] | S | ≤10 |
| 17 | 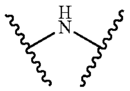 | R | ≤10 |
| 18 | 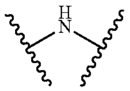 | S | ≤30 |
| 19 | 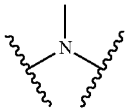 [SMILES: *N(*)C] | R | ≤30 |
| 20 | 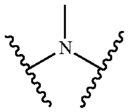 [SMILES: *N(*)C] | S | ≤10 |
| 21 | 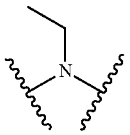 [SMILES: *N(*)CC] | R | ≤30 |
| 22 | 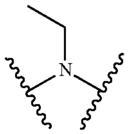 [SMILES: *N(*)CC] | S | ≤30 |
| 23 | 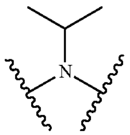 [SMILES: *N(*)C(C)C] | R | ≤10 |
| 24 | 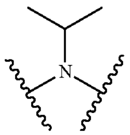 [SMILES: *N(*)C(C)C] | S | ≤10 |

TABLE 2-continued
Inhibitors 15-26. [a]
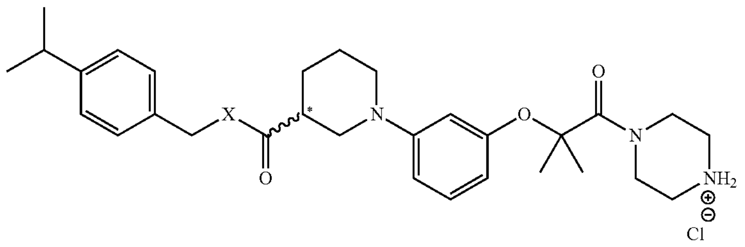
| No. | X | *R/S | $K_i$(μM) |
|---|---|---|---|
| 25 | 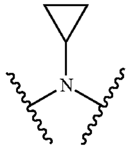 [SMILES: *N(*)C1CC1] | R | ≤5 |
| 26 | 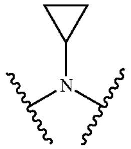 [SMILES: *N(*)C1CC1] | S | ≤10 |
[a] Each set of data was expressed as mean ± standard deviation (n = 3)
TABLE 3
Inhibitors 27-43. [a]
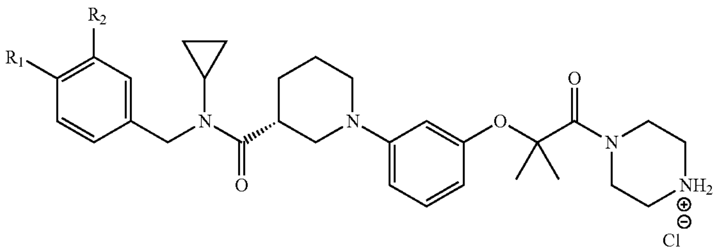
| No. | $R_1$ | $R_2$ | $K_i$(μM) |
|---|---|---|---|
| 27 | H | 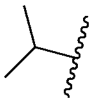 [SMILES: *C(C)C] | <30 |
| 28 | 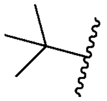 | H | ≤30 |
| 29 | 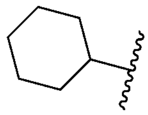 [SMILES: *C1CCCCC1] | H | ≤5 |
| 30 | 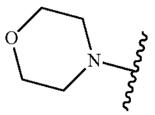 [SMILES: *N1CCOCC1] | H | >90 |

TABLE 3-continued
Inhibitors 27-43. [a]
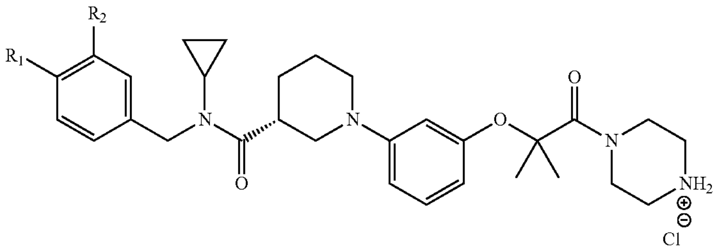
| No. | $R_1$ | $R_2$ | $K_i$(μM) |
|---|---|---|---|
| 31 | 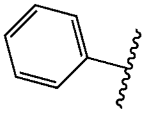 | H | <5 |
| 32 | 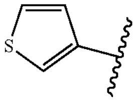 [SMILES: *c1ccsc1] | H | <5 |
| 33 | 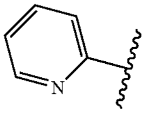 | H | <90 |
| 34 | 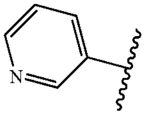 [SMILES: *c1cccnc1] | H | <90 |
| 35 | 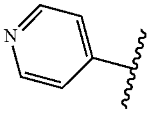 [SMILES: *c1ccncc1] | H | <90 |
| 36 | 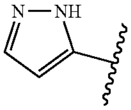 [SMILES: *c1ccn[nH]1] | H | ≤10 |
| 37 | 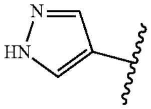 | H | ≤1 |
| 38 | 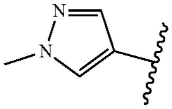 [SMILES: *c1cnn(C)c1] | H | ≤90 |
| 39 | 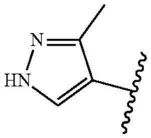 | H | ≤50 |
| 40 | 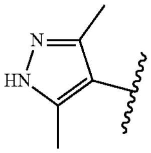 | H | <10 |

TABLE 3-continued
Inhibitors 27-43. [a]
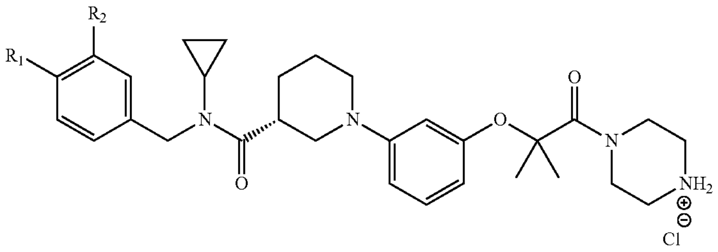
| No. | $R_1$ | $R_2$ | $K_i$(μM) |
| --- | --- | --- | --- |
| 41 | 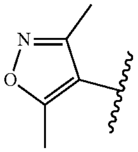 [SMILES: *c1c(C)noc1C] | H | <30 |
| 42 | 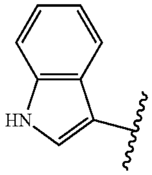 | H | <5 |
| 43 | 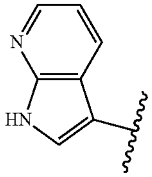 | H | <1 |
[a] Each set of data was expressed as mean ± standard deviation (n = 3)
TABLE 4
Inhibitors 44-53. [a]
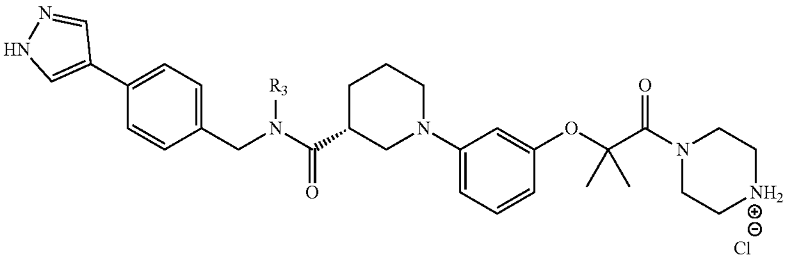
| No. | $R_3$ | $K_i$(μM) | No. | $R_3$ | $K_i$ ± SD |
| --- | --- | --- | --- | --- | --- |
| 44 | H | <90 | 49 | 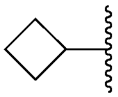 [SMILES: *C1CCC1] | <30 |
| 45 | Me | <30 | 50 | 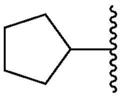 | <10 |

TABLE 4-continued
Inhibitors 44-53. [a]
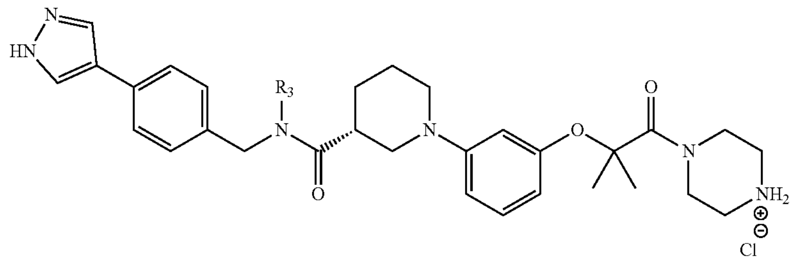
| No. | $R_3$ | $K_i$(μM) | No. | $R_3$ | $K_i$ ± SD |
|---|---|---|---|---|---|
| 46 | Et | <5 | 51 | 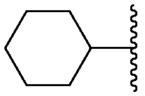 [SMILES: *C1CCCCC1] | <30 |
| 47 | i-Pr | <10 | 52 | 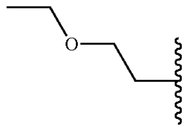 [SMILES: *CCOCC] | <5 |
| 48 | 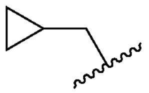 | <90 | 53 | 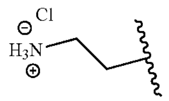 | <90 |
[a] Each set of data was expressed as mean ± standard deviation (n = 3)
TABLE 5
Inhibitors 54-62. [a]
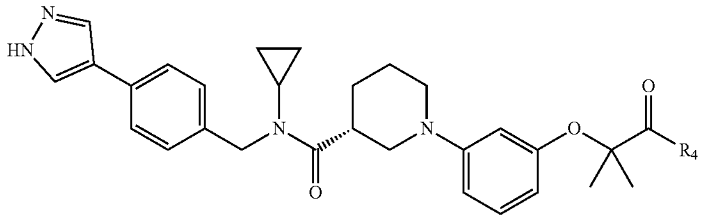
| No. | $R_4$ | $K_i$(μM) |
|---|---|---|
| 54 | 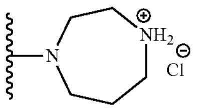 [SMILES: *N1CCC[NH2+]CC1 ; [Cl-]] | < 10 |
| 55 | 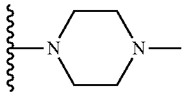 | >90 |
| 56 | 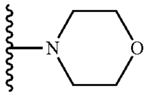 | >90 |
| 57 | 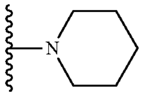 | >90 |

TABLE 5-continued
Inhibitors 54-62. [a]
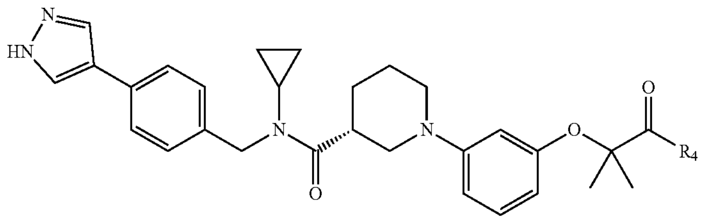
| No. | $R_4$ | $K_i$(μM) |
|---|---|---|
| 58 | 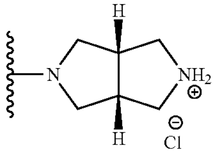 [SMILES: *N1C[C@H]2C[NH2+]C[C@H]2C1 ; [Cl-]] | <30 |
| 59 | 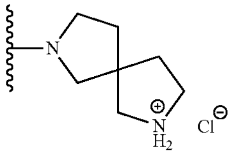 | <5 |
| 60 | 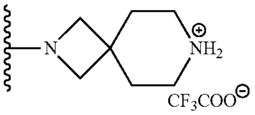 | <30 |
| 61 | 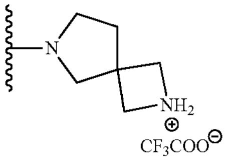 | <30 |
| 62 | 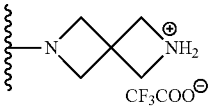 | <90 |
TABLE 6
Inhibitors 63-72. [a]
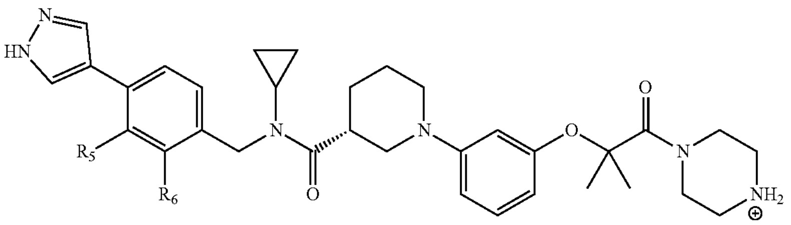 $CF_3COO^{\ominus}$ or $Cl^{\ominus}$
| No. | $R_5$ | $R_6$ | $K_i$(μM) |
|---|---|---|---|
| 63 | H | F | <30 |
| 64 | F | H | <30 |
| 65 | H | Me | <5 |
| 66 | Me | H | <90 |
| 67 | H | Cl | <30 |
| 68 | H | OMe | <5 |

TABLE 6-continued
Inhibitors 63-72. [a]
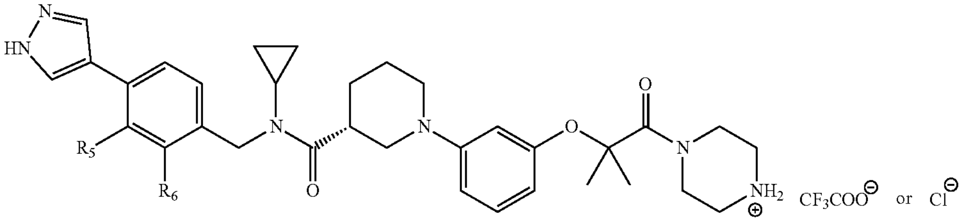
| No. | $R_5$ | $R_6$ | $K_i$(μM) |
|---|---|---|---|
| 69 | OMe | H | <30 |
| 70 | H | $CF_3$ | <10 |
| 71 | $CF_3$ | H | <30 |
| 72 | H | $OCF_3$ | <5 |
TABLE 7
Inhibitors 73-81. [a]
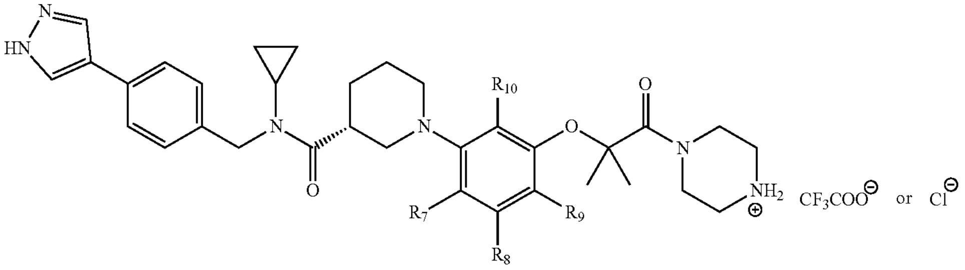
| No. | $R_7$ | $R_8$ | $R_9$ | $R_{10}$ | $K_i$(μM) |
|---|---|---|---|---|---|
| 73 | F | H | H | H | <50 |
| 74 | H | F | H | H | <10 |
| 75 | H | H | F | H | <10 |
| 76 | H | H | H | F | <90 |
| 77 | H | $CF_3$ | H | H | <10 |
| 78 | H | Cl | H | H | <30 |
| 79 | H | CN | H | H | <30 |
| 80 | H | H | Cl | H | <30 |
| 81 | H | H | CN | H | <90 |
TABLE 8
Inhibitors 82-92. [a]
| No. | Structure | $K_i$(μM) |
|---|---|---|
| 82 | 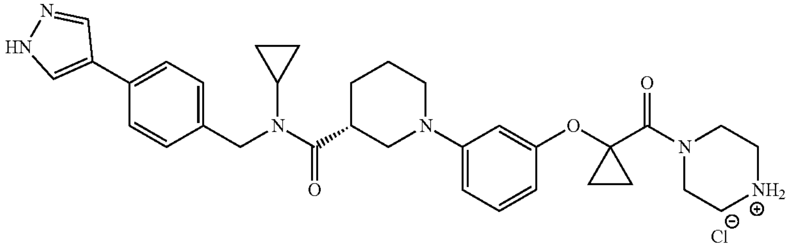 [SMILES: O=C([C@@H]1CCCN(c2cccc(OC3(C(=O)N4CC[NH2+]CC4)CC3)c2)C1)N(Cc1ccc(-c2cn[nH]c2)cc1)C1CC1 ; [Cl-]] | <10 |

TABLE 8-continued
| Inhibitors 82-92. [a] | | |
|---|---|---|
| No. | Structure | $K_i$(μM) |
| 83 | 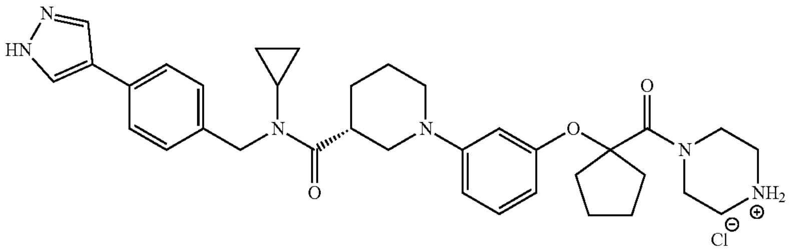 [SMILES: O=C([C@@H]1CCCN(c2cccc(OC3(C(=O)N4CC[NH2+]CC4)CCCC3)c2)C1)N(Cc1ccc(-c2cn[nH]c2)cc1)C1CC1 ; [Cl-]] | <90 |
| 84 | 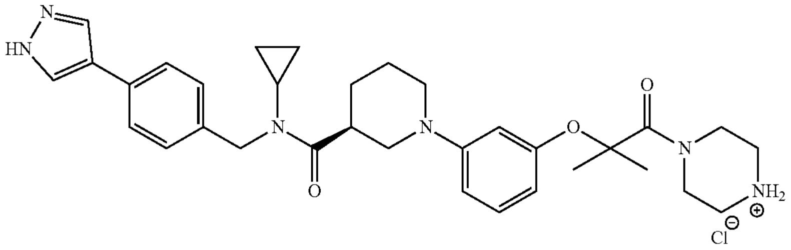 [SMILES: CC(C)(Oc1cccc(N2CCC[C@H](C(=O)N(Cc3ccc(-c4cn[nH]c4)cc3)C3CC3)C2)c1)C(=O)N1CC[NH2+]CC1 ; [Cl-]] | <90 |
| 85 | 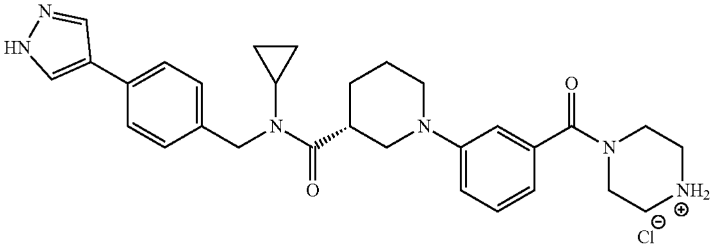 [SMILES: O=C(c1cccc(N2CCC[C@@H](C(=O)N(Cc3ccc(-c4cn[nH]c4)cc3)C3CC3)C2)c1)N1CC[NH2+]CC1 ; [Cl-]] | <90 |
| 86 | 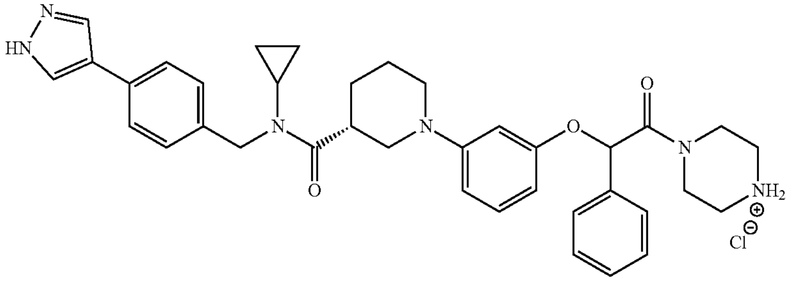 [SMILES: O=C(C(Oc1cccc(N2CCC[C@@H](C(=O)N(Cc3ccc(-c4cn[nH]c4)cc3)C3CC3)C2)c1)c1ccccc1)N1CC[NH2+]CC1 ; [Cl-]] | <30 |
| 87 | 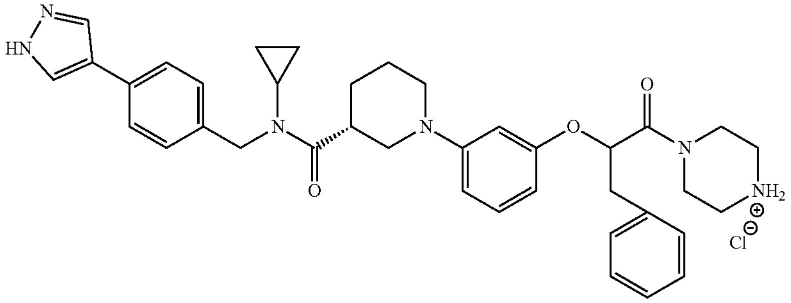 [SMILES: O=C(C(Cc1ccccc1)Oc1cccc(N2CCC[C@@H](C(=O)N(Cc3ccc(-c4cn[nH]c4)cc3)C3CC3)C2)c1)N1CC[NH2+]CC1 ; [Cl-]] | <90 |

TABLE 8-continued
| Inhibitors 82-92. [a] | | |
|---|---|---|
| No. | Structure | $K_i$(μM) |
| 88 | 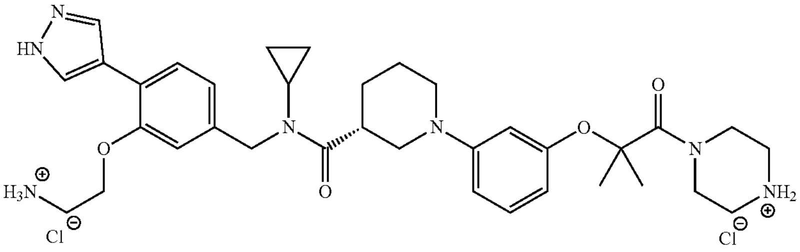 [SMILES: CC(C)(Oc1cccc(N2CCC[C@@H](C(=O)N(Cc3ccc(-c4cn[nH]c4)c(OCC[NH3+])c3)C3CC3)C2)c1)C(=O)N1CC[NH2+]CC1 ; Cl ; [Cl-]] | <5 |
| 89 | 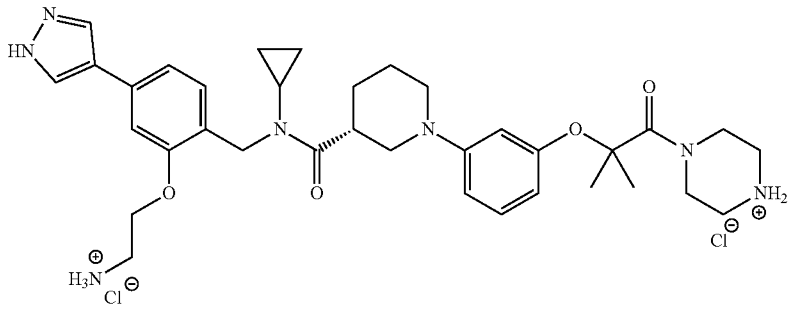 [SMILES: CC(C)(Oc1cccc(N2CCC[C@@H](C(=O)N(Cc3ccc(-c4cn[nH]c4)cc3OCC[NH3+])C3CC3)C2)c1)C(=O)N1CC[NH2+]CC1 ; [Cl-] ; [Cl-]] | <90 |
| 90 | 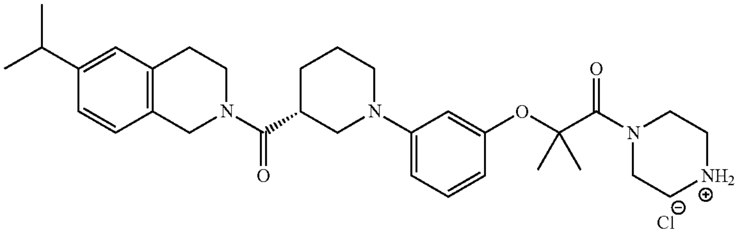 [SMILES: CC(C)c1ccc2c(c1)CCN(C(=O)[C@@H]1CCCN(c3cccc(OC(C)(C)C(=O)N4CC[NH2+]CC4)c3)C1)C2 ; [Cl-]] | <30 |
| 91 | 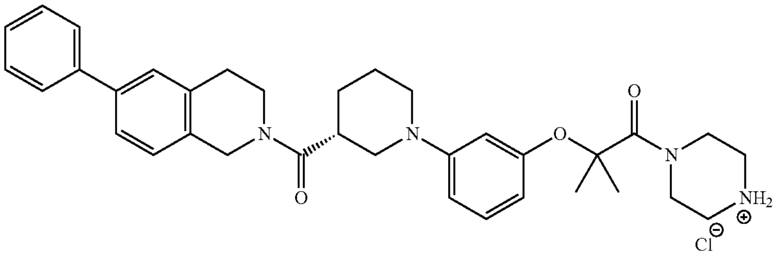 [SMILES: CC(C)(Oc1cccc(N2CCC[C@@H](C(=O)N3CCc4cc(-c5ccccc5)ccc4C3)C2)c1)C(=O)N1CC[NH2+]CC1 ; [Cl-]] | <5 |
| 92 | 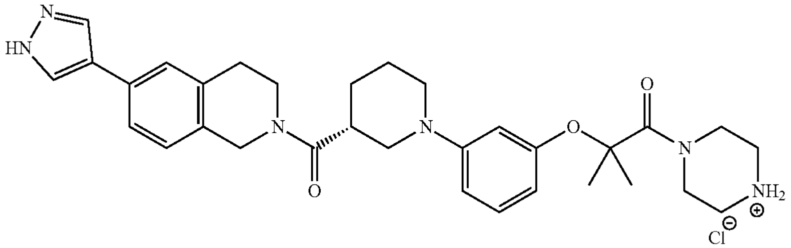 [SMILES: CC(C)(Oc1cccc(N2CCC[C@@H](C(=O)N3CCc4cc(-c5cn[nH]c5)ccc4C3)C2)c1)C(=O)N1CC[NH2+]CC1 ; [Cl-]] | <90 |

TABLE 9

AlphaScreen Assay Results of Inhibitors 93-98.[a]

| Compounds | | Structure | $K_i$ (μM) |
|---|---|---|---|
| 93 | racemic | 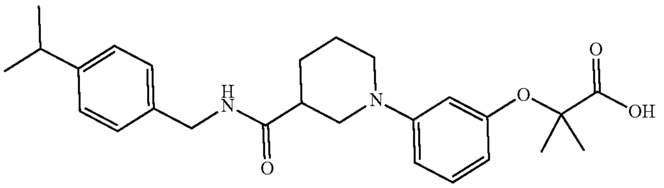 [SMILES: CC(C)c1ccc(CNC(=O)C2CCCN(c3cccc(OC(C)(C)C(=O)O)c3)C2)cc1] | ≤90 |
| 94 | racemic | 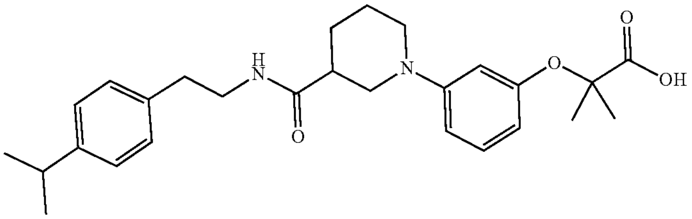 [SMILES: CC(C)c1ccc(CCNC(=O)C2CCCN(c3cccc(OC(C)(C)C(=O)O)c3)C2)cc1] | ≤90 |
| 95 | racemic | 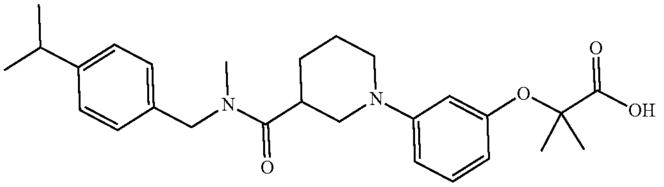 [SMILES: CC(C)c1ccc(CN(C)C(=O)C2CCCN(c3cccc(OC(C)(C)C(=O)O)c3)C2)cc1] | ≤90 |
| 96 | racemic | 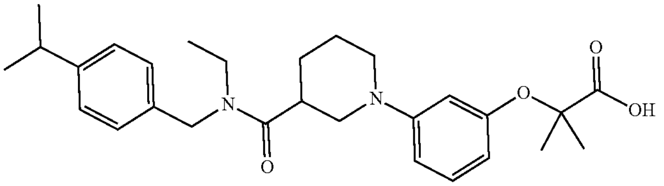 [SMILES: CCN(Cc1ccc(C(C)C)cc1)C(=O)C1CCCN(c2cccc(OC(C)(C)C(=O)O)c2)C1] | ≤90 |
| 97 | racemic | 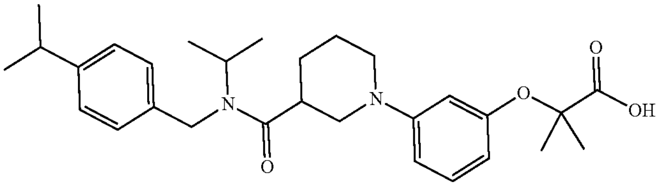 [SMILES: CC(C)c1ccc(CN(C(=O)C2CCCN(c3cccc(OC(C)(C)C(=O)O)c3)C2)C(C)C)cc1] | ≤90 |
| 98 | racemic | 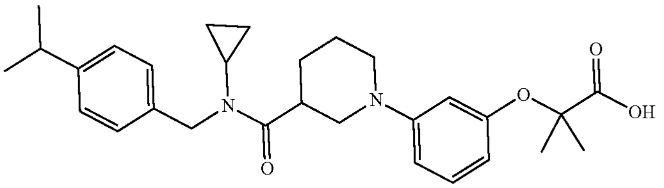 [SMILES: CC(C)c1ccc(CN(C(=O)C2CCCN(c3cccc(OC(C)(C)C(=O)O)c3)C2)C2CC2)cc1] | ≤90 |

[a]Each set of data was expressed as mean ± standard deviation (n = 3).

TABLE 10

AlphaScreen Assay Results of Inhibitors 99-106.[a]

| Compd. | | $R_1$ | $K_i$ ± SD (μM) |
|---|---|---|---|
| 99 | racemic | 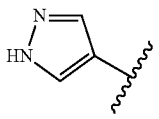 | >90 |

TABLE 10-continued

AlphaScreen Assay Results of Inhibitors 99-106.[a]

| Compd. | | $R_1$ | $K_i$ ± SD (μM) |
|---|---|---|---|
| 100 | racemic | 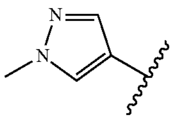 | >90 |

TABLE 10-continued

AlphaScreen Assay Results of Inhibitors 99-106.[a]

| Compd. | | $R_1$ | $K_i$ ± SD (μM) |
|---|---|---|---|
| 101 | racemic | 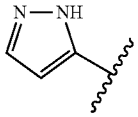 [SMILES: *c1ccn[nH]1] | ≤90 |
| 102 | racemic | 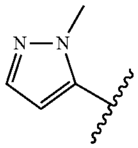 [SMILES: *c1ccnn1C] | >90 |
| 103 | racemic | 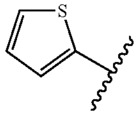 [SMILES: *c1cccs1] | ≤30 |
| 104 | racemic | 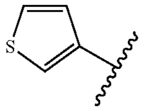 | ≤30 |
| 105 | racemic | 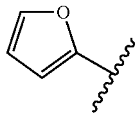 [SMILES: *c1ccco1] | ≤90 |
| 106 | racemic | 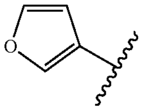 [SMILES: *c1ccoc1] | >90 |

[a]Each set of data was expressed as mean ± standard deviation (n = 3).

TABLE 11

AlphaScreen Assay Results of Inhibitors 107-108.[a]

| Compd. | | Structure | $K_i$ ± SD (μM) |
|---|---|---|---|
| 107 | racemic | 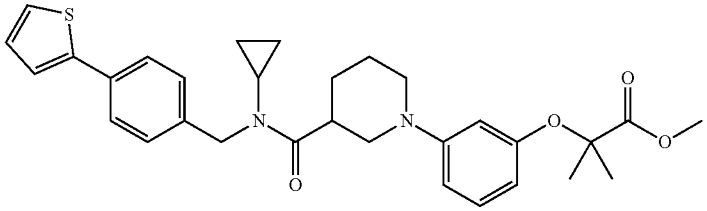 [SMILES: COC(=O)C(C)(C)Oc1cccc(N2CCCC(C(=O)N(Cc3ccc(-c4cccs4)cc3)C3CC3)C2)c1] | >90 |
| 108 | racemic | 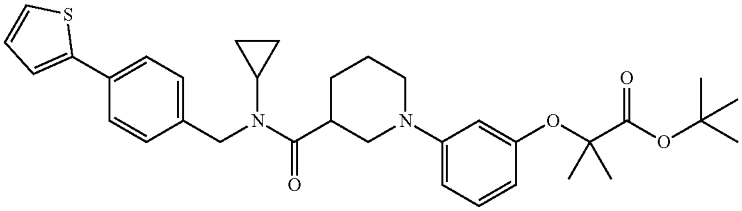 [SMILES: CC(C)(C)OC(=O)C(C)(C)Oc1cccc(N2CCCC(C(=O)N(Cc3ccc(-c4cccs4)cc3)C3CC3)C2)c1] | >90 |

[a]Each set of data was expressed as mean ± standard deviation (n = 3).

TABLE 12

AlphaScreen Assay Results of Inhibitors 109-112.[a]

| Compounds | Structure | $K_i$ (μM) |
|---|---|---|
| 109 | 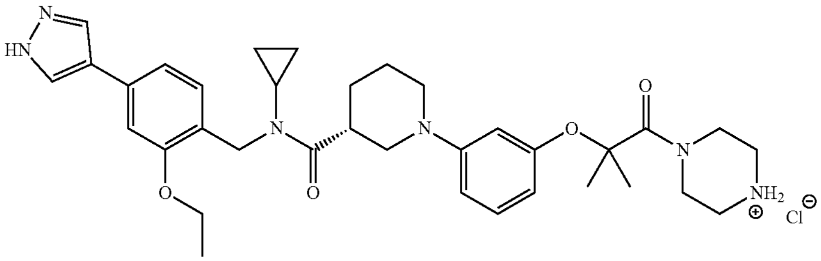 [SMILES: CCOc1cc(-c2cn[nH]c2)ccc1CN(C(=O)[C@@H]1CCCN(c2cccc(OC(C)(C)C(=O)N3CC[NH2+]CC3)c2)C1)C1CC1 ; [Cl-]] | ≤30 |

TABLE 12-continued

| AlphaScreen Assay Results of Inhibitors 109-112.[a] | | |
|---|---|---|
| Compounds | Structure | $K_i$ (μM) |
| 110 | 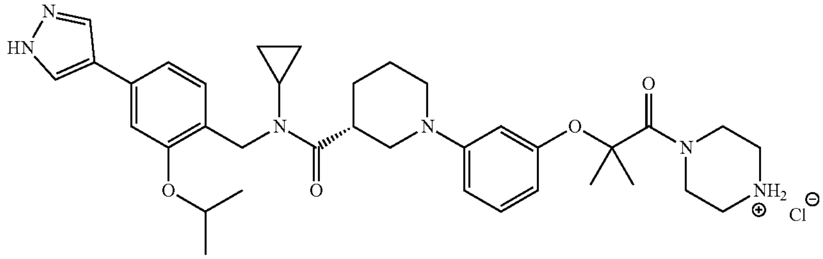 [SMILES: CC(C)Oc1cc(-c2cn[nH]c2)ccc1CN(C(=O)[C@@H]1CCCN(c2cccc(OC(C)(C)C(=O)N3CC[NH2+]CC3)c2)C1)C1CC1 ; [Cl-]] | ≤30 |
| 111 | 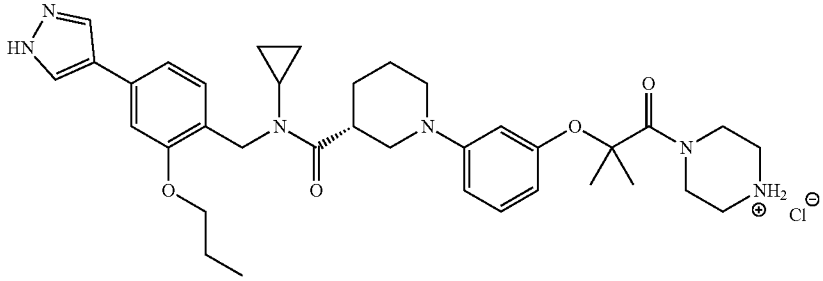 [SMILES: CCCOc1cc(-c2cn[nH]c2)ccc1CN(C(=O)[C@@H]1CCCN(c2cccc(OC(C)(C)C(=O)N3CC[NH2+]CC3)c2)C1)C1CC1 ; [Cl-]] | ≤30 |
| 112 | 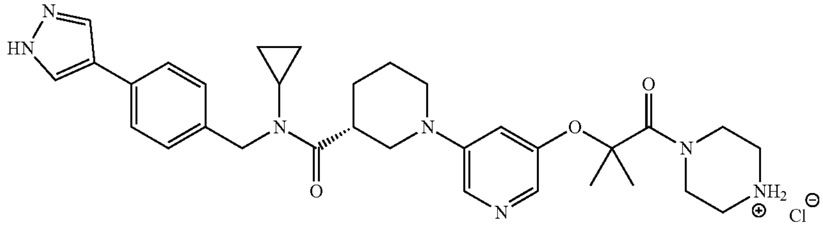 [SMILES: CC(C)(Oc1cncc(N2CCC[C@@H](C(=O)N(Cc3ccc(-c4cn[nH]c4)cc3)C3CC3)C2)c1)C(=O)N1CC[NH2+]CC1 ; [Cl-]] | ≤30 |

[a]Each set of data was expressed as mean ± standard deviation (n = 3).

Methods

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein, in some embodiments, the compounds disclosed herein can inhibit β-catenin/B-cell lymphoma 9 complex. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

In specific examples, the type of cancer is TNBC.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane: sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," Human Gene Therapy, 1999, 10 (18): 17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820, 508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described herein. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Small-Molecule Inhibitors for the β-Catenin/B-Cell Lymphoma 9 Protein-Protein Interaction 1. Design and Chemical Synthesis Some of the compounds synthesized are shown in Tables 1-8.

TABLE 1

Inhibitors 1-14. [a]

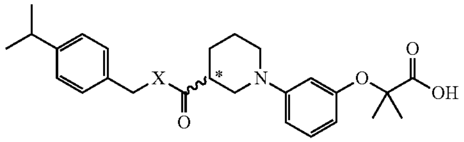

| No. | X | *R/S | $K_i$ (μM) |
|---|---|---|---|
| 1 | 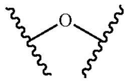 | R | >90 |
| 2 | 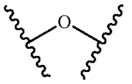 [SMILES: *O*] | S | >90 |
| 3 | 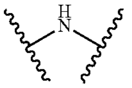 [SMILES: *N*] | R | ≤50 |
| 4 | 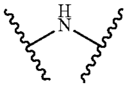 [SMILES: *N*] | S | >90 |
| 5 | 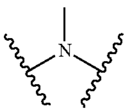 [SMILES: *N(*)C] | R | <50 |
| 6 | 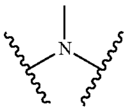 [SMILES: *N(*)C] | S | ≤30 |
| 7 | 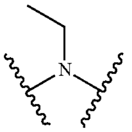 [SMILES: *N(*)CC] | R | >90 |
| 8 | 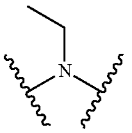 [SMILES: *N(*)CC] | S | >90 |
| 9 | 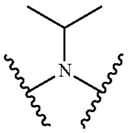 [SMILES: *N(*)C(C)C] | R | >90 |
| 10 | 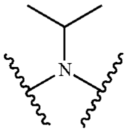 [SMILES: *N(*)C(C)C] | S | ≤50 |
| 11 | 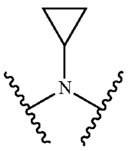 [SMILES: *N(*)C1CC1] | R | ≤50 |

TABLE 1-continued
| Inhibitors 1-14. [a] | | | |
|---|---|---|---|
| 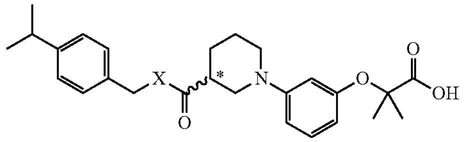 | | | |
| No. | X | *R/S | $K_i$ (μM) |
| 12 | 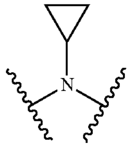 [SMILES: *N(*)C1CC1] | S | >90 |
| 13 | 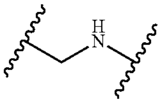 [SMILES: *CN*] | R | ≤50 |
| 14 | 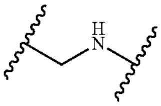 [SMILES: *CN*] | S | ≤90 |
TABLE 2
| Inhibitors 15-26.[a] | | | |
|---|---|---|---|
| 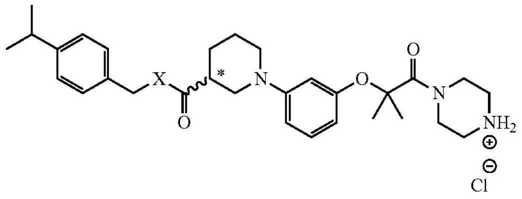 | | | |
| No. | X | *R/S | $K_i$ (μM) |
| 15 | 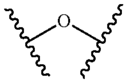 [SMILES: *O*] | R | ≤10 |
| 16 | 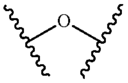 [SMILES: *O*] | S | ≤10 |
| 17 | 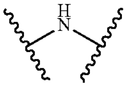 [SMILES: *N*] | R | ≤10 |
| 18 | 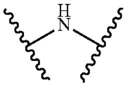 [SMILES: *N*] | S | ≤30 |
| 19 | 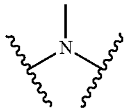 [SMILES: *N(*)C] | R | ≤30 |
TABLE 2-continued
| Inhibitors 15-26.[a] | | | |
|---|---|---|---|
| 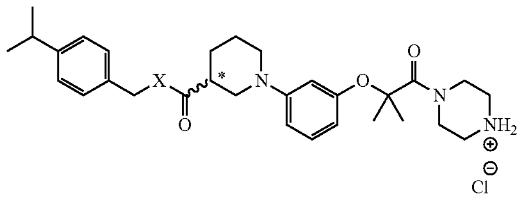 | | | |
| No. | X | *R/S | $K_i$ (μM) |
| 20 | 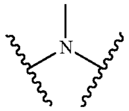 [SMILES: *N(*)C] | S | ≤10 |
| 21 | 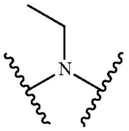 [SMILES: *N(*)CC] | R | ≤30 |
| 22 | 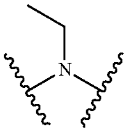 [SMILES: *N(*)CC] | S | ≤30 |
| 23 | 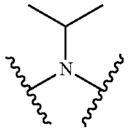 [SMILES: *N(*)C(C)C] | R | ≤10 |
| 24 | 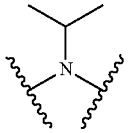 [SMILES: *N(*)C(C)C] | S | ≤10 |
| 25 | 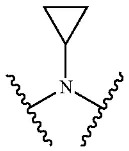 [SMILES: *N(*)C1CC1] | R | ≤5 |
| 26 | 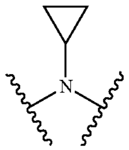 [SMILES: *N(*)C1CC1] | S | ≤10 |
[a]Each set of data was expressed as mean ± standard deviation (n = 3)

TABLE 3
Inhibitors 27-43.[a]
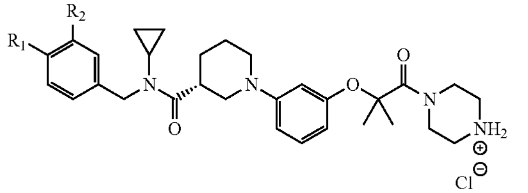
| No. | $R_1$ | $R_2$ | $K_i$ (μM) |
|---|---|---|---|
| 27 | H | 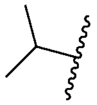 [SMILES: *C(C)C] | ≤30 |
| 28 | 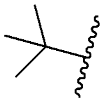 [SMILES: *C(C)(C)C] | H | ≤30 |
| 29 | 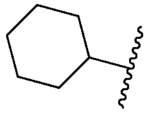 [SMILES: *C1CCCCC1] | H | ≤5 |
| 30 | 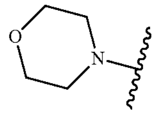 [SMILES: *N1CCOCC1] | H | >90 |
| 31 | 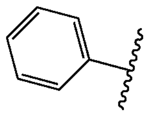 [SMILES: *c1ccccc1] | H | <5 |
| 32 | 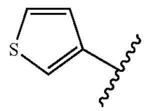 | H | <5 |
| 33 | 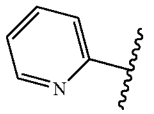 [SMILES: *c1ccccn1] | H | <90 |
| 34 | 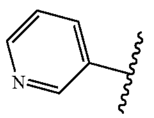 [SMILES: *c1cccnc1] | H | <90 |
| 35 | 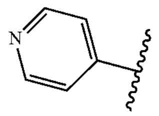 [SMILES: *c1ccncc1] | H | <90 |
| 36 | 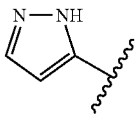 [SMILES: *c1ccn[nH]1] | H | ≤10 |
TABLE 3-continued
Inhibitors 27-43.[a]
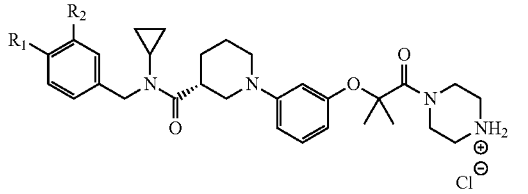
| No. | $R_1$ | $R_2$ | $K_i$ (μM) |
|---|---|---|---|
| 37 | 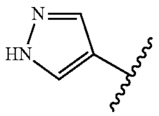 | H | ≤1 |
| 38 | 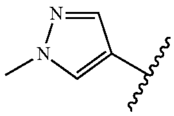 [SMILES: *c1cnn(C)c1] | H | ≤90 |
| 39 | 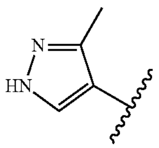 [SMILES: *c1c[nH]nc1C] | H | ≤50 |
| 40 | 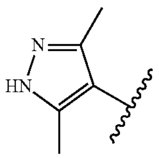 [SMILES: *c1c(C)n[nH]c1C] | H | <10 |
| 41 | 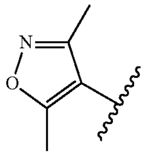 [SMILES: *c1c(C)noc1C] | H | <30 |
| 42 | 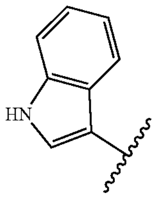 | H | <5 |
| 43 | 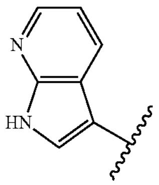 [SMILES: *c1c[nH]c2ncccc12] | H | <1 |
[a]Each set of data was expressed as mean ± standard deviation (n = 3)

TABLE 4
Inhibitors 44-53.[a]
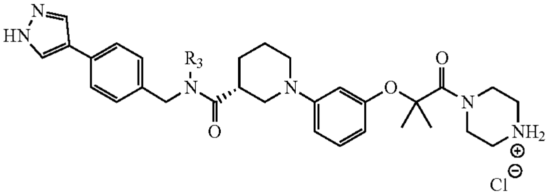
| No. | $R_3$ | $K_i$ (μM) | No. | $R_3$ | $K_i$ ± SD |
|---|---|---|---|---|---|
| 44 | H | <90 | 49 | 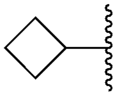 [SMILES: *C1CCC1] | <30 |
| 45 | Me | <30 | 50 | 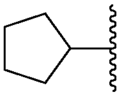 [SMILES: *C1CCCC1] | <10 |
| 46 | Et | <5 | 51 | 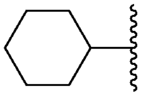 | <30 |
| 47 | i-Pr | <10 | 52 | 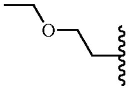 [SMILES: *CCOCC] | <5 |
| 48 | 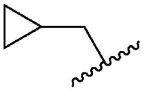 [SMILES: *CC1CC1] | <90 | 53 | 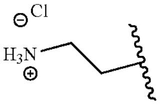 | <90 |
[a]Each set of data was expressed as mean ± standard deviation (n = 3)
TABLE 5
Inhibitors 54-62. [a]
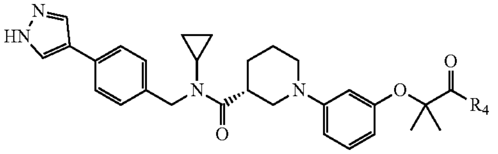
| No. | $R_4$ | $K_i$ (μM) |
|---|---|---|
| 54 | 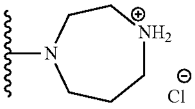 | <10 |
| 55 | 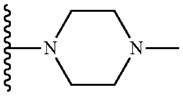 | >90 |
| 56 | 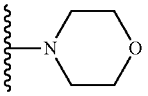 [SMILES: *N1CCOCC1] | >90 |
TABLE 5-continued
Inhibitors 54-62. [a]
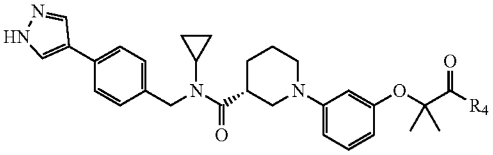
| No. | $R_4$ | $K_i$ (μM) |
|---|---|---|
| 57 | 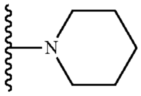 [SMILES: *N1CCCCC1] | >90 |
| 58 | 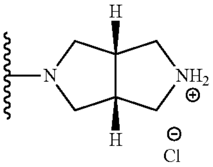 [SMILES: *N1C[C@H]2C[NH2+]C[C@H]2C1 ; [Cl-]] | <30 |
| 59 | 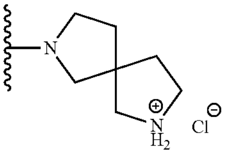 [SMILES: *N1CCC2(CC[NH2+]C2)C1 ; [Cl-]] | <5 |
| 60 | 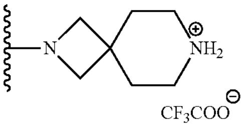 | <30 |
| 61 | 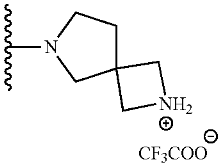 | <30 |
| 62 | 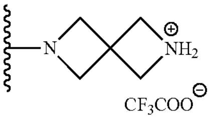 | <90 |
TABLE 6
Inhibitors 63-72. [a]
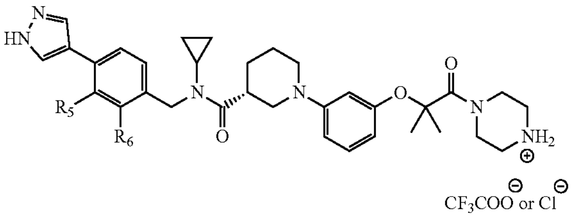
| No. | $R_5$ | $R_6$ | $K_i$ (μM) |
|---|---|---|---|
| 63 | H | F | <30 |
| 64 | F | H | <30 |
| 65 | H | Me | <5 |

TABLE 6-continued
Inhibitors 63-72. [a]
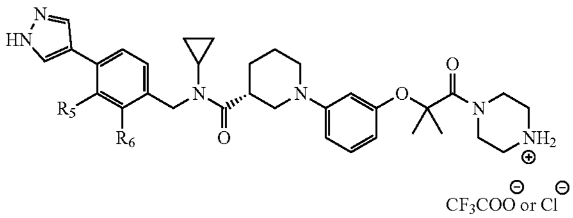
| No. | $R_5$ | $R_6$ | $K_i$ (μM) |
|---|---|---|---|
| 66 | Me | H | <90 |
| 67 | H | Cl | <30 |
| 68 | H | OMe | <5 |
| 69 | OMe | H | <30 |
| 70 | H | $CF_3$ | <10 |
| 71 | $CF_3$ | H | <30 |
| 72 | H | $OCF_3$ | <5 |
TABLE 7
Inhibitors 73-81. [a]
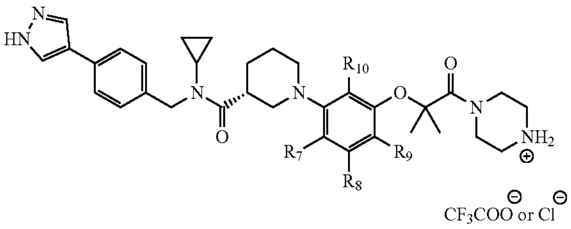
| No. | $R_7$ | $R_8$ | $R_9$ | $R_{10}$ | $K_i$ (μM) |
|---|---|---|---|---|---|
| 73 | F | H | H | H | <50 |
| 74 | H | F | H | H | <10 |
| 75 | H | H | F | H | <10 |
| 76 | H | H | H | F | <90 |
| 77 | H | $CF_3$ | H | H | <10 |
| 78 | H | Cl | H | H | <30 |
| 79 | H | CN | H | H | <30 |
| 80 | H | H | Cl | H | <30 |
| 81 | H | H | CN | H | <90 |
TABLE 8
Inhibitors 82-92. [a]
| No. | Structure | $K_i$ (μM) |
|---|---|---|
| 82 | 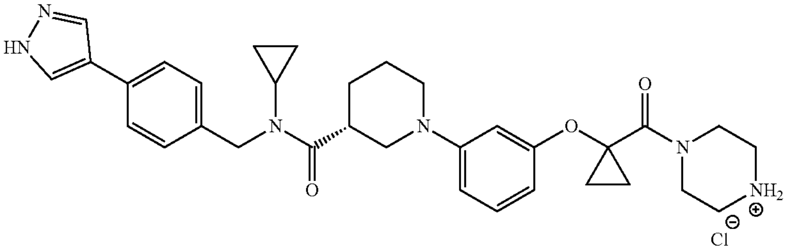 [SMILES: O=C([C@@H]1CCCN(c2cccc(OC3(C(=O)N4CC[NH2+]CC4)CC3)c2)C1)N(Cc1ccc(-c2cn[nH]c2)cc1)C1CC1 ; [Cl-]] | <10 |
| 83 | 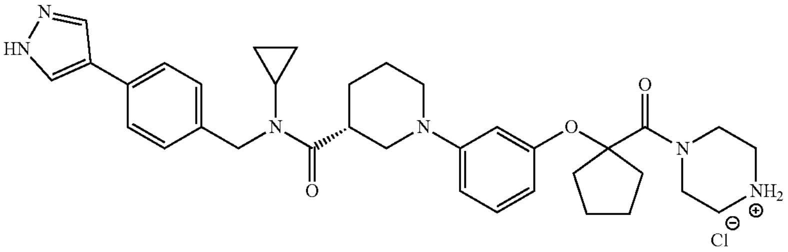 [SMILES: O=C([C@@H]1CCCN(c2cccc(OC3(C(=O)N4CC[NH2+]CC4)CCCC3)c2)C1)N(Cc1ccc(-c2cn[nH]c2)cc1)C1CC1 ; [Cl-]] | <90 |
| 84 | 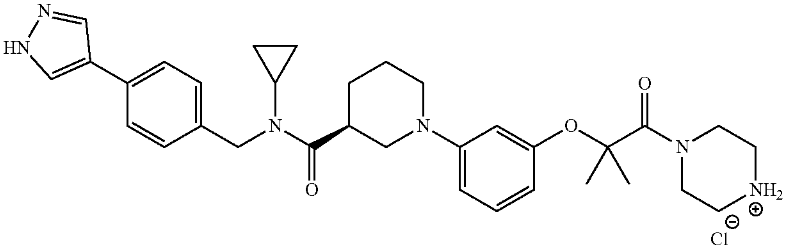 [SMILES: CC(C)(Oc1cccc(N2CCC[C@H](C(=O)N(Cc3ccc(-c4cn[nH]c4)cc3)C3CC3)C2)c1)C(=O)N1CC[NH2+]CC1 ; [Cl-]] | <90 |

TABLE 8-continued
| No. | Structure | $K_i$ (μM) |
|---|---|---|
| | Inhibitors 82-92. [a] | |
| 85 | 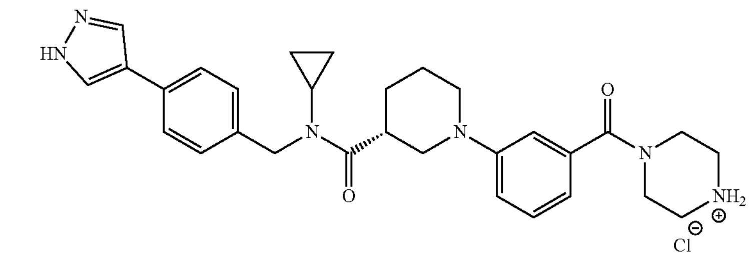 [SMILES: O=C(c1cccc(N2CCC[C@@H](C(=O)N(Cc3ccc(-c4cn[nH]c4)cc3)C3CC3)C2)c1)N1CC[NH2+]CC1 ; [Cl-]] | <90 |
| 86 | 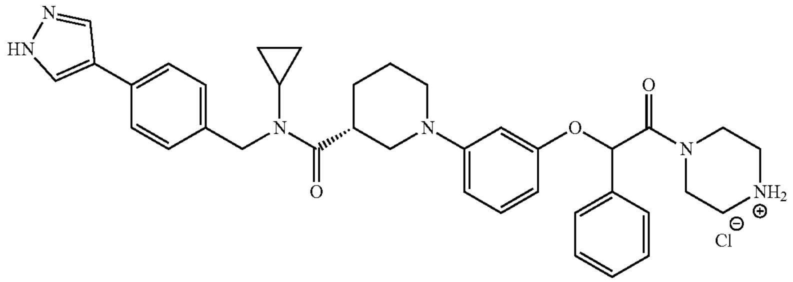 [SMILES: O=C(C(Oc1cccc(N2CCC[C@@H](C(=O)N(Cc3ccc(-c4cn[nH]c4)cc3)C3CC3)C2)c1)c1ccccc1)N1CC[NH2+]CC1 ; [Cl-]] | <30 |
| 87 | 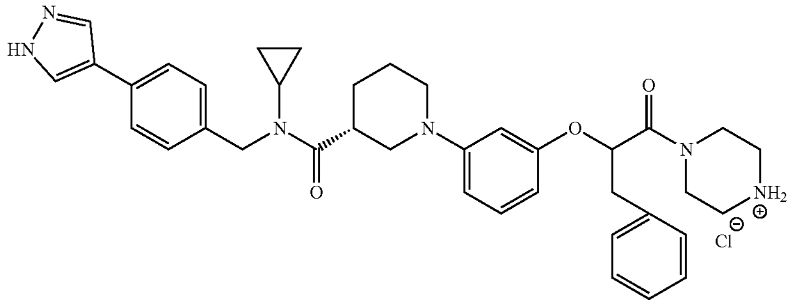 [SMILES: O=C(C(Cc1ccccc1)Oc1cccc(N2CCC[C@@H](C(=O)N(Cc3ccc(-c4cn[nH]c4)cc3)C3CC3)C2)c1)N1CC[NH2+]CC1 ; [Cl-]] | <90 |
| 88 | 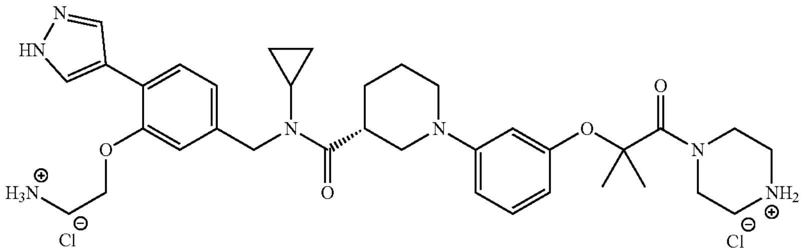 [SMILES: CC(C)(Oc1cccc(N2CCC[C@@H](C(=O)N(Cc3ccc(-c4cn[nH]c4)c(OCC[NH3+])c3)C3CC3)C2)c1)C(=O)N1CC[NH2+]CC1 ; [Cl-] ; [Cl-]] | <5 |
| 89 | 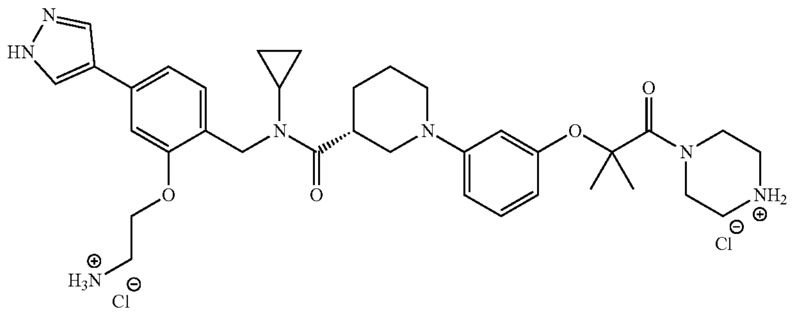 [SMILES: CC(C)(Oc1cccc(N2CCC[C@@H](C(=O)N(Cc3ccc(-c4cn[nH]c4)cc3OCC[NH3+])C3CC3)C2)c1)C(=O)N1CC[NH2+]CC1 ; [Cl-] ; [Cl-]] | <90 |

TABLE 8-continued
| Inhibitors 82-92. [a] | | |
|---|---|---|
| No. | Structure | $K_i$ (μM) |
| 90 | 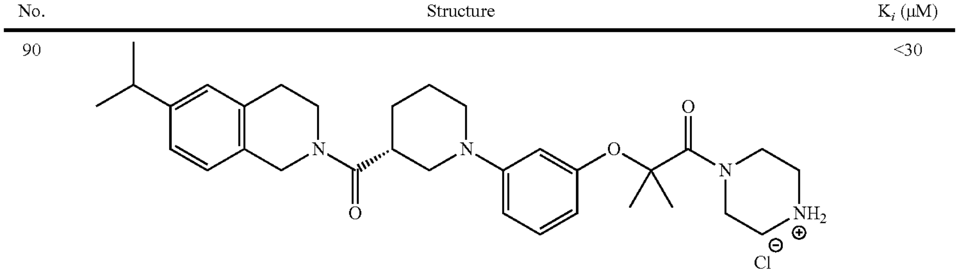 | <30 |
| 91 | 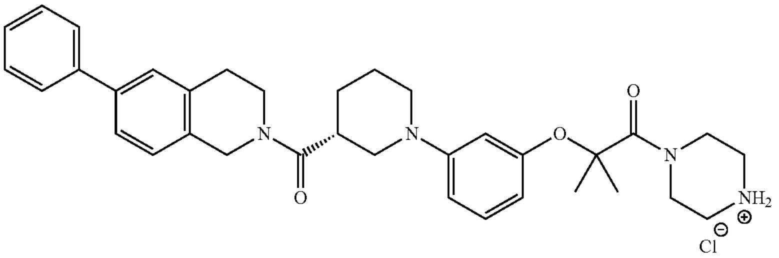 [SMILES: CC(C)(Oc1cccc(N2CCC[C@@H](C(=O)N3CCc4cc(-c5ccccc5)ccc4C3)C2)c1)C(=O)N1CC[NH2+]CC1 ; [Cl-]] | <5 |
| 92 | 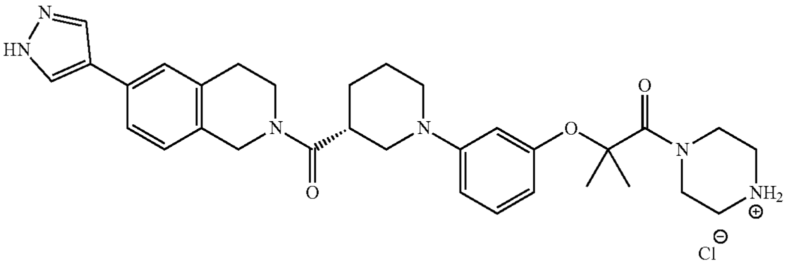 [SMILES: CC(C)(Oc1cccc(N2CCC[C@@H](C(=O)N3CCc4cc(-c5cn[nH]c5)ccc4C3)C2)c1)C(=O)N1CC[NH2+]CC1 ; [Cl-]] | <90 |
TABLE 9
| AlphaScreen Assay Results of Inhibitors 93-98.[a] | | | |
|---|---|---|---|
| Compounds | | Structure | $K_i$ (μM) |
| 93 | racemic | 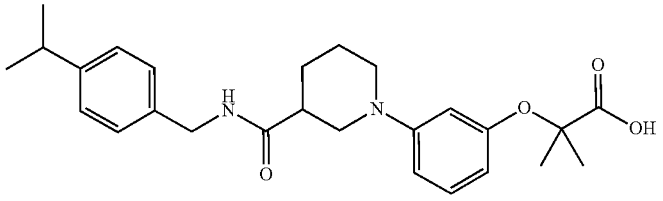 [SMILES: CC(C)c1ccc(CNC(=O)C2CCCN(c3cccc(OC(C)(C)C(=O)O)c3)C2)cc1] | ≤90 |
| 94 | racemic | 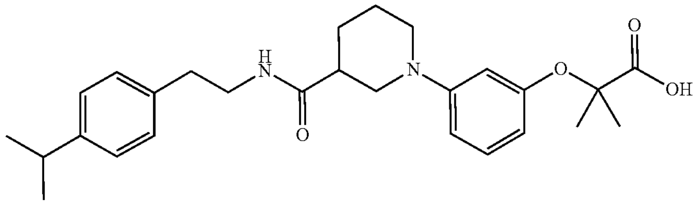 [SMILES: CC(C)c1ccc(CCNC(=O)C2CCCN(c3cccc(OC(C)(C)C(=O)O)c3)C2)cc1] | ≤90 |

TABLE 9-continued

AlphaScreen Assay Results of Inhibitors 93-98.[a]

| Compounds | | Structure | $K_i$ (μM) |
|---|---|---|---|
| 95 | racemic | 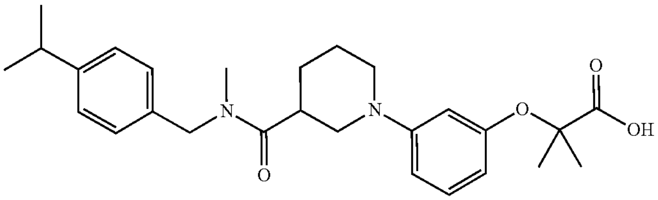 [SMILES: CC(C)c1ccc(CN(C)C(=O)C2CCCN(c3cccc(OC(C)(C)C(=O)O)c3)C2)cc1] | ≤90 |
| 96 | racemic | 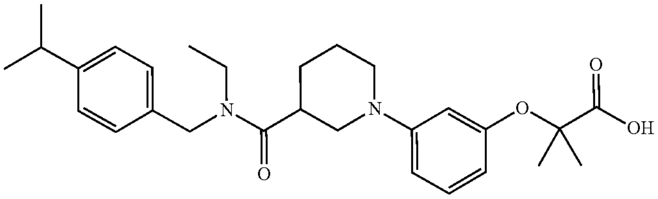 [SMILES: CCN(Cc1ccc(C(C)C)cc1)C(=O)C1CCCN(c2cccc(OC(C)(C)C(=O)O)c2)C1] | ≤90 |
| 97 | racemic | 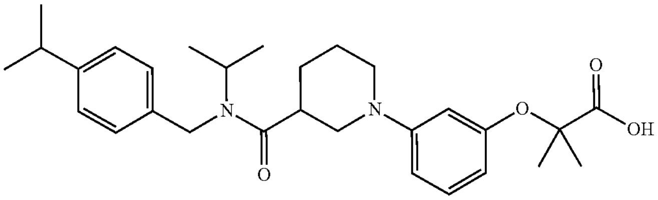 [SMILES: CC(C)c1ccc(CN(C(=O)C2CCCN(c3cccc(OC(C)(C)C(=O)O)c3)C2)C(C)C)cc1] | ≤90 |
| 98 | racemic | 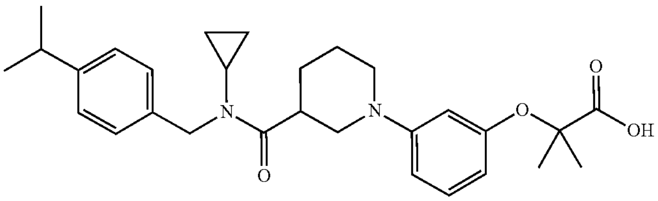 [SMILES: CC(C)c1ccc(CN(C(=O)C2CCCN(c3cccc(OC(C)(C)C(=O)O)c3)C2)C2CC2)cc1] | ≤90 |

[a]Each set of data was expressed as mean ± standard deviation (n = 3).

TABLE 10

AlphaScreen Assay Results of Inhibitors 99-106.[a]

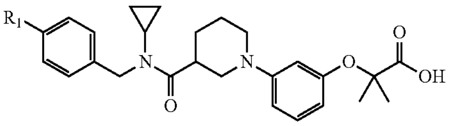

| Compd. | | $R_1$ | $K_i$ ± SD (μM) |
|---|---|---|---|
| 99 | racemic | 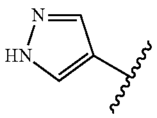 [SMILES: *c1cn[nH]c1] | >90 |
| 100 | racemic | 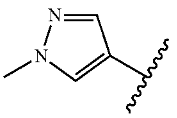 [SMILES: *c1cnn(C)c1] | >90 |

TABLE 10-continued

AlphaScreen Assay Results of Inhibitors 99-106.[a]

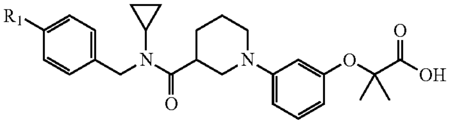

| Compd. | | $R_1$ | $K_i$ ± SD (μM) |
|---|---|---|---|
| 101 | racemic | 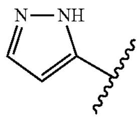 [SMILES: *c1ccn[nH]1] | ≤90 |
| 102 | racemic | 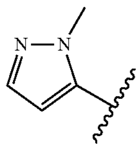 [SMILES: *c1ccnn1C] | >90 |

TABLE 10-continued

AlphaScreen Assay Results of Inhibitors 99-106.[a]

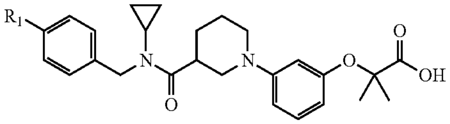

| Compd. | | $R_1$ | $K_i$ ± SD (μM) |
|---|---|---|---|
| 103 | racemic | 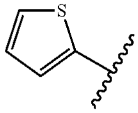 [SMILES: *c1cccs1] | ≤30 |
| 104 | racemic | 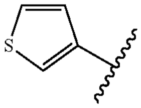 | ≤30 |
| 105 | racemic | 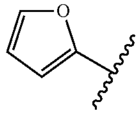 [SMILES: *c1ccco1] | ≤90 |
| 106 | racemic | 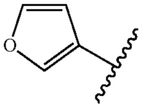 | >90 |

[a]Each set of data was expressed as mean ± standard deviation (n = 3).

TABLE 11

AlphaScreen Assay Results of Inhibitors 107-108.[a]

| Compd. | | Structure | $K_i$ ± SD (μM) |
|---|---|---|---|
| 107 | racemic | 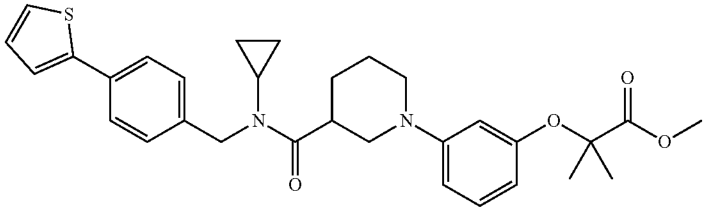 [SMILES: COC(=O)C(C)(C)Oc1cccc(N2CCCC(C(=O)N(Cc3ccc(-c4cccs4)cc3)C3CC3)C2)c1] | >90 |
| 108 | racemic | 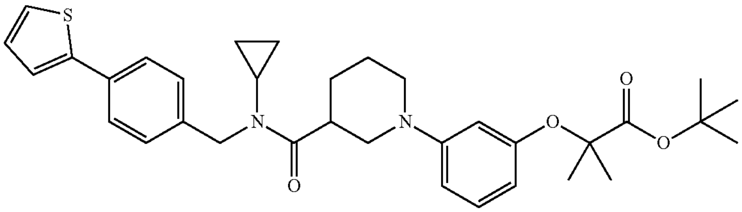 [SMILES: CC(C)(C)OC(=O)C(C)(C)Oc1cccc(N2CCCC(C(=O)N(Cc3ccc(-c4cccs4)cc3)C3CC3)C2)c1] | >90 |

[a]Each set of data was expressed as mean ± standard deviation (n = 3).

TABLE 12

AlphaScreen Assay Results of Inhibitors 109-112.[a]

| Compounds | Structure | $K_i$ (μM) |
|---|---|---|
| 109 | 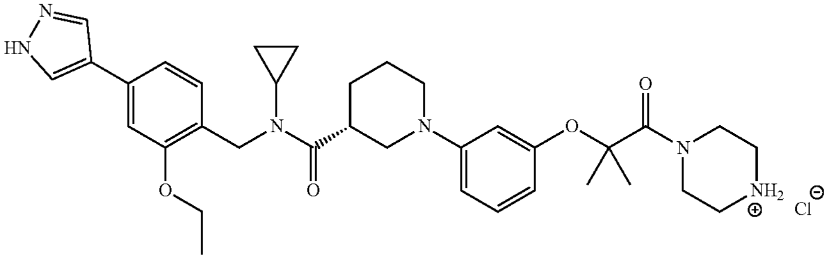 [SMILES: CCOc1cc(-c2cn[nH]c2)ccc1CN(C(=O)[C@@H]1CCCN(c2cccc(OC(C)(C)C(=O)N3CC[NH2+]CC3)c2)C1)C1CC1 ; [Cl-]] | ≤30 |

TABLE 12-continued

AlphaScreen Assay Results of Inhibitors 109-112.[a]

| Compounds | Structure | $K_i$ (μM) |
| --- | --- | --- |
| 110 | 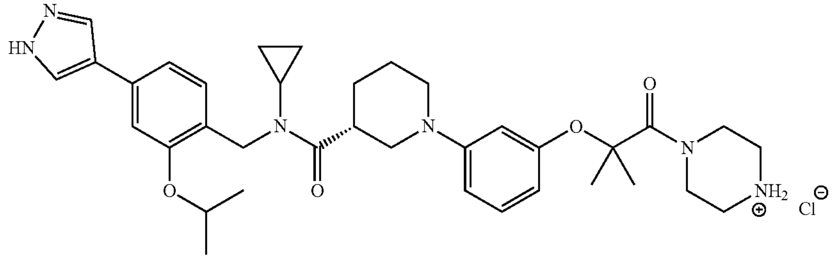 [SMILES: CC(C)Oc1cc(-c2cn[nH]c2)ccc1CN(C(=O)[C@@H]1CCCN(c2cccc(OC(C)(C)C(=O)N3CC[NH2+]CC3)c2)C1)C1CC1 ; [Cl-]] | ≤30 |
| 111 | 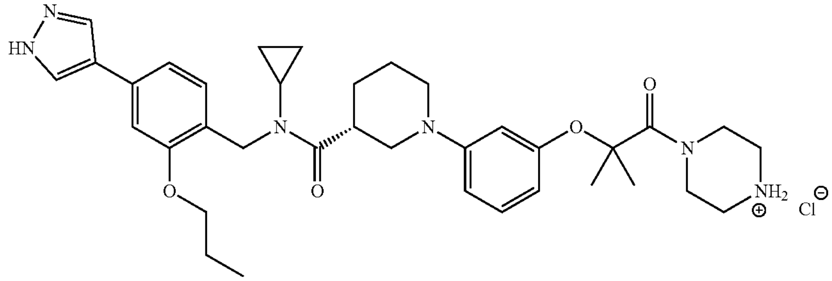 [SMILES: CCCOc1cc(-c2cn[nH]c2)ccc1CN(C(=O)[C@@H]1CCCN(c2cccc(OC(C)(C)C(=O)N3CC[NH2+]CC3)c2)C1)C1CC1 ; [Cl-]] | ≤30 |
| 112 | 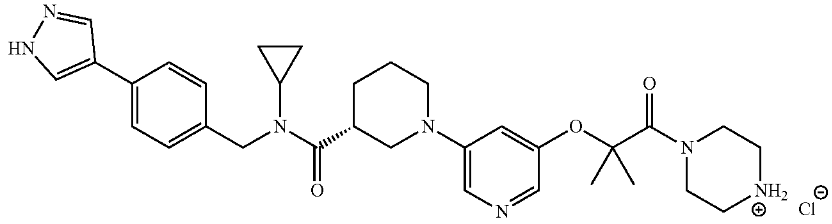 [SMILES: CC(C)(Oc1cncc(N2CCC[C@@H](C(=O)N(Cc3ccc(-c4cn[nH]c4)cc3)C3CC3)C2)c1)C(=O)N1CC[NH2+]CC1 ; [Cl-]] | ≤30 |

[a]Each set of data was expressed as mean ± standard deviation (n = 3).

Synthesis: All reagents were purchased from commercial sources and used as received. $^{1}H$ NMR and $^{13}C$ NMR spectra were recorded on Bruker AVANCEIIIHD 500 (500 MHz) spectrometers (125.7 MHz for $^{13}C$ NMR spectra) in $d_6$-DMSO, $d_6$-acetone, $d_4$-methanol, and $CDCl_3$. Chemical shifts were reported as values in parts per million (ppm), and the reference resonance peaks were set at 7.26 ppm ($CHCl_3$), 3.31 ppm ($CD_2HOD$), 2.50 ppm [$(CD_2H)_2SO$], 2.05 ppm [$(CD_2H)_2CO$] for $^{1}H$ NMR spectra and 77.23 ppm ($CDCl_3$), 49.00 ppm ($CD_3OD$), 39.52 ppm ($d_6$-DMSO), and 29.84 ppm ($d_6$-acetone) for $^{13}C$ NMR spectra. Low-resolution mass spectra were determined on Agilent 6120 single quadrupole MS with 1220 infinity LC system (HPLC-MS) and an ESI source. High-resolution mass spectra were determined on Agilent G6230BA TOF LCMS Mass Spectrometer with a TOF mass detector. Thin-layer chromatography was carried out on E. Merck pre-coated silica gel 60 F254 plates with a UV-visible lamp. Column chromatography was performed with SilicaFlash@F60 (230-400 mesh). The purity of final compounds was determined by HPLC analyses. The instrument was an Agilent 1260 Infinity II HPLC system with a quaternary pump, a vial sampler, and a DAD detector. A Kromasil 300-5-$C_{18}$ column (4.6×250 mm) was used. The DAD detector was set to 254 nm. The purity of all tested compounds was >95%.

Scheme 1. Synthesis of 1-14.

A.

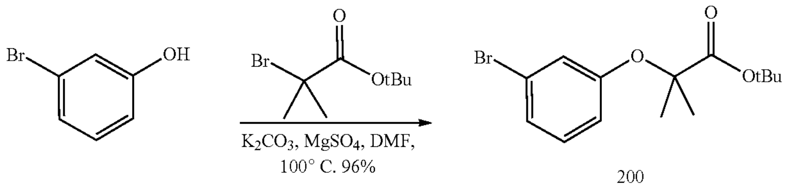

200

-continued
B.
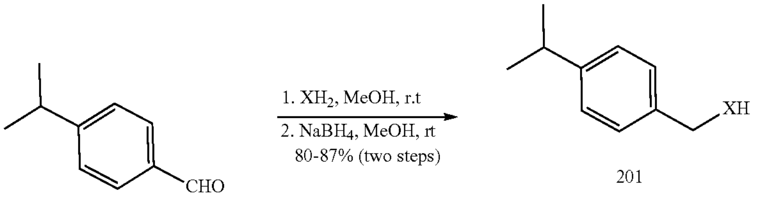
201
201a. X = EtN
201b. X = i-PrN
201c. X = c-PrN
C.
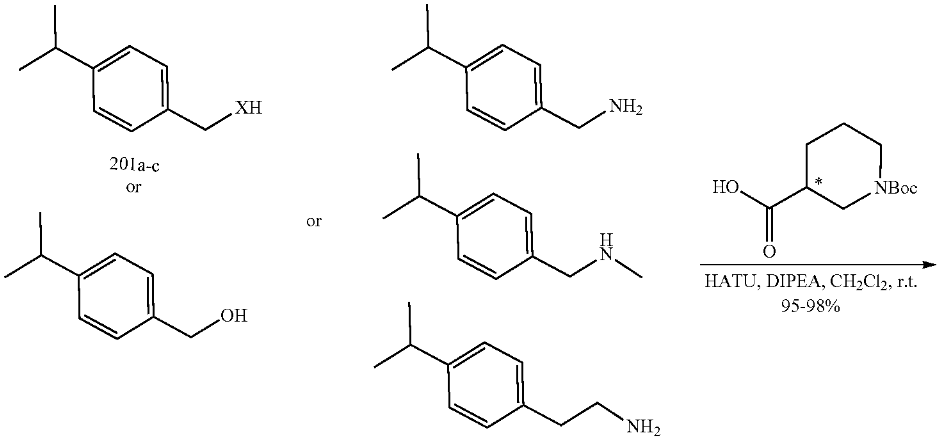
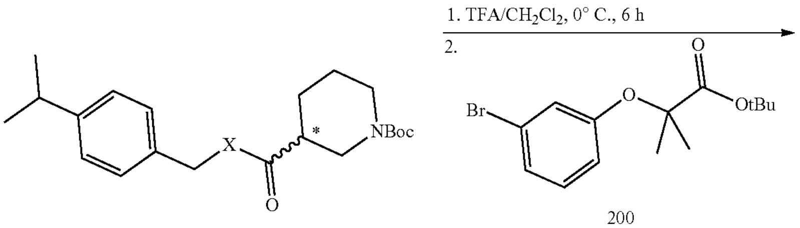
202
200
$Pd_2(dba)_3$, Ruphos
$CsCO_3$, toluene, 80° C.
73-85% (two steps)
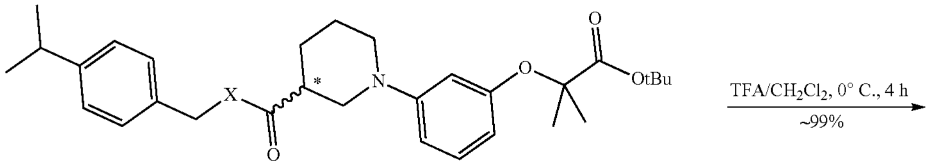
203

-continued

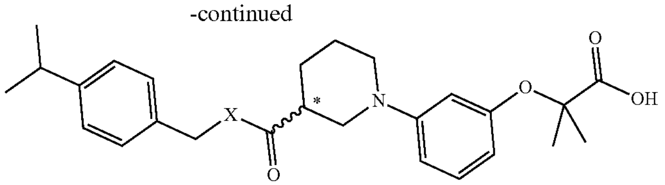

1-14

1. X = O, *R
2. X = O, *S
3. X = NH, *R
4. X = NH, *S
5. X = MeN, *R
6. X = MeN, *S
7. X = EtN, *R
8. X = EtN, *S
9. X = i-PrN, *R
10. X = iPrN, *S
11. X = c-PrN, *R
12. X = c-PrN, *S
13. X = -$CH_2$-NH, *R
14. X = -$CH_2$-NH. *S tert-butyl 2-(3-bromophenoxy)-2-methylpropanoate (200). $^{1}$H NMR (500 MHz, Chloroform-d) δ 7.16-7.04 (m, 2H), 7.01 (dd, J=2.7, 1.3 Hz, 1H), 6.82-6.71 (m, 1H), 1.56 (s, 6H), 1.44 (s, 9H). $^{13}$C NMR (126 MHz, Chloroform-d) δ 172.79, 156.55, 130.10, 124.65, 122.23, 121.82, 117.27, 82.03, 79.83, 27.78, 25.34. MS (ESI) m/z=315.1 [M+H]$^+$. N-(4-isopropylbenzyl) ethanamine (201a). $^{1}$H NMR (500 MHz, Chloroform-d) δ 7.24 (d, J=8.2 Hz, 2H), 7.21-7.16 (m, 2H), 3.76 (s, 2H), 2.89 (hept, J=6.9 Hz, 1H), 2.69 (q, J=7.1 Hz, 2H), 1.25 (d, J=6.9 Hz, 6H), 1.13 (t, J=7.1 Hz, 3H). $^{13}$C NMR (126 MHz, Chloroform-d) δ 147.50, 137.94, 128.12, 126.42, 53.76, 43.72, 33.80, 24.06, 15.33. MS (ESI) m/z=178.2 [M+H]$^+$.

N-(4-isopropylbenzyl) propan-2-amine (201b). $^{1}$H NMR (500 MHz, Chloroform-d) δ 7.26-7.21 (m, 2H), 7.20-7.16 (m, 2H), 3.75 (s, 2H), 3.00-2.65 (m, 2H), 1.24 (d, J=6.9 Hz, 6H), 1.10 (d, J=6.2 Hz, 6H). $^{13}$C NMR (126 MHz, Chloroform-d) δ 147.44, 138.22, 128.07, 126.43, 51.40, 48.10, 33.79, 24.04, 22.97. MS (ESI) m/z=192.3 [M+H]$^+$.

N-(4-isopropylbenzyl)cyclopropanamine (201c). $^{1}$H NMR (500 MHz, Chloroform-d) δ 7.25-7.22 (m, 2H), 7.20-7.17 (m, 2H), 3.81 (s, 2H), 2.90 (hept, J=6.9 Hz, 1H), 2.22-2.12 (m, 1H), 1.25 (d, J=6.9 Hz, 6H), 0.48-0.35 (m, 4H). $^{13}$C NMR (126 MHz, Chloroform-d) δ 147.49, 138.01, 128.16, 126.42, 53.46, 33.81, 30.09, 24.06, 6.48. MS (ESI) m/z=190.2 [M+H]$^+$.

1-(tert-butyl) 3-(4-isopropylbenzyl) (R)-piperidine-1,3-dicarboxylate (202a). $^{1}$H NMR (500 MHz, Chloroform-d) δ 7.20 (dd, J=7.2, 1.2 Hz, 2H), 7.15 (d, J=8.2 Hz, 2H), 5.01 (s, 2H), 4.07 (q, J=7.2 Hz, 1H), 3.85 (d, J=13.3 Hz, 1H), 2.84 (p, J=6.9 Hz, 2H), 2.72 (ddd, J=13.3, 11.4, 3.1 Hz, 1H), 2.41 (ddt, J=10.6, 7.9, 3.9 Hz, 1H), 2.19-1.89 (m, 1H), 1.77-1.48 (m, 2H), 1.37 (s, 10H), 1.18 (d, J=6.9 Hz, 6H). $^{13}$C NMR (126 MHz, Chloroform-d) δ 173.29, 154.67, 149.06, 133.19, 128.27, 126.65, 79.71, 66.28, 45.73, 43.69, 41.49, 33.90, 28.41, 27.41, 24.30, 23.95. MS (ESI) m/z=384.1 [M+Na]$^+$.

1-(tert-butyl) 3-(4-isopropylbenzyl) (S)-piperidine-1,3-dicarboxylate (202b). $^{1}$H NMR (500 MHz, Chloroform-d) δ 7.21 (dd, J=7.2, 1.2 Hz, 2H), 7.15 (d, J=8.2 Hz, 2H), 5.03 (s, 2H), 4.08 (q, J=7.2 Hz, 1H), 3.85 (d, J=13.3 Hz, 1H), 2.84 (p, J=6.9 Hz, 2H), 2.74 (ddd, J=13.3, 11.4, 3.1 Hz, 1H), 2.41 (ddt, J=10.6, 7.9, 3.9 Hz, 1H), 2.18-1.91 (m, 1H), 1.74-1.45 (m, 2H), 1.36 (s, 10H), 1.19 (d, J=6.9 Hz, 6H). MS (ESI) m/z=384.1 [M+Na]$^+$.

tert-butyl (R)-3-((4-isopropylbenzyl)carbamoyl)piperidine-1-carboxylate (202c). $^{1}$H NMR (500 MHz, Chloroform-d) δ 7.14 (s, 4H), 4.37 (d, J=19.2 Hz, 2H), 4.05-3.61 (m, 2H), 3.15 (dd, J=13.5, 9.3 Hz, 1H), 2.86-2.77 (m, 2H), 2.26 (dq, J=9.8, 5.3, 4.9 Hz, 1H), 1.92-1.77 (m, 2H), 1.70-1.53 (m, 1H), 1.38 (s, 10H), 1.22 (d, J=7.0 Hz, 6H). MS (ESI) m/z=383.3 [M+Na]$^+$.

tert-butyl (S)-3-((4-isopropylbenzyl)carbamoyl)piperidine-1-carboxylate (202d). $^{1}$H NMR (500 MHz, Chloroform-d) δ 7.15 (s, 4H), 4.37 (d, J=19.2 Hz, 2H), 4.03-3.60 (m, 2H), 3.14 (dd, J=13.5, 9.3 Hz, 1H), 2.86 (hept, J=6.8 Hz, 2H), 2.28 (dq, J=9.8, 5.3, 4.9 Hz, 1H), 1.91-1.77 (m, 2H), 1.69-1.54 (m, 1H), 1.38 (s, 10H), 1.21 (d, J=7.0 Hz, 6H). $^{13}$C NMR (126 MHz, Chloroform-d) δ 172.92, 154.80, 148.10, 135.59, 127.80, 126.70, 79.81, 45.87, 44.65, 43.22, 43.00, 33.80, 28.37, 27.77, 24.22, 24.00. MS (ESI) m/z=361.3 [M+H]$^+$, 383.3 [M+Na]$^+$.

tert-butyl (R)-3-((4-isopropylbenzyl)(methyl)carbamoyl) piperidine-1-carboxylate (202e). $^{1}$H NMR (500 MHz, Chloroform-d) δ 7.24-7.12 (m, 2H), 7.11-6.89 (m, 2H), 4.51 (s, 2H), 4.16 (s, 1H), 4.06 (s, 1H), 2.95 (s, 2H), 2.90-2.79 (m, 3H), 2.70-2.45 (m, 2H), 2.02-1.54 (m, 3H), 1.53-1.30 (m, 10H), 1.21 (t, J=6.9 Hz, 6H). $^{13}$C NMR (126 MHz, Chloroform-d) δ 173.76, 173.13, 154.69, 154.55, 148.39, 147.96, 134.54, 133.86, 127.91, 126.99, 126.63, 126.21, 79.58, 79.49, 52.83, 50.45, 46.46, 44.30, 39.47, 34.59, 33.83, 33.76, 28.44, 28.39, 28.06, 27.57, 24.74, 24.57, 23.97, 23.95. MS (ESI) m/z=375.3 [M+H]$^+$.

tert-butyl (S)-3-((4-isopropylbenzyl)(methyl)carbamoyl) piperidine-1-carboxylate (202f). $^{1}$H NMR (500 MHz, Chloroform-d) δ 7.24-7.14 (m, 2H), 7.10-6.86 (m, 2H), 4.52 (s, 2H), 4.16 (s, 1H), 4.06 (s, 1H), 2.94 (s, 2H), 2.92-2.80 (m, 3H), 2.69-2.45 (m, 2H), 2.01-1.56 (m, 3H), 1.52-1.30 (m, 10H), 1.21 (t, J=6.9 Hz, 6H). MS (ESI) m/z=375.3 [M+H]$^+$.

tert-butyl (R)-3-(ethyl(4-isopropylbenzyl)carbamoyl)piperidine-1-carboxylate (202g). $^{1}$H NMR (500 MHz, Chloroform-d) δ 7.20-7.14 (m, 1H), 7.14-6.90 (m, 3H), 4.85-3.96 (m, 4H), 3.26 (s, 2H), 2.84 (dp, J=13.7, 6.9 Hz, 2H), 2.60 (tt, J=31.9, 17.1 Hz, 2H), 1.97-1.55 (m, 3H), 1.38 (d, J=30.3 Hz, 10H), 1.19 (dd, J=8.0, 6.9 Hz, 6H), 1.08 (dt, J=48.7, 7.1 Hz, 3H). $^{13}$C NMR (126 MHz, Chloroform-d) δ 173.27, 173.10, 154.63, 154.51, 148.24, 147.80, 135.05, 134.36, 127.76, 126.89, 126.56, 126.16, 79.51, 79.41, 53.43, 49.98, 47.28, 44.63, 43.92, 41.29, 40.62, 39.46, 33.72 (d, J=2.8 Hz), 28.43, 28.37, 28.08, 24.62, 23.97, 23.95, 14.29, 12.59. MS (ESI) m/z=389.3 $[M+H]^+$.

tert-butyl (S)-3-(ethyl(4-isopropylbenzyl)carbamoyl)piperidine-1-carboxylate (202h). $^1$H NMR (500 MHz, Chloroform-d) δ 7.20-7.15 (m, 1H), 7.15-6.84 (m, 3H), 4.90-3.97 (m, 4H), 3.71-3.11 (m, 2H), 2.86 (dh, J=13.7, 6.9 Hz, 2H), 2.74-2.45 (m, 2H), 1.94-1.54 (m, 3H), 1.42 (s, 10H), 1.20 (dd, J=7.7, 6.9 Hz, 6H), 1.17-0.81 (m, 3H). $^{13}$C NMR (126 MHz, Chloroform-d) δ 173.28, 173.12, 154.65, 154.56, 148.26, 147.83, 135.05, 134.37, 127.77, 126.90, 126.57, 126.18, 79.53, 79.44, 53.43, 49.99, 47.29, 46.53, 44.64, 43.77, 41.30, 40.62, 39.51, 33.74, 33.72, 28.44, 28.38, 28.08, 23.98, 23.95, 14.30, 12.59. MS (ESI) m/z=389.3 $[M+H]^+$.

tert-butyl (R)-3-(isopropyl(4-isopropylbenzyl)carbamoyl)piperidine-1-carboxylate (202i). $^1$H NMR (500 MHz, Chloroform-d) δ 7.19-7.12 (m, 1H), 7.12-6.97 (m, 3H), 4.94-3.85 (m, 5H), 3.19-2.20 (m, 4H), 2.04-1.62 (m, 2H), 1.64-1.52 (m, 1H), 1.44 (s, 4H), 1.36 (s, 6H), 1.29-1.10 (m, 9H), 1.04 (d, J=6.8 Hz, 3H). $^{13}$C NMR (126 MHz, Chloroform-d) δ 174.03, 173.29, 154.65, 154.53, 147.79, 146.98, 136.73, 135.99, 126.75, 126.59, 126.33, 125.59, 79.52, 79.37, 53.43, 48.47, 47.13, 46.48, 45.51, 44.59, 43.60, 40.69, 39.74, 33.66, 28.47, 28.37, 28.23, 24.77, 24.41, 24.00, 23.95, 21.96, 21.90, 20.24. MS (ESI) m/z=403.3 $[M+H]^+$, 425.3 $[M+Na]^+$, tert-butyl (S)-3-(isopropyl(4-isopropylbenzyl)carbamoyl) piperidine-1-carboxylate (202j). $^1$H NMR (500 MHz, Chloroform-d) δ 7.23-7.16 (m, 1H), 7.14-7.00 (m, 3H), 4.99-3.90 (m, 5H), 3.17-2.32 (m, 4H), 2.06-1.55 (m, 3H), 1.46 (s, 4H), 1.39 (s, 6H), 1.29-1.10 (m, 9H), 1.07 (d, J=7.0 Hz, 3H). $^{13}$C NMR (126 MHz, Chloroform-d) δ 174.08, 173.33, 154.69, 154.54, 147.84, 147.04, 136.73, 136.03, 126.78, 126.60, 126.36, 125.62, 79:58, 79.43, 48.50, 45.53, 43.63, 40.72, 33.68, 28.50, 28.40, 28.25, 24.83, 24.43, 24.01, 23.97, 21.99, 21.93, 20.27. MS (ESI) m/z=403.3 $[M+H]^+$, 425.3 $[M+Na]^+$ tert-butyl (R)-3-(cyclopropyl(4-isopropylbenzyl)carbamoyl)piperidine-1-carboxylate (202k). $^1$H NMR (500 MHz, Chloroform-d) δ 7.12 (t, J=6.7 Hz, 4H), 4.91-3.94 (m, 4H), 3.19 (tt, J=11.5, 3.8 Hz, 1H), 2.87 (dq, J=13.8, 6.8 Hz, 2H), 2.65 (d, J=69.8 Hz, 2H), 1.90 (d, J=13.3 Hz, 1H), 1.85-1.63 (m, 2H), 1.45 (s, 10H), 1.22 (d, J=6.9 Hz, 6H), 0.97-0.70 (m, 4H). $^{13}$C NMR (126 MHz, Chloroform-d) δ 176.19, 154.67, 147.67, 135.48, 127.65, 126.54, 79.50, 49.36, 47.26, 44.77, 40.35, 33.75, 29.62, 28.46, 27.78, 24.73, 23.99, 9.32. MS (ESI) m/z=401.4 $[M+H]^+$, 423.3 $[M+Na]^+$.

tert-butyl (S)-3-(cyclopropyl(4-isopropylbenzyl)carbamoyl)piperidine-1-carboxylate (202l). $^1$H NMR (500 MHz, Chloroform-d) δ 7.12 (t, J=6.7 Hz, 4H), 4.90-3.93 (m, 4H), 3.18 (tt, J=11.5, 3.8 Hz, 1H), 2.89 (dq, J=13.8, 6.8 Hz, 2H), 2.64 (d, J=69.8 Hz, 2H), 1.89 (d, J=13.3 Hz, 1H), 1.85-1.61 (m, 2H), 1.44 (s, 10H), 1.22 (d, J=6.9 Hz, 6H), 0.97-0.71 (m, 4H). MS (ESI) m/z=401.4 $[M+H]^+$ tert-butyl (R)-3-((4-isopropylphenethyl)carbamoyl)piperidine-1-carboxylate (202m). $^1$H NMR (500 MHz, Chloroform-d) δ 7.11 (dd, J=8.2, 1.8 Hz, 2H), 7.06 (dd, J=8.0, 1.6 Hz, 2H), 6.59-5.92 (m, 1H), 4.11-3.50 (m, 2H), 3.42 (qt, J=13.3, 7.0 Hz, 2H), 3.04 (s, 1H), 2.87-2.80 (m, 1H), 2.75-2.69 (m, 4H), 2.18 (dt, J=12.5, 6.2 Hz, 1H), 1.78 (d, J=8.5 Hz, 1H), 1.55 (t, J=12.7 Hz, 1H), 1.40 (d, J=1.6 Hz, 10H), 1.19 (dd, J=7.0, 1.5 Hz, 6H). MS (ESI) m/z=375.3 $[M+H]^+$, 397.3 $[M+Na]^+$.

tert-butyl (S)-3-((4-isopropylphenethyl)carbamoyl)piperidine-1-carboxylate (202n). $^1$H NMR (500 MHz, Chloroform-d) δ 7.12 (dd, J=8.2, 1.8 Hz, 2H), 7.03 (dd, J=8.0, 1.6 Hz, 2H), 6.59-5.89 (m, 1H), 4.09-3.50 (m, 2H), 3.42 (qt, J=13.3, 7.0 Hz, 2H), 3.04 (s, 1H), 2.87-2.82 (m, 1H), 2.74-2.71 (m, 4H), 2.16 (dt, J=12.5, 6.2 Hz, 1H), 1.78 (d, J=8.5 Hz, 1H), 1.56 (t, J=12.7 Hz, 1H), 1.39 (d, J=1.6 Hz, 10H), 1.20 (dd, J=7.0, 1.5 Hz, 6H). MS (ESI) m/z=375.3 $[M+H]^+$, 397.3 $[M+Na]^+$.

4-isopropylbenzyl (R)-1-(3-((1-(tert-butoxy)-2-methyl-1-oxopropan-2-yl)oxy)phenyl)piperidine-3-carboxylate (203a). $^1$H NMR (500 MHz, Chloroform-d) δ 7.36-7.26 (m, 2H), 7.23 (d, J=8.2 Hz, 2H), 7.08 (t, J=8.2 Hz, 1H), 6.58 (ddd, J=8.3, 2.4, 0.8 Hz, 1H), 6.50 (t, J=2.4 Hz, 1H), 6.32 (ddd, J=8.1, 2.4, 0.8 Hz, 1H), 5.24-5.03 (m, 2H), 3.73 (ddt, J=12.4, 3.2, 1.4 Hz, 1H), 3.46 (ddd, J=12.1, 4.6, 3.0 Hz, 1H), 3.03 (dd, J=12.4, 9.9 Hz, 1H), 2.92 (p, J=6.9 Hz, 1H), 2.80 (ddd, J=12.2, 10.3, 3.2 Hz, 1H), 2.70 (ddd, J=10.0, 6.9, 3.1 Hz, 1H), 2.10-1.97 (m, 1H), 1.80 (ddd, J=8.8, 4.3, 2.4 Hz, 1H), 1.70-1.63 (m, 2H), 1.57 (s, 6H), 1.45 (s, 9H), 1.26 (d, J=7.0 Hz, 6H). $^{13}$C NMR (126 MHz, Chloroform-d) δ 173.68, 173.51, 156.67, 152.50, 148.97, 133.37, 129.12, 128.26, 126.65, 110.53, 109.42, 107.72, 81.49, 79.23, 66.23, 52.04, 49.75, 41.44, 33.91, 27.84, 27.04, 25.52, 25.48, 24.13, 23.98. MS (ESI) m/z=496.3 $[M+H]^+$.

4-isopropylbenzyl(S)-1-(3-((1-(tert-butoxy)-2-methyl-1-oxopropan-2-yl)oxy)phenyl)piperidine-3-carboxylate (203b). $^1$H NMR (500 MHz, Chloroform-d) δ 7.36-7.28 (m, 2H), 7.21 (d, J=8.2 Hz, 2H), 7.08 (t, J=8.2 Hz, 1H), 6.58 (ddd, J=8.3, 2.4, 0.8 Hz, 1H), 6.51 (t, J=2.4 Hz, 1H), 6.32 (ddd, J=8.1, 2.4, 0.8 Hz, 1H), 5.23-5.03 (m, 2H), 3.73 (ddt, J=12.4, 3.2, 1.4 Hz, 1H), 3.46 (ddd, J=12.1, 4.6, 3.0 Hz, 1H), 3.03 (dd, J=12.4, 9.9 Hz, 1H), 2.92 (p, J=6.9 Hz, 1H), 2.80 (ddd, J=12.2, 10.3, 3.2 Hz, 1H), 2.70 (ddd, J=10.0, 6.9, 3.1 Hz, 1H), 2.13-1.99 (m, 1H), 1.80 (ddd, J=8.8, 4.3, 2.4 Hz, 1H), 1.70-1.63 (m, 2H), 1.56 (s, 6H), 1.45 (s, 9H), 1.25 (d, J=7.0 Hz, 6H). MS (ESI) m/z=496.3 $[M+H]^+$.

tert-butyl (R)-2-(3-(3-((4-isopropylbenzyl)carbamoyl)piperidin-1-yl)phenoxy)-2-methylpropanoate (203c). $^1$H NMR (500 MHz, Chloroform-d) δ 7.18 (d, J=1.6 Hz, 4H), 7.06 (t, J=8.2 Hz, 1H), 6.91 (t, J=5.7 Hz, 1H), 6.54 (dd, J=8.3, 2.3 Hz, 1H), 6.48 (t, J=2.3 Hz, 1H), 6.34 (dd, J=8.2, 2.3 Hz, 1H), 4.43 (d, J=5.6 Hz, 2H), 3.39 (dd, J=12.5, 3.6 Hz, 1H), 3.30-3.15 (m, 2H), 3.02 (ddd, J=11.8, 8.4, 3.1 Hz, 1H), 2.88 (p, J=6.9 Hz, 1H), 2.55 (tt, J=8.0, 4.1 Hz, 1H), 2.00-1.73 (m, 3H), 1.66 (tq, J=8.7, 4.4 Hz, 1H), 1.56 (s, 6H), 1.42 (d, J=0.9 Hz, 9H), 1.24 (d, J=6.9 Hz, 6H). MS (ESI) m/z=495.4 $[M+H]^+$.

tert-butyl (S)-2-(3-(3-((4-isopropylbenzyl)carbamoyl)piperidin-1-yl)phenoxy)-2-methylpropanoate (203d). $^1$H NMR (500 MHz, Chloroform-d) δ 7.18 (d, J=1.6 Hz, 4H), 7.06 (t, J=8.2 Hz, 1H), 6.90 (t, J=5.7 Hz, 1H), 6.54 (dd, J=8.3, 2.3 Hz, 1H), 6.49 (t, J=2.3 Hz, 1H), 6.34 (dd, J=8.2, 2.3 Hz, 1H), 4.42 (d, J=5.6 Hz, 2H), 3.39 (dd, J=12.5, 3.6 Hz, 1H), 3.31-3.15 (m, 2H), 3.02 (ddd, J=11.8, 8.4, 3.1 Hz, 1H), 2.88 (p, J=6.9 Hz, 1H), 2.55 (tt, J=8.0, 4.1 Hz, 1H), 2.02-1.72 (m, 3H), 1.66 (tq, J=8.7, 4.4 Hz, 1H), 1.55 (s, 6H), 1.42 (d, J=0.9 Hz, 9H), 1.23 (d, J=6.9 Hz, 6H). $^{13}$C NMR (126 MHz, Chloroform-d) δ 174.06, 173.47, 156.69, 152.47, 148.03, 135.78, 129.22, 127.68, 126.72, 111.11, 110.12, 108.16, 81.60, 79.29, 52.66, 50.58, 43.11, 42.39, 33.81, 27.82, 27.37, 25.52, 25.44, 24.02, 23.47. MS (ESI) m/z=495.4 $[M+H]^+$.

tert-butyl (R)-2-(3-(3-((4-isopropylbenzyl)(methyl)carbamoyl)piperidin-1-yl)phenoxy)-2-methylpropanoate (203e). $^1$H NMR (500 MHz, Chloroform-d) δ 7.17-7.06 (m, 3H), 7.04-6.83 (m, 2H), 6.57-6.30 (m, 2H), 6.21 (ddd, J=16.6, 8.1, 2.2 Hz, 1H), 4.62-4.28 (m, 2H), 3.87-3.51 (m, 2H), 3.00-2.76 (m, 6H), 2.67 (dtd, J=18.5, 12.0, 2.7 Hz, 1H), 2.05-1.61 (m, 4H), 1.54-1.43 (m, 6H), 1.36 (d, J=3.4 Hz, 9H), 1.17 (dd, J=6.9, 3.2 Hz, 6H). $^{13}C$ NMR (126 MHz, Chloroform-d) δ 174.44, 173.81, 173.51, 156.75, 156.73, 152.34, 152.23, 148.42, 148.00, 134.67, 133.96, 129.19, 129.14, 128.00, 127.01, 126.68, 126.22, 110.20, 110.06, 109.26, 109.10, 107.64, 107.49, 81.51, 81.49, 79.26, 79.23, 52.97, 52.52, 52.23, 50.51, 49.98, 49.85, 39.14, 38.96, 34.71, 34.02, 33.79, 33.78, 28.14, 27.82, 27.71, 25.54, 25.54, 25.46, 25.44, 24.43, 24.30, 24.00. MS (ESI) m/z=509.4 $[M+H]^+$.

tert-butyl (S)-2-(3-(3-((4-isopropylbenzyl)(methyl)carbamoyl)piperidin-1-yl)phenoxy)-2-methylpropanoate (203f). $^1H$ NMR (500 MHz, Chloroform-d) δ 7.19-7.04 (m, 3H), 7.04-6.81 (m, 2H), 6.57-6.30 (m, 2H), 6.20 (ddd, J=16.6, 8.1, 2.2 Hz, 1H), 4.62-4.28 (m, 2H), 3.87-3.51 (m, 2H), 3.00-2.76 (m, 6H), 2.67 (dtd, J=18.5, 12.0, 2.7 Hz, 1H), 2.10-1.61 (m, 4H), 1.54-1.43 (m, 6H), 1.38 (d, J=3.4 Hz, 9H), 1.16 (dd, J=6.9, 3.2 Hz, 6H). MS (ESI) m/z=509.4 $[M+H]^+$.

tert-butyl (R)-2-(3-(3-(ethyl(4-isopropylbenzyl)carbamoyl)piperidin-1-yl)phenoxy)-2-methylpropanoate (203g). $^1H$ NMR (500 MHz, Chloroform-d) δ 7.16-7.04 (m, 3H), 7.04-6.87 (m, 2H), 6.54-6.27 (m, 2H), 6.21 (ddd, J=19.7, 7.9, 2.2 Hz, 1H), 4.62-4.31 (m, 2H), 3.75-3.49 (m, 2H), 3.42-3.16 (m, 2H), 3.03-2.52 (m, 4H), 1.96-1.57 (m, 4H), 1.50-1.41 (m, 6H), 1.35 (d, J=3.3 Hz, 9H), 1.16 (dd, J=6.9, 3.5 Hz, 6H), 1.05 (dt, J=25.1, 7.1 Hz, 3H). $^{13}C$ NMR (126 MHz, Chloroform-d) δ 173.96, 173.78, 173.51, 173.48, 156.76, 156.70, 152.40, 152.30, 148.29, 147.86, 135.21, 134.44, 129.19, 129.11, 127.91, 126.93, 126.62, 126.21, 110.20, 110.08, 109.22, 109.03, 107.64, 107.42, 81.48, 81.47, 79.24, 79.21, 52.59, 52.52, 50.13, 50.03, 49.81, 47.34, 41.37, 40.81, 39.18, 39.09, 33.78, 33.76, 28.32, 28.07, 27.82, 25.55, 25.53, 25.48, 25.44, 24.48, 24.31, 24.02, 14.43, 12.72. MS (ESI) m/z=523.4 $[M+H]^+$.

tert-butyl (S)-2-(3-(3-(ethyl(4-isopropylbenzyl)carbamoyl)piperidin-1-yl)phenoxy)-2-methylpropanoate (203h). $^1H$ NMR (500 MHz, Chloroform-d) δ 7.24-7.19 (m, 1H), 7.19-7.12 (m, 2H), 7.11-6.94 (m, 2H), 6.63-6.35 (m, 2H), 6.34-6.21 (m, 1H), 4.80-4.39 (m, 2H), 3.81-3.55 (m, 2H), 3.42 (q, J=7.1 Hz, 1H), 3.31 (qd, J=7.2, 1.9 Hz, 1H), 3.13-2.60 (m, 4H), 2.09-1.67 (m, 4H), 1.57-1.52 (m, 6H), 1.43 (d, J=3.3 Hz, 9H), 1.24 (dd, J=6.9, 3.3 Hz, 6H), 1.13 (dt, J=25.4, 7.1 Hz, 3H). $^{13}C$ NMR (126 MHz, Chloroform-d) δ 173.96, 173.79, 173.53, 173.50, 156.75, 156.70, 152.41, 152.31, 148.31, 147.88, 135.20, 134.43, 129.18, 129.11, 127.91, 126.93, 126.63, 126.20, 110.19, 110.08, 109.20, 109.01, 107.65, 107.43, 81.50, 79.25, 79.21, 52.58, 52.51, 50.12, 50.02, 49.81, 47.33, 41.36, 40.79, 39.19, 39.09, 33.78, 33.76, 28.32, 28.06, 27.82, 25.54, 25.52, 25.47, 25.43, 24.49, 24.32, 24.01, 14.42, 12.71. MS (ESI) m/z=523.4 $[M+H]^+$.

tert-butyl (R)-2-(3-(3-(isopropyl(4-isopropylbenzyl)carbamoyl)piperidin-1-yl)phenoxy)-2-methylpropanoate (203i). $^1H$ NMR (500 MHz, Chloroform-d) δ 7.19 (d, J=8.2 Hz, 1H), 7.15-7.04 (m, 3H), 6.98 (t, J=8.2 Hz, 1H), 6.63-6.21 (m, 3H), 5.07-4.21 (m, 3H), 3.71 (ddt, J=16.2, 12.0, 2.0 Hz, 1H), 3.57 (td, J=9.8, 7.6, 3.0 Hz, 1H), 3.18-2.56 (m, 4H), 2.05-1.63 (m, 4H), 1.59-1.52 (m, 6H), 1.43 (d, J=7.8 Hz, 9H), 1.33-1.00 (m, 12H). $^{13}C$ NMR (126 MHz, Chloroform-d) δ 175.24, 173.17, 172.07, 156.75, 156.49, 148.24, 147.33, 136.04, 135.28, 130.72, 130.52, 126.82, 126.49, 126.47, 126.22, 113.66, 113.43, 112.07, 111.58, 80.20, 79.98, 56.55, 56.08, 55.83, 54.87, 49.20, 46.36, 46.15, 43.95, 38.71, 37.26, 33.70, 33.68, 26.28, 25.79, 25.24, 25.18, 25.01, 24.95, 23.99, 23.90, 22.89, 22.70, 21.78, 21.72, 20.54, 20.24. MS (ESI) m/z=537.4 $[M+H]^+$.

tert-butyl (S)-2-(3-(3-(isopropyl(4-isopropylbenzyl)carbamoyl)piperidin-1-yl)phenoxy)-2-methylpropanoate (203j). $^1H$ NMR (500 MHz, Chloroform-d) δ 7.21-6.94 (m, 4H), 6.71-6.15 (m, 4H), 4.84 (p, J=6.8 Hz, 0.5H), 4.50 (d, J=27.8 Hz, 2H), 4.26 (p, J=6.7 Hz, 0.5H), 3.71 (ddt, J=15.9, 11.3, 2.3 Hz, 1H), 3.61-3.51 (m, 1H), 3.28-2.49 (m, 4H), 2.02-1.61 (m, 4H), 1.62-1.48 (m, 6H), 1.43 (d, J=7.8 Hz, 9H), 1.32-1.15 (m, 9H), 1.11 (dd, J=6.8, 2.9 Hz, 3H). $^{13}C$ NMR (126 MHz, Chloroform-d) δ 174.66, 173.97, 173.53, 173.50, 156.78, 156.64, 152.40, 147.86, 147.02, 136.89, 136.01, 129.20, 129.05, 126.77, 126.68, 126.39, 125.71, 110.17, 110.15, 109.22, 108.98, 107.67, 107.44, 81.50, 81.48, 79.26, 79.20, 52.62, 52.57, 50.09, 49.77, 48.54, 45.81, 45.61, 43.57, 40.23, 39.45, 33.70, 28.50, 28.02, 27.82, 25.54, 25.46, 25.44, 24.60, 24.27, 24.03, 24.00, 23.98, 22.05, 21.93, 20.42. MS (ESI) m/z=537.4 $[M+H]^+$.

tert-butyl (R)-2-(3-(3-(cyclopropyl(4-isopropylbenzyl)carbamoyl)piperidin-1-yl)phenoxy)-2-methylpropanoate (203k). $^1H$ NMR (500 MHz, Chloroform-d) δ 7.20-7.12 (m, 4H), 7.07 (t, J=8.2 Hz, 1H), 6.55 (dd, J=8.2, 2.3 Hz, 1H), 6.49 (t, J=2.4 Hz, 1H), 6.30 (dd, J=8.1, 2.3 Hz, 1H), 4.71-4.37 (m, 2H), 3.85-3.61 (m, 2H), 3.43 (ddt, J=11.0, 7.1, 3.4 Hz, 1H), 2.99 (dd, J=12.4, 10.9 Hz, 1H), 2.88 (p, J=6.9 Hz, 1H), 2.77 (td, J=12.1, 2.6 Hz, 1H), 2.59 (tt, J=6.9, 4.1 Hz, 1H), 2.00-1.89 (m, 1H), 1.88-1.65 (m, 3H), 1.55 (s, 6H), 1.44 (s, 9H), 1.24 (d, J=6.9 Hz, 6H), 0.97-0.75 (m, 4H). $^{13}C$ NMR (126 MHz, Chloroform-d) δ 176.77, 173.50, 156.72, 152.44, 147.61, 135.69, 129.13, 127.64, 126.56, 110.16, 109.13, 107.64, 81.48, 79.24, 52.25, 49.98, 49.46, 39.86, 33.76, 29.73, 27.83, 25.53, 25.48, 24.50, 24.01, 9.40, 9.12. MS (ESI) m/z=535.4 $[M+H]^+$.

tert-butyl (S)-2-(3-(3-(cyclopropyl(4-isopropylbenzyl)carbamoyl)piperidin-1-yl)phenoxy)-2-methylpropanoate (203l). $^1H$ NMR (500 MHz, Chloroform-d) δ 7.20-7.12 (m, 4H), 7.05 (t, J=8.2 Hz, 1H), 6.55 (dd, J=8.2, 2.3 Hz, 1H), 6.49 (t, J=2.4 Hz, 1H), 6.30 (dd, J=8.1, 2.3 Hz, 1H), 4.70-4.37 (m, 2H), 3.85-3.61 (m, 2H), 3.43 (ddt, J=11.0, 7.1, 3.4 Hz, 1H), 2.99 (dd, J=12.4, 10.9 Hz, 1H), 2.88 (p, J=6.9 Hz, 1H), 2.77 (td, J=12.1, 2.6 Hz, 1H), 2.59 (tt, J=6.9, 4.1 Hz, 1H), 2.00-1.89 (m, 1H), 1.88-1.65 (m, 3H), 1.54 (s, 6H), 1.44 (s, 9H), 1.24 (d, J=6.9 Hz, 6H), 0.98-0.72 (m, 4H). MS (ESI) m/z=535.4 $[M+H]^+$.

tert-butyl (R)-2-(3-(3-((4-isopropylphenethyl)carbamoyl)piperidin-1-yl)phenoxy)-2-methylpropanoate (203m). $^1H$ NMR (500 MHz, Chloroform-d) δ 7.18-7.01 (m, 5H), 6.71-6.60 (m, 1H), 6.54-6.45 (m, 2H), 6.36 (dd, J=8.1, 2.2 Hz, 1H), 3.63-3.42 (m, 2H), 3.28-3.13 (m, 2H), 3.10 (ddd, J=11.4, 6.7, 4.2 Hz, 1H), 3.00 (ddd, J=11.8, 7.2, 4.1 Hz, 1H), 2.91-2.81 (m, J=6.7 Hz, 1H), 2.79 (td, J=6.9, 5.1 Hz, 2H), 2.47 (td, J=6.6, 3.3 Hz, 1H), 1.84 (dtd, J=12.1, 7.5, 4.4 Hz, 1H), 1.78-1.67 (m, 1H), 1.65-1.51 (m, 8H), 1.44 (s, 9H), 1.22 (d, J=7.0 Hz, 6H). MS (ESI) m/z=509.4 $[M+H]^+$.

tert-butyl (R)-2-(3-(3-((4-isopropylphenethyl)carbamoyl)piperidin-1-yl)phenoxy)-2-methylpropanoate (203n). $^1H$ NMR (500 MHz, Chloroform-d) δ 7.20-7.01 (m, 5H), 6.69-6.61 (m, 1H), 6.55-6.45 (m, 2H), 6.36 (dd, J=8.1, 2.2 Hz, 1H), 3.64-3.42 (m, 2H), 3.30-3.12 (m, 2H), 3.10 (ddd, J=11.4, 6.7, 4.2 Hz, 1H), 3.01 (ddd,)=11.8, 7.2, 4.1 Hz, 1H), 2.91-2.79 (m, J=6.7 Hz, 1H), 2.79 (td, J=6.9, 5.1 Hz, 2H), 2.46 (td, J=6.6, 3.3 Hz, 1H), 1.84 (dtd, J=12.1, 7.5, 4.4 Hz, 1H), 1.78-1.67 (m, 1H), 1.64-1.51 (m, 8H), 1.45 (s, 9H), 1.22 (d, J=7.0 Hz, 6H). MS (ESI) m/z=509.4 $[M+H]^+$.

(R)-2-(3-(3-(((4-isopropylbenzyl)oxy)carbonyl)piperidin-1-yl)phenoxy)-2-methylpropanoic acid (1). $^1H$ NMR (500 MHz, Chloroform-d) δ 7.27-7.18 (m, 2H), 7.15 (d, J=8.1 Hz, 2H), 7.04 (t, J=8.2 Hz, 1H), 6.58 (ddd, J=8.4, 2.4, 0.8 Hz, 1H), 6.46 (t, J=2.3 Hz, 1H), 6.38-6.19 (m, 1H), 5.04

(d, J=2.4 Hz, 2H), 3.62 (ddt, J=12.5, 3.4, 1.5 Hz, 1H), 3.38 (dd, J=12.3, 4.4 Hz, 1H), 2.98 (dd, J=12.4, 9.8 Hz, 1H), 2.84 (p, J=6.9 Hz, 1H), 2.77-2.71 (m, 1H), 2.68-2.59 (m, 1H), 2.00-1.90 (m, 1H), 1.77-1.67 (m, 1H), 1.67-1.54 (m, 2H), 1.51 (s, 6H), 1.18 (d, J=7.0 Hz, 6H). $^{13}$C NMR (126 MHz, Chloroform-d) δ 177.14, 173.67, 155.18, 152.44, 149.08, 133.24, 129.51, 128.28, 126.67, 111.94, 111.29, 109.44, 79.78, 66.35, 51.97, 49.69, 41.23, 33.90, 26.92, 25.06, 23.96, 23.91. HRMS (ESI) Calcd for $C_{26}H_{33}NO_5$ (M−H)$^-$ 438.2286, found 438.2289. HPLC purity 98.4%, $t_R$=14.17 min.

(S)-2-(3-(3-(((4-isopropylbenzyl)oxy)carbonyl)piperidin-1-yl)phenoxy)-2-methylpropanoic acid (2). $^1$H NMR (500 MHz, Chloroform-d) δ 7.22-7.08 (m, 5H), 6.95-6.84 (m, 2H), 6.74 (dd, J=8.0, 2.2 Hz, 1H), 5.24-4.85 (m, 2H), 3.77-3.60 (m, 1H), 3.51 (d, J=12.1 Hz, 1H), 3.16 (t, J=11.7 Hz, 1H), 3.09-3.03 (m, 1H), 2.96 (td, J=12.1, 3.2 Hz, 1H), 2.84 (p, J=6.9 Hz, 1H), 2.15 (dt, J=12.9, 3.7 Hz, 1H), 2.05-1.92 (m, 1H), 1.85 (dt, J=14.5, 3.5 Hz, 1H), 1.53 (d, J=3.6 Hz, 7H), 1.17 (d, J=6.9 Hz, 6H). $^{13}$C NMR (126 MHz, Chloroform-d) δ 175.68, 171.75, 156.46, 149.36, 145.48, 132.64, 130.61, 126.74, 118.35, 112.92, 111.04, 79.92, 66.96, 55.07, 54.47, 39.73, 33.91, 25.62, 25.21, 24.97, 23.93, 22.84. HRMS (ESI) Calcd for $C_{26}H_{33}NO_5$ (M−H)$^-$ 438.2286, found 438.2291. HPLC purity 98.8%, $t_R$=14.16 min.

(R)-2-(3-(3-((4-isopropylbenzyl)carbamoyl)piperidin-1-yl)phenoxy)-2-methylpropanoic acid (3). $^1$H NMR (500 MHz, Chloroform-d) δ 7.17 (d, J=1.5 Hz, 4H), 7.08 (t, J=8.3 Hz, 1H), 6.91 (t, J=5.8 Hz, 1H), 6.63 (d, J=5.8 Hz, 2H), 6.50 (d, J=8.1 Hz, 1H), 4.56-4.28 (m, 2H), 3.50-3.33 (m, 1H), 3.28 (dt, J=10.3, 4.4 Hz, 1H), 3.19 (dd, J=12.4, 8.6 Hz, 1H), 3.08-2.92 (m, 1H), 2.94-2.78 (m, 1H), 2.65 (dq, J=9.5, 4.8, 4.3 Hz, 1H), 1.90-1.65 (m, 4H), 1.57 (d, J=2.7 Hz, 6H), 1.22 (dd, J=6.9, 1.5 Hz, 6H). $^{13}$C NMR (126 MHz, Chloroform-d) δ 176.64, 173.92, 156.00, 148.21, 135.41, 129.74, 127.74, 126.76, 113.08, 112.13, 109.59, 79.67, 53.43, 51.42, 43.25, 41.93, 33.80, 26.92, 25.20, 25.16, 24.00, 23.15. HRMS (ESI) Calcd for $C_{26}H_{34}N_2O_4$ (M−H)$^-$ 437.2446, found 437.2443. HPLC purity 98.6%, $t_R$=12.48 min.

(S)-2-(3-(3-((4-isopropylbenzyl)carbamoyl)piperidin-1-yl)phenoxy)-2-methylpropanoic acid (4). $^1$H NMR (500 MHz, Methanol-d$_4$) δ 7.19 (d, J=1.0 Hz, 4H), 7.09 (t, J=8.2 Hz, 1H), 6.68-6.62 (m, 1H), 6.53 (t, J=2.3 Hz, 1H), 6.38 (dd, J=8.1, 2.2 Hz, 1H), 4.48-4.23 (m, 2H), 3.62 (ddt, J=12.2, 3.5, 1.6 Hz, 1H), 3.53 (ddt, J=12.5, 3.7, 2.1 Hz, 1H), 3.02-2.82 (m, 2H), 2.81-2.71 (m, 1H), 2.59 (ddd, J=10.5, 6.7, 3.7 Hz, 1H), 2.00-1.90 (m, 1H), 1.80 (qd, J=7.2, 3.4 Hz, 1H), 1.73-1.62 (m, 2H), 1.54 (s, 6H), 1.22 (d, J=7.0 Hz, 6H). $^{13}$C NMR (126 MHz, Methanol-d$_4$) δ 175.12, 156.36, 152.50, 147.69, 135.98, 128.98, 127.17, 126.15, 110.98, 110.62, 108.37, 78.76, 52.60, 50.04, 42.65, 42.34, 33.69, 27.42, 24.42, 24.37, 23.77, 23.06. HRMS (ESI) Calcd for $C_{26}H_{34}N_2O_4$ (M−H)$^-$ 437.2446, found 437.2443. HPLC purity 98.9%, $t_R$=12.51 min.

(R)-2-(3-(3-((4-isopropylbenzyl)(methyl)carbamoyl)piperidin-1-yl)phenoxy)-2-methylpropanoic acid (5). $^1$H NMR (500 MHz, Chloroform-d) δ 9.01 (s, 2H), 7.26-7.19 (m, 2H), 7.19-7.12 (m, 2H), 7.11-7.08 (m, 2H), 7.08-6.98 (m, 1H), 6.86 (ddd, J=26.7, 8.6, 1.9 Hz, 1H), 4.79-4.57 (m, 1H), 4.43 (dd, J=20.4, 15.5 Hz, 1H), 3.70-3.44 (m, 4H), 3.20-2.95 (m, 4H), 2.88 (hept, J=6.9 Hz, 1H), 2.28-1.67 (m, 4H), 1.65-1.55 (m, 6H), 1.23 (dd, J=6.9, 2.0 Hz, 6H). $^{13}$C NMR (126 MHz, Chloroform-d) δ 175.46, 172.68, 171.94, 156.81, 156.69, 148.65, 148.35, 144.78, 144.17, 133.75, 133.50, 130.76, 130.62, 127.89, 127.04, 126.81, 126.52, 119.62, 118.85, 113.58, 113.41, 111.76, 111.49, 80.02, 56.49, 56.25, 55.77, 55.18, 53.35, 50.89, 37.21, 36.96, 34.85, 33.79, 33.76, 25.92, 25.35, 25.30, 25.26, 25.01, 24.97, 23.96, 23.92, 22.72. HRMS (ESI) Calcd for $C_{27}H_{36}N_2O_4$ (M−H)$^-$ 451.2602, found 451.2599. HPLC purity 99.1%, $t_R$=12.99 min.

(S)-2-(3-(3-((4-isopropylbenzyl)(methyl)carbamoyl)piperidin-1-yl)phenoxy)-2-methylpropanoic acid (6). $^1$H NMR (500 MHz, Methanol-d$_4$) δ 7.64-6.67 (m, 8H), 4.72 (dd, J=15.6, 10.1 Hz, 1H), 4.55 (dd, J=54.3, 15.6 Hz, 1H), 3.80-3.25 (m, 5H), 3.05 (s, 2H), 2.97 (s, 1H), 2.89 (dt, J=14.1, 7.3 Hz, 1H), 2.18-1.79 (m, 4H), 1.65-1.49 (m, 6H), 1.23 (dd, J=6.9, 2.4 Hz, 6H). $^{13}$C NMR (126 MHz, Methanol-d$_4$) δ 175.74, 175.65, 174.10, 173.66, 156.97, 156.90, 148.47, 148.16, 134.12, 133.77, 130.39, 130.21, 127.57, 126.71, 126.36, 126.26, 112.98, 112.65, 111.30, 110.86, 79.44, 79.35, 56.91, 53.99, 53.55, 52.68, 50.21, 36.98, 36.45, 33.99, 33.70, 33.67, 33.28, 24.42, 24.26, 23.02, 23.01, 21.81. HRMS (ESI) Calcd for $C_{27}H_{36}N_2O_4$ (M−H)$^-$ 451.2602, found 451.2597. HPLC purity 99.8%, $t_R$=12.98 min.

(R)-2-(3-(3-(ethyl(4-isopropylbenzyl)carbamoyl)piperidin-1-yl)phenoxy)-2-methylpropanoic acid (7). $^1$H NMR (500 MHz, Chloroform-d) δ 7.30-7.18 (m, 3H), 7.16 (d, J=8.1 Hz, 1H), 7.13-7.01 (m, 3H), 6.87 (ddd, J=23.2, 8.2, 2.2 Hz, 1H), 4.66 (dd, J=40.0, 15.8 Hz, 1H), 4.45 (t, J=15.0 Hz, 1H), 3.78-3.21 (m, 6H), 3.20-2.96 (m, 1H), 2.94-2.81 (m, 1H), 2.45-1.64 (m, 4H), 1.60 (t, J=2.7 Hz, 6H), 1.22 (dd, J=6.9, 3.3 Hz, 6H), 1.17 (t, J=7.1 Hz, 2H), 1.10 (t, J=7.1 Hz, 1H). $^{13}$C NMR (126 MHz, Chloroform-d) & 175.31, 172.24, 171.79, 162.29, 162.00, 156.76, 156.64, 148.58, 148.23, 144.13, 134.30, 133.90, 130.78, 130.64, 127.78, 126.99, 126.75, 126.50, 119.88, 119.18, 113.68, 113.54, 112.09, 111.76, 80.11, 79.99, 56.63, 56.41, 55.94, 55.33, 50.63, 47.88, 41.94, 41.87, 37.41, 36.95, 33.78, 33.76, 26.08, 25.77, 25.28, 24.93, 23.97, 23.92, 22.73, 22.68, 14.14, 12.60. HRMS (ESI) Calcd for $C_{28}H_{38}N_2O_4$ (M−H)$^-$ 465.2759, found 465.2758. HPLC purity 98.9%, $t_R$=13.27 min.

(S)-2-(3-(3-(ethyl(4-isopropylbenzyl)carbamoyl)piperidin-1-yl)phenoxy)-2-methylpropanoic acid (8). $^1$H NMR (500 MHz, Chloroform-d) δ 7.24-7.13 (m, 3H), 7.12-7.07 (m, 2H), 7.05-6.65 (m, 3H), 4.64 (d, J=15.2 Hz, 1H), 4.47 (dd, J=29.4, 15.8 Hz, 1H), 3.86-3.12 (m, 6H), 3.10-2.81 (m, 2H), 2.29-1.67 (m, 4H), 1.59 (d, J=4.9 Hz, 6H), 1.23 (dd, J=6.9, 3.2 Hz, 6H), 1.14 (dt, J=34.5, 7.1 Hz, 3H). $^{13}$C NMR (126 MHz, Chloroform-d) δ 175.45, 172.44, 156.36, 156.14, 148.52, 148.16, 134.52, 134.01, 130.42, 130.22, 127.82, 126.99, 126.72, 126.39, 113.02, 112.77, 111.19, 110.73, 80.12, 80.01, 55.33, 54.29, 50.45, 47.73, 41.78, 41.49, 38.05, 37.58, 33.78, 33.76, 26.75, 26.63, 25.24, 25.22, 24.92, 24.91, 23.98, 23.95, 23.27, 14.23, 12.62. HRMS (ESI) Calcd for $C_{28}H_{38}N_2O_4$ (M−H)$^-$ 465.2759, found 465.2763. HPLC purity 98.4%, $t_R$=13.41 min.

(R)-2-(3-(3-(isopropyl(4-isopropylbenzyl)carbamoyl)piperidin-1-yl)phenoxy)-2-methylpropanoic acid (9). $^1$H NMR (500 MHz, Chloroform-d) δ 7.28-7.08 (m, 5H), 7.06 (d, J=8.2 Hz, 1H), 7.02-6.91 (m, 1H), 6.91-6.75 (m, 1H), 4.80 (p, J=6.8 Hz, 0.5H), 4.58 (t, J=16.0 Hz, 1H), 4.40 (t, J=16.8 Hz, 1H), 4.24 (p, J=6.6 Hz, 0.5H), 3.62 (d, J=29.3 Hz, 2H), 3.50 (t, J=14.6 Hz, 1H), 3.38 (t, J=11.5 Hz, 0.5H), 3.14 (dd, J=13.2, 10.1 Hz, 1H), 2.96 (td, J=11.6, 4.4 Hz, 0.5H), 2.87 (dp, J=13.9, 6.9 Hz, 1H), 2.25 (t, J=13.6 Hz, 0.5H), 2.10-1.90 (m, 1H), 1.85-1.38 (m, 8.5H), 1.31-0.82 (m, 12H). $^{13}$C NMR (126 MHz, Chloroform-d) δ 175.24, 173.17, 156.75, 156.49, 148.24, 147.33, 136.04, 135.28, 130.72, 130.52, 126.82, 126.49, 126.47, 126.22, 113.66, 113.43, 112.07, 111.58, 80.20, 79.98, 56.55, 56.08, 55.83, 54.83, 49.20, 46.36, 46.15, 43.95, 38.71, 37.26, 33.70, 33.68, 26.28, 25.79, 25.24, 25.18, 25.01, 24.95, 23.99, 23.90, 22.89, 22.70, 21.78, 21.72, 20.54, 20.24. HRMS (ESI) Calcd for $C_{29}H_{40}N_2O_4$ $(M-H)^-$ 479.2915, found 479.2914. HPLC purity 100%, $t_R$=13.70 min.

(S)-2-(3-(3-(isopropyl(4-isopropylbenzyl)carbamoyl)piperidin-1-yl)phenoxy)-2-methylpropanoic acid (10). $^{1}H$ NMR (500 MHz, Chloroform-d) δ 7.32-7.17 (m, 2H), 7.16-7.01 (m, 4H), 6.99-6.80 (m, 2H), 4.79 (p, J=6.8 Hz, 0.5H), 4.58 (t, J=16.2 Hz, 1H), 4.40 (t, J=16.8 Hz, 1H), 4.23 (q, J=6.6 Hz, 0.5H), 3.63 (d, J=22.0 Hz, 2H), 3.51 (t, J=12.0 Hz, 1H), 3.39 (t, J=11.5 Hz, 0.5H), 3.25-3.09 (m, 1H), 2.98 (td, J=11.7, 4.2 Hz, 0.5H), 2.87 (dp, J=13.9, 6.9 Hz, 1H), 2.26 (t, J=13.6 Hz, 0.5H), 2.14-2.02 (m, 0.5H), 1.96 (d, J=14.5 Hz, 0.5H), 1.77 (d, J=50.9 Hz, 1.5H), 1.58 (t, J=5.4 Hz, 6.5H), 1.45 (d, J=12.6 Hz, 0.5H), 1.29-0.91 (m, 12H). $^{13}C$ NMR (126 MHz, Chloroform-d) δ 156.78, 156.51, 148.26, 147.35, 136.02, 135.26, 130.77, 130.57, 126.82, 126.50, 126.49, 126.23, 113.65, 113.46, 112.12, 111.67, 56.66, 56.23, 55.98, 55.06, 49.21, 46.38, 46.16, 43.96, 38.65, 37.21, 33.70, 33.68, 26.25, 25.75, 25.21, 25.15, 24.99, 24.93, 23.99, 23.89, 22.86, 22.65, 21.78, 21.72, 20.54, 20.25. HRMS (ESI) Calcd for $C_{29}H_{40}N_2O_4$ $(M-H)^-$ 479.2915, found 479.2914. HPLC purity 96.7%, $t_R$=13.67 min.

(R)-2-(3-(3-(cyclopropyl(4-isopropylbenzyl)carbamoyl)piperidin-1-yl)phenoxy)-2-methylpropanoic acid (11). $^{1}H$ NMR (500 MHz, Chloroform-d) δ 7.34-7.22 (m, 1H), 7.22-7.02 (m, 6H), 6.90 (dd, J=8.3, 2.2 Hz, 1H), 4.69 (d, J=14.6 Hz, 1H), 4.44 (d, J=14.4 Hz, 1H), 4.06 (dd, J=13.3, 9.6 Hz, 1H), 3.80-3.46 (m, 3H), 3.14 (td, J=12.5, 3.1 Hz, 1H), 2.89 (p, J=6.9 Hz, 1H), 2.66 (tt, J=6.8, 4.1 Hz, 1H), 2.24 (q, J=13.6 Hz, 1H), 2.13-1.93 (m, 2H), 1.77 (qd, J=13.1, 3.8 Hz, 1H), 1.62 (s, 6H), 1.25 (d, J=6.9 Hz, 6H), 1.13-0.36 (m, 4H). $^{13}C$ NMR (126 MHz, Chloroform-d) δ 175.40, 174.74, 156.68, 147.94, 144.50, 134.91, 130.71, 127.52, 126.68, 119.61, 113.51, 111.79, 80.02, 56.12, 55.83, 49.86, 37.89, 33.76, 30.00, 25.65, 25.32, 24.88, 23.97, 22.94, 9.47, 8.66. HRMS (ESI) Calcd for $C_{29}H_{38}N_2O_4$ $(M-H)^-$ 477.2759, found 477.2753. HPLC purity 97.9%, $t_R$=13.45 min (S)-2-(3-(3-(cyclopropyl(4-isopropylbenzyl)carbamoyl)piperidin-1-yl)phenoxy)-2-methylpropanoic acid (12). $^{1}H$ NMR (500 MHz, Chloroform-d) δ 7.17 (t, J=8.2 Hz, 1H), 7.11-6.92 (m, 6H), 6.80 (dd, J=8.2, 2.1 Hz, 1H), 4.60 (d, J=14.6 Hz, 1H), 4.34 (d, J=14.6 Hz, 1H), 3.96 (ddt, J=10.6, 6.4, 3.2 Hz, 1H), 3.67-3.38 (m, 3H), 3.05 (td, J=12.5, 3.1 Hz, 1H), 2.80 (p, J=6.9 Hz, 1H), 2.57 (ddt, J=10.8, 7.1, 4.1 Hz, 1H), 2.26-2.07 (m, 1H), 1.93 (ddt, J=42.8, 14.6, 3.3 Hz, 2H), 1.67 (qd, J=13.1, 3.8 Hz, 1H), 1.52 (s, 6H), 1.15 (d, J=7.0 Hz, 6H), 1.04-0.53 (m, 4H). $^{13}C$ NMR (126 MHz, Chloroform-d) δ 175.43, 174.77, 156.69, 147.94, 144.49, 134.91, 130.70, 127.51, 126.68, 119.46, 113.56, 111.77, 79.97, 56.12, 55.81, 49.86, 37.89, 33.75, 30.02, 25.63, 25.32, 24.92, 23.97, 22.94, 9.46, 8.66. HRMS (ESI) Calcd for $C_{29}H_{38}N_2O_4$ $(M-H)^-$ 477.2759, found 477.2756. HPLC purity 97.7%, $t_R$=13.46 min (R)-2-(3-(3-((4-isopropylphenethyl)carbamoyl)piperidin-1-yl)phenoxy)-2-methylpropanoic acid (13). $^{1}H$ NMR (500 MHz, Methanol-$d_4$) δ 7.35 (t, J=8.2 Hz, 1H), 7.18-7.09 (m, 4H), 7.04 (dd, J=8.2, 2.2 Hz, 1H), 6.99 (t, J=2.3 Hz, 1H), 6.82 (dd, J=8.3, 2.2 Hz, 1H), 3.56 (ddd, J=15.9, 11.1, 4.3 Hz, 2H), 3.49 (dt, J=14.1, 7.2 Hz, 1H), 3.45-3.33 (m, 2H), 3.31-3.20 (m, 1H), 2.81 (dt, J=29.7, 6.9 Hz, 4H), 1.99-1.80 (m, 3H), 1.61 (s, 6H), 1.20 (dd, J=6.9, 1.1 Hz, 6H). $^{13}C$ NMR (126 MHz, Methanol-$d_4$) δ 175.73, 173.70, 156.90, 146.78, 136.25, 130.22, 128.49, 126.05, 116.62, 112.76, 110.99, 79.35, 56.14, 53.71, 40.38, 34.56, 33.62, 25.68, 24.41, 24.30, 23.10, 23.12, 22.25. HRMS (ESI) Calcd for $C_{27}H_{36}N_2O_4$ $(M-H)^-$ 451.2602, found 451.2602. HPLC purity 98.2%, $t_R$=12.76 min.

(S)-2-(3-(3-((4-isopropylphenethyl)carbamoyl)piperidin-1-yl)phenoxy)-2-methylpropanoic acid (14). $^{1}H$ NMR (500 MHz, Methanol-$d_4$) δ 7.36 (t, J=8.2 Hz, 1H), 7.18-7.09 (m, 4H), 7.05 (dd, J=8.2, 2.2 Hz, 1H), 6.98 (t, J=2.3 Hz, 1H), 6.82 (dd, J=8.3, 2.2 Hz, 1H), 3.57 (ddd, J=15.9, 11.1, 4.3 Hz, 2H), 3.49 (dt, J=14.1, 7.2 Hz, 1H), 3.45-3.33 (m, 2H), 3.30-3.20 (m, 1H), 2.81 (dt, J=29.7, 6.9 Hz, 4H), 1.99-1.80 (m, 3H), 1.61 (s, 6H), 1.20 (dd, J=6.9, 1.1 Hz, 6H). $^{13}C$ NMR (126 MHz, Methanol-$d_4$) δ 175.74, 173.70, 156.90, 146.78, 136.24, 130.22, 128.49, 126.05, 116.62, 112.76, 110.98, 79.35, 56.14, 53.71, 40.37, 34.56, 33.62, 25.68, 24.41, 24.30, 23.11, 23.10, 22.23. HRMS (ESI) Calcd for $C_{27}H_{36}N_2O_4$ $(M-H)^-$ 451.2602, found 451.2600. HPLC purity 98.0%, $t_R$=12.76 min.

Scheme 2. Synthesis of compounds 15-26.

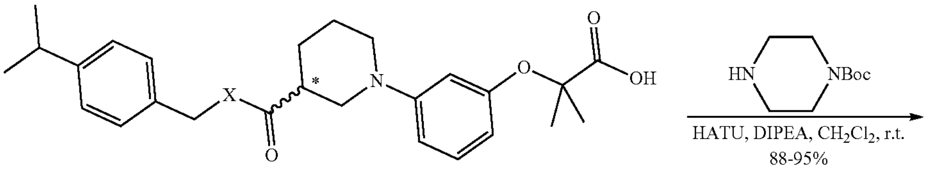

1-12

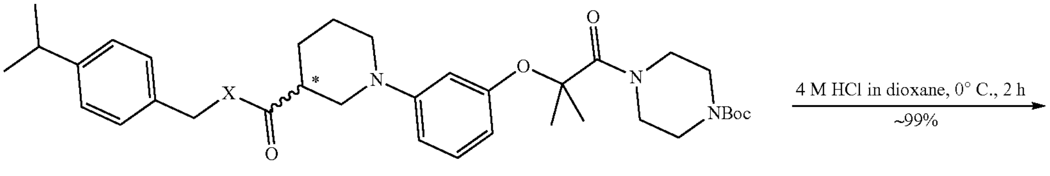

204

-continued

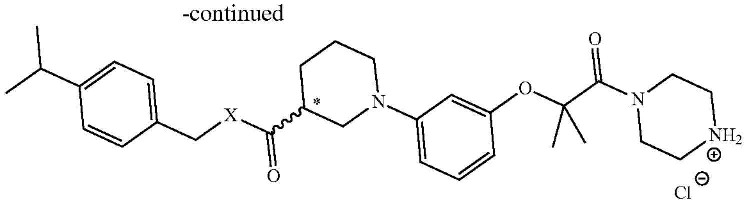

15-26

15. X = O, *R
16. X = O, *S
17. X = NH, *R
18. X = NH, *S
19. X = MeN, *R
20. X = MeN, *S
21. X = EtN, *R
22. X = EtN, *S
23. X = i-PrN, *R
24. X = iPrN, *S
25. X = c-PrN, *R
26. X = c-PrN, *S tert-butyl (R)-4-(2-(3-(3-(((4-isopropylbenzyl)oxy)carbonyl)piperidin-1-yl)phenoxy)-2-methylpropanoyl)piperazine-1-carboxylate (204a). $^{1}$H NMR (500 MHz, Chloroform-d) δ 7.21 (d, J=8.2 Hz, 2H), 7.16-7.07 (m, 2H), 6.98 (t, J=8.2 Hz, 1H), 6.47 (dd, J=8.3, 2.3 Hz, 1H), 6.34 (t, J=2.3 Hz, 1H), 6.20 (dd, J=8.1, 2.3 Hz, 1H), 5.22-4.96 (m, 2H), 3.74 (t, J=5.1 Hz, 2H), 3.62 (dd, J=12.5, 3.5 Hz, 1H), 3.56-3.45 (m, 2H), 3.35 (d, J=12.2 Hz, 1H), 3.26 (d, J=5.6 Hz, 2H), 3.09-2.89 (m, 3H), 2.83 (p, J=6.9 Hz, 1H), 2.75-2.67 (m, 1H), 2.65-2.57 (m, 1H), 2.11-1.91 (m, 1H), 1.72 (ddd, J=9.2, 4.5, 2.4 Hz, 1H), 1.55 (s, 8H), 1.35 (s, 9H), 1.17 (d, J=6.9 Hz, 6H). $^{13}$C NMR (126 MHz, Chloroform-d) δ 173.61, 172.11, 156.18, 154.37, 152.73, 149.01, 133.32, 129.59, 128.26, 126.65, 110.21, 107.30, 105.74, 80.56, 80.07, 66.27, 51.85, 49.54, 45.77, 42.91, 41.31, 33.89, 28.37, 26.99, 26.19, 26.16, 24.05, 23.97. MS (ESI) m/z=608.4 [M+H]$^{+}$, 630.4 [M+Na]$^{+}$.

tert-butyl (S)-4-(2-(3-(3-(((4-isopropylbenzyl)oxy)carbonyl)piperidin-1-yl)phenoxy)-2-methylpropanoyl)piperazine-1-carboxylate (204b). $^{1}$H NMR (500 MHz, Chloroform-d) δ 7.21 (d, J=8.2 Hz, 2H), 7.15 (d, J=8.1 Hz, 2H), 6.98 (t, J=8.2 Hz, 1H), 6.47 (dd, J=8.1, 2.3 Hz, 1H), 6.34 (t, J=2.3 Hz, 1H), 6.20 (dd, J=8.1, 2.3 Hz, 1H), 5.14-4.93 (m, 2H), 3.74 (t, J=5.2 Hz, 2H), 3.67-3.56 (m, 1H), 3.52 (t, J=5.1 Hz, 2H), 3.42-3.31 (m, 1H), 3.25 (t, J=5.3 Hz, 2H), 3.07-2.91 (m, 3H), 2.83 (p, J=6.9 Hz, 1H), 2.76-2.67 (m, 1H), 2.62 (ddd, J=9.9, 6.1, 3.7 Hz, 1H), 2.17-1.88 (m, 1H), 1.73-1.67 (m, 1H), 1.55 (s, 8H), 1.34 (s, 9H), 1.17 (d, J=7.0 Hz, 6H). $^{13}$C NMR (126 MHz, Chloroform-d) δ 173.60, 172.10, 156.18, 154.36, 152.73, 149.00, 133.32, 129.59, 128.27, 126.65, 110.20, 107.29, 105.73, 80.55, 80.06, 66.27, 51.85, 49.54, 45.77, 42.91, 41.31, 33.89, 28.37, 26.99, 26.19, 26.16, 24.05, 23.98. MS (ESI) m/z=608.4 [M+H]$^{+}$, 630.4 [M+Na]$^{+}$.

tert-butyl (R)-4-(2-(3-(3-((4-isopropylbenzyl)carbamoyl)piperidin-1-yl)phenoxy)-2-methylpropanoyl)piperazine-1-carboxylate (204c). $^{1}$H NMR (500 MHz, Chloroform-d) δ 7.14 (d, J=8.2 Hz, 2H), 7.10 (d, J=8.1 Hz, 2H), 6.99 (t, J=8.2 Hz, 1H), 6.88 (s, 1H), 6.45 (dd, J=8.3, 2.2 Hz, 1H), 6.33 (t, J=2.3 Hz, 1H), 6.23 (dd, J=8.1, 2.2 Hz, 1H), 4.37 (qd, J=14.7, 5.6 Hz, 2H), 3.72 (d, J=5.6 Hz, 2H), 3.50-3.36 (m, 3H), 3.33 (dt, J=12.5, 4.4 Hz, 1H), 3.21 (s, 2H), 3.12 (dd, J=12.8, 8.8 Hz, 1H), 2.94 (ddd, J=22.2, 12.9, 4.5 Hz, 3H), 2.82 (p, J=6.9 Hz, 1H), 2.54-2.32 (m, 1H), 1.82 (qd, J=9.1, 3.9 Hz, 2H), 1.67 (dt, J=13.3, 4.8 Hz, 1H), 1.55 (d, J=5.0 Hz, 7H), 1.34 (s, 9H), 1.16 (d, J=7.0 Hz, 6H). $^{13}$C NMR (126 MHz, Chloroform-d) δ 173.68, 172.18, 156.26, 154.33, 152.17, 148.01, 135.95, 129.87, 127.74, 126.67, 110.56, 107.92, 105.22, 80.54, 80.18, 52.47, 50.45, 45.82, 43.11, 42.92, 41.89, 38.62, 33.80, 28.35, 27.35, 26.18, 26.14, 24.02, 23.26. MS (ESI) m/z=607.4 [M+H]$^{+}$.

tert-butyl (S)-4-(2-(3-(3-((4-isopropylbenzyl)carbamoyl)piperidin-1-yl)phenoxy)-2-methylpropanoyl)piperazine-1-carboxylate (204d). $^{1}$H NMR (500 MHz, Chloroform-d) δ 7.21 (d, J=8.4 Hz, 2H), 7.17 (d, J=8.2 Hz, 2H), 7.05 (t, J=8.2 Hz, 1H), 6.95 (s, 1H), 6.51 (dd, J=8.0, 2.2 Hz, 1H), 6.38 (t, J=2.3 Hz, 1H), 6.29 (ddd, J=8.2, 2.4, 0.8 Hz, 1H), 4.44 (qd, J=14.7, 5.7 Hz, 2H), 3.78 (d, J=5.5 Hz, 2H), 3.60-3.41 (m, 3H), 3.41-3.35 (m, 1H), 3.27 (s, 2H), 3.18 (dd, J=12.8, 8.9 Hz, 1H), 3.10-2.95 (m, 3H), 2.88 (p, J=6.9 Hz, 1H), 2.51 (tdd, J=8.8, 4.8, 3.6 Hz, 1H), 1.96-1.82 (m, 2H), 1.73 (dt, J=13.5, 4.5 Hz, 1H), 1.62 (d, J=5.0 Hz, 7H), 1.41 (s, 9H), 1.22 (d, J=7.0 Hz, 6H). $^{13}$C NMR (126 MHz, Chloroform-d) δ 173.68, 172.18, 156.26, 154.33, 152.24, 148.00, 135.97, 129.85, 127.73, 126.67, 110.53, 107.84, 105.16, 80.53, 80.17, 52.42, 50.39, 45.81, 43.10, 42.92, 41.90, 38.61, 33.80, 28.34, 27.36, 26.18, 26.14, 24.02, 23.27. MS (ESI) m/z=607.4 [M+H]$^{+}$.

tert-butyl (R)-4-(2-(3-(3-((4-isopropylbenzyl)(methyl)carbamoyl)piperidin-1-yl)phenoxy)-2-methylpropanoyl)piperazine-1-carboxylate (204e). $^{1}$H NMR (500 MHz, Chloroform-d) δ 7.24-7.10 (m, 3H), 7.09-6.88 (m, 2H), 6.55-6.32 (m, 2H), 6.24 (ddd, J=19.9, 8.1, 2.3 Hz, 1H), 4.84-4.37 (m, 2H), 3.80 (dd, J=10.7, 5.5 Hz, 2H), 3.72-3.53 (m, 4H), 3.32 (d, J=6.0 Hz, 2H), 3.07 (d, J=6.4 Hz, 2H), 3.02-2.92 (m, 4H), 2.92-2.84 (m, 2H), 2.72 (qd, J=12.4, 2.6 Hz, 1H), 1.98-1.66 (m, 4H), 1.68-1.44 (m, 6H), 1.41 (s, 9H), 1.23 (dd, J=6.9, 4.1 Hz, 6H). $^{13}$C NMR (126 MHz, Chloroform-d) δ 174.37, 173.75, 172.08, 156.25, 156.22, 154.34, 152.69, 152.49, 148.43, 148.01, 134.65, 133.94, 129.66, 129.61, 128.00, 127.01, 126.67, 126.20, 109.82, 109.67, 107.08, 106.91, 105.67, 105.52, 80.55, 80.08, 52.96, 52.34, 52.04, 50.51, 49.84, 49.67, 45.76, 42.90, 39.12, 38.86, 38.61, 34.71, 34.03, 33.78, 29.29, 28.36, 28.15, 27.69, 26.18 (d, J=2.5 Hz), 24.46, 24.26, 24.00. MS (ESI) m/z=621.4 [M+H]$^{+}$.

tert-butyl (S)-4-(2-(3-(3-((4-isopropylbenzyl)(methyl)carbamoyl)piperidin-1-yl)phenoxy)-2-methylpropanoyl)piperazine-1-carboxylate (204f). $^{1}$H NMR (500 MHz, Chloroform-d) δ 7.24-7.10 (m, 3H), 7.11-6.93 (m, 2H), 6.59-6.31 (m, 2H), 6.25 (ddd, J=19.9, 8.3, 2.3 Hz, 1H), 4.79-4.44 (m, 2H), 3.90-3.76 (m, 2H), 3.72-3.53 (m, 4H), 3.32 (d, J=6.2 Hz, 2H), 3.07 (d, J=6.3 Hz, 2H), 3.03-2.94 (m, 4H), 2.93-

2.85 (m, 2H), 2.73 (qd, J=12.3, 2.7 Hz, 1H), 2.00-1.70 (m, 4H), 1.71-1.55 (m, 6H), 1.41 (s, 9H), 1.24 (dd, J=6.9, 4.1 Hz, 6H). $^{13}C$ NMR (126 MHz, Chloroform-d) δ 174.38, 173.76, 172.09, 156.26, 156.22, 154.35, 152.69, 152.50, 148.44, 148.02, 134.66, 133.94, 129.66, 129.62, 128.01, 127.02, 126.67, 126.21, 109.83, 109.68, 107.10, 106.92, 105.67, 105.52, 80.56, 80.54, 80.09, 52.96, 52.34, 52.05, 50.52, 49.85, 49.68, 45.77, 42.90, 39.13, 38.87, 38.62, 34.71, 34.04, 33.78, 28.36, 28.15, 27.69, 26.18, 24.47, 24.27, 24.00. MS (ESI) m/z=621.4 $[M+H]^+$.

tert-butyl (R)-4-(2-(3-(3-(ethyl(4-isopropylbenzyl)carbamoyl)piperidin-1-yl)phenoxy)-2-methylpropanoyl)piperazine-1-carboxylate (204g). $^1H$ NMR (500 MHz, Chloroform-d) δ 7.24-7.11 (m, 3H), 7.11-6.89 (m, 2H), 6.65-6.32 (m, 2H), 6.30-6.12 (m, 1H), 4.86-4.43 (m, 2H), 3.80 (dt, J=11.2, 5.2 Hz, 2H), 3.71-3.55 (m, 4H), 3.48-3.24 (m, 4H), 3.17-2.66 (m, 6H), 1.99-1.67 (m, 4H), 1.66-1.52 (m, 7H), 1.42 (s, 9H), 1.24 (dd, J=7.0, 4.2 Hz, 6H), 1.14 (dt, J=27.5, 7.1 Hz, 3H). $^{13}C$ NMR (126 MHz, Chloroform-d) δ 173.91, 173.74, 172.10, 156.27, 156.20, 154.35, 152.70, 152.56, 148.34, 147.91, 135.17, 134.41, 129.66, 129.60, 127.91, 126.94, 126.63, 126.20, 109.85, 109.71, 106.94, 105.75, 105.52, 80.57, 80.54, 80.09, 52.38, 50.12, 49.93, 49.65, 47.34, 45.77, 42.90, 41.37, 40.81, 39.09, 39.04, 33.78, 33.76, 28.36, 28.33, 28.06, 26.18, 24.49, 24.28, 24.01, 14.42, 12.70. MS (ESI) m/z=635.4 $[M+H]^+$.

tert-butyl (S)-4-(2-(3-(3-(ethyl(4-isopropylbenzyl)carbamoyl)piperidin-1-yl)phenoxy)-2-methylpropanoyl)piperazine-1-carboxylate (204h). $^1H$ NMR (500 MHz, Chloroform-d) δ 7.24-7.12 (m, 3H), 7.11-6.88 (m, 2H), 6.62-6.31 (m, 2H), 6.30-6.08 (m, 1H), 4.80-4.40 (m, 2H), 3.80 (dt, J=11.8, 5.1 Hz, 2H), 3.72-3.53 (m, 4H), 3.50-3.26 (m, 4H), 3.21-2.64 (m, 6H), 2.00-1.69 (m, 4H), 1.65-1.52 (m, 7H), 1.41 (s, 9H), 1.23 (dd, J=7.0, 4.3 Hz, 6H), 1.13 (dt, J=27.5, 7.1 Hz, 3H). $^{13}C$ NMR (126 MHz, Chloroform-d) δ 173.90, 173.73, 172.08, 156.27, 156.19, 154.34, 152.70, 152.55, 148.33, 147.90, 135.17, 134.41, 129.66, 129.60, 127.91, 126.94, 126.62, 126.20, 109.84, 109.70, 106.93, 105.73, 105.50, 80.56, 80.53, 80.08, 52.38, 52.38, 50.12, 49.93, 49.64, 47.34, 45.77, 42.90, 41.37, 40.81, 39.08, 39.03, 33.78, 33.76, 28.36, 28.32, 28.06, 26.20, 26.16, 24.48, 24.27, 24.01, 14.42, 12.70. MS (ESI) m/z=635.4 $[M+H]^+$.

tert-butyl (R)-4-(2-(3-(3-(isopropyl(4-isopropylbenzyl)carbamoyl)piperidin-1-yl)phenoxy)-2-methylpropanoyl)piperazine-1-carboxylate (204i). $^1H$ NMR (500 MHz, Chloroform-d) δ 7.22-6.90 (m, 5H), 6.62-6.14 (m, 3H), 4.95-4.19 (m, 3H), 3.90-3.45 (m, 6H), 3.32 (d, J=6.9 Hz, 2H), 3.23-2.54 (m, 6H), 2.00-1.65 (m, 4H), 1.62 (dd, J=7.7, 1.9 Hz, 6H), 1.52-1.39 (m, 10H), 1.34-1.05 (m, 12H). $^{13}C$ NMR (126 MHz, Chloroform-d) δ 174.60, 173.93, 172.10, 156.28, 156.13, 154.35, 154.33, 152.72, 152.62, 147.88, 147.04, 136.85, 136.00, 129.67, 129.56, 126.78, 126.67, 126.38, 125.71, 109.84, 109.73, 106.96, 105.73, 105.49, 80.52, 80.08, 53.43, 52.51, 52.35, 50.02, 49.57, 48.55, 45.82, 45.64, 43.58, 42.89, 40.10, 39.38, 33.70, 28.52, 28.36, 28.02, 26.20, 26.17, 24.63, 24.20, 24.02, 23.99, 22.04, 21.90, 20.43, 20.39. MS (ESI) m/z=649.5 $[M+H]^+$, 671.5 $[M+Na]^+$.

tert-butyl (S)-4-(2-(3-(3-(isopropyl(4-isopropylbenzyl)carbamoyl)piperidin-1-yl)phenoxy)-2-methylpropanoyl)piperazine-1-carboxylate (204j). $^1H$ NMR (500 MHz, Chloroform-d) δ 7.23-6.88 (m, 5H), 6.62-6.05 (m, 3H), 4.95-4.19 (m, 3H), 3.96-3.47 (m, 6H), 3.32 (q, J=6.3, 5.4 Hz, 2H), 3.21-3.03 (m, 2H), 3.00-2.83 (m, 2H), 2.78-2.60 (m, 2H), 2.00-1.66 (m, 4H), 1.62 (dd, J=7.8, 1.9 Hz, 6H), 1.42 (s, 10H), 1.35-0.92 (m, 12H). $^{13}C$ NMR (126 MHz, Chloroform-d) δ 174.61, 173.93, 172.10, 156.28, 156.13, 154.36, 154.33, 152.72, 152.62, 147.89, 147.04, 136.84, 135.99, 129.67, 129.56, 126.78, 126.67, 126.39, 125.71, 109.85, 109.74, 106.96, 105.73, 105.50, 80.56, 80.52, 80.08, 52.51, 52.35, 50.03, 49.58, 48.55, 45.82, 45.65, 43.59, 42.90, 39.39, 33.70, 29.29, 28.52, 28.02, 26.20, 26.17, 24.63, 24.20, 24.02, 23.99, 22.05, 21.90, 20.43, 20.39. MS (ESI) m/z=649.5 $[M+H]^+$, 671.5 $[M+Na]^+$.

tert-butyl (R)-4-(2-(3-(3-(cyclopropyl(4-isopropylbenzyl)carbamoyl)piperidin-1-yl)phenoxy)-2-methylpropanoyl)piperazine-1-carboxylate (204k). $^1H$ NMR (500 MHz, Chloroform-d) δ 7.21-7.13 (m, 4H), 7.07 (t, J=8.2 Hz, 1H), 6.54 (dd, J=8.3, 2.2 Hz, 1H), 6.43 (t, J=2.4 Hz, 1H), 6.28 (dd, J=8.1, 2.3 Hz, 1H), 4.68 (d, J=14.5 Hz, 1H), 4.51 (d, J=14.6 Hz, 1H), 3.83 (q, J=5.5 Hz, 2H), 3.73-3.53 (m, 4H), 3.49-3.28 (m, 3H), 3.17-2.83 (m, 4H), 2.77 (td, J=12.2, 3.0 Hz, 1H), 2.66-2.54 (m, 1H), 2.01-1.92 (m, 1H), 1.89-1.69 (m, 3H), 1.71-1.54 (m, 7H), 1.43 (s, 9H), 1.25 (d, J=6.9 Hz, 6H), 1.02-0.74 (m, 4H). $^{13}C$ NMR (126 MHz, Chloroform-d) δ 176.70, 172.09, 156.23, 154.35, 152.74, 147.64, 135.66, 129.62, 127.65, 126.55, 109.77, 107.01, 105.65, 80.54, 80.09, 52.08, 49.83, 49.48, 45.78, 42.91, 39.85, 33.75, 29.72, 28.36, 27.81, 26.21, 26.15, 24.50, 24.01, 9.50, 9.04. MS (ESI) m/z=647.4 $[M+H]^+$.

tert-butyl (S)-4-(2-(3-(3-(cyclopropyl(4-isopropylbenzyl)carbamoyl)piperidin-1-yl)phenoxy)-2-methylpropanoyl)piperazine-1-carboxylate (204l). $^1H$ NMR (500 MHz, Chloroform-d) δ 7.19-7.11 (m, 4H), 7.06 (t, J=8.2 Hz, 1H), 6.53 (dd, J=8.3, 2.2 Hz, 1H), 6.42 (t, J=2.4 Hz, 1H), 6.27 (dd, J=8.1, 2.3 Hz, 1H), 4.66 (d, J=14.6 Hz, 1H), 4.49 (d, J=14.6 Hz, 1H), 3.81 (q, J=5.5 Hz, 2H), 3.74-3.54 (m, 4H), 3.42 (ddd, J=11.0, 7.4, 3.5 Hz, 1H), 3.32 (s, 2H), 3.16-2.93 (m, 3H), 2.88 (p, J=6.9 Hz, 1H), 2.74 (dd, J=12.2, 2.9 Hz, 1H), 2.60 (ddd, J=6.6, 4.1, 2.4 Hz, 1H), 1.99-1.92 (m, 1H), 1.88-1.67 (m, 4H), 1.63 (d, J=1.3 Hz, 6H), 1.42 (s, 9H), 1.24 (s, 6H), 0.93-0.75 (m, 4H). $^{13}C$ NMR (126 MHz, Chloroform-d) δ 176.71, 172.09, 156.23, 154.35, 152.75, 147.65, 135.66, 129.62, 127.65, 126.56, 109.77, 107.02, 105.67, 80.54, 80.10, 52.08, 49.83, 49.48, 45.79, 42.91, 39.85, 33.76, 29.72, 28.36, 27.81, 26.22, 26.15, 24.50, 24.01, 9.50, 9.04. MS (ESI) m/z=647.4 $[M+H]^+$.

(R)-4-(2-(3-(3-(((4-isopropylbenzyl)oxy)carbonyl)piperidin-1-yl)phenoxy)-2-methylpropanoyl)piperazin-1-ium chloride (15). $^1H$ NMR (500 MHz, Methanol-$d_4$) δ 7.47 (t, J=8.2 Hz, 1H), 7.36-7.26 (m, 3H), 7.26-7.22 (m, 2H), 7.19 (s, 1H), 6.89 (d, J=8.2 Hz, 1H), 5.22-5.07 (m, 2H), 4.03 (d, J=124.2 Hz, 4H), 3.81-3.75 (m, 1H), 3.67-3.60 (m, 2H), 3.52-3.41 (m, 1H), 3.28-2.86 (m, 6H), 2.27-2.01 (m, 3H), 1.85 (q, J=12.8, 12.1 Hz, 1H), 1.67 (d, J=1.6 Hz, 6H), 1.24 (d, J=6.9 Hz, 6H). $^{13}C$ NMR (126 MHz, Methanol-$d_4$) δ 171.62, 156.22, 149.12, 145.12, 133.16, 131.18, 128.26, 126.23, 116.47, 113.64, 110.34, 81.51, 66.60, 55.56, 54.82, 43.15, 42.70, 39.69, 39.55, 33.77, 24.90, 24.84, 24.47, 23.00, 22.41. HRMS (ESI) Calcd for $C_{30}H_{41}N_3O_4$ $(M^+ Na)^+$ 530.2989, found 530.2983. HPLC purity 98.4%, $t_R$=13.34 min.

(S)-4-(2-(3-(3-(((4-isopropylbenzyl)oxy)carbonyl)piperidin-1-yl)phenoxy)-2-methylpropanoyl)piperazin-1-ium chloride (16). $^1H$ NMR (500 MHz, Methanol-$d_4$) δ 7.47 (t, J=8.2 Hz, 1H), 7.35-7.20 (m, 5H), 7.17 (s, 1H), 6.94-6.80 (m, 1H), 5.25-5.07 (m, 2H), 4.02 (d, J=124.6 Hz, 4H), 3.77 (dd, J=12.5, 3.7 Hz, 1H), 3.62 (td, J=9.8, 9.2, 5.0 Hz, 2H), 3.51-3.41 (m, 1H), 3.26-2.85 (m, 6H), 2.29-1.97 (m, 3H), 1.94-1.76 (m, 1H), 1.67 (d, J=1.7 Hz, 6H), 1.24 (d, J=6.9 Hz, 6H). $^{13}C$ NMR (126 MHz, Methanol-$d_4$) δ 171.62, 156.24, 149.13, 133.16, 131.17, 128.26, 126.23, 113.58, 110.29, 81.50, 66.60, 55.55, 54.74, 43.14, 42.64, 39.69, 39.54, 33.78, 24.87, 24.81, 24.45, 22.98, 22.40. HRMS (ESI) Calcd for $C_{30}H_{41}N_3O_4$ ($M^+$ Na)$^+$ 530.2989, found 530.2982. HPLC purity 97.8%, $t_R$=13.34 min.

(R)-4-(2-(3-(3-((4-isopropylbenzyl)carbamoyl)piperidin-1-yl)phenoxy)-2-methylpropanoyl)piperazin-1-ium chloride (17). $^1$H NMR (500 MHz, Methanol-$d_4$) δ 7.52 (t, J=8.3 Hz, 1H), 7.43-7.33 (m, 1H), 7.32-7.12 (m, 5H), 6.99 (dd, J=8.4, 2.2 Hz, 1H), 4.37 (q, J=14.8 Hz, 2H), 4.02 (d, J=117.9 Hz, 4H), 3.71 (td, J=11.0, 10.0, 5.5 Hz, 3H), 3.55 (d, J=8.1 Hz, 1H), 3.25-2.82 (m, 6H), 2.13 (q, J=12.4, 11.3 Hz, 3H), 1.92 (s, 1H), 1.68 (d, J=1.0 Hz, 6H), 1.22 (d, J=6.9 Hz, 6H). $^{13}$C NMR (126 MHz, Methanol-$d_4$) δ 171.51, 156.28, 147.91, 143.93, 135.67, 131.41, 127.30, 126.20, 117.83, 114.17, 111.14, 81.70, 57.47, 43.15, 42.52, 39.62, 33.68, 25.27, 24.88, 24.74, 23.04, 21.92. HRMS (ESI) Calcd for $C_{30}H_{42}N_4O_3$ ($M^+$ Na)$^+$ 529.3149, found 529.3140. HPLC purity 97.6%, $t_R$=10.96 min.

(S)-4-(2-(3-(3-((4-isopropylbenzyl)carbamoyl)piperidin-1-yl)phenoxy)-2-methylpropanoyl)piperazin-1-ium chloride (18). $^1$H NMR (500 MHz, Methanol-$d_4$) δ 7.49 (t, J=8.3 Hz, 1H), 7.32 (d, J=8.2 Hz, 1H), 7.26-7.11 (m, 5H), 7.01-6.72 (m, 1H), 4.43-4.30 (m, 2H), 4.02 (d, J=122.1 Hz, 4H), 3.75-3.46 (m, 4H), 3.27-2.82 (m, 6H), 2.21-1.80 (m, 4H), 1.67 (d, J=1.1 Hz, 6H), 1.22 (d, J=6.9 Hz, 6H). $^{13}$C NMR (126 MHz, Methanol-$d_4$) δ 171.59, 156.26, 147.88, 135.71, 131.26, 127.29, 126.19, 113.86, 110.63, 81.57, 57.00, 54.95, 43.14, 42.50, 39.62, 33.68, 25.47, 24.90, 24.78, 23.05, 22.10. HRMS (ESI) Calcd for $C_{30}H_{42}N_4O_3$ ($M^+$ Na)$^+$ 529.3149, found 529.3140. HPLC purity 100%, $t_R$=10.94 min.

(R)-4-(2-(3-(3-((4-isopropylbenzyl)(methyl)carbamoyl)piperidin-1-yl)phenoxy)-2-methylpropanoyl)piperazin-1-ium chloride (19). $^1$H NMR (500 MHz, Methanol-$d_4$) δ 7.47 (dt, J=25.8, 8.2 Hz, 1H), 7.38-7.01 (m, 6H), 6.90 (d, J=30.1 Hz, 1H), 4.75-4.50 (m, 2H), 4.02 (d, J=122.4 Hz, 4H), 3.78-3.41 (m, 5H), 3.25-2.87 (m, 8H), 2.20-1.79 (m, 4H), 1.70-1.65 (m, 6H), 1.24 (dd, J=6.9, 3.5 Hz, 6H). $^{13}$C NMR (126 MHz, Methanol-$d_4$) δ 171.69, 171.64, 156.30, 148.52, 148.19, 134.08, 131.27, 127.56, 126.70, 126.48, 126.36, 81.59, 52.73, 50.26, 43.13, 34.08, 33.69 (d, J=2.2 Hz), 33.19, 24.89, 24.78, 24.74, 23.01, 23.00. HRMS (ESI) Calcd for $C_{31}H_{44}N_4O_3$ (M+H)$^+$ 521.3486, found 521.3478. HPLC purity 100%, $t_R$=11.37 min (S)-4-(2-(3-(3-((4-isopropylbenzyl)(methyl)carbamoyl)piperidin-1-yl)phenoxy)-2-methylpropanoyl)piperazin-1-ium chloride (20). $^1$H NMR (500 MHz, Methanol-$d_4$) δ 7.59-7.45 (m, 1H), 7.37 (dd, J=28.8, 8.2 Hz, 1H), 7.31-7.14 (m, 5H), 7.07-6.89 (m, 1H), 4.69 (q, J=17.8, 17.4 Hz, 2H), 4.04 (d, J=120.8 Hz, 4H), 3.79-3.51 (m, 5H), 3.27-2.83 (m, 8H), 2.31-1.79 (m, 4H), 1.68 (d, J=3.9 Hz, 6H), 1.24 (dd, J=6.9, 3.3 Hz, 6H). $^{13}$C NMR (126 MHz, Methanol-$d_4$) δ 171.54, 156.30, 148.52, 148.18, 134.07, 133.70, 131.43, 131.34, 127.57, 126.69, 126.60, 126.37, 114.18, 111.13, 81.70, 81.66, 55.13, 52.76, 50.27, 43.14, 42.68, 39.57, 34.13, 33.70, 33.19, 24.92, 24.77, 24.74, 23.03, 23.03. HRMS (ESI) Calcd for $C_{31}H_{44}N_4O_3$ (M+H)$^+$ 521.3486, found 521.3478. HPLC purity 100%, $t_R$=11.37 min (R)-4-(2-(3-(3-(ethyl(4-isopropylbenzyl)carbamoyl)piperidin-1-yl)phenoxy)-2-methylpropanoyl)piperazin-1-ium chloride (21). $^1$H NMR (500 MHz, Methanol-$d_4$) δ 7.48 (dt, J=17.8, 8.1 Hz, 1H), 7.40-7.08 (m, 6H), 6.91 (s, 1H), 4.79-4.36 (m, 2H), 4.03 (d, J=121.8 Hz, 4H), 3.78-3.34 (m, 7H), 3.27-2.79 (m, 5H), 2.30-1.74 (m, 4H), 1.68 (d, J=3.3 Hz, 6H), 1.30-1.11 (m, 9H). $^{13}$C NMR (126 MHz, Methanol-$d_4$) δ 171.62, 171.61, 156.27, 156.27, 148.47, 148.03, 134.61, 134.07, 131.27, 131.19, 127.41, 126.65, 126.61, 126.31, 113.86, 81.60, 81.53, 54.82, 50.32, 43.14, 42.69, 41.88, 41.17, 39.56, 33.68, 24.91, 24.80, 24.79, 23.04, 23.03, 21.90, 13.10, 11.39. HRMS (ESI) Calcd for $C_{32}H_{46}N_4O_3$ (M+H)$^+$ 535.3643, found 535.3640. HPLC purity 98.0%, $t_R$=11.55 min (S)-4-(2-(3-(3-(ethyl(4-isopropylbenzyl)carbamoyl)piperidin-1-yl)phenoxy)-2-methylpropanoyl)piperazin-1-ium chloride (22). $^1$H NMR (500 MHz, Methanol-$d_4$) δ 7.53-7.17 (m, 7H), 6.94 (dd, J=16.6, 8.3 Hz, 1H), 4.43 (d, J=14.8 Hz, 2H), 4.26-3.86 (m, 4H), 3.77-3.36 (m, 7H), 3.28-2.84 (m, 5H), 2.38-1.76 (m, 4H), 1.68 (d, J=3.1 Hz, 6H), 1.25-1.09 (m, 9H). $^{13}$C NMR (126 MHz, Methanol-$d_4$) δ 171.52, 156.26, 148.44, 148.00, 144.42, 134.65, 134.13, 131.36, 131.29, 127.42, 126.74, 126.65, 126.33, 117.31, 114.12, 111.00, 81.64, 81.58, 57.50, 55.11, 50.37, 43.17, 42.70, 41.94, 41.17, 40.28, 39.58, 36.77, 33.68, 24.99, 24.87, 24.86, 23.11, 23.09, 21.93, 13.22, 11.46. HRMS (ESI) Calcd for $C_{32}H_{46}N_4O_3$ (M+H)$^+$ 535.3643, found 535.3639. HPLC purity 100%, $t_R$=11.88 min (R)-4-(2-(3-(3-(isopropyl(4-isopropylbenzyl)carbamoyl)piperidin-1-yl)phenoxy)-2-methylpropanoyl)piperazin-1-ium chloride (23). $^1$H NMR (500 MHz, Methanol-$d_4$) δ 7.46 (dt, J=35.6, 8.2 Hz, 1H), 7.21 (d, J=133.2 Hz, 6H), 7.00-6.79 (m, 1H), 4.73-4.57 (m, 2H), 4.50-4.35 (m, 1H), 4.03 (d, J=124.8 Hz, 4H), 3.81-3.32 (m, 5H), 3.22-2.86 (m, 5H), 2.25-1.77 (m, 4H), 1.67 (t, J=1.6 Hz, 6H), 1.27-1.13 (m, 12H). $^{13}$C NMR (126 MHz, Methanol-$d_4$) δ 171.67, 171.59, 156.27, 156.24, 148.10, 147.21, 136.18, 135.47, 131.30, 131.07, 126.57, 126.26, 126.01, 114.00, 113.45, 110.82, 81.62, 81.42, 54.77, 49.34, 46.18, 43.34, 43.13, 42.69, 39.53, 33.64, 33.62, 24.93, 24.83, 24.77, 23.10, 23.06, 20.58, 20.25, 19.10, 18.90. HRMS (ESI) Calcd for $C_{33}H_{48}N_4O_3$ (M+H)$^+$ 549.3799; found 549.3790. HPLC purity 100%, $t_R$=12.32 min.

(S)-4-(2-(3-(3-(isopropyl(4-isopropylbenzyl)carbamoyl)piperidin-1-yl)phenoxy)-2-methylpropanoyl)piperazin-1-ium chloride (24). $^1$H NMR (500 MHz, Methanol-$d_4$) δ 7.54-7.35 (m, 1H), 7.34-6.70 (m, 7H), 4.76-4.55 (m, 2H), 4.51-4.32 (m, 1H), 4.02 (d, J=124.7 Hz, 4H), 3.77-3.44 (m, 4H), 3.29-2.60 (m, 6H), 2.28-1.73 (m, 4H), 1.67 (d, J=2.9 Hz, 6H), 1.27-1.12 (m, 12H). $^{13}$C NMR (126 MHz, Methanol-$d_4$) δ 171.75, 171.65, 156.28, 156.23, 148.10, 147.23, 136.17, 135.48, 131.21, 130.95, 126.56, 126.25, 126.00, 125.94, 81.57, 81.33, 49.33, 46.09, 43.32, 43.12, 42.69, 33.63 (d, J=2.1 Hz), 24.89, 24.82, 24.75, 23.07, 23.03, 20.54, 20.21, 19.07, 18.85. HRMS (ESI) Calcd for $C_{33}H_{48}N_4O_3$ (M+H)$^+$ 549.3799, found 549.3792. HPLC purity 100%, $t_R$=12.33 min (R)-4-(2-(3-(3-(cyclopropyl(4-isopropylbenzyl)carbamoyl)piperidin-1-yl)phenoxy)-2-methylpropanoyl)piperazin-1-ium chloride (25). $^1$H NMR (500 MHz, Methanol-$d_4$) δ 7.45 (d, J=8.4 Hz, 1H), 7.34-7.02 (m, 6H), 6.87 (s, 1H), 4.47-4.38 (m, 1H), 4.21-3.84 (m, 5H), 3.76-3.38 (m, 5H), 3.26-2.67 (m, 6H), 2.22-1.73 (m, 4H), 1.67 (d, J=2.4 Hz, 6H), 1.23 (d, J=6.9 Hz, 6H), 1.09-0.64 (m, 4H). $^{13}$C NMR (126 MHz, Methanol-$d_4$) δ 171.71, 156.26, 147.81, 135.17, 131.09, 127.16, 126.63, 126.24, 81.45, 49.34, 43.13, 33.67, 29.81, 24.90, 24.78, 23.04, 9.17, 7.36. HRMS (ESI) Calcd for $C_{33}H_{46}N_4O_3$ (M+H)$^+$ 547.3643, found 547.3646. HPLC purity 100%, $t_R$=12.15 min (S)-4-(2-(3-(3-(cyclopropyl(4-isopropylbenzyl)carbamoyl)piperidin-1-yl)phenoxy)-2-methylpropanoyl)piperazin-1-ium chloride (26). $^1$H NMR (500 MHz, Methanol-$d_4$) δ 7.50 (t, J=8.2 Hz, 1H), 7.38-7.14 (m, 6H), 6.93 (d, J=8.2 Hz, 1H), 4.41 (d, J=14.8 Hz, 1H), 4.28-3.79 (m, 5H), 3.79-3.46 (m, 5H), 3.26-2.67 (m, 6H), 2.03 (d, J=112.4 Hz, 4H), 1.68 (d, J=2.5 Hz, 6H), 1.23 (d, J=6.9 Hz, 6H), 1.09-0.85 (m, 4H). $^{13}$C NMR (126 MHz, Methanol-$d_4$) δ 171.63, 156.28, 147.82, 135.14, 131.24, 127.17, 126.24, 97.82, 97.67, 81.58, 62.91, 49.36, 43.13, 33.67, 29.81, 24.90, 24.76, 23.04, 9.24, 7.30. HRMS (ESI) Calcd for $C_{33}H_{46}N_4O_3$ ($M^+$ Na)$^+$ 569.3462, found 569.3457. HPLC purity 100%, $t_R$=12.15 min.

Scheme 3. Synthesis of compounds 27-43.
A.
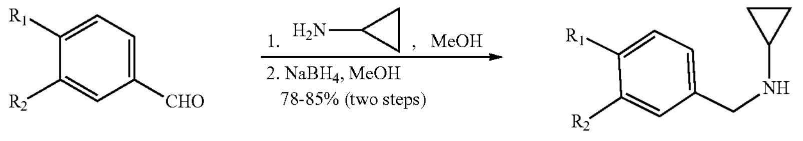
205
205a. $R_1$ = H, $R_2$ = I-Pr
205b. $R_1$ = t-Bu, $R_2$ = H
205c, $R_1$ = cyclohexyl, $R_2$ = H
205d. $R_1$ = morpholino, $R_2$ = H
205e. $R_1$ = Ph, $R_2$ = H
205f. $R_1$ = pyridin-2-yl, $R_2$ = H
205g. $R_1$ = pyridin-3-yl, $R_2$ = H
205h. $R_1$ = pyridin-4-yl, $R_2$ = H
205i. $R_1$ = Br, $R_2$ = H
B.
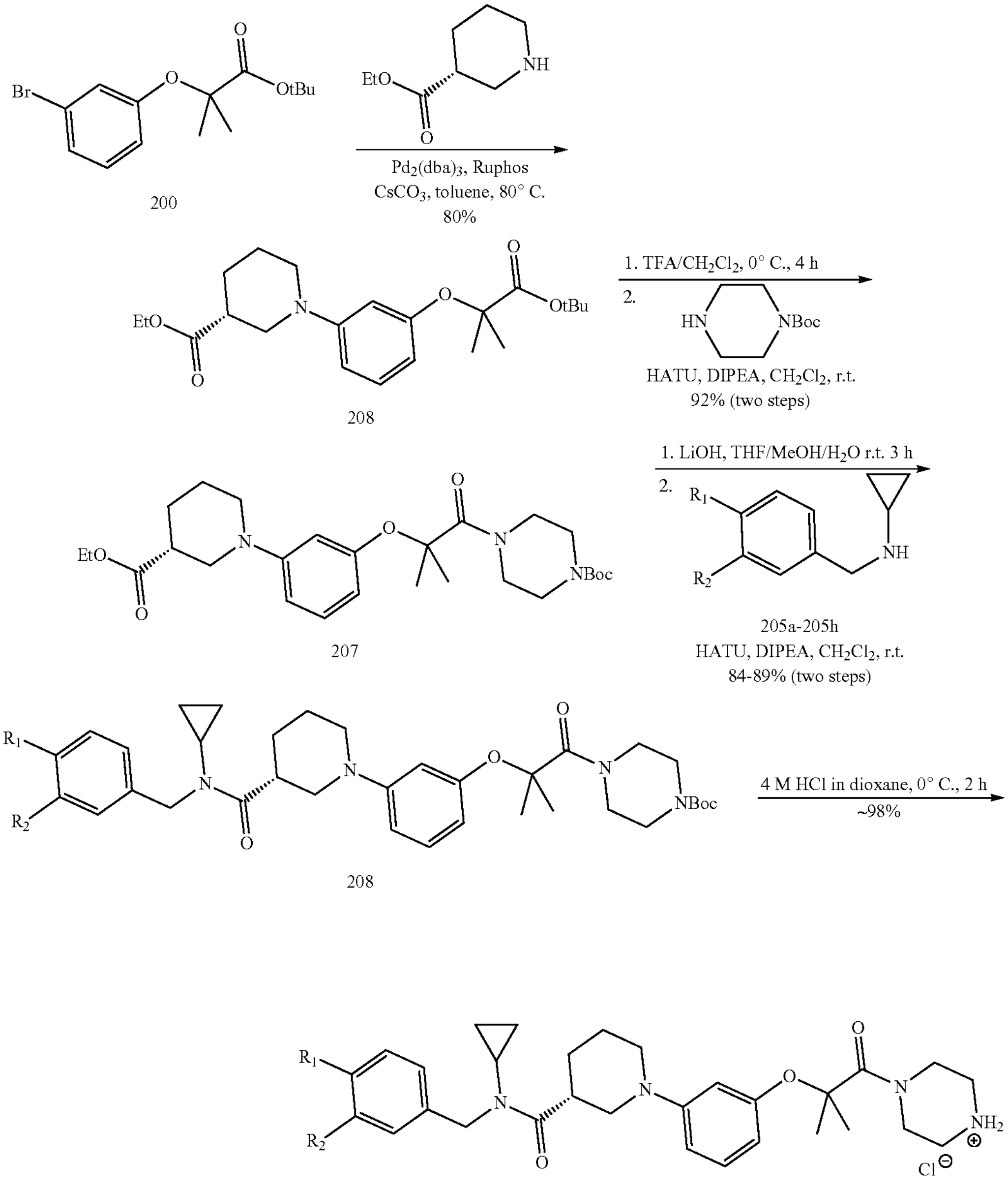
200
208
207
208
27-31, 33-35

-continued
27. $R_1$ = H, $R_2$ = I-Pr
28. $R_1$ = t-Bu, $R_2$ = H
29. $R_1$ = cyclohexyl, $R_2$ = H
30. $R_1$ = morpholino, $R_2$ = H
31. $R_1$ = Ph, $R_2$ = H
33. $R_1$ = pyridin-2-yl, $R_2$ = H
34. $R_1$ = pyridin-3-yl, $R_2$ = H
35. $R_1$ = pyridin-4-yl, $R_2$ = H
C.
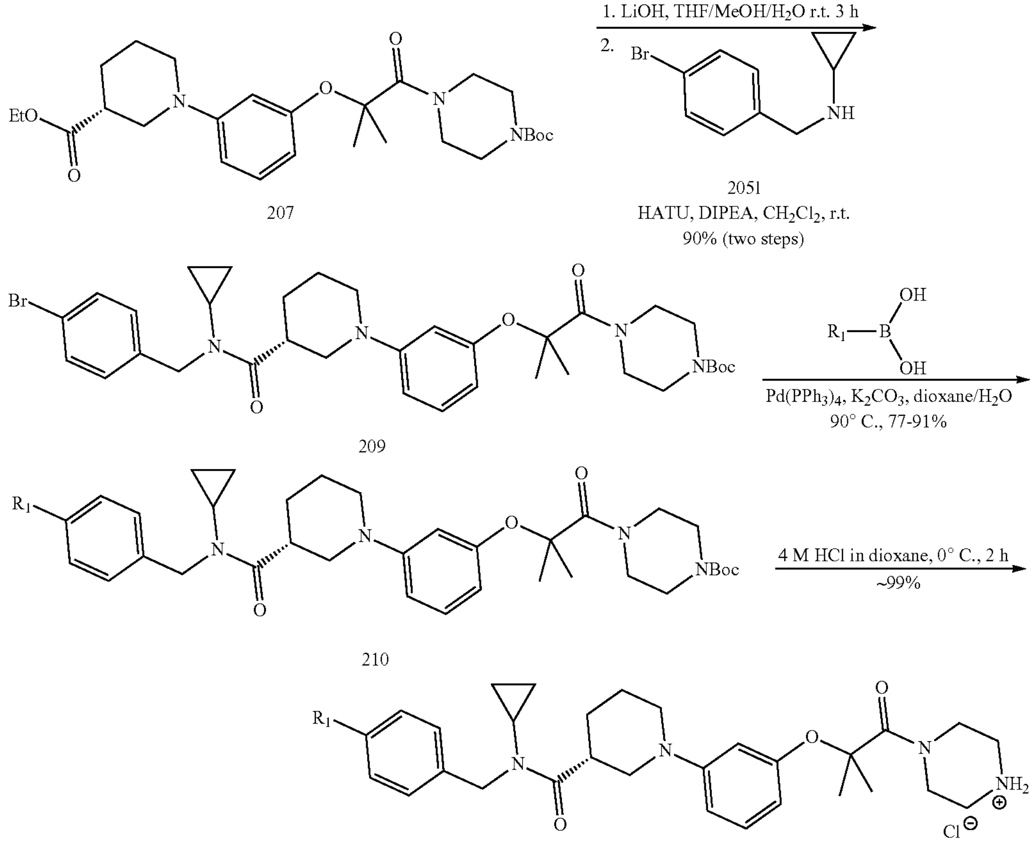
207
209
210
32, 36-43
$R_1$ =
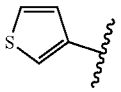
32
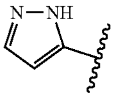
38
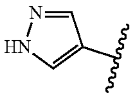
37
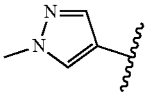
38
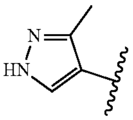
39
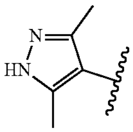
40
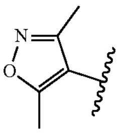
40
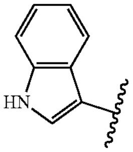
42
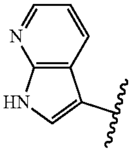
43

N-(3-isopropylbenzyl)cyclopropanamine (205a). $^1$H NMR (500 MHz, Methanol-$d_4$) δ 7.26-7.19 (m, 2H), 7.15-7.05 (m, 2H), 3.77 (s, 2H), 2.95-2.81 (m, J=6.9 Hz, 1H), 2.13 (tt, J=6.8, 3.8 Hz, 1H), 1.25 (d, J=6.9 Hz, 6H), 0.50-0.34 (m, 4H). MS (ESI) m/z=190.2 $[M+H]^+$.

N-(4-(tert-butyl)benzyl)cyclopropanamine (205b). $^1$H NMR (500 MHz, Chloroform-d) δ 7.41-7.33 (m, 2H), 7.30-7.17 (m, 2H), 3.84 (s, 2H), 2.23-2.14 (m, 1H), 1.80 (s, 1H), 1.35 (s, 9H), 0.51-0.37 (m, 4H). MS (ESI) m/z=204.2 $[M+H]^+$.

N-(4-cyclohexylbenzyl)cyclopropanamine (205c). $^1$H NMR (500 MHz, Methanol-$d_4$) δ 7.27-7.20 (m, 2H), 7.19-7.09 (m, 2H), 3.74 (s, 2H), 2.47 (dddd, J=15.9, 12.8, 8.9, 4.9 Hz, 1H), 2.11 (tt, J=6.8, 3.8 Hz, 1H), 1.90-1.79 (m, 4H), 1.75 (dtt, J=12.7, 3.0, 1.6 Hz, 1H), 1.48-1.37 (m, 4H), 1.34-1.21 (m, 1H), 0.49-0.35 (m, 4H). MS (ESI) m/z=230.2 $[M+H]^+$.

N-(4-morpholinobenzyl)cyclopropanamine (205d). $^1$H NMR (500 MHz, Methanol-$d_4$) δ 7.32-7.10 (m, 2H), 6.98-6.83 (m, 2H), 3.88-3.79 (m, 4H), 3.70 (s, 2H), 3.15-3.03 (m, 4H), 2.12 (tt, J=6.8, 3.8 Hz, 1H), 0.48-0.35 (m, 4H). MS (ESI) m/z=233.2 $[M+H]^+$.

N-([1,1'-biphenyl]-4-ylmethyl)cyclopropanamine (205e). $^1$H NMR (500 MHz, Methanol-$d_4$) δ 7.62-7.56 (m, 4H), 7.42 (ddd, J=9.7, 5.3, 2.4 Hz, 4H), 7.33-7.27 (m, 1H), 3.83 (s, 2H), 2.16 (tt, J=6.8, 3.8 Hz, 1H), 0.50-0.36 (m, 4H). MS (ESI) m/z=224.1 $[M+H]^+$.

N-(4-(pyridin-2-yl)benzyl)cyclopropanamine (205f). $^1$H NMR (500 MHz, Chloroform-d) δ 8.68 (dt, J=4.9, 1.3 Hz, 1H), 7.99-7.90 (m, 2H), 7.76-7.68 (m, 2H), 7.44-7.39 (m, 2H), 7.21 (ddd, J=6.7, 4.8, 2.0 Hz, 1H), 3.89 (s, 2H), 2.17 (tt, J=6.6, 3.7 Hz, 1H), 0.48-0.36 (m, 4H). MS (ESI) m/z=225.1 $[M+H]^+$. N-(4-(pyridin-3-yl)benzyl)cyclopropanamine (205g). $^1$H NMR (500 MHz, Chloroform-d) δ 8.84 (dd, J=2.4, 0.9 Hz, 1H), 8.58 (dd, J=4.8, 1.7 Hz, 1H), 7.86 (ddd, J=7.9, 2.4, 1.7 Hz, 1H), 7.57-7.51 (m, 2H), 7.48-7.39 (m, 2H), 7.35 (ddd, J=8.0, 4.8, 0.9 Hz, 1H), 3.90 (s, 2H), 2.23-2.14 (m, 1H), 0.51-0.32 (m, 4H). MS (ESI) m/z=225.1 $[M+H]^+$.

N-(4-(pyridin-4-yl)benzyl)cyclopropanamine (205h). $^1$H NMR (500 MHz, Chloroform-d) δ 8.67-8.59 (m, 2H), 7.66-7.55 (m, 2H), 7.55-7.48 (m, 2H), 7.48-7.42 (m, 2H), 3.90 (s, 2H), 2.22-2.18 (m, 1H), 0.52-0.31 (m, 4H). MS (ESI) m/z=225.1 $[M+H]^+$.

N-(4-bromobenzyl)cyclopropanamine (205i). $^1$H NMR (500 MHz, Chloroform-d) δ 7.46-7.37 (m, 2H), 7.22-7.08 (m, 2H), 3.79 (s, 2H), 2.12 (tt, J=6.5, 3.6 Hz, 1H), 0.49-0.39 (m, 2H), 0.39-0.25 (m, 2H). MS (ESI) m/z=226.0, 228.0 $[M+H]^+$.

ethyl (R)-1-(3-((1-(tert-butoxy)-2-methyl-1-oxopropan-2-yl)oxy)phenyl)piperidine-3-carboxylate (206). $^1$H NMR (500 MHz, Chloroform-d) δ 7.04 (t, J=8.2 Hz, 1H), 6.54 (dd, J=8.1, 2.3 Hz, 1H), 6.45 (t, J=2.4 Hz, 1H), 6.31-6.21 (m, 1H), 4.12 (q, J=7.1 Hz, 2H), 3.67 (ddt, J=12.4, 3.5, 1.5 Hz, 1H), 3.42 (ddd, J=12.3, 4.9, 3.1 Hz, 1H), 2.95 (dd, J=12.4, 9.9 Hz, 1H), 2.80-2.68 (m, 1H), 2.60 (tt, J=10.0, 3.9 Hz, 1H), 2.05-1.93 (m, 1H), 1.74 (th, J=9.2, 3.1 Hz, 1H), 1.69-1.59 (m, 2H), 1.53 (s, 6H), 1.41 (s, 9H), 1.24 (t, J=7.2 Hz, 3H). $^{13}$C NMR (126 MHz, Chloroform-d) δ 173.71, 173.43, 156.64, 152.48, 129.08, 110.40, 109.33, 107.56, 81.40, 79.15, 60.40, 52.05, 49.66, 41.34, 27.78, 26.96, 25.49, 25.42, 24.09, 14.24. MS (ESI) m/z=392.3 $[M+H]^+$, 414.3 $[M+Na]^+$.

tert-butyl (R)-4-(2-(3-(3-(ethoxycarbonyl)piperidin-1-yl)phenoxy)-2-methylpropanoyl)piperazine-1-carboxylate (207). $^1$H NMR (500 MHz, Chloroform-d) δ 7.05 (t, J=8.2 Hz, 1H), 6.55 (dd, J=8.0, 2.3 Hz, 1H), 6.41 (t, J=2.3 Hz, 1H), 6.27 (ddd, J=8.2, 2.5, 0.7 Hz, 1H), 4.15 (q, J=7.1 Hz, 2H), 3.81 (t, J=5.2 Hz, 2H), 3.67 (ddt, J=12.4, 3.5, 1.5 Hz, 1H), 3.59 (t, J=5.2 Hz, 2H), 3.50-3.39 (m, 1H), 3.33 (q, J=5.5 Hz, 2H), 3.07 (t, J=5.2 Hz, 2H), 2.97 (dd, J=12.4, 9.9 Hz, 1H), 2.81-2.70 (m, 1H), 2.62 (tt, J=10.0, 3.9 Hz, 1H), 2.07-1.92 (m, 1H), 1.78 (qq, J=4.9, 3.2, 2.2 Hz, 1H), 1.62 (s, 8H), 1.41 (s, 9H), 1.26 (t, J'=7.1 Hz, 3H). $^{13}$C NMR (126 MHz, Chloroform-d) δ 173.74, 172.10, 156.18, 154.36, 152.75, 129.59, 110.13, 107.29, 105.66, 80.55, 80.07, 60.50, 51.90, 49.50, 45.76, 42.90, 41.29, 28.35, 26.96, 26.18, 26.16, 24.06, 14.26. MS (ESI) m/z=504.3 $[M+H]^+$, 526.3 $[M+Na]^+$.

tert-butyl (R)-4-(2-(3-(3-(cyclopropyl(3-isopropylbenzyl)carbamoyl)piperidin-1-yl)phenoxy)-2-methylpropanoyl)piperazine-1-carboxylate (208a). $^1$H NMR (500 MHz, Chloroform-d) δ 7.16 (t, J=7.5 Hz, 1H), 7.07-6.94 (m, 4H), 6.46 (dd, J=8.4, 2.3 Hz, 1H), 6.35 (t, J=2.4 Hz, 1H), 6.20 (dd, J=8.1, 2.3 Hz, 1H), 4.62 (d, J=14.5 Hz, 1H), 4.45 (d, J=14.5 Hz, 1H), 3.74 (q, J=7.1, 6.1 Hz, 2H), 3.65-3.44 (m, 4H), 3.42-3.16 (m, 3H), 3.08-2.87 (m, 3H), 2.81 (hept, J=7.0 Hz, 1H), 2.69 (td, J=12.1, 2.7 Hz, 1H), 2.50 (tt, J=6.7, 4.2 Hz, 1H), 1.88 (dd, J=10.9, 4.0 Hz, 1H), 1.69 (ddddt, J=24.7, 20.8, 17.3, 8.8, 3.9 Hz, 3H), 1.56 (d, J=1.4 Hz, 6H), 1.35 (s, 9H), 1.17 (d, J=6.9 Hz, 6H), 0.83-0.70 (m, 4H). $^{13}$C NMR (126 MHz, Chloroform-d) δ 176.71, 172.10, 156.23, 154.35, 152.72, 149.12, 138.27, 129.61, 128.44, 125.72, 125.20, 125.12, 109.76, 106.96, 105.67, 80.54, 80.10, 52.06, 49.83, 49.70, 45.77, 42.91, 39.85, 34.03, 29.63, 28.36, 27.76, 26.21, 26.15, 24.50, 24.03, 9.45, 9.10. MS (ESI) m/z=647.5 $[M+H]^+$ tert-butyl (R)-4-(2-(3-(3-((4-(tert-butyl)benzyl)(cyclopropyl)carbamoyl) piperidin-1-yl)phenoxy)-2-methylpropanoyl)piperazine-1-carboxylate (208b). $^1$H NMR (500 MHz, Chloroform-d) δ 7.35-7.29 (m, 2H), 7.18-7.12 (m, 2H), 7.06 (t, J=8.2 Hz, 1H), 6.53 (dd, J=8.3, 2.3 Hz, 1H), 6.42 (t, J=2.3 Hz, 1H), 6.27 (dd, J=8.1, 2.3 Hz, 1H), 4.67 (d, J=14.6 Hz, 1H), 4.49 (d, J=14.6 Hz, 1H), 3.88-3.74 (m, 2H), 3.74-3.49 (m, 4H), 3.43 (tt, J=10.9, 3.5 Hz, 1H), 3.33 (s, 2H), 3.15-2.91 (m, 3H), 2.75 (td, J=12.2, 2.9 Hz, 1H), 2.62 (tt, J=6.6, 4.4 Hz, 1H), 2.00-1.89 (m, 1H), 1.87-1.67 (m, 3H), 1.63 (d, J=1.4 Hz, 6H), 1.42 (s, 9H), 1.30 (s, 9H), 0.89-0.75 (m, 4H). $^{13}$C NMR (126 MHz, Chloroform-d) δ 176.70, 172.09, 156.23, 154.35, 152.75, 149.89, 135.27, 129.62, 127.32, 125.40, 109.78, 107.01, 105.67, 80.55, 80.09, 52.08, 49.83, 49.43, 45.78, 42.91, 39.86, 34.46, 31.38, 29.77, 28.36, 27.83, 26.22, 26.15, 24.50, 9.51, 9.03. MS (ESI) m/z=661.5 $[M+H]^+$ tert-butyl (R)-4-(2-(3-(3-((4-cyclohexylbenzyl)(cyclopropyl)carbamoyl) piperidin-1-yl)phenoxy)-2-methylpropanoyl)piperazine-1-carboxylate (208c). $^1$H NMR (500 MHz, Chloroform-d) δ 7.13 (s, 4H), 7.05 (t, J=8.2 Hz, 1H), 6.52 (dd, J=8.3, 2.3 Hz, 1H), 6.41 (t, J=2.3 Hz, 1H), 6.26 (dd, J=8.2, 2.3 Hz, 1H), 4.65 (d, J=14.6 Hz, 1H), 4.48 (d, J=14.6 Hz, 1H), 3.86-3.72 (m, 2H), 3.71-3.50 (m, 4H), 3.47-3.20 (m, 3H), 3.15-2.92 (m, 3H), 2.75 (td, J=12.2, 2.9 Hz, 1H), 2.66-2.54 (m, 1H), 2.53-2.33 (m, 1H), 1.95 (d, J=11.2 Hz, 1H), 1.90-1.66 (m, 8H), 1.62 (d, J=1.3 Hz, 6H), 1.41 (s, 12H), 1.29-1.18 (m, 2H), 0.91-0.75 (m, 4H). $^{13}$C NMR (126 MHz, Chloroform-d) δ 176.70, 172.09, 156.22, 154.34, 152.74, 146.89, 135.65, 129.62, 127.61, 126.93, 109.77, 107.02, 105.66, 80.53, 80.09, 52.08, 49.83, 49.50, 45.78, 44.21, 42.91, 39.85, 34.47, 29.73, 28.36, 27.80, 26.91, 26.21, 26.16, 24.50, 9.50, 9.04. MS (ESI) m/z=687.5 $[M+H]^+$, 709.4 $[M+Na]^+$ tert-butyl (R)-4-(2-(3-(3-(cyclopropyl(4-morpholinobenzyl)carbamoyl)piperidin-1-yl)phenoxy)-2-methylpropanoyl)piperazine-1-carboxylate (208d). $^1$H NMR (500 MHz, Chloroform-d) δ 7.20-7.11 (m, 2H), 7.05 (t, J=8.2 Hz, 1H), 6.89-6.81 (m, 2H), 6.51 (dd, J=8.4, 2.2 Hz, 1H), 6.40 (t, J=2.3 Hz, 1H), 6.26 (dd, J=8.1, 2.3 Hz, 1H), 4.60 (d, J=14.4 Hz, 1H), 4.45 (d, J=14.4 Hz, 1H), 3.89-3.73 (m, 6H), 3.70-3.49 (m, 4H), 3.45-3.21 (m, 3H), 3.17-2.90 (m, 7H), 2.74 (td, J=12.2, 2.9 Hz, 1H), 2.55 (tt, J=6.8, 4.2 Hz, 1H), 1.92 (d, J=10.8 Hz, 1H), 1.75 (dddd, J=36.9, 15.3, 11.6, 8.3 Hz, 3H), 1.62 (s, 6H), 1.41 (s, 9H), 0.91-0.74 (m, 4H). $^{13}$C NMR (126 MHz, Chloroform-d) δ 176.67, 172.08, 156.23, 154.34, 152.72, 150.34, 129.82, 129.61, 128.88, 115.65, 109.76, 107.02, 105.63, 80.54, 80.09, 66.92, 53.43, 52.07, 49.80, 49.35, 49.07, 45.78, 42.91, 39.82, 29.53, 28.36, 27.78, 26.21, 26.15, 24.47, 9.48, 9.05. MS (ESI) m/z=690.5 $[M+H]^+$ tert-butyl (R)-4-(2-(3-(3-(([1,1'-biphenyl]-4-ylmethyl) (cyclopropyl) carbamoyl) piperidin-1-yl)phenoxy)-2-methylpropanoyl)piperazine-1-carboxylate (208e). $^1$H NMR (500 MHz, Chloroform-d) δ 7.63-7.52 (m, 4H), 7.46-7.39 (m, 2H), 7.37-7.28 (m, 3H), 7.06 (t, J=8.2 Hz, 1H), 6.54 (dd, J=8.3, 2.2 Hz, 1H), 6.43 (t, J=2.4 Hz, 1H), 6.27 (dd, J=8.2, 2.3 Hz, 1H), 4.74 (d, J=14.7 Hz, 1H), 4.57 (d, J=14.7 Hz, 1H), 3.81 (s, 2H), 3.72-3.50 (m, 4H), 3.45 (tt, J=11.0, 3.6 Hz, 1H), 3.32 (s, 2H), 3.13-2.94 (m, 3H), 2.82-2.60 (m, 2H), 2.01-1.94 (m, 1H), 1.88-1.67 (m, 3H), 1.62 (s, 6H), 1.41 (s, 9H), 0.95-0.78 (m, 4H). $^{13}$C NMR (126 MHz, Chloroform-d) δ 176.82, 172.09, 156.24, 154.35, 152.73, 140.82, 140.02, 137.47, 129.65, 128.76, 128.13, 127.28, 127.24, 127.03, 109.79, 107.08, 105.65, 80.54, 80.10, 53.44, 52.09, 49.84, 49.57, 45.79, 42.91, 39.88, 29.84, 28.36, 27.82, 26.21, 26.15, 24.50, 9.54, 9.10. MS (ESI) m/z=681.4 $[M+H]^+$ tert-butyl (R)-4-(2-(3-(3-(cyclopropyl(4-(pyridin-2-yl) benzyl)carbamoyl) piperidin-1-yl)phenoxy)-2-methylpropanoyl)piperazine-1-carboxylate (208f). $^1$H NMR (500 MHz, Chloroform-d) δ 8.67 (dt, J=4.9, 1.3 Hz, 1H), 7.97-7.89 (m, 2H), 7.79-7.65 (m, 2H), 7.34 (d, J=8.1 Hz, 2H), 7.21 (ddd, J=6.6, 4.8, 1.5 Hz, 1H), 7.05 (t, J=8.2 Hz, 1H), 6.52 (dd, J=8.4, 2.3 Hz, 1H), 6.41 (t, J=2.4 Hz, 1H), 6.26 (dd, J=8.1, 2.3 Hz, 1H), 4.75 (d, J=14.6 Hz, 1H), 4.58 (d, J=14.6 Hz, 1H), 3.88-3.73 (m, 2H), 3.73-3.63 (m, 2H), 3.63-3.49 (m, 2H), 3.43 (tt, J=11.0, 3.6 Hz, 1H), 3.32 (s, 2H), 3.14-2.93 (m, 3H), 2.76 (td, J=12.2, 2.8 Hz, 1H), 2.61 (tt, J=6.9, 3.2 Hz, 1H), 2.01-1.89 (m, 1H), 1.89-1.65 (m, 3H), 1.62 (d, J=1.6 Hz, 6H), 1.41 (s, 9H), 0.91-0.77 (m, 4H). $^{13}$C NMR (126 MHz, Chloroform-d) δ 176.81, 172.09, 157.19, 156.24, 154.34, 152.69, 149.68, 139.28, 138.37, 136.73, 129.64, 128.21, 127.12, 122.06, 120.44, 109.77, 107.00, 105.64, 80.54, 80.07, 52.05, 49.80, 49.55, 45.78, 42.90, 39.82, 29.77, 28.35, 27.81, 26.21, 26.14, 24.46, 9.51, 9.06. MS (ESI) m/z=682.4 $[M+H]^+$ tert-butyl (R)-4-(2-(3-(3-(cyclopropyl(4-(pyridin-3-yl) benzyl)carbamoyl) piperidin-1-yl)phenoxy)-2-methylpropanoyl)piperazine-1-carboxylate (208g). $^1$H NMR (500 MHz, Chloroform-d) δ 8.73-8.56 (m, 2H), 7.59 (dd, J=8.1, 1.8 Hz, 2H), 7.51-7.45 (m, 2H), 7.37-7.29 (m, 2H), 7.05 (t, J=8.2 Hz, 1H), 6.52 (dd, J=8.3, 2.3 Hz, 1H), 6.41 (t, J=2.3 Hz, 1H), 6.27 (dd, J=8.2, 2.3 Hz, 1H), 4.74 (d, J=15.1 Hz, 1H), 4.58 (d, J=14.9 Hz, 1H), 3.80 (d, J=6.3 Hz, 2H), 3.72-3.63 (m, 2H), 3.57 (p, J=9.7, 7.7 Hz, 2H), 3.44 (tt, J=11.1, 3.4 Hz, 1H), 3.31 (s, 2H), 3.13-2.95 (m, 3H), 2.81-2.64 (m, 2H), 1.96 (d, J=10.7 Hz, 1H), 1.88-1.69 (m, 3H), 1.41 (d, J=2.4 Hz, 9H), 0.94-0.76 (m, 4H). $^{13}$C NMR (126 MHz, Chloroform-d) δ 176.86, 172.06, 156.25, 154.33, 152.70, 150.25, 147.93, 139.62, 136.89, 129.66, 128.36, 127.18, 121.48, 109.77, 107.21, 105.61, 80.55, 80.10, 52.10, 49.84, 49.69, 45.78, 42.90, 39.88, 29.98, 29.29, 28.35, 27.83, 26.20, 26.15, 24.47, 9.52, 9.10. MS (ESI) m/z=682.4 $[M+H]^+$ tert-butyl (R)-4-(2-(3-(3-(cyclopropyl(4-(pyridin-4-yl) benzyl)carbamoyl) piperidin-1-yl)phenoxy)-2-methylpropanoyl)piperazine-1-carboxylate (208h). $^1$H NMR (500 MHz, Chloroform-d) δ 8.71-8.55 (m, 2H), 7.59 (dd, J=8.1, 1.8 Hz, 2H), 7.52-7.45 (m, 2H), 7.38-7.29 (m, 2H), 7.05 (t, J=8.2 Hz, 1H), 6.52 (dd, J=8.3, 2.3 Hz, 1H), 6.41 (t, J=2.3 Hz, 1H), 6.27 (dd, J=8.2, 2.3 Hz, 1H), 4.74 (d, J=15.1 Hz, 1H), 4.58 (d, J=14.9 Hz, 1H), 3.80 (d, J=6.3 Hz, 2H), 3.73-3.63 (m, 2H), 3.57 (p, J=9.7, 7.7 Hz, 2H), 3.44 (tt, J=11.1, 3.4 Hz, 1H), 3.31 (s, 2H), 3.14-2.94 (m, 3H), 2.75 (td, J=12.1, 3.0 Hz, 1H), 2.67 (tt, J=6.6, 4.0 Hz, 1H), 1.96 (d, J=10.7 Hz, 1H), 1.87-1.68 (m, 3H), 1.62 (s, 6H), 1.41 (d, J=2.4 Hz, 9H), 0.97-0.74 (m, 4H). $^{13}$C NMR (126 MHz, Chloroform-d) δ 176.86, 172.06, 156.25, 154.33, 152.70, 150.25, 147.93, 139.62, 136.89, 129.66, 128.36, 127.18, 121.48, 109.77, 107.21, 105.61, 80.55, 80.10, 52.10, 49.84, 49.69, 45.78, 42.90, 39.88, 29.98, 28.35, 27.83, 26.20, 26.15, 24.47, 9.52, 9.10. MS (ESI) m/z=682.4 $[M+H]^+$ (R)-4-(2-(3-(3-(cyclopropyl(3-isopropylbenzyl)carbamoyl)piperidin-1-yl)phenoxy)-2-methylpropanoyl)piperazin-1-ium chloride (27). $^1$H NMR (500 MHz, Methanol-$d_4$) δ 7.43 (s, 1H), 7.24 (t, J=7.5 Hz, 2H), 7.15-6.99 (m, 4H), 6.81 (s, 1H), 4.93 (s, 1H), 4.41 (d, J=14.8 Hz, 1H), 4.21-3.83 (m, 5H), 3.77-3.68 (m, 2H), 3.68-3.32 (m, 2H), 3.21-2.86 (m, 5H), 2.76 (ddd, J=6.8, 5.5, 3.2 Hz, 1H), 2.19-1.78 (m, 4H), 1.67 (s, 6H), 1.24 (d, J=6.9 Hz, 6H), 1.07-0.85 (m, 4H). $^{13}$C NMR (126 MHz, Methanol-$d_4$) δ 171.78, 156.24, 149.16, 137.79, 130.94, 128.28, 125.02, 124.57, 81.34, 49.61, 43.12, 42.68, 39.49, 33.95, 29.80, 24.92, 24.79, 23.07, 9.15, 7.43. HRMS (ESI) Calcd for $C_{33}H_{46}N_4O_3$ $(M+H)^+$ 547.3643, found 547.3636. HPLC purity 100%, $t_R$=11.93 min (R)-4-(2-(3-(3-((4-(tert-butyl)benzyl)(cyclopropyl)carbamoyl)piperidin-1-yl)phenoxy)-2-methylpropanoyl)piperazin-1-ium chloride (28). $^1$H NMR (500 MHz, Methanol-$d_4$) δ 7.54 (t, J=8.3 Hz, 1H), 7.47-7.33 (m, 3H), 7.29 (s, 1H), 7.19 (d, J=7.9 Hz, 2H), 7.00 (dd, J=8.4, 2.3 Hz, 1H), 4.89 (s, 1H), 4.40 (d, J=14.8 Hz, 1H), 4.02 (d, J=116.9 Hz, 5H), 3.80-3.57 (m, 4H), 3.07 (d, J=107.6 Hz, 4H), 2.84-2.74 (m, 1H), 2.38-1.79 (m, 4H), 1.68 (d, J=2.7 Hz, 6H), 1.30 (s, 9H), 1.12-0.78 (m, 4H). $^{13}$C NMR (126 MHz, Methanol-$d_4$) δ 171.54, 156.30, 150.00, 143.86, 134.70, 131.43, 126.87, 125.13, 118.00, 114.25, 111.30, 81.74, 55.48, 49.31, 43.13, 42.64, 39.56, 33.92, 30.37, 29.84, 24.90, 24.73, 9.30, 7.22. HRMS (ESI) Calcd for $C_{34}H_{48}N_4O_3$ $(M+H)^+$ 561.3799, found 561.3791. HPLC purity 100%, $t_R$=12.49 min (R)-4-(2-(3-(3-((4-cyclohexylbenzyl)(cyclopropyl)carbamoyl)piperidin-1-yl)phenoxy)-2-methylpropanoyl)piperazin-1-ium chloride (29). $^1$H NMR (500 MHz, Methanol-$d_4$) δ 7.46 (t, J=8.2 Hz, 1H), 7.24 (d, J=9.8 Hz, 1H), 7.17 (s, 5H), 6.87 (s, 1H), 4.80 (s, 1H), 4.42 (d, J=14.8 Hz, 1H), 4.25-3.83 (m, 5H), 3.73 (dd, J=12.2, 3.6 Hz, 2H), 3.68-3.40 (m, 2H), 3.24-2.88 (m, 4H), 2.82-2.73 (m, 1H), 2.49 (ddt, J=11.8, 8.5, 3.2 Hz, 1H), 2.21-2.01 (m, 3H), 1.89-1.72 (m, 6H), 1.67 (d, J=2.5 Hz, 6H), 1.47-1.39 (m, 4H), 1.34-1.25 (m, 1H), 1.09-0.84 (m, 4H). $^{13}$C NMR (126 MHz, Methanol-$d_4$) δ 171.72, 156.27, 147.00, 135.16, 131.11, 127.11, 126.66, 113.56, 81.48, 49.37, 44.27, 43.13, 42.71, 34.32, 29.83, 26.59, 25.83, 24.90, 24.79, 9.16, 7.36. HRMS (ESI) Calcd for $C_{36}H_{50}N_4O_3$ $(M+H)^+$ 587.3956, found 587.3948. HPLC purity 99.4%, $t_R$=13.42 min (R)-4-(2-(3-(3-(cyclopropyl(4-morpholinobenzyl)carbamoyl)piperidin-1-yl)phenoxy)-2-methylpropanoyl)piperazin-1-ium chloride (30). $^1$H NMR (500 MHz, Methanol-$d_4$) δ 7.74-7.62 (m, 2H), 7.59-7.41 (m, 4H), 7.35 (s, 1H), 7.03 (dd, J=8.4, 2.3 Hz, 1H), 4.81 (s, 1H), 4.60 (d, J=15.4 Hz, 1H), 4.27-3.84 (m, 9H), 3.81-3.62 (m, 8H), 3.26-2.86 (m, 5H), 2.35-2.09 (m, 3H), 1.95 (s, 1H), 1.68 (d, J=2.3 Hz, 6H), 1.13-0.84 (m, 4H). $^{13}C$ NMR (126 MHz, Methanol-$d_4$) δ 171.47, 156.30, 143.51, 141.23, 140.04, 131.49, 129.02, 120.80, 118.38, 114.40, 111.52, 81.79, 64.17, 55.87, 54.72, 49.31, 43.13, 39.58, 30.19, 24.89, 24.74, 9.15, 7.34. HRMS (ESI) Calcd for $C_{34}H_{47}N_5O_4$ (M+H)+612.3520, found 612.3511. HPLC purity 98.9%, $t_R$=8.94 min (R)-4-(2-(3-(3-(([1,1'-biphenyl]-4-ylmethyl) (cyclopropyl) carbamoyl)piperidin-1-yl)phenoxy)-2-methylpropanoyl)piperazin-1-ium chloride (31). $^1H$ NMR (500 MHz, Methanol-$d_4$) δ 7.64-7.55 (m, 4H), 7.43 (dd, J=8.3, 7.1 Hz, 3H), 7.39-6.62 (m, 6H), 4.88 (d, J=11.1 Hz, 1H), 4.55 (d, J=14.9 Hz, 1H), 4.28-3.79 (m, 5H), 3.74 (dt, J=11.1, 5.4 Hz, 2H), 3.68-3.35 (m, 2H), 3.23-2.82 (m, 5H), 2.23-1.79 (m, 4H), 1.67 (d, J=2.6 Hz, 6H), 1.12-0.79 (m, 4H). $^{13}C$ NMR (126 MHz, Methanol-$d_4$) δ 171.76, 156.26, 140.57, 140.14, 136.96, 131.02, 128.49, 127.66, 127.00, 126.82, 126.47, 81.39, 49.41, 43.11, 42.68, 39.60, 29.93, 24.89, 24.79, 9.16, 7.47. HRMS (ESI) Calcd for $C_{36}H_{44}N_4O_3$ (M+Na)+ 603.3306, found 603.3293. HPLC purity 100%, $t_R$=12.29 min (R)-4-(2-(3-(3-(cyclopropyl(4-(pyridin-2-yl)benzyl)carbamoyl)piperidin-1-yl)phenoxy)-2-methylpropanoyl)piperazin-1-ium chloride (33). $^1H$ NMR (500 MHz, Methanol-$d_4$) δ 8.84 (dd, J=6.0, 1.5 Hz, 1H), 8.68 (td, J=8.0, 1.6 Hz, 1H), 8.41 (d, J=8.2 Hz, 1H), 8.07-8.03 (m, 1H), 7.97 (d, J=8.2 Hz, 2H), 7.61-7.50 (m, 3H), 7.50-7.27 (m, 2H), 7.02 (dd, J=8.4, 2.3 Hz, 1H), 4.93 (s, 1H), 4.68 (d, J=15.6 Hz, 1H), 4.36-3.85 (m, 5H), 3.84-3.66 (m, 4H), 3.27-2.88 (m, 5H), 2.36-1.83 (m, 4H), 1.68 (d, J=2.0 Hz, 6H), 1.13-0.88 (m, 4H). $^{13}C$ NMR (126 MHz, Methanol-$d_4$) δ 171.48, 156.29, 152.36, 146.94, 143.62, 143.24, 141.61, 131.48, 129.66, 128.39, 128.23, 125.87, 125.23, 118.27, 114.39, 111.48, 81.77, 57.82, 55.85, 49.71, 43.13, 42.61, 39.60, 30.33, 24.90, 24.74, 9.21, 7.35. HRMS (ESI) Calcd for $C_{35}H_{43}N_5O_3$ $(M+H)^+$ 582.3439, found 582.3432. HPLC purity 97.1%, $t_R$=8.05 min (R)-4-(2-(3-(3-(cyclopropyl(4-(pyridin-3-yl)benzyl)carbamoyl)piperidin-1-yl)phenoxy)-2-methylpropanoyl)piperazin-1-ium chloride (34). $^1H$ NMR (500 MHz, Methanol-$d_4$) δ 9.20 (d, J=2.1 Hz, 1H), 8.94 (dt, J=8.3, 1.8 Hz, 1H), 8.84 (dt, J=5.6, 1.0 Hz, 1H), 8.19 (dd, J=8.3, 5.7 Hz, 1H), 7.91-7.75 (m, 2H), 7.65-7.23 (m, 5H), 7.03 (dd, J=8.4, 2.3 Hz, 1H), 4.92 (d, J=15.8 Hz, 1H), 4.60 (d, J=15.4 Hz, 1H), 4.35-3.83 (m, 5H), 3.82-3.63 (m, 4H), 3.27-2.73 (m, 5H), 2.43-1.76 (m, 4H), 1.68 (d, J=2.1 Hz, 6H), 1.15-0.86 (m, 4H). $^{13}C$ NMR (126 MHz, Methanol-$d_4$) δ 171.49, 156.30, 144.24, 143.51, 140.57, 140.33, 139.54, 139.36, 132.40, 131.50, 128.36, 127.43, 118.43, 114.42, 111.54, 81.80, 49.52, 43.13, 30.16, 24.89, 24.72, 9.24, 7.27. HRMS (ESI) Calcd for $C_{35}H_{43}N_5O_3$ $(M^+ Na)^+$ 604.3258, found 604.3249. HPLC purity 99.2%, $t_R$=8.21 min (R)-4-(2-(3-(3-(cyclopropyl(4-(pyridin-4-yl)benzyl)carbamoyl)piperidin-1-yl)phenoxy)-2-methylpropanoyl)piperazin-1-ium chloride (35). $^1H$ NMR (500 MHz, Methanol-$d_4$) δ 8.90-8.83 (m, 2H), 8.45-8.38 (m, 2H), 8.00 (d, J=8.3 Hz, 2H), 7.64-7.25 (m, 5H), 7.04 (dd, J=8.4, 2.2 Hz, 1H), 4.93 (d, J=15.7 Hz, 1H), 4.64 (d, J=15.5 Hz, 1H), 4.35-3.85 (m, 5H), 3.83-3.65 (m, 4H); 3.27-2.87 (m, 5H), 2.43-1:85 (m, 4H), 1.68 (d, J=2.0 Hz, 6H), 1.14-0.90 (m, 4H). $^{13}C$ NMR (126 MHz, Methanol-$d_4$) δ 171.48, 157.71, 156.30, 143.46, 142.81, 141.41, 133.21, 131.51, 128.41, 128.14, 124.05, 118.48, 114.45, 111.57, 81.80, 49.65, 43.13, 30.25, 24.89, 24.73, 9.25, 7.30. HRMS (ESI) Calcd for $C_{35}H_{43}N_5O_3$ $(M^+ Na)^+$ 604.3258, found 604.3251. HPLC purity 98.8%, $t_R$=13.07 min tert-butyl (R)-4-(2-(3-(3-((4-bromobenzyl)(cyclopropyl) carbamoyl)piperidin-1-yl)phenoxy)-2-methylpropanoyl) piperazine-1-carboxylate (209). $^1H$ NMR (500 MHz, Chloroform-d) δ 7.47-7.40 (m, 2H), 7.16-7.11 (m, 2H), 7.07 (t, J=8.2 Hz, 1H), 6.53 (dd, J=8.3, 2.2 Hz, 1H), 6.42 (t, J=2.4 Hz, 1H), 6.29 (dd, J=8.1, 2.3 Hz, 1H), 4.63 (d, J=14.7 Hz, 1H), 4.49 (d, J=14.7 Hz, 1H), 3.82 (q, J=4.7 Hz, 2H), 3.72-3.49 (m, 4H), 3.42 (ddt, J=10.9, 7.0, 3.5 Hz, 1H), 3.33 (s, 2H), 3.08 (d, J=5.3 Hz, 2H), 3.02-2.92 (m, 1H), 2.80-2.72 (m, 1H), 2.62 (tt, J=7.0, 3.9 Hz, 1H), 1.99-1.86 (m, 1H), 1.86-1.78 (m, 1H), 1.73 (td, J=11.0, 5.6 Hz, 2H), 1.64 (d, J=1.5 Hz, 6H), 1.43 (s, 9H), 0.96-0.76 (m, 4H). $^{13}C$ NMR (126 MHz, Chloroform-d) δ 176.79, 172.05, 156.24, 154.33, 152.65, 137.49, 131.64, 129.66, 129.50, 120.97, 109.72, 107.16, 105.55, 80.54, 80.09, 52.03, 49.78, 49.35, 45.77, 42.89, 39.81, 38.61, 29.79, 28.35, 27.76, 26.18, 26.16, 24.43, 9.47, 9.09. MS (ESI) m/z=683.3 $[M+H]^+$ tert-butyl (R)-4-(2-(3-(3-(cyclopropyl(4-(thiophen-3-yl) benzyl)carbamoyl) piperidin-1-yl)phenoxy)-2-methylpropanoyl)piperazine-1-carboxylate (210a). $^1H$ NMR (500 MHz, Chloroform-d) δ 7.63-7.51 (m, 2H), 7.46 (t, J=2.2 Hz, 1H), 7.40 (d, J=2.1 Hz, 2H), 7.31-7.27 (m, 2H), 7.09 (t, J=8.2 Hz, 1H), 6.56 (dd, J=8.3, 2.3 Hz, 1H), 6.45 (t, J=2.3 Hz, 1H), 6.30 (dd, J=8.2, 2.3 Hz, 1H), 4.73 (d, J=14.6 Hz, 1H), 4.57 (d, J=14.6 Hz, 1H), 3.83 (s, 2H), 3.70 (t, J=9.3 Hz, 2H), 3.66-3.53 (m, 2H), 3.46 (ddt, J=10.9, 6.9, 3.5 Hz, 1H), 3.35 (s, 2H), 3.18-2.92 (m, 3H), 2.85-2.72 (m, 1H), 2.65 (tt, J=6.5, 3.5 Hz, 1H), 2.03-1.92 (m, 1H), 1.88-1.67 (m, 3H), 1.65 (s, 6H), 1.44 (s, 9H), 0.98-0.79 (m, 4H). $^{13}C$ NMR (126 MHz, Chloroform-d) δ 176.79, 172.09, 156.24, 154.35, 152.72, 141.99, 137.32, 134.74, 129.64, 128.23, 126.59, 126.25, 126.22, 120.15, 109.78, 107.11, 105.65, 80.55, 80.10, 53.42, 52.09, 49.83, 49.56, 45.78, 42.91, 39.87, 29.78, 28.36, 27.81, 26.21, 26.15, 24.49, 9.51, 9.09. MS (ESI) m/z=687.5 $[M+H]^+$ tert-butyl (R)-4-(2-(3-(3-((4-(1H-pyrazol-5-yl)benzyl) (cyclopropyl)carbamoyl) piperidin-1-yl)phenoxy)-2-methylpropanoyl)piperazine-1-carboxylate (210b). $^1H$ NMR (500 MHz, Chloroform-d) δ 7.76-7.66 (m, 2H), 7.61-7.53 (m, 1H), 7.47 (ddd, J=8.4, 6.9, 2.9 Hz, 1H), 7.33-7.24 (m, 2H), 7.07 (t, J=8.2 Hz, 1H), 6.63-6.50 (m, 2H), 6.43 (t, J=2.3 Hz, 1H), 6.29 (dd, J=8.1, 2.3 Hz, 1H), 4.71 (d, J=14.7 Hz, 1H), 4.59 (d, J=14.6 Hz, 1H), 3.89-3.51 (m, 6H), 3.51-3.24 (m, 3H), 3.18-2.89 (m, 3H), 2.77 (td, J=12.1, 2.8 Hz, 1H), 2.63 (td, J=6.8, 3.3 Hz, 1H), 2.05-1.91 (m, 1H), 1.89-1.67 (m, 3H), 1.64 (d, J=1.8 Hz, 6H), 1.43 (s, 9H), 0.94-0.77 (m, 4H). $^{13}C$ NMR (126 MHz, Chloroform-d) δ 176.87, 172.14, 156.21, 154.39, 152.73, 138.07, 132.84, 132.14, 132.06, 131.98, 131.96, 129.66, 128.57, 128.47, 128.18, 125.93, 109.84, 107.21, 105.70, 102.42, 80.54, 80.17, 53.44, 52.18, 49.83, 49.63, 45.78, 42.92, 39.89, 29.79, 28.37, 27.77, 26.18, 24.46, 9.45, 9.13. MS (ESI) m/z=671.5 $[M+H]^+$, 669.4 $[M-H]^-$ tert-butyl (R)-4-(2-(3-(3-((4-(1H-pyrazol-4-yl)benzyl) (cyclopropyl)carbamoyl) piperidin-1-yl)phenoxy)-2-methylpropanoyl)piperazine-1-carboxylate (210c). $^1H$ NMR (500 MHz, Chloroform-d) δ 7.80 (s, 2H), 7.43 (d, J=7.9 Hz, 2H), 7.22 (d, J=7.9 Hz, 2H), 7.05 (t, J=8.2 Hz, 1H), 6.53 (dd, J=8.4, 2.2 Hz, 1H), 6.42 (t, J=2.3 Hz, 1H), 6.27 (dd, J=8.2, 2.3 Hz, 1H), 4.69 (d, J=14.7 Hz, 1H), 4.52 (d, J=14.7 Hz, 1H), 3.88-3.72 (m, 2H), 3.72-3.63 (m, 2H), 3.63-3.52 (m, 2H), 3.44 (tt, J=11.0, 3.5 Hz, 1H), 3.38-3.25 (m, 2H), 3.14-2.91 (m, 3H), 2.76 (td, J'=12.1, 2.8 Hz, 1H), 2.63 (td, J=6.7, 3.2 Hz, 1H), 1.98-1.92 (m, 1H), 1.85-1.67 (m, 3H), 1.62 (s, 6H), 1.41 (s, 9H), 0.94-0.70 (m, 4H). $^{13}C$ NMR (126 MHz, Chloroform-d) δ 176.91, 172.14, 156.23, 154.38, 152.70, 136.55, 131.47, 129.66, 128.21, 125.87, 122.23, 109.82, 107.13, 105.67, 80.55, 80.15, 53.44, 52.10, 49.82, 49.65, 45.78, 42.92, 39.86, 29.85, 28.36, 27.81, 26.21, 26.15, 24.45, 9.49, 9.07. MS (ESI) m/z=671.5 $[M+H]^+$, 669.3 $[M-H]^+$ tert-butyl (R)-4-(2-(3-(3-(cyclopropyl(4-(1-methyl-1H-pyrazol-4-yl)benzyl) carbamoyl)piperidin-1-yl)phenoxy)-2-methylpropanoyl)piperazine-1-carboxylate (210d). $^1$H NMR (500 MHz, Chloroform-d) δ 7.76 (d, J=0.9 Hz, 1H), 7.61 (s, 1H), 7.47-7.37 (m, 2H), 7.25 (d, J=8.0 Hz, 2H), 7.08 (t, J=8.2 Hz, 1H), 6.55 (dd, J=8.3, 2.2 Hz, 1H), 6.44 (t, J=2.3 Hz, 1H), 6.29 (dd, J=8.2, 2.3 Hz, 1H), 4.70 (d, J=14.6 Hz, 1H), 4.55 (d, J=14.6 Hz, 1H), 3.96 (s, 3H), 3.83 (s, 2H), 3.75-3.52 (m, 4H), 3.51-3.24 (m, 3H), 3.15-2.94 (m, 3H), 2.78 (td, J=12.1, 2.9 Hz, 1H), 2.69-2.56 (m, 1H), 1.97 (d, J=11.1 Hz, 1H), 1.90-1.69 (m, 3H), 1.64 (s, 6H), 1.44 (s, 9H), 0.92-0.83 (m, 4H). $^{13}$C NMR (126 MHz, Chloroform-d) δ 176.77, 172.08, 156.23, 154.34, 152.71, 136.70, 136.47, 131.52, 129.64, 128.32, 126.84, 125.64, 122.93, 109.77, 107.10, 105.63, 80.54, 80.10, 53.43, 52.09, 49.82, 49.54, 45.78, 42.90, 39.85, 39.10, 29.72, 28.36, 27.80, 26.20, 26.15, 24.48, 9.50, 9.08. MS (ESI) m/z=685.4 $[M+H]^+$ tert-butyl (R)-4-(2-(3-(3-(cyclopropyl(4-(3-methyl-1H-pyrazol-4-yl)benzyl) carbamoyl)piperidin-1-yl)phenoxy)-2-methylpropanoyl)piperazine-1-carboxylate (210e). $^1$H NMR (500 MHz, Chloroform-d) δ 7.58 (s, 1H), 7.30-7.24 (m, 2H), 7.21-7.13. (m, 2H), 6.99 (t, J=8.2 Hz, 1H), 6.47 (dd, J=8.4, 2.2 Hz, 1H), 6.36 (t, J=2.3 Hz, 1H), 6.20 (dd, J=8.1, 2.3 Hz, 1H), 4.65 (d, J=14.7 Hz, 1H), 4.47 (d, J=14.7 Hz, 1H), 3.82-3.67 (m, 2H), 3.66-3.44 (m, 4H), 3.38 (tt, J=10.9, 3.6 Hz, 1H), 3.26 (s, 2H), 3.07-2.87 (m, 3H), 2.69 (td, J=12.1, 2.8 Hz, 1H), 2.59 (tt, J=10.0, 3.7 Hz, 1H), 2.37 (s, 3H), 1.94-1.84 (m, 1H), 1.80-1.62 (m, 3H), 1.58-1.54 (m, 6H), 1.34 (s, 9H), 0.87-0.68 (m, 4H). $^{13}$C NMR (126 MHz, Chloroform-d) δ 176.90, 172.14, 156.23, 154.37, 152.72, 136.16, 132.43, 129.65, 127.93, 127.48, 119.58, 109.83, 107.12, 105.68, 80.55, 80.15, 52.10, 49.85, 49.65, 45.78, 42.93, 39.87, 29.89, 28.36, 27.83, 26.21, 26.15, 24.47, 11.67, 9.52, 9.05. MS (ESI) m/z=685.4 $[M+H]^+$ tert-butyl (R)-4-(2-(3-(3-(cyclopropyl(4-(3,5-dimethyl-1H-pyrazol-4-yl)benzyl) carbamoyl)piperidin-1-yl)phenoxy)-2-methylpropanoyl)piperazine-1-carboxylate (210f). $^1$H NMR (500 MHz, Chloroform-d) δ 7.22-7.08 (m, 4H), 6.99 (t, J=8.2 Hz, 1H), 6.47 (dd, J=8.3, 2.3 Hz, 1H), 6.36 (t, J=2.3 Hz, 1H), 6.20 (dd, J=8.1, 2.3 Hz, 1H), 4.68 (d, J=14.8 Hz, 1H), 4.48 (d, J=14.8 Hz, 1H), 3.75 (q, J=5.8 Hz, 2H), 3.68-3.45 (m, 4H), 3.40 (tt, J=10.8, 3.4 Hz, 1H), 3.33-3.18 (m, 2H), 3.07-2.84 (m, 3H), 2.77-2.57 (m, 2H), 2.23 (s, 6H), 1.95-1.84 (m, 1H), 1.81-1.61 (m, 3H), 1.56 (d, J=1.7 Hz, 6H), 1.34 (s, 9H), 0.86-0.74 (m, 4H). $^{13}$C NMR (126 MHz, Chloroform-d) δ 176.87, 172.10, 156.23, 154.36, 152.73, 141.85, 136.17, 132.59, 129.64, 129.33, 127.59, 118.00, 109.80, 107.08, 105.68, 80.55, 80.13, 52.10, 49.86, 49.69, 45.78, 42.92, 39.88, 29.96, 27.86, 26.22, 26.13, 24.50, 11.66, 9.54, 9.03. MS (ESI) m/z=699.5 $[M+H]^+$ tert-butyl (R)-4-(2-(3-(3-(cyclopropyl(4-(3,5-dimethyl-isoxazol-4-yl)benzyl) carbamoyl)piperidin-1-yl)phenoxy)-2-methylpropanoyl)piperazine-1-carboxylate (210g). $^1$H NMR (500 MHz, Chloroform-d) δ 7.32-7.28 (m, 2H), 7.25-7.17 (m, 2H), 7.09 (t, J=8.2 Hz, 1H), 6.56 (dd, J=8.2, 2.3 Hz, 1H), 6.45 (t, J=2.3 Hz, 1H), 6.30 (dd, J=8.1, 2.3 Hz, 1H), 4.76 (d, J=14.9 Hz, 1H), 4.58 (d, J=14.9 Hz, 1H), 3.89-3.75 (m, 2H), 3.75-3.67 (m, 2H), 3.61 (s, 2H), 3.48 (tt, J=10.9, 3.6 Hz, 1H), 3.42-3.28 (m, 2H), 3.13-2.95 (m, 3H), 2.85-2.68 (m, 2H), 2.42 (s, 3H), 2.29 (s, 3H), 2.00 (d, J=9.9 Hz, 1H), 1.92-1.68 (m, 3H), 1.65 (d, J=1.7 Hz, 6H), 1.44 (s, 9H), 0.99-0.80 (m, 4H). $^{13}$C NMR (126 MHz, Chloroform-d) δ 176.88, 172.06, 165.16, 158.68, 156.25, 154.35, 152.73, 137.78, 129.65, 129.19, 127.85, 116.31, 109.78, 107.22, 105.65, 80.56, 77.29, 53.43, 52.10, 49.88, 49.75, 45.79, 42.91, 39.90, 30.06, 28.35, 27.87, 26.22, 26.14, 24.51, 11.63, 10.88, 9.53, 9.04. MS (ESI) m/z=700.5 $[M+H]^+$, 722.5 $[M+Na]^+$ tert-butyl (R)-4-(2-(3-(3-((4-(1H-indol-3-yl)benzyl)(cyclopropyl)carbamoyl) piperidin-1-yl)phenoxy)-2-methylpropanoyl)piperazine-1-carboxylate (210h). $^1$H NMR (500 MHz, Chloroform-d) δ 8.22 (d, J=8.3 Hz, 1H), 7.84-7.77 (m, 1H), 7.70 (s, 1H), 7.63-7.55 (m, 2H), 7.39-7.27 (m, 4H), 7.07 (t, J=8.2 Hz, 1H), 6.55 (dd, J=8.2, 2.3 Hz, 1H), 6.43 (t, J=2.3 Hz, 1H), 6.28 (dd, J=8.2, 2.3 Hz, 1H), 4.76 (d, J=14.6 Hz, 1H), 4.58 (d, J=14.7 Hz, 1H), 3.88-3.74 (m, 2H), 3.74-3.65 (m, 2H), 3.59 (s, 2H), 3.46 (tt, J=11.0, 3.6 Hz, 1H), 3.33 (s, 2H), 3.04 (dt, J=23.2, 12.3 Hz, 3H), 2.83-2.73 (m, 1H), 2.68 (td, J=6.7, 3.3 Hz, 1H), 1.99 (d, J=11.7 Hz, 1H), 1.84 (d, J=14.0 Hz, 1H), 1.81-1.73 (m, 2H), 1.69 (s, 11H), 1.63 (s, 7H), 1.42 (s, 10H), 0.95-0.84 (m, 4H). MS (ESI) m/z=720.5 $[M+H]^+$, 718.4 $[M-H]^+$ tert-butyl (R)-4-(2-(3-(3-((4-(1/1-pyrrolo[2,3-b]pyridin-3-yl)benzyl) (cyclopropyl) carbamoyl)piperidin-1-yl)phenoxy)-2-methylpropanoyl)piperazine-1-carboxylate (210i). $^1$H NMR (500 MHz, Chloroform-d) δ 10.65 (s, 1H), 8.38 (dd, J=4.9, 1.5 Hz, 1H), 8.26 (dd, J=8.0, 1.5 Hz, 1H), 7.68-7.57 (m, 2H), 7.55 (d, J=2.0 Hz, 1H), 7.32 (d, J=7.9 Hz, 2H), 7.17 (dd, J=7.9, 4.7 Hz, 1H), 7.06 (t, J=8.2 Hz, 1H), 6.54 (dd, J=8.2, 2.3 Hz, 1H), 6.43 (t, J=2.3 Hz, 1H), 6.27 (dd, J=8.2, 2.3 Hz, 1H), 4.74 (d, J=14.6 Hz, 1H), 4.59 (d, J=14.6 Hz, 1H), 3.89-3.51 (m, 6H), 3.46 (tt, J=11.0, 3.4 Hz, 1H), 3.32 (s, 2H), 3.12-2.96 (m, 3H), 2.86-2.64 (m, 2H), 1.98 (d, J=11.7 Hz, 1H), 1.88-1.72 (m, 3H), 1.62 (s, 6H), 1.41 (s, 9H), 0.96-0.82 (m, 4H). $^{13}$C NMR (126 MHz, Chloroform-d) δ 176.8, 172.1, 156.2, 154.4, 152.7, 149.3, 143.1, 136.3, 133.8, 129.6, 128.4, 128.3, 127.1, 122.1, 118.5, 116.3, 116.1, 109.8, 107.1, 105.7, 80.6, 80.1, 52.1, 49.8, 49.6, 45.8, 42.9, 39.9, 29.8, 28.4, 27.8, 26.2, 26.1, 24.5, 9.5, 9.1. MS (ESI) m/z=721.5 $[M+H]^+$ (R)-4-(2-(3-(3-(cyclopropyl(4-(thiophen-3-yl)benzyl)carbamoyl)piperidin-1-yl)phenoxy)-2-methylpropanoyl)piperazin-1-ium chloride (32). $^1$H NMR (500 MHz, Methanol-$d_4$) δ 7.68-7.55 (m, 3H), 7.51-7.41 (m, 3H), 7.30 (d, J=7.9 Hz, 3H), 7.00 (d, J=127.8 Hz, 2H), 4.87 (d, J=12.4 Hz, 1H), 4.50 (d, J=14.9 Hz, 1H), 4.20-3.82 (m, 5H), 3.74 (ddd, J=12.4, 8.4, 4.0 Hz, 2H), 3.68-3.40 (m, 2H), 3.20-2.81 (m, 5H), 2.20-1.86 (m, 4H), 1.67 (d, J=2.6 Hz, 6H), 1.10-0.88 (m, 4H). $^{13}$C NMR (126 MHz, Methanol-$d_4$) δ 171.71, 156.27, 141.68, 136.61, 134.94, 131.12, 127.68, 126.14, 125.98, 125.63, 119.86, 81.48, 49.44, 43.12, 42.68, 39.53, 29.91, 24.89, 24.78, 9.19, 7.43. HRMS (ESI) Calcd for $C_{34}H_{42}N_4O_3S$ $(M+H)^+$ 609.2870, found 609.2861. HPLC purity 99.4%, $t_R$=11.90 min (R)-4-(2-(3-(3-((4-(1H-pyrazol-5-yl)benzyl)(cyclopropyl)carbamoyl)piperidin-1-yl)phenoxy)-2-methylpropanoyl)piperazin-1-ium chloride (36). $^1$H NMR (500 MHz, Methanol-$d_4$) δ 8.23 (d, J=2.7 Hz, 1H), 7.83 (d, J=8.2 Hz, 2H), 7.64 (ddt, J=9.9, 6.7, 1.8 Hz, 1H), 7.56 (td, J=7.8, 7.4, 2.4 Hz, 2H), 7.46 (d, J=7.9 Hz, 3H), 7.37 (s, 1H), 7.09 (d, J=2.7 Hz, 1H), 7.04 (dd, J=8.4, 2.3 Hz, 1H), 4.91 (s, 1H), 4.59 (d, J=15.4 Hz, 1H), 4.37-3.84 (m, 5H), 3.82-3.63 (m, 4H), 3.26-2.81 (m, 5H), 2.39-1.84 (m, 4H), 1.68 (d, J=2.1 Hz, 6H), 1.14-0.85 (m, 4H). $^{13}$C NMR (126 MHz, Methanol-$d_4$) δ 171.46, 156.30, 147.62, 143.36, 141.04, 134.78, 132.39, 131.71, 131.63, 131.52, 128.63, 128.53, 128.10, 126.73, 125.82, 118.58, 114.49, 111.64, 104.37, 81.81, 55.91, 49.64, 43.13, 42.70, 39.62, 30.17, 24.90, 24.72, 9.26, 7.27. HRMS (ESI) Calcd for $C_{33}H_{42}N_6O_3$ $(M^+ Na)^+$ 593.3211, found 593.3203. HPLC purity 99.1%, $t_R$=9.41 min (R)-4-(2-(3-(3-((4-(1H-pyrazol-4-yl)benzyl)(cyclopropyl)carbamoyl)piperidin-1-yl)phenoxy)-2-methylpropanoyl)piperazin-1-ium chloride (37). $^1$H NMR (500 MHz, Methanol-$d_4$) δ 8.55 (d, J=8.3 Hz, 2H), 7.76-7.62 (m, 2H), 7.56 (t, J=8.3 Hz, 1H), 7.46 (d, J=8.0 Hz, 1H), 7.35 (d, J=7.9 Hz, 3H), 7.04 (dd, J=8.4, 2.3 Hz, 1H), 4.90 (s, 1H), 4.50 (d, J=15.0 Hz, 1H), 4.04 (d, J=128.1 Hz, 5H), 3.82-3.66 (m, 4H), 3.26-2.73 (m, 5H), 2.35-1.84 (m, 4H), 1.68 (d, J=2.2 Hz, 6H), 1.13-0.85 (m, 4H). $^{13}$C NMR (126 MHz, Methanol-$d_4$) δ 171.47, 156.30, 143.36, 137.85, 131.53, 130.68, 128.64, 127.98, 125.95, 123.82, 118.58, 114.49, 111.63, 81.81, 58.25, 55.92, 49.49, 43.13, 42.69, 39.55, 29.99, 24.90, 24.71, 9.30, 7.24. HRMS (ESI) Calcd for $C_{33}H_{42}N_6O_3$ $(M^+ Na)^+$ 593.3211, found 593.3204. HPLC purity 96.8%, $t_R$=9.35 min (R)-4-(2-(3-(3-(cyclopropyl(4-(1-methyl-1H-pyrazol-4-yl)benzyl)carbamoyl) piperidin-1-yl)phenoxy)-2-methylpropanoyl)piperazin-1-ium chloride (38). $^1$H NMR (500 MHz, Methanol-$d_4$) δ 8.11 (s, 1H), 8.00 (d, J=0.9 Hz, 1H), 7.60-7.50 (m, 3H), 7.48-7.37 (m, 1H), 7.37-7.24 (m, 3H), 7.04 (dd, J=8.3, 2.3 Hz, 1H), 4.89 (s, 1H), 4.45 (d, J=14.9 Hz, 1H), 4.23-3.61 (m, 12H), 3.27-2.77 (m, 5H), 2.34-1.79 (m, 4H), 1.68 (d, J=2.6 Hz, 6H), 1.12-0.86 (m, 4H). $^{13}$C NMR (126 MHz, Methanol-$d_4$) δ 171.49, 156.31, 143.36, 136.43, 134.78, 131.53, 130.67, 129.00, 127.84, 125.38, 123.12, 118.58, 114.45, 111.61, 81.82, 49.48, 43.13, 37.51, 29.91, 24.89, 24.70, 9.34, 7.22. HRMS (ESI) Calcd for $C_{34}H_{44}N_6O_3$ $(M^+ Na)^+$ 607.3367, found 607.3356. HPLC purity 98.5%, $t_R$=9.90 min (R)-4-(2-(3-(3-(cyclopropyl(4-(3-methyl-1H-pyrazol-4-yl)benzyl)carbamoyl) piperidin-1-yl)phenoxy)-2-methylpropanoyl)piperazin-1-ium chloride (39). $^1$H NMR (500 MHz, Methanol-$d_4$) δ 8.35 (s, 1H), 7.59-7.47 (m, 4H), 7.39 (t, J=8.0 Hz, 3H), 7.03 (dd, J=8.3, 2.2 Hz, 1H), 4.87 (d, J=15.1 Hz, 1H), 4.54 (d, J=15.2 Hz, 1H), 4.35-3.85 (m, 5H), 3.83-3.67 (m, 4H), 3.28-2.84 (m, 5H), 2.57 (s, 3H), 2.39-1.91 (m, 4H), 1.68 (d, J=2.4 Hz, 6H), 1.16-0.85 (m, 4H). $^{13}$C NMR (126 MHz, Methanol-$d_4$) δ 175.59, 171.43, 156.26, 143.53, 141.81, 137.85, 132.54, 131.51, 128.84, 128.16, 127.87, 127.79, 127.38, 121.57, 118.39, 114.53, 111.61, 81.77, 57.93, 56.00, 49.52, 43.14, 42.67, 39.57, 37.11, 30.11, 24.97, 24.80, 24.03, 21.94, 9.51, 9.31, 7.37. HRMS (ESI) Calcd for $C_{34}H_{44}N_6O_3$ $(M^+ Na)^+$ 585.3548, found 585.3538. HPLC purity 98.7%, $t_R$=9.22 min (R)-4-(2-(3-(3-(cyclopropyl(4-(3,5-dimethyl-1H-pyrazol-4-yl)benzyl)carbamoyl) piperidin-1-yl)phenoxy)-2-methylpropanoyl)piperazin-1-ium chloride (40). $^1$H NMR (500 MHz, Methanol-$d_4$) δ 7.51 (t, J=8.3 Hz, 1H), 7.44-7.31 (m, 5H), 7.27 (s, 1H), 7.00-6.81 (m, 1H), 4.56 (dd, J=15.3, 2.3 Hz, 1H), 4.04 (d, J=122.9 Hz, 5H), 3.85-3.40 (m, 5H), 3.27-2.87 (m, 5H), 2.39 (s, 6H), 2.28-2.09 (m, 3H), 1.95 (d, J=8.1 Hz, 1H), 1.68 (d, J=1.9 Hz, 6H), 1.12-0.90 (m, 4H). $^{13}$C NMR (126 MHz, Methanol-$d_4$) δ 171.60, 156.27, 144.62, 142.92, 138.04, 133.00, 131.28, 129.48, 128.47, 127.62, 119.94, 117.12, 113.95, 110.82, 81.61, 57.27, 55.14, 49.54, 43.13, 42.66, 39.56, 37.39, 30.13, 24.92, 24.78, 24.36, 22.09, 9.19, 9.00, 7.39. HRMS (ESI) Calcd for $C_{35}H_{46}N_6O_3$ $(M^+ Na)^+$ 599.3704, found 599.3691. HPLC purity 96.8%, $t_R$=8.84 min (R)-4-(2-(3-(3-(cyclopropyl(4-(3,5-dimethylisoxazol-4-yl)benzyl)carbamoyl) piperidin-1-yl)phenoxy)-2-methylpropanoyl)piperazin-1-ium chloride (41). $^1$H NMR (500 MHz, Methanol-$d_4$) δ 7.44-7.30 (m, 5H), 7.28-6.56 (m, 3H), 4.87 (d, J=11.8 Hz, 1H), 4.57 (d, J=15.2 Hz, 1H), 4.21-3.82 (m, 5H), 3.78-3.68 (m, 2H), 3.67-3.32 (m, 2H), 3.22-3.08 (m, 2H), 3.01-2.80 (m, 3H), 2.40 (s, 3H), 2.24 (s, 3H), 2.18-1.81 (m, 4H), 1.67 (d, J=1.9 Hz, 6H), 1.09-0.88 (m, 4H). $^{13}$C NMR (126 MHz, Methanol-$d_4$) δ 171.87, 165.50, 158.56, 156.24, 137.57, 130.83, 129.08, 128.97, 127.53, 116.18, 81.25, 49.47, 43.13, 39.52, 30.05, 24.90, 24.83, 10.02, 9.30, 9.03, 7.54. HRMS (ESI) Calcd for $C_{35}H_{45}N_5O_4$ $(M^+ Na)^+$ 622.3364, found 622.3351. HPLC purity 99.5%, $t_R$=10.73 min (R)-4-(2-(3-(3-((4-(1/1-indol-3-yl)benzyl)(cyclopropyl) carbamoyl)piperidin-1-yl)phenoxy)-2-methylpropanoyl) piperazin-1-ium (42). $^1$H NMR (500 MHz, Methanol-$d_4$) δ 7.85 (d, J=7.4 Hz, 1H), 7.65 (d, J=6.1 Hz, 2H), 7.58-7.20 (m, 7H), 7.18-6.96 (m, 3H), 4.45 (d, J=13.5 Hz, 1H), 4.02 (d, J=128.1 Hz, 5H), 3.69 (dd, J=51.6, 20.5 Hz, 4H), 3.26-2.68 (m, 5H), 2.47-1.80 (m, 4H), 1.66 (s, 6H), 1.14-0.81 (m, 4H). $^{13}$C NMR (126 MHz, Methanol-$d_4$) δ 171.48, 156.27, 143.35, 137.27, 135.43, 134.68, 131.63, 127.67, 126.86, 125.37, 122.34, 121.39, 119.37, 118.83, 118.60, 116.24, 114.59, 111.78, 111.40, 81.79, 56.15, 49.68, 43.34, 42.92, 39.69, 30.02, 25.04, 24.84, 21.87, 9.64, 7.44. HRMS (ESI) Calcd for $C_{38}H_{45}N_5O_3$ $(M^+ Na)^+$ 642.3415, found 642.3406. HPLC purity 99.5, $t_R$=11.57 min.

(R)-4-(2-(3-(3-((4-(1/1-pyrrolo[2,3-b]pyridin-3-yl)benzyl) (cyclopropyl) carbamoyl)piperidin-1-yl)phenoxy)-2-methylpropanoyl)piperazin-1-ium chloride (43). $^1$H NMR (500 MHz, Methanol-$d_4$) δ 8.93 (dd, J=8.0, 1.1 Hz, 1H), 8.50 (dd, J=5.9, 1.0 Hz, 1H), 7.97 (s, 1H), 7.74-7.62 (m, 3H), 7.55 (t, J=8.2 Hz, 1H), 7.51 (s, 1H), 7.45-7.29 (m, 3H), 7.01 (dd, J=8.3, 2.2 Hz, 1H), 4.82 (s, 1H), 4.56 (d, J=15.1 Hz, 1H), 4.36-3.85 (m, 5H), 3.83-3.65 (m, 4H), 3.28-2.69 (m, 5H), 2.40-1.88 (m, 4H), 1.67 (d, J=2.6 Hz, 6H), 1.16-0.87 (m, 4H). $^{13}$C NMR (126 MHz, Methanol-$d_4$) δ 175.7, 171.5, 156.3, 143.7, 139.4, 137.3, 137.1, 133.4, 131.5, 131.2, 128.0, 127.4, 126.2, 124.1, 118.2, 118.0, 115.9, 114.4, 111.5, 81.7, 57.9, 55.9, 49.6, 43.1, 42.7, 39.6, 37.2, 30.1, 25.0, 24.8, 24.1, 22.0, 9.3, 7.4. HRMS (ESI) Calcd for $C_{37}H_{44}N_6O_3$ $(M+H)^+$ 621.3548, found 621.3562. HPLC purity 95.9%, $t_R$=9.11 min.

Scheme 4. Synthesis of 44-53
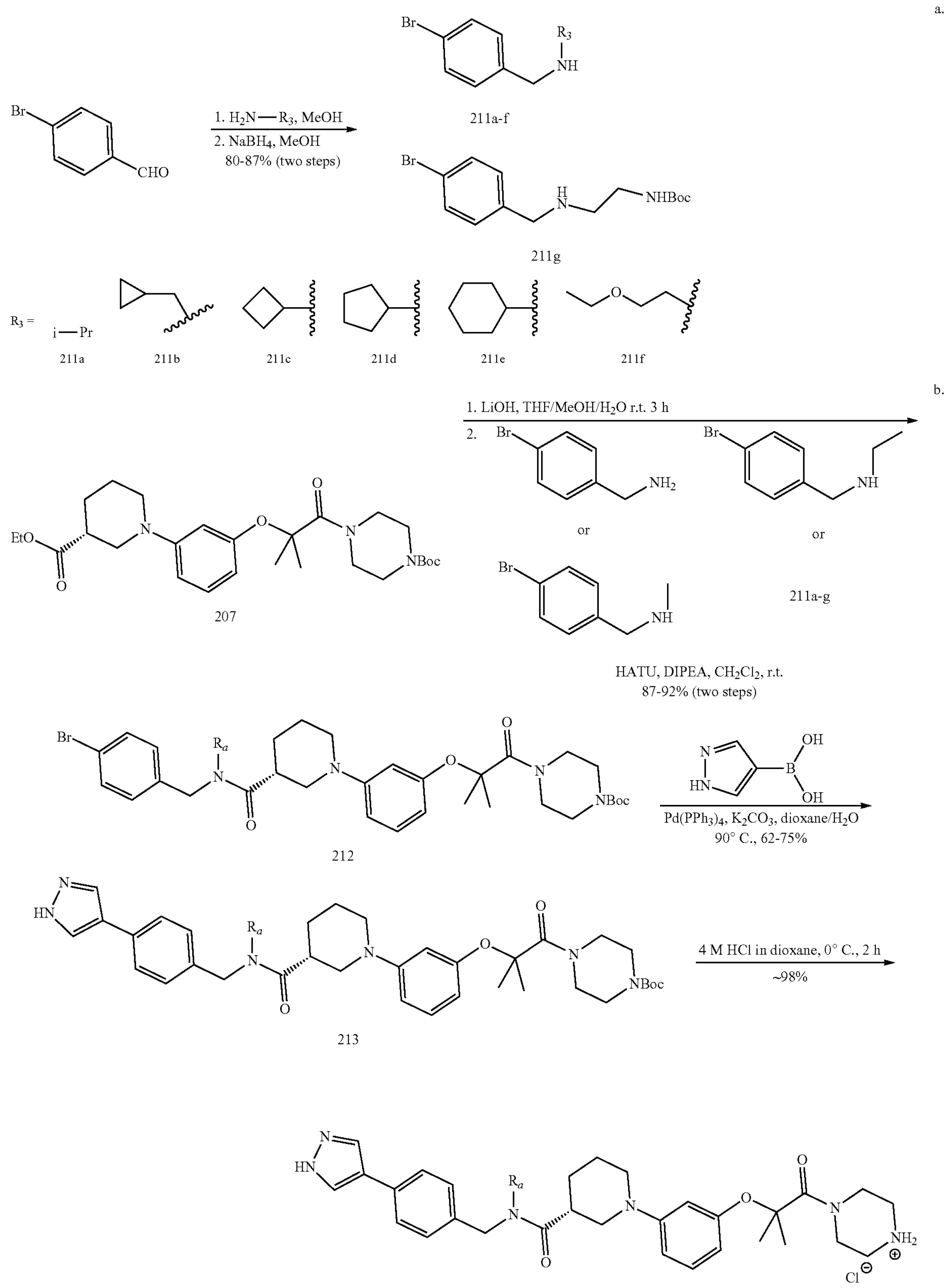
211a-f
211g
211a
211b
211c
211d
211e
211f
207
211a-g
212
213
44-53

-continued

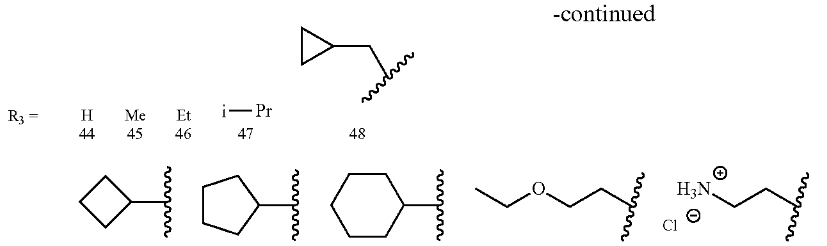

44 45 46 47 48

49 50 51 52 53

N-(4-bromobenzyl) propan-2-amine (211a). $^1$H NMR (500 MHz, Chloroform-d) δ 7.37-7.19 (m, 2H), 7.13-6.95 (m, 2H), 2.73 (hept, J=6.2 Hz, 1H), 0.98 (d, J=6.3 Hz, 6H). $^{13}$C NMR (126 MHz, Chloroform-d) δ 139.91, 131.43, 129.79, 120.53, 50.92, 48.13, 22.96. MS (ESI) m/z=228.1, 230.2 $[M+H]^+$ N-(4-bromobenzyl)-1-cyclopropylmethanamine (211b). $^1$H NMR (500 MHz, Chloroform-d) δ 7.47-7.36 (m, 2H), 7.23-7.12 (m, 2H), 3.77 (s, 2H), 2.47 (d, J=6.8 Hz, 2H), 1.55-1.34 (m, 1H), 1.01-0.92 (m, 1H), 0.53-0.42 (m, 2H), 0.14-0.00 (m, 2H). $^{13}$C NMR (126 MHz, Chloroform-d) δ 139.59, 131.42, 129.77, 120.58, 54.41, 53.14, 11.26, 3.37. MS (ESI) m/z=240.0, 242.0 $[M+H]^+$ N-(4-bromobenzyl)cyclobutanamine (211c). $^1$H NMR (500 MHz, Chloroform-d) δ 7.46-7.38 (m, 2H), 7.21-7.13 (m, 2H), 3.65 (s, 2H), 3.30-3.21 (m, 1H), 2.27-2.09 (m, 2H), 1.73-1.58 (m, 4H), 1.37 (s, 1H). $^{13}$C NMR (126 MHz, Chloroform-d) δ 139.57, 131.40, 129.88, 120.62, 53.60, 50.40, 31.16, 14.77. MS (ESI) m/z=240.1, 242.1 $[M+H]^+$ N-(4-bromobenzyl)cyclopentanamine (211d). $^1$H NMR (500 MHz, Chloroform-d) δ 7.45-7.35 (m, 2H), 7.22-7.12 (m, 2H), 3.71 (s, 2H), 3.08 (p, J=6.6 Hz, 1H), 1.88-1.76 (m, 2H), 1.69 (dqt, J=13.4, 8.5, 2.6 Hz, 2H), 1.60-1.48 (m, 2H), 1.44-1.17 (m, 3H). $^{13}$C NMR (126 MHz, Chloroform-d) δ 139.87, 131.39, 129.86, 120.53, 59.20, 52.06, 33.20, 24.07. MS (ESI) m/z=254.1, 256.1 $[M+H]^+$ N-(4-bromobenzyl)cyclohexanamine (211e). $^1$H NMR (500 MHz, Chloroform-d) δ 7.46-7.40 (m, 2H), 7.22-7.11 (m, 2H), 3.76 (s, 2H), 2.45 (tt, J=10.3, 3.8 Hz, 1H), 1.95-1.83 (m, 2H), 1.80-1.67 (m, 2H), 1.65-1.52 (m, 1H), 1.28-0.94 (m, 6H). $^{13}$C NMR (126 MHz, Chloroform-d) δ 140.12, 131.41, 129.77, 120.47, 56.13, 50.34, 33.60, 26.18, 25.00. MS (ESI) m/z=268.1, 270.1 $[M+H]^+$ N-(4-bromobenzyl)-2-ethoxyethan-1-amine (211f). $^1$H NMR (500 MHz, Chloroform-d) δ 7.47-7.39 (m, 2H), 7.23-7.13 (m, 2H), 3.75 (s, 2H), 3.53 (dd, J=5.6, 4.8 Hz, 2H), 3.48 (q, J=7.0 Hz, 2H), 2.79-2.72 (m, 2H), 1.71 (s, 1H), 1.19 (t, J=7.0 Hz, 3H). $^{13}$C NMR (126 MHz, Chloroform-d) δ 139.43, 131.40, 129.84, 120.61, 69.81, 66.44, 53.24, 48.86, 15.17. MS (ESI) m/z=258.1, 260.1 $[M+H]^+$ tert-butyl(2-((4-bromobenzyl)amino)ethyl) carbamate (211g). $^1$H NMR (500 MHz, Chloroform-d) δ 7.50-7.37 (m, 2H), 7.24-7.09 (m, 2H), 4.89 (s, 1H), 3.73 (s, 2H), 3.23 (q, J=5.8 Hz, 2H), 2.72 (t, J=5.8 Hz, 2H), 1.44 (s, 9H). MS (ESI) m/z=329.1, 331.1 $[M+H]^+$ tert-butyl (R)-4-(2-(3-(3-((4-bromobenzyl)carbamoyl)piperidin-1-yl)phenoxy)-2-methylpropanoyl)piperazine-1-carboxylate (212a). $^1$H NMR (500 MHz, Chloroform-d) δ 7.46-7.37 (m, 2H), 7.30-7.23 (m, 1H), 7.19-7.11 (m, 2H), 7.07 (t, J=8.2 Hz, 1H), 6.50 (dd, J=8.2, 2.2 Hz, 1H), 6.36 (t, J=2.3 Hz, 1H), 6.30 (dd, J=8.2, 2.3 Hz, 1H), 4.49-4.32 (m, 2H), 3.78 (t, J=5.2 Hz, 2H), 3.49 (s, 2H), 3.39 (td, J=15.2, 14.2, 4.0 Hz, 2H), 3.31-3.17 (m, 3H), 3.11-2.94 (m, 3H), 2.52 (tt, J=8.6, 4.0 Hz, 1H), 1.93 (dtd, J=13.4, 9.5, 4.1 Hz, 1H), 1.84 (dq, J=9.1, 5.1 Hz, 1H), 1.69 (td, J=7.8, 3.7 Hz, 1H), 1.62 (d, J=7.7 Hz, 7H), 1.41 (s, 9H). $^{13}$C NMR (126 MHz, Chloroform-d) δ 173.96, 172.35, 156.41, 154.44, 152.11, 138.03, 131.76, 130.09, 129.55, 121.19, 110.53, 108.16, 105.01, 80.63, 80.33, 52.57, 50.58, 45.94, 43.03, 42.75, 41.62, 28.45, 27.32, 26.25, 23.13. MS (ESI) m/z=643.3, 645.3 $[M+H]^+$ tert-butyl (R)-4-(2-(3-(3-((4-bromobenzyl)(methyl)carbamoyl)piperidin-1-yl)phenoxy)-2-methylpropanoyl)piperazine-1-carboxylate (212b). $^1$H NMR (500 MHz, Chloroform-d) δ 7.58-7.35 (m, 2H), 7.17-6.92 (m, 3H), 6.60-6.13 (m, 3H), 4.70-4.36 (m, 2H), 3.86-3.71 (m, 2H), 3.71-3.41 (m, 4H), 3.38-3.17 (m, 2H), 3.10-2.69 (m, 8H), 1.96-1.50 (m, 10H), 1.50-1.30 (m, 9H). MS (ESI) m/z=657.4, 659.3 $[M+H]^+$ tert-butyl (R)-4-(2-(3-(3-((4-bromobenzyl) (ethyl)carbamoyl)piperidin-1-yl)phenoxy)-2-methylpropanoyl)piperazine-1-carboxylate (212c). $^1$H NMR (500 MHz, Chloroform-d) δ 7.52-7.37 (m, 2H), 7.13-6.93 (m, 3H), 6.55-6.16 (m, 3H), 4.64-4.37 (m, 2H), 3.87-3.69 (m, 2H), 3.69-3.48 (m, 4H), 3.48-3.20 (m, 4H), 3.14-2.88 (m, 3H), 2.78 (s, 2H), 1.94-1.49 (m, 10H), 1.40 (s, 9H), 1.12 (dt, J=27.6, 7.1 Hz, 3H). MS (ESI) m/z=671.3 $[M+H]^+$ tert-butyl (R)-4-(2-(3-(3-((4-bromobenzyl) (isopropyl) carbamoyl)piperidin-1-yl)phenoxy)-2-methylpropanoyl) piperazine-1-carboxylate (212d). $^1$H NMR (500 MHz, Chloroform-d) δ 7.54-7.33 (m, 2H), 7.13-6.92 (m, 3H), 6.59-6.16 (m, 3H), 4.91-4.77 (m, 0.5H), 4.57-4.32 (m, 2H), 4.25 (hept, J=6.8 Hz, 0.5H), 3.86-3.46 (m, 6H), 3.31 (s, 2H), 3.15-2.83 (m, 4H), 2.77-2.49 (m, 1H), 2.00-1.57 (m, 10H), 1.41 (d, J=1.9 Hz, 9H), 1.23 (d, J=7.1 Hz, 6H). $^{13}$C NMR (126 MHz, Chloroform-d) δ 174.49, 174.08, 172.06, 156.30, 156.19, 154.34, 152.65, 152.31, 138.75, 137.95, 131.92, 131.44, 129.70, 129.69, 128.59, 127.45, 121.06, 120.33, 109.83, 109.50, 107.21, 107.00, 105.65, 105.33, 80.55 (d, J=2.9 Hz), 80.09, 53.43, 52.39, 52.30, 50.03, 49.46, 48.57, 45.76, 45.54, 45.42, 43.34, 42.89, 40.04, 39.33, 28.48, 28.36, 28.08, 26.17, 24.57, 24.03, 22.00, 21.89, 20.36. MS (ESI) m/z=685.3, 687.3 $[M+H]^+$ tert-butyl (R)-4-(2-(3-(3-((4-bromobenzyl) (cyclopropylmethyl) carbamoyl)piperidin-1-yl)phenoxy)-2-methylpropanoyl)piperazine-1-carboxylate (212e). $^1$H NMR (500 MHz, Chloroform-d) δ 7.51-7.36 (m, 2H), 7.20-7.12 (m, 1H), 7.11-6.92 (m, 2H), 6.55-6.17 (m, 3H), 4.77-4.51 (m, 2H), 3.76 (d, J=25.9 Hz, 3H), 3.69-3.48 (m, 4H), 3.35-3.14 (m, 3H), 3.13-2.85 (m, 4H), 2.77 (s, 1H), 2.43 (d, J=6.8 Hz, 1H), 1.96-1.47 (m, 9H), 1.39 (s, 9H), 0.98-0.79 (m, 1H), 0.60-0.38 (m, 2H), 0.18-0.01 (m, 2H). MS (ESI) m/z=699.3 $[M+H]^+$ tert-butyl (R)-4-(2-(3-(3-((4-bromobenzyl) (cyclobutyl) carbamoyl)piperidin-1-yl)phenoxy)-2-methylpropanoyl) piperazine-1-carboxylate (212f). $^1$H NMR (500 MHz, Chloroform-d) δ 7.49-7.37 (m, 2H), 7.17 (d, J=8.3 Hz, 1H), 7.08-6.91 (m, 2H), 6.55-6.38 (m, 1H), 6.24 (ddd, J=31.1, 8.1, 2.3 Hz, 2H), 4.95-4.37 (m, 2H), 3.89-3.69 (m, 2H), 3.60 (d, J=27.4 Hz, 5H), 3.36-3.21 (m, 3H), 3.12-2.86 (m, 4H), 2.76-2.51 (m, 1H), 2.23-2.04 (m, 5H), 2.01-1.50 (m, 12H), 1.40 (s, 9H). MS (ESI) m/z=697.3 $[M+H]^+$ tert-butyl (R)-4-(2-(3-(3-((4-bromobenzyl) (cyclopentyl) carbamoyl)piperidin-1-yl)phenoxy)-2-methylpropanoyl) piperazine-1-carboxylate (212g). $^1$H NMR (500 MHz, Chloroform-d) δ 7.50-7.34 (m, 3H), 7.21-7.14 (m, 1H), 7.12-6.91 (m, 2H), 6.57-6.18 (m, 2H), 4.56-4.27 (m, 2H), 3.86-3.44 (m, 7H), 3.38-3.18 (m, 2H), 3.15-2.88 (m, 4H), 2.78-2.44 (m, 1H), 1.99-1.27 (m, 27H). MS (ESI) m/z=711.4, 713.3 $[M+H]^+$ tert-butyl (R)-4-(2-(3-(3-((4-bromobenzyl) (cyclohexyl) carbamoyl)piperidin-1-yl)phenoxy)-2-methylpropanoyl) piperazine-1-carboxylate (212h). $^1$H NMR (500 MHz, Chloroform-d) δ 7.52-7.32 (m, 2H), 7.22-6.94 (m, 3H), 6.55-6.18 (m, 3H), 4.60-4.36 (m, 2H), 3.88-3.39 (m, 6H), 3.31 (s, 2H), 3.00 (dtd, J=33.8, 22.3, 21.7, 12.6 Hz, 5H), 2.81-2.38 (m, 1H), 1.97-1.52 (m, 14H), 1.52-0.90 (m, 16H). MS (ESI) m/z=725.4, 727.4 $[M+H]^+$ tert-butyl (R)-4-(2-(3-(3-((4-bromobenzyl) (2-ethoxyethyl)carbamoyl)piperidin-1-yl)phenoxy)-2-methylpropanoyl)piperazine-1-carboxylate (212i). $^1$H NMR (500 MHz, Chloroform-d) δ 7.42-7.36 (m, 2H), 7.21-7.15 (m, 1H), 7.12-7.05 (m, 1H), 7.02 (dt, J=8.2, 4.1 Hz, 1H), 6.54-6.34 (m, 1H), 6.34-6.06 (m, 2H), 4.72-4.41 (m, 2H), 3.82-3.22 (m, 14H), 3.11-2.61 (m, 5H), 1.95-1.64 (m, 4H), 1.62-1.57 (m, 6H), 1.39 (s, 9H), 1.12 (t, J=7.0 Hz, 3H). MS (ESI) m/z=715.4, 717.4 $[M+H]^+$ tert-butyl (R)-4-(2-(3-(3-((4-bromobenzyl) (2-((tert-butoxycarbonyl)amino)ethyl) carbamoyl)piperidin-1-yl)phenoxy)-2-methylpropanoyl)piperazine-1-carboxylate (212j). $^1$H NMR (500 MHz, Chloroform-d) δ 7.45-7.38 (m, 1H), 7.38-7.30 (m, 1H), 7.10-6.85 (m, 3H), 6.48-6.14 (m, 3H), 5.21 (s, 2H), 4.70-4.32 (m, 2H), 3.73 (dt, J=11.0, 4.9 Hz, 2H), 3.62-3.43 (m, 5H), 3.38 (dt, J=13.6, 5.7 Hz, 1H), 3.33-3.14 (m, 4H), 2.98 (dp, J=11.9, 7.1, 5.4 Hz, 2H), 2.93-2.80 (m, 1H), 2.69-2.59 (m, 1H), 1.89-1.61 (m, 3H), 1.59-1.52 (m, 6H), 1.33 (d, J=14.4 Hz, 18H). MS (ESI) m/z=786.5, 788.5 $[M+H]^+$ tert-butyl (R)-4-(2-(3-(3-((4-(1H-pyrazol-4-yl)benzyl) carbamoyl)piperidin-1-yl)phenoxy)-2-methylpropanoyl) piperazine-1-carboxylate (213a). $^1$H NMR (500 MHz, Chloroform-d) δ 7.71 (s, 2H), 7.41-7.28 (m, 2H), 7.26-7.15 (m, 3H), 6.99 (t, J=8.2 Hz, 1H), 6.45 (dd, J=8.2, 2.2 Hz, 1H), 6.32 (t, J=2.3 Hz, 1H), 6.23 (ddd, J=8.2, 2.4, 0.7 Hz, 1H), 4.50-4.31 (m, 2H), 3.71 (t, J=5.2 Hz, 2H), 3.45 (t, J=5.3 Hz, 2H), 3.39 (dd, J=12.9, 3.5 Hz, 1H), 3.30 (dt, J=12.0, 4.2 Hz, 1H), 3.25-3.08 (m, 3H), 3.05-2.88 (m, 3H), 2.50 (tt, J=8.6, 4.1 Hz, 1H), 1.84 (ddtd, J=22.4, 13.4, 9.1, 8.6, 4.6 Hz, 2H), 1.73-1.59 (m, 1H), 1.55 (d, J=8.5 Hz, 7H), 1.33 (s, 9H). $^{13}$C NMR (126 MHz, Chloroform-d) δ 174.14, 172.35, 156.35, 154.46, 152.31, 136.86, 131.78, 130.00, 128.29, 125.96, 122.19, 110.62, 108.13, 105.30, 80.63, 80.33, 52.61, 50.50, 45.89, 43.17, 43.03, 41.92, 28.43, 27.38, 26.27, 26.22, 23.30. MS (ESI) m/z=631.4 $[M+H]^+$ tert-butyl (R)-4-(2-(3-(3-((4-(1H-pyrazol-4-yl)benzyl) (methyl)carbamoyl) piperidin-1-yl)phenoxy)-2-methylpropanoyl)piperazine-1-carboxylate (213b). $^1$H NMR (500 MHz, Chloroform-d) δ 7.84 (d, J=5.9 Hz, 2H), 7.54-7.43 (m, 2H), 7.23 (d, J=7.9 Hz, 1H), 7.18-6.92 (m, 2H), 6.57-6.19 (m, 3H), 4.72-4.47 (m, 2H), 3.87-3.54 (m, 6H), 3.31 (d, J=5.9 Hz, 2H), 3.12-2.95 (m, 6H), 2.90 (tt, J=10.8, 3:3 Hz, 1H); 2.79-2.67 (m, 1H), 2.01-1.68 (m, 4H), 1.65-1.56 (m, 6H), 1.41 (s, 9H). $^{13}$C NMR (126 MHz, Chloroform-d) δ 174.50, 173.96, 172.14, 156.26, 156.22, 154.38, 152.66, 152.44, 135.52, 134.77, 132.14, 131.77, 129.70, 129.65, 128.56, 126.79, 126.27, 125.98, 122.22, 121.96, 109.87, 109.74, 107.02, 105.69, 105.57, 80.57, 80.15, 53.43, 53.04, 52.36, 52.07, 50.63, 49.86, 49.71, 45.76, 42.92, 39.15, 38.95, 34.80, 34.22, 28.37, 28.13, 27.69, 26.19 (d, J=2.4 Hz), 24.44, 24.25. MS (ESI) m/z=645.4 $[M+H]^+$, 643.3 $[M-H]^-$ tert-butyl (R)-4-(2-(3-(3-((4-(1/1-pyrazol-4-yl)benzyl) (ethyl)carbamoyl) piperidin-1-yl)phenoxy)-2-methylpropanoyl)piperazine-1-carboxylate (213c). $^1$H NMR (500 MHz, Chloroform-d) δ 7.83 (d, J=7.6 Hz, 2H), 7.54-7.41 (m, 2H), 7.23 (d, J=7.9 Hz, 1H), 7.17 (d, J=8.0 Hz, 1H), 7.00 (dt, J=58.6, 8.4 Hz, 1H), 6.57-6.19 (m, 3H), 4.74-4.42 (m, 2H), 3.88-3.54 (m, 6H), 3.54-3.16 (m, 4H), 3.16-2.60 (m, 5H), 1.99-1.66 (m, 4H), 1.65-1.56 (m, 6H), 1.41 (s, 9H), 1.16 (dt, J=26.5, 7.1 Hz, 3H). $^{13}$C NMR (126 MHz, Chloroform-d) δ 174.04, 173.95, 172.14, 156.27, 156.20, 154.38, 152.67, 152.48, 136.09, 135.28, 132.03, 131.64, 129.69, 129.63, 128.43, 126.78, 126.19, 125.93, 122.25, 121.98, 109.88, 109.77, 107.16, 105.76, 105.55, 80.58, 80.54, 80.14, 53.43, 52.39, 50.29, 49.93, 49.67, 47.62, 45.77, 42.92, 41.65, 41.11, 39.18, 39.07, 28.37, 28.32, 28.04, 26.21, 26.17, 26.13, 24.46, 24.24, 14.52, 12.77. MS (ESI) m/z=659.5 $[M+H]^+$, 657.5 $[M-H]^-$ tert-butyl (R)-4-(2-(3-(3-((4-(1H-pyrazol-4-yl)benzyl) (isopropyl) carbamoyl) piperidin-1-yl)phenoxy)-2-methylpropanoyl)piperazine-1-carboxylate (213d). $^1$H NMR (500 MHz, Chloroform-d) δ 7.78 (d, J=28.0 Hz, 2H), 7.44 (dd, J=36.8, 7.9 Hz, 2H), 7.18 (d, J=7.8 Hz, 2H), 6.99 (dt, J=79.0, 8.2 Hz, 1H), 6.59-6.12 (m, 3H), 4.88 (hept, J=6.7 Hz, 0.5H), 4.66-4.41 (m, 2H), 4.34-4.23 (m, 0.5H), 3.88-3.49 (m, 6H), 3.31 (dd, J=12.7, 7.0 Hz, 2H), 3.12-2.63 (m, 5H), 2.05-1.66 (m, 4H), 1.61 (dd, J=17.8, 2.6 Hz, 6H), 1.41 (s, 9H), 1.24-1.08 (m, 6H). $^{13}$C NMR (126 MHz, Chloroform-d) δ 174.70, 174.18, 172.15, 156.29, 156.13, 154.38, 152.69, 152.48, 137.67, 136.83, 131.70, 130.96, 129.70, 129.60, 127.18, 126.28, 126.05, 125.74, 122.28, 121.95, 109.90, 109.77, 107.08, 105.77, 105.55, 80.57, 80.52, 80.14, 53.44, 52.48, 52.37, 50.04, 49.62, 48.65, 45.77, 45.64, 43.69, 42.91, 40.13, 39.41, 28.53, 28.36, 28.05, 26.21, 26.17, 26.11, 24.60, 24.14, 22.02, 21.88, 20.43, 20.38. MS (ESI) m/z=673.4 $[M+H]^+$, 671.3 $[M-H]^-$ tert-butyl (R)-4-(2-(3-(3-((4-(1H-pyrazol-4-yl)benzyl) (cyclopropylmethyl) carbamoyl)piperidin-1-yl)phenoxy)-2-methylpropanoyl)piperazine-1-carboxylate (213e). $^1$H NMR (500 MHz, Chloroform-d) δ 7.81 (d, J=10.2 Hz, 2H), 7.48 (d, J=7.9 Hz, 1H), 7.43 (d, J=7.8 Hz, 1H), 7.17 (dd, J=15.1, 7.9 Hz, 2H), 7.00 (dt, J=59.8, 8.3 Hz, 1H), 6.59-6.14 (m, 3H), 4.89-4.59 (m, 2H), 3.84-3.49 (m, 6H), 3.41-2.66 (m, 9H), 2.04-1.67 (m, 4H), 1.59 (d, J=3.6 Hz, 6H), 1.41 (s, 9H), 1.00-0.88 (m, 1H), 0.62-0.38 (m, 2H), 0.18 (dq, J=8.3, 4.6 Hz, 2H). $^{13}$C NMR (126 MHz, Chloroform-d) δ 174.49, 174.03, 172.15, 156.26, 156.18, 154.38, 152.64, 152.47, 135.89, 135.24, 132.04, 131.63, 129.69, 129.64, 128.21, 126.70, 126.13, 125.88, 122.13, 121.87, 109.91, 109.79, 107.14, 107.03, 105.73, 105.54, 80.56, 80.52, 80.15, 53.45, 52.47, 52.35, 51.10, 50.65, 50.05, 49.93, 49.67, 47.97, 45.76, 42.92, 39.22, 39.04, 28.36, 28.27, 28.15, 26.21, 26.15, 24.43, 24.23, 10.65, 9.64, 4.17, 3.74, 3.71, 3.56. MS (ESI) m/z=685.5 $[M+H]^+$, 683.5 $[M-H]^-$ tert-butyl (R)-4-(2-(3-(3-((4-(1H-pyrazol-4-yl)benzyl) (cyclobutyl) carbamoyl) piperidin-1-yl)phenoxy)-2-methylpropanoyl)piperazine-1-carboxylate (213f). $^1$H NMR (500 MHz, Chloroform-d) δ 7.71 (d, J=26.7 Hz, 2H), 7.37 (dd, J=29.7, 7.9 Hz, 2H), 7.11-6.78 (m, 3H), 6.53-6.08 (m, 3H), 4.92-4.35 (m, 3H), 3.82-3.42 (m, 6H), 3.25 (dd, J=12.6, 6.8

Hz, 2H), 3.06-2.55 (m, 5H), 2.18-2.01 (m, 3H), 1.97 (s, 2H), 1.81-1.48 (m, 11H), 1.35 (s, 9H). $^{13}C$ NMR (126 MHz, Chloroform-d) δ 174.81, 174.27, 172.15, 156.28, 156.14, 154.38, 152.67, 152.40, 137.27, 136.66, 131.79, 131.13, 129.70, 129.60, 126.82, 126.16, 126.10, 125.86, 122.20, 121.89, 109.91, 109.75, 107.14, 106.99, 105.73, 105.48, 80.58, 80.52, 80.15, 53.44, 52.50, 52.31, 51.94, 50.04, 49.95, 49.55, 46.84, 45.75, 44.87, 42.92, 40.04, 39.63, 29.96, 29.02, 28.90, 28.36, 28.04, 26.18, 26.12, 24.52, 24.12, 15.05, 14.73. MS (ESI) m/z=685.5 $[M+H]^+$, 683.3 $[M-H]^-$ tert-butyl (R)-4-(2-(3-(3-((4-(1H-pyrazol-4-yl)benzyl)(cyclopentyl) carbamoyl) piperidin-1-yl)phenoxy)-2-methylpropanoyl)piperazine-1-carboxylate (213g). $^1H$ NMR (500 MHz, Chloroform-d) δ 7.80 (s, 1H), 7.72 (s, 1H), 7.47 (d, J=8.0 Hz, 1H), 7.39 (d, J=7.9 Hz, 1H), 7.14 (dd, J=14.2, 7.9 Hz, 2H), 6.98 (dt, J=92.4, 8.2 Hz, 1H), 6.61-6.39 (m, 1H), 6.35-6.11 (m, 2H), 4.95-4.33 (m, 3H), 3.89-3.44 (m, 6H), 3.42-3.21 (m, 2H), 3.14-2.59 (m, 5H), 2.04-1.73 (m, 5H), 1.73-1.51 (m, 12H), 1.41 (s, 10H). $^{13}C$ NMR (126 MHz, Chloroform-d) δ 175.08, 174.43, 172.14, 156.31, 156.12, 154.38, 152.61, 152.44, 137.34, 136.80, 131.74, 131.01, 129.72, 129.60, 126.64, 126.16, 126.08, 125.81, 122.24, 121.94, 109.87, 109.76, 107.02, 105.70, 105.51, 80.59, 80.52, 80.15, 58.78, 55.98, 52.55, 52.41, 49.99, 49.57, 47.11, 45.73, 44.87, 40.18, 39.42, 30.61, 30.39, 29.37, 29.28, 28.52, 28.37, 26.23, 26.16, 26.11, 24.51, 24.13, 23.92, 23.85, 23.77. MS (ESI) m/z=699.4 $[M+H]^+$, 697.3 $[M-H]^-$ tert-butyl (R)-4-(2-(3-(3-((4-(1H-pyrazol-4-yl)benzyl)(cyclohexyl) carbamoyl) piperidin-1-yl)phenoxy)-2-methylpropanoyl)piperazine-1-carboxylate (213h). $^1H$ NMR (500 MHz, Chloroform-d) δ 7.80 (s, 1H), 7.74 (s, 1H), 7.51-7.43 (m, 1H), 7.43-7.33 (m, 1H), 7.17 (t, J=7.8 Hz, 2H), 6.99 (dt, J=82.0, 8.2 Hz, 1H), 6.60-6.15 (m, 3H), 4.66-4.45 (m, 2H), 3.88-3.49 (m, 6H), 3.39-3.19 (m, 2H), 3.15-2.60 (m, 5H), 2.01-1.56 (m, 15H), 1.55 (d, J=3.2 Hz, 15H), 1.14-0.97 (m, 1H). $^{13}C$ NMR (126 MHz, Chloroform-d) δ 174.70, 174.19, 172.14, 156.32, 156.13, 154.38, 152.48 (d, J=2.3 Hz), 137.69, 136.96, 131.65, 130.92, 129.74, 129.61, 127.13, 126.27, 125.98, 125.69, 122.27, 121.95, 109.89, 109.73, 107.05, 106.95, 105.63, 105.53, 80.58, 80.52, 80.14, 57.50, 53.77, 53.44, 52.53, 52.50, 49.87, 49.61, 46.40, 45.73, 44.67, 40.04, 39.31, 32.55, 32.43, 30.80, 28.51, 28.37, 28.10, 26.23, 26.12, 25.94, 25.80, 25.50, 25.21, 24.38, 24.13. MS (ESI) m/z=713.5 $[M+H]^+$, 711.3 $[M-H]^-$ tert-butyl (R)-4-(2-(3-(3-((4-(1H-pyrazol-4-yl)benzyl)(2-ethoxyethyl) carbamoyl)piperidin-1-yl)phenoxy)-2-methylpropanoyl)piperazine-1-carboxylate (213i). $^1H$ NMR (500 MHz, Chloroform-d) δ 7.83 (s, 2H), 7.46 (dd, J=21.2, 7.9 Hz, 2H), 7.22 (d, J=7.9 Hz, 1H), 7.16 (d, J=8.0 Hz, 1H), 6.99 (dt, J=56.4, 8.1 Hz, 1H), 6.61-6.40 (m, 1H), 6.37-6.30 (m, 1H), 6.23 (ddd, J=26.8, 8.2, 2.3 Hz, 1H), 4.83-4.45 (m, 2H), 3.89-3.38 (m, 12H), 3.38-3.23 (m, 2H), 3.15-2.64 (m, 5H), 2.00-1.66 (m, 4H), 1.66-1.52 (m, 6H), 1.41 (s, 9H), 1.16 (td, J=7.0, 4.2 Hz, 3H). MS (ESI) m/z=703.5 $[M+H]^+$, 701.5 $[M-H]^+$ tert-butyl (R)-4-(2-(3-(3-((4-(1H-pyrazol-4-yl)benzyl) (2-((tert-butoxycarbonyl)amino)ethyl)carbamoyl)piperidin-1-yl)phenoxy)-2-methylpropanoyl)piperazine-1-carboxylate (213j). $^1H$ NMR (500 MHz, Chloroform-d) δ 7.82 (d, J=6.3 Hz, 2H), 7.46 (dd, J=18.9, 8.0 Hz, 2H), 7.24-6.91 (m, 3H), 6.57-6.18 (m, 3H), 5.03-4.45 (m, 2H), 3.78 (dt, J=20.9, 5.3 Hz, 2H), 3.69-3.21 (m, 10H), 3.11-2.65 (m, 5H), 1.95-1.71 (m, 3H), 1.65-1.53 (m, 7H), 1.42 (d, J=6.5 Hz, 18H). MS (ESI) m/z=774.5 $[M+H]^+$ (R)-4-(2-(3-(3-((4-(1H-pyrazol-4-yl)benzyl)carbamoyl) piperidin-1-yl)phenoxy)-2-methylpropanoyl)piperazin-1-ium chloride (44). $^1H$ NMR (500 MHz, Methanol-$d_4$) δ 8.50 (s, 2H), 7.71-7.60 (m, 2H), 7.55 (t, J=8.3 Hz, 1H), 7.48-7.27 (m, 4H), 7.03 (dd, J=8.4, 2.3 Hz, 1H), 4.52-4.34 (m, 2H), 4.03 (d, J=118.3 Hz, 4H), 3.76-3.59 (m, 4H), 3.28-2.82 (m, 5H), 2.17 (tdd, J=17.1, 13.0, 7.4 Hz, 3H), 1.94 (d, J=10.8 Hz, 1H), 1.68 (s, 6H). $^{13}C$ NMR (126 MHz, Methanol-$d_4$) δ 171.45, 156.29, 143.41, 138.15, 131.52, 130.66, 128.99, 128.03, 125.81, 123.61, 118.42, 114.38, 111.46, 81.77, 57.72, 55.78, 43.13, 42.39, 39.60, 25.16, 24.88, 24.72, 21.85. HRMS (ESI) Calcd for $C_{30}H_{38}N_6O_3$ (M+Na)+ 553.2898, found 553.2892. HPLC purity 100%, $t_R$=8.11 min (R)-4-(2-(3-(3-((4-(1H-pyrazol-4-yl)benzyl)(methyl)carbamoyl)piperidin-1-yl)phenoxy)-2-methylpropanoyl)piperazin-1-ium chloride (45). $^1H$ NMR (500 MHz, Methanol-$d_4$) δ 8.63 (d, J=1.6 Hz, 2H), 7.78-7.66 (m, 2H), 7.56 (td, J=8.3, 6.3 Hz, 1H), 7.50-7.30 (m, 4H), 7.04 (ddd, J=8.1, 5.7, 2.3 Hz, 1H), 4.84-4.56 (m, 2H), 4.04 (d, J=120.1 Hz, 4H), 3.85-3.54 (m, 6H), 3.13 (s, 4H), 2.99 (s, 2H), 2.37-1.84 (m, 4H), 1.69 (d, J=3.3 Hz, 6H). $^{13}C$ NMR (126 MHz, Methanol-$d_4$) δ 171.46, 156.31 (d, J=1.8 Hz), 143.27, 136.90, 136.40, 131.56, 131.52, 130.79, 128.67, 128.37, 127.58, 126.36, 126.10, 123.92, 118.61, 118.51, 114.51, 114.48, 111.64, 111.55, 81.80, 52.68, 50.27, 43.13, 42.65, 39.57, 34.31, 33.20, 24.92, 24.73, 24.70. HRMS (ESI) Calcd $C_{31}H_{40}N_6O_3$ for (M+Na)+567.3054, found 567.3047. HPLC purity 99.3%, $t_R$=8.48 min (R)-4-(2-(3-(3-((4-(1H-pyrazol-4-yl)benzyl) (ethyl)carbamoyl)piperidin-1-yl)phenoxy)-2-methylpropanoyl)piperazin-1-ium chloride (46). $^1H$ NMR (500 MHz, Methanol-$d_4$) δ 8.45 (d, J=4.4 Hz, 2H), 7.69 (dd, J=29.3, 8.0 Hz, 2H), 7.55 (q, J=8.1 Hz, 1H), 7.49-7.25 (m, 4H), 7.03 (ddd, J=8.8, 6.7, 2.3 Hz, 1H), 4.84-4.47 (m, 2H), 4.31-3.83 (m, 4H), 3.84-3.62 (m, 5H), 3.60-3.41 (m, 2H), 3.28-2.77 (m, 4H), 2.37-1.80 (m, 4H), 1.68 (d, J=3.4 Hz, 6H), 1.20 (dt, J=63.2, 7.1 Hz, 3H). $^{13}C$ NMR (126 MHz, Methanol-$d_4$) δ 171.47, 156.30, 143.35, 136.92, 136.10, 131.53, 130.70, 130.02, 129.42, 128.14, 127.50, 126.13, 125.87, 123.41, 118.49, 118.34, 114.47, 111.60, 111.56, 81.77, 58.29, 55.72, 50.30, 43.13, 42.22, 41.27, 39.60, 24.90, 24.73, 21.39, 13.17, 11.39. HRMS (ESI) Calcd for $C_{32}H_{42}N_6O_3$ $(M^+ Na)^+$ 581.3211, found 581.3204. HPLC purity 99.9%, $t_R$=8.99 min (R)-4-(2-(3-(3-((4-(1H-pyrazol-4-yl)benzyl) (isopropyl) carbamoyl)piperidin-1-yl)phenoxy)-2-methylpropanoyl) piperazin-1-ium chloride (47). $^1H$ NMR (500 MHz, Methanol-$d_4$) δ 8.38 (d, J=9.5 Hz, 2H), 7.76-7.58 (m, 2H), 7.54 (dt, J=12.0, 8.3 Hz, 1H), 7.48-7.23 (m, 4H), 7.02 (ddd, J=13.6, 8.4, 2.3 Hz, 1H), 4.76-4.34 (m, 3H), 4.23-3.57 (m, 9H), 3.27-2.77 (m, 4H), 2.42-1.76 (m, 4H), 1.67 (d, J=3.0 Hz, 6H), 1.31-1.12 (m, 6H). $^{13}C$ NMR (126 MHz, Methanol-$d_4$) δ 171.48, 156.30, 143.39, 138.41, 137.22, 131.52, 131.46, 130.74, 130.61, 128.94, 127.12, 126.89, 126.01, 125.59, 123.40, 122.92, 118.54, 118.10, 114.45, 114.37, 111.52, 111.42, 81.80, 81.73, 55.65, 49.44, 46.25, 43.36, 43.12, 39.44, 24.90, 24.89, 24.71, 24.68, 21.39, 20.52, 20.23, 19.05, 18.86. HRMS (ESI) Calcd for $C_{33}H_{44}N_6O_3$ $(M^+ Na)^+$ 595.3367, found 595.3359. HPLC purity 99.9%, $t_R$=9.35 min (R)-4-(2-(3-(3-((4-(1H-pyrazol-4-yl)benzyl) (cyclopropylmethyl) carbamoyl)piperidin-1-yl)phenoxy)-2-methylpropanoyl)piperazin-1-ium chloride (48).

$^1H$ NMR (500 MHz, Methanol-$d_4$) δ 8.09 (d, J=2.2 Hz, 2H), 7.71-7.61 (m, 1H), 7.61-7.57 (m, 1H), 7.51 (dt, J=22.8, 8.2 Hz, 1H), 7.43-7.13 (m, 4H), 6.96 (ddd, J=22.5, 8.4, 2.3 Hz, 1H), 4.65 (d, J=15.2 Hz, 2H), 4.28-3.82 (m, 4H), 3.79-3.53 (m, 5H), 3.47-3.37 (m, 1H), 3.30-2.83 (m, 5H), 2.29-1.83 (m, 4H), 1.72-1.61 (m, 6H), 1.11-1.00 (m, 1H), 0.65-0.44 (m, 2H), 0.37-0.18 (m, 2H). $^{13}$C NMR (126 MHz, Methanol-$d_4$) δ 170.24, 154.97 (d, J=1.7 Hz), 134.35, 133.77, 130.35, 130.09, 130.00, 129.77, 129.34, 126.49, 125.81, 124.48, 124.19, 116.48, 112.86, 112.71, 109.86, 109.62, 80.39, 80.32, 53.72, 50.30, 49.42, 48.96, 41.81, 41.33, 38.24, 23.58 (d, J=2.3 Hz), 23.43 (d, J=1.6 Hz), 20.35, 8.59, 7.69, 2.32, 1.53, 1.42, 1.27. HRMS (ESI) Calcd for $C_{34}H_{44}N_6O_3$ (M+Na)+607.3367, found 607.3359. HPLC purity 100%, $t_R$=9.81 min (R)-4-(2-(3-(3-((4-(1H-pyrazol-4-yl)benzyl) (cyclobutyl) carbamoyl)piperidin-1-yl)phenoxy)-2-methylpropanoyl) piperazin-1-ium chloride (49). $^1$H NMR (500 MHz, Methanol-$d_4$) δ 8.58 (d, J=2.3 Hz, 2H), 7.70 (dd, J=34.2, 8.0 Hz, 2H), 7.58-7.49 (m, 1H), 7.49-7.22 (m, 4H), 7.02 (ddd, J=10.6, 8.3, 2.3 Hz, 1H), 4.83-4.65 (m, 2H), 4.32-3.32 (m, 10H), 3.26-2.82 (m, 4H), 2.34-1.82 (m, 8H), 1.75-1.64 (m, 8H). $^{13}$C NMR (126 MHz, Methanol-$d_4$) δ 171.46, 156.28, 143.26, 138.78, 138.00, 131.53, 131.49, 130.75, 130.63, 128.95, 128.07, 126.83, 126.75, 126.26, 125.91, 123.93, 123.61, 118.70, 118.34, 114.47, 111.57, 81.81, 52.05, 50.98, 44.47, 43.10, 42.66, 39.56, 29.07, 29.02, 28.37, 28.17, 24.91, 24.67, 14.52, 14.04. HRMS (ESI) Calcd for $C_{34}H_{44}N_6O_3$ ($M^+$ Na)$^+$ 607.3367, found 607.3358. HPLC purity 99.9%, $t_R$=9.74 min (R)-4-(2-(3-(3-((4-(1H-pyrazol-4-yl)benzyl) (cyclopentyl) carbamoyl)piperidin-1-yl)phenoxy)-2-methylpropanoyl)piperazin-1-ium chloride (50). $^1$H NMR (500 MHz, Methanol-$d_4$) δ 8.39 (d, J=9.5 Hz, 2H), 7.66 (dd, J=39.2, 8.1 Hz, 2H), 7.53 (dt, J=11.2, 8.3 Hz, 1H), 7.47-7.21 (m, 4H), 7.01 (ddd, J=13.4, 8.3, 2.3 Hz, 1H), 4.77-4.46 (m, 3H), 4.24-3.72 (m, 7H), 3.70-3.56 (m, 2H), 3.26-2.79 (m, 4H), 2.33-1.79 (m, 6H), 1.67 (d, J=3.9 Hz, 12H). $^{13}$C NMR (126 MHz, Methanol-$d_4$) δ 171.47, 156.29, 143.33, 138.25, 137.28, 131.51, 131.46, 130.74, 130.61, 130.00, 128.87, 126.72, 126.65, 126.05, 125.65, 123.41, 118.60, 118.11, 114.45, 114.36, 111.54, 111.41, 81.80, 81.73, 72.17, 71.05, 60.78, 59.20, 57.41, 55.68, 44.55, 43.11, 39.63, 29.86, 29.65, 28.92, 28.63, 24.89, 24.87, 24.70, 24.68, 23.58, 23.50, 23.28. HRMS (ESI) Calcd for $C_{35}H_{46}N_6O_3$ ($M^+$ Na)$^+$ 621.3524, found 621.3517. HPLC purity 100%, $t_R$=10.17 min (R)-4-(2-(3-(3-((4-(1H-pyrazol-4-yl)benzyl) (cyclohexyl) carbamoyl)piperidin-1-yl)phenoxy)-2-methylpropanoyl) piperazin-1-ium chloride (51). $^1$H NMR (500 MHz, Methanol-$d_4$) δ 8.04 (d, J=6.6 Hz, 2H), 7.67-7.22 (m, 6H), 7.22-6.80 (m, 2H), 4.77-4.30 (m, 3H), 4.19-3.84 (m, 4H), 3.81-3.39 (m, 5H), 3.26-2.87 (m, 4H), 2.32-1.72 (m, 8H), 1.67-1.09 (m, 12H). $^{13}$C NMR (126 MHz, Methanol-$d_4$) δ 171.65, 171.58, 156.29, 156.26, 137.28, 136.40, 131.57, 131.36, 131.15, 130.69, 126.98, 126.60, 125.68, 125.25, 114.06, 113.62, 110.98, 81.68, 81.48, 58.00, 55.12, 46.61, 43.11, 42.64, 39.56, 31.83, 31.66, 30.18, 30.11, 25.61, 25.58, 25.42, 25.35, 25.06, 24.90, 24.87, 24.79, 24.72. HRMS (ESI) Calcd for $C_{36}H_{48}N_6O_3$ ($M^+$ Na)$^+$ 635.3680, found 635.3674. HPLC purity 99.7%, $t_R$=10.73 min (R)-4-(2-(3-(3-((4-(1H-pyrazol-4-yl)benzyl) (2-ethoxyethyl)carbamoyl)piperidin-1-yl)phenoxy)-2-methylpropanoyl)piperazin-1-ium chloride (52). $^1$H NMR (500 MHz, Methanol-$d_4$) δ 8.43 (d, J=4.1 Hz, 2H), 7.68 (dd, J=31.4, 8.0 Hz, 2H), 7.57-7.52 (m, 1H), 7.46-7.28 (m, 4H), 7.02 (ddd, J=7.3, 4.9, 2.2 Hz, 1H), 4.80 (d, J=16.9 Hz, 1H), 4.57 (d, J=15.3 Hz, 1H), 4.22-3.57 (m, 13H), 3.50-3.42 (m, 2H), 3.26-2.81 (m, 4H), 2.30-1.85 (m, 4H), 1.68 (d, J=3.5 Hz, 6H), 1.15 (dt, J=16.7, 7.0 Hz, 3H). $^{13}$C NMR (126 MHz, Methanol-$d_4$) δ 171.47, 156.32, 143.35, 136.92, 131.53, 131.49, 130.71, 129.45, 128.01, 127.44, 126.11, 125.79, 118.41, 118.32, 114.46, 114.43, 111.65, 111.56, 81.80, 81.77, 67.72, 67.34, 66.30, 66.09, 55.70, 43.13, 42.53, 39.54, 24.87, 24.73, 21.41, 14.16, 14.12. HRMS (ESI) Calcd for $C_{34}H_{46}N_6O_4$ (M+H)$^+$ 603.3653, found 603.3650. HPLC purity 99.7%, $t_R$=9.34 min.

(R)-4-(2-(3-(3-((4-(1H-pyrazol-4-yl)benzyl) (2-ammonioethyl)carbamoyl) piperidin-1-yl)phenoxy)-2-methylpropanoyl)piperazin-1-ium chloride (53). $^1$H NMR (500 MHz, Methanol-$d_4$) δ 8.63 (d, J=3.3 Hz, 2H), 7.75 (dd, J=32.8, 7.9 Hz, 2H), 7.59-7.36 (m, 5H), 7.04 (td, J=8.0, 2.1 Hz, 1H), 4.91-4.78 (m, 2H), 4.21-3.50 (m, 12H), 3.28-2.78 (m, 6H), 2.28-1.76 (m, 4H), 1.68 (d, J=4.5 Hz, 6H). $^{13}$C NMR (126 MHz, Methanol-$d_4$) δ 171.36, 156.23, 143.32, 136.86, 136.18, 131.62, 131.56, 130.83, 129.38, 128.90, 128.41, 127.83, 126.42, 126.18, 123.53, 118.76, 118.49, 114.54, 111.52, 111.44, 81.74, 58.15, 55.81, 51.55, 44.48, 44.14, 42.68, 39.60, 38.02, 36.73, 24.91, 24.89, 24.41, 21.71. HRMS (ESI) Calcd for $C_{32}H_{43}N_7O_3$ (M+H)$^+$ 574.3500, found 574.3496. HPLC purity 99.5%, $t_R$=7.77 min.

Scheme 5. Synthesis of 55-57.

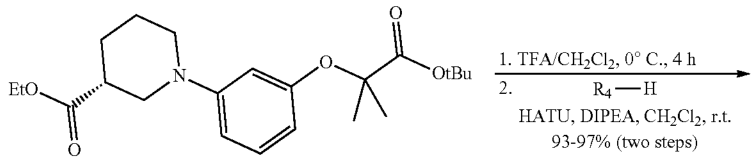

206

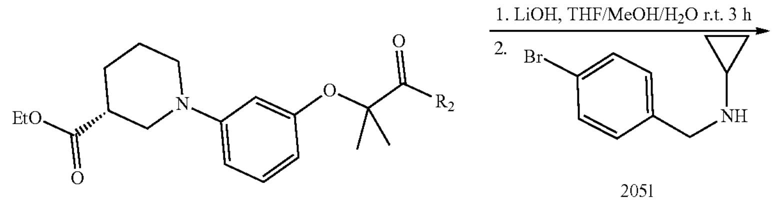

2051

214

HATU, DIPEA, $CH_2Cl_2$, r.t.

80-87% (two steps)

-continued

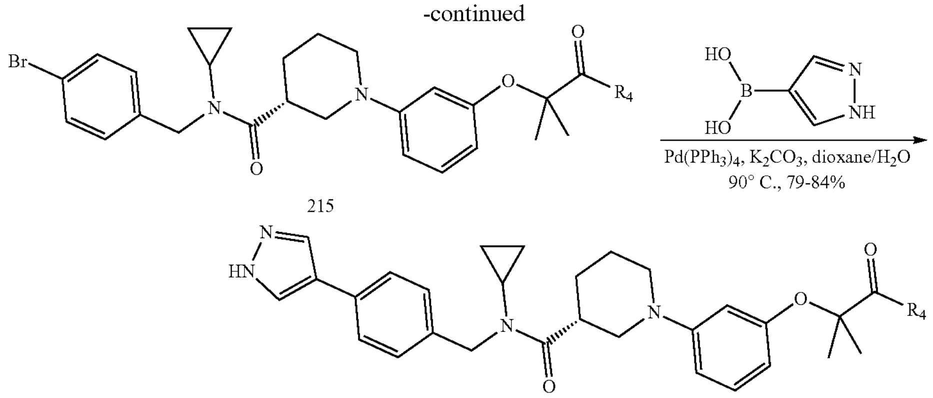

215

55-57

55, 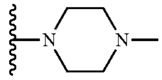

56, 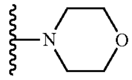

57, 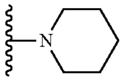

ethyl (R)-1-(3-((2-methyl-1-(4-methylpiperazin-1-yl)-1-oxopropan-2-yl)oxy)phenyl)piperidine-3-carboxylate (214a). $^1$H NMR (500 MHz, Acetone-$d_6$) δ 6.95 (t, J=8.2 Hz, 1H), 6.46 (ddd, J=8.3, 2.3, 0.8 Hz, 1H), 6.31 (t, J=2.3 Hz, 1H), 6.15 (ddd, J=8.1, 2.4, 0.8 Hz, 1H), 4.00 (q, J=7.1 Hz, 2H), 3.70 (s, 2H), 3.55-3.35 (m, 3H), 3.35-3.24 (m, 1H), 2.89 (dd, J=12.4, 9.5 Hz, 1H), 2.69 (ddd, J=12.3, 10.0, 3.2 Hz, 1H), 2.48 (tt, J=9.6, 4.0 Hz, 1H), 2.13 (s, 2H), 1.98 (s, 3H), 1.93 (ddt, J=8.8, 4.4, 2.4 Hz, 2H), 1.87-1.76 (m, 1H), 1.64 (dddd, J=11.5, 6.8, 3.8, 2.0 Hz, 1H), 1.59-1.46 (m, 2H), 1.43 (s, 6H), 1.11 (t, J=7.1 Hz, 3H). $^{13}$C NMR (126 MHz, Acetone-$d_6$) δ 172.96, 170.88, 156.55, 152.83, 129.41, 109.90, 107.95, 105.55, 80.43, 59.91, 54.80, 54.65, 51.92, 49.33, 45.49, 45.24, 42.53, 40.93, 26.78, 25.65, 23.74, 13.70. MS (ESI) m/z=418.3 $[M+H]^+$ ethyl (R)-1-(3-((2-methyl-1-morpholino-1-oxopropan-2-yl)oxy)phenyl) piperidine-3-carboxylate (214b). $^1$H NMR (500 MHz, Chloroform-d) δ 7.03 (t, J=8.2 Hz, 1H), 6.52 (dd, J=8.0, 2.2 Hz, 1H), 6.37 (t, J=2.4 Hz, 1H), 6.28-6.19 (m, 1H), 4.11 (q, J=7.1 Hz, 2H), 3.81 (t, J=4.8 Hz, 2H), 3.68-3.46 (m, 5H), 3.42-3.34 (m, 1H), 3.24 (t, J=4.7 Hz, 2H), 2.95 (dd, J=12.4, 9.8 Hz, 1H), 2.79-2.69 (m, 1H), 2.58 (tt, J=10.0, 3.9 Hz, 1H), 1.96 (dqt, J=6.8, 5.1, 2.3 Hz, 1H), 1.74 (qq, J=8.1, 3.2 Hz, 1H), 1.58 (s, 8H), 1.22 (t, J=7.1 Hz, 3H). $^{13}$C NMR (126 MHz, Chloroform-d) δ 173.62, 171.81, 156.16, 152.73, 129.57, 110.12, 107.41, 105.63, 80.53, 66.79, 66.45, 60.43, 51.93, 49.50, 46.74, 43.31, 41.22, 26.93, 26.09 (d, J=2.8 Hz), 24.01, 14.23. MS (ESI) m/z=405.3 $[M+H]^+$, 831.4 $[2M+Na]^+$ ethyl (R)-1-(3-((2-methyl-1-oxo-1-(piperidin-1-yl) propan-2-yl)oxy)phenyl) piperidine-3-carboxylate (214c). $^1$H NMR (500 MHz, Chloroform-d) δ 7.02 (t, J=8.2 Hz, 1H), 6.51 (ddd, J=8.2, 2.4, 0.8 Hz, 1H), 6.40 (t, J=2.4 Hz, 1H), 6.28 (ddd, J=8.2, 2.4, 0.7 Hz, 1H), 4.12 (q, J=7.2 Hz, 2H), 3.73 (t, J=5.4 Hz, 2H), 3.65 (ddt, J=12.4, 3.6, 1.5 Hz, 1H), 3.53 (t, J=4.9 Hz, 2H), 3.46-3.34 (m, 1H), 2.94 (dd, J=12.4, 9.9 Hz, 1H), 2.80-2.65 (m, 1H), 2.60 (tt, J=10.1, 4.0 Hz, 1H), 2.04-1.93 (m, 1H), 1.82-1.67 (m, 1H), 1.59 (s, 8H), 1.47 (t, J=4.0 Hz, 4H), 1.24 (t, J=7.1 Hz, 5H). $^{13}$C NMR (126 MHz, Chloroform-d) δ 173.73, 171.50, 156.54, 152.62, 129.41, 109.92, 107.77, 105.89, 80.66, 60.42, 52.03, 49.57, 46.62, 44.11, 41.30, 26.98, 26.27, 26.25, 26.15, 25.70, 24.59, 24.06, 14.23. MS (ESI) m/z=403.3 $[M+H]^+$ (R)—N-(4-bromobenzyl)-N-cyclopropyl-1-(3-((2-methyl-1-(4-methylpiperazin-1-yl)-1-oxopropan-2-yl)oxy) phenyl)piperidine-3-carboxamide (215a). $^1$H NMR (500 MHz, Chloroform-d) δ 7.45-7.36 (m, 2H), 7.15-7.08 (m, 2H), 7.05 (t, J=8.2 Hz, 1H), 6.51 (dd, J=8.3, 2.3 Hz, 1H), 6.40 (t, J=2.4 Hz, 1H), 6.28 (dd, J=8.1, 2.3 Hz, 1H), 4.61 (d, J=14.7 Hz, 1H), 4.47 (d, J=14.7 Hz, 1H), 3.85 (s, 2H), 3.67-3.53 (m, 4H), 3.41 (tt, J=11.0, 3.7 Hz, 1H), 2.94 (dd, J=12.4, 10.9 Hz, 1H), 2.79-2.65 (m, 1H), 2.65-2.55 (m, 1H), 2.31 (t, J=5.6 Hz, 2H), 2.17 (s, 3H), 2.08 (d, J=6.5 Hz, 2H), 1.91 (d, J=8.8 Hz, 1H), 1.80 (tt, J=10.8, 4.1 Hz, 1H), 1.76-1.65 (m, 2H), 1.61 (d, J=1.1 Hz, 6H), 0.93-0.74 (m, 4H). $^{13}$C NMR (126 MHz, Chloroform-d) δ 176.85, 171.84, 156.35, 152.68, 137.49, 131.64, 129.60, 129.48, 120.97, 109.79, 107.77, 105.93, 80.66, 54.89, 52.24, 49.88, 49.38, 45.87, 45.58, 42.78, 39.85, 29.82, 27.75, 26.21, 24.48, 9.46, 9.09. MS (ESI) m/z=597.3, 599.3 $[M+H]^+$ (R)—N-(4-bromobenzyl)-N-cyclopropyl-1-(3-((2-methyl-1-morpholino-1-oxopropan-2-yl)oxy)phenyl)piperidine-3-carboxamide (215b). $^1$H NMR (500 MHz, Chloroform-d) δ 7.38-7.32 (m, 2H), 7.07-6.93 (m, 3H), 6.45 (dd, J=8.2, 2.3 Hz, 1H), 6.33 (t, J=2.3 Hz, 1H), 6.21 (dd, J=8.0, 2.3 Hz, 1H), 4.53 (d, J=14.7 Hz, 1H), 4.40 (d, J=14.7 Hz, 1H), 3.83-3.70 (m, 2H), 3.68-3.39 (m, 6H), 3.33 (tt, J=10.9, 3.5 Hz, 1H), 3.18 (d, J=5.3 Hz, 2H), 2.94-2.84 (m, 1H), 2.68-2.60 (m, 1H), 2.53 (tt, J=6.9, 4.0 Hz, 1H), 1.84 (t, J=6.0 Hz, 1H), 1.78-1.59 (m, 3H), 1.54 (d, J=1.8 Hz, 6H), 0.86-0.68 (m, 4H). $^{13}$C NMR (126 MHz, Chloroform-d) δ 176.66, 171.71, 156.19, 152.60, 137.49, 131.56, 129.62, 129.45, 120.87, 109.71, 107.27, 105.45, 80.48, 66.74, 66.40, 52.12, 49.70, 49.28, 46.72, 43.27, 39.72, 29.74, 27.71, 26.07, 24.36, 9.41, 9.03. MS (ESI) m/z=584.3, 586.2 $[M+H]^+$ (R)—N-(4-bromobenzyl)-N-cyclopropyl-1-(3-((2-methyl-1-oxo-1-(piperidin-1-yl) propan-2-yl)oxy)phenyl) piperidine-3-carboxamide (215c). $^{1}$H NMR (500 MHz, Chloroform-d) δ 7.42-7.33 (m, 2H), 7.08 (d, J=8.1 Hz, 2H), 7.02 (t, J=8.2 Hz, 1H), 6.48 (dd, J=8.2, 2.3 Hz, 1H), 6.44 (s, 1H), 6.28 (dd, J=8.2, 2.3 Hz, 1H), 4.57 (d, J=14.7 Hz, 1H), 4.46 (d, J=14.8 Hz, 1H), 3.72 (q, J=5.7 Hz, 2H), 3.67-3.59 (m, 2H), 3.51 (qd, J=13.4, 12.4, 5.7 Hz, 2H), 3.39 (tt, J=10.8, 3.4 Hz, 1H), 2.92 (dd, J=12.5, 10.9 Hz, 1H), 2.76-2.66 (m, 1H), 2.60 (tt, J=7.0, 3.9 Hz, 1H), 1.89 (d, J=9.6 Hz, 1H), 1.83-1.74 (m, 1H), 1.73-1.64 (m, 2H), 1.59 (d, J=1.4 Hz, 6H), 1.51-1.40 (m, 4H), 1.26-1.19 (m, 2H), 0.92-0.72 (m, 4H). $^{13}$C NMR (126 MHz, Chloroform-d) δ 176.73, 171.41, 156.58, 152.50, 137.55, 131.57, 129.49, 129.45, 120.89, 109.45, 107.72, 105.73, 80.61, 52.30, 49.71, 49.34, 46.60, 44.07, 39.78, 29.80, 27.75, 26.28, 26.24, 26.13, 25.70, 24.58, 24.40, 9.38, 9.11. MS (ESI) m/z=582.3, 584.2 $[M+H]^+$ (R)—N-(4-(1H-pyrazol-4-yl)benzyl)-N-cyclopropyl-1-(3-((2-methyl-1-(4-methylpiperazin-1-yl)-1-oxopropan-2-yl)oxy)phenyl)piperidine-3-carboxamide (55). $^{1}$H NMR (500 MHz, Chloroform-d) δ 7.83 (s, 2H), 7.45 (d, J=7.8 Hz, 2H), 7.24 (d, J=7.8 Hz, 2H), 7.06 (t, J=8.2 Hz, 1H), 6.54 (dd, J=8.3, 2.3 Hz, 1H), 6.42 (t, J=2.4 Hz, 1H), 6.28 (dd, J=8.2, 2.3 Hz, 1H), 4.69 (d, J=14.6 Hz, 1H), 4.54 (d, J=14.7 Hz, 1H), 3.87 (s, 2H), 3.73-3.59 (m, 4H), 3.45 (tt, J=11.0, 3.5 Hz, 1H), 2.99 (dd, J=12.4, 11.0 Hz, 1H), 2.75 (td, J=12.1, 3.0 Hz, 1H), 2.64 (ddd, J=10.7, 6.9, 4.1 Hz, 1H), 2.31 (d, J=6.1 Hz, 2H), 2.17 (s, 3H), 2.08 (s, 2H), 1.95 (d, J=10.7 Hz, 1H), 1.85-1.70 (m, 3H), 1.63-1.60 (m, 6H), 0.93-0.80 (m, 4H). $^{13}$C NMR (126 MHz, Chloroform-d) δ 176.87, 171.88, 156.34, 152.72, 136.70, 131.36, 129.59, 128.28, 125.91, 109.85, 107.72, 106.04, 80.67, 54.87, 54.72, 52.30, 49.94, 49.62, 45.86, 45.62, 42.83, 39.90, 29.81, 27.80, 26.23, 26.21, 24.52, 9.50, 9.11. HRMS (ESI) Calcd for $C_{34}H_{44}N_6O_3$ $(M+H)^+$ 585.3548, found 585.3546. HPLC purity 98.5%, $t_R$=9.23 min.

(R)—N-(4-(1H-pyrazol-4-yl)benzyl)-N-cyclopropyl-1-(3-((2-methyl-1-morpholino-1-oxopropan-2-yl)oxy)phenyl) piperidine-3-carboxamide (56). $^{1}$H NMR (500 MHz, Chloroform-d) δ 7.82 (s, 2H), 7.45 (d, J=7.8 Hz, 2H), 7.23 (d, J=7.5 Hz, 2H), 7.08 (t, J=8.2 Hz, 1H), 6.62-6.50 (m, 1H), 6.43 (s, 1H), 6.30 (dd, J=8.3, 2.3 Hz, 1H), 4.69 (d, J=14.6 Hz, 1H), 4.54 (d, J=14.6 Hz, 1H), 3.85 (s, 2H), 3.72-3.53 (m, 6H), 3.46 (s, 1H), 3.28 (q, J=5.4 Hz, 2H), 3.00 (t, J=11.6 Hz, 1H), 2.81-2.72 (m, 1H), 2.63 (tt, J=6.9, 4.1 Hz, 1H), 1.96 (d, J=9.9 Hz, 1H), 1.83 (ddd, J=13.7, 8.4, 5.2 Hz, 1H), 1.79-1.68 (m, 2H), 1.63 (d, J=1.7 Hz, 6H), 0.97-0.79 (m, 4H). $^{13}$C NMR (126 MHz, Methanol-$d_4$) δ 177.59, 172.27, 156.19, 152.55, 136.16, 131.64, 129.49, 127.75, 125.35, 121.96, 109.91, 107.87, 105.30, 80.23, 66.30, 66.10, 52.48, 49.68, 49.18, 46.78, 43.26, 39.64, 29.80, 27.39, 25.11, 25.01, 23.81, 8.50, 8.20. HRMS (ESI) Calcd for $C_{33}H_{41}N_5O_4$ $(M+H)^+$ 572.3231, found 572.3233. HPLC purity 99.4%, $t_R$=10.41 min.

(R)—N-(4-(1H-pyrazol-4-yl)benzyl)-N-cyclopropyl-1-(3-((2-methyl-1-oxo-1-(piperidin-1-yl) propan-2-yl)oxy) phenyl)piperidine-3-carboxamide (57). $^{1}$H NMR (500 MHz, Methanol-$d_4$) δ 7.92 (s, 2H), 7.57-7.51 (m, 2H), 7.24 (d, J=8.1 Hz, 2H), 7.09 (t, J=8.2 Hz, 1H), 6.59 (dd, J=8.3, 2.3 Hz, 1H), 6.44 (t, J=2.3 Hz, 1H), 6.30 (dd, J=8.1, 2.3 Hz, 1H), 4.66-4.56 (m, 2H), 3.81 (p, J=7.2, 6.5 Hz, 2H), 3.72-3.63 (m, 2H), 3.59-3.49 (m, 3H), 2.88 (dd, J=12.3, 10.9 Hz, 1H), 2.78-2.71 (m, 2H), 1.98 (d, J=9.8 Hz, 1H), 1.83 (dq, J=8.6, 2.8 Hz, 1H), 1.72 (qd, J=12.1, 11.7, 3.4 Hz, 2H), 1.59-1.44 (m, 10H), 1.25 (dd, J=7.2, 3.9 Hz, 2H), 0.89 (pd, J=8.5, 7.7, 4.8 Hz, 4H). $^{13}$C NMR (126 MHz, Methanol-$d_4$) δ 177.63, 172.05, 156.44, 152.55, 136.17, 131.63, 129.32, 127.72, 125.34, 121.97, 109.74, 108.18, 105.53, 80.24, 52.53, 49.70, 49.19, 46.65, 44.03, 39.69, 29.81, 27.42, 25.85, 25.42, 25.29, 25.17, 24.06, 23.87, 8.47, 8.22. HRMS (ESI) Calcd for $C_{34}H_{43}N_5O_3$ $(M+H)^+$ 570.3439, found 570.3446. HPLC purity 99.7%, $t_R$=11.52 min.

Scheme 6. Synthesis of 54 and 58-62.

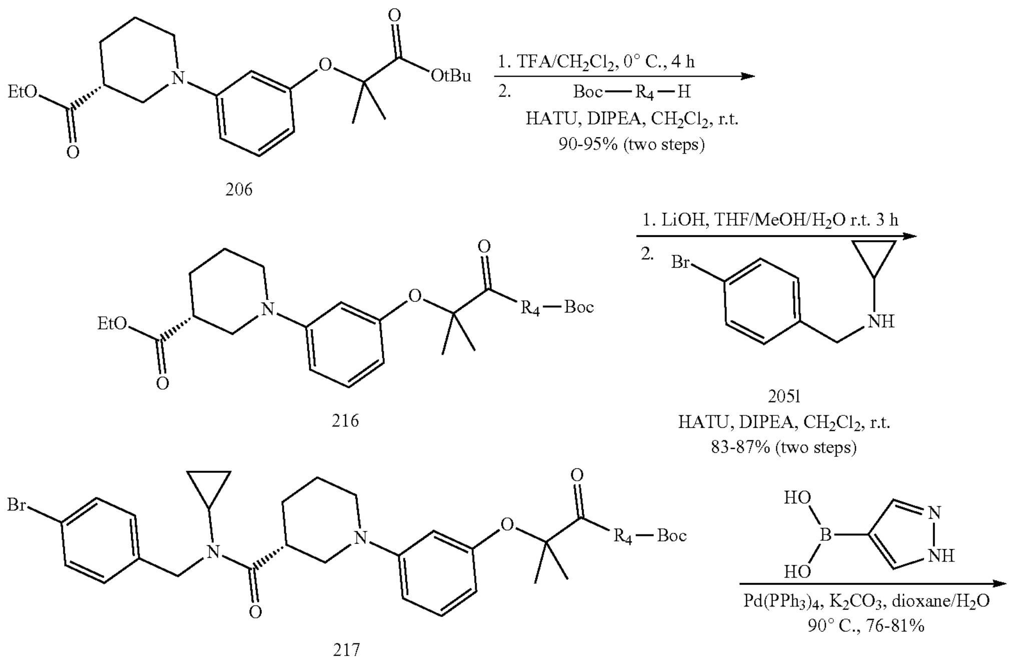

-continued

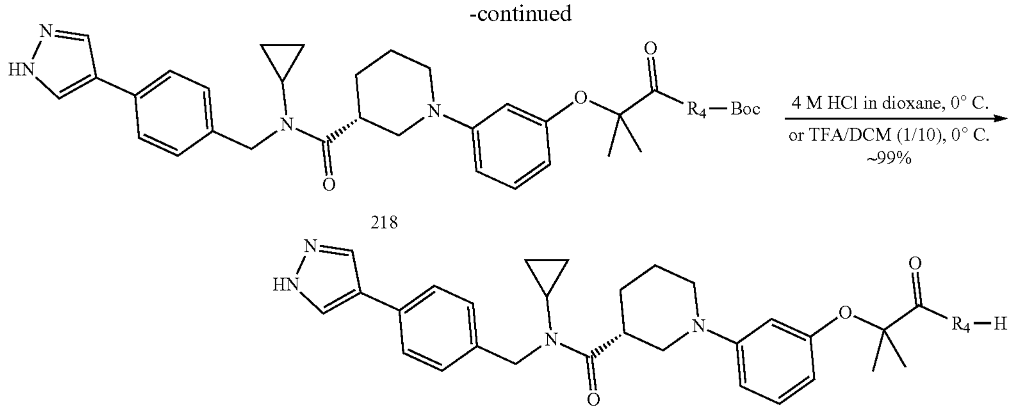

218

TFA or HCl salt

55, 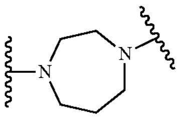 58, 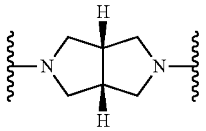 59, 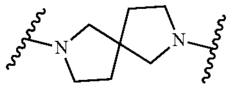

60, 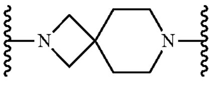 61, 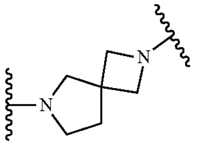 62, 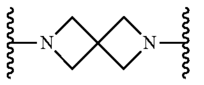

tert-butyl (R)-4-(2-(3-(3-(ethoxycarbonyl)piperidin-1-yl) phenoxy)-2-methylpropanoyl)-1,4-diazepane-1-carboxylate (216a). $^{1}$H NMR (500 MHz, Chloroform-d) δ 7.04 (q, J=8.5 Hz, 1H), 6.53 (ddd, J=8.7, 6.4, 2.3 Hz, 1H), 6.40 (p, J=2.3 Hz, 1H), 6.34-6.17 (m, 1H), 4.14 (q, J=7.1 Hz, 2H), 3.81 (dq, J=18.5, 7.0, 6.6 Hz, 2H), 3.68-3.29 (m, 5H), 3.29-3.03 (m, 3H), 2.96 (tt, J=10.0, 2.4 Hz, 1H), 2.82-2.70 (m, 1H), 2.60 (tt, J=9.9, 3.8 Hz, 1H), 2.06-1.72 (m, 4H), 1.61 (d, J=8.5 Hz, 8H), 1.40 (s, 9H), 1.25 (t, J=7.1 Hz, 3H). MS (ESI) m/z=518.3 [M+H]$^+$ tert-butyl (3aR,6aS)-5-(2-(3-((R)-3-(ethoxycarbonyl)piperidin-1-yl)phenoxy)-2-methylpropanoyl) hexahydropyrrolo[3,4-c]pyrrole-2 (1H)-carboxylate (216b). $^{1}$H NMR (500 MHz, Chloroform-d) δ 7.03 (t, J=8.2 Hz, 1H), 6.53 (dd, J=8.2, 2.2 Hz, 1H), 6.44-6.35 (m, 1H), 6.21 (d, J=7.5 Hz, 1H), 4.18-4.05 (m, 2H), 3.82-3.35 (m, 8H), 3.19-3.05 (m, 1H), 3.05-2.81 (m, 2H), 2.74-2.55 (m, 4H), 1.99 (hept, J=3.9 Hz, 1H), 1.75 (ddq, J=10.7, 7.4, 3.4, 2.7 Hz, 1H), 1.69-1.59 (m, 2H), 1.56 (d, J=4.4 Hz, 6H), 1.39 (s, 9H), 1.24 (t, J=7.1 Hz, 3H). MS (ESI) m/z=530.4 [M+H]$^+$ tert-butyl 7-(2-(3-((R)-3-(ethoxycarbonyl)piperidin-1-yl) phenoxy)-2-methylpropanoyl)-2,7-diazaspiro[4.4]nonane-2-carboxylate (216c). $^{1}$H NMR (500 MHz, Chloroform-d) δ 7.03 (td, J=8.2, 4.4 Hz, 1H), 6.57-6.46 (m, 1H), 6.40 (dq, J=4.5, 2.1 Hz, 1H), 6.22 (ddd, J=8.0, 5.3, 2.4 Hz, 1H), 4.18-4.07 (m, 2H), 3.73-2.90 (m, 11H), 2.75-2.70 (m, 1H), 2.66-2.53 (m, 1H), 2.00 (td, J=10.7, 9.2, 6.1 Hz, 1H), 1.84-1.47 (m, 13H), 1.40 (d, J=8.6 Hz, 9H), 1.24 (t, J=7.1 Hz, 3H). MS (ESI) m/z=544.4 [M+H]$^+$ tert-butyl (R)-2-(2-(3-(3-(ethoxycarbonyl)piperidin-1-yl) phenoxy)-2-methylpropanoyl)-2,7-diazaspiro[3.5]nonane-7-carboxylate (216d). $^{1}$H NMR (500 MHz, Chloroform-d) δ 7.06 (t, J=8.2 Hz, 1H), 6.56 (ddd, J=8.3, 2.4, 0.8 Hz, 1H), 6.42 (t, J=2.3 Hz, 1H), 6.28 (ddd, J=8.2, 2.4, 0.7 Hz, 1H), 4.13 (q, J=7.1 Hz, 2H), 3.89 (s, 2H), 3.72-3.61 (m, 3H), 3.46-3.37 (m, 1H), 3.29-3.12 (m, 4H), 2.97 (dd, J=12.4, 9.8 Hz, 1H), 2.76-2.70 (m, 1H), 2.65-2.54 (m, 1H), 1.99 (dp, J=13.0, 5.1 Hz, 1H), 1.76 (ttd, J=9.0, 6.2, 2.6 Hz, 1H), 1.69-1.57 (m, 2H), 1.57 (s, 10H), 1.39 (s, 9H), 1.24 (t, J=7.1 Hz, 3H). MS (ESI) m/z=544.5 [M+H]$^+$ tert-butyl (R)-6-(2-(3-(3-(ethoxycarbonyl)piperidin-1-yl) phenoxy)-2-methylpropanoyl)-2,6-diazaspiro[3.4]octane-2-carboxylate (216e). $^{1}$H NMR (500 MHz, Chloroform-d) δ 6.95 (td, J=8.2, 4.0 Hz, 1H), 6.49-6.40 (m, 1H), 6.30 (dt, J=5.1, 2.4 Hz, 1H), 6.17-6.05 (m, 1H), 4.05 (qd, J=7.1, 1.4 Hz, 2H), 3.75-3.24 (m, 10H), 2.89 (ddd, J=12.4, 9.8, 6.7 Hz, 1H), 2.65 (s, 1H), 2.56-2.46 (m, 1H), 1.97-1.84 (m, 2H), 1.81 (t, J=7.2 Hz, 1H), 1.67 (tdd, J=11.0, 5.4, 2.6 Hz, 1H), 1.59-1.40 (m, 8H), 1.30 (d, J=7.6 Hz, 9H), 1.16 (dd, J=7.5, 6.8 Hz, 3H). MS (ESI) m/z=530.4 [M+H]$^+$ tert-butyl (R)-6-(2-(3-(3-(ethoxycarbonyl)piperidin-1-yl) phenoxy)-2-methylpropanoyl)-2,6-diazaspiro[3.3]heptane-2-carboxylate (216f). $^{1}$H NMR (500 MHz, Chloroform-d) δ 7.04 (t, J=8.2 Hz, 1H), 6.58-6.51 (m, 1H), 6.38 (t, J=2.4 Hz, 1H), 6.28-6.15 (m, 1H), 4.28 (s, 2H), 4.11 (q, J=7.2 Hz, 2H), 4.06 (s, 2H), 3.92 (d, J=9.3 Hz, 2H), 3.83 (d, J=9.3 Hz, 2H), 3.63 (ddt, J=12.5, 3.4, 1.4 Hz, 1H), 3.45-3.30 (m, 1H), 2.96 (dd, J=12.4, 9.8 Hz, 1H), 2.77-2.71 (m, 1H), 2.59 (tt, J=9.9, 4.0 Hz, 1H), 2.02-1.90 (m, 1H), 1.75 (dqd, J=9.5, 6.3, 2.4 Hz, 1H), 1.68-1.55 (m, 2H), 1.47 (s, 6H), 1.35 (s, 9H), 1.22 (t, J=7.1 Hz, 3H). MS (ESI) m/z=516.4 [M+H]$^+$ tert-butyl (R)-4-(2-(3-(3-((4-bromobenzyl)(cyclopropyl) carbamoyl)piperidin-1-yl)phenoxy)-2-methylpropanoyl)-1,4-diazepane-1-carboxylate (217a). $^{1}$H NMR (500 MHz, Chloroform-d) δ 7.38-7.30 (m, 2H), 7.07-6.92 (m, 3H), 6.43 (td, J=9.0, 2.2 Hz, 1H), 6.34 (d, J=3.4 Hz, 1H), 6.24-6.14 (m, 1H), 4.54 (dd, J=14.9, 3.9 Hz, 1H), 4.40 (dd, J=14.8, 4.4 Hz, 1H), 3.86-3.66 (m, 2H), 3.63-3.54 (m, 2H), 3.45-3.26 (m, 3H), 3.19-2.97 (m, 3H), 2.88 (ddd, J=16.0, 10.6, 4.5 Hz, 1H), 2.68-2.61 (m, 1H), 2.58-2.49 (m, 1H), 1.89-1.50 (m, 13H), 1.34 (s, 9H), 0.85-0.67 (m, 4H). MS (ESI) m/z=697.3, 699.4 [M+H]$^+$ tert-butyl (3aR,6aS)-5-(2-(3-((R)-3-((4-bromobenzyl)(cyclopropyl)carbamoyl) piperidin-1-yl)phenoxy)-2-methylpropanoyl) hexahydropyrrolo[3,4-c]pyrrole-2 (1H)-carboxylate (217b). $^1$H NMR (500 MHz, Chloroform-d) δ 7.44-7.37 (m, 2H), 7.14-7.08 (m, 2H), 7.05 (t, J=8.2 Hz, 1H), 6.52 (dd, J=8.2, 2.4 Hz, 1H), 6.39 (s, 1H), 6.23 (d, J=7.9 Hz, 1H), 4.60 (d, J=14.7 Hz, 1H), 4.47 (d, J=14.7 Hz, 1H), 3.75-3.37 (m, 9H), 3.19-2.83 (m, 3H), 2.76-2.65 (m, 3H), 2.60 (dq, J=7.2, 3.4 Hz, 1H), 1.92-1.67 (m, 4H), 1.59-1.54 (m, 6H), 1.41 (d, J=1.0 Hz, 9H), 0.93-0.74 (m, 4H). MS (ESI) m/z=709.3, 711.3 [M+H]$^+$ tert-butyl 7-(2-(3-((R)-3-((4-bromobenzyl)(cyclopropyl)carbamoyl)piperidin-1-yl)phenoxy)-2-methylpropanoyl)-2,7-diazaspiro[4.4]nonane-2-carboxylate (217c). $^1$H NMR (500 MHz, Chloroform-d) δ 7.38 (dt, J=8.9, 1.9 Hz, 2H), 7.07 (dd, J=8.5, 2.8 Hz, 2H), 7.02 (td, J=8.2, 4.5 Hz, 1H), 6.48 (dq, J=8.2, 2.5 Hz, 1H), 6.38 (q, J=3.2, 2.4 Hz, 1H), 6.20 (td, J=7.5, 7.0, 2.2 Hz, 1H), 4.64-4.50 (m, 1H), 4.49-4.28 (m, 1H), 3.61 (d, J=12.1 Hz, 3H), 3.57-3.45 (m, 2H), 3.45-3.28 (m, 3H), 3.28-3.07 (m, 2H), 3.03 (s, 1H), 2.97-2.85 (m, 1H), 2.77-2.64 (m, 1H), 2.64-2.48 (m, 1H), 1.91-1.52 (m, 14H), 1.38 (d, J=9.4 Hz, 9H), 0.90-0.70 (m, 4H). MS (ESI) m/z=723.4, 725.4 [M+H]$^+$ tert-butyl (R)-2-(2-(3-(3-((4-bromobenzyl)(cyclopropyl)carbamoyl)piperidin-1-yl)phenoxy)-2-methylpropanoyl)-2,7-diazaspiro[3.5]nonane-7-carboxylate (217d). $^1$H NMR (500 MHz, Chloroform-d) δ 7.42-7.33 (m, 2H), 7.13-6.96 (m, 3H), 6.53 (dd, J=8.2, 2.3 Hz, 1H), 6.41 (t, J=2.3 Hz, 1H), 6.28 (dd, J=8.1, 2.3 Hz, 1H), 4.59 (d, J=14.7 Hz, 1H), 4.44 (d, J=14.7 Hz, 1H), 3.87 (s, 2H), 3.71-3.57 (m, 4H), 3.39 (ddt, J=11.0, 7.3, 3.5 Hz, 1H), 3.21 (qdd, J=13.6, 6.7, 4.1 Hz, 4H), 2.93 (dd, J=12.4, 10.9 Hz, 1H), 2.77-2.62 (m, 1H), 2.57 (td, J=7.0, 3.4 Hz, 1H), 1.90 (d, J=8.1 Hz, 1H), 1.79 (tt, J=9.8, 4.7 Hz, 1H), 1.74-1.62 (m, 2H), 1.53-1.35 (m, 19H), 0.91-0.72 (m, 4H). MS (ESI) m/z=723.4, 725.4 [M+H]$^+$ tert-butyl (R)-6-(2-(3-(3-((4-bromobenzyl)(cyclopropyl)carbamoyl)piperidin-1-yl)phenoxy)-2-methylpropanoyl)-2,6-diazaspiro[3.4]octane-2-carboxylate (217e). $^1$H NMR (500 MHz, Chloroform-d) δ 7.38 (dt, J=8.9, 1.8 Hz, 2H), 7.13-7.04 (m, 2H), 7.01 (td, J=8.2, 4.9 Hz, 1H), 6.49 (dd, J=8.3, 2.3 Hz, 1H), 6.36 (q, J=2.5 Hz, 1H), 6.18 (ddd, J=13.0, 8.1, 2.3 Hz, 1H), 4.57 (dd, J=14.7, 10.0 Hz, 1H), 4.43 (dd, J=14.7, 8.6 Hz, 1H), 3.77-3.54 (m, 8H), 3.50-3.45 (m, 2H), 3.37 (td, J=9.8, 8.5, 4.8 Hz, 1H), 2.91 (ddd, J=12.4, 10.9, 7.6 Hz, 1H), 2.69 (td, J=9.8, 9.2, 5.1 Hz, 1H), 2.57 (tq, J=7.2, 3.6 Hz, 1H), 1.94-1.82 (m, 3H), 1.81-1.73 (m, 1H), 1.73-1.60 (m, 2H), 1.56-1.49 (m, 6H), 1.37 (d, J=7.8 Hz, 9H), 0.90-0.69 (m, 4H). MS (ESI) m/z=709.4, 711.4 [M+H]$^+$ tert-butyl (R)-6-(2-(3-(3-((4-bromobenzyl)(cyclopropyl)carbamoyl)piperidin-1-yl)phenoxy)-2-methylpropanoyl)-2,6-diazaspiro[3.3]heptane-2-carboxylate (217f). $^1$H NMR (500 MHz, Chloroform-d) δ 7.42-7.32 (m, 2H), 7.13-6.94 (m, 3H), 6.53 (dd, J=8.3, 2.3 Hz, 1H), 6.38 (t, J=2.4 Hz, 1H), 6.24 (dd, J=8.1, 2.3 Hz, 1H), 4.58 (d, J=14.7 Hz, 1H), 4.44 (d, J=14.7 Hz, 1H), 4.28 (s, 2H), 4.03 (d, J=2.2 Hz, 2H), 3.92 (dd, J'=9.7, 1.6 Hz, 2H), 3.82 (d, J=9.3 Hz, 2H), 3.71-3.53 (m, 2H), 3.38 (ddt, J=11.0, 7.5, 3.6 Hz, 1H), 2.93 (dd, J=12.4, 10.9 Hz, 1H), 2.72 (td, J=11.9, 3.1 Hz, 1H), 2.61-2.42 (m, 1H), 1.90 (d, J=8.9 Hz, 1H), 1.80 (h, J=7.0, 4.8 Hz, 1H), 1.75-1.64 (m, 2H), 1.48 (d, J=1.7 Hz, 6H), 1.36 (s, 9H), 0.89-0.70 (m, 4H). MS (ESI) m/z=695.3, 697.4 [M+H]$^+$ tert-butyl (R)-4-(2-(3-(3-((4-(1H-pyrazol-4-yl)benzyl)(cyclopropyl) carbamoyl)piperidin-1-yl)phenoxy)-2-methylpropanoyl)-1,4-diazepane-1-carboxylate (218a). $^1$H NMR (500 MHz, Chloroform-d) δ 7.81 (s, 2H), 7.44 (d, J=7.8 Hz, 2H), 7.22 (d, J=7.9 Hz, 2H), 7.06 (q, J=8.8, 8.3 Hz, 1H), 6.58-6.47 (m, 1H), 6.47-6.37 (m, 1H), 6.27 (dq, J=8.2, 4.1, 2.4 Hz, 1H), 4.75-4.65 (m, 1H), 4.53 (dd, J=14.8, 10.5 Hz, 1H), 3.82 (tt, J=11.4, 6.0 Hz, 2H), 3.74-3.55 (m, 2H), 3.55-3.30 (m, 3H), 3.30-2.88 (m, 4H), 2.75 (t, J=11.8 Hz, 1H), 2.63 (td, J=5.7, 4.7, 2.6 Hz, 1H), 2.01-1.55 (m, 13H), 1.41 (s, 9H), 0.94-0.76 (m, 4H). MS (ESI) m/z=685.4 [M+H]$^+$, 683.1 [M−H]$^-$ tert-butyl (3aR,6aS)-5-(2-(3-((R)-3-((4-(1H-pyrazol-4-yl)benzyl) (cyclopropyl) carbamoyl)piperidin-1-yl)phenoxy)-2-methylpropanoyl) hexahydropyrrolo[3,4-c]pyrrole-2 (1H)-carboxylate (218b). $^1$H NMR (500 MHz, Chloroform-d) δ 7.85-7.76 (m, 2H), 7.43 (dt, J=8.1, 1.9 Hz, 2H), 7.24-7.18 (m, 2H), 7.05 (t, J=8.3 Hz, 1H), 6.54 (d, J=8.2 Hz, 1H), 6.42 (t, J=2.6 Hz, 1H), 6.23 (d, J=7.8 Hz, 1H), 4.68 (d, J=14.7 Hz, 1H), 4.53 (d, J=14.9 Hz, 1H), 3.81-3.63 (m, 4H), 3.63-3.38 (m, 5H), 3.21-2.84 (m, 3H), 2.84-2.56 (m, 4H), 1.95 (d, J=10.3 Hz, 1H), 1.87-1.77 (m, 1H), 1.72 (q, J=12.4 Hz, 2H), 1.57 (d, J=4.4 Hz, 6H), 1.43-1.39 (m, 9H), 0.93-0.79 (m, 4H). MS (ESI) m/z=697.5 [M+H]$^+$, 695.5 [M−H]$^-$ tert-butyl 7-(2-(3-((R)-3-((4-(1H-pyrazol-4-yl)benzyl)(cyclopropyl)carbamoyl) piperidin-1-yl)phenoxy)-2-methylpropanoyl)-2,7-diazaspiro[4.4]nonane-2-carboxylate (218c). $^1$H NMR (500 MHz, Chloroform-d) δ 7.78 (s, 2H), 7.41 (dd, J=8.1, 1.5 Hz, 2H), 7.19 (d, J=7.9 Hz, 2H), 7.04 (td, J=8.2, 3.3 Hz, 1H), 6.52 (dd, J=8.3, 2.6 Hz, 1H), 6.42 (dd, J=5.5, 3.2 Hz, 1H), 6.22 (td, J=7.6, 2.2 Hz, 1H), 4.73-4.61 (m, 1H), 4.49 (dd, J=14.9, 8.8 Hz, 1H), 3.72-2.89 (m, 12H), 2.80-2.58 (m, 2H), 1.94 (d, J=10.7 Hz, 1H), 1.84-1.48 (m, 13H), 1.41 (d, J=8.3 Hz, 9H), 0.91-0.75 (m, 4H). MS (ESI) m/z=711.6 [M+H]$^+$ tert-butyl (R)-2-(2-(3-(3-((4-(1H-pyrazol-4-yl)benzyl)(cyclopropyl)carbamoyl) piperidin-1-yl)phenoxy)-2-methylpropanoyl)-2,7-diazaspiro[3.5]nonane-7-carboxylate (218d). $^1$H NMR (500 MHz, Chloroform-d) δ 7.82 (s, 2H), 7.48-7.41 (m, 2H), 7.23 (d, J=8.0 Hz, 2H), 7.09 (t, J=8.2 Hz, 1H), 6.57 (dd, J=8.2, 2.3 Hz, 1H), 6.45 (t, J=2.3 Hz, 1H), 6.31 (dd, J=8.2, 2.3 Hz, 1H), 4.69 (d, J=14.6 Hz, 1H), 4.53 (d, J=14.6 Hz, 1H), 3.91 (s, 2H), 3.71-3.64 (m, 4H), 3.45 (tt, J=11.0, 3.5 Hz, 1H), 3.31-3.19 (m, 4H), 2.99 (dd, J=12.4, 10.9 Hz, 1H), 2.75 (dd, J=12.4, 9.2 Hz, 1H), 2.63 (td, J=7.0, 3.3 Hz, 1H), 1.96 (d, J=9.9 Hz, 1H), 1.83 (dt, J=9.9, 3.3 Hz, 1H), 1.80-1.68 (m, 2H), 1.53 (d, J=2.3 Hz, 10H), 1.42 (s, 9H), 0.93-0.80 (m, 4H). MS (ESI) m/z=711.5 [M+H]$^+$ tert-butyl (R)-6-(2-(3-(3-((4-(1H-pyrazol-4-yl)benzyl)(cyclopropyl)carbamoyl) piperidin-1-yl)phenoxy)-2-methylpropanoyl)-2,6-diazaspiro[3.4]octane-2-carboxylate (218e). $^1$H NMR (500 MHz, Chloroform-d) δ 7.80 (s, 2H), 7.46-7.38 (m, 2H), 7.22 (d, J=8.0 Hz, 2H), 7.05 (td, J=8.2, 6.5 Hz, 1H), 6.54 (dt, J=8.5, 2.9 Hz, 1H), 6.44-6.37 (m, 1H), 6.21 (ddd, J=13.1, 8.1, 2.3 Hz, 1H), 4.69 (dd, J=14.7, 5.9 Hz, 1H), 4.53 (dd, J=14.7, 4.3 Hz, 1H), 3.77-3.43 (m, 11H), 3.04-2.90 (m, 1H), 2.75 (tt, J=12.1, 2.5 Hz, 1H), 2.68 (s, 1H), 1.97-1.71 (m, 6H), 1.60-1.54 (m, 6H), 1.41 (d, J=7.8 Hz, 9H), 0.93-0.79 (m, 4H). MS (ESI) m/z=697.5 [M+H]$^+$ tert-butyl (R)-6-(2-(3-(3-((4-(1H-pyrazol-4-yl)benzyl)(cyclopropyl)carbamoyl) piperidin-1-yl)phenoxy)-2-methylpropanoyl)-2,6-diazaspiro[3.3]heptane-2-carboxylate (218f). $^1$H NMR (500 MHz, Chloroform-d) δ 7.82 (s, 2H), 7.48-7.41 (m, 2H), 7.24 (d, J=8.0 Hz, 2H), 7.09 (t, J=8.2 Hz, 1H), 6.58 (dd, J=8.2, 2.3 Hz, 1H), 6.43 (t, J=2.4 Hz, 1H), 6.27 (dd, J=8.1, 2.3 Hz, 1H), 4.68 (d, J=14.6 Hz, 1H), 4.61 (s, 1H), 4.31 (s, 2H), 4.07 (s, 2H), 3.94 (t, J=8.8 Hz, 2H), 3.86 (dd, J=9.5, 2.3 Hz, 2H), 3.67 (d, J=12.3 Hz, 2H), 3.45 (td, J=10.5, 9.0, 5.3 Hz, 1H), 3.00 (dd, J=12.4, 10.9 Hz, 1H), 2.76 (td, J=12.0, 3.0 Hz, 1H), 2.63 (td, J=7.1, 3.5 Hz, 1H), 1.96 (d, J=10.4 Hz, 1H), 1.88-1.79 (m, 1H), 1.79-1.67 (m, 2H), 1.51 (d, J=1.6 Hz, 6H), 1.40 (s, 9H), 0.97-0.79 (m, 4H). MS (ESI) m/z=683.5 [M+H]$^+$ (R)-4-(2-(3-(3-((4-(1H-pyrazol-4-yl)benzyl)(cyclopropyl)carbamoyl)piperidin-1-yl)phenoxy)-2-methylpropanoyl)-1,4-diazepan-1-ium chloride (54). $^1$H NMR (500 MHz, Methanol-d$_4$) δ 8.39 (s, 2H), 7.63 (d, J=7.9 Hz, 2H), 7.54 (t, J=8.2 Hz, 1H), 7.49-7.44 (m, 1H), 7.39-7.30 (m, 3H), 7.03 (dd, J=8.4, 2.3 Hz, 1H), 4.85 (s, 1H), 4.49 (d, J=15.1 Hz, 1H), 4.22 (s, 1H), 3.97 (q, J=6.0 Hz, 8H), 3.31-3.07 (m, 4H), 2.85 (tt, J=7.0, 4.1 Hz, 1H), 2.32-1.93 (m, 6H), 1.69 (d, J=4.5 Hz, 6H), 1.13-0.88 (m, 4H). $^{13}$C NMR (126 MHz, Methanol-d$_4$) δ 175.62, 172.87, 156.41, 143.39, 137.25, 131.50, 130.70, 129.53, 127.91, 125.79, 123.27, 118.58, 114.31, 111.56, 81.89, 57.95, 55.95, 49.50, 45.53, 45.03, 44.01, 43.51, 37.06, 29.99, 25.64, 25.05, 24.93, 23.87, 21.86, 9.33, 7.31. HRMS (ESI) Calcd for $C_{34}H_{44}N_6O_3$ (M+H)$^+$ 585.3548, found 585.3544. HPLC purity 98.6%, $t_R$=9.21 min.

(3aR,6aS)-5-(2-(3-((R)-3-((4-(1H-pyrazol-4-yl)benzyl)(cyclopropyl)carbamoyl) piperidin-1-yl)phenoxy)-2-methylpropanoyl) octahydropyrrolo[3,4-c]pyrrol-2-ium chloride (58). $^1$H NMR (500 MHz, Methanol-d$_4$) δ 8.51 (s, 2H), 7.66 (d, J=7.9 Hz, 2H), 7.55 (t, J=8.2 Hz, 1H), 7.47 (d, J=8.2 Hz, 1H), 7.34 (t, J=8.4 Hz, 3H), 7.02 (dd, J=8.4, 2.2 Hz, 1H), 4.86 (d, J=15.2 Hz, 1H), 4.49 (d, J=15.1 Hz, 1H), 4.26 (s, 1H), 3.88-3.65 (m, 8H), 3.56-3.43 (m, 2H), 3.18-3.03 (m, 3H), 2.86 (tt, J=7.1, 3.9 Hz, 1H), 2.69 (td, J=13.6, 12.9, 6.0 Hz, 1H), 2.27 (d, J=39.9 Hz, 1H), 2.18 (q, J=12.4, 9.7 Hz, 2H), 1.93 (s, 1H), 1.63 (d, J=3.0 Hz, 6H), 1.13-0.88 (m, 4H). $^{13}$C NMR (126 MHz, Methanol-d$_4$) δ 172.16, 156.38, 143.28, 137.62, 131.50, 130.70, 128.97, 127.95, 125.90, 123.57, 118.92, 114.46, 114.40, 111.55, 81.33, 58.10, 55.79, 50.84, 49.73, 49.67, 49.61, 49.50, 48.60, 43.06, 38.91, 37.18, 30.02, 24.19, 23.94, 23.89, 21.97, 9.36, 7.34. HRMS (ESI) Calcd for $C_{35}H_{44}N_6O_3$ (M+H)$^+$ 597.3548, found 597.3553. HPLC purity 98.9%, $t_R$=9.26 min.

7-(2-(3-((R)-3-((4-(1H-pyrazol-4-yl)benzyl)(cyclopropyl)carbamoyl)piperidin-1-yl)phenoxy)-2-methylpropanoyl)-2,7-diazaspiro[4.4]nonan-2-ium chloride (59). $^1$H NMR (500 MHz, Methanol-d$_4$) δ 8.57 (s, 2H), 7.67 (d, J=7.9 Hz, 2H), 7.55-7.33 (m, 5H), 7.00 (dt, J=8.5, 2.7 Hz, 1H), 4.86 (s, 1H), 4.49 (dd, J=15.1, 3.4 Hz, 1H), 4.36-4.06 (m, 1H), 3.84-3.58 (m, 9H), 3.39 (td, J=7.4, 4.1 Hz, 1H), 3.21-3.02 (m, 2H), 2.86 (tt, J=7.0, 3.9 Hz, 1H), 2.37-2.12 (m, 3H), 2.10-1.72 (m, 5H), 1.66-1.62 (m, 6H), 1.11-0.88 (m, 4H). $^{13}$C NMR (126 MHz, Methanol-d$_4$) δ 172.18, 171.90, 156.55, 156.38, 143.37, 143.32, 143.29, 137.82, 137.81, 131.37, 130.69, 128.66, 127.97 (d, J=5.3 Hz), 125.95, 123.76, 118.44, 118.31, 118.03, 117.97, 114.28, 114.21, 111.76, 111.68, 111.52, 111.32, 81.28, 81.26, 81.17, 57.98, 56.06, 56.03, 55.05, 55.04, 52.23, 52.13, 51.51, 51.45, 49.49, 49.29, 46.58, 46.26, 45.89, 45.88, 44.68, 44.61, 37.14, 35.35, 33.62, 33.50, 32.99, 31.92, 30.01, 24.19, 24.14, 24.01, 24.00, 23.89, 23.84, 23.74, 23.65, 21.91, 9.36, 7.30. HRMS (ESI) Calcd for $C_{36}H_{46}N_6O_3$ (M+H)$^+$ 611.3704, found 611.3705. HPLC purity 98.8%, $t_R$=9.31 min.

(R)-2-(2-(3-(3-((4-(1H-pyrazol-4-yl)benzyl)(cyclopropyl)carbamoyl)piperidin-1-yl)phenoxy)-2-methylpropanoyl)-2,7-diazaspiro[3.5]nonan-7-ium 2,2,2-trifluoroacetate (60). $^1$H NMR (500 MHz, Methanol-d$_4$) δ 8.02 (s, 2H), 7.59-7.53 (m, 2H), 7.50 (t, J=8.3 Hz, 1H), 7.32 (dd, J=8.2, 2.2 Hz, 1H), 7.26 (d, J=8.1 Hz, 2H), 7.18 (t, J=2.3 Hz, 1H), 6.97 (dd, J=8.3, 2.3 Hz, 1H), 4.85 (d, J=14.9 Hz, 1H), 4.44 (d, J=15.0 Hz, 1H), 4.10-4.04 (m, 2H), 3.98 (dq, J=9.3, 4.5, 3.8 Hz, 1H), 3.72 (dtd, J=15.4, 12.1, 3.4 Hz, 3H), 3.59-3.51 (m, 1H), 3.08 (td, J=6.3, 5.8, 1.9 Hz, 4H), 2.79 (ddd, J=8.4, 6.1, 3.6 Hz, 1H), 2.21-2.09 (m, 3H), 1.83 (qdt, J=12.7, 8.5, 5.0 Hz, 6H), 1.57 (s, 7H), 1.02-0.86 (m, 4H). $^{13}$C NMR (126 MHz, Methanol-d$_4$) δ 175.70, 173.29, 160.49 (q, J=37.2 Hz), 156.42, 144.39, 136.08, 131.47-131.29 (m), 131.10, 130.63, 127.76, 126.85, 125.77, 125.46, 122.16, 119.65, 117.75, 117.35, 115.04, 113.90, 112.73, 111.18, 81.24, 62.08, 57.70, 57.22, 55.08, 49.45, 40.77, 37.51, 32.53, 30.97, 30.95, 29.80, 24.24, 23.62, 23.46, 22.17, 9.12, 7.34. HRMS (ESI) Calcd for $C_{36}H_{46}N_6O_3$ (M+H)$^+$ 611.3704, found 611.3698. HPLC purity 99.6%, $t_R$=9.22 min.

(R)-6-(2-(3-(3-((4-(1H-pyrazol-4-yl)benzyl)(cyclopropyl)carbamoyl)piperidin-1-yl)phenoxy)-2-methylpropanoyl)-2,6-diazaspiro[3.4]octan-2-ium 2,2,2-trifluoroacetate (61). $^1$H NMR (500 MHz, Methanol-d$_4$) δ 8.02 (s, 2H), 7.58-7.51 (m, 2H), 7.45 (t, J=8.2 Hz, 1H), 7.29-7.23 (m, 3H), 7.14 (dt, J=4.0, 2.3 Hz, 1H), 6.88 (ddd, J=8.1, 5.5, 2.3 Hz, 1H), 4.84 (dd, J=15.0, 3.9 Hz, 1H), 4.43 (d, J=14.9 Hz, 1H), 4.07-3.89 (m, 5H), 3.77-3.51 (m, 8H), 2.78 (tt, J=6.7, 4.4 Hz, 1H), 2.17-2.06 (m, 5H), 1.88 (q, J=7.3 Hz, 1H), 1.61 (d, J=12.0 Hz, 6H), 1.02-0.85 (m, 4H). $^{13}$C NMR (126 MHz, Methanol-d$_4$) δ 175.70, 172.15, 172.11, 160.61 (q, J=36.7, 36.3 Hz), 156.51, 156.35, 144.47 (d, J=21.4 Hz), 136.10, 131.30, 131.19, 131.13, 130.63, 127.78, 127.75, 126.84, 125.76, 125.46, 122.16, 119.70, 117.39, 116.81 (d, J=28.1 Hz), 115.08, 113.72, 113.59, 112.77, 110.59, 81.08, 80.98, 57.09, 55.91, 55.16, 54.99, 54.73, 54.28, 54.15, 53.62, 53.57, 49.45, 45.75, 45.43, 43.42, 40.25, 37.50, 35.78, 31.89, 29.80, 24.28, 24.00, 23.96, 23.80, 23.80, 22.18, 9.11, 7.36. HRMS (ESI) Calcd for $C_{35}H_{44}N_6O_3$ (M+H)$^+$ 597.3548, found 597.3570. HPLC purity 99.2%, $t_R$=9.26 min.

(R)-6-(2-(3-(3-((4-(1H-pyrazol-4-yl)benzyl)(cyclopropyl)carbamoyl)piperidin-1-yl)phenoxy)-2-methylpropanoyl)-2,6-diazaspiro[3.3]heptan-2-ium 2,2,2-trifluoroacetate (62). $^1$H NMR (500 MHz, Methanol-d$_4$) δ 8.01 (s, 2H), 7.57-7.52 (m, 2H), 7.48 (t, J=8.3 Hz, 1H), 7.32 (dd, J=8.0, 2.2 Hz, 1H), 7.26 (d, J=8.1 Hz, 2H), 7.19 (t, J=2.3 Hz, 1H), 6.95 (dd, J=8.2, 2.3 Hz, 1H), 4.85 (d, J=14.9 Hz, 1H), 4.50 (d, J=2.3 Hz, 2H), 4.44 (d, J=15.0 Hz, 1H), 4.21 (d, J=7.7 Hz, 4H), 4.15 (dd, J=11.8, 3.0 Hz, 2H), 4.02-3.93 (m, 1H), 3.78-3.65 (m, 3H), 3.54 (ddd, J=12.3, 8.0, 5.1 Hz, 1H), 2.78 (ddd, J=8.5, 6.1, 3.7 Hz, 1H), 2.13 (ddp, J=14.4, 9.0, 4.4 Hz, 3H), 1.90 (dd, J=15.3, 7.4 Hz, 1H), 1.54 (s, 6H), 1.05-0.87 (m, 4H). $^{13}$C NMR (126 MHz, Methanol-d$_4$) δ 175.74, 172.86, 160.65 (q, J=36.3 Hz), 156.21, 144.42, 136.03, 131.40, 131.09, 130.63, 127.77, 125.45, 118.29, 117.42, 115.11, 114.10 (d, J=2.8 Hz), 111.75, 81.43, 62.27, 57.95, 57.07, 55.07, 55.04, 54.84, 54.82, 49.44, 37.50, 36.08, 29.80, 24.27, 23.56, 23.45, 22.17, 9.11, 7.37. HRMS (ESI) Calcd for $C_{34}H_{42}N_6O_3$ (M+H)$^+$ 583.3391, found 583.3388. HPLC purity 97.3%, $t_R$=9.04 min.

Scheme 7. Synthesis of 63-72.
a.
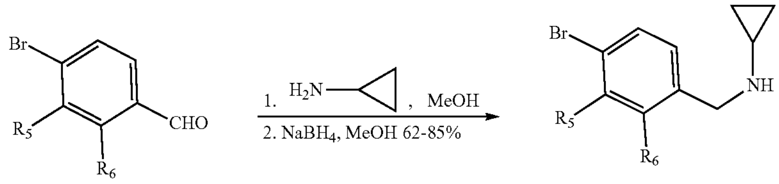
219
219a, $R_5$ = F, $R_6$ = H
219b, $R_5$ = H, $R_5$ = F
219c, $R_5$ = H, $R_5$ = Cl
219d, $R_5$ = Me, $R_6$ = H
219e, $R_5$ = H, $R_6$ = Me
219f, $R_5$ = OMe, $R_6$ = H
219g, $R_5$ = H, $R_6$ = OMe
219h, $R_5$ =$CF_3$, $R_6$ = H
219i, $R_5$ = H, $R_6$ = $CF_3$
219j, $R_5$ = H, $R_6$ = $OCF_3$
b.
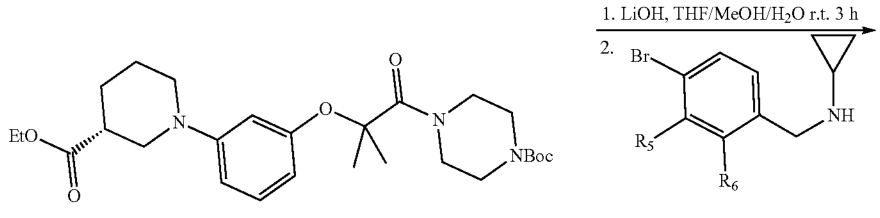
207
219a-219j
HATU, DIPEA, $CH_2Cl_2$, r.t.
85-89% (two steps)
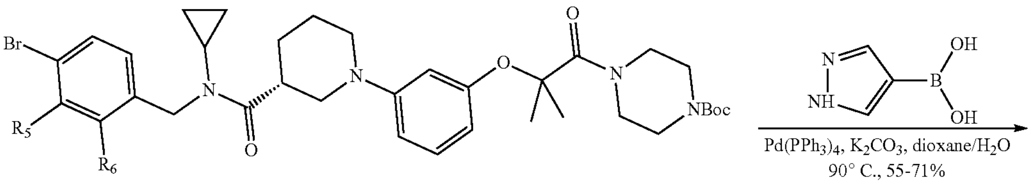
220
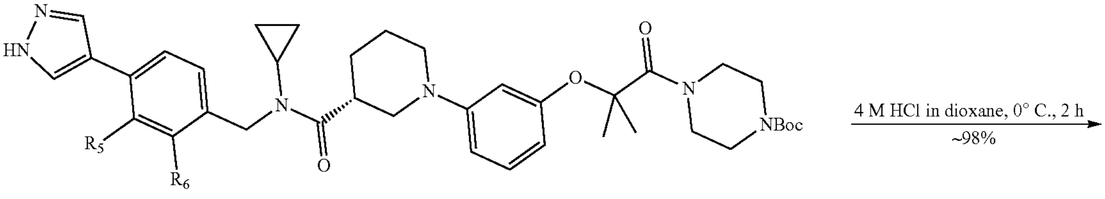
221
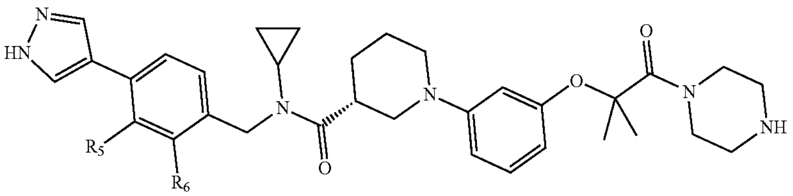
63-72
HCl or $CF_3COOH$ salt -continued 63, $R_5$ = F, $R_6$ = H
64, $R_5$ = H, $R_6$ = F
65, $R_5$ = H, $R_6$ = Cl
66, $R_5$ = Me, $R_6$ = H
67, $R_5$ = H, $R_6$ = Me
68, $R_5$ = OMe, $R_6$ = H
69, $R_5$ = H, $R_6$ = OMe
70, $R_5$ = $CF_3$, $R_6$ = H
71, $R_5$ = H, $R_6$ = $CF_3$
72, $R_5$ = H, $R_6$ = $OCF_3$ N-(4-bromo-3-fluorobenzyl)cyclopropanamine (219a). $^1$H NMR (500 MHz, Chloroform-d) δ 7.46 (dd, J=8.1, 7.1 Hz, 1H), 7.10 (dd, J=9.5, 2.0 Hz, 1H), 7.03-6.87 (m, 1H), 3.80 (s, 2H), 2.13 (tt, J=6.8, 3.6 Hz, 1H), 1.78 (s, 1H), 0.48-0.29 (m, 4H). MS (ESI) m/z=244.0, 246.0 $[M+H]^+$ N-(4-bromo-2-fluorobenzyl)cyclopropanamine (219b). $^1$H NMR (500 MHz, Chloroform-d) δ 7.23-7.09 (m, 3H), 3.77 (d, J=1.1 Hz, 2H), 2.06-1.96 (m, 1H), 1.85-1.64 (m, 1H), 0.44-0.10 (m, 4H). MS (ESI) m/z=244.0, 246.0 $[M+H]^+$ N-(4-bromo-2-chlorobenzyl)cyclopropanamine (219c). $^1$H NMR (500 MHz, Chloroform-d) δ 7.45 (d, J=2.0 Hz, 1H), 7.28 (dd, J=8.2, 2.0 Hz, 1H), 7.22-6.92 (m, 1H), 3.81 (s, 2H), 2.07-1.96 (m, 1H), 1.87 (s, 1H), 0.46-0.13 (m, 4H). MS (ESI) m/z=260.1, 262.1 $[M+H]^+$ N-(4-bromo-3-methylbenzyl)cyclopropanamine (219d). $^1$H NMR (500 MHz, Chloroform-d) δ 7.44 (d, J=8.1 Hz, 1H), 7.17 (d, J=2.2 Hz, 1H), 6.97 (dd, J=8.2, 2.2 Hz, 1H), 3.74 (s, 2H), 2.37 (s, 3H), 2.14-2.08 (m, 1H), 1.89-1.72 (m, 1H), 0.48-0.33 (m, 4H). MS (ESI) m/z=240.1, 242.1 $[M+H]^+$ N-(4-bromo-2-methylbenzyl)cyclopropanamine (219e). $^1$H NMR (500 MHz, Chloroform-d) δ 7.12-6.98 (m, 2H), 6.91 (d, J=8.0 Hz, 1H), 3.55 (s, 2H), 2.10 (s, 3H), 1.93 (ddd, J=10.1, 6.6, 3.6 Hz, 1H), 1.46 (s, 1H), 0.25-0.08 (m, 4H). MS (ESI) m/z=240.1, 242.1 $[M+H]^+$ N-(4-bromo-3-methoxybenzyl)cyclopropanamine (219f). $^1$H NMR (500 MHz, Chloroform-d) δ 7.45 (d, J=8.0 Hz, 1H), 6.88 (d, J=1.9 Hz, 1H), 6.78 (dd, J=8.0, 1.9 Hz, 1H), 3.90 (s, 3H), 3.80 (s, 2H), 2.14 (tt, J=6.5, 3.7 Hz, 1H), 1.82 (s, 1H), 0.49-0.32 (m, 4H). MS (ESI) m/z=256.1, 258.1 $[M+H]^+$ N-(4-bromo-2-methoxybenzyl)cyclopropanamine (219g). $^1$H NMR (500 MHz, Chloroform-d) δ 7.10 (d, J=7.9 Hz, 1H), 7.04 (dd, J=7.9, 1.8 Hz, 1H), 6.99 (d, J=1.8 Hz, 1H), 3.84 (s, 3H), 3.78 (s, 2H), 2.17-1.91 (m, 2H), 0.42-0.31 (m, 4H). MS (ESI) m/z=256.1, 258.1 $[M+H]^+$ N-(4-bromo-3-(trifluoromethyl)benzyl)cyclopropanamine (219h). $^1$H NMR (500 MHz, Chloroform-d) δ 7.68-7.59 (m, 2H), 7.34 (dd, J=8.3, 2.0 Hz, 1H), 3.84 (s, 2H), 2.15-2.08 (m, 1H), 1.83 (s, 1H), 0.49-0.32 (m, 4H). MS (ESI) m/z=294.1, 296.1 $[M+H]^+$ N-(4-bromo-2-(trifluoromethyl)benzyl)cyclopropanamine (219i). $^1$H NMR (500 MHz, Chloroform-d) δ 7.76 (d, J=2.1 Hz, 1H), 7.63 (dd, J=8.3, 2.1 Hz, 1H), 7.47 (d, J=8.2 Hz, 1H), 3.95 (d, J=1.4 Hz, 2H), 2.18-2.08 (m, 1H), 1.81 (s, 1H), 0.50-0.43 (m, 2H), 0.40-0.34 (m, 2H). MS (ESI) m/z=294.1, 296.1 $[M+H]^+$ N-(4-bromo-2-(trifluoromethoxy)benzyl)cyclopropanamine (219j). $^1$H NMR (500 MHz, Chloroform-d) δ 7.43-7.35 (m, 2H), 7.32 (d, J=8.7 Hz, 1H), 3.85 (s, 2H), 2.14-2.07 (m, 1H), 1.85 (s, 1H), 0.47-0.25 (m, 4H). MS (ESI) m/z=310.1, 312.1 $[M+H]^+$ tert-butyl (R)-4-(2-(3-(3-((4-bromo-3-fluorobenzyl)(cyclopropyl)carbamoyl) piperidin-1-yl)phenoxy)-2-methylpropanoyl)piperazine-1-carboxylate (220a). $^1$H NMR (500 MHz, Chloroform-d) δ 7.43 (dd, J=8.2, 4.5 Hz, 1H), 7.07-6.92 (m, 2H), 6.92-6.79 (m, 1H), 6.49 (dd, J=7.8, 4.0 Hz, 1H), 6.37 (s, 1H), 6.24 (dd, J=7.7, 4.0 Hz, 1H), 4.59 (dd, J=14.9, 3.9 Hz, 1H), 4.47-4.32 (m, 1H), 3.77 (s, 2H), 3.69-3.44 (m, 4H), 3.39 (d, J=11.1 Hz, 1H), 3.29 (s, 2H), 3.11-2.97 (m, 2H), 2.93 (dt, J=14.7, 7.1 Hz, 1H), 2.70 (d, J=11.3 Hz, 1H), 2.66-2.54 (m, 1H), 1.90 (d, J=8.7 Hz, 1H), 1.84-1.74 (m, 1H), 1.69 (d, J=11.8 Hz, 2H), 1.62-1.56 (m, 6H), 1.42-1.34 (m, 9H), 0.95-0.68 (m, 4H). $^{13}$C NMR (126 MHz, Chloroform-d) δ 176.85, 172.01, 165.69, 160.01, 158.04, 156.23, 154.31, 152.59, 140.46, 140.42, 133.51, 129.65, 124.49, 124.48, 115.78, 115.61, 109.70, 107.46, 107.29, 107.18, 105.50, 80.51, 80.05, 51.99, 49.74, 49.29, 45.75, 42.86, 39.76, 38.58, 29.95, 28.32, 27.76, 26.14, 24.38, 9.48, 9.06. MS (ESI) m/z=701.3 $[M+H]^+$ tert-butyl (R)-4-(2-(3-(3-((4-bromo-2-fluorobenzyl)(cyclopropyl)carbamoyl) piperidin-1-yl)phenoxy)-2-methylpropanoyl)piperazine-1-carboxylate (220b). $^1$H NMR (500 MHz, Chloroform-d) δ 7.24-7.17 (m, 2H), 7.08 (dt, J=26.6, 8.2 Hz, 2H), 6.51 (dd, J=8.2, 2.3 Hz, 1H), 6.40 (t, J=2.3 Hz, 1H), 6.26 (dd, J=8.2, 2.3 Hz, 1H), 4.65 (d, J=15.1 Hz, 1H), 4.54 (d, J=15.0 Hz, 1H), 3.80 (q, J=5.4 Hz, 2H), 3.71-3.47 (m, 4H), 3.47-3.24 (m, 3H), 3.07 (dq, J=14.9, 5.7, 4.8 Hz, 2H), 2.94 (dd, J=12.5, 10.9 Hz, 1H), 2.73 (td, J=11.9, 3.0 Hz, 1H), 2.63 (tt, J=7.0, 4.0 Hz, 1H), 1.91 (d, J=8.2 Hz, 1H), 1.80 (tt, J=9.6, 4.5 Hz, 1H), 1.76-1.64 (m, 2H), 1.62 (d, J=1.9 Hz, 6H), 1.40 (s, 9H), 0.94-0.73 (m, 4H). $^{13}$C NMR (126 MHz, Chloroform-d) δ 176.92, 172.05, 161.50, 159.50, 156.24, 154.33, 152.64, 131.19, 131.15, 129.66, 127.62, 127.59, 124.62, 124.50, 121.07, 120.99, 119.07, 118.87, 109.73, 107.17, 105.55, 80.54, 80.09, 51.98, 49.79, 45.78, 43.28 (d, J=3.6 Hz), 42.89, 39.85, 29.90, 28.35, 27.73, 26.19, 26.15, 24.41, 9.49, 9.09. MS (ESI) m/z=701.3, 703.3 $[M+H]^+$ tert-butyl (R)-4-(2-(3-(3-((4-bromo-2-chlorobenzyl)(cyclopropyl)carbamoyl) piperidin-1-yl)phenoxy)-2-methylpropanoyl)piperazine-1-carboxylate (220c). $^1$H NMR (500 MHz, Chloroform-d) δ 7.45 (d, J=2.0 Hz, 1H), 7.28 (dd, J=8.3, 2.0 Hz, 1H), 7.00 (t, J=8.2 Hz, 1H), 6.94 (d, J=8.3 Hz, 1H), 6.46 (dd, J=8.3, 2.3 Hz, 1H), 6.35 (t, J=2.3 Hz, 1H), 6.21 (dd, J=8.2, 2.3 Hz, 1H), 4.64 (d, J=15.7 Hz, 1H), 4.55 (d, J=15.7 Hz, 1H), 3.75 (q, J=5.4 Hz, 2H), 3.67-3.44 (m, 4H), 3.38 (tt, J=10.8, 3.8 Hz, 1H), 3.26 (s, 2H), 3.00 (dp, J=14.4, 8.5 Hz, 2H), 2.90 (dd, J=12.5, 10.9 Hz, 1H), 2.77-2.59 (m, 2H), 1.91 (d, J=8.5 Hz, 1H), 1.79-1.61 (m, 3H), 1.56 (d, J=2.4 Hz, 6H), 1.35 (s, 9H), 0.88-0.65 (m, 4H). $^{13}$C NMR (126 MHz, Chloroform-d) δ 176.88, 172.06, 156.25, 154.33, 152.63, 134.91, 133.92, 132.05, 130.18, 130.00, 129.69, 120.94, 109.73, 107.21, 105.53, 80.54, 80.10, 52.05, 49.81, 47.53, 45.78, 42.90, 39.94, 30.28, 28.35, 27.85, 26.19, 26.16, 24.43, 9.49, 9.13. MS (ESI) m/z=717.3 $[M+H]^+$ tert-butyl (R)-4-(2-(3-(3-((4-bromo-3-methylbenzyl)(cyclopropyl)carbamoyl) piperidin-1-yl)phenoxy)-2-methyl-propanoyl)piperazine-1-carboxylate (220d). $^{1}$H NMR (500 MHz, Chloroform-d) δ 7.37 (d, J=8.1 Hz, 1H), 7.03 (d, J=2.2 Hz, 1H), 6.99 (t, J=8.2 Hz, 1H), 6.85 (dd, J=8.1, 2.2 Hz, 1H), 6.45 (dd, J=8.0, 2.2 Hz, 1H), 6.34 (t, J=2.3 Hz, 1H), 6.20 (dd, J=8.2, 2.3 Hz, 1H), 4.53 (d, J=14.6 Hz, 1H), 4.38 (d, J=14.7 Hz, 1H), 3.74 (q, J=5.6 Hz, 2H), 3.66-3.56 (m, 2H), 3.56-3.45 (m, 2H), 3.35 (tt, J=10.9, 3.4 Hz, 1H), 3.30-3.19 (m, 2H), 3.00 (dp, J=13.7, 8.2 Hz, 2H), 2.94-2.83 (m, 1H), 2.71-2.63 (m, 1H), 2.54 (tt, J=6:9, 4.0 Hz, 1H), 2.29 (s, 3H), 1.87 (d, J=9.7 Hz, 1H), 1.80-1.70 (m, 1H), 1.66 (td, J=11.7, 5.7 Hz, 2H), 1.56 (s, 6H), 1.35 (s, 9H), 0.76 (dtd, J=31.4, 11.5, 10.4, 5.6 Hz, 4H). MS (ESI) m/z=697.3, 699.4 [M+H]$^{+}$ tert-butyl (R)-4-(2-(3-(3-((4-bromo-2-methylbenzyl)(cyclopropyl)carbamoyl) piperidin-1-yl)phenoxy)-2-methylpropanoyl)piperazine-1-carboxylate (220e). $^{1}$H NMR (500 MHz, Chloroform-d) δ 7.20-7.07 (m, 2H), 6.95 (t, J=8.2 Hz, 1H), 6.81 (d, J=8.1 Hz, 1H), 6.41 (dd, J=8.2, 2.3 Hz, 1H), 6.31 (t, J=2.3 Hz, 1H), 6.17 (dd, J=8.1, 2.3 Hz, 1H), 4.51 (d, J=15.4 Hz, 1H), 4.35 (d, J=15.3 Hz, 1H), 3.70 (q, J=5.6 Hz, 2H), 3.62-3.52 (m, 2H), 3.47 (dq, J=14.8, 9.3, 7.5 Hz, 2H), 3.34 (tt, J=10.8, 3.4 Hz, 1H), 3.28-3.15 (m, 2H), 3.02-2.91 (m, 2H), 2.91-2.83 (m, 1H), 2.63-2.59 (m, 1H), 2.53 (td, J=6.6, 3.3 Hz, 1H), 2.16 (s, 3H), 1.86 (d, J=9.3 Hz, 1H), 1.70 (ddd, J=15.0, 9.0, 5.8 Hz, 1H), 1.62 (td, J=10.9, 10.2, 5.6 Hz, 2H), 1.52 (d, J=2.1 Hz, 6H), 1.30 (s, 9H), 0.77-0.67 (m, 4H). MS (ESI) m/z=697.3, 699.4 [M+H]$^{+}$ tert-butyl (R)-4-(2-(3-(3-((4-bromo-3-methoxybenzyl) (cyclopropyl)carbamoyl) piperidin-1-yl)phenoxy)-2-methylpropanoyl)piperazine-1-carboxylate (220f). $^{1}$H NMR (500 MHz, Chloroform-d) δ 7.44 (d, J=8.0 Hz, 1H), 7.05 (t, J=8.2 Hz, 1H), 6.79 (d, J=1.9 Hz, 1H), 6.70 (dd, J=8.1, 1.9 Hz, 1H), 6.50 (dd, J=8.7, 2.2 Hz, 1H), 6.39 (d, J=2.5 Hz, 1H), 6.26 (dd, J=8.3, 2.2 Hz, 1H), 4.66 (d, J=14.6 Hz, 1H), 4.44 (d, J=14.6 Hz, 1H), 3.86 (s, 3H), 3.79 (dd, J=12.7, 7.1 Hz, 2H), 3.71-3.61 (m, 2H), 3.61-3.51 (m, 2H), 3.42 (tt, J=11.0, 3.5 Hz, 1H), 3.31 (s, 2H), 3.05 (dq, J=13.6, 8.2, 6.6 Hz, 2H), 2.96 (t, J=11.7 Hz, 1H), 2.78-2.70 (m, 1H), 2.60 (tq, J=6.9, 3.9, 3.3 Hz, 1H), 1.92 (d, J=9.4 Hz, 1H), 1.82 (s, 1H), 1.76-1.68 (m, 2H), 1.62 (s, 6H), 1.41 (s, 9H), 0.92-0.71 (m, 4H). MS (ESI) m/z=713.3, 715.3 [M+H]$^{+}$ tert-butyl (R)-4-(2-(3-(3-((4-bromo-2-methoxybenzyl) (cyclopropyl)carbamoyl) piperidin-1-yl)phenoxy)-2-methylpropanoyl)piperazine-1-carboxylate (220g). $^{1}$H NMR (500 MHz, Chloroform-d) δ 7.02-6.93 (m, 2H), 6.92 (d, J=1.9 Hz, 1H), 6.87 (d, J=8.1 Hz, 1H), 6.47 (dd, J=8.6, 2.2 Hz, 1H), 6.36 (t, J=2.4 Hz, 1H), 6.21 (dd, J=8.1, 2.3 Hz, 1H), 4.55 (d, J=15.4 Hz, 1H), 4.45 (d, J=15.3 Hz, 1H), 3.76 (s, 5H), 3.66-3.58 (m, 2H), 3.56-3.50 (m, 2H), 3.37 (tt, J=10.9, 3.5 Hz, 1H), 3.29 (s, 2H), 3.01 (s, 2H), 2.91 (dd, J=12.5, 11.0 Hz, 1H), 2.68 (dd, J=12.0, 2.8 Hz, 1H), 2.57 (ddt, J=10.9, 7.6, 4.0 Hz, 1H), 1.89 (d, J=9.5 Hz, 1H), 1.79-1.71 (m, 1H), 1.71-1.63 (m, 2H), 1.57 (d, J=2.3 Hz, 6H), 1.35 (s, 9H), 0.80-0.69 (m, 4H). MS (ESI) m/z=713.3, 715.3 [M+H]$^{+}$ tert-butyl (R)-4-(2-(3-(3-((4-bromo-3-(trifluoromethyl) benzyl) (cyclopropyl) carbamoyl)piperidin-1-yl)phenoxy)-2-methylpropanoyl)piperazine-1-carboxylate (220h). $^{1}$H NMR (500 MHz, Chloroform-d) δ 7.60 (d, J=8.2 Hz, 1H), 7.47 (d, J=2.2 Hz, 1H), 7.21 (dd, J=8.2, 2.1 Hz, 1H), 7.01 (t, J=8.2 Hz, 1H), 6.47 (dd, J=8.3, 2.2 Hz, 1H), 6.36 (t, J=2.3 Hz, 1H), 6.23 (dd, J=8.2, 2.3 Hz, 1H), 4.62 (d, J=15.1 Hz, 1H), 4.47 (d, J=15.0 Hz, 1H), 3.82-3.69 (m, 2H), 3.69-3.45 (m, 4H), 3.37 (ddt, J=10.4, 6.7, 3.4 Hz, 1H), 3.33-3.21 (m, 2H), 3.09-2.95 (m, 2H), 2.95-2.87 (m, 1H), 2.72-2.65 (m, 1H), 2.61 (dp, J=7.4, 4.0 Hz, 1H), 1.89 (d, J=8.4 Hz, 1H), 1.77 (tq, J=9.6, 6.5, 4.6 Hz, 1H), 1.74-1.64 (m, 2H), 1.58 (d, J=1.7 Hz, 6H), 1.36 (s, 9H), 0.91-0.69 (m, 4H). MS (ESI) m/z=751.3, 753.3 [M+H]$^{+}$ tert-butyl (R)-4-(2-(3-(3-((4-bromo-2-(trifluoromethyl) benzyl) (cyclopropyl) carbamoyl)piperidin-1-yl)phenoxy)-2-methylpropanoyl)piperazine-1-carboxylate (220i). $^{1}$H NMR (500 MHz, Chloroform-d) δ 7.73 (d, J=2.0 Hz, 1H), 7.59 (dd, J=8.3, 2.0 Hz, 1H), 7.09-6.93 (m, 2H), 6.51 (dd, J=8.3, 2.2 Hz, 1H), 6.45 (s, 1H), 6.26 (dd, J=8.1, 2.3 Hz, 1H), 4.73 (q, J=16.4 Hz, 2H), 3.79 (d, J=6.5 Hz, 2H), 3.73-3.61 (m, 2H), 3.61-3.52 (m, 2H), 3.47 (ddt, J=10.6, 6.6, 3.3 Hz, 1H), 3.30 (t, J=5.4 Hz, 2H), 3.08-3.01 (m, 2H), 2.97 (t, J=11.6 Hz, 1H), 2.80-2.69 (m, 2H), 1.99 (d, J=9.6 Hz, 1H), 1.86-1.78 (m, 1H), 1.60 (d, J=2.8 Hz, 6H), 1.38 (s, 9H), 0.88-0.66 (m, 4H). MS (ESI) m/z=751.3, 753.3 [M+H]$^{+}$ tert-butyl (R)-4-(2-(3-(3-((4-bromo-2-(trifluoromethoxy) benzyl) (cyclopropyl) carbamoyl)piperidin-1-yl)phenoxy)-2-methylpropanoyl)piperazine-1-carboxylate (220j). $^{1}$H NMR (500 MHz, Chloroform-d) δ 7.35 (d, J=7.4 Hz, 2H), 7.08 (d, J=8.3 Hz, 1H), 7.02 (t, J=8.2 Hz, 1H), 6.48 (dd, J=8.3, 2.3 Hz, 1H), 6.38 (t, J=2.3 Hz, 1H), 6.24 (dd, J=8.2, 2.3 Hz, 1H), 4.68-4.49 (m, 2H), 3.77 (q, J=5.5 Hz, 2H), 3.66-3.57 (m, 2H), 3.57-3.49 (m, 2H), 3.39 (tt, J=10.8, 3.6 Hz, 1H), 3.33-3.20 (m, 2H), 3.02 (q, J=6.4, 5.8 Hz, 2H), 2.92 (dd, J=12.5, 10.9 Hz, 1H), 2.78-2.56 (m, 2H), 1.90 (d, J=8.0 Hz, 1H), 1.83-1.73 (m, 1H), 1.73-1.64 (m, 2H), 1.59 (d, J=2.5 Hz, 6H), 1.37 (s, 9H), 0.89-0.71 (m, 4H). MS (ESI) m/z=767.3 [M+H]$^{+}$ tert-butyl (R)-4-(2-(3-(3-(cyclopropyl(3-fluoro-4-(1H-pyrazol-4-yl)benzyl)carbamoyl)piperidin-1-yl)phenoxy)-2-methylpropanoyl)piperazine-1-carboxylate (221a). $^{1}$H NMR (500 MHz, Chloroform-d) δ 7.93 (d, J=1.6 Hz, 2H), 7.49 (t, J=7.9 Hz, 1H), 7.12-6.91 (m, 3H), 6.53 (dd, J=8.2, 2.3 Hz, 1H), 6.42 (t, J=2.4 Hz, 1H), 6.27 (dd, J=8.1, 2.3 Hz, 1H), 4.69 (d, J=14.8 Hz, 1H), 4.50 (d, J=14.8 Hz, 1H), 3.81 (q, J=4.8 Hz, 2H), 3.72-3.50 (m, 4H), 3.44 (tt, J=11.0, 3.5 Hz, 1H), 3.32 (s, 2H), 3.03 (ddd, J=43.0, 13.1, 9.8 Hz, 3H), 2.82-2.63 (m, 2H), 1.96 (d, J=10.4 Hz, 1H), 1.87-1.66 (m, 3H), 1.62 (d, J=1.6 Hz, 6H), 1.41 (s, 9H), 0.86 (dddd, J=38.0, 13.4, 10.9, 5.3 Hz, 4H). $^{13}$C NMR (126 MHz, Chloroform-d) δ 177.0, 172.1, 160.3, 158.3, 156.2, 154.4, 152.7, 138.6, 138.5, 129.7, 127.8, 127.7, 123.55, 123.53, 119.2, 119.1, 115.7, 115.3, 115.1, 109.8, 107.2, 105.7, 80.6, 80.2, 52.1, 49.8, 49.4, 45.8, 42.9, 39.8, 30.0, 28.4, 27.8, 26.2, 26.1, 24.4, 9.5, 9.1. MS (ESI) m/z=689.4 [M+H]$^{+}$, 687.3 [M−H]$^{-}$ tert-butyl (R)-4-(2-(3-(3-(cyclopropyl(2-fluoro-4-(1H-pyrazol-4-yl)benzyl)carbamoyl)piperidin-1-yl)phenoxy)-2-methylpropanoyl)piperazine-1-carboxylate (221b). $^{1}$H NMR (500 MHz, Chloroform-d) δ 7.73 (s, 2H), 7.17-7.04 (m, 3H), 6.99 (t, J=8.2 Hz, 1H), 6.47 (dd, J=8.3, 2.3 Hz, 1H), 6.35 (t, J=2.4 Hz, 1H), 6.20 (dd, J=8.2, 2.3 Hz, 1H), 4.66 (d, J=15.0 Hz, 1H), 4.53 (d, J=15.0 Hz, 1H), 3.74 (p, J=8.2, 6.8 Hz, 2H), 3.67-3.44 (m, 4H), 3.38 (tt, J=10.9, 3.5 Hz, 1H), 3.32-3.18 (m, 2H), 3.09-2.86 (m, 3H), 2.73-2.50 (m, 2H), 1.95-1.60 (m, 4H), 1.60-1.49 (m, 6H), 1.34 (s, 9H), 0.80 (dqd, J=31.5, 10.2, 8.3, 4.4 Hz, 4H). $^{13}$C NMR (126 MHz, Chloroform-d) δ 177.1, 172.2, 162.1, 160.1, 156.2, 154.4, 152.7, 133.8, 133.7, 130.34, 130.30, 129.7, 123.0, 122.8, 121.45, 121.44, 121.2, 112.5, 112.3, 109.9, 107:2, 105.7, 80.5, 80.2, 52.0, 49.8, 45.8, 43.5, 42.9, 39.9, 29.9, 28.3, 27.8, 26.2, 26.1, 24.4, 9.5, 9.1. MS (ESI) m/z=689.4 [M+H]$^{+}$, 687.4 [M−H]$^{-}$ tert-butyl (R)-4-(2-(3-(3-((2-chloro-4-(1H-pyrazol-4-yl) benzyl) (cyclopropyl) carbamoyl)piperidin-1-yl)phenoxy)-2-methylpropanoyl)piperazine-1-carboxylate (221c). $^{1}$H NMR (500 MHz, Chloroform-d) δ 7.75 (s, 2H), 7.45 (d, J=1.8 Hz, 1H), 7.30 (dd, J=7.9, 1.8 Hz, 1H), 7.06 (t, J=7.7 Hz, 2H), 6.62-6.49 (m, 1H), 6.49-6.37 (m, 1H), 6.27 (dd, J=8.1, 2.3 Hz, 1H), 4.77 (d, J=15.6 Hz, 1H), 4.65 (d, J=15.6

Hz, 1H), 3.85-3.47 (m, 7H), 3.40-3.21 (m, 2H), 3.14-2.95 (m, 3H), 2.81-2.64 (m, 2H), 2.05-1.92 (m, 1H), 1.85-1.70 (m, 3H), 1.62 (d, J=2.0 Hz, 6H), 1.40 (s, 9H), 0.92-0.74 (m, 4H). $^{13}$C NMR (126 MHz, Chloroform-d) δ 177.0, 172.1, 156.2, 154.4, 152.6, 133.5, 133.2, 129.7, 129.1, 126.5, 124.2, 120.9, 109.9, 107.23, 105.7, 80.6, 80.2, 53.5, 52.1, 49.9, 47.8, 45.8, 42.9, 40.0, 30.3, 28.3, 27.9, 26.2, 26.1, 24.4, 9.5, 9.1. MS (ESI) m/z=705.4 $[M+H]^+$, 703.3 $[M-H]^-$ tert-butyl (R)-4-(2-(3-(3-(cyclopropyl(3-methyl-4-(1H-pyrazol-4-yl)benzyl)carbamoyl)piperidin-1-yl)phenoxy)-2-methylpropanoyl)piperazine-1-carboxylate (221d). $^1$H NMR (500 MHz, Chloroform-d) δ 7.63-7.57 (m, 2H), 7.24-7.17 (m, 1H), 7.05-6.93 (m, 3H), 6.47 (dd, J=8.3, 2.2 Hz, 1H), 6.36 (t, J=2.4 Hz, 1H), 6.20 (dd, J=8.1, 2.3 Hz, 1H), 4.62 (d, J=14.7 Hz, 1H), 4.45 (d, J=14.7 Hz, 1H), 3.74 (d, J=4.7 Hz, 2H), 3.69-3.57 (m, 2H), 3.52 (s, 2H), 3.44-3.35 (m, 1H), 3.26 (s, 2H), 3.08-2.90 (m, 3H), 2.75-2.65 (m, 1H), 2.63-2.55 (m, 1H), 2.29 (s, 3H), 1.91 (d, J=12.3 Hz, 1H), 1.79-1.63 (m, 3H), 1.59-1.54 (m, 6H), 1.35 (s, 9H), 0.84-0.73 (m, 4H). MS (ESI) m/z=685.4 $[M+H]^+$, 683.4 $[M-H]^+$ tert-butyl (R)-4-(2-(3-(3-(cyclopropyl(2-methyl-4-(1H-pyrazol-4-yl)benzyl)carbamoyl)piperidin-1-yl)phenoxy)-2-methylpropanoyl)piperazine-1-carboxylate (221e). $^1$H NMR (500 MHz, Chloroform-d) δ 7.68 (s, 2H), 7.22-7.15 (m, 2H), 6.99 (t, J=8.2 Hz, 1H), 6.97-6.83 (m, 1H), 6.47 (dd, J=8.3, 2.2 Hz, 1H), 6.37 (t, J=2.3 Hz, 1H), 6.21 (dd, J=8.1, 2.3 Hz, 1H), 4.63 (d, J=15.3 Hz, 1H), 4.45 (d, J=15.3 Hz, 1H), 3.75 (q, J=5.5 Hz, 2H), 3.70-3.63 (m, 1H), 3.63-3.56 (m, 1H), 3.52 (t, J=7.2 Hz, 2H), 3.42 (tt, J=10.9, 3.4 Hz, 1H), 3.26 (s, 2H), 2.98 (ddd, J=35.6, 12.1, 8.1 Hz, 3H), 2.69 (td, J=12.1, 2.7 Hz, 1H), 2.64-2.55 (m, 1H), 2.22 (s, 3H), 2.00-1.89 (m, 1H), 1.79-1.63 (m, 3H), 1.56 (d, J=2.0 Hz, 6H), 1.34 (s, 9H), 0.78 (dddd, J=16.5, 6.5, 4.2, 2.2 Hz, 4H). MS (ESI) m/z=685.4 $[M+H]^+$, 683.4 $[M-H]^-$ tert-butyl (R)-4-(2-(3-(3-(cyclopropyl(3-methoxy-4-(1H-pyrazol-4-yl)benzyl)carbamoyl)piperidin-1-yl)phenoxy)-2-methylpropanoyl)piperazine-1-carboxylate (221f). $^1$H NMR (500 MHz, Chloroform-d) δ 7.98 (s, 2H), 7.46 (d, J=8.1 Hz, 1H), 7.05 (t, J=8.2 Hz, 1H), 6.83 (dt, J=3.9, 1.9 Hz, 2H), 6.52 (dd, J=8.2, 2.2 Hz, 1H), 6.41 (t, J=2.3 Hz, 1H), 6.26 (dd, J=8.1, 2.3 Hz, 1H), 4.73 (d, J=14.6 Hz, 1H), 4.49 (d, J=14.6 Hz, 1H), 3.85 (s, 3H), 3.80 (q, J=5.4 Hz, 2H), 3.74-3.64 (m, 2H), 3.58 (q, J=8.5, 6.8 Hz, 2H), 3.45 (tt, J=11.1, 3.5 Hz, 1H), 3.32 (s, 2H), 3.14-2.96 (m, 3H), 2.76 (td, J=12.1, 2.7 Hz, 1H), 2.62 (tt, J=6.9, 3.3 Hz, 1H), 2.00-1.92 (m, 1H), 1.85-1.70 (m, 3H), 1.62 (s, 6H), 1.41 (s, 9H), 0.91-0.79 (m, 4H). MS (ESI) m/z=701.5 $[M+H]^+$, tert-butyl (R)-4-(2-(3-(3-(cyclopropyl(2-methoxy-4-(1H-pyrazol-4-yl)benzyl)carbamoyl)piperidin-1-yl)phenoxy)-2-methylpropanoyl)piperazine-1-carboxylate (221g). $^1$H NMR (500 MHz, Chloroform-d) δ 7.71 (d, J=16.2 Hz, 2H), 7.00 (d, J=8.2 Hz, 1H), 6.95 (d, J=0.9 Hz, 2H), 6.88 (d, J=10.2 Hz, 1H), 6.47 (dd, J=8.3, 2.2 Hz, 1H), 6.37 (t, J=2.3 Hz, 1H), 6.20 (dd, J=8.1, 2.3 Hz, 1H), 4.62 (d, J=15.4 Hz, 1H), 4.53-4.46 (m, 1H), 3.77 (s, 5H), 3.68-3.57 (m, 2H), 3.53 (dd, J=11.4, 5.7 Hz, 2H), 3.44-3.37 (m, 1H), 3.31-3.20 (m, 2H), 3.08-2.91 (m, 3H), 2.70 (td, J=12.1, 2.7 Hz, 1H), 2.64-2.56 (m, 1H), 1.92 (d, J=11.4 Hz, 1H), 1.78-1.65 (m, 3H), 1.56 (d, J=1.8 Hz, 6H), 1.34 (s, 9H), 0.80-0.71 (m, 4H). MS (ESI) m/z=701.5 $[M+H]^+$, 699.4 $[M-H]^-$ tert-butyl (R)-4-(2-(3-(3-((4-(1H-pyrazol-4-yl)-3-(trifluoromethyl)benzyl) (cyclopropyl) carbamoyl)piperidin-1-yl) phenoxy)-2-methylpropanoyl)piperazine-1-carboxylate (221h). $^1$H NMR (500 MHz, Chloroform-d) δ 7.65-7.58 (m, 2H), 7.52-7.47 (m, 1H), 7.34-7.28 (m, 2H), 7.00 (t, J=8.2 Hz, 1H), 6.47 (dd, J=8.3, 2.3 Hz, 1H), 6.36 (d, J=2.4 Hz, 1H), 6.21 (dd, J=8.2, 2.3 Hz, 1H), 4.69 (d, J=15.0 Hz, 1H), 4.53 (d, J=15.1 Hz, 1H), 3.79-3.65 (m, 2H), 3.62 (dd, J=12.4, 4.9 Hz, 2H), 3.57-3.45 (m, 2H), 3.39 (ddt, J=10.8, 6.7, 3.4 Hz, 1H), 3.26 (s, 2H), 3.08-2.96 (m, 2H), 2.92 (dd, J=12.4, 10.9 Hz, 1H), 2.69 (td, J=12.0, 2.9 Hz, 1H), 2.62 (tt, J=7.2, 4.0 Hz, 1H), 1.90 (d, J=9.7 Hz, 1H), 1.84-1.73 (m, 1H), 1.69 (td, J=10.2, 8.5, 3.1 Hz, 2H), 1.57-1.53 (m, 6H), 1.35 (s, 9H), 0.90-0.73 (m, 4H). MS (ESI) m/z=739.4 $[M+H]^+$ tert-butyl (R)-4-(2-(3-(3-((4-(1H-pyrazol-4-yl)-2-(trifluoromethyl)benzyl) (cyclopropyl) carbamoyl)piperidin-1-yl) phenoxy)-2-methylpropanoyl)piperazine-1-carboxylate (221i). $^1$H NMR (500 MHz, Chloroform-d) δ 7.74 (s, 2H), 7.66 (d, J=1.8 Hz, 1H), 7.51 (d, J=8.2 Hz, 1H), 7.08-6.97 (m, 2H), 6.54-6.46 (m, 1H), 6.39 (d, J=2.4 Hz, 1H), 6.23 (dd, J=8.1, 2.3 Hz, 1H), 4.81 (d, J=16.4 Hz, 1H), 4.71 (d, J=16.3 Hz, 1H), 3.75 (t, J=5.3 Hz, 2H), 3.68 (dd, J=12.2, 3.1 Hz, 1H), 3.65-3.58 (m, 1H), 3.58-3.44 (m, 3H), 3.27 (s, 2H), 2.99 (dt, J=23.3, 11.1 Hz, 3H), 2.74 (ddt, J=16.0, 12.2, 6.8 Hz, 2H), 2.03-1.94 (m, 1H), 1.84-1.67 (m, 3H), 1.57 (d, J=2.5 Hz, 6H), 1.35 (s, 9H), 0.84-0.69 (m, 4H). MS (ESI) m/z=739.4 $[M+H]^+$, 737.4 $[M-H]^+$ tert-butyl (R)-4-(2-(3-(3-((4-(1H-pyrazol-4-yl)-2-(trifluoromethoxy)benzyl) (cyclopropyl) carbamoyl)piperidin-1-yl) phenoxy)-2-methylpropanoyl)piperazine-1-carboxylate (221j). $^1$H NMR (500 MHz, Chloroform-d) δ 7.72 (s, 2H), 7.32-7.24 (m, 2H), 7.12 (d, J=8.0 Hz, 1H), 7.00 (t, J=8.2 Hz, 1H), 6.47 (dd, J=8.2, 2.2 Hz, 1H), 6.36 (t, J=2.3 Hz, 1H), 6.21 (dd, J=8.1, 2.3 Hz, 1H), 4.68 (d, J=15.5 Hz, 1H), 4.56 (d, J=15.4 Hz, 1H), 3.75 (q, J=5.8 Hz, 2H), 3.67-3.57 (m, 2H), 3.57-3.46 (m, 2H), 3.46-3.37 (m, 1H), 3.30-3.21 (m, 2H), 3.08-2.87 (m, 3H), 2.73-2.58 (m, 2H), 1.91 (d, J=11.8 Hz, 1H), 1.79-1.64 (m, 3H), 1.56 (d, J=2.1 Hz, 6H), 1.34 (s, 9H), 0.81-0.73 (m, 4H). MS (ESI) m/z=755.4 $[M+H]^+$, 753.5 $[M-H]^-$ (R)-4-(2-(3-(3-(cyclopropyl(3-fluoro-4-(1H-pyrazol-4-yl)benzyl)carbamoyl) piperidin-1-yl)phenoxy)-2-methylpropanoyl)piperazin-1-ium chloride (63). $^1$H NMR (500 MHz, Methanol-$d_4$) δ 8.18 (s, 2H), 7.68 (t, J=7.9 Hz, 1H), 7.55 (t, J=8.3 Hz, 1H), 7.44 (d, J=8.1 Hz, 1H), 7.33 (s, 1H), 7.18-7.07 (m, 2H), 7.02 (dd, J=8.4, 2.3 Hz, 1H), 4.85 (s, 1H), 4.49 (d, J=15.1 Hz, 1H), 4.03 (d, J=122.6 Hz, 5H), 3.81-3.70 (m, 3H), 3.68-3.63 (m, 1H), 3.27-2.81 (m, 5H), 2.36-1.84 (m, 4H), 1.68 (d, J=2.1 Hz, 6H), 1.12-0.88 (m, 4H). $^{13}$C NMR (126 MHz, Methanol-$d_4$) δ 171.5, 160.3, 158.3, 156.3, 143.5, 138.9, 138.8, 132.1, 131.5, 127.9, 127.8, 123.5, 123.4, 118.3, 116.0, 114.8, 114.6, 114.4, 111.5, 81.8, 55.8, 49.2, 43.1, 42.3, 39.6, 30.0, 24.9, 24.7, 9.3, 7.2. HRMS Calcd for $C_{33}H_{41}FN_6O_3$ $(M+H)^+$ 589.3297, found 589.3286. HPLC purity 100%, $t_R$=9.51 min (R)-4-(2-(3-(3-(cyclopropyl(2-fluoro-4-(1H-pyrazol-4-yl)benzyl)carbamoyl) piperidin-1-yl)phenoxy)-2-methylpropanoyl)piperazin-1-ium chloride (64). $^1$H NMR (500 MHz, Methanol-$d_4$) δ 8.27 (s, 2H), 7.56 (t, J=8.3 Hz, 1H), 7.49-7.39 (m, 3H), 7.39-7.26 (m, 2H), 7.03 (dd, J=8.4, 2.3 Hz, 1H), 4.96 (d, J=13.2 Hz, 1H), 4.50 (d, J=15.2 Hz, 1H), 4.03 (d, J=121.8 Hz, 5H), 3.80-3.71 (m, 3H), 3.69-3.63 (m, 1H), 3.25-2.77 (m, 5H), 2.29-1.86 (m, 4H), 1.68 (d, J=1.3 Hz, 6H), 1.14-0.89 (m, 4H). $^{13}$C NMR (126 MHz, Methanol-$d_4$) δ 171.5, 162.1, 160.2, 156.3, 143.4, 133.0, 132.9, 131.5, 131.0, 130.33, 130.29, 123.0, 122.8, 121.7, 121.32, 121.30, 118.5, 114.4, 112.2, 112.0, 111.5, 81.8, 58.1, 55.7, 43.6, 43.1, 42.6, 39.6, 29.7, 24.9, 24.7, 9.5, 7.3. HRMS (ESI) Calcd for $C_{33}H_{41}FN_6O_3$ $(M+H)^+$ 589.3297, found 589.3288. HPLC purity 100%, $t_R$=9.54 min (R)-4-(2-(3-(3-((2-chloro-4-(1H-pyrazol-4-yl)benzyl) (cyclopropyl) carbamoyl)piperidin-1-yl)phenoxy)-2-methylpropanoyl)piperazin-1-ium chloride (65). $^1$H NMR (500

MHz, Methanol-$d_4$) δ 8.25 (s, 2H), 7.71 (d, J=1.8 Hz, 1H), 7.60-7.51 (m, 2H), 7.45 (d, J=8.2 Hz, 1H), 7.34 (s, 1H), 7.25 (d, J=8.0 Hz, 1H), 7.03 (dd, J=8.4, 2.3 Hz, 1H), 4.93 (d, J=16.0 Hz, 1H), 4.59 (d, J=15.8 Hz, 1H), 4.30-3.84 (m, 5H), 3.77 (dd, J=23.5, 5.3 Hz, 3H), 3.69-3.63 (m, 1H), 3.26-2.77 (m, 5H), 2.37-1.89 (m, 4H), 1.68 (d, J=1.8 Hz, 6H), 1.13-0.86 (m, 4H). $^{13}$C NMR (126 MHz, Methanol-$d_4$) δ 171.5, 156.3, 143.5, 133.25, 133.21, 132.4, 131.5, 131.0, 129.3, 126.2, 124.1, 121.3, 118.5, 114.42, 111.5, 81.8, 55.8, 43.1, 42.7, 39.5, 30.1, 24.9, 24.7, 9.4, 7.3. HRMS Calcd for $C_{33}H_{41}ClN_6O_3$ $(M+H)^+$ 605.3001, found 605.2989. HPLC purity 100%, $t_R$=9.99 min.

(R)-4-(2-(3-(3-(cyclopropyl(3-methyl-4-(1H-pyrazol-4-yl)benzyl)carbamoyl) piperidin-1-yl)phenoxy)-2-methylpropanoyl)piperazin-1-ium 2,2,2-trifluoroacetate (66). $^1$H NMR (500 MHz, Methanol-$d_4$) δ 7.78 (s, 2H), 7.35 (dd, J=16.9, 8.1 Hz, 2H), 7.15 (d, J=1.9 Hz, 1H), 7.09 (dd, J=7.9, 1.9 Hz, 1H), 7.03 (d, J=8.7 Hz, 1H), 6.87 (s, 1H), 6.71-6.64 (m, 1H), 4.79 (d, J=14.9 Hz, 1H), 4.48 (d, J=14.9 Hz, 1H), 4.12 (s, 2H), 3.93-3.77 (m, 3H), 3.75-3.68 (m, 2H), 3.36 (d, J=11.7 Hz, 1H), 3.25-3.07 (m, 3H), 2.91-2.76 (m, 3H), 2.38 (s, 3H), 2.12-1.83 (m, 4H), 1.66 (d, J=1.8 Hz, 6H), 1.00-0.87 (m, 4H). $^{13}$C NMR (126 MHz, Methanol-$d_4$) δ 176.65, 171.94, 160.45, 156.23, 136.41, 135.31, 132.63, 131.04, 130.61, 129.42, 129.07, 124.79, 121.01, 117.45, 115.11, 112.18, 108.13, 81.00, 52.62, 49.28, 43.07, 42.71, 39.50, 38.34, 29.81, 24.88, 24.83, 22.85, 20.08, 8.92, 7.62. HRMS Calcd for $C_{34}H_{44}N_6O_3$ $(M+H)^+$ 585.3548, found 585.3546. HPLC purity 96.1%, $t_R$=9.76 min.

(R)-4-(2-(3-(3-(cyclopropyl(2-methyl-4-(1H-pyrazol-4-yl)benzyl)carbamoyl) piperidin-1-yl)phenoxy)-2-methylpropanoyl)piperazin-1-ium chloride (67). $^1$H NMR (500 MHz, Methanol-$d_4$) δ 8.64 (s, 2H), 7.58-7.54 (m, 2H), 7.51 (td, J=10.4, 9.1, 4.5 Hz, 2H), 7.39 (s, 1H), 7.16 (d, J=7.9 Hz, 1H), 7.04 (dd, J=8.4, 2.2 Hz, 1H), 4.84 (d, J=15.8 Hz, 1H), 4.52 (d, J=15.7 Hz, 1H), 4.37-4.05 (m, 3H), 3.91 (s, 2H), 3.83-3.73 (m, 3H), 3.67 (tdd, J=5.8, 4.0, 1.2 Hz, 1H), 3.25-2.85 (m, 5H), 2.42-1.87 (m, 7H), 1.68 (d, J=2.6 Hz, 6H), 1.14-0.86 (m, 4H). $^{13}$C NMR (126 MHz, Methanol-$d_4$) δ 171.43, 156.27, 143.39, 136.57, 135.76, 131.54, 130.62, 127.88, 127.58, 127.32, 124.14, 123.43, 118.58, 114.54, 111.65, 81.79, 72.17, 71.04, 62.92, 60.78, 58.01, 56.04, 42.68, 39.56, 30.33, 24.94, 24.74, 21.91, 17.95, 9.32, 7.29. HRMS Calcd for $C_{34}H_{44}N_6O_3$ $(M+H)^+$ 585.3548, found 585.3548. HPLC purity 98.8%, $t_R$=9.77 min.

(R)-4-(2-(3-(3-(cyclopropyl(3-methoxy-4-(1H-pyrazol-4-yl)benzyl)carbamoyl) piperidin-1-yl)phenoxy)-2-methylpropanoyl)piperazin-1-ium 2,2,2-trifluoroacetate (68). $^1$H NMR (500 MHz, Methanol-$d_4$) δ 8.09 (s, 2H), 7.56 (d, J=7.8 Hz, 1H), 7.39 (t, J=8.3 Hz, 1H), 7.10 (dd, J=8.3, 2.2 Hz, 1H), 6.94 (d, J=1.7 Hz, 2H), 6.87 (dd, J=7.9, 1.6 Hz, 1H), 6.74 (dd, J=8.2, 2.3 Hz, 1H), 4.84 (s, 1H), 4.47 (d, J=14.9 Hz, 1H), 4.09 (d, J=30.9 Hz, 2H), 3.85 (td, J=9.1, 4.6 Hz, 6H), 3.71 (td, J=11.8, 3.9 Hz, 2H), 3.49-3.37 (m, 1H), 3.27-2.78 (m, 6H), 2.16-1.96 (m, 3H), 1.90-1.82 (m, 1H), 1.66 (d, J=1.3 Hz, 6H), 1.02-0.89 (m, 4H). $^{13}$C NMR (126 MHz, Methanol-$d_4$) δ 176.44, 171.81, 160.53 (d, J=36.5 Hz), 156.25, 156.11, 147.23, 137.54, 132.36, 130.82, 127.26, 119.89, 119.51, 117.87, 117.38, 115.10, 113.84, 112.61, 110.25, 108.80, 81.14, 55.71, 54.53, 53.28, 49.52, 43.06, 42.71, 39.52, 38.10, 29.81, 25.15, 24.87, 24.79, 22.66, 9.00, 7.59. HRMS Calcd for $C_{34}H_{44}N_6O_4$ $(M+H)^+$ 601.3497, found 601.3496. HPLC purity 95.3%, $t_R$=9.60 min.

(R)-4-(2-(3-(3-(cyclopropyl(2-methoxy-4-(1H-pyrazol-4-yl)benzyl)carbamoyl) piperidin-1-yl)phenoxy)-2-methylpropanoyl)piperazin-1-ium chloride (69). $^1$H NMR (500 MHz, Methanol-$d_4$) δ 8.51 (s, 2H), 7.55 (d, J=8.3 Hz, 1H), 7.47 (d, J=8.3 Hz, 1H), 7.35 (d, J=8.5 Hz, 1H), 7.28 (d, J=1.5 Hz, 1H), 7.24 (dd, J=7.8, 1.6 Hz, 1H), 7.16 (d, J=7.7 Hz, 1H), 7.03 (dd, J=8.4, 2.3 Hz, 1H), 4.86 (s, 1H), 4.45 (d, J=15.5 Hz, 1H), 4.27-4.07 (m, 3H), 3.94 (s, 5H), 3.79-3.73 (m, 3H), 3.67 (ddd, J=5.7, 4.3, 1.6 Hz, 1H), 3.08 (d, J=106.3 Hz, 4H), 2.82 (dp, J=6.8, 4.0 Hz, 1H), 2.33-2.14 (m, 3H), 2.09-1.93 (m, 1H), 1.68 (d, J=1.4 Hz, 6H), 1.07-0.84 (m, 4H). $^{13}$C NMR (126 MHz, Methanol-$d_4$) δ 171.45, 157.81, 156.28, 143.42, 131.53, 130.83, 130.57, 128.92, 124.85, 123.74, 118.50, 117.64, 114.49, 111.61, 107.84, 81.79, 62.92, 58.15, 55.93, 54.80, 45.33, 43.13, 42.68, 39.58, 30.00, 24.93, 24.72, 21.80, 9.37, 7.23. HRMS Calcd for $C_{34}H_{44}N_6O_4$ $(M+H)^+$ 601.3497, found 601.3501. HPLC purity 96.4%, $t_R$=9.73 min.

(R)-4-(2-(3-(3-((4-(1H-pyrazol-4-yl)-3-(trifluoromethyl) benzyl) (cyclopropyl) carbamoyl)piperidin-1-yl)phenoxy)-2-methylpropanoyl)piperazin-1-ium 2,2,2-trifluoroacetate (70). $^1$H NMR (500 MHz, Methanol-$d_4$) δ 7.73 (s, 2H), 7.65 (d, J=1.8 Hz, 1H), 7.53-7.46 (m, 2H), 7.39 (t, J=8.3 Hz, 1H), 7.10 (dd, J=8.3, 2.3 Hz, 1H), 6.94 (t, J=2.3 Hz, 1H), 6.74 (dd, J=8.4, 2.3 Hz, 1H), 4.92 (s, 1H), 4.57 (d, J=15.2 Hz, 1H), 4.18-3.83 (m, 5H), 3.72 (td, J=10.2, 8.4, 3.9 Hz, 2H), 3.48-3.39 (m, 1H), 3.28 (d, J=11.1 Hz, 1H), 3.17-2.82 (m, 5H), 2.16-1.96 (m, 3H), 1.84 (dd, J=12.6, 8.4 Hz, 1H), 1.66 (s, 6H), 1.07-0.91 (m, 4H). $^{13}$C NMR (126 MHz, Methanol-$d_4$) δ 176.56, 171.82, 160.49 (d, J=36.4 Hz), 156.25, 137.56, 133.13, 132.53, 130.92, 130.79, 130.74, 127.74 (d, J=29.8 Hz), 127.39, 125.36, 125.07-124.62 (m), 123.19, 118.68, 117.34, 115.03, 112.60, 108.80, 81.12, 55.56, 53.26, 49.12, 43.06, 42.70, 39.50, 38.12, 29.93, 25.16, 24.88, 24.77, 22.65, 9.03, 7.63. HRMS Calcd for $C_{34}H_{41}F_3N_6O_3$ $(M+H)^+$ 639.3265, found 639.3264. HPLC purity 97.0%, $t_R$=10.41 min.

(R)-4-(2-(3-(3-((4-(1H-pyrazol-4-yl)-2-(trifluoromethyl) benzyl) (cyclopropyl) carbamoyl)piperidin-1-yl)phenoxy)-2-methylpropanoyl)piperazin-1-ium 2,2,2-trifluoroacetate (71). $^1$H NMR (500 MHz, Methanol-$d_4$) δ 8.05 (s, 2H), 7.89 (d, J=1.9 Hz, 1H), 7.79 (dd, J=8.2, 1.8 Hz, 1H), 7.43 (t, J=8.3 Hz, 1H), 7.26-7.15 (m, 2H), 7.03 (t, J=2.3 Hz, 1H), 6.82 (dd, J=8.4, 2.3 Hz, 1H), 4.90 (s, 1H), 4.77 (d, J=16.4 Hz, 1H), 4.12 (s, 2H), 4.00-3.78 (m, 4H), 3.73 (dt, J=11.9, 4.3 Hz, 1H), 3.54 (dd, J=12.1, 9.1 Hz, 1H), 3.39 (ddd, J=12.5, 9.5, 4.2 Hz, 1H), 3.14 (s, 2H), 3.01 (ddd, J=7.0, 4.3, 2.9 Hz, 1H), 2.88 (s, 2H), 2.25 (dq, J=13.4, 4.4 Hz, 1H), 2.10 (dh, J=15.9, 4.6, 4.2 Hz, 2H), 1.94 (d, J=8.8 Hz, 1H), 1.67 (d, J=1.6 Hz, 6H), 1.03-0.81 (m, 4H). $^{13}$C NMR (126 MHz, Methanol-$d_4$) δ 176.55, 171.73, 160.56 (q, J=36.6, 36.2 Hz), 156.28, 146.27, 133.81, 132.38 (d, J=2.8 Hz), 132.15, 131.71, 131.63, 131.01, 128.80, 128.63, 128.53, 127.81, 127.66, 127.41, 125.57, 123.40, 122.58 (d, J=6.0 Hz), 120.57, 117.35, 115.04, 113.03, 109.33, 81.27, 56.14, 53.91, 43.05, 42.71, 39.52, 38.03, 30.59, 24.87, 24.76, 22.53, 8.54, 7.17. HRMS Calcd for $C_{34}H_{41}F_3N_6O_3$ $(M^+ Na)^+$ 661.3084, found 661.3085. HPLC purity 99.3%, $t_R$=10.73 min.

(R)-4-(2-(3-(3-((4-(1/I-pyrazol-4-yl)-2-(trifluoromethoxy)benzyl) (cyclopropyl) carbamoyl)piperidin-1-yl) phenoxy)-2-methylpropanoyl)piperazin-1-ium 2,2,2-trifluoroacetate (72). $^1$H NMR (500 MHz, Methanol-$d_4$) δ 8.01 (s, 2H), 7.57 (dd, J=8.1, 1.7 Hz, 1H), 7.52-7.47 (m, 1H), 7.37 (t, J=8.2 Hz, 1H), 7.28 (d, J=8.0 Hz, 1H), 7.06 (d, J=8.2 Hz, 1H), 6.90 (s, 1H), 6.71 (d, J=8.2 Hz, 1H), 4.83 (d, J=15.4 Hz, 1H), 4.61 (d, J=15.5 Hz, 1H), 4.12 (s, 2H), 3.94-3.78 (m, 3H), 3.72 (ddd, J=19.7, 11.9, 3.8 Hz, 2H), 3.38 (t, J=11.1 Hz, 1H), 3.27-3.21 (m, 1H), 3.13 (s, 2H), 2.84 (t, J=9.2 Hz, 3H), 2.18-2.09 (m, 1H), 2.05-1.92 (m, 2H), 1.84 (d, J=11.5 Hz, 1H), 1.66 (s, 6H), 1.00-0.86 (m, 4H). $^{13}$C NMR (126 MHz, Methanol-$d_4$) δ 176.57, 171.90, 160.32 (q, J=36.4 Hz), 156.24, 147.38, 134.01, 131.01, 130.71, 129.70, 128.02, 124.11, 121.72, 120.63, 119.68, 117.54, 117.27, 114.96, 112.36, 108.43, 81.06, 55.29, 52.92, 44.55, 43.07, 42.73, 39.52, 38.35, 29.97, 25.40, 24.87, 24.81, 22.79, 8.89, 7.61. HRMS Calcd for $C_{34}H_{41}F_3N_6O_4$ $(M+H)^+$ 655.3214, found 655.3215. HPLC purity 99.3%, $t_R$=10.76 min.
Scheme 8. Synthesis of 73-81.
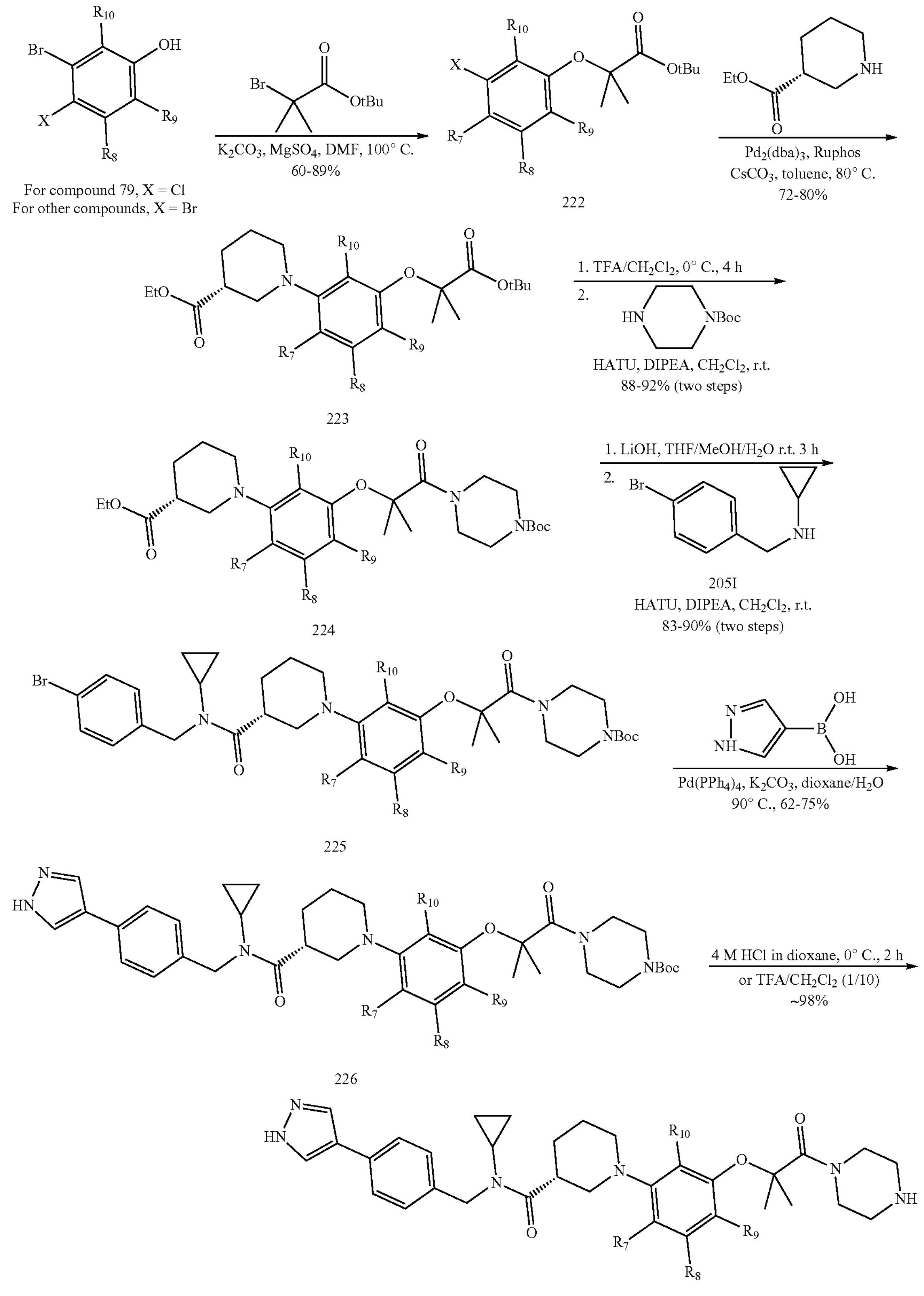
For compound 79, X = Cl
For other compounds, X = Br
222
223
224
205I
225
226
HCl or $CF_3COOH$ salt -continued 73, $R_7$ = F, $R_8$ = H, $R_9$ = H, $R_{10}$ = H
74, $R_7$ = H, $R_8$ = F, $R_9$ = H, $R_{10}$ = H
75, $R_7$ = H, $R_8$ = H, $R_9$ = F, $R_{10}$ = H
76, $R_7$ = H, $R_8$ = H, $R_9$ = H, $R_{10}$ = F
77, $R_7$ = H, $R_8$ = $CF_3$, $R_9$ = H, $R_{10}$ = H
78, $R_7$ = H, $R_8$ = Cl, $R_9$ = H, $R_{10}$ = H
79, $R_7$ = H, $R_8$ = H, $R_9$ = Cl, $R_{10}$ = H
80, $R_7$ = H. $R_8$ = H, $R_9$ = Cl, $R_{10}$ = H
81, $R_7$ = H, $R_8$ = H, $R_9$ = CN, $R_{10}$ = H tert-butyl 2-(3-bromo-4-fluorophenoxy)-2-methylpropanoate (222a). $^1$H NMR (500 MHz, Chloroform-d) δ 7.09 (dd, J=5.7, 3.0 Hz, 1H), 6.98 (dd, J=9.0, 8.1 Hz, 1H), 6.80 (ddd, J=9.0, 3.9, 3.0 Hz, 1H), 1.53 (s, 6H), 1.45 (s, 9H). $^{13}$C NMR (126 MHz, Chloroform-d) δ 172.65, 155.51, 153.59, 152.04 (d, J=2.9 Hz), 124.06, 119.68 (d, J=6.8 Hz), 116.10 (d, J=23.7 Hz), 108.42 (d, J=22.5 Hz), 82.09, 80.42, 27.81, 25.28. MS (ESI) m/z=355.1 [M+Na]$^+$ tert-butyl 2-(3-bromo-5-fluorophenoxy)-2-methylpropanoate (222b). $^1$H NMR (500 MHz, Chloroform-d) δ 6.86 (ddd, J=8.0, 2.3, 1.6 Hz, 1H), 6.79 (ddd, J=2.6, 1.6, 1.1 Hz, 1H), 6.52 (dt, J=10.6, 2.3 Hz, 1H), 1.56 (d, J=7.3 Hz, 6H), 1.45 (s, 9H). $^{13}$C NMR (126 MHz, Chloroform-d) δ 172.35, 162.93 (d, J=248.9 Hz), 157.54 (d, J=11.9 Hz), 122.08 (d, J=12.5 Hz), 117.46 (d, J=3.3 Hz), 112.23 (d, J=24.9 Hz), 105.08 (d, J=24.5 Hz), 82.33, 80.30, 27.75, 25.27. MS (ESI) m/z=355.1 [M+Na]$^+$ tert-butyl 2-(5-bromo-2-fluorophenoxy)-2-methylpropanoate (222c). $^1$H NMR (500 MHz, Chloroform-d) δ 7.12 (d, J=5.9 Hz, 1H), 7.07 (dt, J=7.4, 4.3 Hz, 1H), 6.95 (dt, J=13.3, 6.2 Hz, 1H), 1.57 (t, J=3.5 Hz, 6H), 1.48 (t, J=3.6 Hz, 9H). $^{13}$C NMR (126 MHz, Chloroform-d) δ 172.23, 153.95 (d, J=246.7 Hz), 144.27 (d, J=12.0 Hz), 125.73 (d, J=6.9 Hz), 124.60, 117.60 (d, J=20.8 Hz), 115.60 (d, J=3.9 Hz), 82.21, 81.66, 27.81, 25.05. MS (ESI) m/z=355.0, 357.0 [M+Na]$^+$ tert-butyl 2-(3-bromo-2-fluorophenoxy)-2-methylpropanoate (222d). $^1$H NMR (500 MHz, Chloroform-d) δ 7.18 (ddd, J=7.9, 5.8, 1.6 Hz, 1H), 6.94 (ddd, J=8.3, 7.3, 1.7 Hz, 1H), 6.87 (td, J=8.2, 1.6 Hz, 1H), 1.56 (s, 6H), 1.45 (s, 9H). $^{13}$C NMR (126 MHz, Chloroform-d) δ 172.43, 151.98 (d, J=247.0 Hz), 144.56 (d, J=11.8 Hz), 126.65, 124.06 (d, J=5.0 Hz), 120.55, 109.85 (d, J=19.4 Hz), 81.97, 81.63, 27.80, 25.10. MS (ESI) m/z=355.1, 357.1 [M+Na]$^+$ tert-butyl 2-(3-bromo-5-(trifluoromethyl)phenoxy)-2-methylpropanoate (222e). $^1$H NMR (500 MHz, Chloroform-d) δ 7.35 (td, J=1.6, 0.8 Hz, 1H), 7.16 (t, J=1.9 Hz, 1H), 7.01 (ddd, J=2.3, 1.6, 0.8 Hz, 1H), 1.59 (s, 6H), 1.44 (s, 9H). $^{13}$C NMR (126 MHz, Chloroform-d) δ 172.15, 156.74, 132.72 (q, J=33.0 Hz), 124.61, 124.07, 122.63, 121.90, 121.25 (d, J=4.0 Hz), 114.02 (d, J=3.8 Hz), 82.53, 80.41, 27.70, 25.24. MS (ESI) m/z=405.1, 407.1 [M+Na]$^+$ tert-butyl 2-(3-bromo-5-chlorophenoxy)-2-methylpropanoate (222f). $^1$H NMR (500 MHz, Chloroform-d) δ 7.11 (t, J=1.7 Hz, 1H), 6.89 (dd, J=2.3, 1.6 Hz, 1H), 6.78 (dd, J=2.3, 1.8 Hz, 1H), 1.57 (s, 6H), 1.45 (s, 9H). MS (ESI) m/z=371.1 [M+Na]$^+$ tert-butyl 2-(3-chloro-5-cyanophenoxy)-2-methylpropanoate (222g). $^1$H NMR (500 MHz, Chloroform-d) δ 7.23 (dd, J=1.8, 1.3 Hz, 1H), 7.06 (dd, J=2.4, 1.8 Hz, 1H), 6.99 (dd, J=2.4, 1.3 Hz, 1H), 1.59 (s, 6H), 1.45 (s, 9H). MS (ESI) m/z=318.2 [M+Na]$^+$ tert-butyl 2-(5-bromo-2-chlorophenoxy)-2-methylpropanoate (222h). $^1$H NMR (500 MHz, Chloroform-d) δ 7.22 (dd, J=9.0, 1.3 Hz, 1H), 7.08-6.99 (m, 2H), 1.60 (d, J=1.3 Hz, 6H), 1.47 (d, J=1.3 Hz, 9H). MS (ESI) m/z=371.1 [M+Na]$^+$ tert-butyl 2-(5-bromo-2-cyanophenoxy)-2-methylpropanoate (222i). $^1$H NMR (500 MHz, Chloroform-d) δ 7.41 (d, J=8.2 Hz, 1H), 7.17 (dt, J=8.2, 1.4 Hz, 1H), 7.00 (d, J=1.6 Hz, 1H), 1.66 (d, J=1.3 Hz, 6H), 1.44 (d, J=1.3 Hz, 9H). MS (ESI) m/z=362.1, 364.1 [M+Na]$^+$ ethyl (R)-1-(5-((1-(tert-butoxy)-2-methyl-1-oxopropan-2-yl)oxy)-2-fluorophenyl)piperidine-3-carboxylate (223a). $^1$H NMR (500 MHz, Chloroform-d) δ 6.84 (dd, J=12.0, 8.8 Hz, 1H), 6.55 (dd, J=7.4, 2.9 Hz, 1H), 6.38 (dt, J=8.9, 3.2 Hz, 1H), 4.14 (qd, J=7.2, 1.1 Hz, 2H), 3.51 (ddt, J=11.7, 3.3, 1.4 Hz, 1H), 3.27 (dd, J=11.5, 4.4 Hz, 1H), 2.83 (dd, J=11.5, 10.1 Hz, 1H), 2.76-2.59 (m, 2H), 2.04 (dq, J=12.8, 4.1 Hz, 1H), 1.83 (dp, J=15.5, 3.9 Hz, 1H), 1.73 (dddd, J=17.6, 15.5, 8.2, 4.2 Hz, 1H), 1.52 (s, 7H), 1.45 (s, 9H), 1.26 (td, J=7.2, 0.7 Hz, 3H). MS (ESI) m/z=410.2 [M+H]$^+$ ethyl (R)-1-(3-((1-(tert-butoxy)-2-methyl-1-oxopropan-2-yl)oxy)-5-fluorophenyl)piperidine-3-carboxylate (223b). $^1$H NMR (500 MHz, Chloroform-d) δ 6.30-6.17 (m, 2H), 6.05-5.93 (m, 1H), 4.14 (qq, J=7.1, 1.0 Hz, 2H), 3.72-3.59 (m, 1H), 3.48-3.36 (m, 1H), 3.00 (dd, J=12.5, 9.9 Hz, 1H), 2.79 (ddd, J=13.1, 10.7, 3.2 Hz, 1H), 2.58 (tq, J=11.1, 6.9, 5.2 Hz, 1H), 2.04-1.96 (m, 1H), 1.79-1.71 (m, 1H), 1.70-1.57 (m, 2H), 1.57 (s, 6H), 1.43 (dd, J=2.1, 0.9 Hz, 9H), 1.26 (tq, J=7.1, 1.0 Hz, 3H). MS (ESI) m/z=410.3 [M+H]$^+$, 432.3 [M+Na]$^+$ ethyl (R)-1-(3-((1-(tert-butoxy)-2-methyl-1-oxopropan-2-yl)oxy)-4-fluorophenyl)piperidine-3-carboxylate (223c). $^1$H NMR (500 MHz, Chloroform-d) δ 6.92 (dd, J=10.5, 8.9 Hz, 1H), 6.63 (dd, J=7.3, 2.9 Hz, 1H), 6.54 (dt, J=8.9, 3.3 Hz, 1H), 4.15 (qd, J=7.1, 0.8 Hz, 2H), 3.53 (ddt, J=12.1, 3.6, 1.5 Hz, 1H), 3.33-3.25 (m, 1H), 2.90 (dd, J=12.1, 9.8 Hz, 1H), 2.75-2.57 (m, 2H), 2.03-1.90 (m, 1H), 1.85-1.77 (m, 1H), 1.70-1.60 (m, 2H), 1.53 (d, J=1.3 Hz, 6H), 1.47 (s, 9H), 1.26 (t, J=7.1 Hz, 3H). MS (ESI) m/z=410.3 [M+H]$^+$ ethyl (R)-1-(3-((1-(tert-butoxy)-2-methyl-1-oxopropan-2-yl)oxy)-2-fluorophenyl)piperidine-3-carboxylate (223d). $^1$H NMR (500 MHz, Chloroform-d) δ 6.80 (td, J=8.3, 1.8 Hz, 1H), 6.65-6.50 (m, 2H), 4.07 (q, J=7.1 Hz, 2H), 3.54-3.38 (m, 1H), 3.24 (dt, J=11.9, 3.9 Hz, 1H), 2.79 (t, J=10.9 Hz, 1H), 2.70-2.50 (m, 2H), 1.98 (dt, J=12.8, 4.0 Hz, 1H), 1.83-1.59 (m, 2H), 1.47 (d, J=1.5 Hz, 7H), 1.39 (s, 9H), 1.19 (t, J=7.1 Hz, 3H). MS (ESI) m/z=410.2 [M+H]$^+$, 432.2 [M+Na]$^+$ ethyl (R)-1-(3-((1-(tert-butoxy)-2-methyl-1-oxopropan-2-yl)oxy)-2-(trifluoromethyl)phenyl)piperidine-3-carboxylate (223e). $^1$H NMR (500 MHz, Chloroform-d) δ 6.77 (t, J=1.7 Hz, 1H), 6.58 (t, J=2.2 Hz, 1H), 6.49 (t, J=1.7 Hz, 1H), 4.16 (q, J=7.2 Hz, 2H), 3.73-3.61 (m, 1H), 3.45 (dt, J=12.1, 4.0 Hz, 1H), 3.08 (dd, J=12.5, 9.6 Hz, 1H), 2.86 (ddd, J=12.9, 10.1, 3.2 Hz, 1H), 2.62 (tt, J=9.7, 3.9 Hz, 1H), 2.08-1.98 (m, 1H), 1.85-1.75 (m, 1H), 1.75-1.60 (m, 2H), 1.57 (s, 6H), 1.43 (d, J=0.9 Hz, 9H), 1.27 (t, J=7.1 Hz, 3H). MS (ESI) m/z=460.3 [M+H]$^+$ ethyl (R)-1-(3-((1-(tert-butoxy)-2-methyl-1-oxopropan-2-yl)oxy)-5-chlorophenyl)piperidine-3-carboxylate (223f). $^1$H NMR (500 MHz, Chloroform-d) δ 7.65-7.61 (m, 1H), 7.45-7.38 (m, 2H), 4.16 (q, J=7.2 Hz, 2H), 3.67 (ddt, J=12.7, 3.6, 1.5 Hz, 1H), 3.43 (d, J=12.4 Hz, 1H), 3.01 (dd, J=12.5, 9.9 Hz, 1H), 2.81 (t, J=11.5 Hz, 1H), 2.62 (s, 1H), 2.02 (d, J=9.2 Hz, 1H), 1.82-1.73 (m, 1H), 1.72-1.63 (m, 2H), 1.56 (d, J=1.5 Hz, 6H), 1.45 (s, 9H), 1.28 (t, J=7.1 Hz, 3H). MS (ESI) m/z=426.2 $[M+H]^+$, 448.3 $[M+Na]^+$ ethyl (R)-1-(3-((1-(tert-butoxy)-2-methyl-1-oxopropan-2-yl)oxy)-5-cyanophenyl)piperidine-3-carboxylate (223g). $^1$H NMR (500 MHz, Chloroform-d) δ 6.80 (dd, J=2.5, 1.2 Hz, 1H), 6.65 (t, J=2.3 Hz, 1H), 6.49 (dd, J=2.2, 1.2 Hz, 1H), 4.17 (q, J=7.1 Hz, 2H), 3.66 (ddd, J=12.7, 3.5, 1.8 Hz, 1H), 3.44 (dt, J=12.5, 4.2 Hz, 1H), 3.09 (dd, J=12.7, 9.6 Hz, 1H), 2.87 (ddd, J=13.0, 10.3, 3.1 Hz, 1H), 2.61 (tt, J=9.8, 3.9 Hz, 1H), 2.06-1.95 (m, 1H), 1.84-1.76 (m, 1H), 1.76-1.64 (m, 2H), 1.58-1.54 (m, 6H), 1.45 (s, 9H), 1.29-1.23 (m, 3H). MS (ESI) m/z=417.2 $[M+H]^+$ ethyl (R)-1-(3-((1-(tert-butoxy)-2-methyl-1-oxopropan-2-yl)oxy)-4-chlorophenyl)piperidine-3-carboxylate (223h). $^1$H NMR (500 MHz, Chloroform-d) δ 7.18 (d, J=8.7 Hz, 1H), 6.61-6.50 (m, 2H), 4.19-4.11 (m, 2H), 3.60 (ddt, J=12.3, 3.1, 1.5 Hz, 1H), 3.42-3.32 (m, 1H), 2.95 (dd, J=12.3, 9.9 Hz, 1H), 2.80-2.70 (m, 1H), 2.61 (dq, J=9.9, 5.3, 4.4 Hz, 1H), 2.01 (dt, J=9.8, 5.3 Hz, 1H), 1.78 (dtt, J=11.3, 7.8, 3.1 Hz, 1H), 1.68-1.61 (m, 2H), 1.57 (d, J=1.9 Hz, 6H), 1.46 (d, J=1.4 Hz, 9H), 1.27 (td, J=7.1, 1.3 Hz, 3H). MS (ESI) m/z=426.2 $[M+H]^+$ ethyl (R)-1-(3-((1-(tert-butoxy)-2-methyl-1-oxopropan-2-yl)oxy)-4-cyanophenyl)piperidine-3-carboxylate (223i). $^1$H NMR (500 MHz, Chloroform-d) δ 7.35 (dd, J=8.8, 1.2 Hz, 1H), 6.50 (dd, J=8.8, 2.3 Hz, 1H), 6.33 (d, J=2.2 Hz, 1H), 4.20-4.12 (m, 2H), 3.80-3.70 (m, 1H), 3.52 (dd, J=12.8, 4.7 Hz, 1H), 3.18-3.10 (m, 1H), 2.94 (ddd, J=13.1, 10.5, 2.9 Hz, 1H), 2.56 (tt, J=9.9, 3.9 Hz, 1H), 2.08-1.97 (m, 1H), 1.76 (tt, J=13.8, 3.9 Hz, 2H), 1.63 (s, 6H), 1.56 (dd, J=10.3, 2.8 Hz, 1H), 1.43 (d, J=1.3 Hz, 9H), 1.27 (td, J=7.1, 1.2 Hz, 3H). MS (ESI) m/z=417.2 $[M+H]^+$, 439.3 $[M+Na]^+$ tert-butyl (R)-4-(2-(3-(3-(ethoxycarbonyl)piperidin-1-yl)-4-fluorophenoxy)-2-methylpropanoyl)piperazine-1-carboxylate (224a). $^1$H NMR (500 MHz, Chloroform-d) δ 6.77 (dd, J=11.9, 8.9 Hz, 1H), 6.39 (dd, J=7.3, 3.0 Hz, 1H), 6.26 (dt, J=8.9, 3.1 Hz, 1H), 4.08 (q, J=7.1 Hz, 2H), 3.76 (t, J=5.2 Hz, 2H), 3.54 (t, J=5.1 Hz, 2H), 3.43 (ddt, J=11.7, 3.4, 1.5 Hz, 1H), 3.28 (t, J=5.1 Hz, 2H), 3.19 (dt, J=11.6, 4.1 Hz, 1H), 3.04 (t, J=5.1 Hz, 2H), 2.77 (dd, J=11.7, 9.9 Hz, 1H), 2.69-2.54 (m, 2H), 2.02-1.94 (m, 1H), 1.78 (dp, J=11.5, 3.9 Hz, 1H), 1.72-1.61 (m, 1H), 1.61-1.46 (m, 7H), 1.36 (s, 9H), 1.19 (t, J=7.1 Hz, 3H). $^{13}$C NMR (126 MHz, Chloroform-d) δ 173.54, 171.80, 154.27, 151.58, 151.47 (d, J=2.1 Hz), 149.67, 141.24 (d, J=10.0 Hz), 115.92 (d, J=22.4 Hz), 109.25, 109.00 (d, J=2.7 Hz), 80.82, 80.05, 60.37, 52.97 (d, J=3.6 Hz), 51.00 (d, J=3.0 Hz), 45.74, 42.86, 41.74, 28.28, 26.75, 25.97 (d, J=3.0 Hz), 24.57, 14.15. MS (ESI) m/z=522.4 $[M+H]^+$ tert-butyl (R)-4-(2-(3-(3-(ethoxycarbonyl)piperidin-1-yl)-5-fluorophenoxy)-2-methylpropanoyl)piperazine-1-carboxylate (224b). $^1$H NMR (500 MHz, Chloroform-d) δ 6.21 (dt, J=12.0, 2.1 Hz, 1H), 6.14 (t, J=2.2 Hz, 1H), 5.98 (dt, J=10.4, 2.1 Hz, 1H), 4.13 (q, J=7.2 Hz, 2H), 3.76 (t, J=5.2 Hz, 2H), 3.65-3.52 (m, 3H), 3.42-3.27 (m, 3H), 3.09 (t, J=5.1 Hz, 2H), 3.00 (dd, J=12.6, 9.8 Hz, 1H), 2.78 (ddd, J=13.0, 10.3, 3.1 Hz, 1H), 2.57 (tt, J=9.9, 3.8 Hz, 1H), 2.03-1.95 (m, 1H), 1.79-1.70 (m, 1H), 1.60 (s, 8H), 1.40 (s, 9H), 1.30-1.17 (m, 3H). MS (ESI) m/z=522.4 $[M+H]^+$, 544.4 $[M+Na]^+$ tert-butyl (R)-4-(2-(5-(3-(ethoxycarbonyl)piperidin-1-yl)-2-fluorophenoxy)-2-methylpropanoyl)piperazine-1-carboxylate (224c). $^1$H NMR (500 MHz, Chloroform-d) δ 6.94 (dd, J=10.8, 8.6 Hz, 1H), 6.56-6.41 (m, 2H), 4.15 (q, J=7.1 Hz, 2H), 3.88 (s, 2H), 3.62 (s, 2H), 3.49 (dd, J=12.2, 3.7 Hz, 1H), 3.38 (s, 2H), 3.23 (q, J=5.5, 5.0 Hz, 3H), 2.91 (dd, J=12.1, 9.6 Hz, 1H), 2.73-2.58 (m, 2H), 1.98 (dd, J=9.8, 4.5 Hz, 1H), 1.82-1.76 (m, 1H), 1.63 (s, 8H), 1.43 (s, 9H), 1.26 (t, J=7.1 Hz, 3H). MS (ESI) m/z=522.4 $[M+H]^+$, 544.3 $[M+Na]^+$ tert-butyl (R)-4-(2-(3-(3-(ethoxycarbonyl)piperidin-1-yl)-2-fluorophenoxy)-2-methylpropanoyl)piperazine-1-carboxylate (224d). $^1$H NMR (500 MHz, Chloroform-d) δ 6.85 (td, J=8.3, 1.7 Hz, 1H), 6.67-6.57 (m, 1H), 6.52 (ddd, J=8.5, 7.2, 1.4 Hz, 1H), 4.15 (qd, J=7.1, 1.1 Hz, 2H), 3.88 (s, 2H), 3.62 (s, 2H), 3.53 (ddt, J=11.5, 3.3, 1.5 Hz, 1H), 3.38 (d, J=5.9 Hz, 2H), 3.34-3.26 (m, 1H), 3.21 (s, 2H), 2.87 (dd, J=11.6, 10.1 Hz, 1H), 2.79-2.63 (m, 2H), 2.07 (dt, J=13.3, 4.0 Hz, 1H), 1.84 (dt, J=13.3, 3.7 Hz, 1H), 1.75 (tdd, J=15.1, 9.5, 4.0 Hz, 1H), 1.63 (s, 7H), 1.43 (s, 9H), 1.26 (t, J=7.1 Hz, 3H). MS (ESI) m/z=522.3 $[M+H]^+$, 544.3 $[M+Na]^+$ tert-butyl (R)-4-(2-(3-(3-(ethoxycarbonyl)piperidin-1-yl)-5-(trifluoromethyl)phenoxy)-2-methylpropanoyl)piperazine-1-carboxylate (224e). $^1$H NMR (500 MHz, Chloroform-d) δ 6.74 (t, J=1.7 Hz, 1H), 6.50 (t, J=2.3 Hz, 1H), 6.47 (t, J=1.6 Hz, 1H), 4.14 (q, J=7.1 Hz, 2H), 3.75 (t, J=5.1 Hz, 2H), 3.66-3.50 (m, 3H), 3.39 (dt, J=12.2, 4.2 Hz, 1H), 3.35 (s, 2H), 3.11-3.00 (m, 3H), 2.84 (ddd, J=12.8, 10.0, 3.1 Hz, 1H), 2.59 (tt, J=9.6, 3.8 Hz, 1H), 2.04-1.96 (m, 1H), 1.78 (dddt, J=13.5, 8.5, 4.9, 3.1 Hz, 1H), 1.61 (s, 8H), 1.39 (s, 9H), 1.25 (t, J=7.2 Hz, 3H). MS (ESI) m/z=572.4 $[M+H]^+$, 594.4 $[M+Na]^+$ tert-butyl (R)-4-(2-(3-chloro-5-(3-(ethoxycarbonyl)piperidin-1-yl)phenoxy)-2-methylpropanoyl)piperazine-1-carboxylate (224f). $^1$H NMR (500 MHz, Chloroform-d) δ 6.54 (s, 1H), 6.28 (d, J=7.2 Hz, 2H), 4.17 (q, J=7.1 Hz, 2H), 3.78 (t, J=5.2 Hz, 2H), 3.68-3.56 (m, 3H), 3.43-3.30 (m, 3H), 3.17-3.05 (m, 2H), 3.05-2.96 (m, 1H), 2.85-2.77 (m, 1H), 2.61 (s, 1H), 2.03 (d, J=11.6 Hz, 1H), 1.84-1.74 (m, 1H), 1.62 (s, 8H), 1.43 (s, 9H), 1.28 (t, J=7.1 Hz, 3H). MS (ESI) m/z=538.3 $[M+H]^+$, 560.3 $[M+Na]^+$ tert-butyl (R)-4-(2-(3-cyano-5-(3-(ethoxycarbonyl)piperidin-1-yl)phenoxy)-2-methylpropanoyl)piperazine-1-carboxylate (224g). $^1$H NMR (500 MHz, Chloroform-d) δ 6.77-6.70 (m, 1H), 6.53 (q, J=2.5 Hz, 1H), 6.44 (s, 1H), 4.13 (tq, J=10.8, 6.3, 4.4 Hz, 2H), 3.71 (d, J=6.4 Hz, 2H), 3.58 (d, J=17.0 Hz, 3H), 3.40-3.25 (m, 3H), 3.07 (tt, J=9.4, 4.2 Hz, 3H), 2.89-2.79 (m, 1H), 2.56 (dtt, J=10.1, 6.7, 3.7 Hz, 1H), 1.98 (dq, J=12.4, 4.1 Hz, 1H), 1.79-1.64 (m, 2H), 1.62-1.55 (m, 7H), 1.38 (t, J=3.6 Hz, 9H), 1.23 (qd, J=6.2, 5.2, 2.3 Hz, 3H). MS (ESI) m/z=529.4 $[M+H]^+$, 551.4 $[M+Na]^+$ tert-butyl (R)-4-(2-(2-chloro-5-(3-(ethoxycarbonyl)piperidin-1-yl)phenoxy)-2-methylpropanoyl)piperazine-1-carboxylate (224h). $^1$H NMR (500 MHz, Chloroform-d) δ 7.18 (dd, J=8.8, 1.2 Hz, 1H), 6.54-6.47 (m, 1H), 6.43 (d, J=2.6 Hz, 1H), 4.20-4.11 (m, 2H), 3.81 (t, J=5.1 Hz, 2H), 3.69-3.48 (m, 3H), 3.40-3.23 (m, 3H), 3.12 (s, 2H), 2.96 (dd, J=12.4, 9.7 Hz, 1H), 2.75 (td, J=9.9, 9.2, 5.0 Hz, 1H), 2.60 (dq, J=9.7, 4.6 Hz, 1H), 2.01 (dt, J=13.7, 5.5 Hz, 1H), 1.78 (qd, J=7.1, 6.2, 3.4 Hz, 1H), 1.70-1.62 (m, 8H), 1.43 (d, J=1.3 Hz, 9H), 1.27 (td, J=7.1, 1.2 Hz, 3H). MS (ESI) m/z=538.3 $[M+H]^+$, 560.3 $[M+Na]^+$ tert-butyl (R)-4-(2-(2-cyano-5-(3-(ethoxycarbonyl)piperidin-1-yl)phenoxy)-2-methylpropanoyl)piperazine-1-carboxylate (224i). MS (ESI) m/z=529.4 $[M+H]^+$, 551.3 $[M+Na]^+$. Hydrolysis of 103i gave carboxylate derivative. $^1$H NMR (500 MHz, Chloroform-d) δ 7.37 (d, J=8.7 Hz, 1H), 6.49 (dd, J=8.8, 2.2 Hz, 1H), 6.32 (d, J=2.2 Hz, 1H), 3.78 (d, J=7.4 Hz, 2H), 3.63 (t, J=16.3 Hz, 3H), 3.42-3.27 (m, 4H), 3.11 (dd, J=20.4, 7.3 Hz, 3H), 2.63 (tt, J=8.3, 4.0 Hz, 1H), 2.03-1.95 (m, 1H), 1.88 (dtd, J=11.7, 8.5, 7.8, 3.2 Hz, 1H), 1.84-1.75 (m, 1H), 1.72 (d, J=1.3 Hz, 6H), 1.60 (ddt, J=13.5, 9.4, 5.0 Hz, 1H), 1.43 (s, 9H).

tert-butyl (R)-4-(2-(3-(3-((4-bromobenzyl)(cyclopropyl)carbamoyl)piperidin-1-yl)-4-fluorophenoxy)-2-methylpropanoyl)piperazine-1-carboxylate (225a). $^{1}$H NMR (500 MHz, Chloroform-d) δ 7.39-7.30 (m, 2H), 7.08-6.95 (m, 2H), 6.76 (dd, J=12.0, 8.8 Hz, 1H), 6.41 (dd, J=7.3, 3.0 Hz, 1H), 6.25 (dt, J=8.9, 3.1 Hz, 1H), 4.54 (d, J=14.8 Hz, 1H), 4.38 (d, J=14.7 Hz, 1H), 3.75 (s, 2H), 3.53 (d, J=6.0 Hz, 2H), 3.48-3.35 (m, 2H), 3.34-3.18 (m, 3H), 3.04 (s, 2H), 2.80-2.74 (m, 1H), 2.57 (dtt, J=24.9, 7.0, 3.3 Hz, 2H), 1.91-1.58 (m, 4H), 1.53 (s, 6H), 1.36 (s, 9H), 0.91-0.62 (m, 4H). MS (ESI) m/z=701.3, 703.3 [M+H]$^{+}$ tert-butyl (R)-4-(2-(3-(3-((4-bromobenzyl)(cyclopropyl)carbamoyl)piperidin-1-yl)-5-fluorophenoxy)-2-methylpropanoyl)piperazine-1-carboxylate (225b). $^{1}$H NMR (500 MHz, Chloroform-d) δ 7.48-7.39 (m, 2H), 7.16-7.04 (m, 2H), 6.20 (dt, J=12.1, 2.2 Hz, 1H), 6.15 (d, J=2.3 Hz, 1H), 6.01 (dt, J=10.4, 2.1 Hz, 1H), 4.64 (d, J=14.7 Hz, 1H), 4.46 (d, J=14.7 Hz, 1H), 3.78 (t, J=5.2 Hz, 2H), 3.61 (ddt, J=16.9, 12.8, 6.7 Hz, 4H), 3.42-3.26 (m, 3H), 3.12 (d, J=5.7 Hz, 2H), 2.99 (dd, J=12.6, 11.0 Hz, 1H), 2.83-2.72 (m, 1H), 2.61 (tt, J=6.9, 3.9 Hz, 1H), 1.98-1.89 (m, 1H), 1.81 (ddd, J=14.5, 7.1, 4.1 Hz, 1H), 1.76-1.57 (m, 8H), 1.43 (s, 9H), 0.95-0.76 (m, 4H). MS (ESI) m/z=701.3, 703.3 [M+H]$^{+}$.

tert-butyl (R)-4-(2-(5-(3-((4-bromobenzyl)(cyclopropyl)carbamoyl)piperidin-1-yl)-2-fluorophenoxy)-2-methylpropanoyl)piperazine-1-carboxylate (225c). $^{1}$H NMR (500 MHz, Chloroform-d) δ 7.40-7.30 (m, 2H), 7.06 (d, J=8.1 Hz, 2H), 6.88 (dd, J=10.7, 8.9 Hz, 1H), 6.42 (ddd, J=14.9, 8.0, 3.0 Hz, 2H), 4.53 (d, J=14.7 Hz, 1H), 4.43 (d, J=14.7 Hz, 1H), 3.80 (s, 2H), 3.51 (s, 2H), 3.45-3.22 (m, 5H), 3.22-3.05 (m, 2H), 2.88-2.76 (m, 1H), 2.59 (dqd, J=14.4, 8.1, 6.6, 3.2 Hz, 2H), 1.85 (d, J=10.0 Hz, 1H), 1.81-1.72 (m, 1H), 1.71-1.59 (m, 2H), 1.56 (s, 6H), 1.37 (s, 9H), 0.89-0.68 (m, 4H). MS (ESI) m/z=701.3, 703.3 [M+H]$^{+}$ tert-butyl (R)-4-(2-(3-(3-((4-bromobenzyl)(cyclopropyl)carbamoyl)piperidin-1-yl)-2-fluorophenoxy)-2-methylpropanoyl)piperazine-1-carboxylate (225d). $^{1}$H NMR (500 MHz, Chloroform-d) δ 7.38-7.29 (m, 2H), 7.05-6.97 (m, 2H), 6.83-6.74 (m, 1H), 6.57 (t, J=7.7 Hz, 1H), 6.45 (t, J=7.8 Hz, 1H), 4.59-4.31 (m, 2H), 3.81 (t, J=5.3 Hz, 2H), 3.55 (s, 2H), 3.51-3.42 (m, 1H), 3.42-3.22 (m, 4H), 3.22-3.07 (m, 2H), 2.82 (t, J=11.1 Hz, 1H), 2.70-2.59 (m, 1H), 2.54 (dp, J=7.0, 3.9 Hz, 1H), 1.91-1.83 (m, 1H), 1.83-1.69 (m, 2H), 1.64 (td, J=12.2, 4.7 Hz, 1H), 1.56 (d, J=5.7 Hz, 6H), 1.36 (s, 9H), 0.87-0.71 (m, 4H). MS (ESI) m/z=701.3 [M+H]$^{+}$ tert-butyl (R)-4-(2-(3-(3-((4-bromobenzyl)(cyclopropyl)carbamoyl)piperidin-1-yl)-5-(trifluoromethyl)phenoxy)-2-methylpropanoyl)piperazine-1-carboxylate (225e). $^{1}$H NMR (500 MHz, Chloroform-d) δ 7.45-7.39 (m, 2H), 7.15-7.03 (m, 2H), 6.71 (t, J=1.7 Hz, 1H), 6.54-6.44 (m, 2H), 4.67 (d, J=14.7 Hz, 1H), 4.41 (d, J=14.8 Hz, 1H), 3.75 (d, J=6.0 Hz, 2H), 3.71-3.62 (m, 2H), 3.62-3.48 (m, 2H), 3.38 (tt, J=11.1, 3.5 Hz, 1H), 3.31 (d, J=5.5 Hz, 2H), 3.12-2.99 (m, 3H), 2.86-2.78 (m, 1H), 2.60 (td, J=7.0, 3.3 Hz, 1H), 1.94 (dd, J=12.6, 3.6 Hz, 1H), 1.85-1.66 (m, 3H), 1.63 (d, J=2.0 Hz, 6H), 1.41 (s, 9H), 0.93-0.76 (m, 4H). MS (ESI) m/z=751.3, 753.4 [M+H]$^{+}$ tert-butyl (R)-4-(2-(3-(3-((4-bromobenzyl)(cyclopropyl)carbamoyl)piperidin-1-yl)-5-chlorophenoxy)-2-methylpropanoyl)piperazine-1-carboxylate (225f). $^{1}$H NMR (500 MHz, Chloroform-d) δ 7.40-7.33 (m, 2H), 7.10-7.00 (m, 2H), 6.43 (t, J=2.0 Hz, 1H), 6.21 (dt, J=7.2, 2.2 Hz, 2H), 4.58 (d, J=14.7 Hz, 1H), 4.39 (d, J=14.7 Hz, 1H), 3.71 (d, J=5.4 Hz, 2H), 3.60-3.44 (m, 4H), 3.30 (dq, J=25.6, 6.5, 5.5 Hz, 3H), 3.05 (t, J=4.8 Hz, 2H), 2.94 (dd, J=12.7, 11.0 Hz, 1H), 2.72 (s, 1H), 2.56 (tt, J=6.9, 4.0 Hz, 1H), 1.87 (dd, J=12.2, 3.7 Hz, 1H), 1.77-1.60 (m, 3H), 1.56 (d, J=2.0 Hz, 6H), 1.37 (s, 9H), 0.81-0.75 (m, 4H). MS (ESI) m/z=717.3 [M+H]$^{+}$ tert-butyl (R)-4-(2-(3-(3-((4-bromobenzyl)(cyclopropyl)carbamoyl)piperidin-1-yl)-5-cyanophenoxy)-2-methylpropanoyl)piperazine-1-carboxylate (225g). $^{1}$H NMR (500 MHz, Chloroform-d) δ 7.46-7.38 (m, 2H), 7.15-7.01 (m, 2H), 6.77-6.67 (m, 1H), 6.59-6.52 (m, 1H), 6.48 (s, 1H), 4.65 (d, J=14.7 Hz, 1H), 4.43 (d, J=14.7 Hz, 1H), 3.74 (t, J=5.0 Hz, 2H), 3.67-3.49 (m, 4H), 3.42-3.27 (m, 3H), 3.14-2.97 (m, 3H), 2.84-2.77 (m, 1H), 2.61 (tt, J=6.7, 3.9 Hz, 1H), 1.98-1.90 (m, 1H), 1.83 (dp, J=9.6, 2.8 Hz, 1H), 1.79-1.65 (m, 2H), 1.62 (d, J=2.4 Hz, 6H), 1.42 (d, J=1.6 Hz, 9H), 0.86-0.77 (m, 4H). MS (ESI) m/z=708.3, 710.4 [M+H]$^{+}$ tert-butyl (R)-4-(2-(5-(3-((4-bromobenzyl)(cyclopropyl)carbamoyl)piperidin-1-yl)-2-chlorophenoxy)-2-methylpropanoyl)piperazine-1-carboxylate (225h). $^{1}$H NMR (500 MHz, Chloroform-d) δ 7.45-7.39 (m, 2H), 7.17 (d, J=8.4 Hz, 1H), 7.11 (d, J=8.0 Hz, 2H), 6.43 (d, J=8.1 Hz, 2H), 4.58 (d, J=14.8 Hz, 1H), 4.50 (d, J=14.8 Hz, 1H), 3.78 (s, 2H), 3.53 (td, J=14.3, 13.8, 7.3 Hz, 4H), 3.37 (t, J=10.9 Hz, 1H), 3.29 (s, 2H), 3.09 (d, J=13.3 Hz, 2H), 2.95-2.82 (m, 1H), 2.74-2.57 (m, 2H), 1.91 (d, J=11.5 Hz, 1H), 1.83 (s, 1H), 1.66 (d, J=3.4 Hz, 8H), 1.42 (d, J=1.4 Hz, 9H), 0.92-0.76 (m, 4H). MS (ESI) m/z=717.3 [M+H]$^{+}$ tert-butyl (R)-4-(2-(5-(3-((4-bromobenzyl)(cyclopropyl)carbamoyl)piperidin-1-yl)-2-cyanophenoxy)-2-methylpropanoyl)piperazine-1-carboxylate (225i). $^{1}$H NMR (500 MHz, Chloroform-d) δ 7.45-7.38 (m, 2H), 7.34 (dd, J=8.8, 2.0 Hz, 1H), 7.16-7.07 (m, 2H), 6.41 (dd, J=8.9, 2.2 Hz, 1H), 6.26 (d, J=2.3 Hz, 1H), 4.58 (d, J=14.8 Hz, 1H), 4.48 (d, J=14.8 Hz, 1H), 3.72 (dd, J=23.1, 8.8 Hz, 4H), 3.52 (s, 2H), 3.34-3.19 (m, 3H), 3.19-3.03 (m, 3H), 2.96-2.73 (m, 1H), 2.64 (tq, J=6.3, 3.2, 2.7 Hz, 1H), 1.93 (d, J=12.2 Hz, 1H), 1.84-1.78 (m, 2H), 1.68 (d, J=11.5 Hz, 6H), 1.61-1.52 (m, 1H), 1.41 (d, J=2.0 Hz, 9H), 0.91-0.76 (m, 4H). MS (ESI) m/z=708.3 [M+H]$^{+}$ tert-butyl (R)-4-(2-(3-(3-((4-(1H-pyrazol-4-yl)benzyl)(cyclopropyl)carbamoyl) piperidin-1-yl)-4-fluorophenoxy)-2-methylpropanoyl)piperazine-1-carboxylate (226a). $^{1}$H NMR (500 MHz, Chloroform-d) δ 7.81 (s, 2H), 7.50-7.36 (m, 2H), 7.23-7.14 (m, 2H), 6.84 (dd, J=12.0, 8.8 Hz, 1H), 6.51 (dd, J=7.3, 3.0 Hz, 1H), 6.33 (dt, J=8.9, 3.1 Hz, 1H), 4.72 (d, J=14.7 Hz, 1H), 4.52 (d, J=14.8 Hz, 1H), 3.92-3.74 (m, 2H), 3.68-3.48 (m, 4H), 3.43-3.23 (m, 3H), 3.13 (q, J=5.2 Hz, 2H), 2.88 (t, J=11.0 Hz, 1H), 2.76-2.49 (m, 2H), 2.01-1.70 (m, 4H), 1.62 (s, 6H), 1.44 (s, 9H), 0.98-0.80 (m, 4H). $^{13}$C NMR (126 MHz, Chloroform-d) δ 176.8, 172.0, 154.4, 151.62, 151.60, 151.59, 149.7, 141.4, 141.3, 136.5, 131.5, 131.0, 128.1, 125.8, 122.2, 116.0, 115.8, 109.3, 109.1, 109.0, 80.9, 80.2, 53.93, 53.90, 50.9, 50.8, 49.7, 45.8, 43.0, 40.7, 29.9, 28.4, 27.4, 26.1, 26.0, 25.1, 9.4, 9.0. MS (ESI) m/z=689.4 [M+H]$^{+}$, 687.3 [M−H]$^{-}$ tert-butyl (R)-4-(2-(3-(3-((4-(1H-pyrazol-4-yl)benzyl)(cyclopropyl) carbamoyl)piperidin-1-yl)-5-fluorophenoxy)-2-methylpropanoyl)piperazine-1-carboxylate (226b). $^{1}$H NMR (500 MHz, Chloroform-d) δ 7.79 (s, 2H), 7.42 (d, J=7.9 Hz, 2H), 7.19 (d, J=7.9 Hz, 2H), 6.21 (dt, J=12.1, 2.1 Hz, 1H), 6.15 (d, J=2.2 Hz, 1H), 5.99 (dt, J=10.4, 2.1 Hz, 1H), 4.69 (d, J=14.7 Hz, 1H), 4.49 (d, J=14.7 Hz, 1H), 3.80-3.45 (m, 6H), 3.45-3.26 (m, 3H), 3.17-2.96 (m, 3H), 2.77 (td, J=12.4, 2.5 Hz, 1H), 2.62 (td, J=6.7, 3.3 Hz, 1H), 2.00-1.90 (m, 1H), 1.82-1.58 (m, 9H), 1.40 (s, 9H), 0.93-0.76 (m, 4H). $^{13}$C NMR (126 MHz, Chloroform-d) δ 176.7, 171.6, 165.2, 163.3, 157.1, 157.0, 154.4, 152.9, 152.8, 136.3, 131.6, 128.1, 125.8, 122.1, 100.3, 100.2, 96.5, 96.3, 94.7, 81.0, 80.2, 51.5, 49.7, 49.2, 45.8, 42.9, 39.5, 29.9, 28.3, 27.8, 26.1, 24.2, 9.5, 9.0. MS (ESI) m/z=689.4 $[M+H]^+$, 687.4 $[M-H]^-$ tert-butyl (R)-4-(2-(5-(3-((4-(1H-pyrazol-4-yl)benzyl)(cyclopropyl)carbamoyl) piperidin-1-yl)-2-fluorophenoxy)-2-methylpropanoyl)piperazine-1-carboxylate (226c). $^1$H NMR (500 MHz, Chloroform-d) δ 7.81 (s, 2H), 7.43 (d, J=7.8 Hz, 2H), 7.21 (d, J=7.9 Hz, 2H), 6.94 (dd, J=10.7, 8.7 Hz, 1H), 6.50 (td, J=9.0, 3.1 Hz, 2H), 4.68 (d, J=14.7 Hz, 1H), 4.53 (d, J=14.7 Hz, 1H), 3.87 (s, 2H), 3.65-3.16 (m, 10H), 2.91 (t, J=11.3 Hz, 1H), 2.67 (td, J=9.5, 7.1, 3.0 Hz, 1H), 2.00-1.68 (m, 4H), 1.62 (s, 6H), 1.43 (s, 9H), 0.94-0.77 (m, 4H). $^{13}$C NMR (126 MHz, Chloroform-d) δ 176.7, 171.6, 154.4, 149.1, 148.4, −147.2, 142.9, 142.8, 136.5, 131.4, 128.2, 125.9, 122.2, 116.5, 116.3, 110.7, 109.0, 82.3, 80.2, 53.3, 50.9, 49.7, 45.9, 43.0, 40.1, 29.8, 28.4, 27.5, 26.0, 24.7, 9.5, 9.1. MS (ESI) m/z=689.4 $[M+H]^+$ tert-butyl (R)-4-(2-(3-(3-((4-(1H-pyrazol-4-yl)benzyl)(cyclopropyl) carbamoyl)piperidin-1-yl)-2-fluorophenoxy)-2-methylpropanoyl)piperazine-1-carboxylate (226d). $^1$H NMR (500 MHz, Chloroform-d) δ 7.80 (s, 2H), 7.42 (d, J=8.0 Hz, 2H), 7.20 (d, J=7.9 Hz, 2H), 6.86 (td, J=8.4, 1.5 Hz, 1H), 6.65 (t, J=7.7 Hz, 1H), 6.56-6.45 (m, 1H), 4.68 (d, J=14.9 Hz, 1H), 4.53 (d, J=14.9 Hz, 1H), 3.87 (s, 2H), 3.72-3.52 (m, 3H), 3.51-3.29 (m, 4H), 3.22 (s, 2H), 2.92 (t, J=11.1 Hz, 1H), 2.77-2.56 (m, 2H), 2.02-1.67 (m, 4H), 1.62 (d, J=5.1 Hz, 6H), 1.43 (s, 9H), 0.95-0.81 (m, 4H). $^{13}$C NMR (126 MHz, Chloroform-d) δ 176.9, 171.8, 154.5, 148.1, 146.2, 143.7, 143.6, 142.1, 136.6, 131.4, 131.1, 128.2, 125.9, 123.3, 122.3, 113.0, 112.0, 82.1, 80.2, 54.0, 53.4, 51.4, 49.6, 45.9, 43.1, 40.7, 29.9, 27.5, 26.0, 25.2, 9.4, 9.1. MS (ESI) m/z=689.4 $[M+H]^+$, 687.3 [M−H]

tert-butyl (R)-4-(2-(3-(3-((4-(1H-pyrazol-4-yl)benzyl)(cyclopropyl) carbamoyl)piperidin-1-yl)-5-(trifluoromethyl)phenoxy)-2-methylpropanoyl)piperazine-1-carboxylate (226e). $^1$H NMR (500 MHz, Chloroform-d) δ 7.81 (s, 2H), 7.44 (d, J=8.0 Hz, 2H), 7.22 (d, J=7.9 Hz, 2H), 6.73 (s, 1H), 6.52 (t, J=2.2 Hz, 1H), 6.48 (s, 1H), 4.75 (d, J=14.7 Hz, 1H), 4.48 (d, J=14.7 Hz, 1H), 3.76 (d, J=5.5 Hz, 2H), 3.70 (s, 2H), 3.58 (q, J=5.5 Hz, 2H), 3.42 (tt, J=11.3, 3.5 Hz, 1H), 3.31 (t, J=5.2 Hz, 2H), 3.08 (td, J=10.9, 6.3 Hz, 3H), 2.83 (td, J=12.5, 2.6 Hz, 1H), 2.64 (ddd, J=10.7, 6.7, 4.4 Hz, 1H), 2.01-1.92 (m, 1H), 1.63 (s, 9H), 1.41 (s, 9H), 0.94-0.79 (m, 4H). $^{13}$C NMR (126 MHz, Chloroform-d) δ 176.6, 171.5, 156.5, 154.3, 152.5, 136.5, 132.4, 131.5, 128.2, 125.9, 125.1, 122.9, 122.3, 107.4, 105.9, 81.1, 80.3, 51.5, 49.7, 49.4, 45.8, 42.9, 39.5, 29.8, 28.3, 27.7, 26.0, 24.2, 9.6, 9.0. MS (ESI) m/z=739.5 $[M+H]^+$, 737.5 $[M-H]^-$ tert-butyl (R)-4-(2-(3-(3-((4-(1H-pyrazol-4-yl)benzyl)(cyclopropyl) carbamoyl)piperidin-1-yl)-5-chlorophenoxy)-2-methylpropanoyl)piperazine-1-carboxylate (226f). $^1$H NMR (500 MHz, Chloroform-d) δ 7.81 (s, 2H), 7.46-7.40 (m, 2H), 7.24-7.19 (m, 2H), 6.50 (t, J=1.9 Hz, 1H), 6.26 (d, J=1.9 Hz, 2H), 4.71 (d, J=14.7 Hz, 1H), 4.50 (d, J=14.7 Hz, 1H), 3.76 (d, J=6.0 Hz, 2H), 3.66-3.55 (m, 4H), 3.40 (ddt, J=11.2, 7.2, 3.5 Hz, 1H), 3.33 (s, 2H), 3.10 (d, J=5.5 Hz, 2H), 3.02 (dd, J=12.7, 11.0 Hz, 1H), 2.78 (td, J=12.4, 2.5 Hz, 1H), 2.64 (tt, J=6.8, 4.2 Hz, 1H), 1.95 (d, J=11.8 Hz, 1H), 1.84-1.66 (m, 3H), 1.61 (s, 6H), 1.42 (s, 9H), 0.87-0.82 (m, 4H). MS (ESI) m/z=705.4 $[M+H]^+$, 703.4 $[M-H]^-$ tert-butyl (R)-4-(2-(3-(3-((4-(1H-pyrazol-4-yl)benzyl)(cyclopropyl)carbamoyl) piperidin-1-yl)-5-cyanophenoxy)-2-methylpropanoyl)piperazine-1-carboxylate (226g). $^1$H NMR (500 MHz, Chloroform-d) δ 7.85 (s, 2H), 7.50-7.43 (m, 2H), 7.25 (d, J=8.1 Hz, 2H), 6.75 (d, J=2.2 Hz, 1H), 6.57 (t, J=2.3 Hz, 1H), 6.48 (s, 1H), 4.71 (d, J=14.6 Hz, 1H), 4.52 (d, J=14.6 Hz, 1H), 3.74 (s, 2H), 3.64 (d, J=12.6 Hz, 2H), 3.58 (s, 2H), 3.36 (d, J=34.9 Hz, 3H), 3.13-3.04 (m, 3H), 2.82 (dd, J=13.7, 11.0 Hz, 1H), 2.64 (dt, J=6.6, 2.6 Hz, 1H), 1.98 (d, J=12.7 Hz, 1H), 1.90-1.81 (m, 1H), 1.81-1.66 (m, 2H), 1.65-1.61 (m, 6H), 1.43 (d, J=1.4 Hz, 9H), 0.87-0.80 (m, 4H). MS (ESI) m/z=696.4 $[M+H]^+$, 694.4 $[M-H]^-$ tert-butyl (R)-4-(2-(5-(3-((4-(1H-pyrazol-4-yl)benzyl)(cyclopropyl)carbamoyl) piperidin-1-yl)-2-chlorophenoxy)-2-methylpropanoyl)piperazine-1-carboxylate (226h). $^1$H NMR (500 MHz, Chloroform-d) δ 7.82 (s, 2H), 7.45 (d, J=7.8 Hz, 2H), 7.24 (d, J=7.8 Hz, 2H), 7.18 (d, J=8.6 Hz, 1H), 6.51-6.37 (m, 2H), 4.67 (d, J=14.6 Hz, 1H), 4.54 (d, J=14.7 Hz, 1H), 3.79 (s, 2H), 3.63-3.47 (m, 4H), 3.46-3.36 (m, 1H), 3.29 (s, 2H), 3.18-3.03 (m, 2H), 2.95 (t, J=11.6 Hz, 1H), 2.78-2.63 (m, 2H), 1.94 (d, J=12.2 Hz, 1H), 1.89-1.81 (m, 1H), 1.67 (s, 8H), 1.42 (d, J=1.5 Hz, 9H), 0.90-0.82 (m, 4H). MS (ESI) m/z=705.4 $[M+H]^+$, 703.4 $[M-H]^+$ tert-butyl (R)-4-(2-(5-(3-((4-(1H-pyrazol-4-yl)benzyl)(cyclopropyl)carbamoyl) piperidin-1-yl)-2-cyanophenoxy)-2-methylpropanoyl)piperazine-1-carboxylate (226i). $^1$H NMR (500 MHz, Chloroform-d) δ 7.80 (d, J=1.9 Hz, 2H), 7.47-7.41 (m, 2H), 7.34 (dd, J=8.8, 1.6 Hz, 1H), 7.23-7.17 (m, 2H), 6.42 (dd, J=8.8, 2.0 Hz, 1H), 6.27 (d, J=2.2 Hz, 1H), 4.69 (d, J=14.7 Hz, 1H), 4.51 (d, J=14.7 Hz, 1H), 3.80-3.63 (m, 4H), 3.60-3.47 (m, 2H), 3.30 (ddt, J=27.8, 11.8, 6.6 Hz, 3H), 3.13 (dt, J=21.5, 9.7 Hz, 3H), 2.89 (td, J=12.7, 2.5 Hz, 1H), 2.65 (h, J=6.2 Hz, 1H), 1.97 (q, J=5.0 Hz, 1H), 1.88-1.78 (m, 2H), 1.68 (d, J=6.8 Hz, 6H), 1.60-1.52 (m, 1H), 1.41 (d, J=1.6 Hz, 9H), 0.90-0.78 (m, 4H). MS (ESI) m/z=696.4 $[M+H]^+$, 694.4 $[M-H]^-$ (R)-4-(2-(3-(3-((4-(1H-pyrazol-4-yl)benzyl)(cyclopropyl)carbamoyl)piperidin-1-yl)-4-fluorophenoxy)-2-methylpropanoyl)piperazin-1-ium chloride (73). $^1$H NMR (500 MHz, Methanol-$d_4$) δ 8.55 (s, 2H), 7.73-7.62 (m, 2H), 7.40-7.25 (m, 4H), 6.92 (dt, J=9.3, 3.2 Hz, 1H), 4.84 (s, 1H), 4.52 (d, J=15.0 Hz, 1H), 4.30-3.84 (m, 5H), 3.78 (ddd, J=21.3, 11.6, 4.1 Hz, 2H), 3.71-3.65 (m, 1H), 3.51 (d, J=11.3 Hz, 1H), 3.26-2.92 (m, 4H), 2.83 (ddd, J=8.3, 6.1, 3.7 Hz, 1H), 2.21-1.91 (m, 4H), 1.65 (d, J=3.4 Hz, 6H), 1.10-0.85 (m, 4H). $^{13}$C NMR (126 MHz, Methanol-$d_4$) δ 176.8, 171.6, 152.0, 151.1, 149.2, 137.7, 130.7, 128.8, 128.1, 125.9, 123.8, 117.9, 117.7, 112.3, 81.9, 56.8, 54.2, 49.4, 43.2, 39.6, 36.8, 30.0, 24.8, 24.7, 23.9, 21.7, 9.2, 7.3. HRMS Calcd for $C_{33}H_{41}FN_6O_3$ (M+H)+589.3297, found 589.3285. HPLC purity 100%, $t_R$=10.95 min (R)-4-(2-(3-(3-((4-(1H-pyrazol-4-yl)benzyl)(cyclopropyl)carbamoyl)piperidin-1-yl)-5-fluorophenoxy)-2-methylpropanoyl)piperazin-1-ium chloride (74). $^1$H NMR (500 MHz, Methanol-$d_4$) δ 8.60 (s, 2H), 7.68 (d, J=7.9 Hz, 2H), 7.52-7.08 (m, 4H), 6.75 (d, J=10.0 Hz, 1H), 4.83 (d, J=15.1 Hz, 1H), 4.52 (d, J=15.2 Hz, 1H), 4.29-3.87 (m, 5H), 3.83-3.73 (m, 3H), 3.66-3.61 (m, 1H), 3.13 (d, J=84.7 Hz, 4H), 2.86 (tt, J=7.2, 4.0 Hz, 1H), 2.36-2.24 (m, 1H), 2.17 (ddq, J=27.9, 14.0, 4.3 Hz, 2H), 1.99-1.85 (m, 1H), 1.69 (d, J=2.0 Hz, 6H), 1.12-0.86 (m, 4H). $^{13}$C NMR (126 MHz, Methanol-$d_4$) δ 175.56, 171.03, 164.60, 164.58, 162.63, 162.59, 157.44, 157.42, 157.39, 157.29, 157.27, 144.67, 137.92, 130.68, 128.47, 127.94, 126.00, 123.80, 107.34, 107.05, 105.62, 105.42, 102.64, 102.43, 82.32, 57.50, 55.69, 49.54, 43.15, 42.66, 39.60, 37.24, 30.10, 24.90, 24.71, 24.23, 22.05, 9.32, 7.44. HRMS Calcd for $C_{33}H_{41}FN_6O_3$ $(M^+ Na)^+$ 611.3116, found 611.3116. HPLC purity 98.8%, $t_R$=11.06 min (R)-4-(2-(5-(3-((4-(1H-pyrazol-4-yl)benzyl)(cyclopropyl)carbamoyl)piperidin-1-yl)-2-fluorophenoxy)-2-methylpropanoyl)piperazin-1-ium chloride (75). $^1$H NMR (500 MHz, Methanol-$d_4$) δ 8.49 (s, 2H), 7.70-7.50 (m, 4H), 7.46 (dd, J=10.2, 8.9 Hz, 1H), 7.33 (d, J=7.9 Hz, 2H), 4.83 (s, 1H), 4.51 (d, J=15.1 Hz, 1H), 4.40-3.84 (m, 5H), 3.82-3.71 (m, 3H), 3.69-3.65 (m, 1H), 3.31-3.10 (m, 4H), 2.85 (tt, J=7.1, 4.0 Hz, 1H), 2.44-2.07 (m, 3H), 1.95 (s, 1H), 1.64 (d, J=5.4 Hz, 6H), 1.13-0.84 (m, 4H). $^{13}$C NMR (126 MHz, Methanol-$d_4$) δ 171.2, 156.2, 154.2, 143.3, 143.2, 138.3, 137.6, 130.7, 129.0, 127.9, 127.5, 126.2, 125.9, 123.6, 118.3, 118.1, 117.1, 117.0, 115.7, 84.0, 58.2, 56.1, 49.5, 43.2, 37.1, 30.0, 24.7, 24.6, 23.9, 21.9, 9.3, 7.3. HRMS Calcd for $C_{33}H_{41}FN_6O_3$ (M+H)+589.3297, found 589.3284. HPLC purity 98.5%, $t_R$=9.38 min (R)-4-(2-(3-(3-((4-(1H-pyrazol-4-yl)benzyl)(cyclopropyl)carbamoyl)piperidin-1-yl)-2-fluorophenoxy)-2-methylpropanoyl)piperazin-1-ium chloride (76). $^1$H NMR (500 MHz, Methanol-$d_4$) δ 8.67 (s, 2H), 7.71 (d, J=8.1 Hz, 2H), 7.64-7.56 (m, 1H), 7.37 (dd, J=11.2, 8.3 Hz, 3H), 7.17 (t, J=7.9 Hz, 1H), 4.91 (d, J=15.0 Hz, 1H), 4.52 (d, J=15.0 Hz, 1H), 4.03 (dd, J=126.6, 4.6 Hz, 8H), 3.78-3.70 (m, 1H), 3.17 (d, J=22.1 Hz, 4H), 2.86 (tt, J=6.9, 4.1 Hz, 1H), 2.21 (t, J=4.7 Hz, 4H), 1.67 (s, 6H), 1.10-0.89 (m, 4H). $^{13}$C NMR (126 MHz, Methanol-$d_4$) δ 176.7, 171.1, 147.9, 145.9, 143.94, 143.86, 138.0, 130.9, 130.8, 130.7, 128.3, 128.1, 127.4, 126.4, 126.1, 125.5, 125.5, 124.0, 121.0, 115.6, 83.4, 57.7, 55.2, 49.5, 43.1, 39.7, 36.0, 30.1, 24.78, 24.75, 23.3, 21.1, 9.3, 7.3. HRMS Calcd for $C_{33}H_{41}FN_6O_3$ $(M+H)^+$ 589.3297, found 589.3291. HPLC purity 98.8%, $t_R$=10.32 min (R)-4-(2-(3-(3-((4-(1H-pyrazol-4-yl)benzyl)(cyclopropyl)carbamoyl)piperidin-1-yl)-5-(trifluoromethyl)phenoxy)-2-methylpropanoyl)piperazin-1-ium chloride (77). $^1$H NMR (500 MHz, Methanol-$d_4$) δ 8.54 (s, 2H), 7.67 (d, J=7.9 Hz, 2H), 7.53 (s, 1H), 7.34 (d, J=7.9 Hz, 2H), 7.30 (s, 1H), 7.02 (s, 1H), 4.82 (s, 1H), 4.53 (d, J=15.1 Hz, 1H), 4.16-3.76 (m, 7H), 3.61-3.53 (m, 1H), 3.48-3.39 (m, 1H), 3.23-2.94 (m, 4H), 2.85 (qd, J=6.7, 4.2 Hz, 1H), 2.21-2.03 (m, 3H), 1.94-1.86 (m, 1H), 1.70 (d, J=2.1 Hz, 6H), 1.08-0.87 (m, 4H). $^{13}$C NMR (126 MHz, Methanol-$d_4$) δ 176.25, 171.29, 156.70, 147.17, 137.88, 133.03 (d, J=33.0 Hz), 130.69, 128.70, 127.96, 125.92, 124.37, 123.78, 122.21, 112.45, 109.70, 82.06, 55.68, 53.47, 49.45, 43.11, 42.68, 39.56, 37.79, 30.00, 25.02, 24.77, 24.66, 22.42, 9.10, 7.50. HRMS Calcd for $C_{34}H_{41}F_3N_6O_3$ $(M^+ Na)^+$ 639.3265, found 639.3251. HPLC purity 98.3%, $t_R$=12.13 min (R)-4-(2-(3-(3-((4-(1H-pyrazol-4-yl)benzyl)(cyclopropyl)carbamoyl)piperidin-1-yl)-5-chlorophenoxy)-2-methylpropanoyl)piperazin-1-ium 2,2,2-trifluoroacetate (78). $^1$H NMR (500 MHz, Methanol-$d_4$) δ 7.94 (s, 2H), 7.56-7.49 (m, 2H), 7.28-7.17 (m, 2H), 6.63 (t, J=1.9 Hz, 1H), 6.35 (t, J=2.2 Hz, 1H), 6.29 (t, J=1.9 Hz, 1H), 4.68 (d, J=14.9 Hz, 1H), 4.56 (d, J=14.9 Hz, 1H), 4.10 (s, 2H), 3.83 (s, 2H), 3.73-3.64 (m, 2H), 3.51 (tt, J=10.9, 3.6 Hz, 1H), 3.10 (s, 2H), 3.00-2.85 (m, 3H), 2.82-2.74 (m, 2H), 2.04-1.95 (m, 1H), 1.82 (ddd, J=8.5, 5.7, 2.8 Hz, 1H), 1.72-1.66 (m, 2H), 1.63 (d, J=2.3 Hz, 6H), 0.92-0.85 (m, 4H). $^{13}$C NMR (126 MHz, Methanol-$d_4$) δ 177.35, 171.97, 161.50 (d, J=34.7 Hz), 156.66, 152.95, 136.15, 135.32, 131.61, 130.63, 127.72, 126.04 (d, J=80.4 Hz), 125.36, 121.96, 116.73 (d, J=291.9 Hz), 109.38, 107.16, 102.57, 80.83, 51.44, 49.26, 48.92, 43.11, 42.70, 39.36, 29.84, 27.38, 24.95, 24.78, 23.69, 8.64, 8.08. HRMS Calcd for $C_{33}H_{41}ClN_6O_3$ $(M^+ Na)^+$ 627.2821, found 627.2819. HPLC purity 99.6%, $t_R$=11.77 min.

(R)-4-(2-(3-(3-((4-(1H-pyrazol-4-yl)benzyl)(cyclopropyl)carbamoyl)piperidin-1-yl)-5-cyanophenoxy)-2-methylpropanoyl)piperazin-1-ium 2,2,2-trifluoroacetate (79). $^1$H NMR (500 MHz, Methanol-$d_4$) δ 7.95 (s, 2H), 7.57-7.52 (m, 2H), 7.28-7.23 (m, 2H), 6.96 (dd, J=2.3, 1.2 Hz, 1H), 6.67 (t, J=2.3 Hz, 1H), 6.52 (dd, J=2.3, 1.1 Hz, 1H), 4.69 (d, J=14.9 Hz, 1H), 4.56 (d, J=14.9 Hz, 1H), 4.09 (s, 2H), 3.83 (s, 2H), 3.78-3.70 (m, 2H), 3.51 (tt, J=11.0, 3.6 Hz, 1H), 3.12 (s, 2H), 3.05-2.71 (m, 6H), 2.03 (d, J=10.1 Hz, 1H), 1.89-1.82 (m, 1H), 1.72-1.69 (m, 1H), 1.65 (d, J=3.9 Hz, 6H), 0.95-0.85 (m, 4H). $^{13}$C NMR (126 MHz, Methanol-$d_4$) δ 177.26, 171.74, 161.06 (d, J=35.9 Hz), 156.48, 152.74, 136.17, 131.56, 130.62, 127.73, 126.06 (d, J=85.7 Hz), 121.99, 118.35, 116.50 (d, J=290.8 Hz), 113.44, 112.51, 109.47, 108.21, 81.17, 50.96, 49.27, 48.47, 43.13, 42.66, 39.32, 29.84, 27.34, 24.89, 24.70, 23.65, 8.61, 8.02. HRMS Calcd for $C_{34}H_{41}N_7O_3$ (M+Na)+618.3163, found 618.3161. HPLC purity 97.1%, $t_R$=11.46 min.

(R)-4-(2-(5-(3-((4-(1H-pyrazol-4-yl)benzyl)(cyclopropyl)carbamoyl)piperidin-1-yl)-2-chlorophenoxy)-2-methylpropanoyl)piperazin-1-ium 2,2,2-trifluoroacetate (80). $^1$H NMR (500 MHz, Methanol-$d_4$) δ 8.01 (s, 2H), 7.58-7.54 (m, 2H), 7.40 (d, J=8.8 Hz, 1H), 7.28-7.24 (m, 2H), 6.91 (dd, J=8.8, 2.6 Hz, 1H), 6.70 (d, J=2.6 Hz, 1H), 4.69 (d, J=15.0 Hz, 1H), 4.58 (d, J=14.9 Hz, 1H), 3.98 (d, J=145.2 Hz, 4H), 3.72-3.61 (m, 3H), 3.20-2.93 (m, 6H), 2.80 (tt, J=6.0, 4.3 Hz, 1H), 2.06 (dt, J=12.4, 4.0 Hz, 1H), 1.96 (dt, J=13.1, 3.8 Hz, 1H), 1.89-1.74 (m, 2H), 1.68 (d, J=8.2 Hz, 6H), 0.98-0.86 (m, 4H). $^{13}$C NMR (126 MHz, Methanol-$d_4$) δ 176.77, 171.50, 160.13 (q, J=36.7, 36.3 Hz), 151.24, 147.93, 136.25, 131.30, 131.04, 130.60, 127.73, 126.15 (d, J=94.2 Hz), 125.43, 122.13, 119.42, 118.20, 117.13, 114.83, 112.53, 112.30, 107.11, 82.35, 54.18, 51.43, 49.37, 43.07, 42.72, 39.50, 38.87, 29.85, 26.01, 24.86, 24.76, 23.24, 8.67, 7.88. HRMS Calcd for $C_{33}H_{41}ClN_6O_3$ $(M^+ Na)^+$ 627.2821, found 627.2818. HPLC purity 99.7%, $t_R$=11.14 min.

(R)—N-(4-(1H-pyrazol-4-yl)benzyl)-1-(4-cyano-3-((2-methyl-1-oxo-1-(piperazin-1-yl) propan-2-yl)oxy)phenyl)-N-cyclopropylpiperidine-3-carboxamide 2,2,2-trifluoroacetate (81). $^1$H NMR (500 MHz, Methanol-$d_4$) δ 8.00 (s, 2H), 7.58-7.54 (m, 2H), 7.43 (d, J=8.9 Hz, 1H), 7.26 (d, J=8.2 Hz, 2H), 6.67 (dd, J=9.0, 2.2 Hz, 1H), 6.29 (d, J=2.2 Hz, 1H), 4.62 (s, 2H), 4.09 (d, J=23.3 Hz, 6H), 3.46 (tt, J=10.9, 3.7 Hz, 1H), 3.13-2.91 (m, 6H), 2.81-2.76 (m, 1H), 2.03 (dt, J=12.0, 3.7 Hz, 1H), 1.86-1.74 (m, 2H), 1.69 (d, J=17.2 Hz, 7H), 0.93-0.83 (m, 4H). $^{13}$C NMR (126 MHz, Methanol-$d_4$) δ 176.93, 171.39, 160.47 (q, J=37.4 Hz), 158.42, 154.42, 136.30, 134.68, 131.31, 130.62, 127.79, 126.09 (d, J=78.9 Hz), 125.43, 122.10, 119.63, 117.32, 117.00, 115.02, 108.18, 100.15, 90.17, 82.13, 49.92, 49.29, 43.05, 42.65, 39.45, 39.22, 29.82, 27.85, 27.40, 25.04, 24.54, 23.55, 8.49, 8.23. HRMS Calcd for $C_{34}H_{41}N_7O_3$ $(M^+ Na)^+$ 618.3163, found 618.3162. HPLC purity 99.8%, $t_R$=11.41 min.

Scheme 9. Synthesis of compound 82.
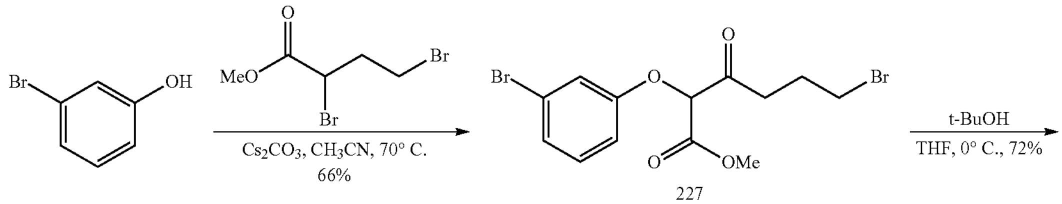
227
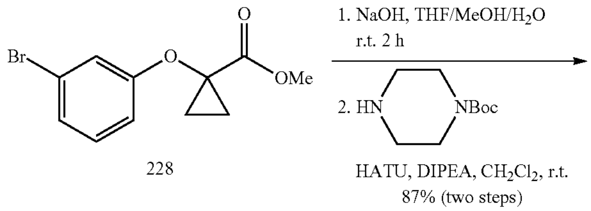
228
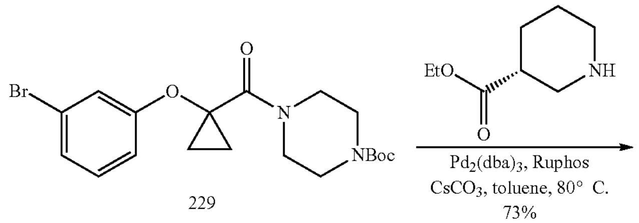
229
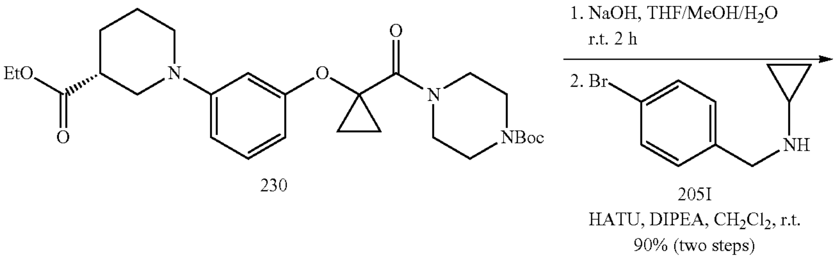
230
2051
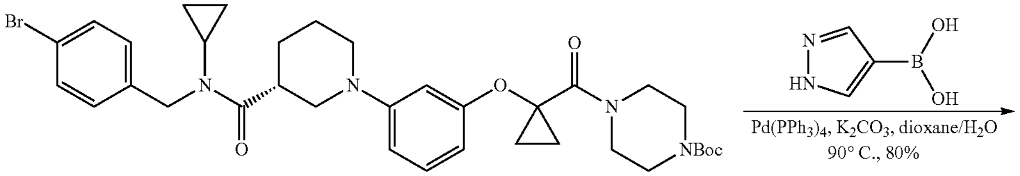
231
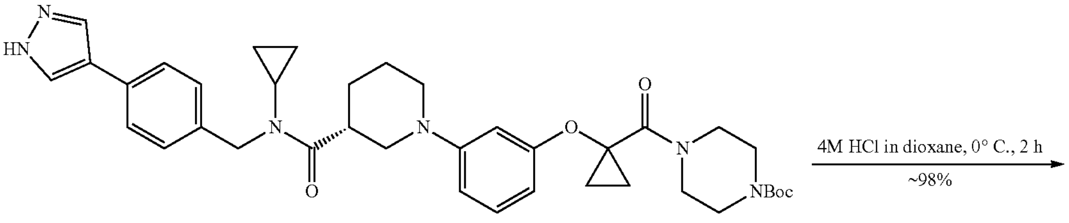
232

-continued

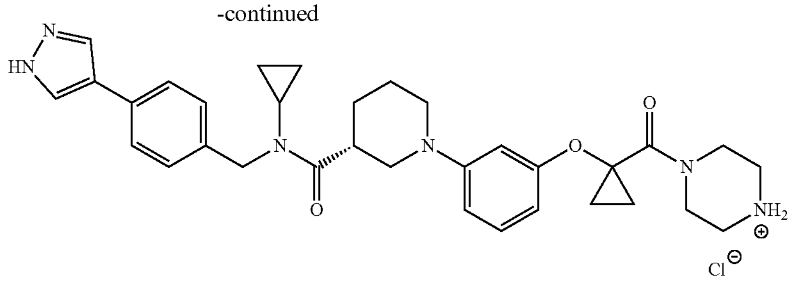

82 methyl 4-bromo-2-(3-bromophenoxy) butanoate (227). $^{1}H$ NMR (500 MHz, Chloroform-d) δ 7.22-7.05 (m, 3H), 6.84 (ddd, J=6.2, 5.0, 3.4 Hz, 1H), 4.86 (dt, J=8.7, 4.4 Hz, 1H), 3.73 (s, 3H), 3.62-3.50 (m, 2H), 2.56-2.37 (m, 2H). MS (ESI) m/z=375.0 $[M+Na]^{+}$ methyl 1-(3-bromophenoxy)cyclopropane-1-carboxylate (228). $^{1}H$ NMR (500 MHz, Chloroform-d) δ 7.15-7.09 (m, 2H), 7.09-7.00 (m, 1H), 6.85 (dt, J=7.0, 2.4 Hz, 1H), 3.72 (s, 3H), 1.67-1.57 (m, 2H), 1.35-1.22 (m, 2H). $^{13}C$ NMR (126 MHz, Chloroform-d) δ 172.21, 158.16, 130.45, 124.74, 122.65, 118.80, 114.14, 58.24, 52.67, 17.40. MS (ESI) m/z=271.0, 273.1 $[M+Na]^{+}$ tert-butyl 4-(1-(3-bromophenoxy)cyclopropane-1-carbonyl)piperazine-1-carboxylate (229). $^{1}H$ NMR (500 MHz, Chloroform-d) δ 7.17-7.06 (m, 3H), 6.98 (dt, J=7.3, 2.3 Hz, 1H), 3.78 (s, 2H), 3.48 (s, 2H), 3.31 (d, J=11.4 Hz, 4H), 1.43 (s, 11H), 1.15-1.05 (m, 2H). $^{13}C$ NMR (126 MHz, Chloroform-d) δ 168.17, 157.91, 154.45, 130.75, 125.00, 122.85, 118.91, 113.79, 80.21, 60.59, 45.73, 42.84, 28.35, 13.34. MS (ESI) m/z=447.1 $[M+Na]^{+}$ tert-butyl (R)-4-(1-(3-(3-(ethoxycarbonyl)piperidin-1-yl)phenoxy)cyclopropane-1-carbonyl)piperazine-1-carboxylate (230). $^{1}H$ NMR (500 MHz, Chloroform-d) δ 7.09 (t, J=8.1 Hz, 1H), 6.60-6.45 (m, 3H), 4.14 (q, J=7.1 Hz, 2H), 3.80 (s, 2H), 3.68 (ddt, J=12.6, 3.4, 1.5 Hz, 1H), 3.58-3.39 (m, 3H), 3.29 (d, J=18.0 Hz, 4H), 2.99 (dd, J=12.4, 9.8 Hz, 1H), 2.85-2.72 (m, 1H), 2.62 (tt, J=10.0, 4.0 Hz, 1H), 2.02-1.95 (m, 1H), 1.77 (tdd, J=8.5, 4.4, 2.1 Hz, 1H), 1.71-1.61 (m, 2H), 1.45-1.39 (m, 11H), 1.25 (t, J=7.1 Hz, 3H), 1.15-1.06 (m, 2H). $^{13}C$ NMR (126 MHz, Chloroform-d) δ 173.74, 168.88, 158.17, 154.49, 152.67, 129.90, 110.12, 105.88, 103.63, 80.09, 60.47, 60.13, 51.91, 49.47, 45.72, 42.82, 41.22, 28.36, 26.98, 23.97, 14.25, 13.37. MS (ESI) m/z=502.3 $[M+H]^{+}$ tert-butyl (R)-4-(1-(3-(3-((4-bromobenzyl)(cyclopropyl)carbamoyl)piperidin-1-yl)phenoxy)cyclopropane-1-carbonyl)piperazine-1-carboxylate (231). $^{1}H$ NMR (500 MHz, Chloroform-d) δ 7.39-7.30 (m, 2H), 7.10-6.96 (m, 3H), 6.56-6.39 (m, 3H), 4.55 (d, J=14.7 Hz, 1H), 4.43 (d, J=14.7 Hz, 1H), 3.76 (s, 2H), 3.68-3.56 (m, 2H), 3.50-3.31 (m, 3H), 3.24 (d, J=23.2 Hz, 4H), 2.95-2.84 (m, 1H), 2.69 (dt, J=12.0, 6.8 Hz, 1H), 2.57 (td, J=7.1, 6.1, 3.7 Hz, 1H), 1.90-1.59 (m, 4H), 1.38 (s, 11H), 1.05 (q, J=5.0, 4.5 Hz, 2H), 0.88-0.67 (m, 4H). MS (ESI) m/z=681.2 $[M+H]^{+}$ tert-butyl (R)-4-(1-(3-(3-((4-(1H-pyrazol-4-yl)benzyl)(cyclopropyl)carbamoyl) piperidin-1-yl)phenoxy)cyclopropane-1-carbonyl)piperazine-1-carboxylate (232). $^{1}H$ NMR (500 MHz, Chloroform-d) δ 7.78 (s, 2H), 7.41 (d, J=7.8 Hz, 2H), 7.20 (d, J=7.9 Hz, 2H), 7.09 (t, J=8.2 Hz, 1H), 6.61-6.41 (m, 3H), 4.69 (d, J=14.7 Hz, 1H), 4.51 (d, J=14.7 Hz, 1H), 3.80 (s, 2H), 3.74-3.62 (m, 2H), 3.44 (ddt, J=14.5, 7.5, 3.8 Hz, 3H), 3.29 (d, J=25.9 Hz, 4H), 3.06-2.90 (m, 1H), 2.75 (td, J=11.9, 2.8 Hz, 1H), 2.64 (qd, J=6.6, 4.3 Hz, 1H), 2.00-1.87 (m, 1H), 1.87-1.64 (m, 3H), 1.42 (s, 11H), 1.10 (q, J=4.8 Hz, 2H), 0.83 (dddd, J=24.3, 12.8, 5.5, 1.8 Hz, 4H). MS (ESI) m/z=669.4 $[M+H]^{+}$ (R)-4-(1-(3-(3-((4-(1H-pyrazol-4-yl)benzyl)(cyclopropyl)carbamoyl)piperidin-1-yl)phenoxy)cyclopropane-1-carbonyl) piperazin-1-ium chloride (82). $^{1}H$ NMR (500 MHz, Methanol-$d_4$) δ 8.60 (s, 2H), 7.68 (d, J=8.0 Hz, 2H), 7.59-7.46 (m, 3H), 7.34 (d, J=7.9 Hz, 2H), 7.29 (dd, J=8.4, 2.3 Hz, 1H), 4.86 (d, J=15.1 Hz, 1H), 4.50 (d, J=15.1 Hz, 1H), 4.30-3.68 (m, 9H), 3.19 (t, J=5.3 Hz, 4H), 2.86 (tt, J=7.1, 4.0 Hz, 1H), 2.38-2.08 (m, 3H), 2.04-1.85 (m, 1H), 1.60-1.50 (m, 2H), 1.27 (td, J=4.5, 2.2 Hz, 2H), 1.14-0.87 (m, 4H). $^{13}C$ NMR (126 MHz, Methanol-$d_4$) δ 175.53, 168.42, 158.29, 143.27, 137.90, 131.65, 130.68, 128.47, 128.00, 126.00, 123.84, 116.63, 114.62, 109.39, 60.64, 57.91, 56.07, 49.48, 43.16, 37.11, 30.03, 23.95, 21.91, 12.51, 12.50, 7.39. HRMS Calcd for $C_{33}H_{40}N_6O_3$ $(M+H)^{+}$ 569.3235, found 569.3231. HPLC purity 99.5%, $t_R$=9.01 min Scheme 10. Synthesis of compound 83.

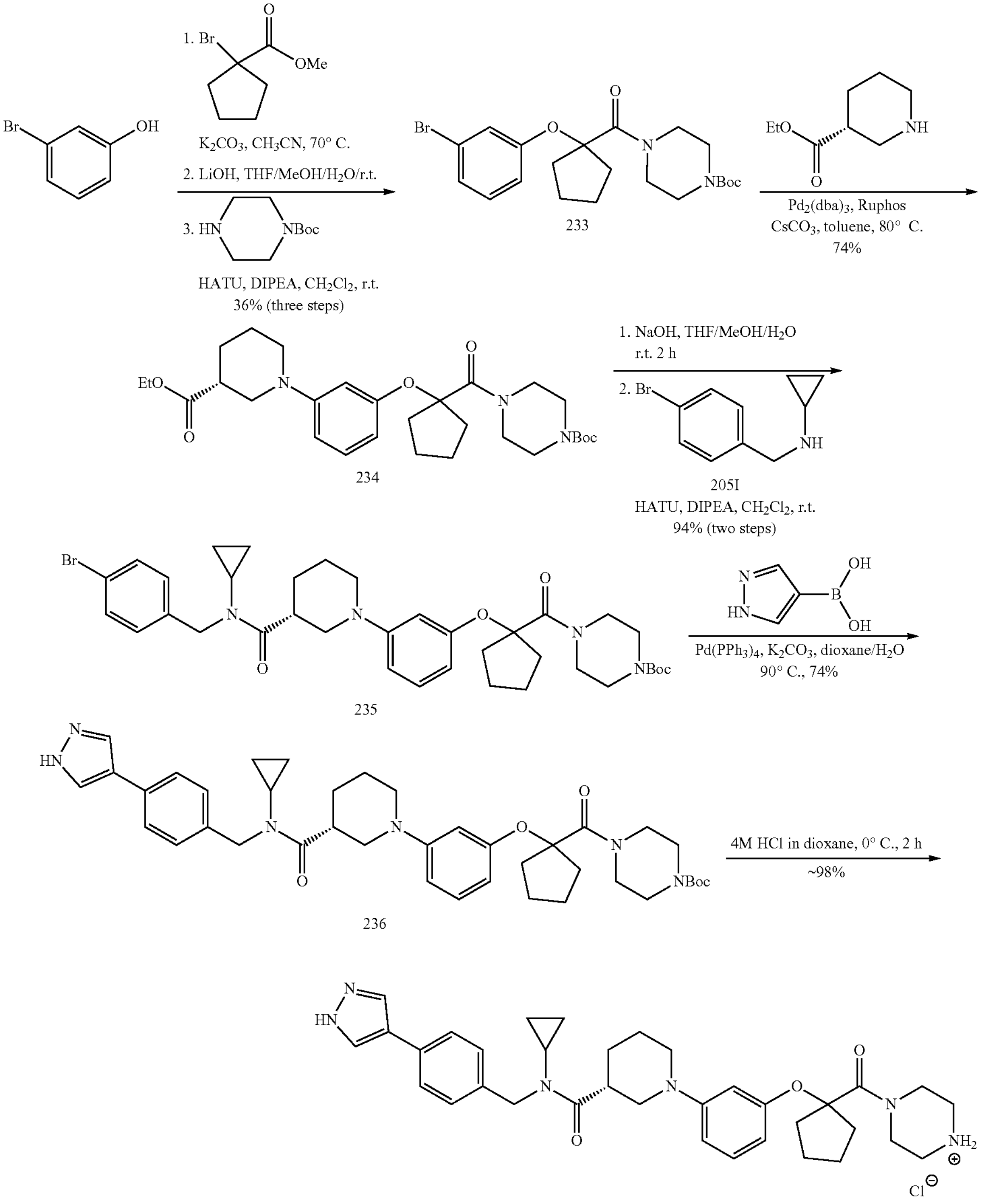

233

234

205I

235

236

83 tert-butyl 4-(1-(3-bromophenoxy)cyclopentane-1-carbonyl)piperazine-1-carboxylate (233). $^1H$ NMR (500 MHz, Chloroform-d) δ 7.04-6.98 (m, 2H), 6.97-6.92 (m, 1H), 6.69 (dt, J=6.9, 2.5 Hz, 1H), 3.65 (t, J=5.2 Hz, 2H), 3.50 (t, J=5.1 Hz, 2H), 3.23 (t, J=5.2 Hz, 2H), 3.11-2.94 (m, 2H), 2.46-2.32 (m, 2H), 2.11-1.97 (m, 2H), 1.78-1.60 (m, 4H), 1.36 (s, 9H). $^{13}C$ NMR (126 MHz, Chloroform-d) δ 171.09, 156.18, 154.25, 130.48, 124.36, 122.73, 119.98, 114.48, 90.63, 80.05, 45.77, 42.96, 37.12, 28.31, 24.72. MS (ESI) m/z=475.1, 477.2 $[M+Na]^+$ tert-butyl (R)-4-(1-(3-(3-(ethoxycarbonyl)piperidin-1-yl)phenoxy)cyclopentane-1-carbonyl)piperazine-1-carboxylate (234). $^1H$ NMR (500 MHz, Chloroform-d) δ 7.05 (t, J=8.2 Hz, 1H), 6.56-6.47 (m, 1H), 6.40 (t, J=2.4 Hz, 1H), 6.28 (ddd, J=8.2, 2.4, 0.7 Hz, 1H), 4.20-4.12 (m, 2H), 3.74 (t, J=5.1 Hz, 2H), 3.68 (ddd, J=12.5, 3.6, 1.7 Hz, 1H), 3.55 (t, J=5.2 Hz, 2H), 3.44 (dt, J=12.5, 3.9 Hz, 1H), 3.27 (t, J=5.2 Hz, 2H), 3.16-3.05 (m, 2H), 2.97 (dd, J=12.4, 9.9 Hz, 1H), 2.84-2.72 (m, 1H), 2.63 (tt, J=10.0, 4.0 Hz, 1H), 2.49-2.38 (m, 2H), 2.18-2.08 (m, 2H), 2.03-1.98 (m, 1H), 1.84-1.75 (m, 3H), 1.75-1.69 (m, 2H), 1.68-1.63 (m, 2H), 1.42 (s, 9H), 1.31-1.25 (m, 3H). MS (ESI) m/z=530.4 $[M+H]^+$ tert-butyl (R)-4-(1-(3-(3-((4-bromobenzyl)(cyclopropyl) carbamoyl)piperidin-1-yl)phenoxy)cyclopentane-1-carbonyl)piperazine-1-carboxylate (235). $^1$H NMR (500 MHz, Chloroform-d) δ 7.46-7.41 (m, 2H), 7.11 (dd, J=8.6, 2.6 Hz, 2H), 7.05 (t, J=8.2 Hz, 1H), 6.49 (dd, J=8.3, 2.2 Hz, 1H), 6.39 (t, J=2.4 Hz, 1H), 6.27 (dd, J=8.1, 2.3 Hz, 1H), 4.63-4.46 (m, 2H), 3.72 (d, J=5.2 Hz, 2H), 3.64 (d, J=12.3 Hz, 2H), 3.52 (s, 2H), 3.40 (tt, J=10.9, 3.6 Hz, 1H), 3.32-3.18 (m, 2H), 3.08 (d, J=5.3 Hz, 2H), 2.94 (t, J=11.6 Hz, 1H), 2.73 (td, J=12.0, 2.9 Hz, 1H), 2.66-2.57 (m, 1H), 2.48-2.36 (m, 2H), 2.16-2.06 (m, 2H), 1.91 (s, 1H), 1.85-1.64 (m, 7H), 1.41 (s, 9H), 0.88-0.75 (m, 4H). MS (ESI) m/z=709.3, 711.3 $[M+H]^+$ tert-butyl (R)-4-(1-(3-(3-((4-(1H-pyrazol-4-yl)benzyl) (cyclopropyl)carbamoyl) piperidin-1-yl)phenoxy)cyclopentane-1-carbonyl)piperazine-1-carboxylate (236). $^1$H NMR (500 MHz, Chloroform-d) δ 7.78 (s, 2H), 7.42 (d, J=7.8 Hz, 2H), 7.20 (d, J=7.9 Hz, 2H), 7.04 (t, J=8.2 Hz, 1H), 6.50 (dd, J=8.3, 2.2 Hz, 1H), 6.40 (t, J=2.3 Hz, 1H), 6.26 (dd, J=8.1, 2.3 Hz, 1H), 4.69 (d, J=14.7 Hz, 1H), 4.51 (d, J=14.7 Hz, 1H), 3.79-3.60 (m, 4H), 3.60-3.39 (m, 3H), 3.25 (t, J=5.3 Hz, 2H), 3.09 (q, J=5.1, 4.3 Hz, 2H), 3.03-2.92 (m, 1H), 2.81-2.59 (m, 2H), 2.41 (dq, J=14.9, 7.3 Hz, 2H), 2.15-2.05 (m, 2H), 2.00-1.89 (m, 1H), 1.85-1.62 (m, 7H), 1.40 (s, 9H), 0.84 (dtq, J=19.0, 8.4, 4.3, 3.0 Hz, 4H). MS (ESI) m/z=697.4 $[M+H]^+$, 695.3 $[M-H]^-$ (R)-4-(1-(3-(3-((4-(1/1-pyrazol-4-yl)benzyl)(cyclopropyl)carbamoyl)piperidin-1-yl)phenoxy)cyclopentane-1-carbonyl) piperazin-1-ium chloride (83). $^1$H NMR (500 MHz, Methanol-$d_4$) δ 8.34 (s, 2H), 7.63 (d, J=8.1 Hz, 2H), 7.52 (t, J=8.3 Hz, 1H), 7.43 (dd, J=8.3, 2.1 Hz, 1H), 7.36-7.28 (m, 3H), 7.00 (dd, J=8.4, 2.3 Hz, 1H), 4.85 (s, 1H), 4.48 (d, J=15.0 Hz, 1H), 4.14 (d, J=60.1 Hz, 3H), 3.85-3.65 (m, 6H), 3.04 (d, J=70.0 Hz, 4H), 2.85 (tt, J=6.9, 4.1 Hz, 1H), 2.52 (ddt, J=20.6, 14.0, 7.3 Hz, 2H), 2.31-2.14 (m, 5H), 1.95 (t, J=10.5 Hz, 1H), 1.86-1.73 (m, 4H), 1.11-0.87 (m, 4H). $^{13}$C NMR (126 MHz, Methanol-$d_4$) δ 175.60, 171.23, 156.53, 143.49, 137.07, 132.43, 132.41, 131.71, 131.63, 131.49, 130.69, 129.77, 128.66, 128.57, 127.90, 127.29, 125.75, 123.10, 117.10, 114.00, 110.43, 91.07, 57.97, 55.93, 49.49, 43.24, 43.16, 42.64, 39.48, 36.94, 36.79, 29.98, 24.47, 23.89, 21.86, 9.33, 7.33. HRMS Calcd for $C_{35}H_{44}N_6O_3$ $(M+H)^+$ 597.3548, found 597.3545. HPLC purity 99.6%, $t_R$=9.79 min Scheme 11. Synthesis of compound 84.

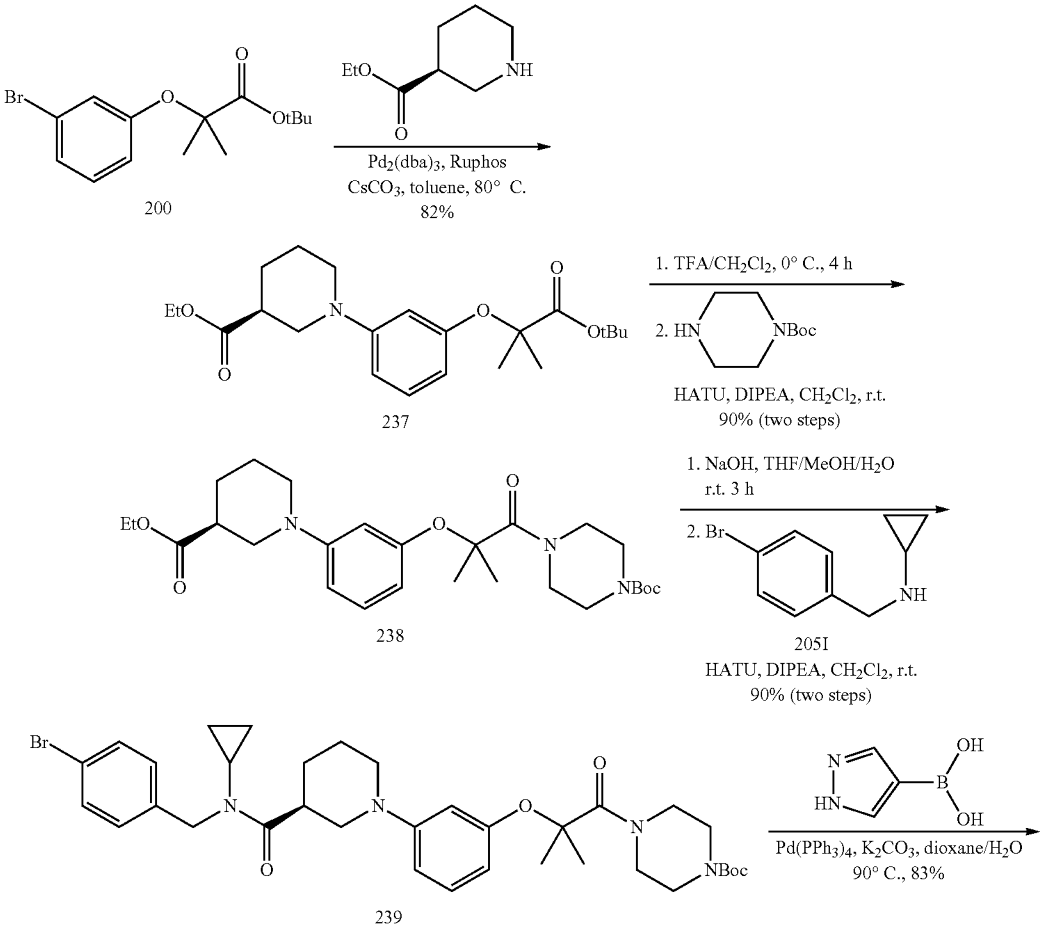

-continued

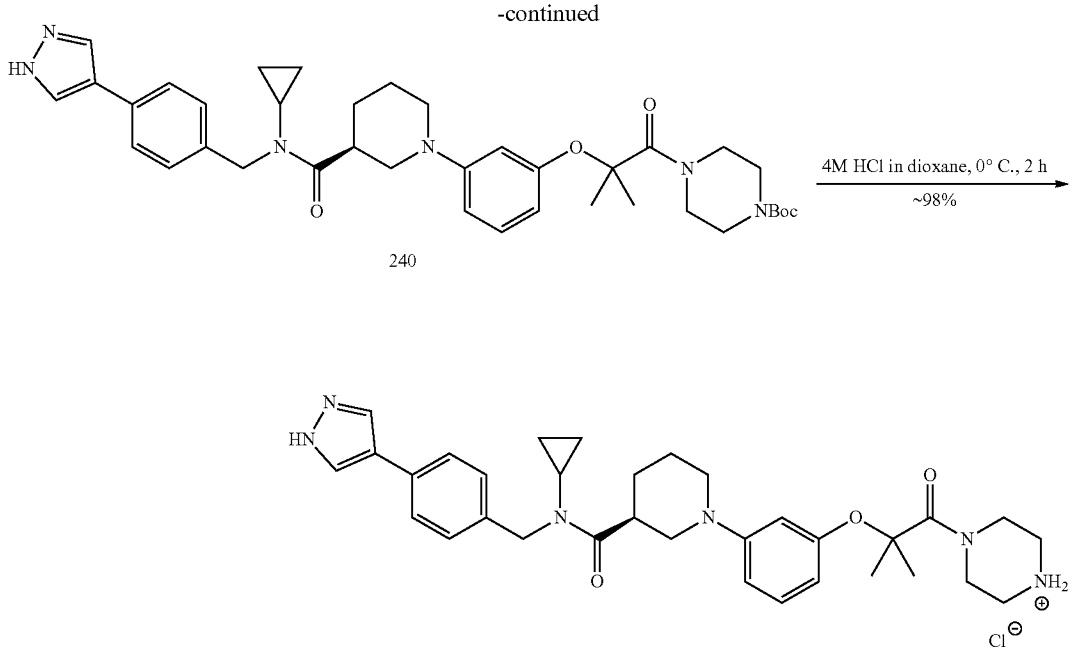

240

84 ethyl(S)-1-(3-((1-(tert-butoxy)-2-methyl-1-oxopropan-2-yl)oxy)phenyl)piperidine-3-carboxylate (237). $^1$H NMR (500 MHz, Chloroform-d) δ 7.07 (t, J=8.2 Hz, 1H), 6.57 (ddd, J=8.3, 2.4, 0.8 Hz, 1H), 6.48 (t, J=2.4 Hz, 1H), 6.30 (ddd, J=8.1, 2.3, 0.8 Hz, 1H), 4.20-4.11 (m, 2H), 3.70 (ddt, J=12.3, 3.5, 1.5 Hz, 1H), 3.51-3.42 (m, 1H), 2.97 (dd, J=12.4, 10.0 Hz, 1H), 2.77 (tdd, J=10.2, 4.5, 3.1 Hz, 1H), 2.66-2.56 (m, 1H), 2.06-1.95 (m, 1H), 1.82-1.72 (m, 1H), 1.72-1.62 (m, 2H), 1.55 (s, 6H), 1.44 (s, 9H), 1.27 (t, J=7.1 Hz, 3H). $^{13}$C NMR (126 MHz, Chloroform-d) δ 173.84, 173.52, 156.65, 152.50, 129.10, 110.43, 109.33, 107.63, 81.51, 79.21, 60.47, 52.06, 49.69, 41.41, 27.82, 27.00, 25.51, 25.44, 24.14, 14.26. MS (ESI) m/z=392.2 [M+H]$^+$ tert-butyl (S)-4-(2-(3-(3-(ethoxycarbonyl)piperidin-1-yl) phenoxy)-2-methylpropanoyl)piperazine-1-carboxylate (238). $^1$H NMR (500 MHz, Chloroform-d) δ 7.04 (t, J=8.2 Hz, 1H), 6.54 (dd, J=8.2, 2.3 Hz, 1H), 6.40 (t, J=2.3 Hz, 1H), 6.29-6.21 (m, 1H), 4.14 (q, J=7.1 Hz, 2H), 3.80 (t, J=5.1 Hz, 2H), 3.66 (ddt, J=12.4, 3.5, 1.5 Hz, 1H), 3.58 (d, J=5.3 Hz, 2H), 3.46-3.37 (m, 1H), 3.32 (d, J=5.4 Hz, 2H), 3.06 (t, J=5.2 Hz, 2H), 2.97 (dd, J=12.4, 9.9 Hz, 1H), 2.82-2.68 (m, 1H), 2.61 (tq, J=12.2, 4.3 Hz, 1H), 2.05-1.94 (m, 1H), 1.77 (dddd, J=10.5, 9.1, 5.3, 3.5 Hz, 1H), 1.61 (s, 8H), 1.40 (s, 9H), 1.25 (t, J=7.1 Hz, 3H). $^{13}$C NMR (126 MHz, Chloroform-d) δ 173.71, 172.08, 156.17, 154.34, 152.74, 129.58, 110.12, 107.29, 105.64, 80.54, 80.05, 60.49, 51.89, 49.49, 45.75, 42.89, 41.27, 28.34, 26.94, 26.17, 26.15, 24.05, 14.25. MS (ESI) m/z=504.3 [M+H]$^+$ tert-butyl (S)-4-(2-(3-(3-((4-bromobenzyl)(cyclopropyl) carbamoyl)piperidin-1-yl)phenoxy)-2-methylpropanoyl) piperazine-1-carboxylate (239). $^1$H NMR (500 MHz, Chloroform-d) δ 7.42-7.34 (m, 2H), 7.08 (d, J=8.4 Hz, 2H), 7.02 (t, J=8.2 Hz, 1H), 6.48 (dd, J=8.5, 2.3 Hz, 1H), 6.37 (t, J=2.4 Hz, 1H), 6.23 (dd, J=8.2, 2.3 Hz, 1H), 4.58 (d, J=14.7 Hz, 1H), 4.44 (d, J=14.7 Hz, 1H), 3.77 (d, J=7.2 Hz, 2H), 3.61 (d, J=12.5 Hz, 2H), 3.57-3.46 (m, 2H), 3.37 (tt, J=10.9, 3.5 Hz, 1H), 3.31 (s, 2H), 3.07-2.96 (m, 2H), 2.96-2.84 (m, 1H), 2.69 (dd, J=12.0, 3.0 Hz, 1H), 2.56 (td, J=6.6, 3.2 Hz, 1H), 1.89 (d, J=10.9 Hz, 1H), 1.77 (ddd, J=11.6, 7.3, 4.2 Hz, 1H), 1.74-1.65 (m, 2H), 1.58 (d, J=1.4 Hz, 6H), 1.37 (s, 9H), 0.90-0.72 (m, 4H). $^{13}$C NMR (126 MHz, Chloroform-d) δ 176.78, 172.02, 156.21, 154.30, 152.62, 137.47, 131.61, 129.64, 129.47, 120.93, 109.72, 107.17, 105.49, 80.50, 80.06, 52.03, 49.76, 49.33, 45.75, 42.87, 39.77, 38.58, 29.78, 28.33, 27.73, 26.15, 24.39, 9.45, 9.06. MS (ESI) m/z=683.4, 685.3 [M+H]$^+$ tert-butyl (S)-4-(2-(3-(3-((4-(1/1-pyrazol-4-yl)benzyl) (cyclopropyl)carbamoyl) piperidin-1-yl)phenoxy)-2-methylpropanoyl)piperazine-1-carboxylate (240). $^1$H NMR (500 MHz, Chloroform-d) δ 7.80 (s, 2H), 7.49-7.38 (m, 2H), 7.22 (d, J=8.0 Hz, 2H), 7.05 (t, J=8.2 Hz, 1H), 6.53 (dd, J=8.3, 2.2 Hz, 1H), 6.42 (t, J=2.4 Hz, 1H), 6.27 (dd, J=8.2, 2.3 Hz, 1H), 4.69 (d, J=14.7 Hz, 1H), 4.53 (d, J=14.7 Hz, 1H), 3.88-3.73 (m, 2H), 3.73-3.64 (m, 2H), 3.64-3.50 (m, 2H), 3.44 (ddt, J=11.0, 7.0, 3.5 Hz, 1H), 3.32 (s, 2H), 3.14-2.95 (m, 3H), 2.76 (td, J=12.1, 2.8 Hz, 1H), 2.63 (tt, J=6.8, 3.2 Hz, 1H), 1.95 (d, J=10.9 Hz, 1H), 1.85-1.71 (m, 3H), 1.62 (s, 6H), 1.41 (s, 9H), 0.92-0.78 (m, 4H). MS (ESI) m/z=671.4 [M+H]$^+$, 669.4 [M−H]$^-$ (S)-4-(2-(3-(3-((4-(1H-pyrazol-4-yl)benzyl)(cyclopropyl) carbamoyl)piperidin-1-yl)phenoxy)-2-methylpropanoyl) piperazin-1-ium chloride (84). $^1$H NMR (500 MHz, Methanol-d$_4$) δ 8.52 (s, 2H), 7.66 (d, J=8.0 Hz, 2H), 7.55 (t, J=8.2 Hz, 1H), 7.50 (dd, J=8.1, 2.1 Hz, 1H), 7.40 (s, 1H), 7.33 (d, J=7.9 Hz, 2H), 7.03 (dd, J=8.4, 2.3 Hz, 1H), 4.85 (d, J=15.1 Hz, 1H), 4.50 (d, J=15.1 Hz, 1H), 4.36-3.85 (m, 5H), 3.82-3.67 (m, 4H), 3.28-2.75 (m, 5H), 2.40-2.08 (m, 3H), 1.95 (d, J=12.2 Hz, 1H), 1.68 (d, J=2.1 Hz, 6H), 1.15-0.84 (m, 4H). $^{13}$C NMR (126 MHz, Methanol-d$_4$) δ 171.42, 156.26, 143.43, 137.66, 131.53, 130.70, 128.91, 127.94, 125.92, 123.59, 118.49, 114.55, 111.65, 81.78, 58.00, 56.04, 49.52, 43.13, 42.67, 39.58, 37.07, 30.05, 24.97, 24.78, 23.92, 21.88, 9.33, 7.35. HRMS Calcd for $C_{33}H_{42}N_6O_3$ (M+H)$^+$ 571.3391, found 571.3389. HPLC purity 98.8%, $t_R$=9.34 min Scheme 12. Synthesis of compound 85.

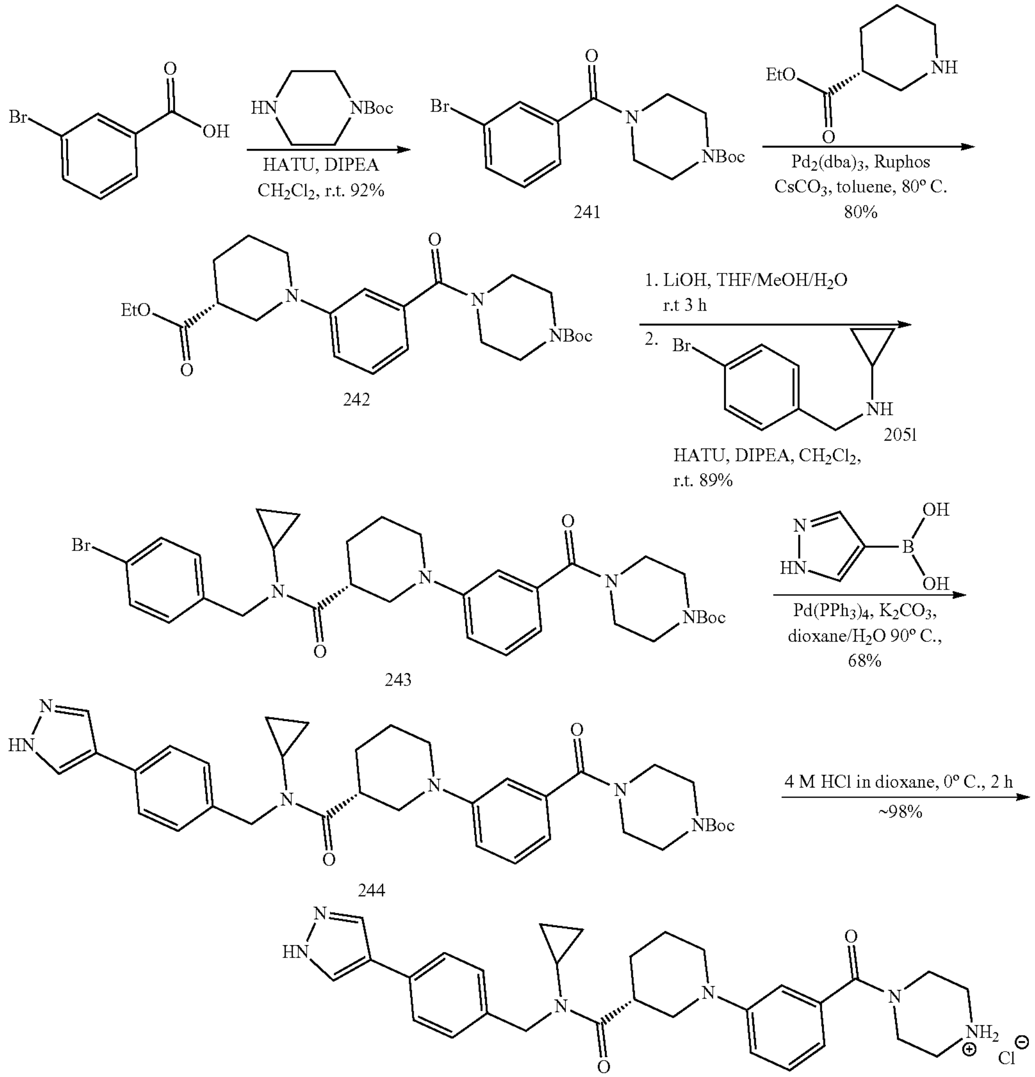

85 tert-butyl 4-(3-bromobenzoyl)piperazine-1-carboxylate (241). $^1$H NMR (500 MHz, Chloroform-d) δ 7.60-7.51 (m, 2H), 7.35-7.27 (m, 2H), 3.82-3.26 (m, 8H), 1.47 (s, 9H).

tert-butyl (R)-4-(3-(3-(ethoxycarbonyl)piperidin-1-yl) benzoyl)piperazine-1-carboxylate (242). $^1$H NMR (500 MHz, Chloroform-d) δ 7.23-7.12 (m, 1H), 6.92 (ddd, J=8.4, 2.6, 0.9 Hz, 1H), 6.88 (dd, J=2.5, 1.4 Hz, 1H), 6.72 (dt, J=7.4, 1.2 Hz, 1H), 4.09 (q, J=7.1 Hz, 2H), 3.65 (ddt, J=12.4, 3.5, 1.5 Hz, 3H), 3.49-3.22 (m, 7H), 2.99 (dd, J=12.4, 9.8 Hz, 1H), 2.83-2.75 (m, 1H), 2.58 (tt, J=9.8, 3.9 Hz, 1H), 2.00-1.92 (m, 1H), 1.74 (dqt, J=8.2, 3.7, 2.0 Hz, 1H), 1.64-1.56 (m, 2H), 1.40 (s, 9H), 1.20 (t, J=7.1 Hz, 3H). MS (ESI) m/z=446.3 $[M+H]^+$, 468.3 $[M+Na]^+$ tert-butyl (R)-4-(3-(3-((4-bromobenzyl)(cyclopropyl)carbamoyl)piperidin-1-yl)benzoyl)piperazine-1-carboxylate (243). $^1$H NMR (500 MHz, Chloroform-d) δ 7.41-7.32 (m, 2H), 7.19 (d, J=4.8 Hz, 1H), 7.09-7.00 (m, 2H), 6.93-6.81 (m, 2H), 6.71 (d, J=7.4 Hz, 1H), 4.60 (d, J=14.7 Hz, 1H), 4.36 (d, J=14.7 Hz, 1H), 3.75-3.52 (m, 4H), 3.52-3.20 (m, 7H), 3.02-2.92 (m, 1H), 2.81-2.64 (m, 1H), 2.51 (tt, J=7.0, 4.0 Hz, 1H), 1.88 (d, J=9.3 Hz, 1H), 1.82-1.73 (m, 1H), 1.66 (tt, J=9.8, 2.4 Hz, 2H), 1.40 (s, 9H), 0.86-0.69 (m, 4H).

tert-butyl (R)-4-(3-(3-((4-(1/1-pyrazol-4-yl)benzyl)(cyclopropyl)carbamoyl) piperidin-1-yl)benzoyl)piperazine-1-carboxylate (244). $^1$H NMR (500 MHz, Chloroform-d) δ 7.71 (s, 2H), 7.39-7.31 (m, 2H), 7.22-7.09 (m, 3H), 6.95-6.84 (m, 2H), 6.71 (dt, J=7.4, 1.1 Hz, 1H), 4.64 (d, J=14.7 Hz, 1H), 4.43 (d, J=14.7 Hz, 1H), 3.65 (t, J=13.2 Hz, 4H), 3.50-3.15 (m, 7H), 3.00 (dd, J=12.4, 10.9 Hz, 1H), 2.75 (td, J=12.2, 2.8 Hz, 1H), 2.54 (ddt, J=10.5, 6.8, 4.0 Hz, 1H), 1.92-1.83 (m, 1H), 1.78-1.58 (m, 3H), 1.39 (s, 9H), 0.86-0.71 (m, 4H). MS (ESI) m/z=613.4 $[M+H]^+$, 611.4 $[M-H]^-$ (R)-4-(3-(3-((4-(1H-pyrazol-4-yl)benzyl)(cyclopropyl) carbamoyl)piperidin-1-yl)benzoyl) piperazin-1-ium chloride (85). $^1$H NMR (500 MHz, Methanol-$d_4$) δ 8.66 (s, 2H), 8.06 (s, 1H), 8.01-7.92 (m, 1H), 7.77-7.66 (m, 4H), 7.35 (d, J=7.9 Hz, 2H), 4.86 (d, J=15.2 Hz, 1H), 4.52 (d, J=15.1 Hz, 1H), 4.27 (s, 1H), 3.96-3.65 (m, 8H), 3.36 (d, J=6.5 Hz, 4H), 2.87 (tt, J=7.1, 4.0 Hz, 1H), 2.39-2.15 (m, 3H), 2.04-1.89 (m, 1H), 1.13-0.89 (m, 4H). $^{13}$C NMR (126 MHz, Methanol-$d_4$)

δ 168.89, 142.31, 138.14, 136.61, 131.00, 130.69, 129.00, 128.15, 128.03, 126.04, 124.09, 123.14, 120.69, 72.16, 71.04, 62.92, 60.78, 57.92, 56.00, 49.47, 42.96, 42.42, 37.11, 30.03, 23.91, 21.88, 9.31, 7.38. HRMS Calcd for $C_{30}H_{36}N_6O_2$ $(M^+ Na)^+$ 535.2792, found 535.2790. HPLC purity 98.8%, $t_R$=8.07 min.
Scheme 13. Synthesis of compound 86 and 87.
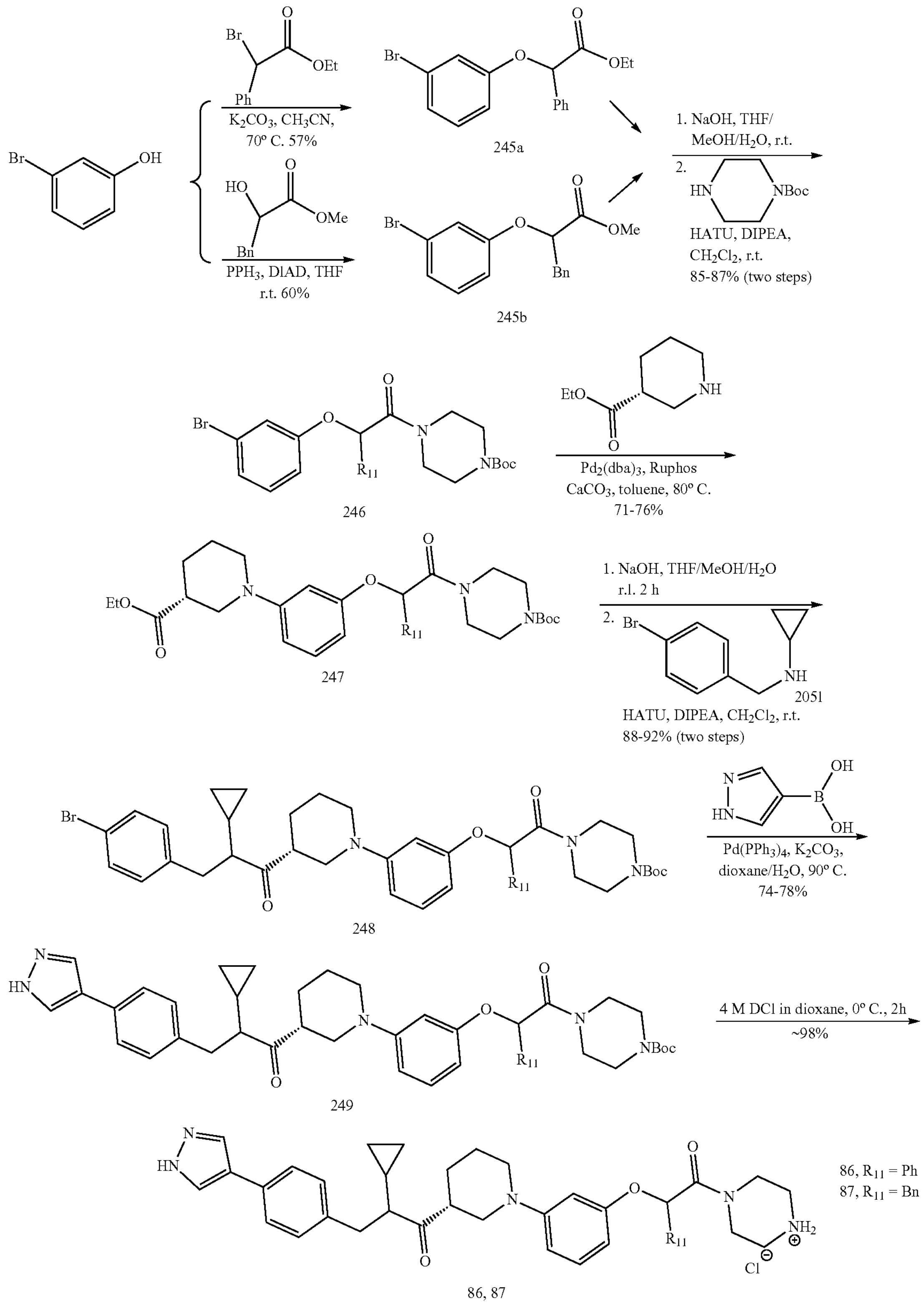

ethyl 2-(3-bromophenoxy)-2-phenylacetate (245a). $^1$H NMR (500 MHz, Chloroform-d) δ 7.58-7.53 (m, 2H), 7.45-7.36 (m, 3H), 7.18-7.07 (m, 3H), 6.89 (dt, J=6.8, 2.6 Hz, 1H), 5.60 (s, 1H), 4.29-4.12 (m, 2H), 1.22 (t, J=7.1 Hz, 3H). MS (ESI) m/z=335.0, 337.1 [M+H]$^+$ methyl 2-(3-bromophenoxy)-3-phenylpropanoate (245b). $^1$H NMR (500 MHz, Chloroform-d) δ 7.28-7.12 (m, 5H), 7.05-6.94 (m, 2H), 6.94-6.87 (m, 1H), 6.65 (pd, J=4.1, 2.4 Hz, 1H), 4.70 (t, J=6.4 Hz, 1H), 3.62 (s, 3H), 3.15 (d, J=6.4 Hz, 2H). MS (ESI) m/z=335.0, 337.0 [M+H]$^+$ tert-butyl 4-(2-(3-bromophenoxy)-2-phenylacetyl)piperazine-1-carboxylate (246a). $^1$H NMR (500 MHz, Chloroform-d) δ 7.43 (dt, J=8.2, 1.1 Hz, 2H), 7.37-7.31 (m, 2H), 7.31-7.23 (m, 1H), 7.16-7.11 (m, 1H), 7.11 (s, 2H), 6.90 (dt, J=7.4, 2.3 Hz, 1H), 5.84 (s, 1H), 3.53-3.12 (m, 6H), 2.98 (t, J=5.2 Hz, 2H), 1.34 (s, 9H). MS (ESI) m/z=475.1, 477.1 [M+H]$^+$ tert-butyl 4-(2-(3-bromophenoxy)-3-phenylpropanoyl)piperazine-1-carboxylate (246b). $^1$H NMR (500 MHz, Chloroform-d) δ 7.28-7.13 (m, 5H), 7.08-7.00 (m, 2H), 6.96-6.86 (m, 1H), 6.72 (dt, J=7.0, 2.4 Hz, 1H), 4.95 (t, J=6.6 Hz, 1H), 3.57-3.09 (m, 9H), 2.84 (ddd, J=13.3, 7.0, 3.6 Hz, 1H), 1.37 (s, 9H). MS (ESI) m/z=489.1, 491.1 [M+H]$^+$ tert-butyl 4-(2-(3-((R)-3-(ethoxycarbonyl)piperidin-1-yl)phenoxy)-2-phenylacetyl)piperazine-1-carboxylate (247a). $^1$H NMR (500 MHz, Chloroform-d) δ 7.54 (dd, J=7.3, 1.8 Hz, 2H), 7.44-7.37 (m, 2H), 7.36-7.30 (m, 1H), 7.15 (t, J=8.2 Hz, 1H), 6.66-6.56 (m, 2H), 6.50 (dd, J=8.2, 2.3 Hz, 1H), 5.93 (s, 1H), 4.17 (q, J=7.1 Hz, 2H), 3.72 (ddd, J=12.4, 3.7, 1.5 Hz, 1H), 3.61-3.22 (m, 7H), 3.03 (ddd, J=12.2, 8.2, 2.1 Hz, 3H), 2.88-2.76 (m, 1H), 2.69-2.56 (m, 1H), 2.03 (d, J=3.9 Hz, 1H), 1.84-1.75 (m, 1H), 1.73-1.63 (m, 2H), 1.41 (s, 9H), 1.27 (t, J=7.1 Hz, 3H). MS (ESI) m/z=552.3 [M+H]$^+$ tert-butyl 4-(2-(3-((R)-3-(ethoxycarbonyl)piperidin-1-yl)phenoxy)-3-phenylpropanoyl)piperazine-1-carboxylate (247b). $^1$H NMR (500 MHz, Chloroform-d) δ 7.25-7.19 (m, 4H), 7.18-7.09 (m, 1H), 7.02 (t, J=8.2 Hz, 1H), 6.48 (dt, J=8.3, 1.5 Hz, 1H), 6.37 (t, J=2.4 Hz, 1H), 6.23 (dd, J=8.1, 2.3 Hz, 1H), 4.96 (t, J=6.6 Hz, 1H), 4.08 (qd, J=7.1, 0.8 Hz, 2H), 3.58 (dddd, J=16.6, 12.1, 6.4, 3.3 Hz, 2H), 3.49-3.21 (m, 5H), 3.21-3.02 (m, 4H), 2.92 (dd, J=12.4, 9.8 Hz, 1H), 2.82-2.66 (m, 2H), 2.54 (tdd, J=7.2, 5.1, 2.2 Hz, 1H), 1.96-1.90 (m, 1H), 1.75-1.64 (m, 1H), 1.64-1.53 (m, 2H), 1.35 (s, 9H), 1.21-1.17 (m, 3H). MS (ESI) m/z=566.3 [M+H]$^+$ tert-butyl 4-(2-(3-((R)-3-((4-bromobenzyl)(cyclopropyl)carbamoyl)piperidin-1-yl)phenoxy)-2-phenylacetyl)piperazine-1-carboxylate (248a). $^1$H NMR (500 MHz, Chloroform-d) δ 7.51 (ddt, J=8.3, 1.5, 0.9 Hz, 2H), 7.44-7.34 (m, 4H), 7.34-7.29 (m, 1H), 7.18-7.01 (m, 3H), 6.61 (d, J=2.4 Hz, 1H), 6.56 (dd, J=8.3, 2.2 Hz, 1H), 6.47 (dd, J=8.1, 2.2 Hz, 1H), 5.90 (d, J=4.5 Hz, 1H), 4.63 (dd, J=14.7, 5.9 Hz, 1H), 4.43 (dd, J=14.7, 6.4 Hz, 1H), 3.68 (t, J=12.9 Hz, 2H), 3.53 (q, J=6.9, 5.4 Hz, 3H), 3.46-3.18 (m, 4H), 3.07-2.94 (m, 3H), 2.75 (s, 1H), 2.58 (tdd, J=10.5, 6.9, 4.9 Hz, 1H), 1.91 (s, 1H), 1.85-1.76 (m, 1H), 1.76-1.63 (m, 2H), 1.38 (s, 9H), 0.93-0.71 (m, 4H). MS (ESI) m/z=731.3, 733.3 [M+H]$^+$ tert-butyl 4-(2-(3-((R)-3-((4-bromobenzyl)(cyclopropyl)carbamoyl)piperidin-1-yl)phenoxy)-3-phenylpropanoyl)piperazine-1-carboxylate (248b). $^1$H NMR (500 MHz, Chloroform-d) δ 7.41-7.31 (m, 2H), 7.27-7.21 (m, 4H), 7.19-7.14 (m, 1H), 7.07-6.95 (m, 3H), 6.52-6.42 (m, 1H), 6.37 (d, J=2.7 Hz, 1H), 6.22 (dd, J=8.3, 2.2 Hz, 1H), 4.95 (q, J=6.2 Hz, 1H), 4.59 (dd, J=14.7, 5.0 Hz, 1H), 4.37 (dd, J=14.7, 7.1 Hz, 1H), 3.64-3.50 (m, 3H), 3.44 (dq, J=9.5, 2.8 Hz, 1H), 3.40-3.23 (m, 4H), 3.22-3.12 (m, 3H), 3.09 (d, J=10.3 Hz, 1H), 2.95-2.86 (m, 1H), 2.68 (dd, J=12.5, 2.6 Hz, 1H), 2.51 (dtt, J=10.8, 7.0, 4.0 Hz, 1H), 1.85 (d, J=10.0 Hz, 1H), 1.76-1.57 (m, 4H), 1.36 (s, 9H), 0.87-0.65 (m, 4H). MS (ESI) m/z=745.3, 747.3 [M+H]$^+$ tert-butyl 4-(2-(3-((R)-3-((4-(1H-pyrazol-4-yl)benzyl)(cyclopropyl)carbamoyl) piperidin-1-yl)phenoxy)-2-phenylacetyl)piperazine-1-carboxylate (249a). $^1$H NMR (500 MHz, Chloroform-d) δ 7.79 (s, 2H), 7.52 (d, J=7.6 Hz, 2H), 7.47-7.42 (m, 2H), 7.41-7.35 (m, 2H), 7.35-7.28 (m, 1H), 7.22 (d, J=8.0 Hz, 2H), 7.15 (t, J=8.2 Hz, 1H), 6.65 (s, 1H), 6.60 (dd, J=8.3, 2.3 Hz, 1H), 6.49 (dd, J=8.1, 2.3 Hz, 1H), 5.93 (d, J=2.9 Hz, 1H), 4.71 (d, J=14.7 Hz, 1H), 4.52 (d, J=15.0 Hz, 1H), 3.72 (d, J=12.3 Hz, 2H), 3.55 (s, 3H), 3.50-3.19 (m, 4H), 3.12-2.97 (m, 3H), 2.81 (t, J=11.9 Hz, 1H), 2.62 (tt, J=6.8, 4.2 Hz, 1H), 1.96 (d, J=11.2 Hz, 1H), 1.87-1.67 (m, 3H), 1.41 (s, 9H), 0.92-0.79 (m, 4H). MS (ESI) m/z=719.4 [M+H]$^+$ tert-butyl 4-(2-(3-((R)-3-((4-(1H-pyrazol-4-yl)benzyl)(cyclopropyl)carbamoyl) piperidin-1-yl)phenoxy)-3-phenylpropanoyl)piperazine-1-carboxylate (249b). $^1$H NMR (500 MHz, Acetone-$d_6$) δ 8.00 (s, 2H), 7.58 (d, J=7.9 Hz, 2H), 7.38 (dt, J=7.9, 1.4 Hz, 2H), 7.34-7.18 (m, 5H), 7.09 (t, J=8.2 Hz, 1H), 6.66-6.53 (m, 1H), 6.49 (t, J=2.3 Hz, 1H), 6.33 (dd, J=8.1, 2.2 Hz, 1H), 5.21 (td, J=6.7, 4.3 Hz, 1H), 4.72 (dd, J=14.9, 8.8 Hz, 1H), 4.54 (dd, J=14.8, 9.5 Hz, 1H), 3.75 (t, J=14.7 Hz, 2H), 3.64-3.43 (m, 5H), 3.36 (s, 2H), 3.23 (d, J=6.8 Hz, 3H), 3.05-2.90 (m, 2H), 2.90-2.70 (m, 3H), 1.82-1.63 (m, 3H), 1.43 (s, 9H), 0.90-0.83 (m, 4H). MS (ESI) m/z=733.4 [M+H]$^+$ 4-(2-(3-((R)-3-((4-(1H-pyrazol-4-yl)benzyl)(cyclopropyl)carbamoyl)piperidin-1-yl)phenoxy)-2-phenylacetyl) piperazin-1-ium chloride (86). $^1$H NMR (500 MHz, Methanol-$d_4$) δ 8.40 (s, 2H), 7.65-7.57 (m, 5H), 7.54-7.39 (m, 5H), 7.30 (d, J=7.6 Hz, 2H), 7.19 (dt, J=8.4, 2.8 Hz, 1H), 6.47 (d, J=13.8 Hz, 1H), 4.83 (d, J=15.2 Hz, 1H), 4.49 (d, J=15.1 Hz, 1H), 4.33-3.93 (m, 3H), 3.84-3.63 (m, 7H), 3.41-3.33 (m, 1H), 3.14 (s, 1H), 2.83 (tt, J=9.4, 4.7 Hz, 2H), 2.40-2.05 (m, 3H), 1.96 (dd, J=23.4, 12.2 Hz, 1H), 1.13-0.85 (m, 4H). $^{13}$C NMR (126 MHz, Methanol-$d_4$) δ 175.45, 167.84, 158.53, 158.44, 143.12, 137.30, 134.44, 134.35, 131.37, 131.35, 130.72, 129.45, 129.35, 129.32, 129.01, 127.92, 127.89, 127.87, 127.39, 126.08, 125.82, 123.29, 117.61, 117.49, 113.77, 113.71, 108.91, 108.67, 77.34, 77.31, 72.16, 71.04, 62.93, 60.78, 57.84, 57.64, 56.27, 56.03, 49.49, 42.82, 42.48, 42.08, 38.80, 37.18, 30.02, 24.09, 22.02, 9.38, 9.35, 7.45. HRMS Calcd for $C_{38}H_{44}N_6O_3$ ($M^+$ Na)$^+$ 641.3211, found 641.3204. HPLC purity 100%, $t_R$=9.37 min.

4-(2-(3-((R)-3-((4-(1H-pyrazol-4-yl)benzyl)(cyclopropyl)carbamoyl)piperidin-1-yl)phenoxy)-3-phenylpropanoyl) piperazin-1-ium chloride (87). $^1$H NMR (500 MHz, Methanol-$d_4$) δ 8.27 (s, 2H), 7.60 (d, J=8.0 Hz, 2H), 7.53-7.48 (m, 1H), 7.42-7.27 (m, 9H), 7.07 (dt, J=8.4, 2.5 Hz, 1H), 5.58 (dt, J=17.0, 6.9 Hz, 1H), 4.82 (d, J=10.3 Hz, 1H), 4.48 (dd, J=15.1, 12.4 Hz, 1H), 4.25 (s, 1H), 4.09-3.92 (m, 1H), 3.85-3.66 (m, 7H), 3.30-3.14 (m, 4H), 3.03 (dd, J=11.8, 6.3 Hz, 1H), 2.82 (tt, J=7.2, 4.0 Hz, 1H), 2.59 (dt, J=40.3, 9.9 Hz, 1H), 2.29 (d, J=12.1 Hz, 3H), 1.93 (t, J=11.4 Hz, 1H), 1.10-0.84 (m, 4H). $^{13}$C NMR (126 MHz, Methanol-$d_4$) δ 175.53, 169.12, 169.09, 158.35, 158.32, 143.23, 143.20, 136.88, 136.86, 135.56, 135.55, 131.50, 130.71, 130.08, 129.68, 129.67, 128.45, 127.85, 127.84, 127.10, 127.09, 125.70, 122.90, 117.24, 117.04, 113.82, 113.72, 108.66, 108.33, 75.43, 75.36, 72.16, 71.03, 60.78, 57.72, 56.04, 49.50, 42.77, 41.96, 38.55, 38.48, 37.10, 30.00, 24.04, 21.96, 9.40, 9.35, 7.40. HRMS Calcd for $C_{37}H_{42}N_6O_3$ (M+Na)+655.3367, found 655.3363. HPLC purity 100%, $t_R$=9.37 min Scheme 14. Synthesis of compounds 88 and 89.
a.
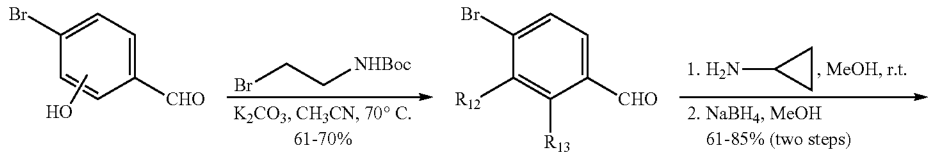
250
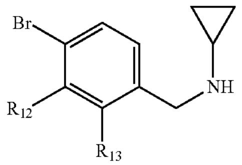
251
251a, $R_{12}$ = 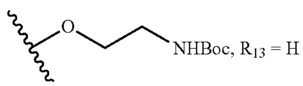, $R_{13}$ = H
251b, $R_{12}$ = H, $R_{13}$ = 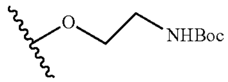
b.
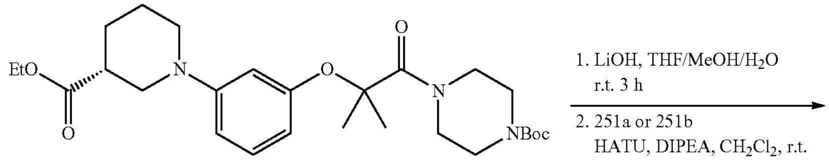
207
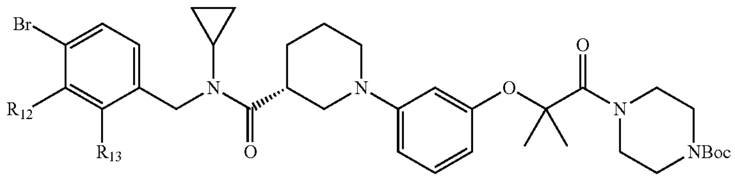
252
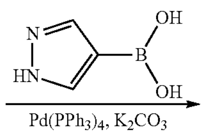
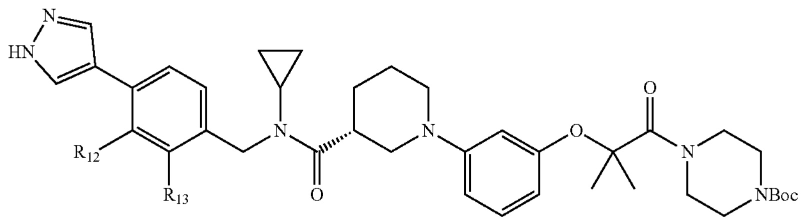
253
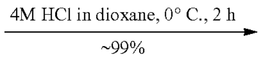

-continued

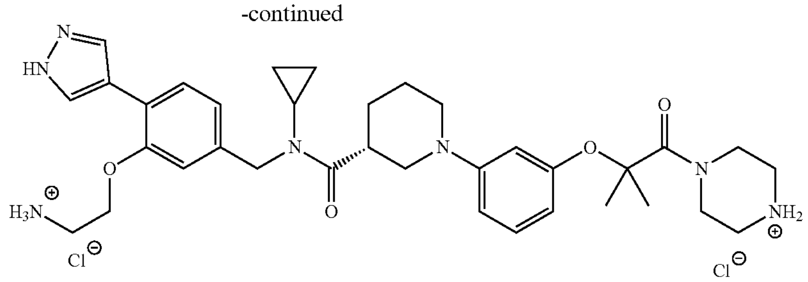

88

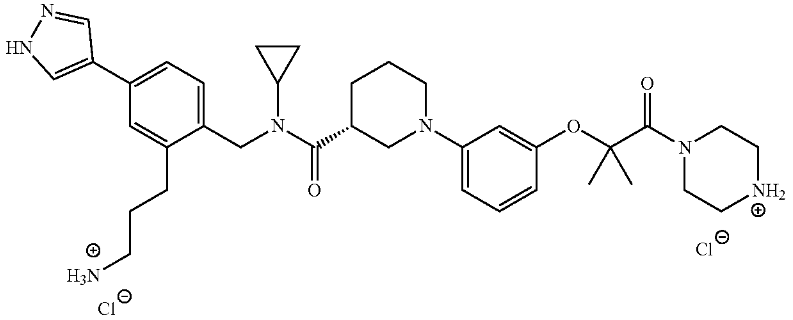

89 tert-butyl(2-(2-bromo-5-formylphenoxy)ethyl) carbamate (250a). $^1$H NMR (500 MHz, Chloroform-d) δ 9.92 (s, 1H), 7.72 (d, J=7.9 Hz, 1H), 7.42-7.29 (m, 2H), 5.06 (d, J=6.6 Hz, 1H), 4.14 (t, J=5.2 Hz, 2H), 3.61 (q, J=5.5 Hz, 2H), 1.44 (s, 9H). MS (ESI) m/z=366.1, 368.2 $[M+Na]^+$ tert-butyl(2-(5-bromo-2-formylphenoxy)ethyl) carbamate (250b). $^1$H NMR (500 MHz, Chloroform-d) δ 10.32 (d, J=0.8 Hz, 1H), 7.58 (d, J=8.2 Hz, 1H), 7.12-6.98 (m, 2H), 5.35 (t, J=6.1 Hz, 1H), 4.07 (t, J=5.3 Hz, 2H), 3.55 (q, J=5.5 Hz, 2H), 1.38 (s, 9H). MS (ESI) m/z=366.1, 368.2 $[M+Na]^+$ tert-butyl(2-(2-bromo-5-((cyclopropylamino)methyl)phenoxy)ethyl) carbamate (251a). $^1$H NMR (500 MHz, Chloroform-d) δ 7.46 (d, J=8.0 Hz, 1H), 6.88 (d, J=1.9 Hz, 1H), 6.81 (dd, J=8.0, 1.9 Hz, 1H), 5.09 (s, 1H), 4.08 (t, J=5.1 Hz, 2H), 3.78 (s, 2H), 3.58 (q, J=5.4 Hz, 2H), 2.17-2.07 (m, 1H), 1.74 (s, 1H), 1.45 (s, 9H), 0.49-0.35 (m, 4H). MS (ESI) m/z=385.2, 387.2 $[M+H]^+$ tert-butyl(2-(5-bromo-2-((cyclopropylamino)methyl)phenoxy)ethyl) carbamate (251b). $^1$H NMR (500 MHz, Chloroform-d) δ 7.11 (d, J=8.0 Hz, 1H), 7.05 (dd, J=7.9, 1.8 Hz, 1H), 6.98 (d, J=1.8 Hz, 1H), 5.48 (s, 1H), 4.06 (t, J=5.1 Hz, 2H), 3.79 (s, 2H), 3.52 (q, J=5.4 Hz, 2H), 2.09 (tt, J=6.4, 3.8 Hz, 1H), 1.44 (s, 9H), 0.47-0.31 (m, 4H). MS (ESI) m/z=385.2, 387.2 $[M+H]^+$ tert-butyl (R)-4-(2-(3-(3-((4-bromo-3-(2-((tert-butoxycarbonyl)amino) ethoxy)benzyl) (cyclopropyl) carbamoyl)piperidin-1-yl)phenoxy)-2-methylpropanoyl)piperazine-1-carboxylate (252a). $^1$H NMR (500 MHz, Chloroform-d) δ 7.44 (dd, J=8.1, 2.6 Hz, 1H), 7.05 (t, J=8.2 Hz, 1H), 6.79 (dd, J=9.3, 1.9 Hz, 1H), 6.71 (dd, J=8.1, 1.9 Hz, 1H), 6.50 (dd, J=8.4, 2.3 Hz, 1H), 6.39 (q, J=3.3, 2.4 Hz, 1H), 6.26 (dd, J=8.1, 2.3 Hz, 1H), 5.10 (d, J=6.8 Hz, 1H), 4.66 (d, J=14.7 Hz, 1H), 4.38 (d, J=14.7 Hz, 1H), 4.05 (dt, J=16.8, 5.1 Hz, 2H), 3.84-3.76 (m, 2H), 3.66-3.52 (m, 6H), 3.40 (tt, J=10.9, 3.7 Hz, 1H), 3.30 (s, 2H), 3.05 (d, J=6.3 Hz, 2H), 2.95 (dd, J=12.4, 10.9 Hz, 1H), 2.74 (dd, J=12.4, 9.5 Hz, 1H), 2.60 (tt, J=6.9, 4.0 Hz, 1H), 1.91 (d, J=8.8 Hz, 1H), 1.85-1.77 (m, 1H), 1.77-1.67 (m, 2H), 1.61 (d, J=1.4 Hz, 6H), 1.43 (s, 9H), 1.40 (s, 9H), 0.91-0.75 (m, 4H). MS (ESI) m/z=842.4 $[M+H]^+$ tert-butyl (R)-4-(2-(3-(3-((4-bromo-2-(2-((tert-butoxycarbonyl)amino) ethoxy)benzyl) (cyclopropyl) carbamoyl)piperidin-1-yl)phenoxy)-2-methylpropanoyl)piperazine-1-carboxylate (252b). $^1$H NMR (500 MHz, Chloroform-d) δ 7.09-7.00 (m, 3H), 6.97 (dd, J=3.9, 1.7 Hz, 1H), 6.49 (dd, J=8.2, 2.2 Hz, 1H), 6.38 (t, J=2.3 Hz, 1H), 6.26 (dd, J=7.9, 2.3 Hz, 1H), 5.82 (s, 1H), 4.68 (d, J=14.7 Hz, 1H), 4.48 (d, J=14.7 Hz, 1H), 4.00 (t, J=4.9 Hz, 2H), 3.80 (d, J=4.0 Hz, 2H), 3.58 (dt, J=56.5, 8.1 Hz, 6H), 3.43-3.25 (m, 3H), 3.06 (s, 2H), 3.01-2.90 (m, 1H), 2.77-2.72 (m, 1H), 2.50 (s, 1H), 1.89 (d, J=11.9 Hz, 1H), 1.84-1.67 (m, 3H), 1.62 (s, 6H), 1.42 (d, J=11.3 Hz, 18H), 0.90-0.80 (m, 4H). MS (ESI) m/z=842.4 $[M+H]^+$ tert-butyl (R)-4-(2-(3-(3-((3-(2-((tert-butoxycarbonyl) amino) ethoxy)-4-(1H-pyrazol-4-yl)benzyl)(cyclopropyl) carbamoyl)piperidin-1-yl)phenoxy)-2-methylpropanoyl) piperazine-1-carboxylate (253a). $^1$H NMR (500 MHz, Chloroform-d) δ 8.01 (s, 2H), 7.49 (d, J=7.8 Hz, 1H), 7.06 (t, J=8.2 Hz, 1H), 6.91-6.81 (m, 2H), 6.52 (dd, J=8.4, 2.2 Hz, 1H), 6.40 (t, J=2.3 Hz, 1H), 6.27 (dd, J=8.1, 2.3 Hz, 1H), 4.93 (s, 1H), 4.70 (d, J=14.6 Hz, 1H), 4.49 (d, J=14.6 Hz, 1H), 4.09 (t, J=5.2 Hz, 2H), 3.87-3.74 (m, 2H), 3.72-3.49 (m, 6H), 3.49-3.37 (m, 1H), 3.31 (s, 2H), 3.06 (s, 2H), 3.03-2.93 (m, 1H), 2.79-2.69 (m, 1H), 2.63 (td, J=7.1, 3.5 Hz, 1H), 1.95 (d, J=10.6 Hz, 1H), 1.87-1.71 (m, 3H), 1.62 (s, 6H), 1.42 (d, J=8.0 Hz, 18H), 0.95-0.79 (m, 4H). MS (ESI) m/z=830.1 $[M+H]^+$ tert-butyl (R)-4-(2-(3-(3-((2-(2-((tert-butoxycarbonyl) amino) ethoxy)-4-(1H-pyrazol-4-yl)benzyl)(cyclopropyl) carbamoyl)piperidin-1-yl)phenoxy)-2-methylpropanoyl) piperazine-1-carboxylate (253b). $^1$H NMR (500 MHz, Chloroform-d) δ 7.80 (s, 2H), 7.15 (d, J=7.7 Hz, 1H), 7.11-7.03 (m, 2H), 6.94 (d, J=1.6 Hz, 1H), 6.51 (d, J=8.3 Hz, 1H), 6.41 (s, 1H), 6.26 (d, J=7.8 Hz, 1H), 5.90 (s, 1H), 4.75 (d, J=14.5 Hz, 1H), 4.55 (d, J=14.5 Hz, 1H), 4.06 (t, J=5.0 Hz, 2H), 3.85-3.72 (m, 2H), 3.71-3.65 (m, 2H), 3.61-3.52 (m, 4H), 3.43 (s, 1H), 3.32 (s, 2H), 3.11-2.97 (m, 3H), 2.77 (t, J=12.0 Hz, 1H), 2.53 (d, J=8.5 Hz, 1H), 1.93 (d, J=11.4

Hz, 1H), 1.81-1.71 (m, 3H), 1.62 (s, 6H), 1.43 (d, J=15.9 Hz, 18H), 0.89-0.84 (m, 4H). MS (ESI) m/z=830.1 $[M+H]^+$ (R)-4-(2-(3-(3-((3-(2-ammonioethoxy)-4-(1H-pyrazol-4-yl)benzyl) (cyclopropyl) carbamoyl)piperidin-1-yl)phenoxy)-2-methylpropanoyl)piperazin-1-ium chlorine (88). $^1$H NMR (500 MHz, Methanol-$d_4$) δ 8.62 (s, 2H), 7.67-7.53 (m, 2H), 7.51-7.38 (m, 2H), 7.14-6.91 (m, 3H), 4.81 (d, J=40.2 Hz, 1H), 4.52 (d, J=15.2 Hz, 1H), 4.42 (q, J=5.1 Hz, 2H), 4.31-3.87 (m, 5H), 3.86-3.69 (m, 4H), 3.52 (t, J=4.8 Hz, 2H), 3.26-2.69 (m, 5H), 2.40-1.83 (m, 4H), 1.68 (d, J=4.1 Hz, 6H), 1.16-0.84 (m, 4H). $^{13}$C NMR (126 MHz, Methanol-$d_4$) δ 171.46, 156.26, 154.77, 143.43, 139.75, 132.51, 131.55, 128.69, 120.67, 118.47, 117.78, 114.55, 111.89, 111.61, 81.77, 65.21, 56.07, 49.71, 43.13, 42.68, 39.57, 38.88, 37.17, 30.16, 24.96, 24.79, 24.02, 21.99, 9.40, 7.29. HRMS Calcd for $C_{35}H_{47}N_7O_4$ $(M^+ Na)^+$ 652.3582, found 652.3575. HPLC purity 98.8%, $t_R$=8.37 min.

(R)-4-(2-(3-(3-((2-(2-ammonioethoxy)-4-(1/I-pyrazol-4-yl)benzyl) (cyclopropyl) carbamoyl)piperidin-1-yl)phenoxy)-2-methylpropanoyl)piperazin-1-ium chlorine (89). $^1$H NMR (500 MHz, Methanol-$d_4$) δ 8.45 (s, 2H), 7.60-7.49 (m, 2H), 7.43 (s, 1H), 7.37-7.23 (m, 3H), 7.07-6.95 (m, 1H), 5.04 (d, J=15.1 Hz, 1H), 4.52-4.33 (m, 3H), 4.31-3.81 (m, 6H), 3.81-3.69 (m, 3H), 3.51-3.41 (m, 2H), 3.27-2.60 (m, 5H), 2.31 (d, J=13.1 Hz, 1H), 2.18 (tt, J=14.8, 4.2 Hz, 2H), 1.92 (d, J=12.4 Hz, 1H), 1.68 (d, J=3.8 Hz, 6H), 1.18-0.90 (m, 4H). $^{13}$C NMR (126 MHz, Methanol-$d_4$) δ 171.47, 156.33, 156.24, 143.55, 131.58, 131.48, 130.95, 130.12, 124.64, 123.09, 118.63, 118.39, 114.56, 111.73, 109.33, 81.78, 64.41, 57.48, 56.18, 44.77, 43.12, 42.69, 39.05, 37.68, 29.67, 24.90, 24.78, 24.34, 22.34, 9.80, 7.44. HRMS Calcd for $C_{35}H_{47}N_7O_4$ $(M+H)^+$ 630.3762, found 630.3757. HPLC purity 99.0%, $t_R$=8.45 min.

Scheme 15. Synthesis of compounds 90 and 91.

a.

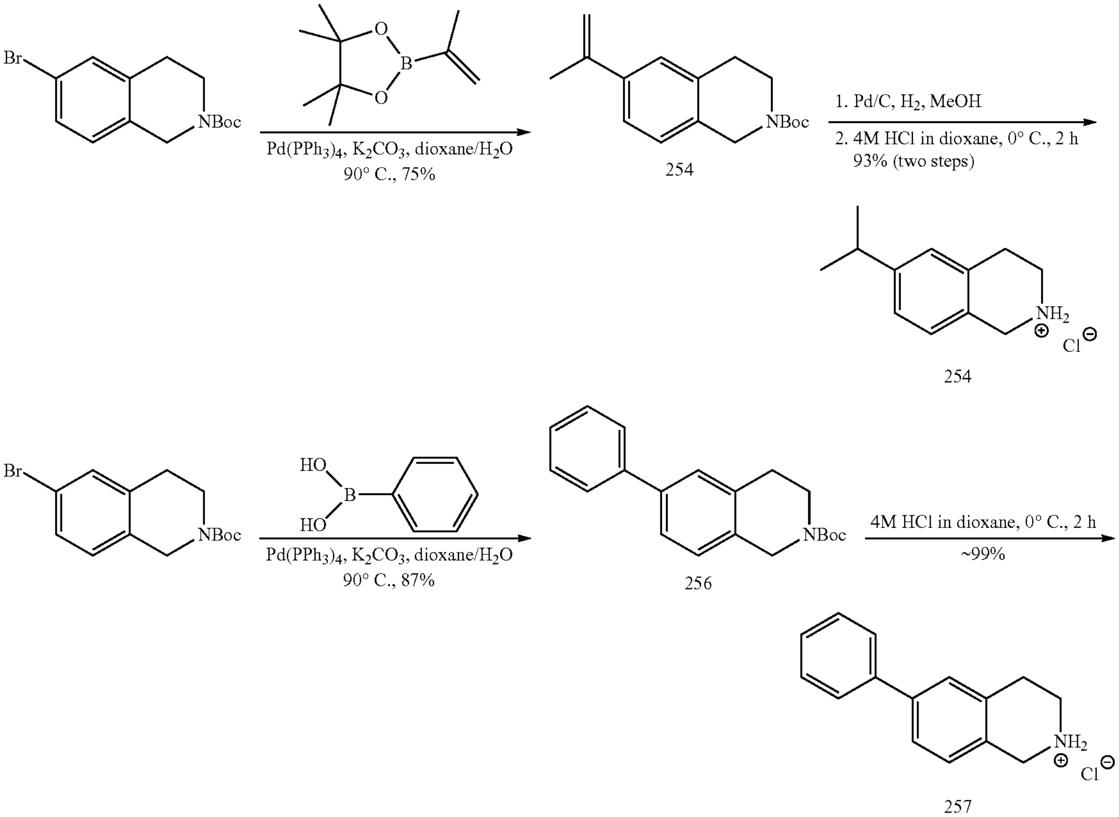

b.

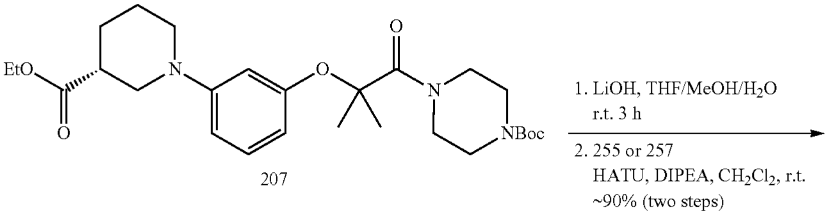

-continued

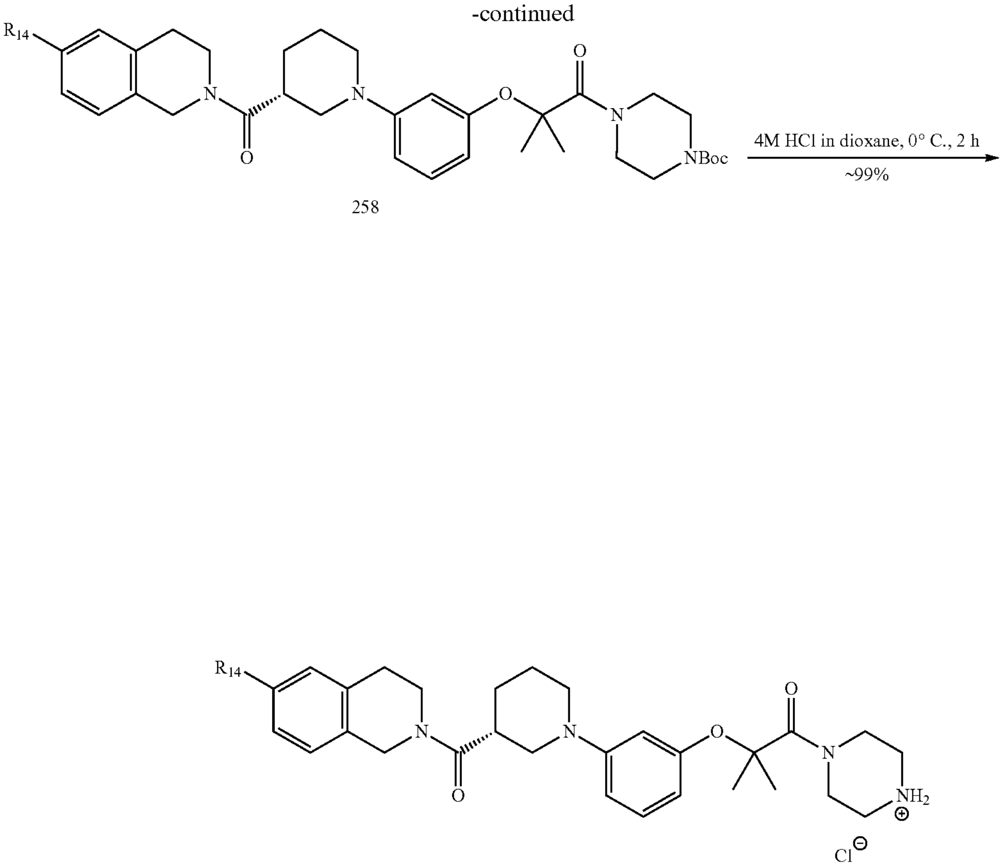

258

90-91
90, $R_{14}$ = i-Pr
91, $R_{14}$ = Ph tert-butyl 6-(prop-1-en-2-yl)-3,4-dihydroisoquinoline-2 (1H)-carboxylate (254). $^1$H NMR (500 MHz, Chloroform-d) δ 7.30 (dd, J=8.0, 1.9 Hz, 1H), 7.23 (d, J=1.9 Hz, 1H), 7.07 (d, J=8.0 Hz, 1H), 5.35 (d, J=1.4 Hz, 1H), 5.07 (p, J=1.5 Hz, 1H), 4.58 (s, 2H), 3.66 (t, J=6.1 Hz, 2H), 2.84 (t, J=5.9 Hz, 2H), 2.20-2.05 (m, 3H), 1.51 (d, J=1.4 Hz, 9H). MS (ESI) m/z=296.2 $[M+Na]^+$. Reduction of double bond of 254 under $H_2$ using Pd/C in methanol and then removal of Boc by 4 M HCl in dioxane yielded 255, which was used directly in next step.

tert-butyl 6-phenyl-3,4-dihydroisoquinoline-2 (1H)-carboxylate (256). $^1$H NMR (500 MHz, Chloroform-d) δ 7.61-7.53 (m, 2H), 7.51-7.40 (m, 3H), 7.40-7.29 (m, 2H), 7.19 (d, J=8.0 Hz, 1H), 4.63 (s, 2H), 3.71 (d, J=7.7 Hz, 2H), 2.91 (t, J=6.0 Hz, 2H), 1.52 (s, 9H). MS (ESI) m/z=332.1 $[M+Na]^+$. Removal of Boc of 256 by 4 M HCl in dioxane yielded 257, which was used directly in next step.

tert-butyl (R)-4-(2-(3-(3-(6-isopropyl-1,2,3,4-tetrahydroisoquinoline-2-carbonyl)piperidin-1-yl)phenoxy)-2-methylpropanoyl)piperazine-1-carboxylate (258a). $^1$H NMR (500 MHz, Chloroform-d) δ 7.12-6.94 (m, 4H), 6.52 (td, J=8.5, 2.3 Hz, 1H), 6.41 (dt, J=4.7, 2.4 Hz, 1H), 6.27 (dt, J=8.2, 2.0 Hz, 1H), 4.73-4.56 (m, 2H), 3.90-3.71 (m, 4H), 3.71-3.47 (m, 4H), 3.33 (s, 2H), 3.09 (p, J=7.2, 6.0 Hz, 2H), 3.01-2.80 (m, 5H), 2.76-2.66 (m, 1H), 1.92 (t, J=10.6 Hz, 1H), 1.84-1.69 (m, 3H), 1.63 (d, J=2.9 Hz, 6H), 1.42 (s, 9H), 1.26-1.22 (m, 6H). MS (ESI) m/z=633.4 $[M+H]^+$ tert-butyl (R)-4-(2-methyl-2-(3-(3-(6-phenyl-1,2,3,4-tetrahydroisoquinoline-2-carbonyl)piperidin-1-yl)phenoxy)propanoyl)piperazine-1-carboxylate (258b). $^1$H NMR (500 MHz, Chloroform-d) δ 7.67-7.49 (m, 2H), 7.44 (dd, J=8.6, 6.8 Hz, 3H), 7.40-7.37 (m, 1H), 7.37-7.29 (m, 1H), 7.22 (dd, J=18.9, 8.0 Hz, 1H), 7.11-7.00 (m, 1H), 6.59-6.48 (m, 1H), 6.42 (p, J=2.3 Hz, 1H), 6.28 (dd, J=8.1, 2.2 Hz, 1H), 4.82-4.62 (m, 2H), 3.95-3.75 (m, 4H), 3.68 (t, J=13.1 Hz, 2H), 3.59 (s, 2H), 3.33 (s, 2H), 3.15-3.04 (m, 2H), 3.04-2.87 (m, 4H), 2.79-2.67 (m, 1H), 1.94 (d, J=12.1 Hz, 1H), 1.87-1.72 (m, 3H), 1.63 (d, J=2.7 Hz, 6H), 1.42 (s, 9H). MS (ESI) m/z=667.4 $[M+H]^+$ (R)-4-(2-(3-(3-(6-isopropyl-1,2,3,4-tetrahydroisoquinoline-2-carbonyl)piperidin-1-yl)phenoxy)-2-methylpropanoyl)piperazin-1-ium chlorine (90). $^1$H NMR (500 MHz, Methanol-$d_4$) δ 7.52-6.73 (m, 7H), 4.77-4.62 (m, 2H), 4.22-3.80 (m, 6H), 3.77-3.34 (m, 5H), 3.22-2.84 (m, 7H), 1.94 (d, J=110.6 Hz, 4H), 1.72-1.56 (m, 6H), 1.23 (d, J=6.9 Hz, 6H). $^{13}$C NMR (126 MHz, Methanol-$d_4$) δ 171.77, 156.26, 147.82, 147.46, 134.40, 133.89, 131.00, 129.99, 126.23, 126.04, 125.92, 125.79, 124.45, 124.34, 81.36, 44.00, 43.37, 43.13, 40.46, 33.69, 29.20, 27.92, 24.89, 24.79, 23.03. HRMS Calcd for $C_{32}H_{44}N_4O_3$ $(M+H)^+$ 533.3486, found 533.3471. HPLC purity 100%, $t_R$=11.52 min.

(R)-4-(2-methyl-2-(3-(3-(6-phenyl-1,2,3,4-tetrahydroisoquinoline-2-carbonyl)piperidin-1-yl)phenoxy) propanoyl) piperazin-1-ium chlorine (91). $^1$H NMR (500 MHz, Methanol-$d_4$) δ 7.64-7.54 (m, 2H), 7.52-7.38 (m, 5H), 7.37-7.21 (m, 3H), 7.14 (s, 1H), 6.88 (s, 1H), 4.84-4.67 (m, 2H), 4.26-3.81 (m, 6H), 3.77-3.40 (m, 5H), 3.22-2.82 (m, 6H), 2.22-1.80 (m, 4H), 1.67 (t, J=2.7 Hz, 6H). $^{13}$C NMR (126 MHz, Methanol-d$_4$) δ 171.69, 156.27, 140.55, 140.52, 140.09, 139.76, 135.09, 134.59, 131.73, 131.61, 131.13, 128.47, 127.03, 126.99, 126.83, 126.63, 126.55, 126.48, 126.46, 126.40, 124.93, 124.85, 113.49, 81.47, 54.17, 44.01, 43.31, 43.12, 40.38, 39.53, 29.24, 27.97, 24.90, 24.77. HRMS Calcd for $C_{35}H_{42}N_4O_3$ $(M+H)^+$ 567.3330, found 567.3319. HPLC purity 99.5%, $t_R$=11.79 min.

7.32 (m, 1H), 7.32-7.27 (m, 1H), 7.14 (dd, J=14.4, 7.9 Hz, 1H), 7.06 (td, J=8.3, 3.0 Hz, 1H), 6.54 (t, J=8.4 Hz, 1H), 6.43 (d, J=6.0 Hz, 1H), 6.28 (dt, J=8.4, 2.6 Hz, 1H), 4.78-4.61 (m, 2H), 3.91-3.76 (m, 4H), 3.72-3.50 (m, 4H), 3.33 (d, J=5.9 Hz, 2H), 3.07 (d, J=6.6 Hz, 2H), 3.03-2.83 (m, 4H), 2.74 (td, J=11.8, 3.2 Hz, 1H), 1.94 (t, J=11.5 Hz, 1H), 1.87-1.69 (m, 3H), 1.63 (d, J=2.3 Hz, 6H), 1.41 (s, 9H). MS (ESI) m/z=657.4 $[M+H]^+$

Scheme 16. Synthesis of compound 92.

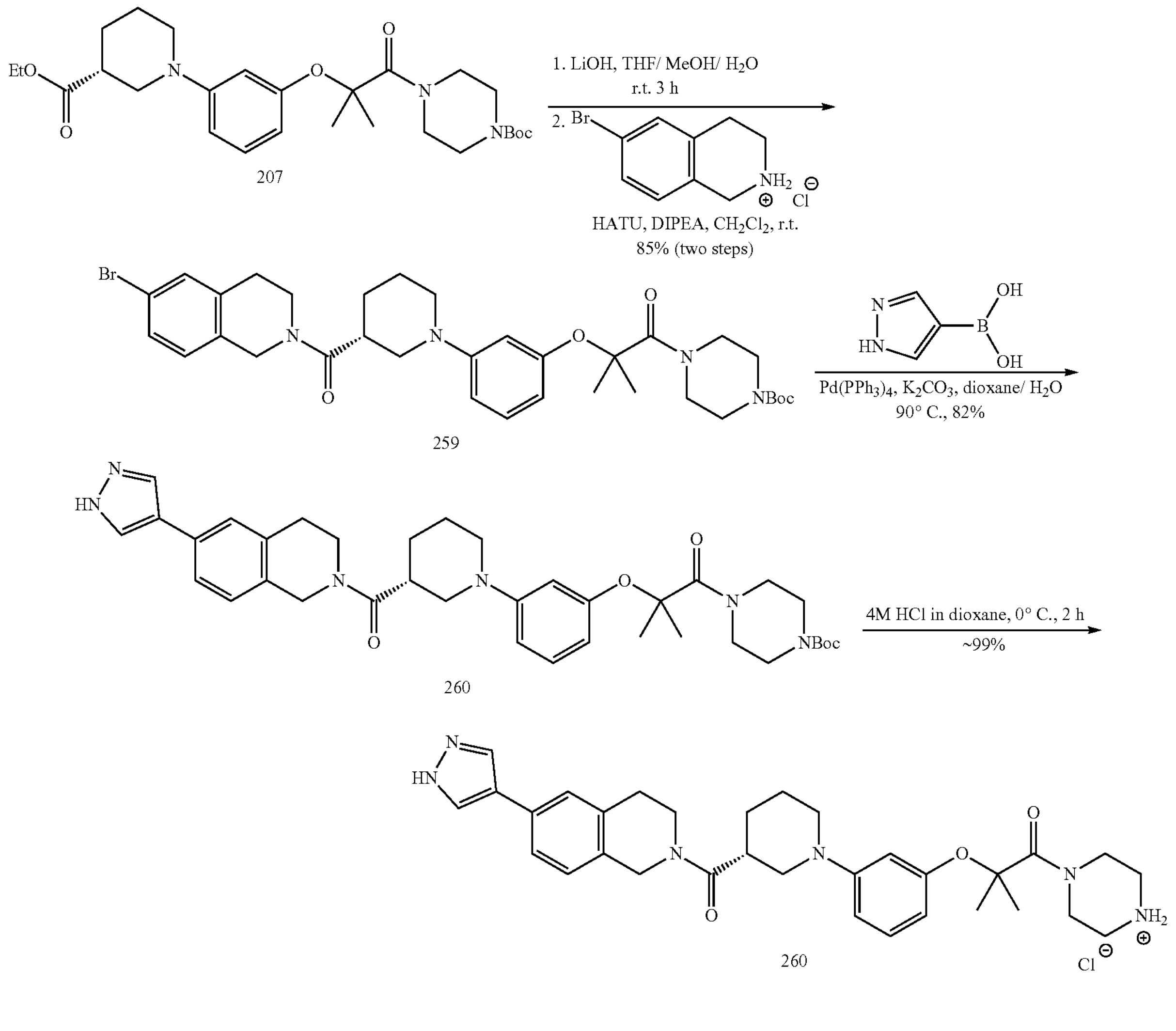

207

259

260

260 tert-butyl (R)-4-(2-(3-(3-(6-bromo-1,2,3,4-tetrahydroisoquinoline-2-carbonyl)piperidin-1-yl)phenoxy)-2-methylpropanoyl)piperazine-1-carboxylate (259). $^1$H NMR (500 MHz, Chloroform-d) δ 7.33-7.23 (m, 2H), 7.09-6.92 (m, 2H), 6.50 (t, J=9.5 Hz, 1H), 6.39 (d, J=8.6 Hz, 1H), 6.26 (dd, J=8.2, 2.2 Hz, 1H), 4.63 (d, J=20.0 Hz, 2H), 3.87-3.69 (m, 4H), 3.64 (d, J=10.8 Hz, 2H), 3.57 (d, J=5.2 Hz, 2H), 3.31 (d, J=5.3 Hz, 2H), 3.05 (d, J=6.0 Hz, 2H), 2.99-2.84 (m, 3H), 2.82 (t, J=3.4 Hz, 1H), 2.72 (dt, J=12.3, 6.2 Hz, 1H), 1.90 (dd, J=19.2, 8.0 Hz, 1H), 1.85-1.67 (m, 3H), 1.61 (d, J=2.6 Hz, 6H), 1.40 (s, 9H). MS (ESI) m/z=669.3, 671.3 $[M+H]^+$ tert-butyl (R)-4-(2-(3-(3-(6-(1H-pyrazol-4-yl)-1,2,3,4-tetrahydroisoquinoline-2-carbonyl)piperidin-1-yl)phenoxy)-2-methylpropanoyl)piperazine-1-carboxylate (260). $^1$H NMR (500 MHz, Chloroform-d) δ 7.84 (d, J=3.0 Hz, 2H), 7.40-

(R)-4-(2-(3-(3-(6-(1H-pyrazol-4-yl)-1,2,3,4-tetrahydroisoquinoline-2-carbonyl)piperidin-1-yl)phenoxy)-2-methylpropanoyl)piperazin-1-ium chloride (92). $^1$H NMR (500 MHz, Methanol-d$_4$) δ 8.37 (d, J=3.1 Hz, 2H), 7.60-7.48 (m, 3H), 7.44 (dd, J=6.5, 3.9 Hz, 1H), 7.37-7.20 (m, 2H), 7.03 (dt, J=8.4, 2.1 Hz, 1H), 4.84-4.69 (m, 2H), 4.24-3.83 (m, 6H), 3.80-3.62 (m, 5H), 3.27-2.87 (m, 6H), 2.33-1.83 (m, 4H), 1.68 (d, J=1.4 Hz, 6H). $^{13}$C NMR (126 MHz, Methanol-d$_4$) δ 171.48, 156.32, 143.40, 135.43, 134.94, 131.92, 131.77, 131.53, 130.70, 129.58, 129.19, 126.91, 126.71, 125.66, 125.44, 123.86, 123.77, 118.44, 114.41, 111.50, 81.80, 44.02, 43.23, 43.14, 40.29, 29.08, 27.85, 24.89, 24.70. HRMS Calcd for $C_{32}H_{40}N_6O_3$ $(M+H)^+$ 557.3235, found 557.3233. HPLC purity 99.4%, $t_R$=8.62 min.

Scheme 17. Synthesis of 93-98.
A.
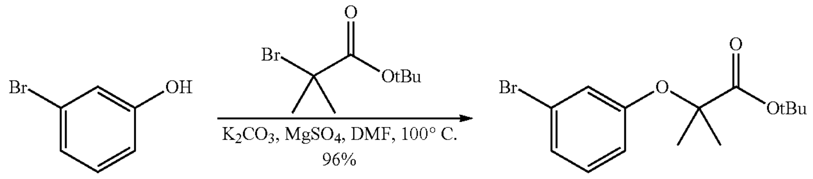
200
B.
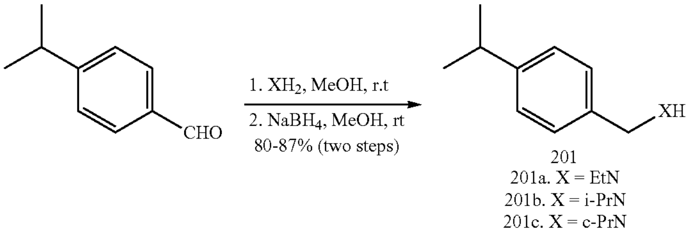
201
201a. X = EtN
201b. X = i-PrN
201c. X = c-PrN
C.
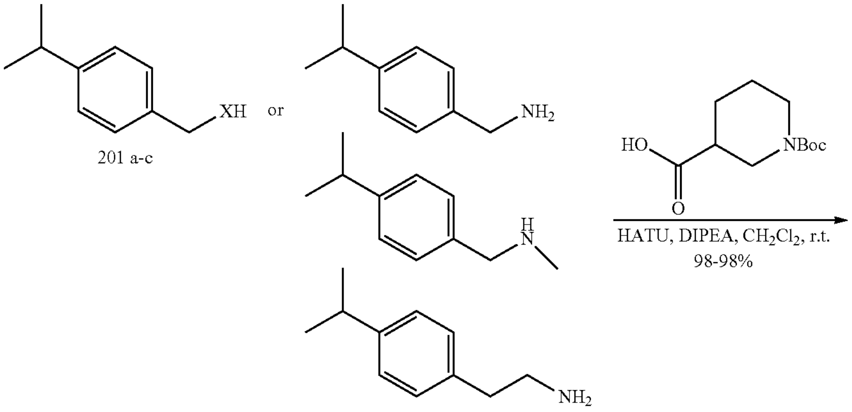
201 a-c
or
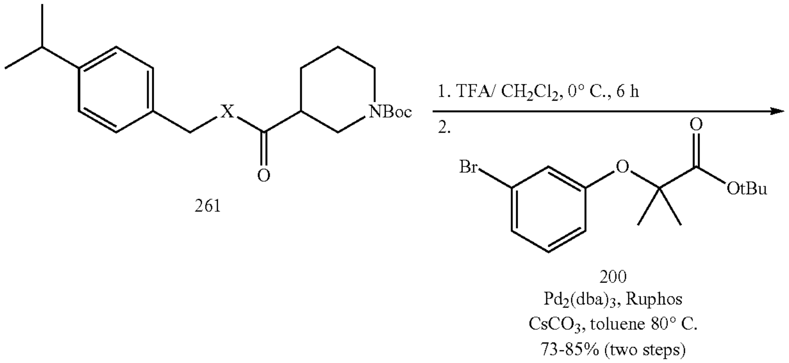
261
200
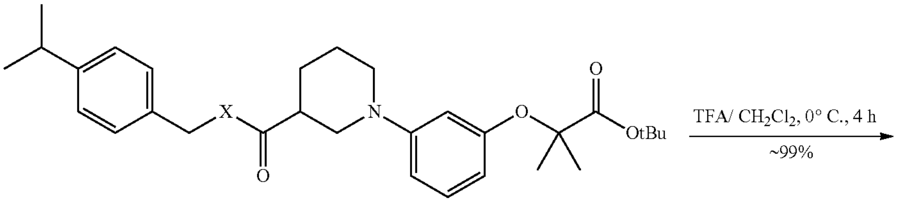
262

-continued

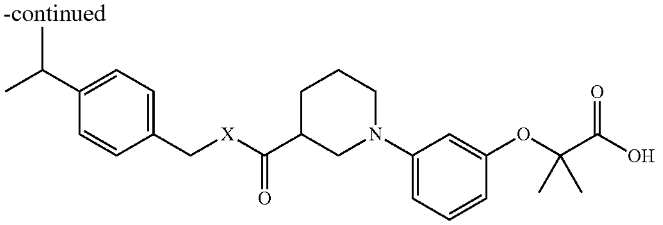

93-98
93. X = NH
94. X = $-CH_2-NH$
95. X = MeN
96. X = EtN
97. X = i-PrN
98. X = c-PrN tert-butyl 2-(3-bromophenoxy)-2-methylpropanoate (200). $^1H$ NMR (500 MHz, Chloroform-d) δ 7.16-7.04 (m, 2H), 7.01 (dd, J=2.7, 1.3 Hz, 1H), 6.82-6.71 (m, 1H), 1.56 (s, 6H), 1.44 (s, 9H). $^{13}C$ NMR (126 MHz, Chloroform-d) δ 172.79, 156.55, 130.10, 124.65, 122.23, 121.82, 117.27, 82.03, 79.83, 27.78, 25.34. MS (ESI) m/z=315.1 $[M+H]^+$.

N-(4-isopropylbenzyl) ethanamine (201a). $^1H$ NMR (500 MHz, Chloroform-d) δ 7.24 (d, J=8.2 Hz, 2H), 7.21-7.16 (m, 2H), 3.76 (s, 2H), 2.89 (hept, J=6.9 Hz, 1H), 2.69 (q, J=7.1 Hz, 2H), 1.25 (d, J=6.9 Hz, 6H), 1.13 (t, J=7.1 Hz, 3H). $^{13}C$ NMR (126 MHz, Chloroform-d) δ 147.50, 137.94, 128.12, 126.42, 53.76, 43.72, 33.80, 24.06, 15.33. MS (ESI) m/z=178.2 $[M+H]^+$.

N-(4-isopropylbenzyl) propan-2-amine (201b). $^1H$ NMR (500 MHz, Chloroform-d) δ 7.26-7.21 (m, 2H), 7.20-7.16 (m, 2H), 3.75 (s, 2H), 3.00-2.65 (m, 2H), 1.24 (d, J=6.9 Hz, 6H), 1.10 (d, J=6.2 Hz, 6H). $^{13}C$ NMR (126 MHz, Chloroform-d) δ 147.44, 138.22, 128.07, 126.43, 51.40, 48.10, 33.79, 24.04, 22.97. MS (ESI) m/z=192.3 $[M+H]^+$.

N-(4-isopropylbenzyl)cyclopropanamine (201c). $^1H$ NMR (500 MHz, Chloroform-d) δ 7.25-7.22 (m, 2H), 7.20-7.17 (m, 2H), 3.81 (s, 2H), 2.90 (hept, J=6.9 Hz, 1H), 2.22-2.12 (m, 1H), 1.25 (d, J=6.9 Hz, 6H), 0.48-0.35 (m, 4H). $^{13}C$ NMR (126 MHz, Chloroform-d) δ 147.49, 138.01, 128.16, 126.42, 53.46, 33.81, 30.09, 24.06, 6.48. MS (ESI) m/z=190.2 $[M+H]^+$.

tert-butyl 3-((4-isopropylbenzyl)carbamoyl)piperidine-1-carboxylate (261a). $^1H$ NMR (500 MHz, Chloroform-d) δ 7.15 (s, 4H), 4.37 (d, J=19.2 Hz, 2H), 4.03-3.60 (m, 2H), 3.14 (dd, J=13.5, 9.3 Hz, 1H), 2.86 (hept, J=6.8 Hz, 2H), 2.28 (dq, J=9.8, 5.3, 4.9 Hz, 1H), 1.91-1.77 (m, 2H), 1.69-1.54 (m, 1H), 1.38 (s, 10H), 1.21 (d, J=7.0 Hz, 6H). $^{13}C$ NMR (126 MHz, Chloroform-d) δ 172.92, 154.80, 148.10, 135.59, 127.80, 126.70, 79.81, 45.87, 44.65, 43.22, 43.00, 33.80, 28.37, 27.77, 24.22, 24.00. MS (ESI) m/z=361.3 $[M+H]^+$, 383.3 $[M+Na]^+$.

tert-butyl 3-((4-isopropylphenethyl)carbamoyl)piperidine-1-carboxylate (261b). $^1H$ NMR (500 MHz, Chloroform-d) δ 7.12 (dd, J=8.2, 1.8 Hz, 2H), 7.03 (dd, J=8.0, 1.6 Hz, 2H), 6.59-5.89 (m, 1H), 4.09-3.50 (m, 2H), 3.42 (qt, J=13.3, 7.0 Hz, 2H), 3.04 (s, 1H), 2.87-2.82 (m, 1H), 2.74-2.71 (m, 4H), 2.16 (dt, J=12.5, 6.2 Hz, 1H), 1.78 (d, J=8.5 Hz, 1H), 1.56 (t, J=12.7 Hz, 1H), 1.39 (d, J=1.6 Hz, 10H), 1.20 (dd, J=7.0, 1.5 Hz, 6H). MS (ESI) m/z=375.3 $[M+H]^+$, 397.3 $[M+Na]^+$.

tert-butyl 3-((4-isopropylbenzyl)(methyl)carbamoyl)piperidine-1-carboxylate (261c). $^1H$ NMR (500 MHz, Chloroform-d) δ 7.24-7.12 (m, 2H), 7.11-6.89 (m, 2H), 4.51 (s, 2H), 4.16 (s, 1H), 4.06 (s, 1H), 2.95 (s, 2H), 2.90-2.79 (m, 3H), 2.70-2.45 (m, 2H), 2.02-1.54 (m, 3H), 1.53-1.30 (m, 10H), 1.21 (t, J=6.9 Hz, 6H). $^{13}C$ NMR (126 MHz, Chloroform-d) δ 173.76, 173.13, 154.69, 154.55, 148.39, 147.96, 134.54, 133.86, 127.91, 126.99, 126.63, 126.21, 79.58, 79.49, 52.83, 50.45, 46.46, 44.30, 39.47, 34.59, 33.83, 33.76, 28.44, 28.39, 28.06, 27.57, 24.74, 24.57, 23.97, 23.95. MS (ESI) m/z=375.3 $[M+H]^+$.

tert-butyl 3-(ethyl(4-isopropylbenzyl)carbamoyl)piperidine-1-carboxylate (261d). $^1H$ NMR (500 MHz, Chloroform-d) δ 7.20-7.14 (m, 1H), 7.14-6.90 (m, 3H), 4.85-3.96 (m, 4H), 3.26 (s, 2H), 2.84 (dp, J=13.7, 6.9 Hz, 2H), 2.60 (tt, J=31.9, 17.1 Hz, 2H), 1.97-1.55 (m, 3H), 1.38 (d, J=30.3 Hz, 10H), 1.19 (dd, J=8.0, 6.9 Hz, 6H), 1.08 (dt, J=48.7, 7.1 Hz, 3H). $^{13}C$ NMR (126 MHz, Chloroform-d) δ 173.27, 173.10, 154.63, 154.51, 148.24, 147.80, 135.05, 134.36, 127.76, 126.89, 126.56, 126.16, 79.51, 79.41, 53.43, 49.98, 47.28, 44.63, 43.92, 41.29, 40.62, 39.46, 33.72 (d, J=2.8 Hz), 28.43, 28.37, 28.08, 24.62, 23.97, 23.95, 14.29, 12.59. MS (ESI) m/z=389.3 $[M+H]^+$.

tert-butyl 3-(isopropyl(4-isopropylbenzyl)carbamoyl)piperidine-1-carboxylate (261e). $^1H$ NMR (500 MHz, Chloroform-d) δ 7.19-7.12 (m, 1H), 7.12-6.97 (m, 3H), 4.94-3.85 (m, 5H), 3.19-2.20 (m, 4H), 2.04-1.62 (m, 2H), 1.64-1.52 (m, 1H), 1.44 (s, 4H), 1.36 (s, 6H), 1.29-1.10 (m, 9H), 1.04 (d, J=6.8 Hz, 3H). $^{13}C$ NMR (126 MHz, Chloroform-d) δ 174.03, 173.29, 154.65, 154.53, 147.79, 146.98, 136.73, 135.99, 126.75, 126.59, 126.33, 125.59, 79.52, 79.37, 53.43, 48.47, 47.13, 46.48, 45.51, 44.59, 43.60, 40.69, 39.74, 33.66, 28.47, 28.37, 28.23, 24.77, 24.41, 24.00, 23.95, 21.96, 21.90, 20.24. MS (ESI) m/z=403.3 $[M+H]^+$, 425.3 $[M+Na]^+$, tert-butyl 3-(cyclopropyl(4-isopropylbenzyl)carbamoyl)piperidine-1-carboxylate (261f). $^1H$ NMR (500 MHz, Chloroform-d) δ 7.12 (t, J=6.7 Hz, 4H), 4.91-3.94 (m, 4H), 3.19 (tt, J=11.5, 3.8 Hz, 1H), 2.87 (dq, J=13.8, 6.8 Hz, 2H), 2.65 (d, J=69.8 Hz, 2H), 1.90 (d, J=13.3 Hz, 1H), 1.85-1.63 (m, 2H), 1.45 (s, 10H), 1.22 (d, J=6.9 Hz, 6H), 0.97-0.70 (m, 4H). $^{13}C$ NMR (126 MHz, Chloroform-d) δ 176.19, 154.67, 147.67, 135.48, 127.65, 126.54, 79.50, 49.36, 47.26, 44.77, 40.35, 33.75, 29.62, 28.46, 27.78, 24.73, 23.99, 9.32. MS (ESI) m/z=401.4 $[M+H]^+$, 423.3 $[M+Na]^+$.

tert-butyl 2-(3-(3-((4-isopropylbenzyl)carbamoyl)piperidin-1-yl)phenoxy)-2-methylpropanoate (262a). $^1H$ NMR (500 MHz, Chloroform-d) δ 7.18 (d, J=1.6 Hz, 4H), 7.06 (t, J=8.2 Hz, 1H), 6.90 (t, J=5.7 Hz, 1H), 6.54 (dd, J=8.3, 2.3 Hz, 1H), 6.49 (t, J=2.3 Hz, 1H), 6.34 (dd, J=8.2, 2.3 Hz, 1H), 4.42 (d, J=5.6 Hz, 2H), 3.39 (dd, J=12.5, 3.6 Hz, 1H), 3.31-3.15 (m, 2H), 3.02 (ddd, J=11.8, 8.4, 3.1 Hz, 1H), 2.88 (p, J=6.9 Hz, 1H), 2.55 (tt, J=8.0, 4.1 Hz, 1H), 2.02-1.72 (m, 3H), 1.66 (tq, J=8.7, 4.4 Hz, 1H), 1.55 (s, 6H), 1.42 (d, J=0.9 Hz, 9H), 1.23 (d, J=6.9 Hz, 6H). $^{13}$C NMR (126 MHz, Chloroform-d) δ 174.06, 173.47, 156.69, 152.47, 148.03, 135.78, 129.22, 127.68, 126.72, 111.11, 110.12, 108.16, 81.60, 79.29, 52.66, 50.58, 43.11, 42.39, 33.81, 27.82, 27.37, 25.52, 25.44, 24.02, 23.47. MS (ESI) m/z=495.4 $[M+H]^+$.

tert-butyl 2-(3-(3-((4-isopropylphenethyl)carbamoyl)piperidin-1-yl)phenoxy)-2-methylpropanoate (262b). $^1$H NMR (500 MHz, Chloroform-d) δ 7.18-7.01 (m, 5H), 6.71-6.60 (m, 1H), 6.54-6.45 (m, 2H), 6.36 (dd, J=8.1, 2.2 Hz, 1H), 3.63-3.42 (m, 2H), 3.28-3.13 (m, 2H), 3.10 (ddd, J=11.4, 6.7, 4.2 Hz, 1H), 3.00 (ddd, J=11.8, 7.2, 4.1 Hz, 1H), 2.91-2.81 (m, J=6.7 Hz, 1H), 2.79 (td, J=6.9, 5.1 Hz, 2H), 2.47 (td, J=6.6, 3.3 Hz, 1H), 1.84 (dtd, J=12.1, 7.5, 4.4 Hz, 1H), 1.78-1.67 (m, 1H), 1.65-1.51 (m, 8H), 1.44 (s, 9H), 1.22 (d, J=7.0 Hz, 6H). MS (ESI) m/z=509.4 $[M+H]^+$.

tert-butyl 2-(3-(3-((4-isopropylbenzyl)(methyl)carbamoyl)piperidin-1-yl)phenoxy)-2-methylpropanoate (262c). $^1$H NMR (500 MHz, Chloroform-d) δ 7.17-7.06 (m, 3H), 7.04-6.83 (m, 2H), 6.57-6.30 (m, 2H), 6.21 (ddd, J=16.6, 8.1, 2.2 Hz, 1H), 4.62-4.28 (m, 2H), 3.87-3.51 (m, 2H), 3.00-2.76 (m, 6H), 2.67 (dtd, J=18.5, 12.0, 2.7 Hz, 1H), 2.05-1.61 (m, 4H), 1.54-1.43 (m, 6H), 1.36 (d, J=3.4 Hz, 9H), 1.17 (dd, J=6.9, 3.2 Hz, 6H). $^{13}$C NMR (126 MHz, Chloroform-d) δ 174.44, 173.81, 173.51, 156.75, 156.73, 152.34, 152.23, 148.42, 148.00, 134.67, 133.96, 129.19, 129.14, 128.00, 127.01, 126.68, 126.22, 110.20, 110.06, 109.26, 109.10, 107.64, 107.49, 81.51, 81.49, 79.26, 79.23, 52.97, 52.52, 52.23, 50.51, 49.98, 49.85, 39.14, 38.96, 34.71, 34.02, 33.79, 33.78, 28.14, 27.82, 27.71, 25.54, 25.54, 25.46, 25.44, 24.43, 24.30, 24.00. MS (ESI) m/z=509.4 $[M+H]^+$.

tert-butyl 2-(3-(3-(ethyl(4-isopropylbenzyl)carbamoyl)piperidin-1-yl)phenoxy)-2-methylpropanoate (262d). $^1$H NMR (500 MHz, Chloroform-d) δ 7.16-7.04 (m, 3H), 7.04-6.87 (m, 2H), 6.54-6.27 (m, 2H), 6.21 (ddd, J=19.7, 7.9, 2.2 Hz, 1H), 4.62-4.31 (m, 2H), 3.75-3.49 (m, 2H), 3.42-3.16 (m, 2H), 3.03-2.52 (m, 4H), 1.96-1.57 (m, 4H), 1.50-1.41 (m, 6H), 1.35 (d, J=3.3 Hz, 9H), 1.16 (dd, J=6.9, 3.5 Hz, 6H), 1.05 (dt, J=25.1, 7.1 Hz, 3H). $^{13}$C NMR (126 MHz, Chloroform-d) δ 173.96, 173.78, 173.51, 173.48, 156.76, 156.70, 152.40, 152.30, 148.29, 147.86, 135.21, 134.44, 129.19, 129.11, 127.91, 126.93, 126.62, 126.21, 110.20, 110.08, 109.22, 109.03, 107.64, 107.42, 81.48, 81.47, 79.24, 79.21, 52.59, 52.52, 50.13, 50.03, 49.81, 47.34, 41.37, 40.81, 39.18, 39.09, 33.78, 33.76, 28.32, 28.07, 27.82, 25.55, 25.53, 25.48, 25.44, 24.48, 24.31, 24.02, 14.43, 12.72. MS (ESI) m/z=523.4 $[M+H]^+$.

tert-butyl (R)-2-(3-(3-(isopropyl(4-isopropylbenzyl)carbamoyl)piperidin-1-yl)phenoxy)-2-methylpropanoate (262e). $^1$H NMR (500 MHz, Chloroform-d) δ 7.19 (d, J=8.2 Hz, 1H), 7.15-7.04 (m, 3H), 6.98 (t, J=8.2 Hz, 1H), 6.63-6.21 (m, 3H), 5.07-4.21 (m, 3H), 3.71 (ddt, J=16.2, 12.0, 2.0 Hz, 1H), 3.57 (td, J=9.8, 7.6, 3.0 Hz, 1H), 3.18-2.56 (m, 4H), 2.05-1.63 (m, 4H), 1.59-1.52 (m, 6H), 1.43 (d, J=7.8 Hz, 9H), 1.33-1.00 (m, 12H). $^{13}$C NMR (126 MHz, Chloroform-d) δ 175.24, 173.17, 172.07, 156.75, 156.49, 148.24, 147.33, 136.04, 135.28, 130.72, 130.52, 126.82, 126.49, 126.47, 126.22, 113.66, 113.43, 112.07, 111.58, 80.20, 79.98, 56.55, 56.08, 55.83, 54.87, 49.20, 46.36, 46.15, 43.95, 38.71, 37.26, 33.70, 33.68, 26.28, 25.79, 25.24, 25.18, 25.01, 24.95, 23.99, 23.90, 22.89, 22.70, 21.78, 21.72, 20.54, 20.24. MS (ESI) m/z=537.4 $[M+H]^+$.

tert-butyl (R)-2-(3-(3-(cyclopropyl(4-isopropylbenzyl)carbamoyl)piperidin-1-yl)phenoxy)-2-methylpropanoate (262f). $^1$H NMR (500 MHz, Chloroform-d) δ 7.20-7.12 (m, 4H), 7.07 (t, J=8.2 Hz, 1H), 6.55 (dd, J=8.2, 2.3 Hz, 1H), 6.49 (t, J=2.4 Hz, 1H), 6.30 (dd, J=8.1, 2.3 Hz, 1H), 4.71-4.37 (m, 2H), 3.85-3.61 (m, 2H), 3.43 (ddt, J=11.0, 7.1, 3.4 Hz, 1H), 2.99 (dd, J=12.4, 10.9 Hz, 1H), 2.88 (p, J=6.9 Hz, 1H), 2.77 (td, J=12.1, 2.6 Hz, 1H), 2.59 (tt, J=6.9, 4.1 Hz, 1H), 2.00-1.89 (m, 1H), 1.88-1.65 (m, 3H), 1.55 (s, 6H), 1.44 (s, 9H), 1.24 (d, J=6.9 Hz, 6H), 0.97-0.75 (m, 4H). $^{13}$C NMR (126 MHz, Chloroform-d) δ 176.77, 173.50, 156.72, 152.44, 147.61, 135.69, 129.13, 127.64, 126.56, 110.16, 109.13, 107.64, 81.48, 79.24, 52.25, 49.98, 49.46, 39.86, 33.76, 29.73, 27.83, 25.53, 25.48, 24.50, 24.01, 9.40, 9.12. MS (ESI) m/z=535.4 $[M+H]^+$.

2-(3-(3-((4-isopropylbenzyl)carbamoyl)piperidin-1-yl)phenoxy)-2-methylpropanoic acid (93). $^1$H NMR (500 MHz, Chloroform-d) δ 7.30 (t, J=5.9 Hz, 1H), 7.19 (t, J=8.2 Hz, 1H), 7.14 (s, 4H), 7.08-6.96 (m, 2H), 6.84 (dd, J=8.3, 2.1 Hz, 1H), 4.39 (dd, J=14.7, 6.1 Hz, 1H), 4.24 (dd, J=14.7, 5.4 Hz, 1H), 3.56-3.35 (m, 3H), 3.18 (dtd, J=31.6, 12.0, 11.5, 3.5 Hz, 2H), 2.86 (hept, J=6.9 Hz, 1H), 2.17-2.02 (m, 1H), 2.02-1.86 (m, 2H), 1.86-1.74 (m, 1H), 1.57 (s, 6H), 1.20 (d, J=7.0 Hz, 6H). $^{13}$C NMR (126 MHz, Chloroform-d) δ 175.91, 171.84, 156.79, 148.18, 144.27, 135.09, 130.74, 127.66, 126.72, 118.97, 113.37, 111.34, 79.82, 56.79, 55.44, 43.25, 40.98, 33.78, 25.41, 25.24, 25.12, 23.98, 22.49. HRMS (ESI) Calcd for $(M-H)^-$ 437.2446, found 437.2443. HPLC purity 99.7%, $t_R$=12.69 min.

2-(3-(3-((4-isopropylphenethyl)carbamoyl)piperidin-1-yl)phenoxy)-2-methylpropanoic acid (94). $^1$H NMR (500 MHz, Methanol-$d_4$) δ 7.35 (t, J=8.2 Hz, 1H), 7.18-7.09 (m, 4H), 7.04 (dd, J=8.2, 2.2 Hz, 1H), 6.99 (t, J=2.3 Hz, 1H), 6.82 (dd, J=8.3, 2.2 Hz, 1H), 3.56 (ddd, J=15.9, 11.1, 4.3 Hz, 2H), 3.49 (dt, J=14.1, 7.2 Hz, 1H), 3.45-3.33 (m, 2H), 3.31-3.20 (m, 1H), 2.81 (dt, J=29.7, 6.9 Hz, 4H), 1.99-1.80 (m, 3H), 1.61 (s, 6H), 1.20 (dd, J=6.9, 1.1 Hz, 6H). $^{13}$C NMR (126 MHz, Methanol-$d_4$) δ 175.73, 173.70, 156.90, 146.78, 136.25, 130.22, 128.49, 126.05, 116.62, 112.76, 110.99, 79.35, 56.14, 53.71, 40.38, 34.56, 33.62, 25.68, 24.41, 24.30, 23.10, 23.12, 22.25. HRMS (ESI) Calcd for $C_{27}H_{36}N_2O_4$ $(M-H)^-$ 451.2602, found 451.2602. HPLC purity 98.0%, $t_R$=12.76 min.

2-(3-(3-((4-isopropylbenzyl)(methyl)carbamoyl)piperidin-1-yl)phenoxy)-2-methylpropanoic acid (95). $^1$H NMR (500 MHz, Chloroform-d) δ 9.01 (s, 2H), 7.26-7.19 (m, 2H), 7.19-7.12 (m, 2H), 7.11-7.08 (m, 2H), 7.08-6.98 (m, 1H), 6.86 (ddd, J=26.7, 8.6, 1.9 Hz, 1H), 4.79-4.57 (m, 1H), 4.43 (dd, J=20.4, 15.5 Hz, 1H), 3.70-3.44 (m, 4H), 3.20-2.95 (m, 4H), 2.88 (hept, J=6.9 Hz, 1H), 2.28-1.67 (m, 4H), 1.65-1.55 (m, 6H), 1.23 (dd, J=6.9, 2.0 Hz, 6H). $^{13}$C NMR (126 MHz, Chloroform-d) δ 175.46, 172.68, 171.94, 156.81, 156.69, 148.65, 148.35, 144.78, 144.17, 133.75, 133.50, 130.76, 130.62, 127.89, 127.04, 126.81, 126.52, 119.62, 118.85, 113.58, 113.41, 111.76, 111.49, 80.02, 56.49, 56.25, 55.77, 55.18, 53.35, 50.89, 37.21, 36.96, 34.85, 33.79, 33.76, 25.92, 25.35, 25.30, 25.26, 25.01, 24.97, 23.96, 23.92, 22.72. HRMS (ESI) Calcd for $C_{27}H_{36}N_2O_4$ $(M-H)^-$ 451.2602, found 451.2599. HPLC purity 99.1%, $t_R$=12.99 min.

2-(3-(3-(ethyl(4-isopropylbenzyl)carbamoyl)piperidin-1-yl)phenoxy)-2-methylpropanoic acid (96). $^1$H NMR (500 MHz, Chloroform-d) δ 7.30-7.18 (m, 3H), 7.16 (d, J=8.1 Hz, 1H), 7.13-7.01 (m, 3H), 6.87 (ddd, J=23.2, 8.2, 2.2 Hz, 1H), 4.66 (dd, J=40.0, 15.8 Hz, 1H), 4.45 (t, J=15.0 Hz, 1H), 3.78-3.21 (m, 6H), 3.20-2.96 (m, 1H), 2.94-2.81 (m, 1H), 2.45-1.64 (m, 4H), 1.60 (t, J=2.7 Hz, 6H), 1.22 (dd, J=6.9, 3.3 Hz, 6H), 1.17 (t, J=7.1 Hz, 2H), 1.10 (t, J=7.1 Hz, 1H). $^{13}$C NMR (126 MHz, Chloroform-d) δ 175.31, 172.24, 171.79, 162.29, 162.00, 156.76, 156.64, 148.58, 148.23, 144.13, 134.30, 133.90, 130.78, 130.64, 127.78, 126.99, 126.75, 126.50, 119.88, 119.18, 113.68, 113.54, 112.09, 111.76, 80.11, 79.99, 56.63, 56.41, 55.94, 55.33, 50.63, 47.88, 41.94, 41.87, 37.41, 36.95, 33.78, 33.76, 26.08, 25.77, 25.28, 24.93, 23.97, 23.92, 22.73, 22.68, 14.14, 12.60. HRMS (ESI) Calcd for $C_{28}H_{38}N_2O_4$ $(M-H)^-$ 465.2759, found 465.2758. HPLC purity 98.9%, $t_R$=13.27 min.

2-(3-(3-(isopropyl(4-isopropylbenzyl)carbamoyl)piperidin-1-yl)phenoxy)-2-methylpropanoic acid (97). $^1$H NMR (500 MHz, Chloroform-d) δ 7.28-7.08 (m, 5H), 7.06 (d, J=8.2 Hz, 1H), 7.02-6.91 (m, 1H), 6.91-6.75 (m, 1H), 4.80 (p, J=6.8 Hz, 0.5H), 4.58 (t, J=16.0 Hz, 1H), 4.40 (t, J=16.8 Hz, 1H), 4.24 (p, J=6.6 Hz, 0.5H), 3.62 (d, J=29.3 Hz, 2H), 3.50 (t, J=14.6 Hz, 1H), 3.38 (t, J=11.5 Hz, 0.5H), 3.14 (dd, J=13.2, 10.1 Hz, 1H), 2.96 (td, J=11.6, 4.4 Hz, 0.5H), 2.87 (dp, J=13.9, 6.9 Hz, 1H), 2.25 (t, J=13.6 Hz, 0.5H), 2.10-1.90 (m, 1H), 1.85-1.38 (m, 8.5H), 1.31-0.82 (m, 12H). $^{13}$C NMR (126 MHz, Chloroform-d) δ 175.24, 173.17, 156.75, 156.49, 148.24, 147.33, 136.04, 135.28, 130.72, 130.52, 126.82, 126.49, 126.47, 126.22, 113.66, 113.43, 112.07, 111.58, 80.20, 79.98, 56.55, 56.08, 55.83, 54.83, 49.20, 46.36, 46.15, 43.95, 38.71, 37.26, 33.70, 33.68, 26.28, 25.79, 25.24, 25.18, 25.01, 24.95, 23.99, 23.90, 22.89, 22.70, 21.78, 21.72, 20.54, 20.24. HRMS (ESI) Calcd for $C_{29}H_{40}N_2O_4$ $(M-H)^-$ 479.2915, found 479.2914. HPLC purity 100%, $t_R$=13.70 min.

(R)-2-(3-(3-(cyclopropyl(4-isopropylbenzyl)carbamoyl)piperidin-1-yl)phenoxy)-2-methylpropanoic acid (98). $^1$H NMR (500 MHz, Chloroform-d) δ 7.34-7.22 (m, 1H), 7.22-7.02 (m, 6H), 6.90 (dd, J=8.3, 2.2 Hz, 1H), 4.69 (d, J=14.6 Hz, 1H), 4.44 (d, J=14.4 Hz, 1H), 4.06 (dd, J=13.3, 9.6 Hz, 1H), 3.80-3.46 (m, 3H), 3.14 (td, J=12.5, 3.1 Hz, 1H), 2.89 (p, J=6.9 Hz, 1H), 2.66 (tt, J=6.8, 4.1 Hz, 1H), 2.24 (q, J=13.6 Hz, 1H), 2.13-1.93 (m, 2H), 1.77 (qd, J=13.1, 3.8 Hz, 1H), 1.62 (s, 6H), 1.25 (d, J=6.9 Hz, 6H), 1.13-0.36 (m, 4H). $^{13}$C NMR (126 MHz, Chloroform-d) δ 175.40, 174.74, 156.68, 147.94, 144.50, 134.91, 130.71, 127.52, 126.68, 119.61, 113.51, 111.79, 80.02, 56.12, 55.83, 49.86, 37.89, 33.76, 30.00, 25.65, 25.32, 24.88, 23.97, 22.94, 9.47, 8.66. HRMS (ESI) Calcd for $C_{29}H_{38}N_2O_4$ $(M-H)^-$ 477.2759, found 477.2753. HPLC purity 97.9%, $t_R$=13.45 min Scheme 18. Synthesis of 99-106

A.

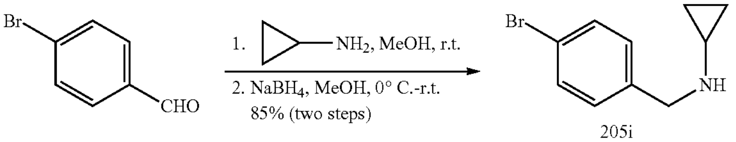

205i

B.

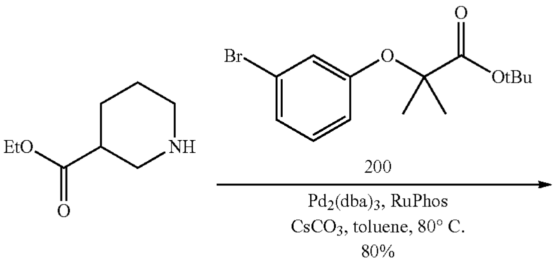

200

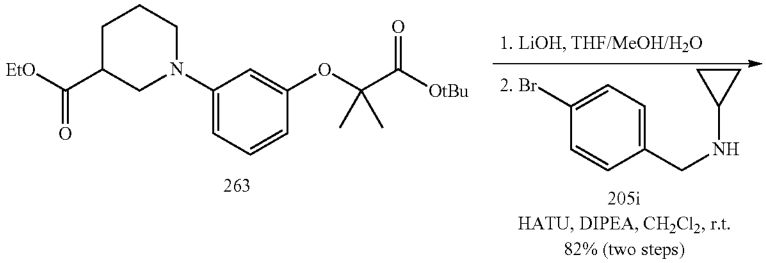

263

205i

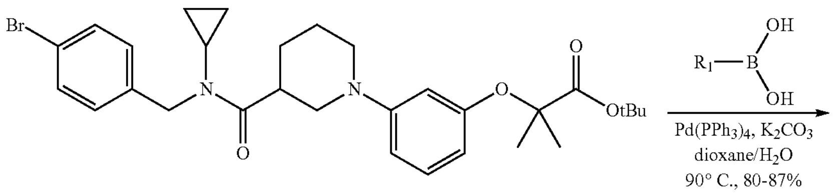

264

-continued

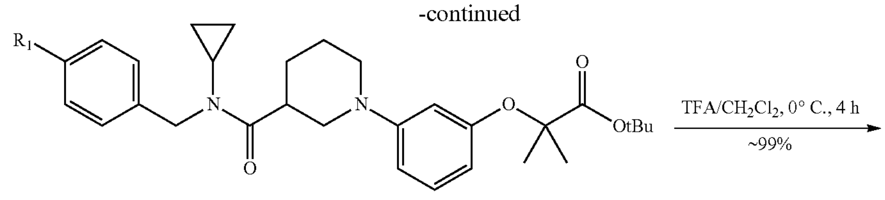

265

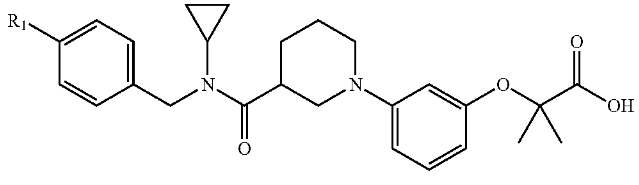

99-106

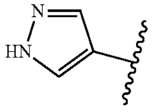 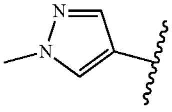 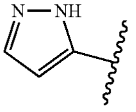 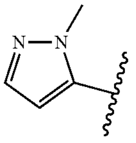

99 100 101 102

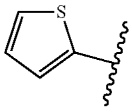 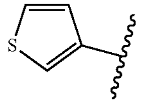 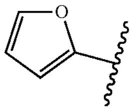 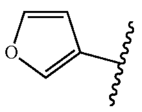

103 104 105 106

N-(4-bromobenzyl)cyclopropanamine (205i). $^1$H NMR (500 MHz, Chloroform-d) δ 7.46-7.37 (m, 2H), 7.22-7.08 (m, 2H), 3.79 (s, 2H), 2.12 (tt, J=6.5, 3.6 Hz, 1H), 0.49-0.39 (m, 2H), 0.39-0.25 (m, 2H). MS (ESI) m/z=226.0, 228.0 $[M+H]^+$.

ethyl 1-(3-((1-(tert-butoxy)-2-methyl-1-oxopropan-2-yl) oxy)phenyl)piperidine-3-carboxylate (263). $^1$H NMR (500 MHz, Chloroform-d) δ 7.04 (t, J=8.2 Hz, 1H), 6.54 (dd, J=8.1, 2.3 Hz, 1H), 6.45 (t, J=2.4 Hz, 1H), 6.31-6.21 (m, 1H), 4.12 (q, J=7.1 Hz, 2H), 3.67 (ddt, J=12.4, 3.5, 1.5 Hz, 1H), 3.42 (ddd, J=12.3, 4.9, 3.1 Hz, 1H), 2.95 (dd, J=12.4, 9.9 Hz, 1H), 2.80-2.68 (m, 1H), 2.60 (tt, J=10.0, 3.9 Hz, 1H), 2.05-1.93 (m, 1H), 1.74 (th, J=9.2, 3.1 Hz, 1H), 1.69-1.59 (m, 2H), 1.53 (s, 6H), 1.41 (s, 9H), 1.24 (t, J=7.2 Hz, 3H). MS (ESI) m/z=392.3 $[M+H]^+$, 414.3 $[M+Na]^+$.

tert-butyl 2-(3-(3-((4-bromobenzyl)(cyclopropyl)carbamoyl)piperidin-1-yl)phenoxy)-2-methylpropanoate (264). $^1$H NMR (500 MHz, Chloroform-d) δ 7.42 (d, J=8.3 Hz, 2H), 7.11 (d, J=8.3 Hz, 2H), 7.07 (t, J=8.2 Hz, 1H), 6.54 (d, J=8.2 Hz, 1H), 6.48 (s, 1H), 6.30 (d, J=8.1 Hz, 1H), 4.59 (d, J=14.7 Hz, 1H), 4.49 (d, J=14.7 Hz, 1H), 3.67 (d, J=12.1 Hz, 2H), 3.42 (s, 1H), 2.97 (t, J=11.6 Hz, 1H), 2.76 (t, J=11.0 Hz, 1H), 2.58 (s, 1H), 1.91 (d, J=8.5 Hz, 1H), 1.76 (dt, J=32.5, 8.6 Hz, 3H), 1.55 (d, J=1.9 Hz, 6H), 1.43 (d, J=2.0 Hz, 9H), 0.91-0.74 (m, 4H). MS (ESI) m/z=571.2, 573.2 $[M+H]^+$.

tert-butyl 2-(3-(3-((4-(1H-pyrazol-4-yl)benzyl)(cyclopropyl)carbamoyl)piperidin-1-yl)phenoxy)-2-methylpropanoate (265a). $^1$H NMR (500 MHz, Chloroform-d) δ 7.78 (s, 2H), 7.42 (d, J=8.1 Hz, 2H), 7.20 (d, J=8.1 Hz, 2H), 7.07 (t, J=8.2 Hz, 1H), 6.56 (d, J=8.2 Hz, 1H), 6.49 (t, J=2.2 Hz, 1H), 6.30 (d, J=8.1 Hz, 1H), 4.67 (d, J=14.7 Hz, 1H), 4.55 (d, J=14.8 Hz, 1H), 3.69 (t, J=11.3 Hz, 2H), 3.46 (t, J=10.9 Hz, 1H), 3.04-2.97 (m, 1H), 2.77 (t, J=11.0 Hz, 1H), 2.62 (dt, J=6.6, 2.8 Hz, 1H), 1.94 (d, J=10.6 Hz, 1H), 1.83-1.67 (m, 3H), 1.55 (s, 6H), 1.43 (s, 9H), 0.89-0.81 (m, 4H). MS (ESI) m/z=559.4 $[M+H]^+$ tert-butyl 2-(3-(3-(cyclopropyl(4-(1-methyl-1H-pyrazol-4-yl)benzyl)carbamoyl)piperidin-1-yl)phenoxy)-2-methylpropanoate (265b). $^1$H NMR (500 MHz, Chloroform-d) δ 7.50 (s, 1H), 7.36 (d, J=8.0 Hz, 2H), 7.29 (d, J=7.8 Hz, 2H), 7.07 (t, J=8.2 Hz, 1H), 6.55 (d, J=8.0 Hz, 1H), 6.49 (s, 1H), 6.29 (d, J=8.0 Hz, 2H), 4.65 (q, J=15.0 Hz, 2H), 3.88 (s, 3H), 3.76-3.64 (m, 2H), 3.46 (t, J=10.5 Hz, 1H), 2.99 (t, J=11.5 Hz, 1H), 2.77 (t, J=11.7 Hz, 1H), 2.69-2.65 (m, 1H), 1.95 (d, J=11.0 Hz, 1H), 1.82-1.70 (m, 3H), 1.54 (s, 6H), 1.43 (s, 9H), 0.94-0.79 (m, 4H). MS (ESI) m/z=573.4 $[M+H]^+$, 595.4 $[M+Na]^+$.

tert-butyl 2-(3-(3-((4-(1H-pyrazol-5-yl)benzyl)(cyclopropyl)carbamoyl)piperidin-1-yl)phenoxy)-2-methylpropanoate (265c). $^1$H NMR (500 MHz, Chloroform-d) δ 7.71 (d, J=8.0 Hz, 2H), 7.65 (d, J=1.4 Hz, 2H), 7.24 (d, J=8.1 Hz, 2H), 7.06 (t, J=8.2 Hz, 1H), 6.59-6.51 (m, 2H), 6.48 (t, J=2.2 Hz, 1H), 6.29 (d, J=8.1 Hz, 1H), 4.69 (d, J=14.7 Hz, 1H), 4.54 (d, J=14.7 Hz, 1H), 3.68 (t, J=9.5 Hz, 2H), 3.44 (t, J=10.9 Hz, 1H), 3.05-2.96 (m, 1H), 2.77 (t, J=11.9 Hz, 1H), 2.63-2.54 (m, 1H), 1.93 (d, J=10.7 Hz, 1H), 1.75 (ddd, J=29.2, 17.1, 8.6 Hz, 3H), 1.54 (s, 6H), 1.42 (s, 9H), 0.88-0.78 (m, 4H). MS (ESI) m/z=559.4 $[M+H]^+$ tert-butyl 2-(3-(3-(cyclopropyl(4-(1-methyl-1H-pyrazol-5-yl)benzyl)carbamoyl)piperidin-1-yl)phenoxy)-2-methylpropanoate (265d). $^1$H NMR (500 MHz, Chloroform-d) δ 7.72 (s, 1H), 7.57 (s, 1H), 7.39 (d, J=7.9 Hz, 2H), 7.20 (d, J=7.8 Hz, 2H), 7.05 (t, J=8.2 Hz, 1H), 6.54 (d, J=8.2 Hz, 1H), 6.47 (s, 1H), 6.28 (d, J=8.0 Hz, 1H), 4.63 (d, J=14.6 Hz, 1H), 4.56-4.51 (m, 1H), 3.90-3.88 (m, 3H), 3.71-3.63 (m, 2H), 3.41 (d, J=10.7 Hz, 1H), 2.98 (t, J=11.7 Hz, 1H), 2.75 (t, J=11.4 Hz, 1H), 2.61--2.55 (m, 1H), 1.92 (d, J=10.8 Hz, 1H), 1.74 (dq, J=26.8, 15.7, 11.2 Hz, 3H), 1.53 (s, 6H), 1.41 (d, J=1.2 Hz, 9H), 0.83 (ddd, J=25.3, 13.1, 8.0 Hz, 4H). MS (ESI) m/z=573.4 $[M+H]^+$ tert-butyl 2-(3-(3-(cyclopropyl(4-(thiophen-2-yl)benzyl)carbamoyl)piperidin-1-yl)phenoxy)-2-methylpropanoate (265e). $^1$H NMR (500 MHz, Chloroform-d) δ 7.50-7.43 (m, 2H), 7.19 (dd, J=3.6, 1.2 Hz, 1H), 7.18 (s, 3H), 7.02-6.92 (m, 2H), 6.47 (dd, J=8.3, 2.3 Hz, 1H), 6.41 (t, J=2.4 Hz, 1H), 6.22 (dd, J=8.1, 2.2 Hz, 1H), 4.58 (d, J=14.7 Hz, 1H), 4.47 (d, J=14.7 Hz, 1H), 3.66-3.55 (m, 2H), 3.36 (tt, J=10.9, 3.4 Hz, 1H), 2.92 (dd, J=12.5, 10.9 Hz, 1H), 2.68 (td, J=12.1, 2.7 Hz, 1H), 2.52 (tt, J=6.9, 4.1 Hz, 1H), 1.89-1.83 (m, 1H), 1.74-1.59 (m, 3H), 1.46 (s, 6H), 1.34 (s, 9H), 0.83-0.65 (m, 4H). MS (ESI) m/z=575.4 $[M+H]^+$ tert-butyl 2-(3-(3-(cyclopropyl(4-(thiophen-3-yl)benzyl)carbamoyl)piperidin-1-yl)phenoxy)-2-methylpropanoate (265f). $^1$H NMR (500 MHz, Chloroform-d) δ 7.47-7.40 (m, 2H), 7.32 (dd, J=2.6, 1.7 Hz, 1H), 7.29-7.22 (m, 2H), 7.19-7.10 (m, 2H), 6.97 (t, J=8.2 Hz, 1H), 6.45 (dd, J=8.2, 2.3 Hz, 1H), 6.39 (t, J=2.4 Hz, 1H), 6.20 (dd, J=8.0, 2.2 Hz, 1H), 4.57 (d, J=14.6 Hz, 1H), 4.47 (d, J=14.8 Hz, 1H), 3.64-3.53 (m, 2H), 3.34 (tt, J=11.2, 3.4 Hz, 1H), 2.90 (dd, J=12.5, 10.9 Hz, 1H), 2.67 (td, J=12.1, 2.7 Hz, 1H), 2.51 (tt, J=6.9, 4.1 Hz, 1H), 1.88-1.80 (m, 1H), 1.73-1.57 (m, 3H), 1.44 (s, 6H), 1.33 (s, 9H), 0.81-0.66 (m, 4H). MS (ESI) m/z=575.4 $[M+H]^+$.

tert-butyl 2-(3-(3-(cyclopropyl(4-(furan-2-yl)benzyl)carbamoyl)piperidin-1-yl)phenoxy)-2-methylpropanoate (265g). $^1$H NMR (500 MHz, Chloroform-d) δ 7.58-7.50 (m, 2H), 7.37 (d, J=1.7 Hz, 1H), 7.21-7.15 (m, 2H), 6.99 (t, J=8.2 Hz, 1H), 6.57-6.51 (m, 1H), 6.48 (dd, J=8.2, 2.3 Hz, 1H), 6.41 (t, J=2.3 Hz, 1H), 6.37 (dd, J=3.4, 1.8 Hz, 1H), 6.22 (dd, J=8.1, 2.2 Hz, 1H), 4.59 (d, J=14.7 Hz, 1H), 4.47 (d, J=14.7 Hz, 1H), 3.65-3.56 (m, 2H), 3.36 (tt, J=11.1, 3.5 Hz, 1H), 2.92 (dd, J=12.5, 10.9 Hz, 1H), 2.69 (td, J=12.1, 2.7 Hz, 1H), 2.51 (tt, J=6.9, 4.1 Hz, 1H), 1.90-1.81 (m, 1H), 1.76-1.61 (m, 3H), 1.47 (s, 6H), 1.35 (s, 9H), 0.82-0.69 (m, 4H). MS (ESI) m/z=559.4 $[M+H]^+$ tert-butyl 2-(3-(3-(cyclopropyl(4-(furan-3-yl)benzyl)carbamoyl)piperidin-1-yl)phenoxy)-2-methylpropanoate (265h). $^1$H NMR (500 MHz, Chloroform-d) δ 7.74 (t, J=1.2 Hz, 1H), 7.52-7.42 (m, 3H), 7.27 (dd, J=8.9, 7.0 Hz, 2H), 7.09 (t, J=8.2 Hz, 1H), 6.71 (dd, J=1.9, 0.9 Hz, 1H), 6.58 (dd, J=8.2, 2.3 Hz, 1H), 6.52 (t, J=2.3 Hz, 1H), 6.33 (dd, J=8.1, 2.3 Hz, 1H), 4.68 (d, J=14.7 Hz, 1H), 4.59 (d, J=14.7 Hz, 1H), 3.78-3.67 (m, 2H), 3.47 (tt, J=11.2, 3.6 Hz, 1H), 3.03 (dd, J=12.5, 10.9 Hz, 1H), 2.80 (td, J=12.1, 2.8 Hz, 1H), 2.63 (tt, J=6.9, 4.1 Hz, 1H), 2.00-1.90 (m, 1H), 1.86-1.72 (m, 3H), 1.57 (s, 6H), 1.46 (s, 9H), 0.92-0.80 (m, 4H). MS (ESI) m/z=559.4 $[M+H]^+$2-(3-(3-((4-(1H-pyrazol-4-yl)benzyl)(cyclopropyl)carbamoyl)piperidin-1-yl)phenoxy)-2-methylpropanoic acid (99). $^1$H NMR (500 MHz, DMSO-$d_6$) δ 8.02 (s, 2H), 7.55 (d, J=8.1 Hz, 2H), 7.16 (dd, J=7.9, 5.9 Hz, 3H), 6.73 (s, 1H), 6.56 (s, 1H), 6.34 (s, 1H), 4.63 (d, J=15.0 Hz, 1H), 4.40 (d, J=15.0 Hz, 1H), 3.76-3.67 (m, 1H), 3.65 (d, J=12.4 Hz, 1H), 3.48 (s, 1H), 2.92 (d, J=52.1 Hz, 2H), 2.70 (tt, J=6.8, 4.1 Hz, 1H), 1.94 (d, J=11.3 Hz, 1H), 1.79 (d, J=13.0 Hz, 1H), 1.70-1.57 (m, 2H), 1.49 (d, J=3.1 Hz, 6H), 0.90-0.75 (m, 4H). $^{13}$C NMR (126 MHz, DMSO-$d_6$) δ 175.59, 156.75, 136.50, 131.96, 131.21, 130.10, 128.03, 125.66, 121.42, 78.77, 52.98, 48.96, 38.89, 29.90, 27.39, 25.60, 25.54, 23.94, 9.50, 8.73. HRMS (ESI) Calcd for $C_{29}H_{34}N_4O_4$ (M−H): 501.2507, found 501.2512. HPLC purity 99.1%, $t_R$=10.83 min 2-(3-(3-(cyclopropyl(4-(1-methyl-1H-pyrazol-4-yl)benzyl)carbamoyl)piperidin-1-yl)phenoxy)-2-methylpropanoic acid (100). $^1$H NMR (500 MHz, Chloroform-d) δ 7.52 (d, J=2.0 Hz, 1H), 7.39-7.32 (m, 2H), 7.29 (d, J=8.1 Hz, 2H), 7.09 (t, J=8.2 Hz, 1H), 6.63 (dd, J=8.2, 2.2 Hz, 1H), 6.60 (s, 1H), 6.41 (dd, J=8.1, 2.2 Hz, 1H), 6.29 (d, J=1.9 Hz, 1H), 4.70 (d, J=14.9 Hz, 1H), 4.59 (d, J=14.9 Hz, 1H), 3.87 (s, 3H), 3.65 (dd, J=12.7, 3.5 Hz, 2H), 3.49 (s, 1H), 3.00 (t, J=11.6 Hz, 1H), 2.81-2.70 (m, 1H), 2.66 (tt, J=7.0, 4.0 Hz, 1H), 1.96 (d, J=8.0 Hz, 1H), 1.87-1.67 (m, 3H), 1.59 (s, 6H), 0.96-0.78 (m, 4H). $^{13}$C NMR (126 MHz, Chloroform-d) δ 177.06, 176.64, 155.83, 152.29, 143.43, 138.82, 138.37, 129.47, 129.33, 128.95, 127.80, 111.39, 110.96, 108.95, 106.04, 79.50, 52.34, 50.40, 49.77, 39.79, 37.38, 30.09, 27.67, 25.29, 25.15, 24.41, 9.49, 9.10. HRMS (ESI) Calcd for $C_{30}H_{36}N_4O_4$ $(M-H)^-$ 515.2664, found 515.2673. HPLC purity 99.5%, $t_R$=11.58 min 2-(3-(3-((4-(1H-pyrazol-5-yl)benzyl)(cyclopropyl)carbamoyl)piperidin-1-yl)phenoxy)-2-methylpropanoic acid (101). $^1$H NMR (500 MHz, DMSO-$d_6$) δ 7.74 (d, J=8.1 Hz, 2H), 7.70 (d, J=2.2 Hz, 1H), 7.22 (d, J=8.0 Hz, 2H), 7.14 (t, J=8.2 Hz, 1H), 6.78-6.63 (m, 2H), 6.55 (s, 1H), 6.33 (d, J=8.1 Hz, 1H), 4.65 (d, J=15.2 Hz, 1H), 4.44 (d, J=15.1 Hz, 1H), 3.78-3.69 (m, 1H), 3.65 (d, J=11.9 Hz, 1H), 3.47 (s, 1H), 2.91 (d, J=53.2 Hz, 2H), 2.73 (tt, J=6.9, 4.1 Hz, 1H), 1.95 (d, J=11.1 Hz, 1H), 1.84-1.56 (m, 3H), 1.49 (d, J=3.1 Hz, 6H), 0.92-0.70 (m, 4H). $^{13}$C NMR (126 MHz, DMSO-$d_6$) δ 175.99, 175.60, 156.75, 138.23, 133.21, 131.63, 130.07, 127.88, 125.71, 110.74, 107.82, 102.30, 78.75, 52.81, 50.43, 49.08, 38.92, 29.99, 27.45, 25.59, 25.55, 23.97, 9.48, 8.74. HRMS (ESI) Calcd for $C_{29}H_{34}N_4O_4$ $(M-H)^-$ 501.2507, found 501.2511. HPLC purity 99.5%, $t_R$=10.91 min 2-(3-(3-(cyclopropyl(4-(1-methyl-1H-pyrazol-5-yl)benzyl)carbamoyl)piperidin-1-yl)phenoxy)-2-methylpropanoic acid (102). $^1$H NMR (500 MHz, Chloroform-d) δ 7.79-7.72 (m, 1H), 7.58 (s, 1H), 7.46-7.36 (m, 2H), 7.20 (d, J=7.9 Hz, 2H), 7.09 (t, J=8.2 Hz, 1H), 6.63 (dd, J=8.2, 2.2 Hz, 1H), 6.56 (t, J=2.3 Hz, 1H), 6.45-6.35 (m, 1H), 4.67 (d, J=14.6 Hz, 1H), 4.51 (d, J=14.6 Hz, 1H), 3.93 (s, 3H), 3.64 (t, J=8.4 Hz, 2H), 3.46 (s, 1H), 2.99 (t, J=11.6 Hz, 1H), 2.79-2.69 (m, 1H), 2.58 (tt, J=6.8, 4.0 Hz, 1H), 1.93 (d, J=7.9 Hz, 1H), 1.86-1.68 (m, 3H), 1.58 (s, 6H), 0.91-0.76 (m, 4H). $^{13}$C NMR (126 MHz, Chloroform-d) δ 176.95, 176.57, 155.65, 152.32, 136.59, 136.38, 131.42, 129.48, 128.28, 127.00, 125.67, 122.91, 111.52, 111.15, 109.08, 79.63, 52.27, 50.36, 49.57, 39.77, 39.02, 29.78, 27.62, 25.22, 25.12, 24.42, 9.51, 9.04. HRMS (ESI) Calcd for $C_{30}H_{36}N_4O_4$ $(M-H)^-$ 515.2664, found 515.2674. HPLC purity 99.8%, $t_R$=11.57 min 2-(3-(3-(cyclopropyl(4-(thiophen-2-yl)benzyl)carbamoyl)piperidin-1-yl)phenoxy)-2-methylpropanoic acid (103). $^1$H NMR (500 MHz, Chloroform-d) δ 7.50-7.45 (m, 2H), 7.21 (dd, J=3.6, 1.2 Hz, 1H), 7.19-7.17 (m, 1H), 7.14 (d, J=8.0 Hz, 2H), 7.02-6.97 (m, 2H), 6.56 (dd, J=8.2, 2.3 Hz, 1H), 6.50 (d, J=2.4 Hz, 1H), 6.33 (dd, J=8.1, 2.3 Hz, 1H), 4.64 (d, J=14.7 Hz, 1H), 4.42 (d, J=14.7 Hz, 1H), 3.56 (d, J=11.6 Hz, 2H), 3.41 (tt, J=11.4, 3.6 Hz, 1H), 2.93 (t, J=11.6 Hz, 1H), 2.65 (td, J=11.9, 3.3 Hz, 1H), 2.51 (tt, J=6.9, 4.0 Hz, 1H), 1.85 (d, J=7.8 Hz, 1H), 1.74-1.62 (m, 3H), 1.50 (s, 6H), 0.83-0.71 (m, 4H). $^{13}$C NMR (126 MHz, Chloroform-d) δ 177.23, 177.06, 155.80, 152.12, 144.06, 137.48, 133.36, 129.49, 128.27, 128.03, 126.11, 124.74, 123.03, 111.51, 111.17, 109.14, 79.44, 52.36, 50.56, 49.60, 39.68, 29.87, 27.58, 25.27, 25.19, 24.35, 9.56, 8.98. HRMS (ESI) Calcd for $C_{30}H_{34}N_2O_4S$ $(M-H)^-$ 517.2167, found 517.2176. HPLC purity 99.2%, $t_R$=13.56 min 2-(3-(3-(cyclopropyl(4-(thiophen-3-yl)benzyl)carbamoyl)piperidin-1-yl)phenoxy)-2-methylpropanoic acid (104). $^1$H NMR (500 MHz, Chloroform-d) δ 7.48-7.44 (m, 2H), 7.35 (t, J=2.2 Hz, 1H), 7.29 (d, J=2.1 Hz, 2H), 7.18-7.15 (m, 2H), 7.00 (t, J=8.2 Hz, 1H), 6.56 (dd, J=8.2, 2.3 Hz, 1H), 6.51 (t, J=2.4 Hz, 1H), 6.33 (dd, J=8.1, 2.2 Hz, 1H), 4.64 (d, J=14.7 Hz, 1H), 4.44 (d, J=14.6 Hz, 1H), 3.61-3.51 (m, 2H), 3.42 (ddd, J=11.2, 7.4, 3.5 Hz, 1H), 2.98-2.89 (m, 1H), 2.65

(td, J=11.8, 3.4 Hz, 1H), 2.51 (tt, J=6.9, 4.1 Hz, 1H), 1.86 (d, J=7.8 Hz, 1H), 1.74-1.62 (m, 3H), 1.50 (s, 6H), 0.82-0.70 (m, 4H). $^{13}C$ NMR (126 MHz, Chloroform-d) δ 177.14, 177.05, 155.81, 152.08, 141.95, 137.06, 134.78, 129.49, 128.20, 126.61, 126.25, 120.19, 111.54, 111.25, 109.14, 79.44, 52.39, 50.62, 49.63, 39.68, 29.88, 27.55, 25.27, 25.18, 24.35, 9.54, 8.99. HRMS (ESI) Calcd for $C_{30}H_{34}N_2O_4S$ (M−H): 517.2167, found 517.2170. HPLC purity 99.9%, $t_R$=13.43 min 2-(3-(3-(cyclopropyl(4-(furan-2-yl)benzyl)carbamoyl)piperidin-1-yl)phenoxy)-2-methylpropanoic acid (105). $^1H$ NMR (500 MHz, Chloroform-d) δ 7.64-7.58 (m, 2H), 7.45 (d, J=1.7 Hz, 1H), 7.24 (d, J=8.1 Hz, 2H), 7.12-7.07 (m, 1H), 6.64 (dd, J=12.7, 5.9 Hz, 2H), 6.57 (t, J=2.4 Hz, 1H), 6.46 (dd, J=3.3, 1.8 Hz, 1H), 6.41 (dd, J=8.1, 2.2 Hz, 1H), 4.72 (d, J=14.6 Hz, 1H), 4.49 (d, J=14.7 Hz, 1H), 3.70-3.60 (m, 2H), 3.48 (s, 1H), 3.01 (t, J=11.6 Hz, 1H), 2.73 (dt, J=11.9, 6.3 Hz, 1H), 2.58 (tt, J=6.6, 4.0 Hz, 1H), 1.94 (d, J=8.5 Hz, 1H), 1.82-1.70 (m, 3H), 1.58 (s, 6H), 0.89-0.78 (m, 4H). $^{13}C$ NMR (126 MHz, Chloroform-d) δ 176.99, 155.58, 153.75, 152.20, 142.03, 137.32, 129.89, 129.54, 128.12, 124.00, 113.93, 111.40, 109.25, 104.93, 79.65, 52.29, 50.48, 49.63, 39.72, 29.80, 27.59, 25.18, 25.10, 24.39, 9.56, 8.96. HRMS (ESI) Calcd for $C_{30}H_{34}N_2O_5$ $(M-H)^-$ 501.2395, found 501.2405. HPLC purity 96.0%, $t_R$=13.22 min 2-(3-(3-(cyclopropyl(4-(furan-3-yl)benzyl)carbamoyl)piperidin-1-yl)phenoxy)-2-methylpropanoic acid (106). $^1H$ NMR (500 MHz, Chloroform-d) δ 7.71 (t, J=1.2 Hz, 1H), 7.46 (t, J=1.7 Hz, 3H), 7.22 (d, J=8.0 Hz, 2H), 7.09 (t, J=8.2 Hz, 1H), 6.72-6.62 (m, 2H), 6.58 (t, J=2.4 Hz, 1H), 6.41 (dd, J=8.0, 2.2 Hz, 1H), 4.71 (d, J=14.7 Hz, 1H), 4.50 (d, J=14.6 Hz, 1H), 3.70-3.57 (m, 2H), 3.48 (d, J=11.0 Hz, 1H), 3.01 (t, J=11.7 Hz, 1H), 2.74 (td, J=12.1, 11.6, 3.4 Hz, 1H), 2.58 (ddt, J=9.6, 6.8, 4.0 Hz, 1H), 1.94 (d, J=8.6 Hz, 1H), 1.84-1.70 (m, 3H), 1.58 (s, 6H), 0.90-0.77 (m, 4H). $^{13}C$ NMR (126 MHz, Chloroform-d) δ 176.99, 176.85, 155.60, 152.15, 143.68, 138.45, 136.96, 131.35, 129.52, 128.22, 126.12, 126.05, 111.66, 111.39, 109.23, 108.79, 79.62, 52.32, 50.53, 49.61, 39.71, 29.82, 27.58, 25.20, 25.12, 24.38, 9.55, 8.98. HRMS (ESI) Calcd for $C_{30}H_{34}N_2O_5$ $(M-H)^-$ 501.2395, found 501.2404. HPLC purity 98.8%, $t_R$=13.06 min Scheme 19. Synthesis of 107-108.

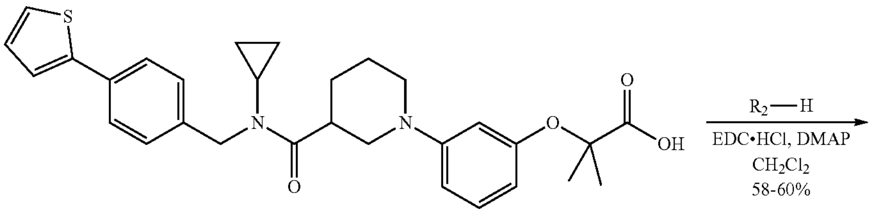

103

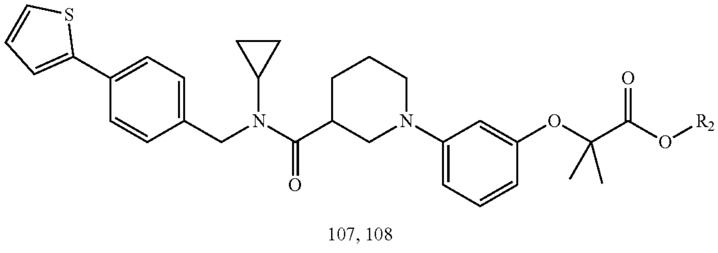

107, 108

107. $R_2$ = Me
108. $R_2$ = tBu methyl 2-(3-(3-(cyclopropyl(4-(thiophen-2-yl)benzyl)carbamoyl)piperidin-1-yl)phenoxy)-2-methylpropanoate (107). $^1$H NMR (500 MHz, Chloroform-d) δ 7.58-7.53 (m, 2H), 7.29-7.24 (m, 4H), 7.09-7.04 (m, 2H), 6.64-6.54 (m, 1H), 6.48 (s, 1H), 6.25 (dd, J=8.2, 2.2 Hz, 1H), 4.67 (d, J=14.7 Hz, 1H), 4.57 (d, J=14.8 Hz, 1H), 3.74 (s, 3H), 3.71-3.66 (m, 2H), 3.45 (s, 1H), 3.01 (t, J=11.7 Hz, 1H), 2.82-2.74 (m, 1H), 2.61 (ddt, J=10.8, 6.9, 4.0 Hz, 1H), 2.01-1.93 (m, 1H), 1.77 (ddd, J=20.6, 17.2, 8.3 Hz, 3H), 1.58 (s, 6H), 0.91-0.82 (m, 4H). $^{13}$C NMR (126 MHz, Chloroform-d) δ 176.82, 175.03, 156.36, 144.11, 137.69, 133.32, 129.43, 128.28, 128.01, 126.11, 124.71, 123.00, 110.67, 109.34, 107.94, 78.95, 52.47, 52.27, 50.07, 49.50, 39.80, 29.77, 27.78, 25.47, 25.39, 24.42, 9.47, 9.14. HRMS (ESI) Calcd for $C_{31}H_{36}N_2O_{48}$ $(M+H)^+$ 533.2469, found 533.2469. HPLC purity 99.0%, $t_R$=14.44 min tert-butyl 2-(3-(3-(cyclopropyl(4-(thiophen-2-yl)benzyl)carbamoyl)piperidin-1-yl)phenoxy)-2-methylpropanoate (108). $^1$H NMR (500 MHz, Chloroform-d) δ 7.53-7.42 (m, 2H), 7.24-7.12 (m, 4H), 7.04-6.93 (m, 2H), 6.48 (dd, J=8.2, 2.3 Hz, 1H), 6.41 (t, J=2.3 Hz, 1H), 6.22 (dd; J=8.1, 2.3 Hz, 1H), 4.59 (d, J=14.7 Hz, 1H), 4.48 (d, J=14.7 Hz, 1H), 3.69-3.51 (m, 2H), 3.37 (tt, J=10.9, 3.0 Hz, 1H), 2.99-2.82 (m, 1H), 2.70 (td, J=12.2, 2.8 Hz, 1H), 2.59-2.44 (m, 1H), 1.86 (d, J=11.3 Hz, 1H), 1.75-1.63 (m, 3H), 1.47 (s, 6H), 1.35 (s, 9H), 0.85-0.66 (m, 4H). $^{13}$C NMR (126 MHz, Chloroform-d) δ 176.89, 173.53, 156.73, 152.41, 144.12, 137.74, 133.29, 129.18, 128.28, 128.02, 126.10, 124.71, 122.99, 110.17, 109.15, 107.60, 81.52, 79.24, 52.25, 49.98, 49.51, 39.85, 29.79, 27.86, 27.83, 25.53, 25.47, 24.48, 9.46, 9.14. HRMS (ESI) Calcd for $C_{34}H_{42}N_2O_4S$ $(M+H)^+$ 575.2938 HPLC purity 100%, $t_R$=15.31 min Scheme 20. Synthesis of 109-111.

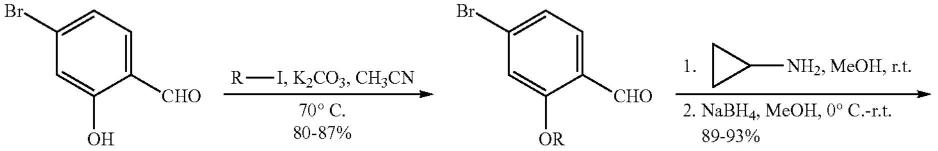

266

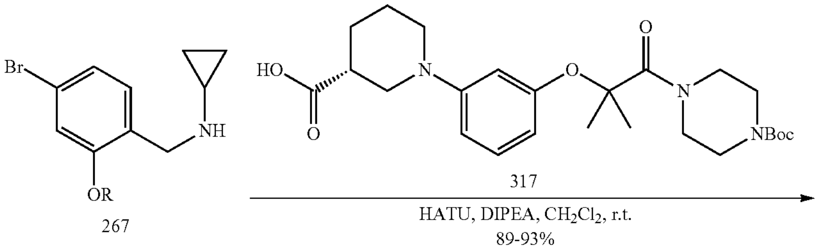

267

317

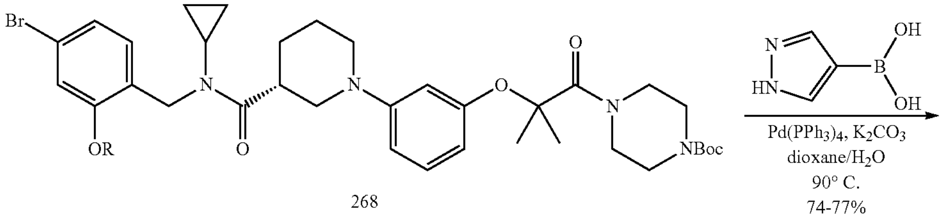

268

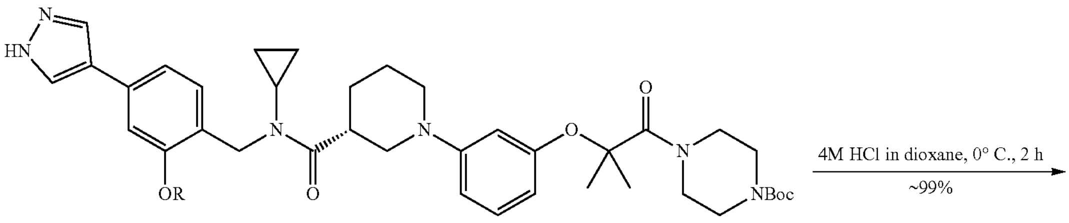

269

-continued

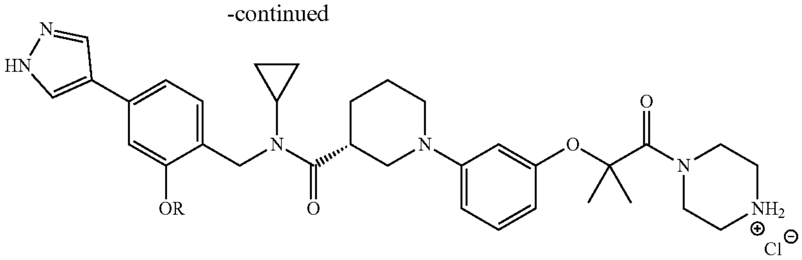

109-111

109 R = 

110 R = 

111 R = 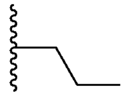

4-Bromo-2-ethoxybenzaldehyde (266a). Yield 87%, $^1$H NMR (500 MHz, $CDCl_3$) δ 10.42 (d, J=0.8 Hz, 1H), 7.68 (d, J=8.2 Hz, 1H), 7.19-7.05 (m, 2H), 4.14 (q, J=7.0 Hz, 2H), 1.48 (t, J=7.0 Hz, 3H). MS (ESI) 229.1, 231.0 $(M+H)^+$.

4-Bromo-2-isopropoxybenzaldehyde (266b). Yield 80%, $^1$H NMR (500 MHz, $CDCl_3$) δ 10.41 (d, J=0.8 Hz, 1H), 7.68 (dd, J=7.9, 0.6 Hz, 1H), 7.17-7.05 (m, 2H), 4.71-4.56 (m, 1H), 1.41 (d, J=6.1 Hz, 6H). MS (ESI) 243.1, 245.0 $(M+H)^+$.

4-Bromo-2-propoxybenzaldehyde (266c). Yield 85%, $^1$H NMR (500 MHz, $CDCl_3$) δ 10.37 (d, J=0.8 Hz, 1H), 7.68-7.50 (m, 1H), 7.11-6.94 (m, 2H), 3.96 (t, J=6.4 Hz, 2H), 1.81 (dtd, J=13.8, 7.4, 6.4 Hz, 2H), 1.00 (t, J=7.4 Hz, 3H). MS (ESI) 243.1, 245.0 $(M+H)^+$.

N-(4-Bromo-2-ethoxybenzyl)cyclopropanamine (267a). Yield 66%, $^1$H NMR (500 MHz, $CDCl_3$) δ 7.09 (d, J=7.9 Hz, 1H), 7.02 (dd, J=7.9, 1.8 Hz, 1H), 6.97 (d, J=1.8 Hz, 1H), 4.04 (q, J=7.0 Hz, 2H), 3.78 (s, 2H), 2.05 (tt, J=6.5, 3.7 Hz, 1H), 1.44 (t, J=7.0 Hz, 3H), 0.45-0.28 (m, 4H). MS (ESI) 270.1, 272.1 $(M+H)^+$.

N-(4-Bromo-2-isopropoxybenzyl)cyclopropanamine (267b). Yield 61%, $^1$H NMR (500 MHz, $CDCl_3$) δ 7.02 (d, J=7.8 Hz, 1H), 6.99-6.76 (m, 2H), 4.48 (pd, J=6.0, 0.6 Hz, 1H), 3.68 (s, 2H), 1.97 (tt, J=6.5, 3.7 Hz, 2H), 1.29 (d, J=6.1 Hz, 6H), 0.40-0.18 (m, 4H). MS (ESI) 284.1, 286.0 (M+H)+

N-(4-Bromo-2-propoxybenzyl)cyclopropanamine (267c). Yield 63%, $^1$H NMR (500 MHz, $CDCl_3$) δ 7.02 (d, J=7.9 Hz, 1H), 6.95 (dd, J=7.9, 1.8 Hz, 1H), 6.90 (d, J=1.8 Hz, 1H), 3.86 (t, J=6.4 Hz, 2H), 3.71 (s, 2H), 2.03-1.90 (m, 2H), 1.77 (dtd, J=13.8, 7.4, 6.4 Hz, 2H), 0.99 (t, J=7.4 Hz, 3H), 0.39-0.10 (m, 4H). MS (ESI) 284.1, 286.0 $(M+H)^+$.

tert-Butyl (R)-4-(2-(3-(3-((4-bromo-2-ethoxybenzyl)(cyclopropyl)carbamoyl)piperidin-1-yl)phenoxy)-2-methylpropanoyl)piperazine-1-carboxylate (268a). Yield 93%, $^1$H NMR (500 MHz, $CDCl_3$) δ 6.99 (t, J=8.2 Hz, 1H), 6.94 (dd, J=8.1, 1.8 Hz, 1H), 6.90-6.78 (m, 2H), 6.45 (dd, J=8.3, 2.3 Hz, 1H), 6.35 (t, J=2.3 Hz, 1H), 6.21-6.11 (m, 1H), 4.53 (s, 1H), 4.45 (d, J=15.5 Hz, 1H), 3.95 (q, J=7.0 Hz, 2H), 3.73 (p, J=6.9, 6.3 Hz, 2H), 3.65-3.56 (m, 2H), 3.54-3.45 (m, 2H), 3.36 (td, J=10.9, 5.4 Hz, 1H), 3.31-3.18 (m, 2H), 2.99 (tt, J=13.8, 6.7 Hz, 2H), 2.93-2.82 (m, 1H), 2.69-2.49 (m, 2H), 1.93-1.83 (m, 1H), 1.83-1.71 (m, 1H), 1.70-1.60 (m, 2H), 1.56 (d, J=2.4 Hz, 6H), 1.35 (d, J=4.7 Hz, 12H), 0.81-0.67 (m, 4H). MS (ESI) 727.3, 729.4 $(M+H)^+$.

tert-Butyl (R)-4-(2-(3-(3-((4-bromo-2-isopropoxybenzyl)(cyclopropyl)carbamoyl)piperidin-1-yl)phenoxy)-2-methylpropanoyl)piperazine-1-carboxylate (268b). Yield 89%, $^1$H NMR (500 MHz, $CDCl_3$) δ 6.99 (t, J=8.2 Hz, 1H), 6.96-6.89 (m, 2H), 6.86 (d, J=8.0 Hz, 1H), 6.46 (dd, J=8.3, 2.3 Hz, 1H), 6.35 (t, J=2.4 Hz, 1H), 6.20 (dd, J=8.1, 2.3 Hz, 1H), 4.56-4.41 (m, 3H), 3.74 (t, J=5.5 Hz, 2H), 3.64-3.45 (m, 4H), 3.44-3.33 (m, 1H), 3.26 (s, 2H), 3.08-2.95 (m, 2H), 2.90 (dd, J=12.5, 11.0 Hz, 1H), 2.68 (td, J=12.1, 3.0 Hz, 1H), 2.61 (tt, J=6.8, 4.3 Hz, 1H), 1.89 (d, J=9.5 Hz, 1H), 1.77-1.72 (m, 1H), 1.65 (d, J=7.0 Hz, 2H), 1.56 (d, J=2.4 Hz, 6H), 1.35 (s, 9H), 1.28 (d, J=6.0 Hz, 6H), 0.79-0.65 (m, 4H). MS (ESI) 741.4, 743.4 $(M+H)^+$.

tert-Butyl (R)-4-(2-(3-(3-((4-bromo-2-propoxybenzyl)(cyclopropyl)carbamoyl)piperidin-1-yl)phenoxy)-2-methylpropanoyl)piperazine-1-carboxylate (268c). Yield 92%, $^1$H NMR (500 MHz, $CDCl_3$) δ 7.07 (t, J=8.2 Hz, 1H), 7.03 (dd, J=8.1, 1.8 Hz, 1H), 6.97 (d, J=1.8 Hz, 1H), 6.92 (d, J=8.1 Hz, 1H), 6.54 (dd, J=8.3, 2.3 Hz, 1H), 6.43 (t, J=2.3 Hz, 1H), 6.28 (dd, J=8.2, 2.3 Hz, 1H), 4.63 (d, J=15.6 Hz, 1H), 4.55 (d, J=15.5 Hz, 1H), 3.93 (t, J=6.5 Hz, 2H), 3.82 (p, J=9.2, 7.4 Hz, 2H), 3.74-3.64 (m, 2H), 3.64-3.55 (m, 2H), 3.45 (ddt, J=10.8, 7.0, 3.6 Hz, 1H), 3.34 (s, 2H), 3.17-3.03 (m, 2H), 2.98 (dd, J=12.5, 10.9 Hz, 1H), 2.78-2.67 (m, 2H), 2.00-1.91 (m, 1H), 1.86-1.79 (m, 3H), 1.79-1.70 (m, 2H), 1.64 (d, J=2.4 Hz, 6H), 1.43 (s, 9H), 1.06 (t, J=7.4 Hz, 3H), 0.90-0.77 (m, 4H). MS (ESI) 741.4, 743.4 $(M+H)^+$.

tert-Butyl (R)-4-(2-(3-(3-(cyclopropyl(2-ethoxy-4-(1H-pyrazol-4-yl)benzyl)carbamoyl)piperidin-1-yl)phenoxy)-2-methylpropanoyl)piperazine-1-carboxylate (269a). Yield 77%, $^1$H NMR (500 MHz, $CDCl_3$) δ 7.75 (s, 2H), 7.07 (q, J=9.5, 8.9 Hz, 1H), 7.04-7.00 (m, 2H), 6.97-6.90 (m, 1H), 6.56 (dd, J=8.4, 2.3 Hz, 1H), 6.45 (t, J=2.4 Hz, 1H), 6.28 (dd, J=8.2, 2.3 Hz, 1H), 4.72 (d, J=15.4 Hz, 1H), 4.63-4.56 (m, 1H), 4.07 (q, J=6.9 Hz, 2H), 3.88-3.54 (m, 6H), 3.50 (tt, J=11.0, 3.5 Hz, 1H), 3.44-3.28 (m, 2H), 3.06 (ddd, J=36.7, 14.7, 7.9 Hz, 3H), 2.85-2.70 (m, 2H), 2.07-1.97 (m, 1H), 1.86-1.70 (m, 3H), 1.64 (d, J=2.1 Hz, 6H), 1.43 (d, J=7.1 Hz, 12H), 0.90-0.78 (m, 4H). MS (ESI) 715.5 $(M+H)^+$.

tert-Butyl (R)-4-(2-(3-(3-(cyclopropyl(2-isopropoxy-4-(1H-pyrazol-4-yl)benzyl)carbamoyl)piperidin-1-yl)phenoxy)-2-methylpropanoyl)piperazine-1-carboxylate (269b). Yield 74%, $^1$H NMR (500 MHz, $CDCl_3$) δ 7.67 (s, 2H), 7.02-6.87 (m, 4H), 6.48 (dd, J=8.3, 2.3 Hz, 1H), 6.37 (t, J=2.3 Hz, 1H), 6.20 (dd, J=8.1, 2.3 Hz, 1H), 4.65-4.44 (m, 3H), 3.82-3.46 (m, 6H), 3.42 (tt, J=11.1, 3.7 Hz, 1H), 3.26 (s, 2H), 2.98 (ddd, J=38.9, 12.1, 8.8 Hz, 3H), 2.74-2.61 (m, 2H), 1.97-1.85 (m, 1H), 1.81-1.63 (m, 3H), 1.56 (d, J=2.2 Hz, 6H), 1.35 (s, 9H), 1.29 (dd, J=6.1, 1.2 Hz, 6H), 0.76 (dt, J=8.8, 6.0 Hz, 4H). MS (ESI) 729.4 $(M+H)^+$.

tert-Butyl (R)-4-(2-(3-(3-(cyclopropyl(2-propoxy-4-(1H-pyrazol-4-yl)benzyl)carbamoyl)piperidin-1-yl)phenoxy)-2-methylpropanoyl)piperazine-1-carboxylate (269c). Yield 74%, $^1$H NMR (500 MHz, $CDCl_3$) δ 7.70 (s, 2H), 7.00 (t, J=8.2 Hz, 1H), 6.95 (d, J=0.9 Hz, 2H), 6.87 (s, 1H), 6.52-6.40 (m, 1H), 6.40-6.32 (m, 1H), 6.21 (dd, J=8.1, 2.3 Hz, 1H), 4.64 (d, J=15.5 Hz, 1H), 4.55 (d, J=15.6 Hz, 1H), 3.91 (t, J=6.5 Hz, 2H), 3.80-3.70 (m, 2H), 3.69-3.59 (m, 2H), 3.52 (d, J=12.0 Hz, 2H), 3.42 (s, 1H), 3.26 (s, 2H), 3.09-2.89 (m, 3H), 2.74-2.63 (m, 2H), 1.93 (d, J=11.1 Hz, 1H), 1.78 (h, J=7.0 Hz, 3H), 1.73-1.62 (m, 2H), 1.56 (d, J=2.2 Hz, 6H), 1.35 (s, 9H), 1.00 (d, J=7.4 Hz, 3H), 0.82-0.71 (m, 4H). MS (ESI) 729.4 $(M+H)^+$.

(R)-4-(2-(3-(3-(Cyclopropyl(2-ethoxy-4-(1H-pyrazol-4-yl)benzyl)carbamoyl)piperidin-1-yl)phenoxy)-2-methylpropanoyl)piperazin-1-ium chloride (109). Yield ~99%, $^1$H NMR (500 MHz, MeOD) δ 8.58 (s, 2H), 7.58 (t, J=8.2 Hz, 1H), 7.50 (dd, J=8.2, 2.1 Hz, 1H), 7.44-7.37 (m, 1H), 7.32-7.21 (m, 2H), 7.14 (d, J=7.8 Hz, 1H), 7.04 (dd, J=8.3, 2.3 Hz, 1H), 4.79 (d, J=15.7 Hz, 1H), 4.54 (d, J=15.6 Hz, 1H), 4.22 (hept, J=10.0, 9.1 Hz, 5H), 4.01-3.85 (m, 2H), 3.85-3.65 (m, 4H), 3.28-2.85 (m, 5H), 2.25 (dddd, J=38.7, 19.1, 9.7, 5.2 Hz, 3H), 2.02-1.85 (m, 1H), 1.69 (s, 6H), 1.47 (t, J=7.0 Hz, 3H), 1.15-0.86 (m, 4H). $^{13}$C NMR (126 MHz, MeOD) δ 171.55, 157.00, 156.25, 143.43, 131.62, 130.75, 129.96, 128.54, 125.31, 123.91, 118.40, 117.65, 114.56, 111.59, 108.77, 81.75, 63.79, 58.01, 56.13, 43.10, 39.59, 37.19, 30.44, 24.98, 24.78, 22.04, 13.96, 9.32, 7.40.

(R)-4-(2-(3-(3-(Cyclopropyl(2-isopropoxy-4-(1H-pyrazol-4-yl)benzyl)carbamoyl)piperidin-1-yl)phenoxy)-2-methylpropanoyl)piperazin-1-ium chloride (110). Yield ~99%, $^1$H NMR (500 MHz, MeOD) δ 8.58 (s, 2H), 7.58 (t, J=8.2 Hz, 1H), 7.51 (dd, J=8.2, 2.1 Hz, 1H), 7.41 (d, J=2.3 Hz, 1H), 7.31 (d, J=1.5 Hz, 1H), 7.24 (dd, J=7.8, 1.5 Hz, 1H), 7.14 (d, J=7.9 Hz, 1H), 7.04 (dd, J=8.4, 2.4 Hz, 1H), 4.83 (p, J=6.0 Hz, 1H), 4.75 (d, J=15.7 Hz, 1H), 4.54 (d, J=15.7 Hz, 1H), 4.32-4.09 (m, 3H), 4.06-3.86 (m, 2H), 3.86-3.66 (m, 4H), 3.26-2.75 (m, 5H), 2.25 (dddt, J=40.2, 19.2, 9.4, 5.1 Hz, 3H), 2.01 (q, J=12.1, 11.1 Hz, 1H), 1.69 (s, 6H), 1.39 (d, J=6.1 Hz, 6H), 1.11-0.84 (m, 4H). $^{13}$C NMR (126 MHz, MeOD) δ 171.54, 156.25, 155.89, 143.44, 131.62, 130.76, 129.87, 128.72, 126.29, 123.91, 118.39, 117.68, 114.56, 111.59, 110.42, 81.75, 70.34, 62.92, 58.00, 56.13, 45.46, 43.20, 43.10, 39.59, 37.22, 30.49, 24.98, 24.78, 21.18, 9.29, 7.43.

(R)-4-(2-(3-(3-(Cyclopropyl(2-propoxy-4-(1H-pyrazol-4-yl)benzyl)carbamoyl)piperidin-1-yl)phenoxy)-2-methylpropanoyl)piperazin-1-ium chloride (111). Yield ~99%, $^1$H NMR (500 MHz, MeOD) δ 8.50 (s, 2H), 7.57 (t, J=8.3 Hz, 1H), 7.50 (dd, J=8.2, 2.1 Hz, 1H), 7.43-7.34 (m, 1H), 7.28-7.17 (m, 2H), 7.11 (d, J=7.8 Hz, 1H), 7.04 (dd, J=8.3, 2.3 Hz, 1H), 4.78 (d, J=15.8 Hz, 1H), 4.57 (d, J=15.8 Hz, 1H), 4.33-4.02 (m, 5H), 4.01-3.85 (m, 2H), 3.84-3.64 (m, 5H), 3.25-2.91 (m, 4H), 2.37-2.12 (m, 3H), 2.06-1.92 (m, 1H), 1.87 (p, J=7.0 Hz, 2H), 1.69 (s, 6H), 1.14-0.84 (m, 7H). $^{13}$C NMR (126 MHz, MeOD) δ 171.55, 157.02, 156.25, 143.46, 131.61, 130.77, 130.34, 128.21, 125.08, 123.67, 118.37, 117.57, 114.54, 111.57, 108.69, 81.74, 69.67, 57.97, 56.12, 43.10, 39.59, 37.23, 30.49, 24.98, 24.78, 22.39, 9.76, 9.23, 7.36.

Scheme 21. Synthesis of 112.

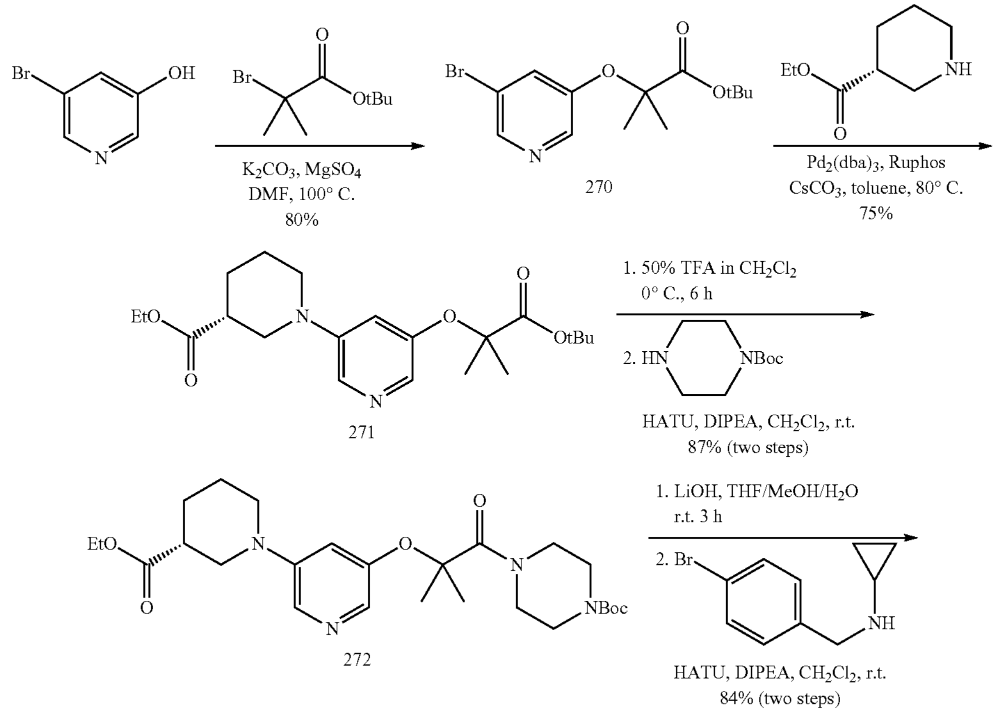

-continued

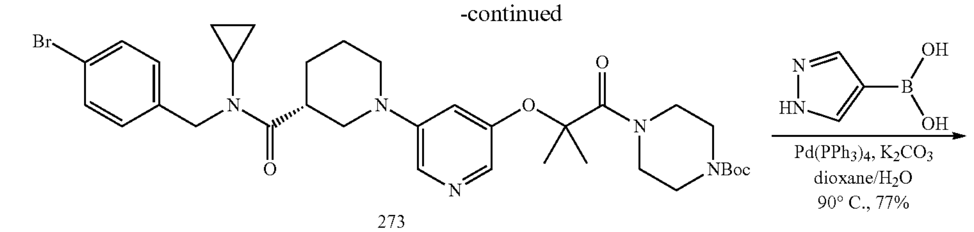

273

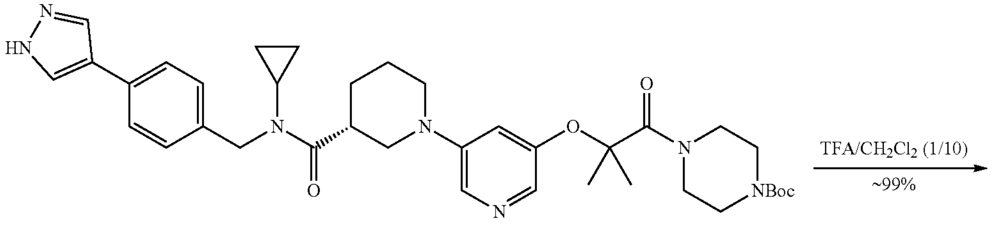

274

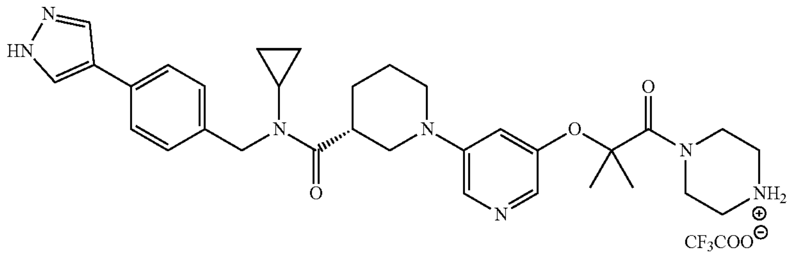

112 tert-Butyl 2-((5-bromopyridin-3-yl)oxy)-2-methylpropanoate (270). Yield 80%. $^1$H NMR (500 MHz, $CDCl_3$) δ 8.23 (d, J=1.9 Hz, 1H), 8.11 (d, J=2.6 Hz, 1H), 7.26 (dd, J=2.6, 1.9 Hz, 1H), 1.53 (s, 6H), 1.38 (s, 9H). MS (ESI) 316.0, 318.1 $(M+H)^+$.

Ethyl (R)-1-(5-((1-(tert-butoxy)-2-methyl-1-oxopropan-2-yl)oxy)pyridin-3-yl)piperidine-3-carboxylate (271). Yield 75%, $^1$H NMR (500 MHz, $CDCl_3$) δ 7.91 (d, J=2.5 Hz, 1H), 7.63 (d, J=2.3 Hz, 1H), 6.69 (t, J=2.4 Hz, 1H), 4.10 (q, J=7.1 Hz, 2H), 3.61 (ddd, J=12.6, 3.5, 1.7 Hz, 1H), 3.38 (dt, J=12.2, 4.2 Hz, 1H), 3.00 (dd, J=12.5, 9.7 Hz, 1H), 2.88-2.72 (m, 1H), 2.57 (tt, J=9.9, 3.9 Hz, 1H), 2.01-1.90 (m, 1H), 1.78-1.70 (m, 1H), 1.67-1.55 (m, 2H), 1.51 (s, 6H), 1.39 (s, 9H), 1.21 (t, J=7.2 Hz, 3H). MS (ESI) 393.2 $(M+H)^+$.

tert-Butyl (R)-4-(2-((5-(3-(ethoxycarbonyl)piperidin-1-yl)pyridin-3-yl)oxy)-2-methylpropanoyl)piperazine-1-carboxylate (272). Yield 87%. $^1$H NMR (500 MHz, $CDCl_3$) δ 7.90 (d, J=2.4 Hz, 1H), 7.62 (d, J=2.4 Hz, 1H), 6.62 (t, J=2.4 Hz, 1H), 4.10 (q, J=7.2 Hz, 2H), 3.72 (s, 2H), 3.63-3.51 (m, 3H), 3.40-3.24 (m, 3H), 3.13-2.98 (m, 3H), 2.80 (ddd, J=12.9, 10.2, 3.2 Hz, 1H), 2.57 (tt, J=9.8, 3.9 Hz, 1H), 2.01-1.89 (m, 1H), 1.75 (ddt, J=11.6, 6.1, 3.0 Hz, 1H), 1.58 (s, 8H), 1.36 (s, 9H), 1.21 (t, J=7.1 Hz, 3H). MS (ESI) 505.3 $(M+H)^+$.

tert-Butyl (R)-4-(2-((5-(3-((4-bromobenzyl)(cyclopropyl)carbamoyl)piperidin-1-yl)pyridin-3-yl)oxy)-2-methylpropanoyl)piperazine-1-carboxylate (273). Yield 84%, 1H NMR (500 MHz, $CDCl_3$) δ 7.87 (d, J=2.4 Hz, 1H), 7.61 (d, J=2.3 Hz, 1H), 7.42-7.30 (m, 2H), 7.10-7.00 (m, 2H), 6.59 (t, J=2.4 Hz, 1H), 4.57 (d, J=14.7 Hz, 1H), 4.40 (d, J=14.8 Hz, 1H), 3.71 (d, J=5.8 Hz, 2H), 3.62-3.48 (m, 4H), 3.36-3.21 (m, 3H), 3.06 (t, J=5.2 Hz, 2H), 2.97 (dd, J=12.6, 11.0 Hz, 1H), 2.75 (td, J=12.4, 2.9 Hz, 1H), 2.54 (tt, J=7.1, 3.9 Hz, 1H), 1.92-1.82 (m, 1H), 1.81-1.54 (m, 9H), 1.36 (s, 9H), 0.88-0.67 (m, 4H). MS (ESI) 684.3, 686.2 $(M+H)^+$.

tert-Butyl (R)-4-(2-((5-(3-((4-(1H-pyrazol-4-yl)benzyl)(cyclopropyl)carbamoyl)piperidin-1-yl)pyridin-3-yl)oxy)-2-methylpropanoyl)piperazine-1-carboxylate (274). Yield 77%, $^1$H NMR (500 MHz, $CDCl_3$) δ 7.89 (d, J=2.4 Hz, 1H), 7.74 (s, 2H), 7.61 (d, J=2.4 Hz, 1H), 7.41-7.33 (m, 2H), 7.14 (d, J=8.1 Hz, 2H), 6.61 (t, J=2.4 Hz, 1H), 4.61 (d, J=14.7 Hz, 1H), 4.47 (d, J=14.7 Hz, 1H), 3.78-3.44 (m, 6H), 3.37 (tt, J=11.2, 3.6 Hz, 1H), 3.26 (d, J=5.6 Hz, 2H), 3.12-2.96 (m, 3H), 2.75 (td, J=12.3, 2.7 Hz, 1H), 2.62-2.51 (m, 1H), 1.94-1.87 (m, 1H), 1.80-1.53 (m, 9H), 1.35 (s, 9H), 0.86-0.73 (m, 4H). MS (ESI) 672.4 $(M+H)^+$.

(R)-4-(2-((5-(3-((4-(1H-pyrazol-4-yl)benzyl)(cyclopropyl)carbamoyl)piperidin-1-yl)pyridin-3-yl)oxy)-2-methylpropanoyl)piperazin-1-ium chloride (112). Yield ~99%. $^1$H NMR (500 MHz, MeOD) δ 8.18 (d, J=2.4 Hz, 1H), 8.10 (s, 2H), 7.65 (d, J=2.0 Hz, 1H), 7.62-7.53 (m, 2H), 7.36 (t, J=2.4 Hz, 1H), 7.28 (d, J=8.1 Hz, 2H), 4.75 (d, J=14.9 Hz, 1H), 4.54 (d, J=15.0 Hz, 1H), 4.18-3.78 (m, 6H), 3.54 (tt, J=10.6, 3.7 Hz, 1H), 3.32-3.28 (m, 1H), 3.25-3.05 (m, 5H), 2.86-2.79 (m, 1H), 2.15-2.04 (m, 1H), 1.93 (dt, J=13.2, 3.3 Hz, 1H), 1.87-1.69 (m, 8H), 0.98-0.81 (m, 4H). $^{13}$C NMR (126 MHz, MeOD) δ 176.82, 170.60, 160.57 (q, J=37.3 Hz), 154.60, 149.42, 136.56, 130.81, 130.61, 127.80, 125.50, 123.72-121.83 (m), 118.57, 117.31, 115.49, 115.00, 83.20, 49.36, 49.14, 42.99, 38.87, 29.89, 26.91, 24.60, 24.38, 23.26, 8.66, 7.88.

Scheme 22. Synthesis of One of the Celebron (CBRN) Ligands.

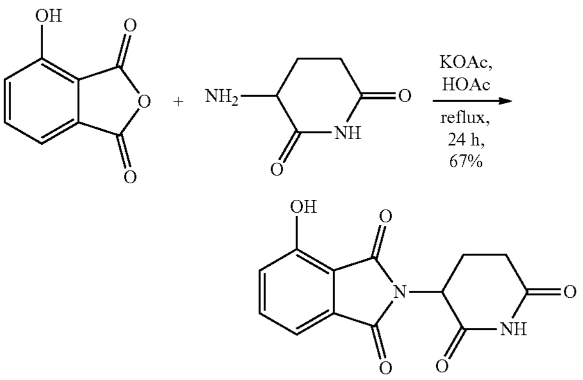

301

2-(2,6-dioxopiperidin-3-yl)-4-hydroxyisoindoline-1,3-dione (301). In a round-bottom flask, 3-hydroxyphthalic anhydride (2.0 g, 12.2 mmol, 1.0 eq), KOAc (3.72 g, 37.82 mmol, 3.1 eq) and 3-aminoperidine-2,6-dione hydrochloride (2.2 g, 13.4 mmol, 1.1 eq) were mixed in acetic acid (40 mL). The resulting reaction mixture was heated to reflux for 24 h. After cooling to ambient temperature, solvent was evaporated and washed with water to yield brown solid which was purified by recrystallization with MeOH with to give the desired product 301 (2.23 g, 67%). $^1H$ NMR (500 MHz, DMSO-$d_6$) δ 11.17 (s, 1H), 11.08 (s, 1H), 7.65 (dd, J=8.4, 7.2 Hz, 1H), 7.36-7.29 (m, 1H), 7.25 (dd, J=8.4, 0.8 Hz, 1H), 5.07 (dd, J=12.8, 5.5 Hz, 1H), 2.88 (ddd, J=16.9, 13.8, 5.5 Hz, 1H), 2.62-2.54 (m, 2H), 2.02 (ddq, J=10.5, 5.5, 3.1, 2.5 Hz, 1H). $^{13}C$ NMR (126 MHz, DMSO-$d_6$) δ 170.01, 167.02, 165.81, 155.46, 136.39, 133.16, 123.56, 114.37, 114.30, 48.65, 30.97, 22.04.

Scheme 23. Synthesis of one of the von Hippel-Lindau E3 ligase (VHL) ligands.

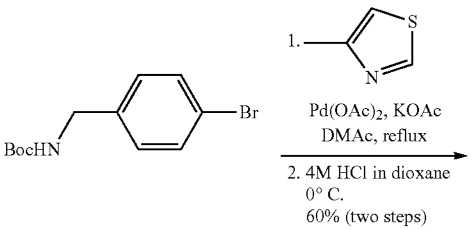

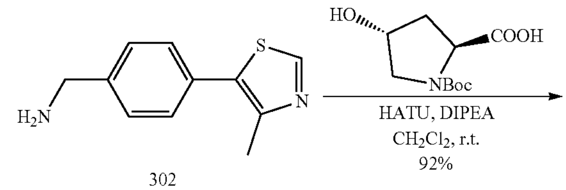

302

-continued

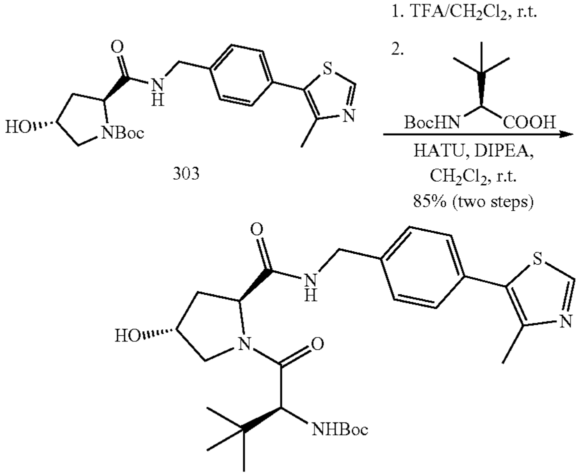

303

304

(4-(4-methylthiazol-5-yl)phenyl) methanamine (302). A solution of tert-butyl (4-bromobenzyl) carbamate (1 eq), 4-methylthiazole (2 eq), $Pd(OAc)_2$ (1%), and KOAc (2 eq) in N,N-dimethylacetamide (DMAc) was refluxed under Ar overnight. The mixture was concentrated and purified by flash chromatography to yield pure compound, which was added to 4 M HCl in dioxane and stirred at 0° C. for 4 h. The mixture was concentrated and ethyl acetate and saturated $NaHCO_3$ were added. The organic phase was washed by brine and dried over $Na_2SO_4$ and concentrated to yield compound 302 (yield 60%). $^1H$ NMR (500 MHz, $CD_3OD$) δ 8.87 (s, 1H), 7.43 (s, 4H), 3.84 (s, 2H), 2.47 (s, 3H). MS (ESI) 205.2 $(M+H)^+$.

tert-butyl(2S,4R)-4-hydroxy-2-((4-(4-methylthiazol-5-yl) benzyl)carbamoyl) pyrrolidine-1-carboxylate (303). To a solution of 302 (1 eq) and (2S,4R)-1-(tert-butoxycarbonyl)-4-hydroxypyrrolidine-2-carboxylic acid (1 eq) in $CH_2Cl_2$ were added HATU (1.5 eq) and DIPEA (2 eq). The mixture was stirred at room temperature overnight. Water was added to the mixture and the organic phase was concentrated and purified by flash chromatography to yield 303 (yield 92%). $^1H$ NMR (400 MHz, $CDCl_3$) δ 8.67 (s, 1H), 7.42-7.29 (m, 4H), 4.48 (d, J=16.7 Hz, 4H), 3.51 (dd, J=11.0, 4.7 Hz, 2H), 2.59-2.44 (m, 4H), 2.03 (d, J=7.4 Hz, 2H), 1.43 (s, 9H). MS (ESI) 418.3 $(M+H)^+$.

tert-butyl ((S)-1-((2S,4R)-4-hydroxy-2-((4-(4-methylthiazol-5-yl)benzyl)carbamoyl) pyrrolidin-1-yl)-3,3-dimethyl-1-oxobutan-2-yl) carbamate (304). Compound 303 (1 eq) was dissolved in TFA/$CH_2Cl_2$ (1/10) and stirred at room temperature for 6 h. The mixture was concentrated and redissolved in $CH_2Cl_2$. (S)-2-((tert-butoxycarbonyl)amino)-3,3-dimethylbutanoic acid (1 eq), HATU (1.5 eq), and DIPEA (2 eq) were added to the mixture and stirred at room temperature overnight. Water was added and organic phase was concentrated and purified by flash chromatography to produce 304 (yield 85%). $^1H$ NMR (500 MHz, $CDCl_3$) δ 8.61 (s, 1H), 7.28 (q, J=8.2 Hz, 4H), 5.08 (d, J=9.0 Hz, 1H), 4.71 (t, J=7.9 Hz, 1H), 4.57-4.41 (m, 2H), 4.25 (dd, J=14.9, 5.1 Hz, 1H), 4.06 (t, J=10.8 Hz, 2H), 3.49 (dd, J=11.4, 3.5 Hz, 1H), 2.55 (ddd, J=12.8, 7.8, 4.6 Hz, 1H), 2.45 (s, 3H), 2.06 (dd, J=13.6, 8.3 Hz, 1H), 1.34 (s, 9H), 0.84 (s, 9H).

Scheme 24. Synthesis of celebron (CBRN) ligand with link A.

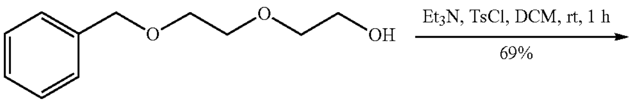

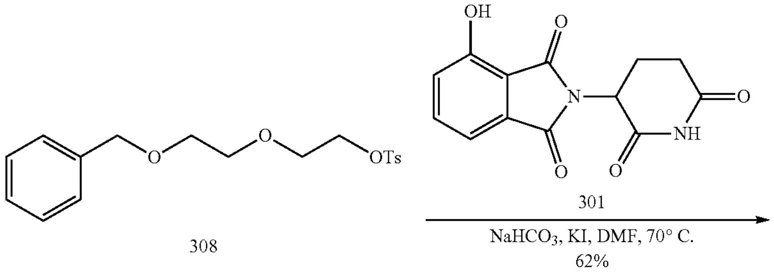

301

308

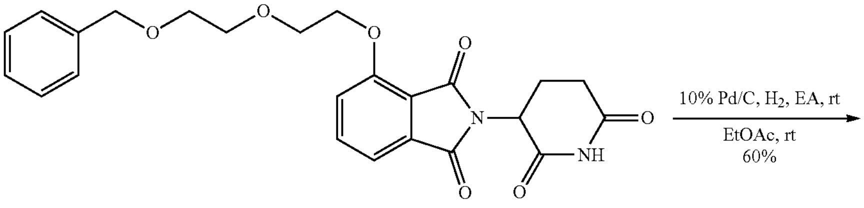

306

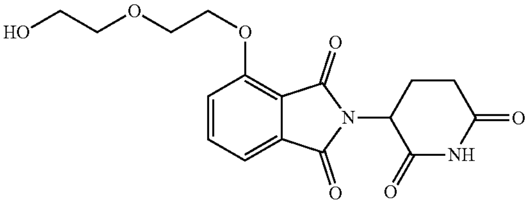

307

2-(2-(benzyloxy) ethoxy)ethyl 4-methylbenzenesulfonate (305). To a solution of alcohol (1.0 eq) was added $Et_3N$ (3.0 eq) and TsCl (1.5 eq) at 0° C. The mixture was stirred at room temperature for 1 h. Then mixture was concentrated under reduced pressure to remove the solvent. The residue was purified by column chromatography. The title compound 305 (2.44 g, 69%) was synthesized. $^1H$ NMR (500 MHz, Chloroform-d) δ 7.79 (d, J=8.3 Hz, 2H), 7.37-7.25 (m, 7H), 4.53 (s, 2H), 4.20-4.14 (m, 2H), 3.72-3.67 (m, 2H), 3.63-3.59 (m, 2H), 3.59-3.54 (m, 2H), 2.42 (s, 3H). $^{13}C$ NMR (126 MHz, Chloroform-d) δ 144.77, 138.12, 133.00, 129.81, 128.39, 127.97, 127.72, 127.65, 73.28, 70.81, 69.37, 69.27, 68.70, 21.63.

4-(2-(2-(benzyloxy) ethoxy) ethoxy)-2-(2,6-dioxopiperidin-3-yl) isoindoline-1,3-dione (306). To a solution of compound 301 (0.14 g, 0.5 mmol), compound 305 (1.0 mmol) in DMF (4.0 mL) was added $NaHCO_3$ (84 mg, 1.0 mmol) and KI (10 mg). The reaction mixture was stirred at 70° C. for 12 h prior to being taken up in ethyl acetate and water. The organic layer was separated, dried, and evaporated. The residue was purified by column chromatography to afford the desired product. The title compound 306 (0.14 g, 62%) was synthesized. $^1H$ NMR (500 MHz, Chloroform-d) δ 8.11 (s, 1H), 7.37 (dd, J=8.5, 7.3 Hz, 1H), 7.18 (dd, J=7.3, 0.7 Hz, 1H), 7.07-7.05 (m, 3H), 7.02-6.98 (m, 2H), 4.68 (dd, J=12.3, 5.4 Hz, 1H), 4.29 (s, 2H), 4.09 (dd, J=5.3, 4.3 Hz, 2H), 3.72-3.65 (m, 2H), 3.57-3.50 (m, 2H), 3.42-3.35 (m, 2H), 2.63-2.40 (m, 3H), 1.87-1.76 (m, 1H). $^{13}C$ NMR (126 MHz, Chloroform-d) δ 171.13, 168.17, 167.01, 165.59, 156.46, 138.23, 136.44, 133.73, 128.35, 127.75, 127.60, 119.62, 117.32, 116.14, 73.23, 71.19, 69.54, 69.45, 69.35, 49.10, 31.38, 22.59.

2-(2,6-dioxopiperidin-3-yl)-4-(2-(2-hydroxyethoxy) ethoxy) isoindoline-1,3-dione (307). To a solution of alcohol with compound 306 in ethyl acetate was added 10% Pd/C (0.1 eq, weight). After evacuating and flushing the flask with hydrogen gas three times, the reaction mixture was stirred under hydrogen atmosphere for 3 h. Upon completion, Pd/C was removed via filtration. The filtrate was concentrated under vacuum and the crude product was purified via column chromatography to give the desired product. The title compound 307 (0.024 g, 60%) was synthesized. $^1H$ NMR (500 MHz, Chloroform-d) δ 8.39 (s, 1H), 7.67 (dd, J=8.5, 7.3 Hz, 1H), 7.46 (dd, J=7.3, 0.7 Hz, 1H), 7.23 (dd, J=8.5, 0.7 Hz, 1H), 4.97 (dd, J=12.4, 5.3 Hz, 1H), 4.37-4.30 (m, 2H), 4.00-3.95 (m, 2H), 3.77 (t, J=4.8 Hz, 2H), 3.75-3.70 (m, 2H), 2.90-2.70 (m, 4H), 2.13-2.07 (m, 1H). $^{13}C$ NMR (126 MHz, Chloroform-d) δ 171.12, 168.20, 166.98, 165.93, 156.37, 136.61, 133.78, 119.23, 117.40, 116.29, 72.75, 69.05, 68.98, 61.77, 49.19, 31.42, 22.61.

133.04, 129.82, 128.38, 127.99, 127.75, 127.62, 73.25, 70.79, 70.70, 70.60, 69.43, 69.26, 68.71, 21.65.

4-(2-(2-(2-(benzyloxy) ethoxy) ethoxy) ethoxy)-2-(2,6-dioxopiperidin-3-yl) isoindoline-1,3-dione (309). To a solution of compound 301 (0.14 g, 0.5 mmol), compound 308 (1.0 mmol) in DMF (4.0 mL) was added $NaHCO_3$ (84 mg, Scheme 25. Synthesis of celebron (CBRN) ligand with link B.

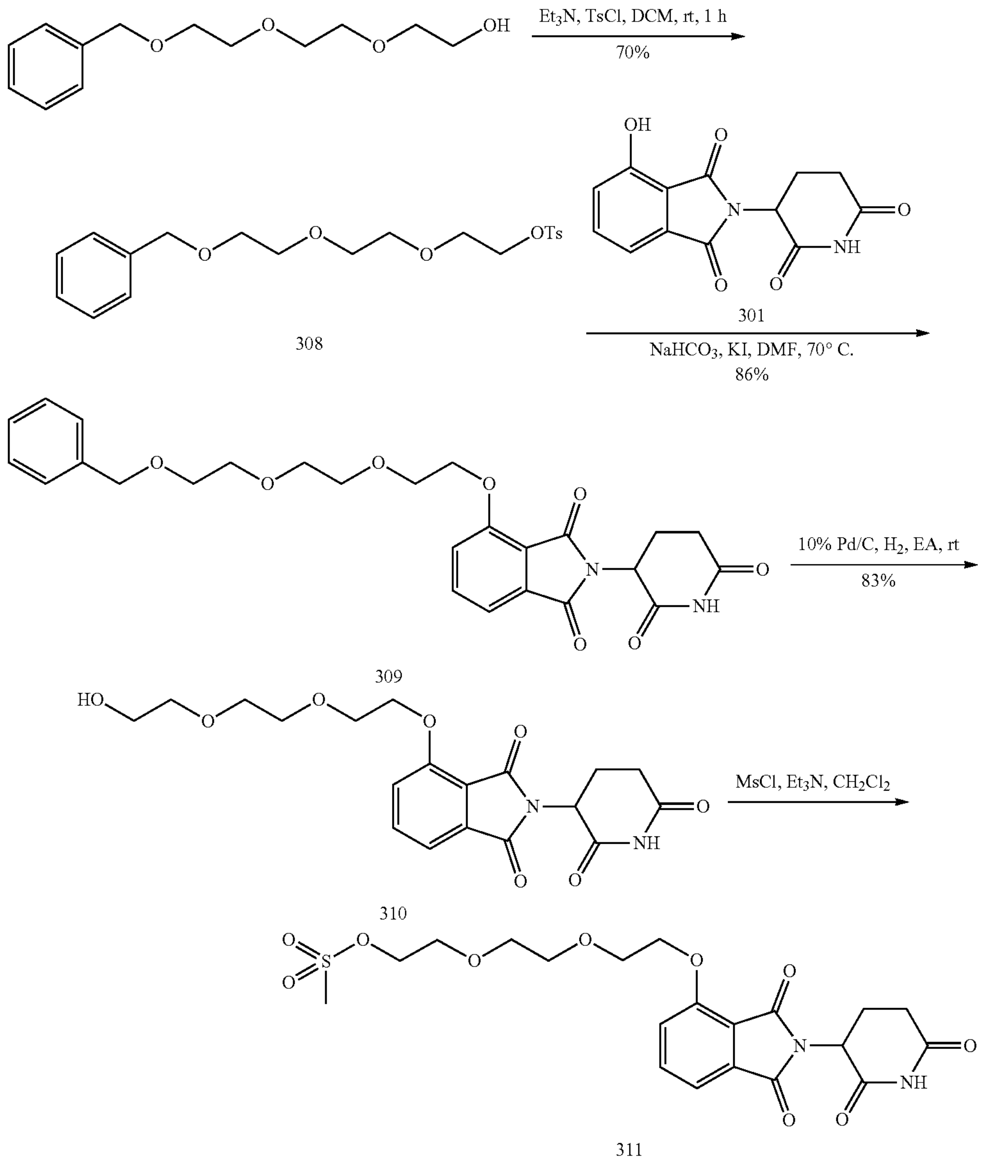

2-(2-(2-(benzyloxy) ethoxy) ethoxy)ethyl 4-methylbenzenesulfonate (308). To a solution of alcohol (1.0 eq) was added $Et_3N$ (3.0 eq) and TsCl (1.5 eq) at 0° C. The mixture was stirred at room temperature for 1 h. Then mixture was concentrated under reduced pressure to remove the solvent. The residue was purified by column chromatography. The title compound 308 (5.5 g, 70%) was synthesized. $^{1}H$ NMR (500 MHz, Chloroform-d) & 7.70-7.64 (m, 2H), 7.24-7.14 (m, 7H), 4.44 (s, 2H), 4.06-4.01 (m, 2H), 3.59-3.55 (m, 2H), 3.54-3.51 (m, 2H), 3.51-3.48 (m, 2H), 3.47 (s, 4H), 2.31 (s, 3H). $^{13}C$ NMR (126 MHz, Chloroform-d) δ 144.78, 138.25, 1.0 mmol) and KI (10 mg). The reaction mixture was stirred at 70° C. for 12 h prior to being taken up in ethyl acetate and water. The organic layer was separated, dried, and evaporated. The residue was purified by column chromatography to afford the desired product. The title compound 309 (1.5 g, 86%) was synthesized. $^{1}H$ NMR (500 MHz, Chloroform-d) δ 8.09 (s, 1H), 7.67 (dd, J=8.5, 7.3 Hz, 1H), 7.49-7.46 (m, 1H), 7.36-7.34 (m, 4H), 7.30-7.28 (m, 2H), 5.01-4.90 (m, 1H), 4.58 (s, 2H), 4.37 (dd, J=5.7, 4.0 Hz, 2H), 3.99-3.94 (m, 2H), 3.83-3.78 (m, 2H), 3.71-3.68 (m, 4H), 3.67-3.63 (m, 3H), 2.93-2.72 (m, 3H), 2.16-2.09 (m, 1H). $^{13}C$ NMR (126 MHz, Chloroform-d) δ 170.87, 167.99, 167.01, 165.59, 156.52, 138.31, 136.48, 133.77, 128.39, 128.37, 127.80, 127.76, 127.63, 119.64, 117.36, 116.18; 73.26, 71.19, 70.75, 70.68, 69.48, 69.46, 69.36, 53.47, 49.14, 31.42, 22.64.

2-(2,6-dioxopiperidin-3-yl)-4-(2-(2-(2-hydroxyethoxy) ethoxy) ethoxy) isoindoline-1,3-dione (310). To a solution of compound 309 in ethyl acetate was added 10% Pd/C (0.1 eq, weight). After evacuating and flushing the flask with hydrogen gas three times, the reaction mixture was stirred under hydrogen atmosphere for 3 h. Upon completion, Pd/C was removed via filtration. The filtrate was concentrated under vacuum and the crude product was purified via column chromatography to give the desired product. The title compound 310 (1.02 g, 83%) was synthesized. $^1$H NMR (500 MHz, Chloroform-d) δ 8.22 (s, 1H), 7.67 (dd, J=8.5, 7.3 Hz, 1H), 7.47 (dd, J=7.3, 0.7 Hz, 1H), 7.28-7.24 (m, 2H), 4.95 (dd, J=12.3, 5.4 Hz, 1H), 4.39-4.33 (m, 2H), 3.99-3.92 (m, 2H), 3.83-3.78 (m, 2H), 3.75-3.66 (m, 4H), 3.64-3.58 (m, 2H), 2.92-2.69 (m, 3H), 2.54 (t, J=6.2 Hz, 1H), 2.15-2.08 (m, 1H). $^{13}$C NMR (126 MHz, Chloroform-d) δ 170.98, 168.12, 166.99, 165.72, 156.42, 136.55, 133.81, 119.47, 117.40, 116.28, 72.51, 71.26, 70.44, 69.36, 61.80, 49.18, 31.43, 22.66.

2-(2-(2-((2-(2,6-dioxopiperidin-3-yl)-1,3-dioxoisoindolin-4-yl)oxy) ethoxy) ethoxy)ethyl methanesulfonate (311). To a solution of compound 310 (0.04 g, 0.1 mmol) and MsCl (23 mg, 0.2 mmol) in dry DCM (2.0 mL) was added TEA (30 mg, 0.3 mmol) dropwise at 0° C. Then the mixture was stirred for 1 h at 0° C. The reaction mixture was stirred at 0° C. for 1 h prior to being taken up in DCM and water. The organic layer was separated, dried, and evaporated. The residue was purified by column chromatography to afford the desired product 311 (0.05 g). $^1$H NMR (500 MHz, Chloroform-d) δ 8.48 (s, 1H), 7.67 (dd, J=8.5, 7.2 Hz, 1H), 7.46 (dd, J=7.3, 0.7 Hz, 1H), 7.24 (d, J=8.5 Hz, 1H), 4.95 (dd, J=12.0, 5.4 Hz, 1H), 4.37-4.30 (m, 4H), 3.95-3.90 (m, 2H), 3.81-3.75 (m, 4H), 3.71-3.67 (m, 2H), 3.04 (s, 3H), 2.89-2.69 (m, 3H), 2.11 (ddd, J=7.8, 5.8, 2.1 Hz, 1H). $^{13}$C NMR (126 MHz, Chloroform-d) δ 171.21, 168.34, 166.98, 165.61, 156.32, 136.54, 133.82, 119.26, 117.30, 116.19, 71.17, 70.54, 69.41, 69.27, 69.21, 69.01, 49.15, 37.61, 31.38, 22.63.

Scheme 26. Synthesis of celebron (CBRN) ligand with link C.

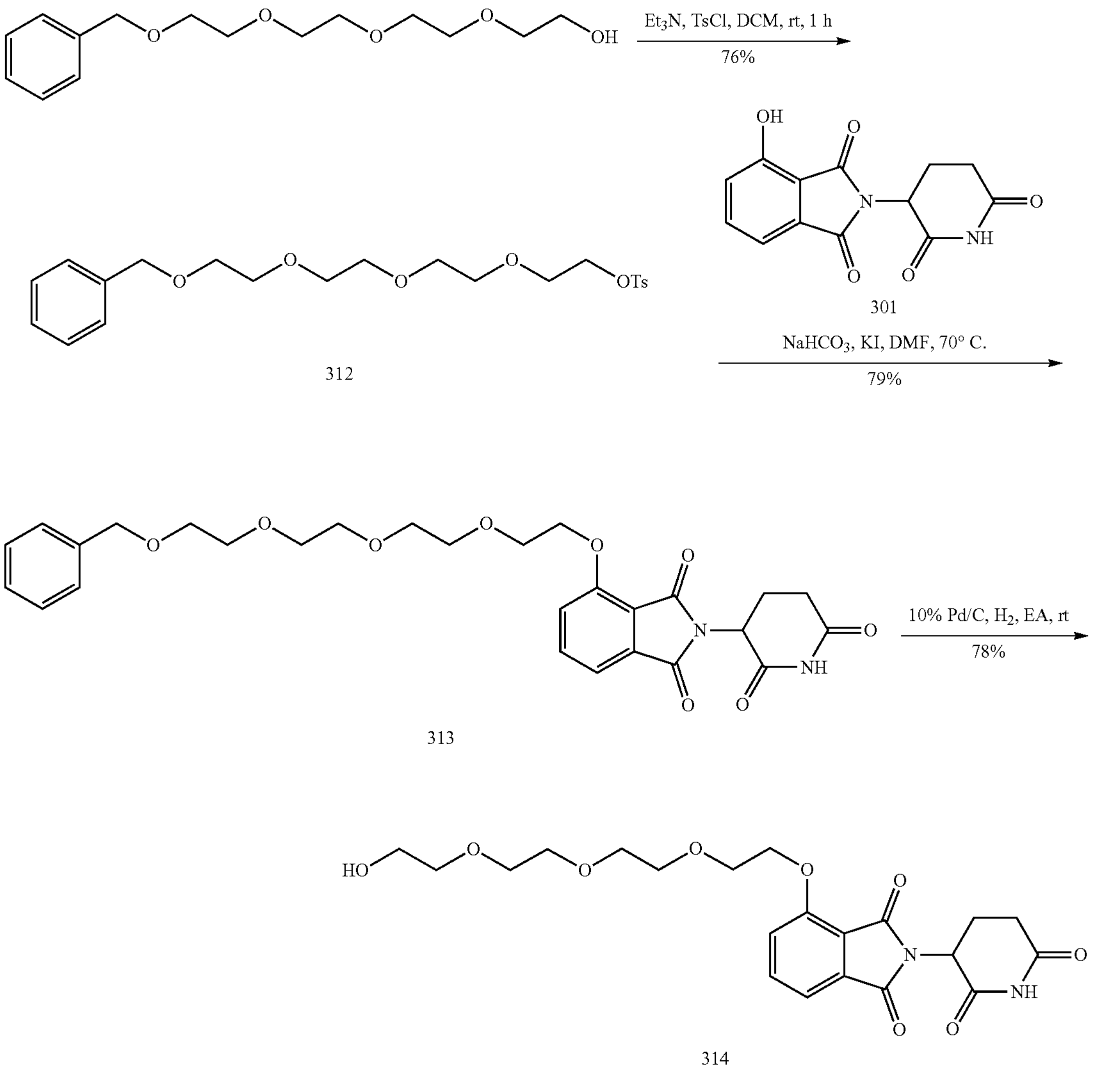

301

312

313

314

1-phenyl-2,5,8,11-tetraoxatridecan-13-yl 4-methylbenzenesulfonate (312). To a solution of alcohol (1.0 eq) was added $Et_3N$ (3.0 eq) and TsCl (1.5 eq) at 0° C. The mixture was stirred at room temperature for 1 h. Then mixture was concentrated under reduced pressure to remove the solvent. The residue was purified by column chromatography. The title compound 312 (4.99 g, 75.85%) was synthesized. $^1H$ NMR (500 MHz, Chloroform-d) δ 7.83-7.75 (m, 2H), 7.36-7.30 (m, 6H), 7.30-7.26 (m, 1H), 4.56 (s, 2H), 4.17-4.11 (m, 2H), 3.69-3.65 (m, 4H), 3.65-3.61 (m, 6H), 3.60-3.55 (m, 4H), 2.43 (s, 3H). $^{13}C$ NMR (126 MHz, Chloroform-d) δ 144.78, 138.31, 133.08, 129.82, 128.37, 128.00, 127.75, 127.60, 73.26, 70.78, 70.67, 70.66, 70.57, 69.48, 69.26, 68.70, 21.65.

2-(2,6-dioxopiperidin-3-yl)-4-((1-phenyl-2,5,8,11-tetraoxatridecan-13-yl)oxy) isoindoline-1,3-dione (313). To a solution of compound 301 (0.14 g, 0.5 mmol), compound 312 (1.0 mmol) in DMF (4.0 mL) was added $NaHCO_3$ (84 mg, 1.0 mmol) and KI (10 mg). The reaction mixture was stirred at 70° C. for 12 h prior to being taken up in ethyl acetate and water. The organic layer was separated, dried, and evaporated. The residue was purified by column chromatography to afford the desired product. The title compound 313 (1.51 g, 79%) was synthesized. $^1H$ NMR (500 MHz, Chloroform-d) δ 8.21 (s, 1H), 7.65 (dd, J=8.4, 7.3 Hz, 1H), 7.45 (dd, J=7.3, 0.7 Hz, 1H), 7.35-7.31 (m, 4H), 7.27-7.24 (m, 2H), 4.93 (dd, J=12.3, 5.4 Hz, 1H), 4.55 (d, J=2.2 Hz, 2H), 4.36-4.31 (m, 2H), 3.95-3.91 (m, 2H), 3.79-3.75 (m, 2H), 3.68-3.64 (m, 8H), 3.64-3.61 (m, 2H), 2.90-2.68 (m, 3H), 2.14-2.07 (m, 1H). $^{13}C$ NMR (126 MHz, Chloroform-d) δ 170.94, 168.04, 167.01, 165.57, 156.50, 138.29, 136.46, 133.78, 128.38, 128.36, 127.77, 127.75, 127.61, 119.63, 117.36, 116.16, 73.24, 71.18, 70.69, 70.66, 70.64, 70.60, 69.49, 69.42, 69.35, 49.13, 31.41, 22.65.

2-(2,6-dioxopiperidin-3-yl)-4-(2-(2-(2-(2-hydroxyethoxy) ethoxy) ethoxy) ethoxy) isoindoline-1,3-dione (314). To a solution of compound 313 in ethyl acetate was added 10% Pd/C (0.1 eq, weight). After evacuating and flushing the flask with hydrogen gas three times, the reaction mixture was stirred under hydrogen atmosphere for 3 h. Upon completion, Pd/C was removed via filtration. The filtrate was concentrated under vacuum and the crude product was purified via column chromatography to give the desired product. The title compound 314 (0.98 g, 78%) was synthesized. $^1H$ NMR (500 MHz, Chloroform-d) δ 8.34 (s, 1H), 7.67 (dd, J=8.5, 7.3 Hz, 1H), 7.46 (d, J=7.3 Hz, 1H), 7.27 (d, J=8.8 Hz, 1H), 4.95 (dd, J=12.2, 5.3 Hz, 1H), 4.38-4.33 (m, 2H), 3.94 (dd, J=5.3, 4.2 Hz, 2H), 3.82-3.77 (m, 2H), 3.72-3.64 (m, 8H), 3.62-3.57 (m, 2H), 2.91-2.69 (m, 3H), 2.66 (d, J=6.5 Hz, 1H), 2.16-2.08 (m, 1H). $^{13}C$ NMR (126 MHz, Chloroform-d) δ 171.06, 168.17, 167.02, 165.64, 156.48, 136.50, 133.80, 119.55, 117.38, 116.19, 72.50, 71.18, 70.62, 70.59, 70.38, 69.38, 61.75, 49.16, 31.42, 22.68.

Scheme 27. Synthesis of one β-catenin degrader

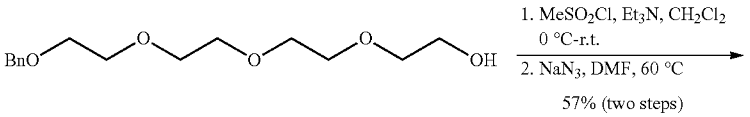

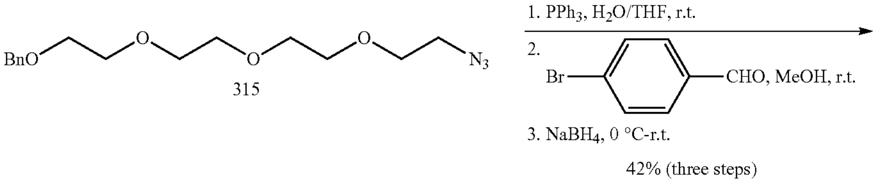

315

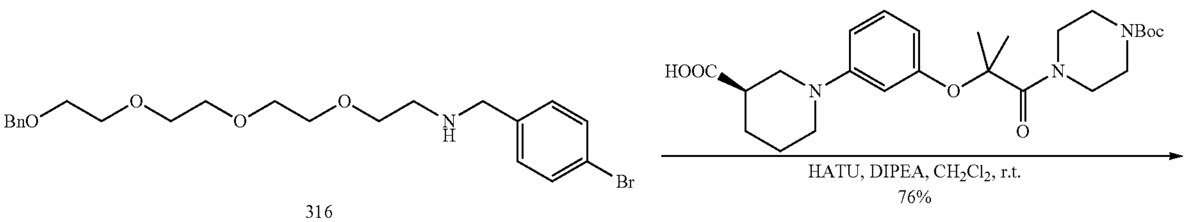

316

-continued
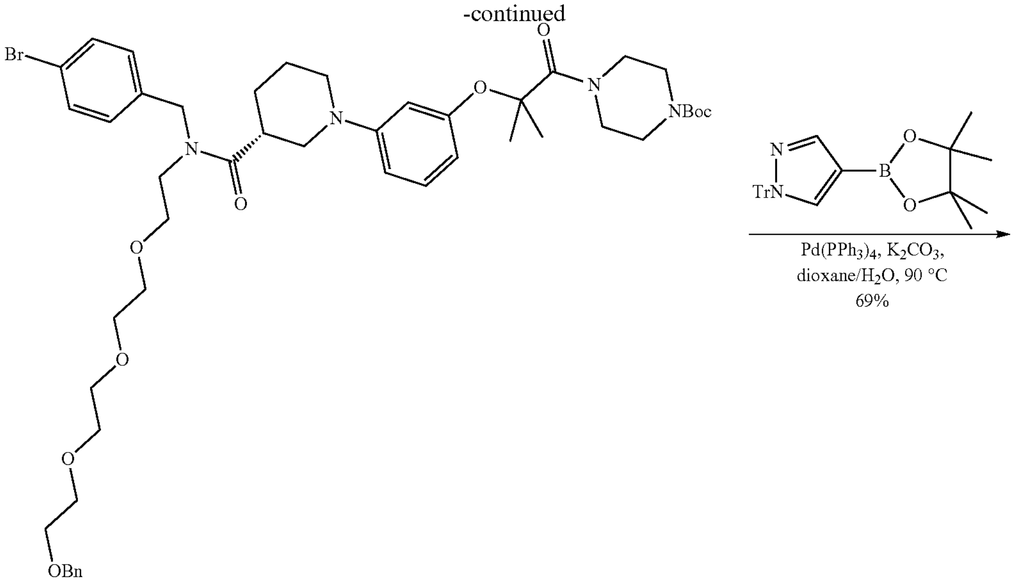
318
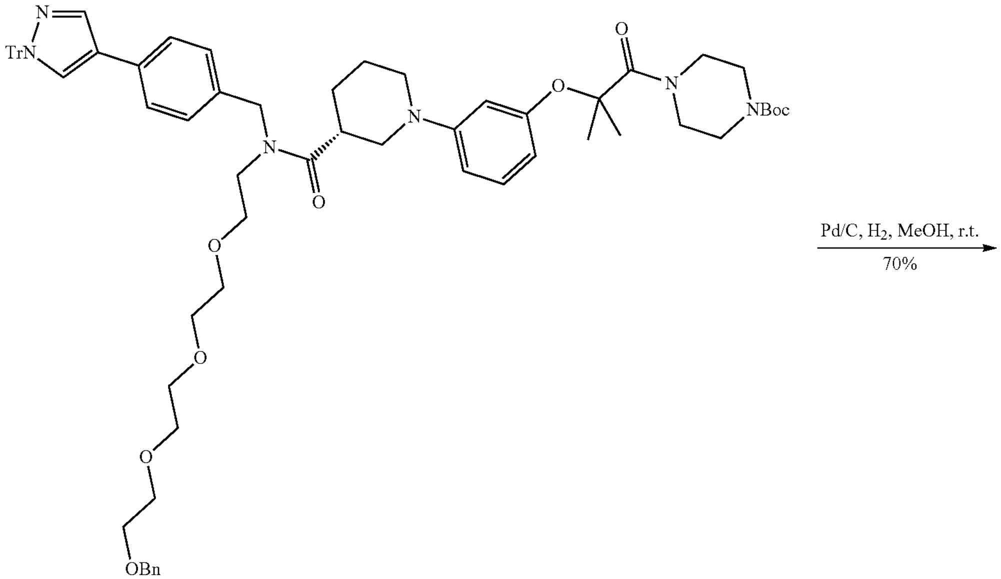
319

-continued
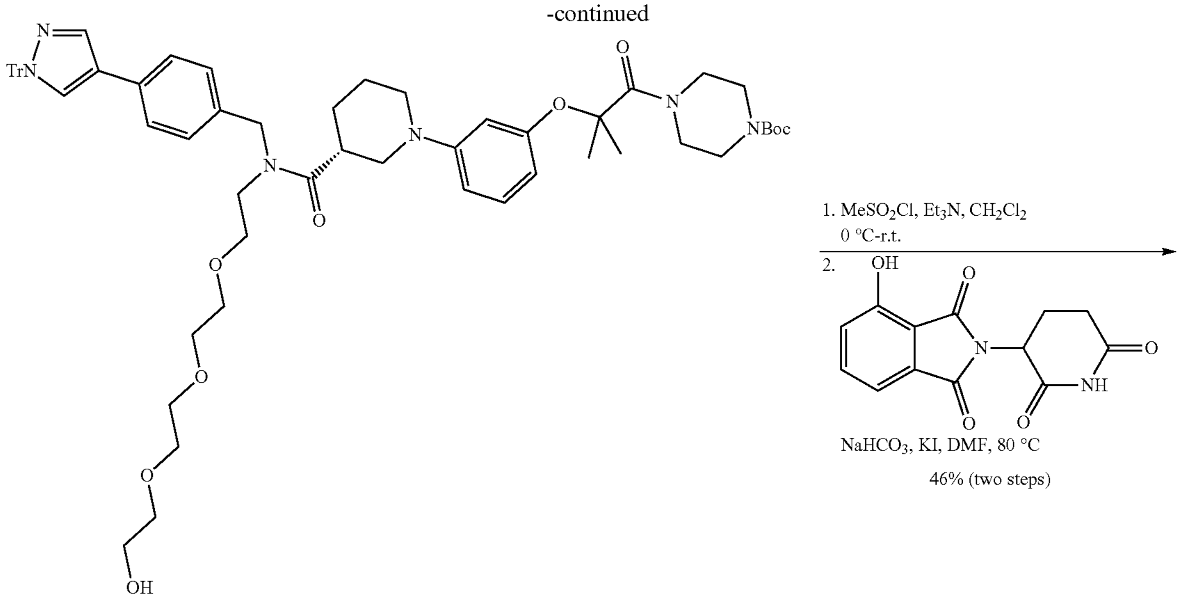
320
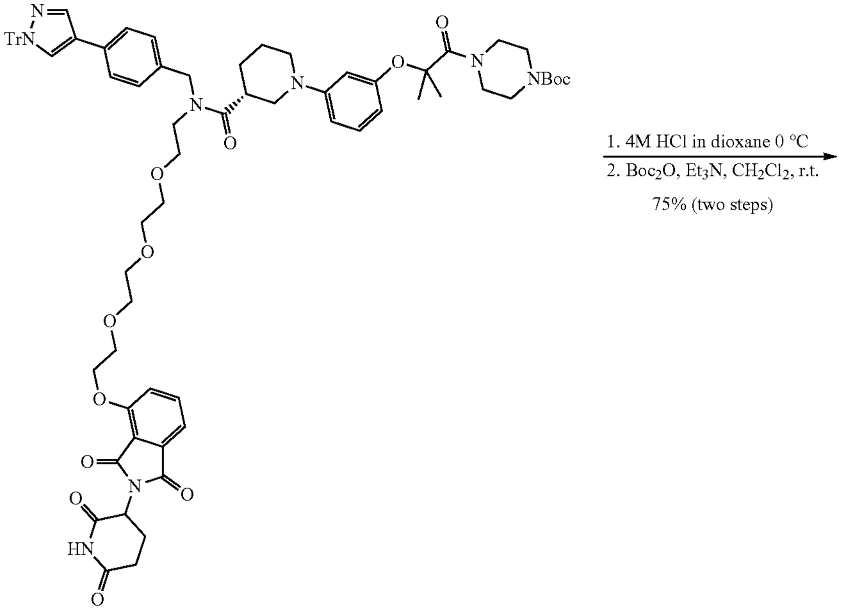
321

-continued

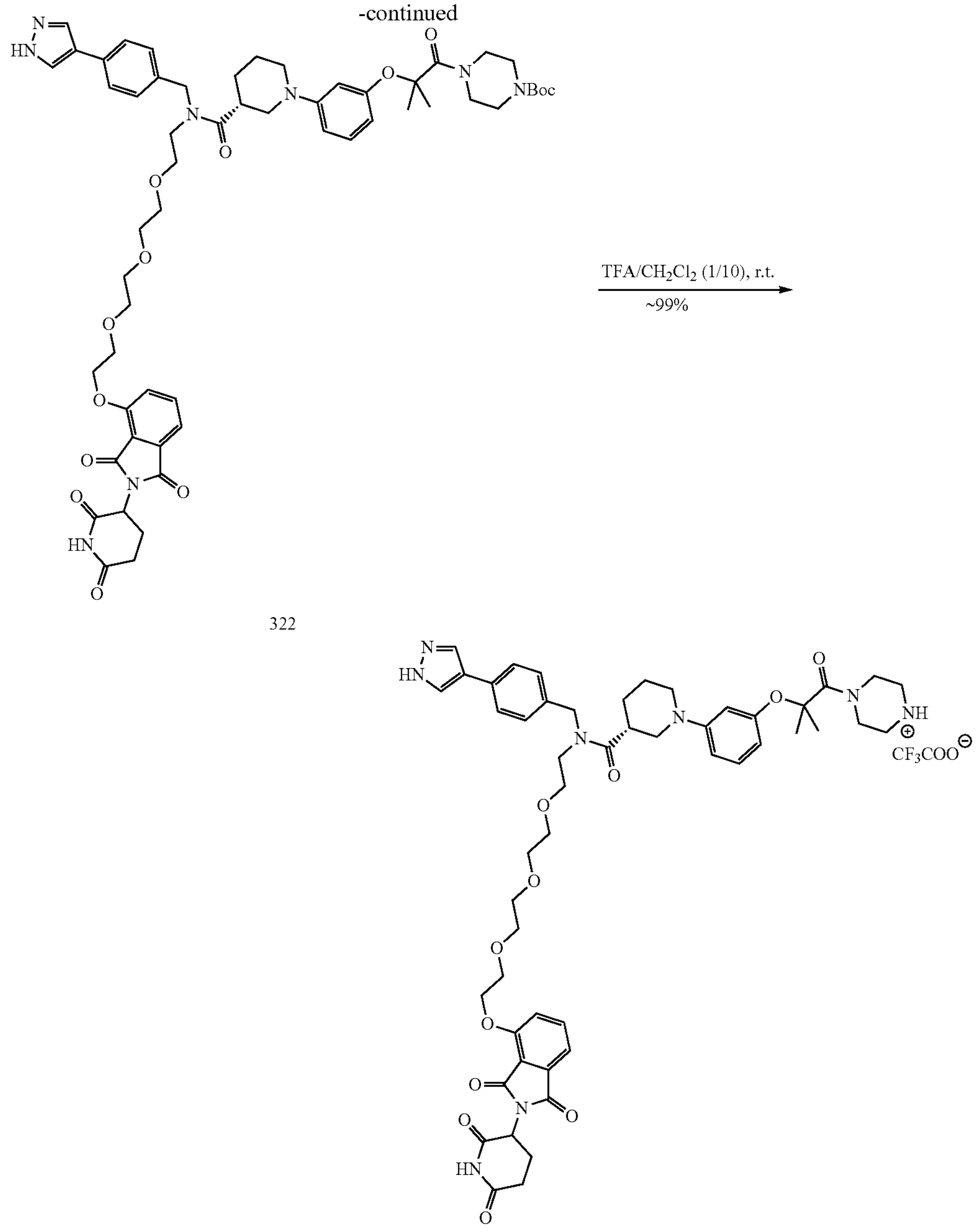

322

300

13-azido-1-phenyl-2,5,8,11-tetraoxatridecane (315). $MeSO_2Cl$ (1.5 eq) was added dropwise to a stirred solution of 1-phenyl-2,5,8,11-tetraoxatridecan-13-ol (1 eq) and $Et_3N$ (1.5 eq) in anhydrous $CH_2Cl_2$ at 0° C. under Ar. The reaction was allowed to warm to room temperature and stirred for 2 h. The reaction mixture was poured into methanol and concentrated in vacuo, and then was diluted with diethyl ether, washed with water and brine. The combined organic phase was then dried over anhydrous $MgSO_4$, then filtered and concentrated. The resulting mixture was dissolved in DMF and $NaN_3$ (3 eq) was added to the solution. The mixture was stirred at 60° C. for 12 h. The solution was concentrated and went through the silica column to yield compound 315 (yield 57%). $^1H$ NMR (500 MHz, $CDCl_3$) δ 7.38-7.18 (m, 5H), 4.60-4.49 (m, 2H), 3.64 (ddd, J=12.6, 6.4, 3.2 Hz, 14H), 3.34 (dd, J=5.3, 2.9 Hz, 2H).

N-(4-bromobenzyl)-1-phenyl-2,5,8,11-tetraoxatridecan-13-amine (316). $PPh_3$ (2 eq) and water (1.5 eq) were added to a stirred solution of 315 (1 eq) in THF under Ar. The reaction was stirred under Ar for 16 h. The mixture was concentrated in vacuo to afford oil, which was purified by flash chromatography to remove the triphenylphosphine oxide. The obtained amine was added to a solution of 4-bromobenzaldehyde (2 eq) in MeOH and stirred at RT overnight. Then $NaBH_4$ (2 eq) was added to the mixture at 0° C. After completion of the reaction, water and ethyl acetate were added and the organic phase was washed by brine and purified by flash chromatography to yield compound 316 (yield 42%). $^1H$ NMR (500 MHz, $CDCl_3$) δ 7.45

(d, J=8.4 Hz, 2H), 7.39-7.33 (m, 4H), 7.32-7.28 (m, 1H), 7.27-7.18 (m, 2H), 4.58 (s, 2H), 3.78 (s, 2H), 3.72-3.60 (m, 14H), 2.80 (dd, J=5.6, 4.8 Hz, 2H).

tert-butyl (R)-4-(2-(3-(3-((4-bromobenzyl) (1-phenyl-2,5,8,11-tetraoxatridecan-13-yl)carbamoyl)piperidin-1-yl)phenoxy)-2-methylpropanoyl)piperazine-1-carboxylate (318). Compound 317 was synthesized by Scheme 3 from compound 207. A solution of compound 316 (1 eq) and compound 317 (1 eq) in $CH_2Cl_2$ was added HATU (1.5 eq) and DIPEA (2 eq) under Ar. The mixture was stirred at room temperature overnight. Then the mixture was washed with water and concentrated under vacuo and purified by silica column to yield compound 318 (yield 76%). $^1$H NMR (500 MHz, $CDCl_3$) δ 7.50-7.43 (m, 1H), 7.43-7.37 (m, 1H), 7.35-7.21 (m, 5H), 7.11 (d, J=8.3 Hz, 1H), 7.05 (d, J=8.0 Hz, 2H), 6.59-6.18 (m, 3H), 4.68 (s, 1H), 4.54 (d, J=1.9 Hz, 2H), 3.88-3.71 (m, 2H), 3.66-3.45 (m, 21H), 3.32 (s, 2H), 3.14-2.83 (m, 4H), 2.73 (dd, J=21.4, 8.7 Hz, 1H), 1.93 (d, J=11.2 Hz, 4H), 1.65-1:60 (m, 6H), 1.42 (s, 9H).

tert-butyl (R)-4-(2-methyl-2-(3-(3-((1-phenyl-2,5,8,11-tetraoxatridecan-13-yl) (4-(1-trityl-1H-pyrazol-4-yl)benzyl) carbamoyl)piperidin-1-yl)phenoxy) propanoyl)piperazine-1-carboxylate (319). A solution of 318 (1 eq), 4-(4,4,5,5-tetramethyl-1,3,2-dioxaborolan-2-yl)-1-trityl-1H-pyrazole (2 eq), $Pd(PPh_3)_4$ (10%), and $K_2CO_3$ (2 eq) in dioxane and water was stirred at 90° C. under Ar overnight. Then the mixture was concentrated and ethyl acetate and water were added. The organic phase was washed by brine and concentrated. The resulting mixture was purified by silica column to yield compound 319 (yield 69%). $^1$H NMR (500 MHz, $CDCl_3$) δ 7.98-7.88 (m, 1H), 7.70 (ddd, J=12.0, 8.3, 1.4 Hz, 2H), 7.66-7.60 (m, 1H), 7.59-7.46 (m, 3H), 7.43 (dd, J=10.2, 8.0 Hz, 1H), 7.41-7.25 (m, 15H), 7.25-7.11 (m, 7H), 4.77-4.65 (m, 1H), 4.56 (d, J=1.7 Hz, 2H), 3.96-2.53 (m, 30H), 1.91-1.61 (m, 10H), 1.45 (d, J=2.8 Hz, 9H).

tert-butyl (R)-4-(2-(3-(3-((2-(2-(2-(2-hydroxyethoxy) ethoxy) ethoxy)ethyl) (4-(1-trityl-1H-pyrazol-4-yl)benzyl) carbamoyl)piperidin-1-yl)phenoxy)-2-methylpropanoyl) piperazine-1-carboxylate (320). Compound 319 (1 eq) and Pd/C in MeOH was stirred overnight under $H_2$ at room temperature. Then Pd/C was filtered out and the solution was concentrated and purified by silica column to yield compound 320 (70%). $^1$H NMR (500 MHz, $CDCl_3$) δ 7.85 (d, J=10.5 Hz, 1H), 7.54 (d, J=13.9 Hz, 1H), 7.47-7.15 (m, 15H), 7.16-6.95 (m, 8H), 4.66 (dd, J=15.6, 7.9 Hz, 1H), 3.83-2.80 (m, 30H), 1.82-1.50 (m, 10H), 1.35 (d, J=3.2 Hz, 9H).

tert-butyl 4-(2-(3-((3R)-3-((2-(2-(2-(2-((2-(2,6-dioxopiperidin-3-yl)-1,3-dioxoisoindolin-4-yl)oxy) ethoxy) ethoxy) ethoxy)ethyl) (4-(1-trityl-1H-pyrazol-4-yl)benzyl)carbamoyl)piperidin-1-yl)phenoxy)-2-methylpropanoyl)piperazine-1-carboxylate (321). $MeSO_2Cl$ (2 eq) was added dropwise to a stirred solution of 320 (1 eq) and $Et_3N$ (2 eq) in anhydrous $CH_2Cl_2$ at 0° C. under Ar. The reaction was allowed to warm to room temperature and stirred for 6 h. The reaction mixture was poured into methanol and concentrated in vacuo, and then was diluted with diethyl ether, washed with water and brine. The combined organic phase was then dried over anhydrous $MgSO_4$, then filtered and concentrated and used directly in next step. The obtained mixture was added to a solution of compound 301 (2 eq), $NaHCO_3$ (4 eq) and KI (0.1 eq) in DMF and stirred at 80° C. overnight. The mixture was concentrated and purified by flash chromatography to yield compound 321 (46%). $^1$H NMR (500 MHz, $CDCl_3$) δ 7.89-7.80 (m, 1H), 7.58-7.48 (m, 2H), 7.39-7.21 (m, 14H), 7.18-6.80 (m, 10H), 6.51-6.08 (m, 3H), 4.91-4.78 (m, 1H), 4.69-4.43 (m, 2H), 4.23 (dq, J=5.1, 2.8 Hz, 2H), 3.84 (q, J=3.7, 2.4 Hz, 2H), 3.77-3.63 (m, 4H), 3.63-3.33 (m, 14H), 3.25 (s, 2H), 3.06-2.82 (m, 4H), 2.80-2.56 (m, 4H), 2.00 (ddt, J=10.7, 5.5, 2.8 Hz, 1H), 1.84 (s, 2H), 1.80-1.59 (m, 1H), 1.55 (s, 6H), 1.34 (s, 9H).

tert-butyl 4-(2-(3-((3R)-3-((4-(1H-pyrazol-4-yl)benzyl) (2-(2-(2-(2-((2-(2,6-dioxopiperidin-3-yl)-1,3-dioxoisoindolin-4-yl)oxy) ethoxy) ethoxy) ethoxy)ethyl)carbamoyl)piperidin-1-yl)phenoxy)-2-methylpropanoyl)piperazine-1-carboxylate (322). Compound 321 (1 eq) was stirred in 4 M HCl in dioxane at 0° C. for 4 h and concentrated. The resulting mixture was dissolved in $CH_2Cl_2$ and $Boc_2O$ (1.5 eq) and $Et_3N$ (2 eq) were added. The mixture was stirred at room temperature for 20 min. Then water was added and the organic phase was concentrated and purified by silica column to yield compound 322 (yield 75%). $^1$H NMR (500 MHz, $CDCl_3$) δ 9.05-8.60 (m, 1H), 7.77 (s, 1H), 7.54 (ddt, J=8.4, 7.2, 2.8 Hz, 1H), 7.41-7.29 (m, 3H), 7.18-7.05 (m, 3H), 7.00-6.81 (m, 1H), 6.54-6.06 (m, 3H), 4.88 (ddd, J=12.1, 5.4, 2.0 Hz, 1H), 4.72-4.45 (m, 2H), 4.21 (q, J=4.6 Hz, 2H), 3.90-3.77 (m, 2H), 3.77-3.36 (m, 18H), 3.25 (s, 2H), 3.08-2.54 (m, 8H), 2.02 (ddd, J=10.5, 6.0, 3.4 Hz, 1H), 1.84 (dd, J=39.3, 11.0 Hz, 1H), 1.76-1.58 (m, 2H), 1.54 (dd, J=14.8, 1.9 Hz, 6H), 1.35 (s, 9H).

4-(2-(3-((3R)-3-((4-(1H-pyrazol-4-yl)benzyl) (2-(2-(2-(2-((2-(2,6-dioxopiperidin-3-yl)-1,3-dioxoisoindolin-4-yl) oxy) ethoxy) ethoxy) ethoxy)ethyl)carbamoyl)piperidin-1-yl)phenoxy)-2-methylpropanoyl)piperazin-1-ium 2,2,2-trifluoroacetate (300).

Compound 322 was dissolved in TFA/$CH_2Cl_2$ (1/10) and stirred at room temperature for 4 h. The mixture was concentrated and $CH_2Cl_2$ was added three more times and concentrated. The final mixture was dissolved in water and dried by lyophilizer to yield compound 300 (yield 99%). $^1$H NMR (500 MHz, MeOD) δ 8.00 (s, 2H), 7.72 (ddd, J=23.8, 8.5, 7.3 Hz, 1H), 7.55 (ddd, J=10.9, 8.1, 3.0 Hz, 2H), 7.45-7.34 (m, 2H), 7.34-7.10 (m, 3H), 7.02-6.38 (m, 3H), 5.14-5.02 (m, 1H), 4.85 (s, 1H), 4.77 (dd, J=15.8, 8.5 Hz, 1H), 4.57 (dd, J=15.3, 2.3 Hz, 1H), 4.33 (dt, J=9.8, 3.9 Hz, 2H), 4.12 (s, 2H), 3.94-3.43 (m, 18H), 3.13 (s, 3H), 2.96-2.77 (m, 3H), 2.77-2.60 (m, 2H), 2.13-1.70 (m, 5H), 1.68-1.58 (m, 6H). $^{13}$C NMR (126 MHz, MeOD) δ 175.10, 173.17, 172.18, 171.99, 170.19, 170.10, 167.13, 166.00, 165.97, 156.35, 156.31, 156.22, 156.13, 136.58, 136.48, 135.61, 133.67, 133.62, 127.82, 127.78, 126.89, 126.86, 125.64, 125.38, 119.42, 116.83, 116.80, 115.30, 115.26, 80.95, 80.69, 70.68, 70.62, 70.58, 70.23, 70.16, 70.11, 70.05, 70.02, 69.11, 69.07, 69.03, 68.73, 68.05, 51.93, 49.03, 49.00, 48.37, 43.13, 42.74, 39.45, 30.75, 24.96, 24.92, 24.88, 22.95, 22.26.

2. Biological Characterization

Inhibitor Selectivity between β-Catenin/BCL9 and β-Catenin/E-Cadherin PPIs. Selective inhibition of β-catenin/BCL9 PPI while leaving β-catenin/E-cadherin PPI unaffected is extremely important, because the formation of β-catenin/E-cadherin complex is critical for cell-cell adhesion and the interface of β-catenin to interact with BCL9 is also used to bind E-cadherin. Compound 37 was assessed for its selectivity between β-catenin/BCL9 and β-catenin/E-cadherin PPIs using the AlphaScreen selectivity assay. As shown in FIG. 1A, this compound exhibited 229-fold selectivity for β-catenin/BCL9 over β-catenin/E-cadherin PPIs.

Figures 1B, 1C, 1D, 1E, 1F, 1G:
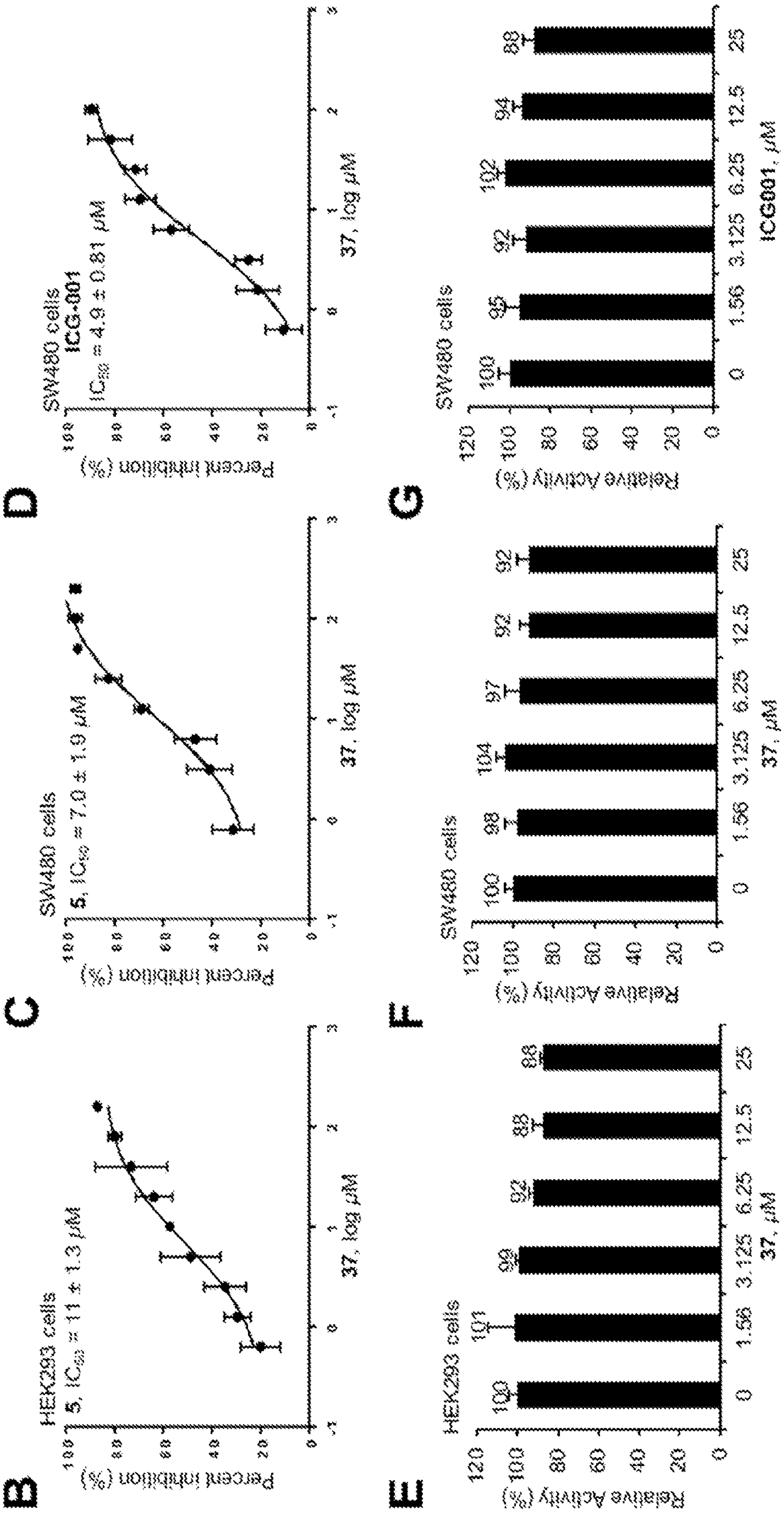

Inhibition of β-Catenin/BCL9/Tcf Transcriptional Activity. Wnt-specific TOPFlash/FOPFlash luciferase reporter assays were performed to evaluate the effects of inhibitor 37 on β-catenin-dependent transcriptional activity, and three cell lines were used including human embryonic kidney cell line 293 (HEK293) transfected with pcDNA3.1-β-catenin to activate β-catenin signaling, colorectal cancer cell line SW480 with hyperactive Wnt/β-catenin signaling, and WNT3a stimulated triple negative breast cancer (TNBC) cell line MDA-MB-468. For the TOPFlash reporter construct, the firefly luciferase reporter gene was placed downstream of three wild-type Tcf binding sites. For the FOPFlash reporter construct, the firefly luciferase reporter gene was place downstream of three mutant Tcf binding sites. The high expression of firefly luciferase in TOPFlash assays was controlled by tandem Tcf binding sites. The *renilla* luciferase reporter construct (pCMV-RL) was used as the internal control to normalize luciferase reporter signals and eliminate systematic errors such as cell viability, transfection effect, etc. As shown in FIG. 1B, compound 37 suppressed the TOPFlash luciferase activities in HEK293 cells in a dose-dependent manner with an $IC_{50}$ of 10.8 μM. The negative control 55 did not show any activity at 200 μM in HEK293 cells. Compound 37 also dose-dependently suppressed the TOPFlash luciferase activities in SW480 cells and MDA-MB-468 cells with $IC_{50}$ values of 7.0 and 6.3 μM, respectively (FIG. 1C), which is comparable with that displayed by the β-catenin/CBP inhibitor ICG-001 ($IC_{50=4.9}$ μM, FIG. 1D). Further FOPFlash luciferase reporter assays revealed compound 37 did not show obvious inhibitory activity at 25 μM in all these three cell lines (FIG. 1E, 1F). All the results indicated 37 selectively inhibits Wnt/β-catenin signaling transactivation without general inhibition of transcription.

Figures 2A, 2B:
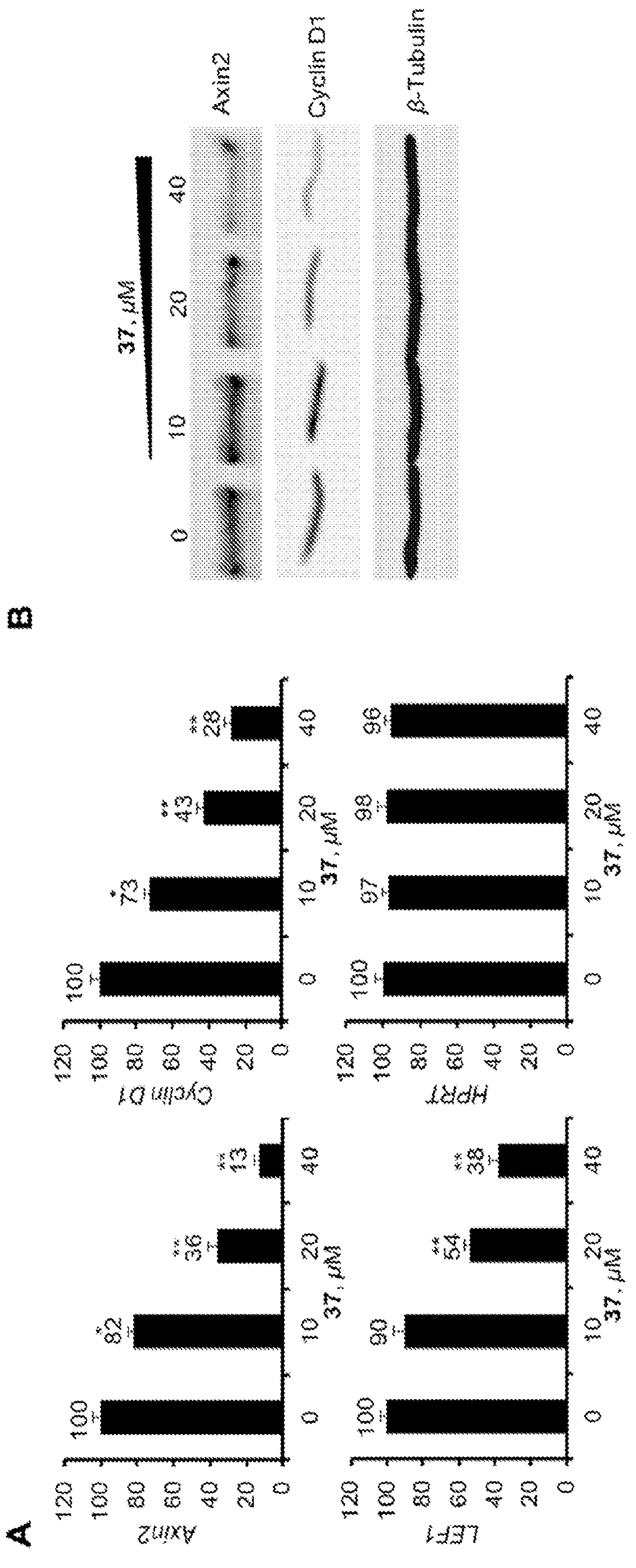
FIG. 2A shows qPCR studies to determine the changes of mRNA expression of Axin2, cyclin D1, and LEF1 in SW480 cells in response to inhibitor 37 at different concentrations. House-keeper gene HPRT was used as the reference.
FIG. 2B shows Western blot analysis to monitor the change of protein expression of Axin2 and cyclin D1 in response to different concentrations of inhibitor 37 in SW480 cells. β-Tubulin was used as the internal reference.
Figures 2C, 2D:
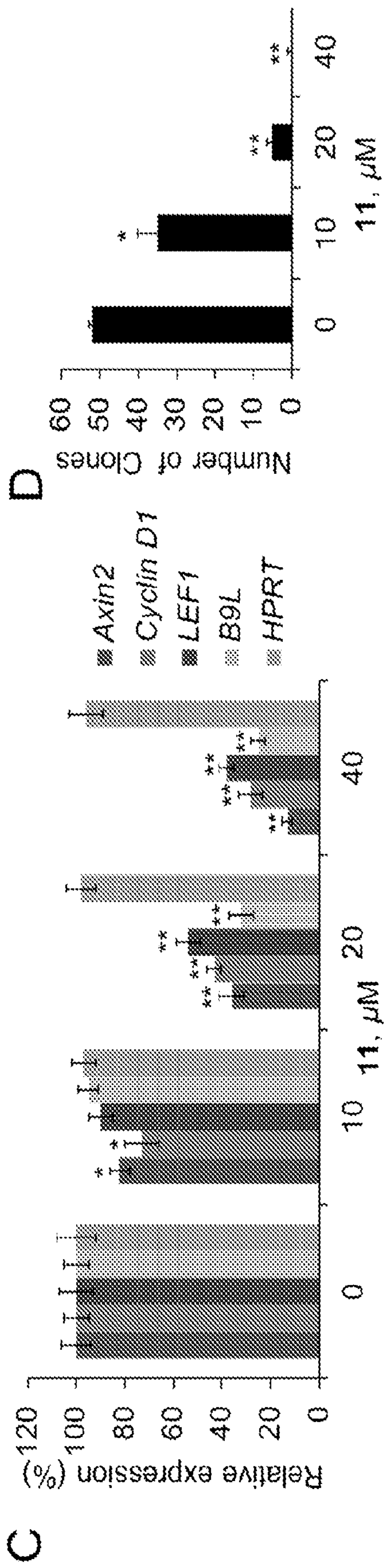
FIG. 2C shows qPCR to determine the changes of mRNA expression of AXIN2, cyclicn D1, LEF1, and B9L in response to different concentrations of 37 using Wnt 3a-activated MDA-MB-468 cells. House-keeper gene HPRT was used as the negative control.
FIG. 2D shows the effect of inhibitor 37 on clonogenic growth of MDA-MB-231 cells. * $P<0.05$, ** $P<0.01$, as determined by the unpaired, two-tailed Student t test. Each experiment was performed in duplicate.

Inhibition of Expression of Wnt/β-Catenin Target Genes. The inhibitory activity of 37 on Wnt/β-catenin signaling was further investigated by monitoring the transcript levels of Wnt-specific target gene Axin2 and two other Wnt/β-catenin target genes cyclin D1 and LEF1. Quantitative real-time PCR (qPCR) results show that 37 dose-dependently inhibited transcription of all these Wnt target genes without affecting expression of house-keeper genes, such as HPRT (FIG. 2A). At 20 μM, compound 37 reduced Wnt target gene transcripts to 36% (Axin2), 43% (cyclin D1), and 54% (LEF1) of the DMSO-treated control.

Consistent with the qPCR studies, Western blot experiments indicated that the protein expression levels of Axin2 and cyclin D1 were significantly decreased in a dose-dependent manner after treatment of 37 without affecting the internal control β-tubulin (FIG. 2B).

Figures 3A, 3B:
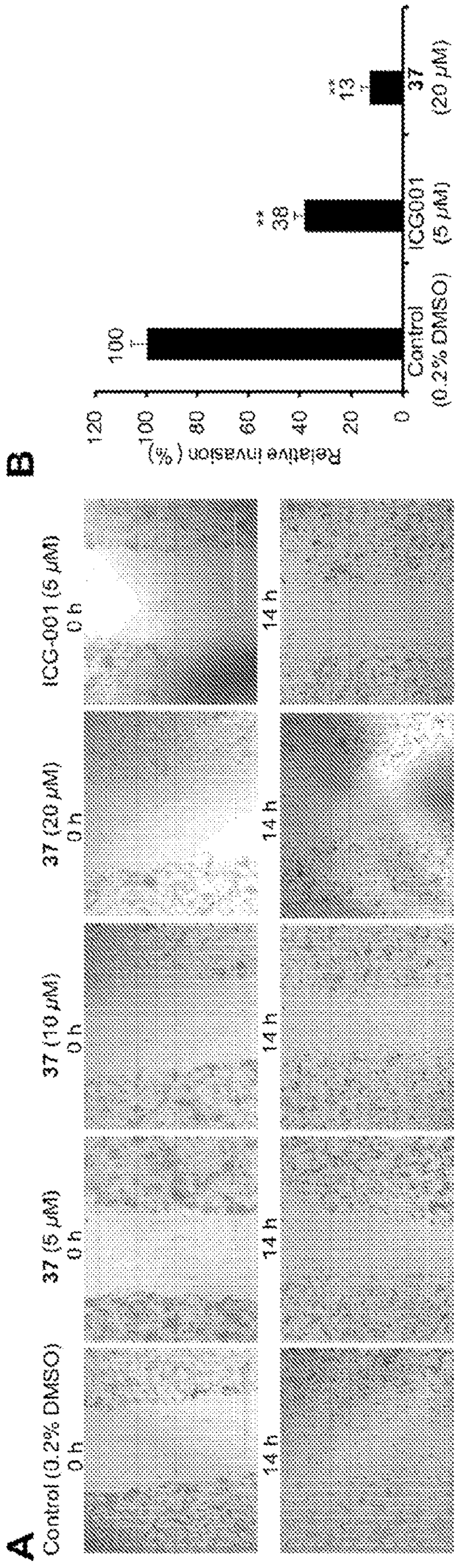
FIG. 3A is a wound-healing assays showing that inhibitor 37 inhibited migration of human TNBC MDA-MB-231 cells induced by serum (10% in media). Control, 0.2% DMSO in 10% FBS. Mitomycin (10 μg/mL) was added to inhibit cell proliferation and allow examination of the effects on cell migration.
FIG. 3B shows matrigel invasion assays showed that 37 (20 μM) inhibited invasion of human TNBC MDA-MB-231 cells. Control, 0.2% DMSO in 10% FBS. ** $P<0.01$, as determined by the unpaired, two-tailed Student t test. Each experiment was performed in duplicate.

Inhibition of Migration and Invasion of Cancer Cells Induced by β-Catenin Signaling β-Catenin signaling induces and maintains migration, invasion and of cancer cells, including TNBC cells. Scratch wound healing and Matrigel invasion assays using TNBC MDA-MB-231 cells were conducted. As shown in FIG. 3A, compound 37 can effectively inhibit TNBC cell migration in a dose-dependent manner. At 20 μM, 37 can also reduce TNBC cell invasion to 13% of the DMSO-treated control (FIG. 3B).

Figures 4A, 4B, 4C, 4D:
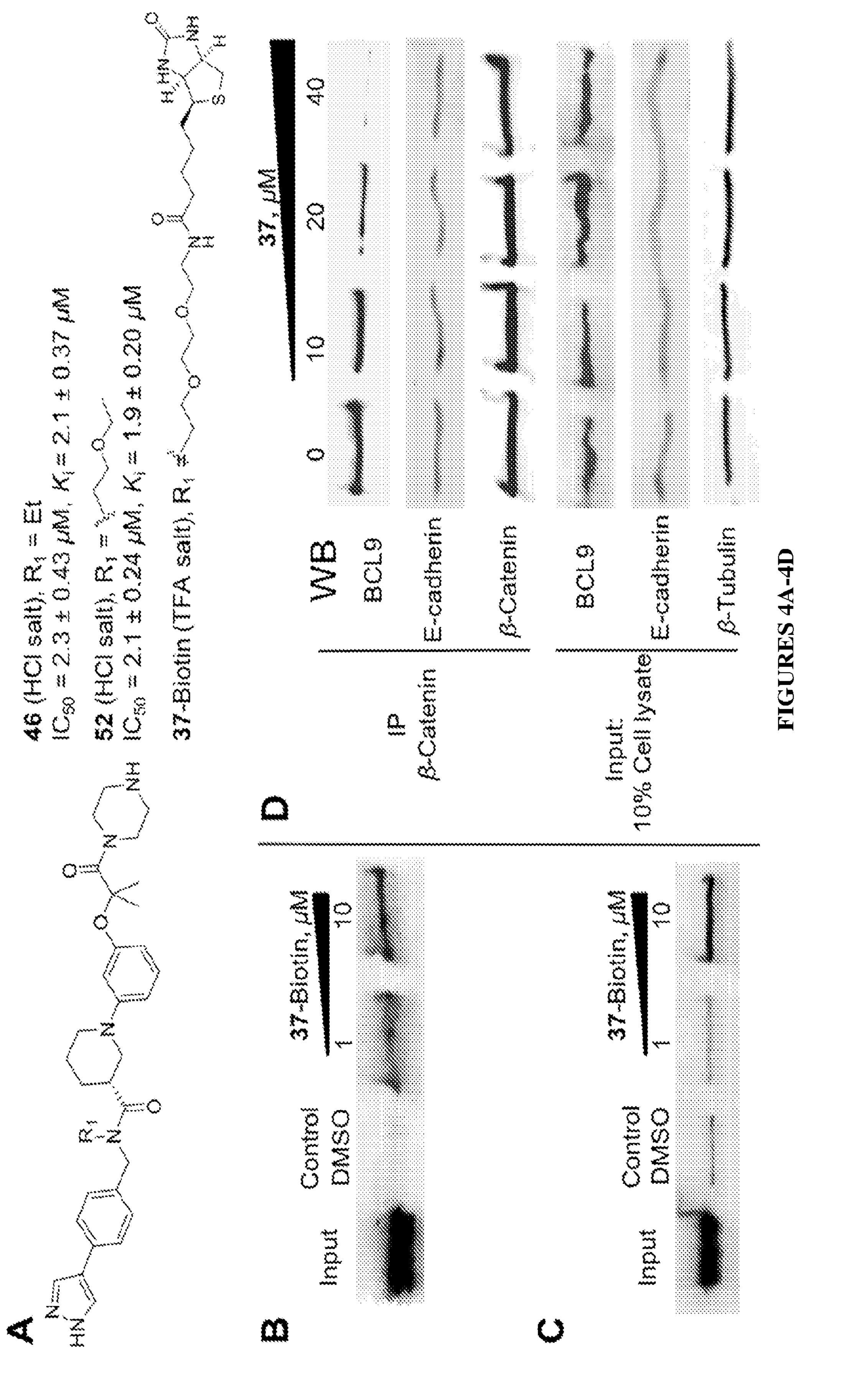
FIG. 4A shows structures and AlphaScreen results of compounds 46 and 52, and the structure of 37-Biotin, TFA: trifluoroacetic acid. Purified full-length β-catenin (FIG. 4B) and SW480 cell lysate (FIG. 4C) were incubated with 37-Biotin, followed by streptavidin pull-down experiment. The levels of β-catenin associated with 37-Biotin were analyzed by Western blot analysis. Input: 5% full-length β-catenin (FIG. 4B), 5% of cell lysate (FIG. 4C).
FIG. 4D shows co-IP experiments to evaluate the disruption of the β-catenin/BCL9 and β-catenin/E-cadherin PPI by inhibitor 37 in HCT116 cells. IP, immunoprecipitation; input, 10% of the cell lysate. Each experiment was performed in duplicate.

Target Engagement. The structure-activity relationship (SAR) indicated that the compounds with linear alkyl $R_1$ substitutions, such as 46 and 52, maintained the inhibitory activities (FIG. 4A). Biotinylated-37 (37-Biotin) in FIG. 4A was synthesized and incubated with purified full-length β-catenin and SW480 cell lysates, respectively. The proteins that bind with 37-Biotin were pulled down by streptavidin-conjugated beads and examined by Western blot analyses using β-catenin-specific antibody. As shown in FIG. 4B, 37-Biotin can bind with purified full-length β-catenin in a dose-dependent manner starting at a concentration of 1 μM. 37-Biotin also effectively bound with β-catenin in SW480 cell lysate at 10 UM (FIG. 4C). Co-immunoprecipitation (Co-IP) experiments were conducted to evaluate the effects of 37 on disruption of the β-catenin/BCL9 PPI in Wnt/β-catenin hyperactive HCT116 cancer cells. As shown in FIG. 4D, inhibitor 37 disrupted the β-catenin/BCL9 PPI in a dose-dependent manner, while the input and immunoprecipitation controls were constant in different experiments. A parallel experiment indicated that 37 did not affect the β-catenin/E-cadherin PPI at the concentrations that were sufficient to disrupt the β-catenin/BCL9 PPI, confirming its excellent selectivity for β-catenin/BCL9 over β-catenin/E-cadherin PPIs (FIG. 4D).

FIG. 5A shows hepatic microsome stability of compound 11 and positive control sunitinib. FIG. 5B shows mouse PK data of compound 11. Male C57BL/6 mice were administrated with 11 through intravenous injection (iv) via tail vein or through oral gavage (po).

Protein Expression and Purification. Full-length β-catenin (residues 1-781) were cloned into a pET-28b vector carrying a C-terminal 6× histidine (Novagen), and transformed into *E. coli* BL21 DE3 (Novagen). Cells were cultured in LB medium with 50 μg/mL kanamycin until the OD600 was approximately 0.8, and then protein expression was induced with 400 UM of IPTG at 20° C. overnight. Cells were lysed by sonication. The proteins were purified by three steps of chromatography, including Ni-NTA affinity chromatography (30210, Qiagen), HiTrap Q HP anion exchange chromatography (17-1154-01, GE Healthcare Life Science) and size-exclusion chromatography with a HiLoad 26/600 Superdex 200 μg column (28-9893-36, GE Healthcare Life Science), using an AKTA Pure FPLC (GE Healthcare Life Science) system. Protein was eluted in a buffer containing 20 mM of Tris (pH 8.5), 100 mM NaCl, and 2 mM DTT. The purity of β-catenin was greater than 95% as determined by SDS-PAGE gel analyses. Thermal-shift assays were performed on an CFX96 Real Time System (Bio-Rad) to monitor protein stability and detect protein aggregation. Protein unfolding was evaluated through measurement of the fluorescence changes of fluorescent dye Sypro Orange when interacting with β-catenin proteins. A temperature increment of 1°/min was applied. All proteins were stable and no aggregation was observed under storage or assay conditions. Proteins were aliquoted and stored at −80° C.

BCL9 Peptide Synthesis and Purification. Human BCL9 (residues 350-375), N-terminally biotinylated human BCL9 (residues 350-375), human E-cadherin (residues 824-877), and N-terminally biotinylated human E-cadherin (residues 824-877) were synthesized by InnoPep Inc. (San Diego, CA, www.innopep.com). All synthesized peptides were purified by HPLC with purity>95%. The structures were validated by LC/MS. The sequences of the peptides are as follows (Ahx, 6-aminohexanoic acid).

| Peptide | Sequence |
|---|---|
| BCL9 26-mer | H-$^{350}$GLSQEQLEHRERSLQTLRDIQRMLFP$^{375}$-$NH_2$ (SEQ ID NO: 1) |
| Biotinylated BCL9 26-mer | Biotin-Ahx-$^{350}$GLSQEQLEHRERSLQTLRDIQRMLFP$^{375}$-$NH_2$ (SEQ ID NO: 2) |
| E-cadherin 54-mer | H-$^{824}$APPYDSLLVFDYEGSGSEAASLSSLNSSESDKDQD YDYLNEWGNRFKKLADMYG$^{877}$-$NH_2$ (SEQ ID NO: 3) |

-continued

| Peptide | Sequence |
|---|---|
| Biotinylated E-cadherin 54-mer | Biotin-$^{824}$APPYDSLLVFDYEGSGSEAASLSSLNSSESDKDQD YDYLNEWGNRFKKLADMYG$^{877}$-$NH_2$ (SEQ ID NO: 4) |

AlphaScreen Assays of 8-Catenin and BCL9 Interaction. Experiments were performed in white opaque 384-well plates from PerkinElmer (Waltham, MA), and the samples were read on a Synergy 2 plate reader (Biotek, Winooski, VT) with excitation at 680 nm and emission at 570 nm. The standard AlphaScreen protocol was used with a sensitivity setting of 200. All dilutions were made in 1× assay buffer containing 25 mM Hepes (pH 7.4), 100 mM NaCl, 0.01% Triton X-100 and 0.1% BSA to minimize nonspecific interactions. For the competitive inhibition assays of the β-catenin/BCL9 PPI, The Max average signal in AlphaScreen assay was with a standard deviation of, Min average signal was with a standard deviation of, and the Z-factor was 0.8. the negative control (equivalent to 0% inhibition) refers to 5.0 nM biotinylated BCL9, 40 nM $His_6$-tagged β-catenin, and 10 μg/mL donor and acceptor beads in a final volume of 25 μL assay buffer, but no tested inhibitor present. The positive control (equivalent to 100% inhibition) refers to 5.0 nM biotinylated BCL9 and 10 μg/mL donor and acceptor beads in a final volume of 25 μL assay buffer. For the competitive inhibition assays of the β-catenin/E-cadherin PPI, the negative control (equivalent to 0% inhibition) refers to 10 nM biotinylated E-cadherin, 40 nM $His_6$-tagged β-catenin, and 10 μg/mL donor and acceptor beads in a final volume of 25 μL assay buffer. The positive control (equivalent to 100% inhibition) of the β-catenin/E-cadherin PPI refers to 10 nM biotinylated E-cadherin and 10 μg/mL donor and acceptor beads in a final volume of 25 μL assay buffer.

For the β-catenin/BCL9 assay, 5 nM biotinylated BCL9 and 40 nM $His_6$-tagged β-catenin were incubated in assay buffer at 4° C. for 30 min. For the β-catenin/E-cadherin assay, 10 nM biotinylated human E-cadherin, and 40 nM $His_6$-tagged human β-catenin were added and incubated in assay buffer at 4° C. for 30 min. Different concentrations of the tested inhibitor were added and incubated in 20 AL assay buffer at 4° C. for another 1 h. All of the assay plates were covered and gently mixed on an orbital shaker. The donor and acceptor beads were then added to the plates to a final concentration of 10 μg/mL in 25 AL assay buffer. The mixture was incubated for 1 h at 4° C. before detection. The $IC_{50}$ value was determined by nonlinear least-square analysis of GraphPad Prism 5.0. The $K_1$ values were derived from the $IC_{50}$ values using a method reported by Nikolovska-Coleska et al. The equation used is $K_i=[I]_{50}/([L]_{50}/K_d+[P]_0/K_d+1)$ (Where $[I]_{50}$ denotes the concentration of the free inhibitor at 50% inhibition, $[L]_{50}$ is the concentration of the free labeled ligand at 50% inhibition, $[P]_0$ is the concentration of the free protein at 0% inhibition, and $K_d$ is the dissociation constant of the protein-ligand complex). All of the experiments were performed in triplicate and carried out in the presence of 1% DMSO for small-molecule inhibitors. Each compound was assayed at least by two independent experiments. The results were expressed as mean±standard deviation. The inhibitor selectivity for β-catenin/BCL9 over β-catenin/E-cadherin interactions was defined as the ratio of the respective $K_1$ value of β-catenin/E-cadherin interactions over that of β-catenin/BCL9 interactions.

Cell Transfection and Luciferase Assay. FuGENE6 (E269A, Promega) 96 well plate format was used for the transfection of HEK293 and SW480 cells according to the manufacturer's instruction. HEK293 cells were co-transfected with 45 ng TOPFlash or FOPFlash reporter gene, 135 ng pcDNA3.1-β-catenin, and 20 ng pCMV-RL normalization reporter gene. SW480 cells were co-transfected with 60 ng the TOPFlash or FOPFlash firefly luciferase reporter gene and 40 ng *renilla* luciferase pCMV-RL normalization reporter. Cells were cultured in DMEM and 10% FBS at 37° C. for 24 h, and different concentrations of inhibitors or DMSO was added. After 24 h, the luciferase reporter activity was measured using the Dual-Glo system (E2940, Promega). Normalized luciferase activity in response to the treatment with inhibitors was compared with that obtained from the cells treated with DMSO. Experiments were performed in triplicate.

Quantitative Real Time PCR analysis. SW480 cells at $1\times10^6$/mL were treated with inhibitors at different concentrations for 24 h. Total RNAs were extracted with TRIzol (15596026, Life Technologies), and the cDNA was synthesized with the superscript III first-strand kit (18080-051, Invitrogen). qPCR experiments were performed using the iQTM SYBR green supermix kit (170-8880, BIO-RAD) on an CFX96 Real Time System (BIO-RAD). The threshold cycle (CT) values were normalized to that of internal reference GAPDH. Experiments were performed in triplicate. The primer pairs are shown below

| | | |
|---|---|---|
| human GAPDH | forward | 5'-GAAGGTGAAGGTCGGAGTC-3' (SEQ ID NO: 5) |
| | reverse | 5'-GAAGATGGTGATGGGATTTC-3' (SEQ ID NO: 6) |
| human HPRT | forward | 5'-GCTATAAATTCTTTGCTGACCTGCTG-3' (SEQ ID NO: 7) |
| | reverse | 5'-AATTACTTTTATGTCCCCTGTTGACTGG-3' (SEQ ID NO: 8) |
| human AXIN2 | forward | 5'-AGTGTGAGGTCCACGGAAAC-3' (SEQ ID NO: 9) |
| | reverse | 5'-CTTCACACTGCGATGCATTT-3' (SEQ ID NO: 10) |
| human LEF1 | forward | 5'-GACGAGATGATCCCCTTCAA-3' (SEQ ID NO: 11) |
| | reverse | 5'-AGGGCTCCT GAGAGGTTTGT-3' (SEQ ID NO: 12) |
| human cyclin D1 | forward | 5'-ACAAACAGATCATCCGCAAACAC-3' (SEQ ID NO: 13) |
| | reverse | 5'-TGTTGGGGCTCCTCAGGTTC-3' (SEQ ID NO: 14) |

Western Blotting. SW480 cells at $1\times10^6$ cells/mL were treated with different concentrations of inhibitors for 24 h. Cells were lysed in buffer containing 50 mM Tris (pH 7.4), 150 mM NaCl, 1% Nonidet P-40, 0.5% sodium deoxycholate, 0.1% SDS, and protease inhibitors. After centrifugation at 12,000 rpm for 20 min at 4° C., the supernatant was loaded onto an 8% SDS polyacrylamide gel for electrophoretic analysis. Separated proteins were transferred onto nitrocellulose membranes for immunoblot analysis. The antibodies against Axin2 (MA5-15015, Thermo Fisher) cyclin D1 (sc-853, Santa Cruz Biotechnology, Inc.), and β-tubulin (sc-55529, Santa Cruz Biotechnology, Inc) were incubated with the membranes overnight at 4° C., respectively. IRDye 680LT goat anti-mouse IgG (827-11080, LiCOR) or IRDye 800CW goat anti-rabbit IgG (827-08365, LiCOR) was used as the secondary antibody. The images were detected by the Odyssey Infrared Imaging System (LiCOR). Experiments were performed in duplicate.

Pull-Down Experiments. Adherent β-catenin signaling hyperactive SW480 cancer cells (70-80% confluency) in T75 flask were lysed first in 1 mL buffer A containing 50 mM Tris (pH 7.4), 150 mM NaCl, 1% Nonidet P-40, 2 mM EDTA, and protease inhibitors. Cell debris was removed by centrifugation at 10,000 g for 20 min at 4° C. In 500 μL SW480 cell lysates or 3 μg FLBcatenin protein in 300 μL buffer B (20 mM Tris pH 7.4, 150 mM NaCl, 0.05% NP-40), 1 μM or 10 UM biotinylated inhibitor was added in and incubated at 4° C. for 3 h. Then, 25 μL Streptavidin Sepharose beads (S-1638, Sigma) were added to the lysate mixture and rotated at 4° C. for 2 h. The lysate mixture was centrifuged at 4000 rpm for 2 min at 4° C. The beads were washed with buffer B for 4 times. The beads were resuspended in 60 μL of 2×SDS sample buffer. After boiling, the samples were loaded onto 8% SDS polyacrylamide gel for electrophoretic analysis. Separated proteins were transferred onto nitrocellulose membranes for immunoblot analysis. The antibody against β-catenin (610153, BD Biosciences) were incubated with the membranes. IRDye 680LT goat anti-mouse IgG (827-11080, LiCOR) was used as the secondary antibody. The images were detected by the Odyssey Infrared Imaging System (LiCOR). Experiments were performed in duplicate.

Co-Immunoprecipitation Experiments. 8-Catenin signaling hyperactive HCT116 cancer cells at $1\times10^6$/mL were treated with different concentrations of the inhibitor for 24 h. Cells were then lysed in buffer containing 50 mM Tris, pH 7.4, 150 mM NaCl, 1% Nonidet P-40, 2 mM EDTA, and protease inhibitors. The cell lysates were then preadsorbed to A/G plus agarose (sc-2003, Santa Cruz Biotechnology) at 4° C. for 1 h. Preadsorbed lysates were incubated with a specific primary antibody against β-catenin (610153, BD Biosciences) overnight at 4° C. A/G plus agarose was then added to the lysate mixture and incubated for 3 h. The beads were washed four times with the lysis buffer at 4° C. The bound protein was eluted by boiling in the SDS sample buffer and loaded onto 8% SDS polyacrylamide gel for electrophoretic analysis. Separated proteins were transferred onto nitrocellulose membranes for immunoblot analysis. The antibodies against BCL9 (ab37305, Abcam), β-catenin (610153, BD Biosciences), E-cadherin (610404, BD Biosciences) and β-tubulin (sc-55529, Santa Cruz Biotechnology, Inc.) were incubated with the membranes, respectively. IRDye 680LT goat anti mouse IgG (827-11080, LiCOR) and IRDye 800CW goat anti rabbit IgG (926-32211, LiCOR) were used as the secondary antibodies. The images were detected by the Odyssey Infrared Imaging System (LiCOR). Experiments were performed in duplicate.

Hepatic microsomal stability. Microsome stability was evaluated by incubating 1 μM compound with 1 mg/ml hepatic microsomes (human, rat, or mouse) in 100 mM potassium phosphate buffer, pH 7.4. The reactions were held at 37° C. with continuous shaking. The reaction was initiated by adding NADPH (1 mM final concentration). The final incubation volume was 300 μL, and 40 μL aliquots were removed at 0, 5, 10, 20, 40, and 60 min. The removed aliquot was added to 160 μL acetonitrile to stop the reaction and precipitate the protein. NADPH dependence of the reaction was evaluated in parallel incubations without NADPH. At the end of the assay, the samples are centrifuged through a 0.45 micron filter plate (MSRLN0450, Millipore Multiscreen Solventer low binding PTFE hydrophilic plates) and analyzed by LC-MS/MS. The data was log transformed, and the results are reported as half-life and intrinsic clearance.

In vivo pharmacokinetics. All procedure described are covered under existing protocols and have been approved by the Scripps Florida IACUC to be conducted in the Scripps vivarium, which is fully AAALAC accredited. Pharmacokinetics were determined in n=3 male C57BL/6 mice. Compounds were dosed as indicated via intravenous (i.v.) injection via tail vein or oral (p.o.) gavage. 25 μL blood was collected via a small nick in the tail using heparin-coated hematocrit capillary tubes which were sealed with wax and kept on ice until plasma was generated by centrifugation using a refrigerated centrifuge equipped with a hematocrit rotor. Dose levels are provided as described. Time points for determination of pharmacokinetic parameters were 5 min (i.v. only), 15 min, 30 min, 1 h, 2 h, 4 h, 6 h, 8 h, and 24 h (p.o.). Plasma concentrations were determined via LC-MS/MS using an eight-point standard curve between 2 and 2,000 ng/mL prepared in mouse plasma. Pharmacokinetic analysis was done with WinNonLin, Pharsight Inc. using a noncompartmental model.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

In some embodiments of Formula I, I-A, I-B or I-C, $R_{12}$ is selected from hydrogen, hydroxyl, halogen, cyano, $C_1$-$C_3$ alkyl, $C_1$-$C_3$ alkoxy, or $C_1$-$C_3$ alkylhalide.

In some embodiments of Formula I, I-A, I-B or I-C, at least one of $R_{11}$ and $R_{12}$ are hydrogen.

In some embodiments of Formula I, I-A, I-B or I-C, both $R_{13}$ and $R_{14}$ can be independently selected from hydrogen, hydroxyl, halogen, cyano, $C_1$-$C_6$ alkyl, $C_1$-$C_6$ alkoxy, $C_1$-$C_6$ alkylhalide, aryl, heteroaryl, a linker conjugated to a PROTAC moiety, or $R_{13}$ and $R_{14}$ combine together with the atoms to which they are attached to form a cycloalkyl, a heterocycloalkyl, or a heterocycloalkenyl. $R_{13}$ and $R_{14}$ are optionally and independently substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl.

In some embodiments of Formula I, I-A, I-B or I-C, $R_{15}$ is absent. In some embodiments of Formula I, I-A, I-B or I-C, $R_{15}$ can be selected from hydroxyl, halogen, cyano, $C_1$-$C_6$ alkyl, $C_1$-$C_6$ alkoxy, $C_1$-$C_6$ alkylhalide, or a linker conjugated to a PROTAC moiety.

In some embodiments of Formula I, I-A, I-B or I-C, $R_{16}$ for each occurrence can be independently selected from halogen, hydroxyl, carboxyl, amino, cyano, nitro, isocyano, alkyl, haloalkyl, haloalkoxy, a linker conjugated to a PROTAC moiety, cycloalkyl, heterocycloalkyl, aryl, or heteroaryl.

As described herein, the compound can have a chiral designation of R or S or in some cases, is a racemic mixture.

For example, the compound can be as described below in Tables 1-8:

What is claimed is:

1. A compound having a structure according to Formula I-B,

Formula I-B

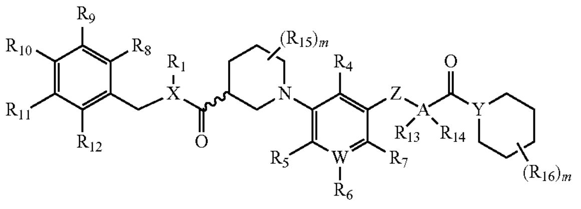

wherein m is independently for each occurrence 0, 1, or 2;

W is selected from C or N, wherein when W is N, then $R_6$ is absent;

X is selected from O, N;

Y is selected from O, N;

Z is absent or O;

A is absent or selected from $C_1$-$C_3$ alkyl;

$R_1$ is absent or selected from hydrogen, halogen, $C_1$-$C_6$ alkyl, $C_1$-$C_6$ alkoxy, $C_1$-$C_6$ haloalkyl, $C_1$-$C_6$ haloalkoxy, $C_1$-$C_6$ alkylamine, $C_3$-$C_6$ cycloalkyl, $C_3$-$C_6$ cycloalkenyl, heteroaryl, or a linker conjugated to a PROTAC moiety; wherein $R_1$ is optionally substituted with halogen, hydroxyl, carboxyl, amino, cyano, nitro, isocyano, alkyl, haloalkyl, haloalkoxy, a linker conjugated to a PROTAC moiety, cycloalkyl, heterocycloalkyl, aryl, or heteroaryl;

$R_4$, $R_5$, $R_6$, and $R_7$ are independently selected from hydrogen, hydroxyl, halogen, cyano, $C_1$-$C_3$ alkyl, $C_1$-$C_3$ alkoxy, $C_1$-$C_3$ alkylhalide, or a linker conjugated to a PROTAC moiety;

$R_8$ and $R_9$ are independently selected from hydrogen, $C_1$-$C_6$ alkyl, $C_1$-$C_6$ alkoxy, $C_3$-$C_8$ cycloalkyl, a $C_1$-$C_7$ heterocycloalkyl, $C_5$-$C_8$ aryl, $C_1$-$C_8$ heteroaryl, a linker conjugated to a PROTAC moiety, or $R_1$ and $R_8$ combine together with the atoms to which they are attached to form a heterocycloalkyl, or a heterocycloalkenyl, wherein $R_8$ and $R_9$ are optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

$R_{10}$ is selected from hydrogen, $C_1$-$C_6$ alkyl, $C_1$-$C_6$ alkoxy, $C_3$-$C_{10}$ cycloalkyl, a $C_2$-$C_8$ heterocycloalkyl, $C_5$-$C_{10}$ aryl, $C_2$-$C_8$ heteroaryl, or a linker conjugated to a PROTAC moiety, wherein $R_{10}$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

$R_{11}$ and $R_{12}$ are independently selected from hydrogen, hydroxyl, halogen, cyano, $C_1$-$C_3$ alkyl, $C_1$-$C_3$ alkoxy, $C_1$-$C_3$ heteroalkyl, $C_1$-$C_3$ alkylhalide, or a linker conjugated to a PROTAC moiety;

$R_{13}$ and $R_{14}$ are independently selected from hydrogen, hydroxyl, halogen, cyano, $C_1$-$C_6$ alkyl, $C_1$-$C_6$ alkoxy, $C_1$-$C_6$ alkylhalide, aryl, heteroaryl, a linker conjugated to a PROTAC moiety, or $R_{13}$ and $R_{14}$ combine together with the atoms to which they are attached to form a cycloalkyl, a heterocycloalkyl, or a heterocycloalkenyl, wherein $R_{13}$ and $R_{14}$ are optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl, $R_{15}$ is absent or for each occurrence, independently selected from hydroxyl, halogen, cyano, $C_1$-$C_6$ alkyl, $C_1$-$C_6$ alkoxy, $C_1$-$C_6$ alkylhalide, aryl, heteroaryl, a linker conjugated to a PROTAC moiety, wherein $R_{15}$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl, and $R_{16}$ for each occurrence is independently selected from halogen, hydroxyl, carboxyl, amino, cyano, nitro, isocyano, alkyl, haloalkyl, haloalkoxy, a linker conjugated to a PROTAC moiety, cycloalkyl, heterocycloalkyl, aryl, or heteroaryl.

2. A compound having Formula I-C,

Formula I-C

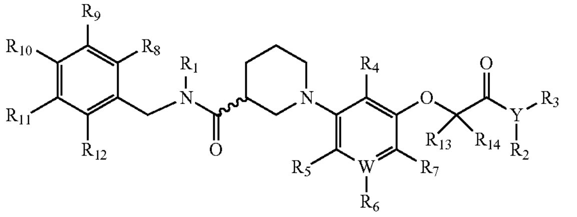

wherein

W is selected from C or N, wherein when W is N, then $R_6$ is absent;

Y is N;

$R_1$ is selected from hydrogen, halogen, $C_1$-$C_6$ alkyl, $C_1$-$C_6$ alkoxy, $C_1$-$C_6$ haloalkyl, $C_1$-$C_6$ haloalkoxy, $C_1$-$C_6$ alkylamine, $C_2$-$C_6$ ether, $C_3$-$C_6$ cycloalkyl, $C_3$-$C_6$ cycloalkenyl, heteroaryl, or a linker conjugated to a PROTAC moiety; wherein $R_1$ is optionally substituted with halogen, hydroxyl, carboxyl, amino, cyano, nitro, isocyano, alkyl, haloalkyl, haloalkoxy, cycloalkyl, heterocycloalkyl, aryl, or heteroaryl;

$R_2$ and $R_3$ are independently selected from hydrogen, $C_1$-$C_6$ alkyl, $C_3$-$C_{10}$ cycloalkyl, a $C_2$-$C_8$ heterocycloalkyl, $C_5$-$C_{10}$ aryl, $C_2$-$C_8$ heteroaryl, a linker conjugated to a PROTAC moiety, or $R_2$ and $R_3$ combine together with the atoms to which they are attached to form a heterocycloalkyl, a heterocycloalkenyl, or a heteroaryl, wherein $R_2$ and $R_3$ are optionally substituted with halogen, hydroxyl, carboxyl, amino, cyano, nitro, isocyano, alkyl, haloalkyl, haloalkoxy, cycloalkyl, heterocycloalkyl, aryl, or heteroaryl;

$R_4$, $R_5$, $R_6$, and $R_7$ are independently selected from hydrogen, hydroxyl, halogen, cyano, $C_1$-$C_3$ alkyl, $C_1$-$C_3$ alkoxy, $C_1$-$C_3$ alkylhalide, or a linker conjugated to a PROTAC moiety;

$R_8$ and $R_9$ are independently selected from hydrogen, $C_1$-$C_6$ alkyl, $C_1$-$C_6$ alkoxy, $C_3$-$C_8$ cycloalkyl, a $C_1$-$C_7$ heterocycloalkyl, $C_5$-$C_8$ aryl, $C_1$-$C_8$ heteroaryl, a linker conjugated to a PROTAC moiety, or $R_1$ and $R_8$ combine together with the atoms to which they are attached to form a heterocycloalkyl, or a heterocycloalkenyl, wherein $R_8$ and $R_9$ are optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

$R_{10}$ is selected from hydrogen, $C_1$-$C_6$ alkyl, $C_1$-$C_6$ alkoxy, $C_3$-$C_{10}$ cycloalkyl, a $C_2$-$C_8$ heterocycloalkyl, $C_5$-$C_{10}$ aryl, $C_2$-$C_8$ heteroaryl, or a linker conjugated to a PROTAC moiety, wherein $R_{10}$ is optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl;

$R_{11}$ and $R_{12}$ are independently selected from hydrogen, hydroxyl, halogen, cyano, $C_1$-$C_3$ alkyl, $C_1$-$C_3$ alkoxy, $C_1$-$C_3$ heteroalkyl, $C_1$-$C_3$ alkylhalide, or a linker conjugated to a PROTAC moiety;

$R_{13}$ and $R_{14}$ are independently selected from hydrogen, hydroxyl, halogen, cyano, $C_1$-$C_6$ alkyl, $C_1$-$C_6$ alkoxy, $C_1$-$C_6$ alkylhalide, aryl, alkylaryl, heteroaryl, alkylheteroaryl, a linker conjugated to a PROTAC moiety, or $R_{13}$ and $R_{14}$ combine together with the atoms to which they are attached to form a cycloalkyl, a cycloalkenyl, a heterocycloalkyl, or a heterocycloalkenyl, wherein $R_{13}$ and $R_{14}$ are optionally substituted with halogen, hydroxyl, amino, cyano, nitro, isocyano, carboxyl, hydroxyl, alkyl, alkoxy, alkenyl, haloalkyl, haloalkoxy, cycloalkyl, heterocycloalkyl, aryl, or heteroaryl.

3. The compound according to claim 2, wherein the compound of Formula I comprises at least one linker conjugated to a PROTAC moiety, wherein the linker conjugated to the PROTAC moiety comprises a linker selected from a substituted or unsubstituted $C_4$-$C_{24}$ alkyl, a substituted or unsubstituted $C_4$-$C_{24}$ alkoxy, and the PROTAC moiety is selected from a cereblon binder or a von Hippel-Lindau E3 ligase (VHL) ligand.

4. The compound according to claim 2, having a chiral designation of S.

5. The compound according to claim 2, wherein W is C.

6. The compound according to claim 2, wherein $R_{13}$ and $R_{14}$ are independently selected from hydrogen and $C_1$-$C_6$ alkyl.

7. The compound according to claim 2, wherein $R_1$ is selected from hydrogen, $C_1$-$C_6$ alkyl, $C_1$-$C_6$ alkoxy, or $C_3$-$C_6$ cycloalkyl.

8. The compound according to claim 2, wherein $R_2$ and $R_3$ combine together with the atoms to which they are attached to form a heterocycloalkyl, a heterocycloalkenyl, or a heteroaryl.

9. The compound according to claim 2, wherein Y is O, $R_2$ is absent and $R_3$ is selected from hydrogen, $C_1$-$C_6$ alkyl, or a linker conjugated to a PROTAC moiety.

10. The compound according to claim 6, wherein $R_2$ and $R_3$ combine together with the atoms to which they are attached to form a heterocycloalkyl, wherein $R_2$ and $R_3$ are optionally substituted with halogen, hydroxyl, carboxyl, amino, cyano, nitro, isocyano, alkyl, haloalkyl, haloalkoxy, cycloalkyl, heterocycloalkyl, aryl, or heteroaryl.

11. The compound according to claim 2, wherein $R_4$, $R_5$, $R_6$, $R_7$, $R_8$, $R_9$, $R_{11}$, and $R_{12}$ are all hydrogen.

12. The compound according to claim 11, wherein $R_{10}$ is selected from $C_1$-$C_6$ alkyl, $C_1$-$C_6$ alkoxy, $C_3$-$C_{10}$ cycloalkyl, a $C_2$-$C_8$ heterocycloalkyl, $C_5$-$C_{10}$ aryl, $C_2$-$C_8$ heteroaryl, or a linker conjugated to a PROTAC moiety.

13. The compound according to claim 2, wherein $R_{10}$ is selected from $C_1$-$C_6$ alkyl, $C_1$-$C_6$ alkoxy, or $C_2$-$C_8$ heteroaryl.

14. A pharmaceutical composition comprising a therapeutically effective amount of a compound of claim 2, or a pharmaceutically acceptable salt thereof, and a pharmaceutically acceptable carrier.

15. A method for the treatment of a disorder of uncontrolled cellular proliferation comprising the step of administering to the mammal an effective amount of a compound of claim 2, or a pharmaceutically acceptable salt thereof.

16. The method of claim 15, wherein the disorder is cancer.

17. The method of claim 16, wherein the cancer is selected from breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm.

18. A method for inhibiting protein-protein interactions of b-catenin and B-cell lymphoma 9 in at least one cell, comprising the step of contacting the at least one cell with an effective amount of a compound of claim 2, or a pharmaceutically acceptable salt thereof.

19. The compound according to claim 2, wherein the compound is:
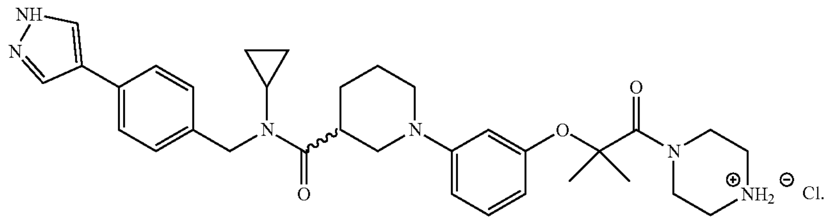 [SMILES: CC(C)(Oc1cccc(N2CCCC(C(=O)N(Cc3ccc(-c4cn[nH]c4)cc3)C3CC3)C2)c1)C(=O)N1CCNCC1]
* * * * *

SEQUENCE LISTING

```
<160> NUMBER OF SEQ ID NOS: 14

<210> SEQ ID NO 1
<211> LENGTH: 26
<212> TYPE: PRT
<213> ORGANISM: Artificial sequence
<220> FEATURE:
<223> OTHER INFORMATION: Description of sequence: Peptide, name:
      BCL9 26-mer
<220> FEATURE:
<221> NAME/KEY: SITE
<222> LOCATION: (26)
<223> OTHER INFORMATION: terminal is NH2

<400> SEQUENCE: 1

Gly Leu Ser Gln Glu Gln Leu Glu His Arg Glu Arg Ser Leu Gln Thr
1               5                   10                  15

Leu Arg Asp Ile Gln Arg Met Leu Phe Pro
            20                  25


<210> SEQ ID NO 2
<211> LENGTH: 27
<212> TYPE: PRT
<213> ORGANISM: Artificial sequence
<220> FEATURE:
<223> OTHER INFORMATION: Description of sequence: Peptide, name:
      Biotinylated BCL9 26-mer
<220> FEATURE:
<221> NAME/KEY: SITE
<222> LOCATION: (1)
<223> OTHER INFORMATION: Ahx
<220> FEATURE:
<221> NAME/KEY: SITE
<222> LOCATION: (1)
<223> OTHER INFORMATION: Biotinylated
<220> FEATURE:
<221> NAME/KEY: SITE
<222> LOCATION: (27)
<223> OTHER INFORMATION: terminal is NH2

<400> SEQUENCE: 2

Xaa Gly Leu Ser Gln Glu Gln Leu Glu His Arg Glu Arg Ser Leu Gln
1               5                   10                  15

Thr Leu Arg Asp Ile Gln Arg Met Leu Phe Pro
            20                  25


<210> SEQ ID NO 3
<211> LENGTH: 54
<212> TYPE: PRT
<213> ORGANISM: Artificial sequence
<220> FEATURE:
<223> OTHER INFORMATION: Description of sequence: Peptide, name:
      E-cadherin 54-mer
<220> FEATURE:
<221> NAME/KEY: SITE
<222> LOCATION: (54)
<223> OTHER INFORMATION: terminal is NH2

<400> SEQUENCE: 3

Ala Pro Pro Tyr Asp Ser Leu Leu Val Phe Asp Tyr Glu Gly Ser Gly
1               5                   10                  15

Ser Glu Ala Ala Ser Leu Ser Ser Leu Asn Ser Ser Glu Ser Asp Lys
            20                  25                  30

Asp Gln Asp Tyr Asp Tyr Leu Asn Glu Trp Gly Asn Arg Phe Lys Lys
        35                  40                  45

Leu Ala Asp Met Tyr Gly
    50
```

<210> SEQ ID NO 4
<211> LENGTH: 54
<212> TYPE: PRT
<213> ORGANISM: Artificial sequence
<220> FEATURE:
<223> OTHER INFORMATION: Description of sequence: Peptide, name:
      Biotinylated E-cadherin 54-mer
<220> FEATURE:
<221> NAME/KEY: SITE
<222> LOCATION: (1)
<223> OTHER INFORMATION: Biotinylated
<220> FEATURE:
<221> NAME/KEY: SITE
<222> LOCATION: (54)
<223> OTHER INFORMATION: terminal is NH2

<400> SEQUENCE: 4

```
Ala Pro Pro Tyr Asp Ser Leu Leu Val Phe Asp Tyr Glu Gly Ser Gly
1               5                   10                  15

Ser Glu Ala Ala Ser Leu Ser Ser Leu Asn Ser Ser Glu Ser Asp Lys
            20                  25                  30

Asp Gln Asp Tyr Asp Tyr Leu Asn Glu Trp Gly Asn Arg Phe Lys Lys
        35                  40                  45

Leu Ala Asp Met Tyr Gly
    50
```

<210> SEQ ID NO 5
<211> LENGTH: 19
<212> TYPE: DNA
<213> ORGANISM: Artificial sequence
<220> FEATURE:
<223> OTHER INFORMATION: Description of sequence: Primer, name: human
      GAPDH, direction: forward

<400> SEQUENCE: 5
gaaggtgaag gtcggagtc 19

<210> SEQ ID NO 6
<211> LENGTH: 20
<212> TYPE: DNA
<213> ORGANISM: Artificial sequence
<220> FEATURE:
<223> OTHER INFORMATION: Description of sequence: Primer, name: human
      GAPDH, direction: reverse

<400> SEQUENCE: 6
gaagatggtg atgggatttc 20

<210> SEQ ID NO 7
<211> LENGTH: 26
<212> TYPE: DNA
<213> ORGANISM: Artificial sequence
<220> FEATURE:
<223> OTHER INFORMATION: Description of sequence: Primer, name: human
      HPRT, direction: forward

<400> SEQUENCE: 7
gctataaatt ctttgctgac ctgctg 26

<210> SEQ ID NO 8
<211> LENGTH: 28
<212> TYPE: DNA
<213> ORGANISM: Artificial sequence
<220> FEATURE:
<223> OTHER INFORMATION: Description of sequence: Primer, name: human
      HPRT, direction: reverse -continued

<400> SEQUENCE: 8
aattactttt atgtcccctg ttgactgg 28

<210> SEQ ID NO 9
<211> LENGTH: 20
<212> TYPE: DNA
<213> ORGANISM: Artificial sequence
<220> FEATURE:
<223> OTHER INFORMATION: Description of sequence: Primer, name: human AXIN2, direction: forward

<400> SEQUENCE: 9
agtgtgaggt ccacggaaac 20

<210> SEQ ID NO 10
<211> LENGTH: 20
<212> TYPE: DNA
<213> ORGANISM: Artificial sequence
<220> FEATURE:
<223> OTHER INFORMATION: Description of sequence: Primer, name: human AXIN2, direction: reverse

<400> SEQUENCE: 10
cttcacactg cgatgcattt 20

<210> SEQ ID NO 11
<211> LENGTH: 20
<212> TYPE: DNA
<213> ORGANISM: Artificial sequence
<220> FEATURE:
<223> OTHER INFORMATION: Description of sequence: Primer, name: human LEF1, direction: forward

<400> SEQUENCE: 11
gacgagatga tcccccttcaa 20

<210> SEQ ID NO 12
<211> LENGTH: 20
<212> TYPE: DNA
<213> ORGANISM: Artificial sequence
<220> FEATURE:
<223> OTHER INFORMATION: Description of sequence: Primer, name: human LEF1, direction: reverse

<400> SEQUENCE: 12
agggctcctg agaggtttgt 20

<210> SEQ ID NO 13
<211> LENGTH: 23
<212> TYPE: DNA
<213> ORGANISM: Artificial sequence
<220> FEATURE:
<223> OTHER INFORMATION: Description of sequence: Primer, name: human cyclin D1, direction: forward

<400> SEQUENCE: 13
acaaacagat catccgcaaa cac 23

<210> SEQ ID NO 14
<211> LENGTH: 20
<212> TYPE: DNA
<213> ORGANISM: Artificial sequence -continued

```
<220> FEATURE:
<223> OTHER INFORMATION: Description of sequence: Primer, name: human
      cyclin D1, direction: reverse

<400> SEQUENCE: 14

tgttggggct cctcaggttc                                              20
```